US012553029B2

(12) United States Patent
Fardis et al.

(10) Patent No.: US 12,553,029 B2
(45) Date of Patent: *Feb. 17, 2026

(54) TREATMENT OF NSCLC PATIENTS WITH TUMOR INFILTRATING LYMPHOCYTE THERAPIES

(71) Applicant: Iovance Biotherapeutics, Inc., San Carlos, CA (US)

(72) Inventors: Maria Fardis, San Carlos, CA (US); Friedrich-Reinhard Graf Finck Von Finckenstein, San Carlos, CA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,755

(22) Filed: May 24, 2024

(65) Prior Publication Data

US 2024/0368543 A1 Nov. 7, 2024

Related U.S. Application Data

(63) Continuation of application No. 18/247,877, filed as application No. PCT/US2021/053841 on Oct. 6, 2021.

(60) Provisional application No. 63/146,402, filed on Feb. 5, 2021, provisional application No. 63/127,027, filed on Dec. 17, 2020, provisional application No. 63/088,282, filed on Oct. 6, 2020.

(51) Int. Cl.

| | |
|---|---|
| ***C12N 5/078*** | (2010.01) |
| ***A61K 31/664*** | (2006.01) |
| ***A61K 35/17*** | (2015.01) |
| ***A61K 38/20*** | (2006.01) |
| ***A61K 40/10*** | (2025.01) |
| ***A61K 40/11*** | (2025.01) |
| ***A61K 40/24*** | (2025.01) |
| ***A61K 40/33*** | (2025.01) |
| ***A61K 40/35*** | (2025.01) |
| ***A61K 40/42*** | (2025.01) |
| ***A61P 35/00*** | (2006.01) |
| ***C07K 16/28*** | (2006.01) |
| ***C12N 5/0781*** | (2010.01) |
| ***C12N 5/0783*** | (2010.01) |

(52) U.S. Cl.

CPC .......... *C12N 5/0634* (2013.01); *A61K 31/664* (2013.01); *A61K 35/17* (2013.01); *A61K 38/2013* (2013.01); *A61K 40/10* (2025.01); *A61K 40/11* (2025.01); *A61K 40/24* (2025.01); *A61K 40/33* (2025.01); *A61K 40/35* (2025.01); *A61K 40/42* (2025.01); *A61P 35/00* (2018.01); *C07K 16/2809* (2013.01); *C12N 5/0635* (2013.01); *C12N 5/0636* (2013.01); *C12N 5/0646* (2013.01); *A61K 2239/55* (2023.05); *C12N 2501/2302* (2013.01); *C12N 2501/515* (2013.01); *C12N 2502/11* (2013.01)

(58) Field of Classification Search

None

See application file for complete search history.

(56) References Cited

U.S. PATENT DOCUMENTS

| | | | |
|---|---|---|---|
| 4,704,692 | A | 11/1987 | Ladner |
| 4,766,106 | A | 8/1988 | Katre et al. |
| 4,897,355 | A | 1/1990 | Eppstein et al. |
| 4,902,502 | A | 2/1990 | Nitecki et al. |
| 4,946,778 | A | 8/1990 | Ladner et al. |
| 5,019,034 | A | 5/1991 | Weaver et al. |
| 5,089,261 | A | 2/1992 | Nitecki et al. |
| 5,126,132 | A | 6/1992 | Rosenberg |
| 5,128,257 | A | 7/1992 | Baer |
| 5,137,817 | A | 8/1992 | Busta et al. |
| 5,173,158 | A | 12/1992 | Schmukler |
| 5,206,344 | A | 4/1993 | Katre et al. |
| 5,232,856 | A | 8/1993 | Firth |
| 5,273,525 | A | 12/1993 | Hofmann |
| 5,279,833 | A | 1/1994 | Rose |
| 5,304,120 | A | 4/1994 | Crandell et al. |
| 5,318,514 | A | 6/1994 | Hofmann |
| 5,443,983 | A | 8/1995 | Ochoa et al. |
| 5,459,127 | A | 10/1995 | Felgner et al. |
| 5,593,875 | A | 1/1997 | Wurm et al. |
| 5,631,237 | A | 5/1997 | Dzau et al. |
| 5,648,260 | A | 7/1997 | Winter et al. |
| 5,714,350 | A | 2/1998 | Co et al. |
| 5,739,277 | A | 4/1998 | Presta et al. |

(Continued)

FOREIGN PATENT DOCUMENTS

CN 102816734 A 12/2012
CN 106244538 A 12/2016

(Continued)

OTHER PUBLICATIONS

Santos et al (ARPMD, 6:49-69, 2011).*

(Continued)

*Primary Examiner* — Brad Duffy

(74) *Attorney, Agent, or Firm* — Melissa J. Brayman

(57) ABSTRACT

The present invention provides improved and/or shortened processes and methods for preparing TILs in order to prepare therapeutic populations of TILs with increased therapeutic efficacy for the treatment of non-small cell lung carcinoma (NSCLC), wherein the NSCLC is refractory to treatment with an anti-PD-1 antibody and/or anti-PD-L1 antibody and/or VEGF inhibitor, or wherein the NSCLC has a predetermined tumor proportion score (TPS).

20 Claims, 44 Drawing Sheets

Specification includes a Sequence Listing.

(56) References Cited

U.S. PATENT DOCUMENTS

| | | | |
|---|---|---|---|
| 5,766,902 | A | 6/1998 | Craig et al. |
| 5,811,097 | A | 9/1998 | Allison et al. |
| 5,824,778 | A | 10/1998 | Ishikawa et al. |
| 5,834,250 | A | 11/1998 | Wells et al. |
| 5,855,887 | A | 1/1999 | Allison et al. |
| 5,869,046 | A | 2/1999 | Presta et al. |
| 5,898,031 | A | 4/1999 | Crooke |
| 5,908,635 | A | 6/1999 | Thierry |
| 5,928,893 | A | 7/1999 | Kang et al. |
| 5,955,365 | A | 9/1999 | Szoka, Jr. et al. |
| 5,976,567 | A | 11/1999 | Wheeler et al. |
| 5,977,318 | A | 11/1999 | Linsley et al. |
| 6,010,613 | A | 1/2000 | Walters et al. |
| 6,025,337 | A | 2/2000 | Truong et al. |
| 6,051,227 | A | 4/2000 | Allison et al. |
| 6,056,938 | A | 5/2000 | Unger et al. |
| 6,078,490 | A | 6/2000 | Walters |
| 6,096,871 | A | 8/2000 | Presta et al. |
| 6,100,071 | A | 8/2000 | Davis-Smyth et al. |
| 6,107,094 | A | 8/2000 | Crooke |
| 6,110,490 | A | 8/2000 | Thierry |
| 6,121,022 | A | 9/2000 | Presta et al. |
| 6,194,551 | B1 | 2/2001 | Idusogie et al. |
| 6,207,156 | B1 | 3/2001 | Kuchroo et al. |
| 6,210,669 | B1 | 4/2001 | Aruffo et al. |
| 6,242,195 | B1 | 6/2001 | Idusogie et al. |
| 6,277,375 | B1 | 8/2001 | Ward |
| 6,303,121 | B1 | 10/2001 | Kwon |
| 6,350,861 | B1 | 2/2002 | Co et al. |
| 6,352,694 | B1 | 3/2002 | June et al. |
| 6,362,325 | B1 | 3/2002 | Kwon |
| 6,375,929 | B1 | 4/2002 | Thomas, Jr. et al. |
| 6,410,517 | B1 | 6/2002 | Truong et al. |
| 6,475,994 | B2 | 11/2002 | Tomalia et al. |
| 6,479,626 | B1 | 11/2002 | Kim et al. |
| 6,489,458 | B2 | 12/2002 | Hackett et al. |
| 6,506,559 | B1 | 1/2003 | Fire et al. |
| 6,528,624 | B1 | 3/2003 | Idusogie et al. |
| 6,534,055 | B1 | 3/2003 | June et al. |
| 6,534,261 | B1 | 3/2003 | Cox, III et al. |
| 6,534,484 | B1 | 3/2003 | Wheeler et al. |
| 6,538,124 | B1 | 3/2003 | Idusogie et al. |
| 6,569,997 | B1 | 5/2003 | Kwon |
| 6,607,882 | B1 | 8/2003 | Cox, III et al. |
| 6,627,442 | B1 | 9/2003 | Humeau et al. |
| 6,682,736 | B1 | 1/2004 | Hanson et al. |
| 6,706,289 | B2 | 3/2004 | Lewis et al. |
| 6,737,056 | B1 | 5/2004 | Presta |
| 6,746,838 | B1 | 6/2004 | Choo et al. |
| 6,794,136 | B1 | 9/2004 | Eisenberg et al. |
| 6,821,505 | B2 | 11/2004 | Ward |
| 6,824,978 | B1 | 11/2004 | Cox, III et al. |
| 6,866,997 | B1 | 3/2005 | Choo et al. |
| 6,867,041 | B2 | 3/2005 | Berenson et al. |
| 6,884,879 | B1 | 4/2005 | Baca et al. |
| 6,887,466 | B2 | 5/2005 | June et al. |
| 6,887,673 | B2 | 5/2005 | Kunkel et al. |
| 6,903,185 | B2 | 6/2005 | Kim et al. |
| 6,905,680 | B2 | 6/2005 | June et al. |
| 6,905,681 | B1 | 6/2005 | June et al. |
| 6,905,685 | B2 | 6/2005 | Kwon |
| 6,933,113 | B2 | 8/2005 | Case |
| 6,974,863 | B2 | 12/2005 | Kwon |
| 6,979,539 | B2 | 12/2005 | Cox, III et al. |
| 6,984,720 | B1 | 1/2006 | Korman et al. |
| 6,998,253 | B1 | 2/2006 | Presta et al. |
| 7,013,219 | B2 | 3/2006 | Case et al. |
| 7,030,215 | B2 | 4/2006 | Liu et al. |
| 7,056,704 | B2 | 6/2006 | Tuschl et al. |
| 7,060,269 | B1 | 6/2006 | Baca et al. |
| 7,078,196 | B2 | 7/2006 | Tuschl et al. |
| 7,083,784 | B2 | 8/2006 | Dall'Acqua et al. |
| 7,109,003 | B2 | 9/2006 | Hanson et al. |
| 7,132,281 | B2 | 11/2006 | Hanson et al. |
| 7,144,575 | B2 | 12/2006 | June et al. |
| 7,148,342 | B2 | 12/2006 | Tolentino et al. |
| 7,169,901 | B2 | 1/2007 | Baca et al. |
| 7,175,843 | B2 | 2/2007 | June et al. |
| 7,189,705 | B2 | 3/2007 | Lam et al. |
| 7,214,493 | B2 | 5/2007 | Kunkel et al. |
| 7,220,719 | B2 | 5/2007 | Case et al. |
| 7,227,004 | B2 | 6/2007 | Kim |
| 7,232,566 | B2 | 6/2007 | June et al. |
| 7,241,573 | B2 | 7/2007 | Choo et al. |
| 7,241,574 | B2 | 7/2007 | Choo et al. |
| 7,282,564 | B2 | 10/2007 | Mello et al. |
| 7,288,638 | B2 | 10/2007 | Jure-Kunkel et al. |
| 7,297,334 | B2 | 11/2007 | Baca et al. |
| 7,432,249 | B2 | 10/2008 | Crooke |
| 7,432,250 | B2 | 10/2008 | Crooke |
| 7,479,269 | B2 | 1/2009 | June et al. |
| 7,504,101 | B2 | 3/2009 | Weinberg |
| 7,538,095 | B2 | 5/2009 | Fire et al. |
| 7,550,140 | B2 | 6/2009 | Bakker et al. |
| 7,560,438 | B2 | 7/2009 | Fire et al. |
| 7,572,631 | B2 | 8/2009 | Berenson et al. |
| 7,585,849 | B2 | 9/2009 | Liu et al. |
| 7,595,376 | B2 | 9/2009 | Kim et al. |
| 7,622,444 | B2 | 11/2009 | Weinberg |
| 7,687,070 | B2 | 3/2010 | Gebeyehu et al. |
| 7,696,175 | B2 | 4/2010 | Epstein et al. |
| 7,943,743 | B2 | 5/2011 | Korman et al. |
| 7,951,365 | B2 | 5/2011 | Winqvist et al. |
| 7,960,515 | B2 | 6/2011 | Min et al. |
| 8,007,785 | B2 | 8/2011 | Winqvist et al. |
| 8,008,449 | B2 | 8/2011 | Korman et al. |
| 8,034,334 | B2 | 10/2011 | Dudley et al. |
| 8,133,983 | B2 | 3/2012 | Bakker et al. |
| 8,168,757 | B2 | 5/2012 | Finnefrock et al. |
| 8,206,702 | B2 | 6/2012 | Winqvist et al. |
| 8,211,424 | B2 | 7/2012 | Winqvist et al. |
| 8,211,425 | B2 | 7/2012 | Winqvist et al. |
| 8,217,149 | B2 | 7/2012 | Irving et al. |
| 8,236,930 | B2 | 8/2012 | Min et al. |
| 8,287,856 | B2 | 10/2012 | Li et al. |
| 8,287,857 | B2 | 10/2012 | Dudley et al. |
| 8,337,850 | B2 | 12/2012 | Ahrens et al. |
| 8,354,509 | B2 | 1/2013 | Carven et al. |
| 8,383,099 | B2 | 2/2013 | Dudley et al. |
| 8,450,460 | B2 | 5/2013 | Hill et al. |
| 8,580,247 | B2 | 11/2013 | Li et al. |
| 8,586,526 | B2 | 11/2013 | Gregory et al. |
| 8,617,884 | B2 | 12/2013 | Berenson et al. |
| 8,686,119 | B2 | 4/2014 | Rotem-Yehudar et al. |
| 8,697,359 | B1 | 4/2014 | Zhang |
| 8,735,553 | B1 | 5/2014 | Li et al. |
| 8,771,945 | B1 | 7/2014 | Zhang |
| 8,779,108 | B2 | 7/2014 | Queva et al. |
| 8,809,050 | B2 | 8/2014 | Vera et al. |
| 8,821,867 | B2 | 9/2014 | Ahrens et al. |
| 8,865,406 | B2 | 10/2014 | Zhang et al. |
| 8,871,445 | B2 | 10/2014 | Cong et al. |
| 8,895,308 | B1 | 11/2014 | Zhang et al. |
| 8,906,616 | B2 | 12/2014 | Zhang et al. |
| 8,907,053 | B2 | 12/2014 | Sasikumar et al. |
| 8,921,519 | B2 | 12/2014 | Hill et al. |
| 8,932,814 | B2 | 1/2015 | Cong et al. |
| 8,945,839 | B2 | 2/2015 | Zhang |
| 8,956,860 | B2 | 2/2015 | Vera et al. |
| 8,962,804 | B2 | 2/2015 | Williams et al. |
| 8,993,233 | B2 | 3/2015 | Zhang et al. |
| 8,999,641 | B2 | 4/2015 | Zhang et al. |
| 9,006,399 | B2 | 4/2015 | Liu et al. |
| 9,018,230 | B2 | 4/2015 | Mano et al. |
| 9,028,824 | B2 | 5/2015 | Min et al. |
| 9,044,442 | B2 | 6/2015 | Sasikumar et al. |
| 9,074,185 | B2 | 7/2015 | Dudley et al. |
| 9,080,171 | B2 | 7/2015 | Khvorova et al. |
| 9,096,642 | B2 | 8/2015 | Sasikumar et al. |
| 9,163,085 | B2 | 10/2015 | Liu et al. |
| 9,340,599 | B2 | 5/2016 | Hill et al. |
| 9,359,420 | B2 | 6/2016 | Hill et al. |
| 9,458,508 | B2 | 10/2016 | Morris et al. |
| 9,468,678 | B2 | 10/2016 | Ahrens et al. |

(56) References Cited

U.S. PATENT DOCUMENTS

| | | | |
|---|---|---|---|
| 9,476,028 | B2 | 10/2016 | Karlsson-Parra et al. |
| 9,528,088 | B2 | 12/2016 | Berenson et al. |
| 9,687,510 | B2 | 6/2017 | Borrello et al. |
| 9,777,261 | B2 | 10/2017 | Kim et al. |
| 9,790,490 | B2 | 10/2017 | Zhang et al. |
| 9,792,403 | B2 | 10/2017 | Sun et al. |
| 9,844,569 | B2 | 12/2017 | Gros et al. |
| 9,914,783 | B1 | 3/2018 | Afar et al. |
| 10,087,464 | B2 | 10/2018 | Hayes et al. |
| 10,130,659 | B2 | 11/2018 | Wardell |
| 10,144,779 | B2 | 12/2018 | Van Dijk et al. |
| 10,155,945 | B2 | 12/2018 | Knopov |
| 10,183,979 | B2 | 1/2019 | Alvarez et al. |
| 10,363,273 | B2 | 7/2019 | Wardell |
| 10,517,894 | B2 | 12/2019 | Frank |
| 10,537,595 | B2 | 1/2020 | Wardell |
| 10,633,654 | B2 | 4/2020 | Pavco et al. |
| 10,653,723 | B1 | 5/2020 | Wardell |
| 10,905,718 | B2 | 2/2021 | Wardell |
| 10,913,948 | B2 | 2/2021 | Khvorova |
| 10,918,666 | B2 | 2/2021 | Wardell |
| 10,925,900 | B2 | 2/2021 | Wardell et al. |
| 10,933,094 | B2 | 3/2021 | Wardell |
| 10,946,044 | B2 | 3/2021 | Wardell |
| 10,946,045 | B2 | 3/2021 | Wardell |
| 10,953,046 | B2 | 3/2021 | Wardell |
| 10,953,047 | B2 | 3/2021 | Wardell |
| 11,013,770 | B1 | 5/2021 | Wardell |
| 11,026,974 | B2 | 6/2021 | Frank |
| 11,168,303 | B2 | 11/2021 | Wardell |
| 11,168,304 | B2 | 11/2021 | Wardell |
| 11,220,670 | B2 | 1/2022 | Simpson-Abelson |
| 11,254,913 | B1 | 2/2022 | Wardell |
| 11,293,009 | B2 | 4/2022 | Simpson-Abelson |
| 11,351,198 | B2 | 6/2022 | Frank |
| 11,357,841 | B2 | 6/2022 | Ritthipichai |
| 11,401,507 | B2 | 8/2022 | Simpson-Abelson |
| 11,433,097 | B2 | 9/2022 | Fardis |
| 11,517,592 | B1 | 12/2022 | Wardell |
| 11,529,372 | B1 | 12/2022 | Wardell |
| 11,541,077 | B2 | 1/2023 | Wardell |
| 11,631,483 | B2 | 4/2023 | Brooks |
| 11,713,446 | B2 | 8/2023 | Chartier-Courtaud |
| 11,819,517 | B2 | 11/2023 | Wardell |
| 2002/0039581 | A1 | 4/2002 | Carreno et al. |
| 2002/0076747 | A1 | 6/2002 | Price et al. |
| 2002/0086014 | A1 | 7/2002 | Korman et al. |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2004/0110704 | A1 | 6/2004 | Yamane et al. |
| 2004/0265839 | A1 | 12/2004 | Mello et al. |
| 2005/0095244 | A1 | 5/2005 | Jure-Kunkel et al. |
| 2005/0100913 | A1 | 5/2005 | Mello et al. |
| 2005/0106717 | A1 | 5/2005 | Wilson et al. |
| 2005/0201994 | A1 | 9/2005 | Korman et al. |
| 2006/0024798 | A1 | 2/2006 | Mello et al. |
| 2008/0050342 | A1 | 2/2008 | Fire et al. |
| 2008/0055443 | A1 | 3/2008 | Okamoto et al. |
| 2008/0081373 | A1 | 4/2008 | Fire et al. |
| 2008/0248576 | A1 | 10/2008 | Fire et al. |
| 2009/0028857 | A1 | 1/2009 | Li et al. |
| 2009/0131360 | A1 | 5/2009 | Woolf et al. |
| 2010/0136030 | A1 | 6/2010 | Salah-Eddine et al. |
| 2010/0143918 | A1 | 6/2010 | Guo et al. |
| 2010/0203056 | A1 | 8/2010 | Irving et al. |
| 2010/0221737 | A1 | 9/2010 | Gu et al. |
| 2010/0266617 | A1 | 10/2010 | Carven et al. |
| 2010/0285013 | A1 | 11/2010 | Li et al. |
| 2011/0008369 | A1 | 1/2011 | Finnefrock et al. |
| 2011/0027218 | A1 | 2/2011 | Hill et al. |
| 2011/0039914 | A1 | 2/2011 | Pavco et al. |
| 2011/0052530 | A1 | 3/2011 | Dudley et al. |
| 2011/0111494 | A1 | 5/2011 | Hill et al. |
| 2011/0136228 | A1 | 6/2011 | Vera et al. |
| 2011/0201118 | A1 | 8/2011 | Yang et al. |
| 2012/0244133 | A1 | 9/2012 | Rosenberg et al. |
| 2013/0022600 | A1 | 1/2013 | Li et al. |
| 2013/0034559 | A1 | 2/2013 | Queva et al. |
| 2013/0045200 | A1 | 2/2013 | Irving et al. |
| 2013/0045201 | A1 | 2/2013 | Irving et al. |
| 2013/0045202 | A1 | 2/2013 | Irving et al. |
| 2013/0102075 | A1 | 4/2013 | Vera et al. |
| 2013/0108651 | A1 | 5/2013 | Carven et al. |
| 2013/0109843 | A1 | 5/2013 | Carven et al. |
| 2013/0115617 | A1 | 5/2013 | Wilson |
| 2013/0117869 | A1 | 5/2013 | Duchateau et al. |
| 2013/0131141 | A1 | 5/2013 | Khvorova et al. |
| 2013/0131142 | A1 | 5/2013 | Khvorova et al. |
| 2013/0315884 | A1 | 11/2013 | Galetto et al. |
| 2014/0227237 | A1 | 8/2014 | June et al. |
| 2014/0294898 | A1 | 10/2014 | Miller et al. |
| 2014/0295426 | A1 | 10/2014 | Albelda et al. |
| 2014/0328791 | A1 | 11/2014 | Bossard et al. |
| 2014/0341917 | A1 | 11/2014 | Nastri et al. |
| 2014/0377284 | A1 | 12/2014 | Simons et al. |
| 2014/0377739 | A1 | 12/2014 | Welch et al. |
| 2015/0056193 | A1 | 2/2015 | Crosby et al. |
| 2015/0073024 | A1 | 3/2015 | Sasikumar et al. |
| 2015/0073042 | A1 | 3/2015 | Sasikumar et al. |
| 2015/0087581 | A1 | 3/2015 | Sasikumar et al. |
| 2015/0110734 | A1 | 4/2015 | Hill et al. |
| 2015/0125491 | A1 | 5/2015 | Sasikumar et al. |
| 2015/0126709 | A1 | 5/2015 | Hill et al. |
| 2015/0126710 | A1 | 5/2015 | Hill et al. |
| 2015/0132288 | A1 | 5/2015 | Simons et al. |
| 2015/0175966 | A1 | 6/2015 | Vera et al. |
| 2015/0190506 | A1 | 7/2015 | Cheung et al. |
| 2015/0203871 | A1 | 7/2015 | Juillerat et al. |
| 2015/0320798 | A1 | 11/2015 | Borrello et al. |
| 2016/0010058 | A1 | 1/2016 | Gros et al. |
| 2016/0120906 | A1 | 5/2016 | Galetto et al. |
| 2016/0208216 | A1 | 7/2016 | Vera et al. |
| 2016/0215262 | A1 | 7/2016 | Powell |
| 2016/0304873 | A1 | 10/2016 | Wolfson et al. |
| 2017/0044496 | A1 | 2/2017 | Sarnaik et al. |
| 2017/0081635 | A1 | 3/2017 | Sarnaik et al. |
| 2017/0107490 | A1 | 4/2017 | Maeurer |
| 2017/0114321 | A1 | 4/2017 | Berenson et al. |
| 2017/0152478 | A1 | 6/2017 | Rosenberg et al. |
| 2017/0258838 | A1 | 9/2017 | Borrello et al. |
| 2018/0127715 | A1 | 5/2018 | Veerapathran et al. |
| 2018/0148690 | A1 | 5/2018 | Gros et al. |
| 2018/0187150 | A1 | 7/2018 | De Larichaudy |
| 2018/0207201 | A1 | 7/2018 | Wardell et al. |
| 2018/0228841 | A1 | 8/2018 | Frank et al. |
| 2018/0280436 | A1 | 10/2018 | Wardell et al. |
| 2018/0282694 | A1 | 10/2018 | Wardell et al. |
| 2018/0363066 | A1 | 12/2018 | Chalmers et al. |
| 2019/0000070 | A1 | 1/2019 | De Larichaudy et al. |
| 2019/0002546 | A1 | 1/2019 | Li et al. |
| 2019/0048096 | A1 | 2/2019 | Hermann et al. |
| 2019/0048341 | A1 | 2/2019 | Cardia et al. |
| 2019/0062706 | A1 | 2/2019 | Almaasbak et al. |
| 2019/0136186 | A1 | 5/2019 | Germeroth et al. |
| 2019/0201334 | A1 | 7/2019 | Hakim et al. |
| 2019/0211337 | A1 | 7/2019 | Khvorova et al. |
| 2019/0275133 | A1 | 9/2019 | Charych et al. |
| 2019/0298801 | A1 | 10/2019 | Kerwin et al. |
| 2019/0307796 | A1 | 10/2019 | Delgoffe |
| 2019/0343918 | A1 | 11/2019 | Graham et al. |
| 2020/0024350 | A1 | 1/2020 | Van Dijk et al. |
| 2020/0121719 | A1 | 4/2020 | Lotze et al. |
| 2020/0181220 | A1 | 6/2020 | Ptacin et al. |
| 2020/0223907 | A1 | 7/2020 | Balakrishnan et al. |
| 2020/0270334 | A1 | 8/2020 | Deane et al. |
| 2020/0299644 | A1 | 9/2020 | Frank et al. |
| 2020/0330601 | A1 | 10/2020 | Ptacin et al. |

(56) References Cited

U.S. PATENT DOCUMENTS

| | | | |
|---|---|---|---|
| 2020/0347350 | A1 | 11/2020 | Karyampudi et al. |
| 2021/0038684 | A1 | 2/2021 | Losey et al. |

FOREIGN PATENT DOCUMENTS

| | | | |
|---|---|---|---|
| CN | 106591232 | A | 4/2017 |
| CN | 107384867 | A | 11/2017 |
| EP | 0154316 | B1 | 9/1989 |
| EP | 0401384 | A1 | 12/1990 |
| EP | 0404097 | B1 | 9/1996 |
| EP | 0672141 | B1 | 5/2003 |
| EP | 0928290 | B1 | 3/2005 |
| EP | 1212422 | B1 | 2/2007 |
| EP | 1309726 | B1 | 12/2009 |
| EP | 1539929 | B1 | 4/2013 |
| EP | 1176195 | B1 | 5/2013 |
| EP | 2925329 | A1 | 10/2015 |
| EP | 3188740 | A1 | 7/2017 |
| EP | 3365434 | A1 | 8/2018 |
| EP | 3368659 | A1 | 9/2018 |
| EP | 3487990 | A1 | 5/2019 |
| JP | 2022-512915 | A | 2/2022 |
| JP | 2023-544199 | A | 10/2023 |
| WO | WO 88/007089 | | 9/1988 |
| WO | WO 93/011161 | | 6/1993 |
| WO | WO 95/012673 | | 5/1995 |
| WO | WO 95/021925 | | 8/1995 |
| WO | WO 96/014339 | | 5/1996 |
| WO | WO 96/040915 | | 12/1996 |
| WO | WO 97/020574 | | 6/1997 |
| WO | WO 98/005787 | | 2/1998 |
| WO | WO 98/023289 | | 6/1998 |
| WO | WO 98/030679 | | 7/1998 |
| WO | WO 98/042752 | | 10/1998 |
| WO | WO 99/032619 | | 7/1999 |
| WO | WO 99/051642 | | 10/1999 |
| WO | WO 99/054342 | | 10/1999 |
| WO | WO 99/058572 | | 11/1999 |
| WO | WO 00/009560 | | 2/2000 |
| WO | WO 00/032767 | | 6/2000 |
| WO | WO 00/037504 | | 6/2000 |
| WO | WO 00/042072 | | 7/2000 |
| WO | WO 01/014424 | | 3/2001 |
| WO | WO 01/029058 | | 4/2001 |
| WO | WO 2002/44215 | A2 | 6/2002 |
| WO | WO 2002/060919 | A2 | 8/2002 |
| WO | WO 2003/035835 | A2 | 5/2003 |
| WO | WO 2003/074569 | A2 | 9/2003 |
| WO | WO 2003/086459 | A1 | 10/2003 |
| WO | WO 2004/016750 | A2 | 2/2004 |
| WO | WO 2004/029207 | A2 | 4/2004 |
| WO | WO 2004/035607 | A2 | 4/2004 |
| WO | WO 2004/035752 | A2 | 4/2004 |
| WO | WO 2004031370 | A1 | 4/2004 |
| WO | WO 2004/063351 | A2 | 7/2004 |
| WO | WO 2004/074455 | A2 | 9/2004 |
| WO | WO 2004/081021 | A2 | 9/2004 |
| WO | WO 2005/040217 | A2 | 10/2004 |
| WO | WO 2004/099249 | A2 | 11/2004 |
| WO | WO 2005/012359 | A2 | 2/2005 |
| WO | WO 2005/070963 | A1 | 8/2005 |
| WO | WO 2005/077981 | A2 | 8/2005 |
| WO | WO 2005/092380 | A2 | 10/2005 |
| WO | WO 2005/092925 | A2 | 10/2005 |
| WO | WO 2005/123780 | A2 | 12/2005 |
| WO | WO 2006/009649 | A2 | 1/2006 |
| WO | WO 2006/012168 | A2 | 2/2006 |
| WO | WO 2006/019447 | A1 | 2/2006 |
| WO | WO 2006/029219 | A2 | 3/2006 |
| WO | WO 2006/047350 | A2 | 5/2006 |
| WO | WO 2006/085967 | A2 | 8/2006 |
| WO | WO 2006/121168 | A2 | 11/2006 |
| WO | WO 2006/121810 | A2 | 11/2006 |
| WO | WO 2007/067959 | A2 | 6/2007 |
| WO | WO 2007/0123737 | A2 | 11/2007 |
| WO | WO 2008/025516 | A2 | 3/2008 |
| WO | WO 2008/156712 | A1 | 12/2008 |
| WO | WO 2009/007120 | A2 | 1/2009 |
| WO | WO 2009040789 | A2 | 4/2009 |
| WO | WO 2009/100140 | A1 | 8/2009 |
| WO | WO 2010/003766 | A2 | 1/2010 |
| WO | WO 2010/010051 | A1 | 1/2010 |
| WO | WO 2010/020618 | A1 | 2/2010 |
| WO | WO 2010/042433 | A1 | 4/2010 |
| WO | WO 2010/058426 | A2 | 5/2010 |
| WO | WO 2010/078966 | A1 | 7/2010 |
| WO | WO 2010/093928 | A2 | 8/2010 |
| WO | WO 2010/097597 | A1 | 9/2010 |
| WO | WO 2010/148223 | A2 | 12/2010 |
| WO | WO 2011072088 | A2 | 6/2011 |
| WO | WO 2012/027328 | A3 | 3/2012 |
| WO | WO 2012/032433 | A1 | 3/2012 |
| WO | WO 2012/065086 | A1 | 5/2012 |
| WO | WO 2012/120125 | A1 | 9/2012 |
| WO | WO 2012129201 | A1 | 9/2012 |
| WO | WO 2012/177788 | A1 | 12/2012 |
| WO | WO 2013/028231 | A1 | 2/2013 |
| WO | WO 2013/038191 | A2 | 3/2013 |
| WO | WO 2013057500 | A1 | 4/2013 |
| WO | WO 2013/070634 | A1 | 5/2013 |
| WO | WO 2013088147 | A1 | 6/2013 |
| WO | WO 2013173835 | A1 | 11/2013 |
| WO | WO 2013188427 | A1 | 12/2013 |
| WO | WO 2014/006113 | A1 | 1/2014 |
| WO | WO 2014/148895 | A1 | 9/2014 |
| WO | WO 2014210036 | A1 | 12/2014 |
| WO | WO 2015009604 | A1 | 1/2015 |
| WO | WO 2015/033301 | A1 | 3/2015 |
| WO | WO 2015/036927 | A1 | 3/2015 |
| WO | WO 2015/044900 | A1 | 4/2015 |
| WO | WO 2015/119923 | A1 | 8/2015 |
| WO | WO 2015157636 | A1 | 10/2015 |
| WO | WO 2015188839 | A1 | 12/2015 |
| WO | WO 2015189356 | A1 | 12/2015 |
| WO | WO 2015189357 | A1 | 12/2015 |
| WO | WO 2016053338 | A1 | 4/2016 |
| WO | WO 2016096903 | A1 | 6/2016 |
| WO | 2017008019 | A1 | 1/2017 |
| WO | WO 2017001784 | A1 | 1/2017 |
| WO | WO 2017048614 | A1 | 3/2017 |
| WO | WO 2018005712 | A1 | 1/2018 |
| WO | WO 2018081473 | A1 | 5/2018 |
| WO | WO 2018/106884 | A1 | 6/2018 |
| WO | WO 2018102761 | A1 | 6/2018 |
| WO | WO 2018/132496 | A1 | 7/2018 |
| WO | WO 2018129332 | A1 | 7/2018 |
| WO | WO 2018170188 | A2 | 9/2018 |
| WO | WO 2018182817 | A1 | 10/2018 |
| WO | WO 2018/204760 | A1 | 11/2018 |
| WO | WO 2018209115 | A1 | 11/2018 |
| WO | WO 2018226714 | A1 | 12/2018 |
| WO | 2020096682 | A2 | 3/2020 |
| WO | 2020096986 | A2 | 5/2020 |
| WO | WO 2020/096988 | A2 | 5/2020 |
| WO | 2022076952 | A1 | 4/2022 |

OTHER PUBLICATIONS

Kanda et al (AO, 00:1-9, 2016).*

Shah et al (Oncotarget, 9(4):4375-4284, 2018.*

Robertson et al (Immuno-Oncology Technology, 3:1-7, 2019).*

Abdullah et al (Cancer, 118:3455-3467, 2012).*

Ahmad, Z. et al., "scFv Antibody: Principles and Clinical Application," Clin. & Dev. Immunol., 2012, 980250, doi:10.1155/2012/980250, 15 pages.

Augustyns, K., et al., "Incorporation of hexose nucleoside analogues into oligonucleotides: synthesis, base-pairing properties and enzymatic stability," Nucl. Acids. Res., 1992, 20(18):4711-4716.

Beane, J. et al., "Clinical Scale Zinc Finger Nuclease-mediated Gene Editing of PD-1 in Tumor Infiltrating Lymphocytes for the Treatment of Metastatic Melanoma," Molecular Therapy, Aug. 2015, 23(8):1380-1390.

(56) References Cited

OTHER PUBLICATIONS

Bergan, R. et al., "Electroporation enhances c-myc antisense oligodeoxynucleotide efficacy," Nucleic Acids Research, 1993, 21(15):3567-3573.
Bird, R. et al., "Single Chain Antibody Variable Regions," TIBTECH, Apr. 1991, 9: 132-137.
Bird, R., et al., "Single-Chain Antigen-Binding Proteins," Science, Oct. 21, 1988, 242:423-426.
Bose, R. et al., "Activating HER2 Mutations in HER2 Gene Amplification Negative Breast Cancer," Cancer Discov., Feb. 2013, 3(2):224-237.
Brahmer, J. et al., "Clinical activitgy and biomarkers of MEDI4736, an anti-PD-L1 antibody, in patients with NSCLC," J. Clin. Oncol., May 2014, 32(15):8021, 2 pages.
Byrne, M. et al., "Novel Hydrophobically Modified Asymmetric RNAi Compounds (sd-rxRNA) Demonstrate Robust Efficacy in the Eye," J. Ocular Pharmacology and Therapeutics, 2013, 00:00, 1-10.
Camacho, L. et al., "Phase 1 clinical trial of anti-CTLA4 human monoclonal antibody CP-675,206 in patients (pts) with advanced solid malignancies," J. Clin. Oncology, Jul. 15, 2004, 22(14):2505-2505, 4 pages.
Carmeliet, P. et al., "Angiogenesis in cancer and other diseases," Sep. 14, 2000, Nature, 407:249-257.
Cepko, C. et al., "Transduction of Genes Using Retrovirus Vectors," Current Protocols in Molecular Biology, 1996, 9.9.1-9.9.16.
Chen, C. et al., "High-Efficiency Transformation of Mammalian Cells by Plasmid DNA," Molecular and Cellular Biology, Aug. 1987, 7(8):2745-2752.
Cox, D. et al., "Therapeutic Genome Editing: Prospects and Challenges," Nat. Med., Feb. 2015, 21(2):121-131.
Curti, B. et al., "OX40 is a potent immune stimulating target in late stage cancer patients," Dec. 15, 2013, Cancer Res., 73(24):7189-7198.
De Marco, A., "Biotechnological applications of recombinant single-domain antibody fragments," Microbial Cell Factories, 2011, 10:44, 1-14.
Dominguez-Villar, M. et al., "Regulatory T cells in autoimmune diseases," Nat. Immunology, Jul. 2018, 19(7):665-673.
Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.
Dudley, et al., "Adoptive Cell Therapy for Patients with Metastatic Melanoma: Evaluation of Intensive Myeloablative Chemoradiation Preparative Regimens", J. Clin. Oncol., Nov. 2008, 26(32), 5233-39.
Dudley, et al., "Cancer Regression and Autoimmunity in Patients After Clonal Repopulation with Antitumor Lymphocytes", Science, Oct. 2002, 298, 850-54.
Dull T. et al., "A Third-Generation Lentivirus Vector with a Conditional Packaging System," Journal of Virology, Nov. 1998, 72(11):8463-8471.
Eisenhauer, E.A. et al., "New response evaluation criteria in solid tumours: Revised RECIST guideline," European Journal of Cancer, 2009, 45:228-247.
Eton, O. et al., "A Phase II Study of 'Decrescendo' Interleukin-2 plus Interferon-α-2a in Patients with Progressive Metastatic Melanoma after Chemotherapy," Cancer, Apr. 1, 2000, 88(7):1703-1709.
FDA, "Tissue Guidances," http://www.fda.gov/cber/guidelines.htm, 3 pages.
Fehniger, T. et al., "Interleukin 15: biology and relevance to human disease," Blood, Jan. 1, 2001, 97(1):14-32.
Felgner, P. et al., "Lipofection: A highly efficient, lipid-mediated DNA-transfection procedure," Proc. Natl. Acad. Sci. USA, Nov. 1987, 84:7413-7417.
Ferrara, N. et al., "Discovery and Development of Bevacizumab, an Anti-VEGF Antibody for Treating Cancer," Nature Reviews Drug Discovery, May 2004, 3:391-400.
Fisher, T. et al., "Targeting of 4-1BB by monoclonal antibody PF-05082566 enhances T-cell function and promotes anti-tumor activity," Cancer Immunolog. & Immunother., 2012, 61:1721-1733.
Fry, T. et al., "Interleukin-7: from bench to clinic," Blood, Jun. 1, 2002, 99(11):3892-3904.
Fuerst, M., "Metastatic Melanoma: Immunotherapy with Pembrolizumab Induces Durable Responses," Oncology Times, Jul. 10, 2014, 36:35-36.
Gandhi, L. et al., "Pembrolizumab plus Chemotherapy in Metastatic Non-Small-Cell Lung Cancer," N Engl J Med, 2018, 378(22):2078-2092.
Gieffers, C. et al., "APG350 Induces Superior Clustering of TRAIL Receptors and Shows Therapeutic Antitumor Efficacy Independent of Cross-Linking via Fcγ Receptors," Mol. Cancer Therapeutics, Dec. 2013, 12(12):2735-2747.
Graham, F. L. et al., "A New Technique for the Assay of Infectivity of Human Adenovirus 5 DNA," Virology, 1973, 52:456-467.
Hackett, P. et al., "A Transposon and Transposase System for Human Application," Molecular Therapy, Apr. 2010, 18(4):674-683.
Hartemann, A. et al., "Low-dose interleukin 2 in patients with type 1 diabetes: a phase 1/2 randomised, double-blind, placebo-controlled trial," Lancet Diabetes Endocrinol., Dec. 2013, 1:295-305.
Hellmann, M.D. et al., "Nivolumab plus Ipilimumab in Advanced Non-Small-Cell Lung Cancer," N Engl J Med, Nov. 21, 2019, 381(21):2020-2031.
Holliger, P. et al., "'Diabodies': Small bivalent and bispecific antibody fragments," Proc. Natl. Acad. Sci. USA, Jul. 1993, 90:6444-6448.
Horn, L. et al., "EML4-ALK: Honing In on a New Target in Non-Small-Cell Lung Cancer," J Clin Oncol., Sep. 10, 2009, 27(26):4232-4235.
Hosse, R. et al., "A new generation of protein display scaffolds for molecular recognition," Protein Science, 2006, 15:14-27.
FDA, "Guidance, Compliance & Regulatory Information (Biologics)," downloaded Oct. 29, 2024, 4 pages, https://www.fda.gov/vaccines-blood-biologics/quidance-compliance-regulatory-information-biologics.
Hurwitz, A. et al., "CTLA-4 blockade synergizes with tumor-derived granulocyte-macrophage colony-stimulating factor for treatment of an experimental mammary carcinoma," Proc. Natl. Acad. Sci. USA, Aug. 1998, 95(17):10067-10071.
Huston, J., et al., "Protein engineering of antibody binding sites: Recovery of specific activity in an anti-digoxin single-chain Fv analogue produced in *Escherichia coli*," Proc. Natl. Acad. Sci. USA, Aug. 1988, 85:5879-5883.
Jaeger, H. et al., "Physics of the Granular State," Science, Mar. 20, 1992, 255:1523-1531.
Jones, P. et al., "Replacing the complementarity-determining regions in a human antibody with those from a mouse," Nature, May 29, 1986, 321:522-525.
Keir, M. et al., "PD-1 and Its Ligands in Tolerance and Immunity," Annu. Rev. Immunol., 2008, 26:677-704.
Khvorova et al., "The chemical evolution of oligonucleotide therapies of clinical utility," Nat. Biotechnol., Mar. 2017, 35(3):238-248.
Kim, S., "Animal Models of Cancer in the Head and Neck Region," Clinical and Experimental Otorhinolaryngology, Jun. 2009, 2(2):55-60.
Koide, A. et al., "The Fibronectin Type III Domain as a Scaffold for Novel Binding Properties," J. Mol. Biol., 1998, 284:1141-1151.
Lee, D. et al., "4-1BB Signaling Activates the T Cell Factor 1 Effector/b-Catenin Pathway with Delayed Kinetics via ERK Signaling and Delayed PI3K/AKT Activation to Promote the Proliferation of $CD8^+$ T Cells," PLOS One, Jul. 2013, 8(7):e69677, 11 pages.
Levine, B. et al., "Gene transfer in humans using a conditionally replicating lentiviral vector," PNAS, Nov. 14, 2006, 103(46):17372-17377.
Ligtenberg, M. et al., "Self-Delivering RNAi Targeting PD-1 Improves Tumor-Specific T Cell Functionality for Adoptive Cell Therapy of Malignant Melanoma," Mol. Therapy, Jun. 2018, 26(6):1482-1493.

(56) References Cited

OTHER PUBLICATIONS

Malek, T., "The Biology of Interleukin-2," Annu. Rev. Immunol., 2008, 26:453-79.
McDermott, D. et al., "New treatments: immunotherapy and targeted therapy," Cancer Treatment Rev., 2014, 40:1056-64.
Metzker, M., "Sequence technologies—the next generation," Nature Reviews Genetics, Jan. 2010, 11:31-46.
Meuwissen, R. et al., "Mouse models for human lung cancer," Genes & Development, 2005, 19:643-664.
Mok, T. S. K. et al., "Pembrolizumab versus chemotherapy for previously untreated, PD-L1-expressing, locally advanced or metastatic non-small-cell lung cancer (Keynote-042): a randomized, open-label, controlled, phase 3 trial," Lancet, 2019, 393:1819-1830.
Mokyr, M. et al., "Realization of the Therapeutic Potential of CTLA-4 Blockade in Low-Dose Chemotherapy-treated Tumor-bearing Mice," Cancer Res., Dec. 1, 1998, 58:5301-5304.
Molina, J. et al., "Non-Small Cell Lung Cancer: Epidemiology, Risk Factors, Treatment, and Survivorship," Mayo Clin Proc., 2008, 83(5):584-594.
Monnier, P. et al., "In Vivo Applications of Single Chain Fv (Variable Domain) (scFv) Fragments," Antibodies, 2013, 2:193-208.
Morgensztern, D., "Keynote-042 and the role for single agent pembrolizumab in patients with PD-L1 tumor proportion score 1-49%," J Thorac Dis, 2019, 11 (Suppl 15):S1963-S1965.
Musin, O., "The problem of the twenty-five spheres," Russ. Math. Surv., 2003, 58:794-795.
NIH—U.S. National Library of Medicine, "A Study Of PF-05082566 As A Single Agent And In Combination With Rituximab," ClinicalTrials.gov Identifier: NCT01307267, Mar. 17, 2020, 27 pages.
NIH—U.S. National Library of Medicine, "Safety, Tolerability, Pharmacokinetics, and Immunoregulatory Study of Urelumab (BMS-663513) in Subjects With Advanced and/or Metastatic Solid Tumors and Relapsed/Refractory B-cell Non-Hodgkin's Lymphoma," ClinicalTrials.gov Identifier: NCT01471210, Apr. 19, 2017, 12 pages.
NIH—U.S. National Library of Medicine, "Combination Study of Urelumab and Rituximab in Patients With B-cell Non-Hodgkins Lymphoma," ClinicalTrials.gov Identifier: NCT01775631, Mar. 31, 2017, 10 pages.
NIH—U.S. National Library of Medicine, "Combination Study of Urelumab and Cetuximab in Patients With Advanced/Metastatic Colorectal Cancer or Advanced/Metastatic Head and Neck Cancer," ClinicalTrials.gov Identifier: NCT02110082, Apr. 19, 2017, 11 pages.
NIH—U.S. National Library of Medicine, "An Investigational Immuno-therapy Study to Determine the Safety of Urelumab Given in Combination With Nivolumab in Solid Tumors and B-cell Non-Hodgkin's Lymphoma," ClinicalTrials.gov Identifier: NCT02253992, Oct. 5, 2020, 11 pages.
NIH—U.S. National Library of Medicine, "Study Of OX40 Agonist PF-04518600 Alone And In Combination With 4-1BB Agonist PF-05082566," ClinicalTrials.gov Identifier: NCT02315066, Apr. 21, 2022, 39 pages.
NIH—U.S. National Library of Medicine, "A Phase 1 Study of MEDI0562 in Adult Subjects With Selected Advanced Solid Tumors," ClinicalTrials.gov Identifier: NCT02318394, Mar. 31, 2017, 10 pages.
NIH—U.S. National Library of Medicine, "A Study of PF-05082566 In Combination With Mogamulizumab In Patients With Advanced Solid Tumors," ClinicalTrials.gov Identifier: NCT02444793, Feb. 27, 2019, 22 pages.
NIH—U.S. National Library of Medicine, "A Study Of Avelumab In Combination With Other Cancer Immunotherapies In Advanced Malignancies (JAVELIN Medley)," ClinicalTrials.gov Identifier: NCT02554812, Jun. 23, 2023, 8 pages.
NIH—U.S. National Library of Medicine, "Combination Study of Urelumab and Rituximab in Patients With B-cell Non-Hodgkins Lymphoma," ClinicalTrials.gov Identifier: NCT02705482, Mar. 31, 2017, 10 pages.
NIH—U.S. National Library of Medicine, Study of Autologous Tumor Infiltrating Lymphocytes in Patients With Solid Tumors, ClinicalTrials.gov Identifier: NCT03645928, Oct. 29, 2024, 5 pages.
Nelson, B., "IL-2, Regulatory T Cells, and Tolerance," J. Immunol., 2004, 172:3983-3988.
Nosaki, K. et al., "Safety and efficacy of pembrolizumab monotherapy in elderly patients with PD-L1-positive advanced non-small-cell lung cancer: Pooled analysis from the Keynote-010, Keynote-024, and Keynote-042 studies," Lung Cancer, 2019, 135:188-195.
O'Day, S. et al., "Advantages of Concurrent Biochemistry Modified by Decrescendo Interleukin-2, Granulocyte Colony-Stimulating Factor, and Tamoxifen for Patients With Metastatic Melanoma," J. Clin. Oncol., Sep. 1999, 17(9):2752-2761.
Okuma, Y. et al., "Soluble Programmed Cell Death Ligand 1 as a Novel Biomarker for Nivolumab Therapy for Non-Small-cell Lung Cancer," Clinical Lung Cancer, 2018, 19(5):410-417.
Pacheco, J., "Keynote-407: changing the way we treat stage IV squamous non-small cell lung cancer," Transl Lung Cancer Res, 2020, 9(1):148-153.
Page, D. et al., "Immune Modulation in Cancer with Antibodies," Ann. Rev. Med., 2014, 65:185-202.
Paz-Ares, L. et al., "Pembrolizumab plus Chemotherapy for Squamous Non-Small-Cell Lung Cancer," N Engl J Med, 2018, 379:2040-2051.
Pilon-Thomas, S. et al., "Brief Communication: Efficacy of Adoptive Cell Transfer of Tumor Infiltrating Lymphocytes after Lymphopenia Induction for Metastatic Melanoma," J Immunother., Oct. 2012, 35(8):615-620.
Presta, L., "Antibody engineering," Current Opinion in Structural Biology, 1992, 2:593-596.
Pulford, K. et al., "Anaplastic Lymphoma Kinase Proteins in Growth Control and Cancer," Journal of Cellular Physiology, 2004, 199:330-358.
Raag, R. et al., "Single Chain Fvs," The FASEB Journal, Jan. 1999, 9:73-80.
Radvanyi, L. et al., "Specific lymphocyte subsets predict response to adoptive cell therapy using expanded autologous tumor-infiltrating lymphocytes in metastatic melanoma patients," Clin Cancer Res., Dec. 15, 2012, 18(24):6758-6770.
Reck, M. et al., "Pembrolizumab versus Chemotherapy for PD-L1-Positive Non-Small-Cell Lung Cancer," N Engl J Med, Nov. 10, 2016, 375(19):1823-1833.
Riechmann, L. et al., "Reshaping human antibodies for therapy," Nature, Mar. 24, 1988, 332:323-329.
Robert, C., et al., "Anti-programmed-death-receptor-1 treatment with pembrolizumab in ipilimumab-refractory advanced melanoma: a randomised dose-comparison cohort of a phase 1 trial," Lancet, Sep. 20, 2014, 384:1109-17.
Rose, J K et al., "A new cationic liposome reagent mediating nearly quantitative transfection of animal cells," Biotechniques, Apr. 1991, 10(4):520-525.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenzwaig, M. et al., "Immunological and clinical effects of low-dose interleukin-2 across 11 autoimmune diseases in a single, open clinical trial," HAL Open Science, Ann. Rheum. Dis., 2019, 78, 209-217, 2018-214229, hal-01960735.
Ruby, C. et al., "OX40-Enhanced Tumor Rejection and Effector T Cell Differentiation Decreases with Age," J. Immunol, 2009, 182:1481-1489.
Sano, D. et al., "Xenograft models of head and neck cancers," Head & Neck Oncology, 2009, 1:32, pp. 1-6.
Santegoets, S. et al., "IL-21 promotes the expansion of $CD27^+$ $CD28^+$ tumor infiltrating lymphocytes with high cytotoxic potential and low collateral expansion of regulatory T cells," Journal of Translational Medicine, 2013, 11:37, pp. 1-10.
Schiller, J. et al., Comparison of Four Chemotherapy Regimens for Advanced Non-Small-Cell Lung Cancer, N Engl J Med, Jan. 10, 2002, 346(2):92-98.

(56) References Cited

OTHER PUBLICATIONS

Segal, N. et al., "Results from an Integrated Safety Analysis of Urelumab, an Agonist Anti-CD137 Monoclonal Antibody," Clin. Cancer Res., Apr. 15, 2017, 23(8):1929-1936.
Shields, R. et al., "Lack of Fucose on Human IgG1 N-Linked Oligosaccharide Improves Binding to Human FcγRIII and Antibody-dependent Cellular Toxicity," The Journal of Biological Chemistry, Jul. 26, 2002, 277(30):26733-26740.
Siegel, R. et al., "Cancer Statistics," CA Cancer J Clin, 2015, 65:5-29.
Smith, C. et al., "Ex vivo expansion of human T cells for adoptive immunotherapy using the novel Xeno-free CTS Immune Cell Serum Replacement," Clinical & Translational Immunology, 2015, 4(e31), doi:10.1038/cti.2014.31.
Socinski, M.A. et al., "Atezolizumab for First-Line Treatment of Metastatic Nonsquamous NSCLC," New Engl J Med, 2018, 378:2288-301.
Spolski, R. et al., "Interleukin-21: a double-edged sword with therapeutic potential," Nature Reviews—Drug Discovery, May 2014, 13:379-395.
Steinke, J. et al., "Th2 cytokines and asthma Interleukin-4: its role in the pathogenesis of asthma, and targeting it for asthma treatment with interleukin-4 receptor antagonists," Respir. Res., 2001, 2:66-70.
Swartz, M. et al., "Tumor Microenvironment Complexity: Emerging Roles in Cancer Therapy," Cancer Res., May 15, 2012, 72(10):2473-2480.
Tarentino A. et al., "The Isolation and Structure of the Core Oligosaccharide Sequences of IgM," Biochemistry, 1975, 14(25):5516-5523.
Thomas, A. et al., "Immunotherapy for non-small-cell lung cancer," Exp. Opin. Biol. Ther., May 30, 2014, 14:(8)1061-1064.
Topalian, S. et al., "Safety, Activity, and Immune Correlates of Anti-PD-1 Antibody in Cancer," N. Eng. J. Med., Jun. 28, 2012, 366(26):2443-2454.
Tsong, T., "Electroporation of cell membranes," Biophys. J., Aug. 1991, 60:297-306.
Umaña, P. et al., "Engineered glycoforms of an antineuroblastoma IgG1 with optimized antibodydependent cellular cytotoxic activity," Nature Biotechnology, Feb. 17, 1999, 17:176-180.
Vecchiarelli, S. et al., "Circulating programmed death ligand-1 (cPD-L1) in non-small-cell lung cancer (NSCLC)," Oncotarget, 2018, 9(25):17554-17563.
Viteri, S. et al., "Keynote 407: the combination of pembrolizumab and chemotherapy cracks the shell of squamous cell lung cancer," Transl Lung Cancer Res, 2020, 9(3):828-832.
Vitt, U. et al., "Evolution and Classification of Cystine Knot-Containing Hormones and Related Extracellular Signaling Molecules," Molecular Endocrinology, 2001, 15(5):681-694.
Wang, C. et al., "In Vitro Characterization of the Anti-PD-1 Antibody Nivolumab, BMS-936558, and In Vivo Toxicology in Non-Human Primates", Cancer Immunology Research, Sep. 2014, 2(9):846-856.
Ward, E. S. et al., "Binding activities of a repertoire of single immunoglobulin variable domains secreted from *Escherichia coli*," Nature, Oct. 12, 1989, 341:544-546.
Weber, J. et al., "Safety, Efficacy, and Biomarkers of Nivolumab With Vaccine in Ipilimumab-Refractory or -Naive Melanoma," J. Clin. Oncology, Dec. 1, 2013, 31(34):4311-4318.
Weinberg, A. et al., "Anti-OX40 (CD134) Administration to Non-human Primates: Immunostimulatory Effects and Toxicokinetic Study," J. Immunother. Nov./Dec. 2006, 29(6):575-585.
Wigler, M. et al., "DNA-mediated transfer of the adenine phosphoribosyltransferase locus into mammalian cells," Proc. Natl. Acad. Sci. USA, Mar. 1979, 76(3):1373-1376.
Yamane-Ohnuki, N. et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biology and Bioengineering, Sep. 5, 2004, 87(5):614-622.
Zufferey, R. et al., "Multiply attenuated lentiviral vector achieves efficient gene delivery in vivo," Nature Biotechnology, Sep. 1997, 15:871-875.
Zuo, W.J. et al., "Dual Characteristics of Novel HER2 Kinase Domain Mutations in Response to HER-2-Targeted Therapies in Human Breast Cancer," Clin Cancer Res, Oct. 1, 2016, 22(19):4859-4869.
NCT03374839, ClinicalTrials.gov.
Katz, Steven C et al. "Phase I Hepatic Immunotherapy for Metastases Study of Intra-Arterial Chimeric Antigen Receptor-Modified T-cell Therapy for CEA+ Liver Metastases." Clinical cancer research : an official journal of the American Association for Cancer Research vol. 21,14 (2015): 3149-59. doi: 10.1158/1078-0432.CCR-14-1421.
Akkök, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.
Andersen, Rikke et al. "Long-Lasting Complete Responses in Patients with Metastatic Melanoma after Adoptive Cell Therapy with Tumor-Infiltrating Lymphocytes and an Attenuated IL2 Regimen." Clinical cancer research : an official journal of the American Association for Cancer Research vol. 22,15 (2016): 3734-45. doi:10.1158/1078-0432.CCR-15-1879.
Axelsson et al., "Cryopreserved peripheral blood mononuclear cells are suitable for the assessment of immunological markers in type 1 diabetic children", Cryobiology, Aug. 2008, 57, 201-208.
Bajgain, P. et al., "Optimizing the production of suspension cells using the G-Rex "M" series", Molecular Therapy—Methods and Clinical Development, vol. 1, Jan. 1, 2014.
Baruch et al., "Adoptive T cell therapy: An overview of obstacles and opportunities : ACT Obstacles and Opportunities", Cancer, vol. 123, No. S11, May 19, 2017, pp. 2154-2162.
Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).
Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):0F1-0F9 (2013).
Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.
Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS One, vol. 8, No. 4, Apr. 1, 2013, 25 pages.
Chang C.-H. et al., "Metabolic competition in the tumor microenvironment is a driver of cancer progression", Cell., Sep. 10, 2015, vol. 162, No. 6, pp. 1229-1241.
Chang et al., "Emerging concepts in immunotherapy T-cell metabolism as a therapeutic target", Nat. Immunol., Apr. 2016, 17(4), 364-368.
Donia, M et al., "Characterization and comparison of 'standard' and 'young' tumour-infiltrating lymphocytes for adoptive cell therapy at a Danish translational research institution." Scandinavian journal of immunology vol. 75,2 (2012): 157-67.
Donia, M, et al.. "Simplified protocol for clinical-grade tumor-infiltrating lymphocyte manufacturing with use of the Wave bioreactor", Cytotherapy. Aug. 2014;16(8):1117-20. doi: 10.1016/j.jcyt.2014.02.004; PubMed PMID: 24831841.
Dudley et al., "CD8+ Enriched "Young" Tumor Infiltrating Lymphocytes Can Mediate Regression of Metastatic Melanoma" Clin Cancer Res, 16:6122-6131 (2010).
Dudley et al., "Generation of Tumor-Infiltrating Lymphocyte Cultures for Use in Adoptive Transfer Therapy for Melanoma Patients," J Immunother., 2003: 26(4): 332-342.
Forget et al., "Activation and propagation of tumor infiltrating lymphocytes on clinical-grade designer artificial antigen presenting

(56) References Cited

OTHER PUBLICATIONS cells for adoptive immunotherapy of melanoma", Journal of Immunotherapy, vol. 37 No. 9, Nov. 1, 2014, pp. 448-460.
Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.
Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.
Garaud, Soizic et al. "A simple and rapid protocol to non-enzymatically dissociate fresh human tissues for the analysis of infiltrating lymphocytes." Journal of visualized experiments : JoVE , 94 52392. Dec. 6, 2014, doi:10.3791/52392.
Gassner, et al., "Fludarabine modulates composition and function of the T Cell pool in patients with chronic lymphocytic leukaemia", Cancer. Immunol. Immunother., 2011, 60, 75-85.
Gattinoni, et al., "Adoptive immunotherapy for cancer: building on success", Nat. Rev. Immunol. May 2006, 6(5), 383-393.
Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.
Glassman, A B, and C E Bennett. "Cryopreservation of human lymphocytes: a brief review and evaluation of an automated liquid nitrogen freezer." Transfusion vol. 19,2 (1979): 178-81. doi:10.1046/j.1537-2995.1979.19279160289.x.
Goff et al., "Tumor Infiltrating Lymphocyte Therapy for Metastatic Melanoma: Analysis of Tumors Resected for TIL", J. Immunother, Oct. 2010, 33(8), 840-847.
Goff SL, et al., "Randomized, Prospective Evaluation Comparing Intensity of Lymphodepletion Before Adoptive Transfer of Tumor-Infiltrating Lymphocytes for Patients With Metastatic Melanoma", J Clin Oncol. Jul. 10, 2016;34(20):2389-79.
Hall et al., "Expansion of tumor-infiltrating lymphocytes (TIL) from human pancreatic tumors", Journal for Immuno Therapy of Cancer, vol. 4, No. 1, pp. 1-12.
Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.
Henning AL, et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.
Hernandez-Chacon et al., "Costimulation through the CD137/4-1BB Pathway Protects Human Melanoma Tumor-infiltrating Lymphocytes from Activation-induced Cell Death and Enhances Anti-tumor Effector Function", Journal of Immuno Therapy, vol. 34, No. 3, Apr. 1, 2011, pp. 236-250.
Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.
Huang et al., "Survival, Persistence, and Progressive Differentiation of Adoptively Transferred Tumor-Reactive T Cells Associated with Tumor Regression"; J. Immunother, 28(3), 258-267 (2005).
Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.
International Search Report and Written Opinion for International Patent Application No. PCT/US2017/058610 dated Mar. 8, 2018, 13 pages.
International Search Report and Written Opinion for International Patent Application No. PCT/US2018/012633 dated May 25, 2018, 14 pages.
International Search Report and Written Opinion for International Patent Application No. PCT/US2018/040474 dated Nov. 14, 2018, 17 pages.
Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.
Iyer, R.K. et al., "Industrializing Autologous Adoptive Immunotherapies: Manufacturing Advances and Challenges", Frontiers in Medicine, vol. 5, May 23, 2018.
Jia He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.
Jin et al., "Enhanced clinical-scale manufacturing of TCR transduced T-cells using closed culture system modules", Journal of Transactional Medicine, col. 16. No. 1, Jan. 24, 2018.
Jin et al., "Simplified method of the growth of human tumor infiltrating lymphocytes in gas-permiable flasks to numbers needed for patient treatment", J. Immunotherapy, 2012, 35:283-292.
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Lee et al., "Tumor-Infiltrating Lymphocytes in Melanoma", Curr Oncol Rep. Aug. 2012, 14, 468-474.
Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.
Meng, Qingda et al. "Expansion of Tumor-reactive T Cells From Patients With Pancreatic Cancer." Journal of immunotherapy (Hagerstown, Md. : 1997) vol. 39,2 (2016): 81-9. doi:10.1097/CJI.0000000000000111.
Merhavi-Shoham et al., "Adoptive Cell Therapy for Metastatic Melanoma", Cancer Journal, vol. 23, No. 1, Jan. 1, 2017.
Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Muranski, et al., "Increased intensity lymphodepletion and adoptive immunotherapy—how far can we go?", Nat. Clin. Pract. Oncol., Dec. 2006, 3, 668-681.
Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.
Peng, Weiyi et al. "PD-1 blockade enhances T-cell migration to tumors by elevating IFN-γ inducible chemokines." Cancer research vol. 72,20 (2012): 5209-18. doi:10.1158/0008-5472.CAN-12-1187.
Riddell, et al., "Restoration of Viral Immunity in Immunodeficient Humans by the Adoptive Transfer of T Cell Clones", Science, Jul. 1992, 257, 238-41.
Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rosenberg SA, Dudley ME. Adoptive cell therapy for the treatment of patients with metastatic melanoma. Curr Opin Immunol. Apr. 2009;21(2):233-40.
Rosenberg, "IL-2: The First Effective Immunotherapy for Human Cancer," The Journal of Immunology, col. 192, No. 12, Jun. 6, 2014.
Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.
Rosenberg, S A et al. "Treatment of patients with metastatic melanoma with autologous tumor-infiltrating lymphocytes and

(56) References Cited

OTHER PUBLICATIONS interleukin 2." Journal of the National Cancer Institute vol. 86,15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.
Rufer N, et al., "Telomere length dynamics in human lymphocyte subpopulations measured by flow cytometry", Nat Biotechnol. Aug. 1998;16(8):743-7. PubMed PMID: 9702772.
Sadeghi, et al., "Rapid expansion of T cells: Effects of culture and cryopreservation and improtance of short-term cell recovery", Acta Oncologica 2013, 52, 978-986.
Schiltz, P M et al. "Characterization of tumor-infiltrating lymphocytes derived from human tumors for use as adoptive immunotherapy of cancer." Journal of immunotherapy (Hagerstown, Md. : 1997) vol. 20,5 (1997): 377-86. doi:10.1097/00002371-199709000-00007.
Shen X,et al.. Persistence of tumor infiltrating lymphocytes in adoptive immunotherapy correlates with telomere length. J Immunother. Jan. 2007;30(1):123-9. PubMed PMID:17198091; PubMed Central PMCID: PMC2151201.
Somerville RP, et al.. Clinical scale rapid expansion of lymphocytes for adoptive cell transfer therapy in the WAVE® bioreactor. J Transl Med. Apr. 4, 2012;10:69.
Spiess, P J et al. "In vivo antitumor activity of tumor-infiltrating lymphocytes expanded in recombinant interleukin-2." Journal of the National Cancer Institute vol. 79,5 (1987): 1067-75.
Tran et al., "Minimally Cultured tumor-infiltrating lymphocytes display optimal characteristics for adoptive cell therapy", 2008, J. Immunother., Oct. 2008 31(8), 742-751.
Tsoukas et al., "Activation of resting T lymphocytes by anti-CD3 (T3) antibodies in the absence of monocytes", J. Immunol. 1985, 135, 1719.
Van den Bossche, J. et al. "Metabolic Characterization of Polarized M1 and M2 Bone Marrow-derived Macrophages Using Real-time Extracellular Flux Analysis." Journal of visualized experiments : JoVE ,105 53424. Nov. 28, 2015, doi:10.3791/53424.
Wang & Riviere, "Manufacture of tumor- and virus-specific T lymphocytes for adoptive cell therapies", Cancer Gene Therapy, 2015, 22: 85-94.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Wilson Wolf—Superior Cell Culture Devices, G-Rex, Oct. 31, 2016.
Wu, Richard et al. "Adoptive T-cell therapy using autologous tumor-infiltrating lymphocytes for metastatic melanoma: current status and future outlook." Cancer journal (Sudbury, Mass.) vol. 18,2 (2012): 160-75. doi:10.1097/PPO.0b013e31824d4465.
Ye, et al., "Engineered Artificial antigen presenting cells facilitate direct and efficient expansion of tumor infiltrating lymphocytes", J. Translat. Med. 2011, 9(131), 13 pages.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.
Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.
Ameratunga, M. et al., "PD-L1 and Tumor Infiltrating Lymphocytes as Prognostic Markers in Resected NSCLC," PLOS One, Apr. 22, 2016, vol. 11, No. 4., p. e0153954.
Anonymous, "Nivolumab and Tumor Infiltrating Lymphocytes (TIL) in Advanced Non-Small Cell Lung Cancer—Full Text View—Clinicaltrials.gov", Jan. 6, 2017, Retrieved from the Internet: URL:https://clinicaltrials.gov/ct2/show/NCT03215810 [retrieved on Jan. 20, 2022].
Anonymous, "T Cell Receptor Immunotherapy for Patients with Metastatic Non-small Cell Lung Cancer—Full Text View—Clinicaltrials.gov", Jul. 12, 2017, Retrieved from the Internet: URL:https://clinicaltrials.gov/ct2/show/NCT02133196 [retrieved on Jan. 20, 2022].
Black, R. et al., "Updates in Oncology: Part 1 NSCLC: An Update of Driver Mutations, Their Role in Pathogenesis and Clinical Significance," Oct. 2015, Rhode Island Medical Journal, pp. 25-28, Retrieved from the Internet: URL: http://rimed.org/rimedicaljournal/2015/10/2015-10-25-onc-black.pdf [retrieved on Jan. 24, 2022].
Brahmer J. et al., "Progression after the next line of therapy (PFS2) and updated OS among patients (pts) with advanced NSCLC and PD-L1 tumor proportion score (TPS) >=50% enrolled I Keynote-024" Journal of Clinical Oncology, May 20, 2017, vol. 35, No. 15 supplement. p. 9000 URL:https://ascopubs.org/doi/10.1200/JCO.2017.35.15_suppl.9000 [retrieved on Jan. 24, 2022].
Chen, J. et al., "Optimal Management of Patients with Advanced NSCLC Harboring High PD-L1 Expression and Driver Mutations," Current Treatment Options in Oncology, Jun. 25, 2020, vol. 21, No. 7, p. 60.
De Mello et al., "Immunotherapy in Patients with Advanced Non-Small Cell Lung Cancer Lacking Driver Mutations and Future Perspectives," Cancers, 2022, vol. 14, No. 1., p. 122.
Teixido, C. et al., "PD-L1 expression testing in non-small cell lung cancer," Ther Adv Med Oncol, 2018, vol. 10, No. 1, pp. 1-17.

* cited by examiner

Figure 1

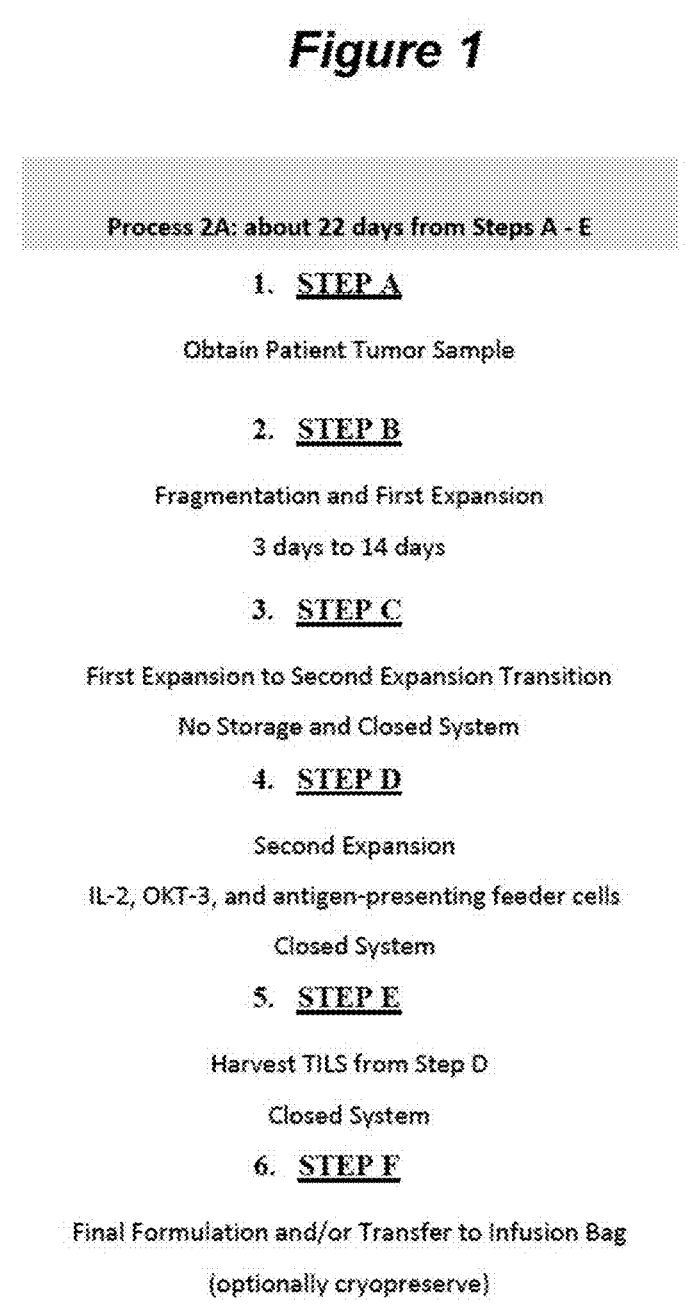

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

Figure 5

| Process 1C: 43-55 Days for Steps A - E | Process 2A: about 22 days from Steps A - E |
|---|---|
| 1. **STEP A**<br>Obtain Patient Tumor Sample | 1. **STEP A**<br>Obtain Patient Tumor Sample |
| 2. **STEP B**<br>Fragmentation and First Expansion<br>11 days to 21 days | 2. **STEP B**<br>Fragmentation and First Expansion<br>3 days to 14 days |
| 3. **STEP C**<br>First Expansion to Second Expansion Transition<br>Optional Storage until Selection | 3. **STEP C**<br>First Expansion to Second Expansion Transition<br>No Storage and Closed System |
| 4. **STEP D**<br>Second Expansion<br>IL-2, OKT-3, antigen-presenting feeder cells<br>Optionally repeat one or more times | 4. **STEP D**<br>Second Expansion<br>IL-2, OKT-3, and antigen-presenting feeder cells<br>Closed System |
| 5. **STEP E**<br>Harvest TILS from Step D | 5. **STEP E**<br>Harvest TILS from Step D<br>Closed System |
| 6. **STEP F**<br>Final Formulation and/or Transfer to Infusion Bag | 6. **STEP F**<br>Final Formulation and/or Transfer to Infusion Bag<br>(optionally cryopreserve) |

Figure 6

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40×10$^6$ TIL | • Pre-REP TIL directly move to REP on day 11<br>• REP requires 25-200×10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5×10$^6$ TIL and 5×10$^8$ PBMC feeders per flask on REP day 0<br>• Split to 18-36 flasks on REP day 7<br>• 14 day duration | • 1 GREX-500M flask on day 11<br>• 25-200×10$^8$ TIL and 5x10$^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system' | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in $LN_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

*Figure 8A*

| Process 2A: about 22 days from Steps A - E | Process GEN 3: about 14-18 days from Steps A - E |
|---|---|
| **STEP A**<br>Obtain Patient Tumor Sample<br>(optionally can be frozen before Step B) | **STEP A**<br>Obtain Patient Tumor Sample<br>(optionally can be frozen before Step B) |
| **STEP B**<br>First Expansion<br>(physical fragmentation to at least 40 fragments per container grown for about 3 days to 14 days with media comprising IL-2) | **STEP B**<br>Priming First Expansion<br>(physical fragmentation of up to 60 fragments per container grown for about 1 days to 7 days with media comprising IL-2, OKT-3, and antigen-presenting feeder cells) |
| **STEP C**<br>First Expansion to Second Expansion Transition<br>(Step B TILs directly move to Step D, optionally on Step B day 11) | **STEP C**<br>Priming First Expansion to Rapid Second Expansion Transition<br>(Step B TILs directly move to Step D on day 7) |
| **STEP D**<br>Second Expansion<br>(TILs grown in growth media medium comprising IL-2, OKT-3, and antigen-presenting feeder cells in a closed container) | **STEP D**<br>Rapid Second Expansion<br>(TILs grown in growth media medium comprising IL-2, OKT-3, and 2X antigen-presenting feeder cells; Days 10-11 scale up and add additional IL-2) |
| **STEP E**<br>Harvest TILS from Step D<br>(TILs harvested via closed system) | **STEP E**<br>Harvest TILS from Step D |
| **STEP F**<br>Final Formulation and/or Transfer to Infusion Bag<br>(optionally cryopreserve) | STEP F<br>Final Formulation and/or Transfer to Infusion Bag<br>(optionally cryopreserve) |

*Figure 8B*

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to 7 days with media comprising IL-2, OKT-3, and antigen-presenting feeder cells)

STEP C
Priming First Expansion to Rapid Second Expansion Transition
(Step B TILs directly move to Step D on day 7)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Final Formulation and/or Transfer to Infusion Bag
(optionally cryopreserve)

*Figure 8C*

| **Embodiment GEN 3.0: about 14-18 days from Steps A - E** | **Embodiment GEN 3.1 control: about 14-18 days from Steps A - E** | **Embodiment GEN 3.1 Test/F: about 14-18 days from Steps A - E** |
|---|---|---|
| **STEP A**<br>Obtain Patient Tumor Sample (optionally can be frozen before Step B) | **STEP A**<br>Obtain Patient Tumor Sample (optionally can be frozen before Step B) | **STEP A**<br>Obtain Patient Tumor Sample (optionally can be frozen before Step B) |
| **STEP B**<br>Priming First Expansion (physical fragmentation of up to 60 fragments per container grown for about 1 days to 7/8 days with media comprising IL-2) | **STEP B**<br>Priming First Expansion (physical fragmentation of up to 60 fragments per container grown for about 1 days to 7/8 days with media comprising IL-2, and OKT-3) | **STEP B**<br>Priming First Expansion (physical fragmentation of up to 60 fragments per container grown for about 1 days to 7/8 days with media comprising IL-2, OKT-3, and antigen-presenting feeder cells) |
| **STEP C**<br>Priming First Expansion to Rapid Second Expansion Transition (Step B TILs directly move to Step D on day 7/8) | **STEP C**<br>Priming First Expansion to Rapid Second Expansion Transition (Step B TILs directly move to Step D on day 7/8) | **STEP C**<br>Priming First Expansion to Rapid Second Expansion Transition (Step B TILs directly move to Step D on day 7/8) |
| **STEP D**<br>Rapid Second Expansion (TILs grown in growth media medium comprising IL-2, OKT-3, and antigen-presenting feeder cells; Days 10-11 scale up and add additional IL-2) | **STEP D**<br>Rapid Second Expansion (TILs grown in growth media medium comprising IL-2, OKT-3, and 2X antigen-presenting feeder cells; Days 10-11 scale up and add additional IL-2) | **STEP D**<br>Rapid Second Expansion (TILs grown in growth media medium comprising IL-2, OKT-3, and 2X antigen-presenting feeder cells; Days 10-11 scale up and add additional IL-2) |
| **STEP E**<br>Harvest TILS from Step D | **STEP E**<br>Harvest TILS from Step D | **STEP E**<br>Harvest TILS from Step D |
| **STEP F**<br>Final Formulation and/or Transfer to Infusion Bag (optionally cryopreserve) | **STEP F**<br>Final Formulation and/or Transfer to Infusion Bag (optionally cryopreserve) | **STEP F**<br>Final Formulation and/or Transfer to Infusion Bag (optionally cryopreserve) |

*Figure 8D*

Modified Gen 2-like Process: about 22 days from Steps A - E

STEP A
Obtain Patient Tumor Sample
(optionally can be frozen before Step B;
optionally tumor sample can be a core/small biopsy)

STEP B1
Initial Culture
physical fragmentation of up to 60 tumor fragments or up to 10 cores/small biopsies per container, TILs grown for 3 days in growth medium comprising IL-2

STEP B2
Priming First Expansion
TILs grown for 8 days in growth medium comprising IL-2, OKT-3, and antigen-presenting feeder cells)

STEP C
Priming First Expansion to Rapid Second Expansion Transition
(Step B TILs directly move to Step D on day 11)

STEP D
Rapid Second Expansion
(volume reduced; TILs grown in growth media medium comprising IL-2, OKT-3, and 50X antigen-presenting feeder cells; Day 16 scale up and add additional IL-2)

STEP E
Harvest TILS from Step D

STEP F
Final Formulation and/or Transfer to Infusion Bag
(optionally cryopreserve)

| STEP | Gen 2 | Gen 2.1 | Gen 3.0 Optimized |
|---|---|---|---|
| **Pre REP- day 0** | ≤ 50 fragments/ 1 G-Rex<br>100MCS - **11 days** | ≤ 180 fragments/ 3 G-Rex,<br>Pre-formulated CM1 warmed media<br>100MCS - **11 days** | ***Fresh or Frozen Tumor***<br>Whole tumor with ≤ 30 fragments up to 60 fragments per 1 G-Rex.<br>100MCS (up to 4 G-Rex),<br>preformulated warmed media - **7 days. Pre REP, Feeders 2.5 E8 cells + OKT-3 (30ng/mL)** |
| **REP Initiation** | Direct to REP- Day 11-<br>**<200 E6 TIL**<br>1 G-Rex 500MCS | Direct to REP- Day 11-<br>**<200 E6 TIL**<br>Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 5 E8 cells +OKT-3 (30ng/mL)** |
| **TIL propagation or Scale up** | 1 to 5 G-REX 500MCS<br>**Split day 16** | 2 to 5 G-REX 500MCS<br>Pre-formulated CM4 warmed media<br>**Split day 16** | From G-REX 100MCS transfer TIL suspension to G-REX 500MCS, up to 4 GREX 500 MCS- Standard media or Defined Media (Serum Free)<br>**Scale up on day 10 or 11** |
| **Harvest** | **Harvest day 22,**<br>LOVO-automated cell washer | **Harvest day 22,**<br>LOVO-automated cell washer (5 wash cycle) | **Harvest day 14 or 16**<br>LOVO- automated cell washer (5 wash cycle) |
| **Final formulation** | Cryopreserved Product<br>300IU/ml IL2- CS10 in $LN_2$,<br>multiple aliquots | Cryopreserved Product<br>300IU/ml IL2- CS10 in $LN_2$,<br>multiple aliquots | Cryopreserved product<br>300IU/ml IL-2- CS10 in $LN_2$,<br>multiple aliquots |
| **Process time** | **22 days** | **22 days** | **16 days** |

*Figure 11*

| Process Day | Conditions | Gen 3.1 |
|---|---|---|
| Day 0- pre REP initiation | Media CM1 | 500 mL |
| | IL-2 (6000 IU/mL) | + |
| | OKT-3 (30ng/mL) | + |
| | Feeders (250 E+06) | + |

| Process Day | Conditions | Gen 3.1 |
|---|---|---|
| Day 7- REP initiation | Media CM2 | 500 mL |
| | IL-2 (6000 IU/mL) | + |
| | OKT-3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

*Figure 12*

*Figure 13*

| Process Comparison | Key Process Changes | Benefit |
|---|---|---|
| **Gen 2 : Gen 2.1** | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| **Gen 2.1 : Gen 3.1** | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

*Figure 14*

| Process Comparison | Key Process Changes | Desired Improvement | Criteria for Success | Outcome |
|---|---|---|---|---|
| **Gen 2 : Gen 3.0** | • 14-16 days<br>• Initiate REP with fragments up to 4 flask.<br>• 100MCS scales to 500MCS | • Increased potency<br>• Improved phenotype<br>• Decreased process time | • Increase potency as measured by INF-g ✓<br>• Comparable phenotype ✓<br>• Comparable Dose ✓<br>• Comparable purity ✓ ( feeder cell )<br>• Maintain clonal diversity ✓ | • Potency increased over Gen2<br>• Improved expression of CD28 on CD8 cells<br>• Maximum capacity of flask reached by day 16 on Gen 3.1<br>• Reduced feeder cell usage<br>• Increased diversity |

*Figure 15*

| Process | Gen 2 | Gen 3 |
|---|---|---|
| L4054 | Standard Media | Standard Media |
| L4055 | Standard Media | Standard Media |
| M1085T | Standard Media | Standard Media |

| Process | Gen 3 | Gen 3.1 control | Gen 3.1 |
|---|---|---|---|
| L4063 | Standard Media | Standard Media | Standard Media |
| L4064 | Defined Media | Defined Media | Defined Media |

Standard Media:
Pre REP: CM1
REP initiation : CM2
Split or Scale up : CM4

Defined Media:
CTS Optimizer (Serum Free Media) in each day of the process

*Figure 20*

| Process Day | Conditions | Gen 3.1 Test |
|---|---|---|
| Day 0- pre REP initiation | Media CM1 | 500 mL |
| | IL-2 (6000 IU/mL) | + |
| | OKT-3 (15 ug) | + |
| | Feeders (250 E+06) | + |

| Process Day | Conditions | Gen 3.1 Test |
|---|---|---|
| Day 7- REP initiation | Media CM2 | 500 mL |
| | IL-2 (6000 IU/mL) | + |
| | OKT-3 (30 ug) added on Day 7 | + |
| | Feeders Added on Day 7 | 500 E06 |
| | Total Feeders at Day | 750 E+06 |

| Process Day | Conditions | Gen 3.1 Test |
|---|---|---|
| Day 9-11 –Scale Up | From G-REX 100MCS transfer TIL suspension to 1 G-REX 500MCS ( up to 3 GREX 500MCS) | Yes |
| Day 16- Harvest | LOVO- automated cell washer | Yes |

| | Gen 2 | Gen 3 |
|---|---|---|
| Total Culture Time | 22d | 16-17d |
| Pre-REP | | |
| Fragments/flask | ≤60 fragments in 1 flask | ≤60 fragments in up to 4 flasks |
| Media volume | 1L - Single addition | 1L - 2 x 500mL additions |
| Target preREP cell numbers | ≤200e6 TIL | All cell carried through continuous process |
| Screening | No screen | No screen |
| Selection of flasks | No selection | Bac-T sterility, visual inspection for contaminants |
| REP/Scale up | | |
| Feeders | | Reduced by ≥40% |
| Media | Contains HSAB | Defined |
| Scale up | Pooled culture Volume reduce to 500mL on Day 5 split up to 5 flasks (2500 cm2) | Flasks scaled linearly and treated as subcomponents. |
| OKT3 | 150ug | ≤180ug at max scale |
| IL-2 | High dose | High dose |
| Number of flasks | 1-5 | 1-4 |
| Harvest/volume reduction | Closed 10:1 | Closed 10:1 |
| Concentrate/wash | LOVO 100:1 | LOVO 1000:1 |
| Formulation | 1:1 CS10 (5% DMSO) | 1:1 CS10 (5% DMSO) |
| Shipment | Vapor phase LN | Vapor phase LN |
| Infusion | Thawed IV gravity | Thawed IV gravity |

*Figure 23A*

| | Gen 2 | Gen 3 |
|---|---|---|
| Total Culture Time | 22d | 16-17d |
| Pre-REP | | |
| Fragments/flask | ≤60 fragments in 1 flask | ≤60 fragments in up to 4 flasks |
| Media volume | 1L - Single addition | 1L - 2 x 500mL additions |
| Target preREP cell numbers | ≤200e6 TIL | All cell carried through continuous process |
| Screening | No screen | No screen |
| Selection of flasks | No selection | Bac-T sterility, visual inspection for contaminants |
| REP/Scale up | | |
| Feeders | | Reduced by ≥40% |
| Media | Contains HSAB | Defined |
| Scale up | Pooled culture<br>Volume reduce to 500mL on Day 5 split up to 5 flasks (2500 cm2) | Flasks scaled linearly and treated as subcomponents. |
| OKT3 | 150ug | ≤180ug at max scale |
| IL-2 | High dose | High dose |
| Number of flasks | 1-5 | 1-4 |
| Harvest/volume reduction | Closed 10:1 | Closed 10:1 |
| Concentrate/wash | LOVO 100:1 | LOVO 1000:1 |
| Formulation | 1:1 CS10<br>(5% DMSO) | 1:1 CS10<br>(5% DMSO) |
| Shipment | Vapor phase LN | Vapor phase LN |
| Infusion | Thawed IV gravity | Thawed IV gravity |

*Figure 23B*

*Figure 28*

| STEP | Gen 2 | Gen 2.1 | Gen 3.0 |
|---|---|---|---|
| **Pre REP- day 0** | ≤ 50 fragments/ 1 G-Rex<br>100MCS - **11 days** | ≤ 180 fragments/ 3 G-Rex,<br>Pre-formulated CM1 warmed media<br>100MCS - **11 days** | ***Fresh or Frozen Tumor***<br>Whole tumor with ≤ 30 fragments up to 60 fragments per 1 G-Rex<br>100MCS (up to 4 G-Rex),<br>preformulated warmed media - **7 days. Pre REP, Feeders 250e6 cells + OKT-3 (15ug)** |
| **REP Initiation** | Direct to REP- Day 11-<br>**<200e$^6$ TIL**<br>1 G-Rex 500MCS | Direct to REP- Day 11-<br>**<200 e$^6$ TIL**<br>Pre-formulated CM2 warmed media in one G-Rex 500MCS | Direct to REP- Day **7-all cells TIL- same G-Rex 100MCS (100MCS up to 4 GREX), Standard media or Defined Media (Serum free). Addition Feeders 500e6 cells +OKT-3 (30ug)** |
| **TIL propagation or Scale up** | 1 to 5 G-REX 500MCS<br>**Split day 16** | 2 to 5 G-REX 500MCS<br>Pre-formulated CM4 warmed media<br>**Split day 16** | From G-REX 100MCS transfer TIL suspension to G-REX 500MCS , up to 4 GREX 500 MCS- Standard media or Defined Media (Serum Free)<br>**Scale up on day 10 or 11** |
| **Harvest** | **Harvest day 22,**<br>LOVO-automated cell washer | **Harvest day 22,**<br>LOVO-automated cell washer (5 wash cycle) | **Harvest day 14 or 16**<br>LOVO- automated cell washer (5 wash cycle) |
| **Final formulation** | Cryopreserved Product<br>300IU/ml IL2- CS10 in $LN_2$,<br>multiple aliquots | Cryopreserved Product<br>300IU/ml IL2- CS10 in $LN_2$,<br>multiple aliquots | Cryopreserved product<br>300IU/ml IL-2-CS10 in $LN_2$,<br>multiple aliquots |
| **Process time** | **22 days** | **22 days** | **16 days** |

*Figure 29*

| Process Comparison | Process Changes | Differences |
|---|---|---|
| Gen 2 : Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| Gen 2.1 : Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

*Figure 30*

Table 2. Description of Gen 3 optimization conditions.

| Process Day | Conditions | Gen 3.0 | Gen 3.1 control | Gen 3.1 Test |
|---|---|---|---|---|
| **Day 0 :** Tumor Fragment Isolation and Activation | Media (*) | 500 mL | 500 mL | 500 mL |
| | IL-2 | 6000 IU/mL | 6000 IU/mL | 6000 IU/mL |
| | OKT-3 | - | 15 ug | 15 ug |
| | Feeders | - | - | 2.5E+06 |
| **Process Day** | **Conditions** | **Gen 3.0** | **Gen 3.1 control** | **Gen 3.1 Test** |
| **Day 7- 8 :** TIL Culture Reactivation | Media (*) | 500 mL | 500 mL | 500 mL |
| | IL-2 | 6000 IU/mL | 6000 IU/mL | 6000 IU/mL |
| | OKT-3 | 30 ug | 30 ug | 30 ug |
| | Feeders | 1 E+09 | 500 E+06 | 500E+06 |
| | Total Feeders added through Day 7 | 1 E+09 | 500 E+06 | 750E+06 |
| **Process Day** | **Conditions** | **Gen 3.0** | **Gen 3.1 control** | **Gen 3.1 Test** |
| **Day 10-11 :** **Culture Scale Up** | From GREX 100 transfer whole TIL suspension to 1 GREX 500 containing 4L media with IL-2 (3000 IU/mL) | | | |
| **Process Day** | **Conditions** | **Gen 3.0** | **Gen 3.1 control** | **Gen 3.1 Test** |
| **Day 16 –17:** **Harvest/Wash/Formulate** | LOVO automated cell washer and cryopreservation with CS10. | | | |

(*) Media can be standard media or CTS serum free media.

*Figure 32*

| Step | Process Gen 3-Optimized |
|---|---|
| **Day 0**<br>**Tumor isolation and Activation** | ≤240 fragments<br>≤60 fragments/flask<br>≤4 flasks<br>≤2L media (500mL/flask)<br>IL-2 (6000IU/mL)<br>$2.5x10^8$ feeder cells/flask<br>15ug OKT3/flask |
| **Day 7 - 8**<br>**Reactivation** | Fresh TIL direct to REP<br>Activate entire culture<br>$5x10^8$ feeder cells<br>30 ug OKT3/flask<br>G-Rex 100MCS<br>Add 500mL media+ IL-2(6000IU/mL) |
| **Day 10 – 11**<br>**Scale up or TIL Sub-culture** | ≤4 G-REX 500MCS<br>Scale up entire culture transferring 1L from GREX 100MCS into GREX 500MCS<br>and add 4L of media +IL-2 (3000 IU/mL) /flask |
| **Day 16 -17**<br>**Harvest** | Harvest<br>LOVO- automated cell washer<br>Cryopreservation on Plasmalyte 1% HSA: CS10 |

*Figure 33*

| Test | Acceptance Criteria | Gen 3.1Test vs Gen 3.0 Process |
|---|---|---|
| Cell Count (TVC) | Gen 3.1 > 30% to Process Gen 3.0 | Met |
| % Viability | ≥70% Viability | Met |
| Immunophenotyping (%CD3+/ %CD45+) | ≤5% difference between Gen 3.1 and Gen 3.0 process | Met |
| IFNγ secretion | Gen 3.1 ≥ to Process Gen 3.0 | Met |

*Figure 1* *Diagram of Study Design*

*Figure 37*

Each PD-1/PD-L1 antibody was FDA approved in the setting of its own unique PD-L1 assay, with its own unique method of interpretation.

| | Pembro (Merck)[1,2] | Atezo (Roche)[3-6] | Nivo (BMS)[7-9] | Durva (AstraZeneca)[10-12] |
|---|---|---|---|---|
| Assay | PD-L1 IHC 22C3 pharmDx (Mouse mAb anti-PD-L1 clone 22C3, extracellular epitope)[1] | VENTANA PD-L1 (SP142) (Rabbit mAb anti-PD-L1 clone SP142, cytoplasmic epitope)[4] | PD-L1 IHC 28-8 pharmDx (Rabbit mAb anti-PD-L1 clone 28-828-8, extracellular epitope)[7] | VENTANA PD-L1 (SP263) (Rabbit mAb clone SP263, cytoplasmic epitope) |
| Manufacturer | Dako (Agilent) | Ventana (Roche) | Dako (Agilent) | Ventana (AZN) |
| Type | Companion Diagnostic[3] | | Complementary diagnostic[3,9] | |
| Scoring System | **TPS**- % viable tumor cells that exhibit PD-L1 staining at any intensity / Total # of tumor cells[2] | Percentage of PD-L1 expressing **Tumor Cells (TCs) or Immune Cells (ICs)**[4] | Percentage of PD-L1 expressing **TCs** | |

| Subgroups | Pembrolizumab-KEYNOTE Studies | Atezolizumab- IMpower, Poplar Studies[4] | Nivolumab- CHECKMATE studies | Durvalumab- PACIFIC[11,12] |
|---|---|---|---|---|
| High PD-L1 | ≥50% by TPS | TC3 or IC3 = TC ≥ 50% or IC ≥ 10% PD-L1+ | PD-L1 ≥ 1% by TPS | ≥25% by TPS |
| Low PD-L1 | 1-49% by TPS | TC1/2 or IC1/2 = ≥ 1% TC/IC and <50% TC or <10% IC PDL1+[4] | | |
| Negative PD-L1 | <1% by TPS | TC0 and IC0 = TC and IC < 1% PD-L1+ | <1% by TPS | <1% by TPS |

TPS: Tumor Proportion Score; TCs: Tumor Cells; ICs: Tumor-Infiltrating Immune Cells; A companion diagnostic is essential for safe and effective use of the drug. A complementary diagnostic aids to inform risk/benefit but is not required to use the drug.

SEQUENCE LISTING

```
Sequence total quantity: 267
SEQ ID NO: 1            moltype = AA  length = 450
FEATURE                 Location/Qualifiers
REGION                  1..450
                        note = amino acid sequence of the heavy chain of muromonab
source                  1..450
                        mol_type = protein
                        organism = synthetic construct
SEQUENCE: 1
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSSA  120
KTTAPSVYPL APVCGGTTGS SVTLGCLVKG YFPEPVTLTW NSGSLSSGVH TFPAVLQSDL  180
YTLSSSVTVT SSTWPSQSIT CNVAHPASST KVDKKIEPRP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 2            moltype = AA  length = 213
FEATURE                 Location/Qualifiers
REGION                  1..213
                        note = amino acid sequence of the light chain of muromonab
source                  1..213
                        mol_type = protein
                        organism = synthetic construct
SEQUENCE: 2
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRADT APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 3            moltype = AA  length = 134
FEATURE                 Location/Qualifiers
REGION                  1..134
                        note = amino acid sequence of a recombinant human IL-2
                         protein
source                  1..134
                        mol_type = protein
                        organism = synthetic construct
SEQUENCE: 3
MAPTSSSTKK TQLQLEHLLL DLQMILNGIN NYKNPKLTRM LTFKFYMPKK ATELKHLQCL  60
EEELKPLEEV LNLAQSKNFH LRPRDLISNI NVIVLELKGS ETTFMCEYAD ETATIVEFLN  120
RWITFCQSII STLT                                                    134

SEQ ID NO: 4            moltype = AA  length = 132
FEATURE                 Location/Qualifiers
REGION                  1..132
                        note = amino acid sequence of aldesleukin
source                  1..132
                        mol_type = protein
                        organism = synthetic construct
SEQUENCE: 4
PTSSSTKKTQ LQLEHLLLDL QMILNGINNY KNPKLTRMLT FKFYMPKKAT ELKHLQCLEE  60
ELKPLEEVLN LAQSKNFHLR PRDLISNINV IVLELKGSET TFMCEYADET ATIVEFLNRW  120
ITFSQSIIST LT                                                      132

SEQ ID NO: 5            moltype = AA  length = 133
FEATURE                 Location/Qualifiers
REGION                  1..133
                        note = IL-2 form
```

```
source                  1..133
                        mol_type = protein
                        organism = synthetic construct
SEQUENCE: 5
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 6            moltype = AA  length = 303
FEATURE                 Location/Qualifiers
REGION                  1..303
                        note = amino acid sequence of nemvaleukin alfa
source                  1..303
                        mol_type = protein
                        organism = synthetic construct
SEQUENCE: 6
SKNFHLRPRD LISNINVIVL ELKGSETTFM CEYADETATI VEFLNRWITF SQSIISTLTG  60
GSSSTKKTQL QLEHLLLDLQ MILNGINNYK NPKLTRMLTF KFYMPKKATE LKHLQCLEEE  120
LKPLEEVLNL AQGSGGGSEL CDDDPPEIPH ATFKAMAYKE GTMLNCECKR GFRRIKSGSL  180
YMLCTGNSSH SSWDNQCQCT SSATRNTTKQ VTPQPEEQKE RKTTEMQSPM QPVDQASLPG  240
HCREPPPWEN EATERIYHFV VGQMVYYQCV QGYRALHRGP AESVCKMTHG KTRWTQPQLI  300
CTG                                                                303

SEQ ID NO: 7            moltype = AA  length = 452
FEATURE                 Location/Qualifiers
REGION                  1..452
                        note = IL-2 form
source                  1..452
                        mol_type = protein
                        organism = synthetic construct
SEQUENCE: 7
MDAMKRGLCC VLLLCGAVFV SARRPSGRKS SKMQAFRIWD VNQKTFYLRN NQLVAGYLQG  60
PNVNLEEKID VVPIEPHALF LGIHGGKMCL SCVKSGDETR LQLEAVNITD LSENRKQDKR  120
FAFIRSDSGP TTSFESAACP GWFLCTAMEA DQPVSLTNMP DEGVMVTKFY FQEDESGSGG  180
ASSESSASSD GPHPVITESR ASSESSASSD GPHPVITESR EPKSSDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 8            moltype = AA  length = 16
FEATURE                 Location/Qualifiers
REGION                  1..16
                        note = mucin domain polypeptide
source                  1..16
                        mol_type = protein
                        organism = synthetic construct
SEQUENCE: 8
SESSASSDGP HPVITP                                                  16

SEQ ID NO: 9            moltype = AA  length = 130
FEATURE                 Location/Qualifiers
REGION                  1..130
                        note = amino acid sequence of a recombinant human IL-4
                         protein
source                  1..130
                        mol_type = protein
                        organism = synthetic construct
SEQUENCE: 9
MHKCDITLQE IIKTLNSLTE QKTLCTELTV TDIFAASKNT TEKETFCRAA TVLRQFYSHH  60
EKDTRCLGAT AQQFHRHKQL IRFLKRLDRN LWGLAGLNSC PVKEANQSTL ENFLERLKTI  120
MREKYSKCSS                                                         130

SEQ ID NO: 10           moltype = AA  length = 153
FEATURE                 Location/Qualifiers
REGION                  1..153
                        note = amino acid sequence of a recombinant human IL-7
                         protein
source                  1..153
                        mol_type = protein
                        organism = synthetic construct
SEQUENCE: 10
MDCDIEGKDG KQYESVLMVS IDQLLDSMKE IGSNCLNNEF NFFKRHICDA NKEGMFLFRA  60
ARKLRQFLKM NSTGDFDLHL LKVSEGTTIL LNCTGQVKGR KPAALGEAQP TKSLEENKSL  120
KEQKKLNDLC FLKRLLQEIK TCWNKILMGT KEH                                153

SEQ ID NO: 11           moltype = AA  length = 115
FEATURE                 Location/Qualifiers
REGION                  1..115
```

```
                          note = amino acid sequence of a recombinant human IL-15
                           protein
source                    1..115
                          mol_type = protein
                          organism = synthetic construct
SEQUENCE: 11
MNWVNVISDL KKIEDLIQSM HIDATLYTES DVHPSCKVTA MKCFLLELQV ISLESGDASI  60
HDTVENLIIL ANNSLSSNGN VTESGCKECE ELEEKNIKEF LQSFVHIVQM FINTS       115

SEQ ID NO: 12             moltype = AA  length = 132
FEATURE                   Location/Qualifiers
REGION                    1..132
                          note = amino acid sequence of a recombinant human IL-21
                           protein
source                    1..132
                          mol_type = protein
                          organism = synthetic construct
SEQUENCE: 12
MQDRHMIRMR QLIDIVDQLK NYVNDLVPEF LPAPEDVETN CEWSAFSCFQ KAQLKSANTG  60
NNERIINVSI KKLKRKPPST NAGRRQKHRL TCPSCDSYEK KPPKEFLERF KSLLQKMIHQ  120
HLSSRTHGSE DS                                                      132

SEQ ID NO: 13             moltype = AA  length = 153
FEATURE                   Location/Qualifiers
REGION                    1..153
                          note = IL-2 sequence
source                    1..153
                          mol_type = protein
                          organism = synthetic construct
SEQUENCE: 13
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 14             moltype = AA  length = 133
FEATURE                   Location/Qualifiers
REGION                    1..133
                          note = IL-2 mutein sequence
source                    1..133
                          mol_type = protein
                          organism = synthetic construct
SEQUENCE: 14
APTSSSTKKT QLQLEHLLLD LQMILNGINN YKNPKLTAML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 15             moltype = AA  length = 133
FEATURE                   Location/Qualifiers
REGION                    1..133
                          note = IL-2 mutein sequence
source                    1..133
                          mol_type = protein
                          organism = synthetic construct
SEQUENCE: 15
APTSSSTKKT QLQLEHLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 16             moltype = AA  length = 145
FEATURE                   Location/Qualifiers
REGION                    1..145
                          note = HCDR1_IL-2 for IgG.IL2R67A.H1
source                    1..145
                          mol_type = protein
                          organism = synthetic construct
SEQUENCE: 16
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GMSVG                                        145

SEQ ID NO: 17             moltype = AA  length = 16
FEATURE                   Location/Qualifiers
REGION                    1..16
                          note = HCDR2 for IgG.IL2R67A.H1
source                    1..16
                          mol_type = protein
                          organism = synthetic construct
SEQUENCE: 17
DIWWDDKKDY NPSLKS                                                  16
```

```
SEQ ID NO: 18          moltype = AA  length = 10
FEATURE                Location/Qualifiers
REGION                 1..10
                       note = HCDR3 for IgG.IL2R67A.H1
source                 1..10
                       mol_type = protein
                       organism = synthetic construct
SEQUENCE: 18
SMITNWYFDV                                                    10

SEQ ID NO: 19          moltype = AA  length = 141
FEATURE                Location/Qualifiers
REGION                 1..141
                       note = HCDR1_IL-2 kabat for IgG.IL2R67A.H1
source                 1..141
                       mol_type = protein
                       organism = synthetic construct
SEQUENCE: 19
APTSSSTKKT QLQLEHLLLD LQMILNGINN YKNPKLTAML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSTSGMSV G                                       141

SEQ ID NO: 20          moltype = AA  length = 16
FEATURE                Location/Qualifiers
REGION                 1..16
                       note = HCDR2 kabat for IgG.IL2R67A.H1
source                 1..16
                       mol_type = protein
                       organism = synthetic construct
SEQUENCE: 20
DIWWDDKKDY NPSLKS                                             16

SEQ ID NO: 21          moltype = AA  length = 10
FEATURE                Location/Qualifiers
REGION                 1..10
                       note = HCDR3 kabat for IgG.IL2R67A.H1
source                 1..10
                       mol_type = protein
                       organism = synthetic construct
SEQUENCE: 21
SMITNWYFDV                                                    10

SEQ ID NO: 22          moltype = AA  length = 142
FEATURE                Location/Qualifiers
REGION                 1..142
                       note = HCDR1_IL-2 clothia for IgG.IL2R67A.H1
source                 1..142
                       mol_type = protein
                       organism = synthetic construct
SEQUENCE: 22
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GM                                      142

SEQ ID NO: 23          moltype = AA  length = 5
FEATURE                Location/Qualifiers
REGION                 1..5
                       note = HCDR2 clothia for IgG.IL2R67A.H1
source                 1..5
                       mol_type = protein
                       organism = synthetic construct
SEQUENCE: 23
WWDDK                                                         5

SEQ ID NO: 24          moltype = AA  length = 10
FEATURE                Location/Qualifiers
REGION                 1..10
                       note = HCDR3 clothia for IgG.IL2R67A.H1
source                 1..10
                       mol_type = protein
                       organism = synthetic construct
SEQUENCE: 24
SMITNWYFDV                                                    10

SEQ ID NO: 25          moltype = AA  length = 143
FEATURE                Location/Qualifiers
REGION                 1..143
                       note = HCDR1_IL-2 IMGT for IgG.IL2R67A.H1
```

```
source                  1..143
                        mol_type = protein
                        organism = synthetic construct
SEQUENCE: 25
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GMS                                          143

SEQ ID NO: 26           moltype = AA  length = 7
FEATURE                 Location/Qualifiers
REGION                  1..7
                        note = HCDR2 IMGT for IgG.IL2R67A.H1
source                  1..7
                        mol_type = protein
                        organism = synthetic construct
SEQUENCE: 26
IWWDDKK                                                            7

SEQ ID NO: 27           moltype = AA  length = 12
FEATURE                 Location/Qualifiers
REGION                  1..12
                        note = HCDR3 IMGT for IgG.IL2R67A.H1
source                  1..12
                        mol_type = protein
                        organism = synthetic construct
SEQUENCE: 27
ARSMITNWYF DV                                                      12

SEQ ID NO: 28           moltype = AA  length = 253
FEATURE                 Location/Qualifiers
REGION                  1..253
                        note = VH chain for IgG.IL2R67A.H1
source                  1..253
                        mol_type = protein
                        organism = synthetic construct
SEQUENCE: 28
QVTLRESGPA LVKPTQTLTL TCTFSGFSLA PTSSSTKKTQ LQLEHLLLDL QMILNGINNY  60
KNPKLTAMLT FKFYMPKKAT ELKHLQCLEE ELKPLEEVLN LAQSKNFHLR PRDLISNINV  120
IVLELKGSET TFMCEYADET ATIVEFLNRW ITFCQSIIST LTSTSGMSVG WIRQPPGKAL  180
EWLADIWWDD KKDYNPSLKS RLTISKDTSK NQVVLKVTNM DPADTATYYC ARSMITNWYF  240
DVWGAGTTVT VSS                                                     253

SEQ ID NO: 29           moltype = AA  length = 533
FEATURE                 Location/Qualifiers
REGION                  1..533
                        note = heavy chain for IgG.IL2R67A.H1
source                  1..533
                        mol_type = protein
                        organism = synthetic construct
SEQUENCE: 29
QMILNGINNY KNPKLTAMLT FKFYMPKKAT ELKHLQCLEE ELKPLEEVLN LAQSKNFHLR  60
PRDLISNINV IVLELKGSET TFMCEYADET ATIVEFLNRW ITFCQSIIST LTSTSGMSVG  120
WIRQPPGKAL EWLADIWWDD KKDYNPSLKS RLTISKDTSK NQVVLKVTNM DPADTATYYC  180
ARSMITNWYF DVWGAGTTVT VSSASTKGPS VFPLAPSSKS TSGGTAALGC LVKDYFPEPV  240
TVSWNSGALT SGVHTFPAVL QSSGLYSLSS VVTVPSSSLG TQTYICNVNH KPSNTKVDKR  300
VEPKSCDKTH TCPPCPAPEL LGGPSVFLFP PKPKDTLMIS RTPEVTCVVV AVSHEDPEVK  360
FNWYVDGVEV HNAKTKPREE QYNSTYRVVS VLTVLHQDWL NGKEYKCKVS NKALAAPIEK  420
TISKAKGQPR EPQVYTLPPS REEMTKNQVS LTCLVKGFYP SDIAVEWESN GQPENNYKTT  480
PPVLDSDGSF FLYSKLTVDK SRWQQGNVFS CSVMHEALHN HYTQKSLSLS PGK          533

SEQ ID NO: 30           moltype = AA  length = 10
FEATURE                 Location/Qualifiers
REGION                  1..10
                        note = LCDR1 kabat for IgG.IL2R67A.H1
source                  1..10
                        mol_type = protein
                        organism = synthetic construct
SEQUENCE: 30
KAQLSVGYMH                                                         10

SEQ ID NO: 31           moltype = AA  length = 7
FEATURE                 Location/Qualifiers
REGION                  1..7
                        note = LCDR2 kabat for IgG.IL2R67A.H1
source                  1..7
                        mol_type = protein
                        organism = synthetic construct
SEQUENCE: 31
DTSKLAS                                                            7
```

```
SEQ ID NO: 32          moltype = AA  length = 9
FEATURE                Location/Qualifiers
REGION                 1..9
                       note = LCDR3 kabat for IgG.IL2R67A.H1
source                 1..9
                       mol_type = protein
                       organism = synthetic construct
SEQUENCE: 32
FQGSGYPFT                                                         9

SEQ ID NO: 33          moltype = AA  length = 6
FEATURE                Location/Qualifiers
REGION                 1..6
                       note = LCDR1 chothia for IgG.IL2R67A.H1
source                 1..6
                       mol_type = protein
                       organism = synthetic construct
SEQUENCE: 33
QLSVGY                                                            6

SEQ ID NO: 34          moltype =   length =
SEQUENCE: 34
000

SEQ ID NO: 35          moltype = AA  length = 6
FEATURE                Location/Qualifiers
REGION                 1..6
                       note = LCDR3 chothia for IgG.IL2R67A.H1
source                 1..6
                       mol_type = protein
                       organism = synthetic construct
SEQUENCE: 35
GSGYPF                                                            6

SEQ ID NO: 36          moltype = AA  length = 106
FEATURE                Location/Qualifiers
REGION                 1..106
                       note = VL chain
source                 1..106
                       mol_type = protein
                       organism = synthetic construct
SEQUENCE: 36
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIK                106

SEQ ID NO: 37          moltype = AA  length = 213
FEATURE                Location/Qualifiers
REGION                 1..213
                       note = light chain
source                 1..213
                       mol_type = protein
                       organism = synthetic construct
SEQUENCE: 37
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 38          moltype = AA  length = 583
FEATURE                Location/Qualifiers
REGION                 1..583
                       note = light chain
source                 1..583
                       mol_type = protein
                       organism = synthetic construct
SEQUENCE: 38
QVTLRESGPA LVKPTQTLTL TCTFSGFSLA PTSSSTKKTQ LQLEHLLLDL QMILNGINNY  60
KNPKLTRMLT AKFYMPKKAT ELKHLQCLEE ELKPLEEVLN LAQSKNFHLR PRDLISNINV  120
IVLELKGSET TFMCEYADET ATIVEFLNRW ITFCQSIIST LTSTSGMSVG WIRQPPGKAL  180
EWLADIWWDD KKDYNPSLKS RLTISKDTSK NQVVLKVTNM DPADTATYYC ARSMITNWYF  240
DVWGAGTTVT VSSASTKGPS VFPLAPSSKS TSGGTAALGC LVKDYFPEPV TVSWNSGALT  300
SGVHTFPAVL QSSGLYSLSS VVTVPSSSLG TQTYICNVNH KPSNTKVDKR VEPKSCDKTH  360
TCPPCPAPEL LGGPSVFLFP PKPKDTLMIS RTPEVTCVVV AVSHEDPEVK FNWYVDGVEV  420
HNAKTKPREE QYNSTYRVVS VLTVLHQDWL NGKEYKCKVS NKALAAPIEK TISKAKGQPR  480
EPQVYTLPPS REEMTKNQVS LTCLVKGFYP SDIAVEWESN GQPENNYKTT PPVLDSDGSF  540
FLYSKLTVDK SRWQQGNVFS CSVMHEALHN HYTQKSLSLS PGK                   583

SEQ ID NO: 39          moltype = AA  length = 213
```

```
FEATURE                Location/Qualifiers
REGION                 1..213
                       note = light chain
source                 1..213
                       mol_type = protein
                       organism = synthetic construct
SEQUENCE: 39
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 40          moltype = AA  length = 255
FEATURE                Location/Qualifiers
REGION                 1..255
                       note = amino acid sequence of human 4-1BB
source                 1..255
                       mol_type = protein
                       organism = synthetic construct
SEQUENCE: 40
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                   255

SEQ ID NO: 41          moltype = AA  length = 256
FEATURE                Location/Qualifiers
REGION                 1..256
                       note = amino acid sequence of murine 4-1BB
source                 1..256
                       mol_type = protein
                       organism = synthetic construct
SEQUENCE: 41
MGNNCYNVVV IVLLLVGCEK VGAVQNSCDN CQPGTFCRKY NPVCKSCPPS TFSSIGGQPN  60
CNICRVCAGY FRFKKFCSST HNAECECIEG FHCLGPQCTR CEKDCRPGQE LTKQGCKTCS  120
LGTFNDQNGT GVCRPWTNCS LDGRSVLKTG TTEKDVVCGP PVVSFSPSTT ISVTPEGGPG  180
GHSLQVLTLF LALTSALLLA LIFITLLFSV LKWIRKKFPH IFKQPFKKTT GAAQEEDACS  240
CRCPQEEEGG GGGYEL                                                  256

SEQ ID NO: 42          moltype = AA  length = 441
FEATURE                Location/Qualifiers
REGION                 1..441
                       note = heavy chain for the 4-1BB agonist monoclonal
                        antibody utomilumab (PF-05082566)
source                 1..441
                       mol_type = protein
                       organism = synthetic construct
SEQUENCE: 42
EVQLVQSGAE VKKPGESLRI SCKGSGYSFS TYWISWVRQM PGKGLEWMGK IYPGDSYTNY  60
SPSFQGQVTI SADKSISTAY LQWSSLKASD TAMYYCARGY GIFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS NFGTQTYTCN VDHKPSNTKV DKTVERKCCV ECPPCPAPPV AGPSVFLFPP  240
KPKDTLMISR TPEVTCVVVD VSHEDPEVQF NWYVDGVEVH NAKTKPREEQ FNSTFRVVSV  300
LTVVHQDWLN GKEYKCKVSN KGLPAPIEKT ISKTKGQPRE PQVYTLPPSR EEMTKNQVSL  360
TCLVKGFYPS DIAVEWESNG QPENNYKTTP PMLDSDGSFF LYSKLTVDKS RWQQGNVFSC  420
SVMHEALHNH YTQKSLSLSP G                                            441

SEQ ID NO: 43          moltype = AA  length = 214
FEATURE                Location/Qualifiers
REGION                 1..214
                       note = light chain for the 4-1BB agonist monoclonal
                        antibody utomilumab (PF-05082566)
source                 1..214
                       mol_type = protein
                       organism = synthetic construct
SEQUENCE: 43
SYELTQPPSV SVSPGQTASI TCSGDNIGDQ YAHWYQQKPG QSPVLVIYQD KNRPSGIPER  60
FSGSNSGNTA TLTISGTQAM DEADYYCATY TGFGSLAVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 44          moltype = AA  length = 116
FEATURE                Location/Qualifiers
REGION                 1..116
                       note = heavy chain variable region (VH) for the 4-1BB
                        agonist monoclonal antibody utomilumab (PF-05082566).
source                 1..116
                       mol_type = protein
```

```
                        organism = synthetic construct
SEQUENCE: 44
EVQLVQSGAE VKKPGESLRI SCKGSGYSFS TYWISWVRQM PGKGLEWMGK IYPGDSYTNY  60
SPSFQGQVTI SADKSISTAY LQWSSLKASD TAMYYCARGY GIFDYWGQGT LVTVSS      116

SEQ ID NO: 45           moltype = AA  length = 108
FEATURE                 Location/Qualifiers
REGION                  1..108
                        note = light chain variable region (VL) for the 4-1BB
                         agonist monoclonal antibody utomilumab (PF-05082566).
source                  1..108
                        mol_type = protein
                        organism = synthetic construct
SEQUENCE: 45
SYELTQPPSV SVSPGQTASI TCSGDNIGDQ YAHWYQQKPG QSPVLVIYQD KNRPSGIPER  60
FSGSNSGNTA TLTISGTQAM DEADYYCATY TGFGSLAVFG GGTKLTVL               108

SEQ ID NO: 46           moltype = AA  length = 6
FEATURE                 Location/Qualifiers
REGION                  1..6
                        note = heavy chain CDR1 for the 4-1BB agonist monoclonal
                         antibody utomilumab (PF-05082566)
source                  1..6
                        mol_type = protein
                        organism = synthetic construct
SEQUENCE: 46
STYWIS                                                             6

SEQ ID NO: 47           moltype = AA  length = 17
FEATURE                 Location/Qualifiers
REGION                  1..17
                        note = heavy chain CDR2 for the 4-1BB agonist monoclonal
                         antibody utomilumab (PF-05082566)
source                  1..17
                        mol_type = protein
                        organism = synthetic construct
SEQUENCE: 47
KIYPGDSYTN YSPSFQG                                                 17

SEQ ID NO: 48           moltype = AA  length = 8
FEATURE                 Location/Qualifiers
REGION                  1..8
                        note = heavy chain CDR3 for the 4-1BB agonist monoclonal
                         antibody utomilumab (PF-05082566)
source                  1..8
                        mol_type = protein
                        organism = synthetic construct
SEQUENCE: 48
RGYGIFDY                                                           8

SEQ ID NO: 49           moltype = AA  length = 11
FEATURE                 Location/Qualifiers
REGION                  1..11
                        note = light chain CDR1 for the 4-1BB agonist monoclonal
                         antibody utomilumab (PF-05082566)
source                  1..11
                        mol_type = protein
                        organism = synthetic construct
SEQUENCE: 49
SGDNIGDQYA H                                                       11

SEQ ID NO: 50           moltype = AA  length = 7
FEATURE                 Location/Qualifiers
REGION                  1..7
                        note = light chain CDR2 for the 4-1BB agonist monoclonal
                         antibody utomilumab (PF-05082566)
source                  1..7
                        mol_type = protein
                        organism = synthetic construct
SEQUENCE: 50
QDKNRPS                                                            7

SEQ ID NO: 51           moltype = AA  length = 11
FEATURE                 Location/Qualifiers
REGION                  1..11
                        note = light chain CDR3 for the 4-1BB agonist monoclonal
                         antibody utomilumab (PF-05082566)
source                  1..11
                        mol_type = protein
```

```
                         organism = synthetic construct
SEQUENCE: 51
ATYTGFGSLA V                                                      11

SEQ ID NO: 52            moltype = AA  length = 448
FEATURE                  Location/Qualifiers
REGION                   1..448
                         note = heavy chain for the 4-1BB agonist monoclonal
                          antibody urelumab (BMS-663513)
source                   1..448
                         mol_type = protein
                         organism = synthetic construct
SEQUENCE: 52
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                    448

SEQ ID NO: 53            moltype = AA  length = 216
FEATURE                  Location/Qualifiers
REGION                   1..216
                         note = light chain for the 4-1BB agonist monoclonal
                          antibody urelumab (BMS-663513)
source                   1..216
                         mol_type = protein
                         organism = synthetic construct
SEQUENCE: 53
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF CGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 54            moltype = AA  length = 120
FEATURE                  Location/Qualifiers
REGION                   1..120
                         note = heavy chain variable region (VH) for the 4-1BB
                          agonist monoclonal antibody urelumab (BMS-663513)
source                   1..120
                         mol_type = protein
                         organism = synthetic construct
SEQUENCE: 54
MKHLWFFLLL VAAPRWVLSQ VQLQQWGAGL LKPSETLSLT CAVYGGSFSG YYWSWIRQSP  60
EKGLEWIGEI NHGGYVTYNP SLESRVTISV DTSKNQFSLK LSSVTAADTA VYYCARDYGP  120

SEQ ID NO: 55            moltype = AA  length = 110
FEATURE                  Location/Qualifiers
REGION                   1..110
                         note = light chain variable region (VL) for the 4-1BB
                          agonist monoclonal antibody urelumab (BMS-663513)
source                   1..110
                         mol_type = protein
                         organism = synthetic construct
SEQUENCE: 55
MEAPAQLLFL LLLWLPDTTG EIVLTQSPAT LSLSPGERAT LSCRASQSVS SYLAWYQQKP  60
GQAPRLLIYD ASNRATGIPA RFSGSGSGTD FTLTISSLEP EDFAVYYCQQ            110

SEQ ID NO: 56            moltype = AA  length = 5
FEATURE                  Location/Qualifiers
REGION                   1..5
                         note = heavy chain CDR1 for the 4-1BB agonist monoclonal
                          antibody urelumab (BMS-663513)
source                   1..5
                         mol_type = protein
                         organism = synthetic construct
SEQUENCE: 56
GYYWS                                                             5

SEQ ID NO: 57            moltype = AA  length = 16
FEATURE                  Location/Qualifiers
REGION                   1..16
                         note = heavy chain CDR2 for the 4-1BB agonist monoclonal
                          antibody urelumab (BMS-663513)
source                   1..16
                         mol_type = protein
                         organism = synthetic construct
```

```
SEQUENCE: 57
EINHGGYVTY NPSLES                                                    16

SEQ ID NO: 58          moltype = AA  length = 13
FEATURE                Location/Qualifiers
REGION                 1..13
                       note = heavy chain CDR3 for the 4-1BB agonist monoclonal
                        antibody urelumab (BMS-663513)
source                 1..13
                       mol_type = protein
                       organism = synthetic construct
SEQUENCE: 58
DYGPGNYDWY FDL                                                       13

SEQ ID NO: 59          moltype = AA  length = 11
FEATURE                Location/Qualifiers
REGION                 1..11
                       note = light chain CDR1 for the 4-1BB agonist monoclonal
                        antibody urelumab (BMS-663513)
source                 1..11
                       mol_type = protein
                       organism = synthetic construct
SEQUENCE: 59
RASQSVSSYL A                                                         11

SEQ ID NO: 60          moltype = AA  length = 7
FEATURE                Location/Qualifiers
REGION                 1..7
                       note = light chain CDR2 for the 4-1BB agonist monoclonal
                        antibody urelumab (BMS-663513)
source                 1..7
                       mol_type = protein
                       organism = synthetic construct
SEQUENCE: 60
DASNRAT                                                              7

SEQ ID NO: 61          moltype = AA  length = 11
FEATURE                Location/Qualifiers
REGION                 1..11
                       note = light chain CDR3 for the 4-1BB agonist monoclonal
                        antibody urelumab (BMS-663513)
source                 1..11
                       mol_type = protein
                       organism = synthetic construct
SEQUENCE: 61
QQRSDWPPAL T                                                         11

SEQ ID NO: 62          moltype = AA  length = 230
FEATURE                Location/Qualifiers
REGION                 1..230
                       note = Fc domain for a TNFRSF agonist fusion protein
source                 1..230
                       mol_type = protein
                       organism = synthetic construct
SEQUENCE: 62
KSCDKTHTCP PCPAPELLGG PSVFLFPPKP KDTLMISRTP EVTCVVVDVS HEDPEVKFNW  60
YVDGVEVHNA KTKPREEQYN STYRVVSVLT VLHQDWLNGK EYKCKVSNKA LPAPIEKTIS  120
KAKGQPREPQ VYTLPPSREE MTKNQVSLTC LVKGFYPSDI AVEWESNGQP ENNYKTTPPV  180
LDSDGSFFLY SKLTVDKSRW QQGNVFSCSV MHEALHNHYT QKSLSLSPGK             230

SEQ ID NO: 63          moltype = AA  length = 22
FEATURE                Location/Qualifiers
REGION                 1..22
                       note = linker for a TNFRSF agonist fusion protein
source                 1..22
                       mol_type = protein
                       organism = synthetic construct
SEQUENCE: 63
GGPGSSKSCD KTHTCPPCPA PE                                             22

SEQ ID NO: 64          moltype = AA  length = 22
FEATURE                Location/Qualifiers
REGION                 1..22
                       note = linker for a TNFRSF agonist fusion protein
source                 1..22
                       mol_type = protein
                       organism = synthetic construct
SEQUENCE: 64
GGSGSSKSCD KTHTCPPCPA PE                                             22
```

```
SEQ ID NO: 65           moltype = AA  length = 27
FEATURE                 Location/Qualifiers
REGION                  1..27
                        note = linker for a TNFRSF agonist fusion protein
source                  1..27
                        mol_type = protein
                        organism = synthetic construct
SEQUENCE: 65
GGPGSSSSSS SKSCDKTHTC PPCPAPE                                        27

SEQ ID NO: 66           moltype = AA  length = 27
FEATURE                 Location/Qualifiers
REGION                  1..27
                        note = linker for a TNFRSF agonist fusion protein
source                  1..27
                        mol_type = protein
                        organism = synthetic construct
SEQUENCE: 66
GGSGSSSSSS SKSCDKTHTC PPCPAPE                                        27

SEQ ID NO: 67           moltype = AA  length = 29
FEATURE                 Location/Qualifiers
REGION                  1..29
                        note = linker for a TNFRSF agonist fusion protein
source                  1..29
                        mol_type = protein
                        organism = synthetic construct
SEQUENCE: 67
GGPGSSSSSS SSSKSCDKTH TCPPCPAPE                                      29

SEQ ID NO: 68           moltype = AA  length = 29
FEATURE                 Location/Qualifiers
REGION                  1..29
                        note = linker for a TNFRSF agonist fusion protein
source                  1..29
                        mol_type = protein
                        organism = synthetic construct
SEQUENCE: 68
GGSGSSSSSS SSSKSCDKTH TCPPCPAPE                                      29

SEQ ID NO: 69           moltype = AA  length = 23
FEATURE                 Location/Qualifiers
REGION                  1..23
                        note = linker for a TNFRSF agonist fusion protein
source                  1..23
                        mol_type = protein
                        organism = synthetic construct
SEQUENCE: 69
GGPGSSSGSGS DKTHTCPPCP APE                                           23

SEQ ID NO: 70           moltype = AA  length = 23
FEATURE                 Location/Qualifiers
REGION                  1..23
                        note = linker for a TNFRSF agonist fusion protein
source                  1..23
                        mol_type = protein
                        organism = synthetic construct
SEQUENCE: 70
GGPGSSGSGS DKTHTCPPCP APE                                            23

SEQ ID NO: 71           moltype = AA  length = 21
FEATURE                 Location/Qualifiers
REGION                  1..21
                        note = linker for a TNFRSF agonist fusion protein
source                  1..21
                        mol_type = protein
                        organism = synthetic construct
SEQUENCE: 71
GGPSSSGSDK THTCPPCPAP E                                              21

SEQ ID NO: 72           moltype = AA  length = 25
FEATURE                 Location/Qualifiers
REGION                  1..25
                        note = linker for a TNFRSF agonist fusion protein
source                  1..25
                        mol_type = protein
                        organism = synthetic construct
SEQUENCE: 72
```

```
GGSSSSSSSS GSDKTHTCPP CPAPE                                    25

SEQ ID NO: 73           moltype = AA  length = 246
FEATURE                 Location/Qualifiers
REGION                  1..246
                        note = Fc domain for a TNFRSF agonist fusion protein
source                  1..246
                        mol_type = protein
                        organism = synthetic construct
SEQUENCE: 73
METDTLLLWV LLLWVPAGNG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPG                                                         246

SEQ ID NO: 74           moltype = AA  length = 11
FEATURE                 Location/Qualifiers
REGION                  1..11
                        note = linker for a TNFRSF agonist fusion protein
source                  1..11
                        mol_type = protein
                        organism = synthetic construct
SEQUENCE: 74
SGSGSGSGSG S                                                   11

SEQ ID NO: 75           moltype = AA  length = 12
FEATURE                 Location/Qualifiers
REGION                  1..12
                        note = linker for a TNFRSF agonist fusion protein
source                  1..12
                        mol_type = protein
                        organism = synthetic construct
SEQUENCE: 75
SSSSSSGSGS GS                                                  12

SEQ ID NO: 76           moltype = AA  length = 16
FEATURE                 Location/Qualifiers
REGION                  1..16
                        note = linker for a TNFRSF agonist fusion protein
source                  1..16
                        mol_type = protein
                        organism = synthetic construct
SEQUENCE: 76
SSSSSSGSGS GSGSGS                                              16

SEQ ID NO: 77           moltype = AA  length = 254
FEATURE                 Location/Qualifiers
REGION                  1..254
                        note = 4-1BB ligand (4-1BBL) amino acid sequence
source                  1..254
                        mol_type = protein
                        organism = synthetic construct
SEQUENCE: 77
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                254

SEQ ID NO: 78           moltype = AA  length = 168
FEATURE                 Location/Qualifiers
REGION                  1..168
                        note = soluble portion of 4-1BBL polypeptide
source                  1..168
                        mol_type = protein
                        organism = synthetic construct
SEQUENCE: 78
LRQGMFAQLV AQNVLLIDGP LSWYSDPGLA GVSLTGGLSY KEDTKELVVA KAGVYYVFFQ  60
LELRRVVAGE GSGSVSLALH LQPLRSAAGA AALALTVDLP PASSEARNSA FGFQGRLLHL  120
SAGQRLGVHL HTEARARHAW QLTQGATVLG LFRVTPEIPA GLPSPRSE           168

SEQ ID NO: 79           moltype = AA  length = 118
FEATURE                 Location/Qualifiers
REGION                  1..118
                        note = heavy chain variable region (VH) for the 4-1BB
                         agonist antibody 4B4-1-1 version 1
source                  1..118
                        mol_type = protein
```

```
                          organism = synthetic construct
SEQUENCE: 79
QVQLQQPGAE LVKPGASVKL SCKASGYTFS SYWMHWVKQR PGQVLEWIGE INPGNGHTNY  60
NEKFKSKATL TVDKSSSTAY MQLSSLTSED SAVYYCARSF TTARGFAYWG QGTLVTVS    118

SEQ ID NO: 80             moltype = AA  length = 107
FEATURE                   Location/Qualifiers
REGION                    1..107
                          note = light chain variable region (VL) for the 4-1BB
                           agonist antibody 4B4-1-1 version 1
source                    1..107
                          mol_type = protein
                          organism = synthetic construct
SEQUENCE: 80
DIVMTQSPAT QSVTPGDRVS LSCRASQTIS DYLHWYQQKS HESPRLLIKY ASQSISGIPS  60
RFSGSGSGSD FTLSINSVEP EDVGVYYCQD GHSFPPTFGG GTKLEIK                107

SEQ ID NO: 81             moltype = AA  length = 119
FEATURE                   Location/Qualifiers
REGION                    1..119
                          note = heavy chain variable region (VH) for the 4-1BB
                           agonist antibody 4B4-1-1 version 2
source                    1..119
                          mol_type = protein
                          organism = synthetic construct
SEQUENCE: 81
QVQLQQPGAE LVKPGASVKL SCKASGYTFS SYWMHWVKQR PGQVLEWIGE INPGNGHTNY  60
NEKFKSKATL TVDKSSSTAY MQLSSLTSED SAVYYCARSF TTARGFAYWG QGTLVTVSA   119

SEQ ID NO: 82             moltype = AA  length = 108
FEATURE                   Location/Qualifiers
REGION                    1..108
                          note = light chain variable region (VL) for the 4-1BB
                           agonist antibody 4B4-1-1 version 2
source                    1..108
                          mol_type = protein
                          organism = synthetic construct
SEQUENCE: 82
DIVMTQSPAT QSVTPGDRVS LSCRASQTIS DYLHWYQQKS HESPRLLIKY ASQSISGIPS  60
RFSGSGSGSD FTLSINSVEP EDVGVYYCQD GHSFPPTFGG GTKLEIKR               108

SEQ ID NO: 83             moltype = AA  length = 120
FEATURE                   Location/Qualifiers
REGION                    1..120
                          note = heavy chain variable region (VH) for the 4-1BB
                           agonist antibody H39E3-2
source                    1..120
                          mol_type = protein
                          organism = synthetic construct
SEQUENCE: 83
MDWTWRILFL VAAATGAHSE VQLVESGGGL VQPGGSLRLS CAASGFTFSD YWMSWVRQAP  60
GKGLEWVADI KNDGSYTNYA PSLTNRFTIS RDNAKNSLYL QMNSLRAEDT AVYYCARELT  120

SEQ ID NO: 84             moltype = AA  length = 109
FEATURE                   Location/Qualifiers
REGION                    1..109
                          note = light chain variable region (VL) for the 4-1BB
                           agonist antibody H39E3-2
source                    1..109
                          mol_type = protein
                          organism = synthetic construct
SEQUENCE: 84
MEAPAQLLFL LLLWLPDTTG DIVMTQSPDS LAVSLGERAT INCKSSQSLL SSGNQKNYLW  60
YQQKPGQPPK LLIYYASTRQ SGVPDRFSGS GSGTDFTLTI SSLQAEDVA              109

SEQ ID NO: 85             moltype = AA  length = 277
FEATURE                   Location/Qualifiers
REGION                    1..277
                          note = amino acid sequence of human OX40
source                    1..277
                          mol_type = protein
                          organism = synthetic construct
SEQUENCE: 85
MCVGARRLGR GPCAALLLLG LGLSTVTGLH CVGDTYPSND RCCHECRPGN GMVSRCSRSQ  60
NTVCRPCGPG FYNDVVSSKP CKPCTWCNLR SGSERKQLCT ATQDTVCRCR AGTQPLDSYK  120
PGVDCAPCPP GHFSPGDNQA CKPWTNCTLA GKHTLQPASN SSDAICEDRD PPATQPQETQ  180
GPPARPITVQ PTEAWPRTSQ GPSTRPVEVP GGRAVAAILG LGLVLGLLGP LAILLALYLL  240
RRDQRLPPDA HKPPGGGSFR TPIQEEQADA HSTLAKI                          277
```

```
SEQ ID NO: 86          moltype = AA  length = 272
FEATURE                Location/Qualifiers
REGION                 1..272
                       note = amino acid sequence of murine OX40
source                 1..272
                       mol_type = protein
                       organism = synthetic construct
SEQUENCE: 86
MYVWVQQPTA LLLLGLTLGV TARRLNCVKH TYPSGHKCCR ECQPGHGMVS RCDHTRDTLC  60
HPCETGFYNE AVNYDTCKQC TQCNHRSGSE LKQNCTPTQD TVCRCRPGTQ PRQDSGYKLG  120
VDCVPCPPGH FSPGNNQACK PWTNCTLSGK QTRHPASDSL DAVCEDRSLL ATLLWETQRP  180
TFRPTTVQST TVWPRTSELP SPPTLVTPEG PAFAVLLGLG LGLLAPLTVL LALYLLRKAW  240
RLPNTPKPCW GNSFRTPIQE EHTDAHFTLA KI                                272

SEQ ID NO: 87          moltype = AA  length = 451
FEATURE                Location/Qualifiers
REGION                 1..451
                       note = heavy chain for the OX40 agonist monoclonal antibody
                        tavolixizumab (MEDI-0562)
source                 1..451
                       mol_type = protein
                       organism = synthetic construct
SEQUENCE: 87
QVQLQESGPG LVKPSQTLSL TCAVYGGSFS SGYWNWIRKH PGKGLEYIGY ISYNGITYHN  60
PSLKSRITIN RDTSKNQYSL QLNSVTPEDT AVYYCARYKY DYDGGHAMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 88          moltype = AA  length = 214
FEATURE                Location/Qualifiers
REGION                 1..214
                       note = light chain for the OX40 agonist monoclonal antibody
                        tavolixizumab (MEDI-0562)
source                 1..214
                       mol_type = protein
                       organism = synthetic construct
SEQUENCE: 88
DIQMTQSPSS LSASVGDRVT ITCRASQDIS NYLNWYQQKP GKAPKLLIYY TSKLHSGVPS  60
RFSGSGSGTD YTLTISSLQP EDFATYYCQQ GSALPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 89          moltype = AA  length = 118
FEATURE                Location/Qualifiers
REGION                 1..118
                       note = heavy chain variable region (VH) for the OX40
                        agonist monoclonal antibody tavolixizumab (MEDI-0562)
source                 1..118
                       mol_type = protein
                       organism = synthetic construct
SEQUENCE: 89
QVQLQESGPG LVKPSQTLSL TCAVYGGSFS SGYWNWIRKH PGKGLEYIGY ISYNGITYHN  60
PSLKSRITIN RDTSKNQYSL QLNSVTPEDT AVYYCARYKY DYDGGHAMDY WGQGTLVT    118

SEQ ID NO: 90          moltype = AA  length = 108
FEATURE                Location/Qualifiers
REGION                 1..108
                       note = light chain variable region (VL) for the OX40
                        agonist monoclonal antibody tavolixizumab (MEDI-0562)
source                 1..108
                       mol_type = protein
                       organism = synthetic construct
SEQUENCE: 90
DIQMTQSPSS LSASVGDRVT ITCRASQDIS NYLNWYQQKP GKAPKLLIYY TSKLHSGVPS  60
RFSGSGSGTD YTLTISSLQP EDFATYYCQQ GSALPWTFGQ GTKVEIKR               108

SEQ ID NO: 91          moltype = AA  length = 9
FEATURE                Location/Qualifiers
REGION                 1..9
                       note = heavy chain CDR1 for the OX40 agonist monoclonal
                        antibody tavolixizumab (MEDI-0562)
source                 1..9
                       mol_type = protein
                       organism = synthetic construct
SEQUENCE: 91
```

```
GSFSSGYWN                                                    9

SEQ ID NO: 92          moltype = AA  length = 13
FEATURE                Location/Qualifiers
REGION                 1..13
                       note = heavy chain CDR2 for the OX40 agonist monoclonal
                        antibody tavolixizumab (MEDI-0562)
source                 1..13
                       mol_type = protein
                       organism = synthetic construct
SEQUENCE: 92
YIGYISYNGI TYH                                               13

SEQ ID NO: 93          moltype = AA  length = 14
FEATURE                Location/Qualifiers
REGION                 1..14
                       note = heavy chain CDR3 for the OX40 agonist monoclonal
                        antibody tavolixizumab (MEDI-0562)
source                 1..14
                       mol_type = protein
                       organism = synthetic construct
SEQUENCE: 93
RYKYDYDGGH AMDY                                              14

SEQ ID NO: 94          moltype = AA  length = 8
FEATURE                Location/Qualifiers
REGION                 1..8
                       note = light chain CDR1 for the OX40 agonist monoclonal
                        antibody tavolixizumab (MEDI-0562)
source                 1..8
                       mol_type = protein
                       organism = synthetic construct
SEQUENCE: 94
QDISNYLN                                                     8

SEQ ID NO: 95          moltype = AA  length = 11
FEATURE                Location/Qualifiers
REGION                 1..11
                       note = light chain CDR2 for the OX40 agonist monoclonal
                        antibody tavolixizumab (MEDI-0562)
source                 1..11
                       mol_type = protein
                       organism = synthetic construct
SEQUENCE: 95
LLIYYTSKLH S                                                 11

SEQ ID NO: 96          moltype = AA  length = 8
FEATURE                Location/Qualifiers
REGION                 1..8
                       note = light chain CDR3 for the OX40 agonist monoclonal
                        antibody tavolixizumab (MEDI-0562)
source                 1..8
                       mol_type = protein
                       organism = synthetic construct
SEQUENCE: 96
QQGSALPW                                                     8

SEQ ID NO: 97          moltype = AA  length = 444
FEATURE                Location/Qualifiers
REGION                 1..444
                       note = heavy chain for the OX40 agonist monoclonal antibody
                        11D4
source                 1..444
                       mol_type = protein
                       organism = synthetic construct
SEQUENCE: 97
EVQLVESGGG LVQPGGSLRL SCAASGFTFS SYSMNWVRQA PGKGLEWVSY ISSSSSTIDY  60
ADSVKGRFTI SRDNAKNSLY LQMNSLRDED TAVYYCARES GWYLFDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSNFGTQTYT CNVDHKPSNT KVDKTVERKC CVECPPCPAP PVAGPSVFLF  240
PPKPKDTLMI SRTPEVTCVV VDVSHEDPEV QFNWYVDGVE VHNAKTKPRE EQFNSTFRVV  300
SVLTVVHQDW LNGKEYKCKV SNKGLPAPIE KTISKTKGQP REPQVYTLPP SREEMTKNQV  360
SLTCLVKGFY PSDIAVEWES NGQPENNYKT TPPMLDSDGS FFLYSKLTVD KSRWQQGNVF  420
SCSVMHEALH NHYTQKSLSL SPGK                                   444

SEQ ID NO: 98          moltype = AA  length = 180
FEATURE                Location/Qualifiers
REGION                 1..180
                       note = light chain for the OX40 agonist monoclonal antibody
```

```
                         11D4
source                  1..180
                        mol_type = protein
                        organism = synthetic construct
SEQUENCE: 98
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180

SEQ ID NO: 99           moltype = AA  length = 118
FEATURE                 Location/Qualifiers
REGION                  1..118
                        note = heavy chain variable region (VH) for the OX40
                         agonist monoclonal antibody 11D4
source                  1..118
                        mol_type = protein
                        organism = synthetic construct
SEQUENCE: 99
EVQLVESGGG LVQPGGSLRL SCAASGFTFS SYSMNWVRQA PGKGLEWVSY ISSSSSTIDY  60
ADSVKGRFTI SRDNAKNSLY LQMNSLRDED TAVYYCARES GWYLFDYWGQ GTLVTVSS    118

SEQ ID NO: 100          moltype = AA  length = 107
FEATURE                 Location/Qualifiers
REGION                  1..107
                        note = light chain variable region (VL) for the OX40
                         agonist monoclonal antibody 11D4
source                  1..107
                        mol_type = protein
                        organism = synthetic construct
SEQUENCE: 100
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPPTFGG GTKVEIK                107

SEQ ID NO: 101          moltype = AA  length = 5
FEATURE                 Location/Qualifiers
REGION                  1..5
                        note = heavy chain CDR1 for the OX40 agonist monoclonal
                         antibody 11D4
source                  1..5
                        mol_type = protein
                        organism = synthetic construct
SEQUENCE: 101
SYSMN                                                              5

SEQ ID NO: 102          moltype = AA  length = 17
FEATURE                 Location/Qualifiers
REGION                  1..17
                        note = heavy chain CDR2 for the OX40 agonist monoclonal
                         antibody 11D4
source                  1..17
                        mol_type = protein
                        organism = synthetic construct
SEQUENCE: 102
YISSSSSTID YADSVKG                                                 17

SEQ ID NO: 103          moltype = AA  length = 9
FEATURE                 Location/Qualifiers
REGION                  1..9
                        note = heavy chain CDR3 for the OX40 agonist monoclonal
                         antibody 11D4
source                  1..9
                        mol_type = protein
                        organism = synthetic construct
SEQUENCE: 103
ESGWYLFDY                                                          9

SEQ ID NO: 104          moltype = AA  length = 11
FEATURE                 Location/Qualifiers
REGION                  1..11
                        note = light chain CDR1 for the OX40 agonist monoclonal
                         antibody 11D4
source                  1..11
                        mol_type = protein
                        organism = synthetic construct
SEQUENCE: 104
RASQGISSWL A                                                       11

SEQ ID NO: 105          moltype = AA  length = 7
FEATURE                 Location/Qualifiers
```

```
REGION                  1..7
                        note = light chain CDR2 for the OX40 agonist monoclonal
                         antibody 11D4
source                  1..7
                        mol_type = protein
                        organism = synthetic construct
SEQUENCE: 105
AASSLQS                                                             7

SEQ ID NO: 106          moltype = AA  length = 9
FEATURE                 Location/Qualifiers
REGION                  1..9
                        note = light chain CDR3 for the OX40 agonist monoclonal
                         antibody 11D4
source                  1..9
                        mol_type = protein
                        organism = synthetic construct
SEQUENCE: 106
QQYNSYPPT                                                           9

SEQ ID NO: 107          moltype = AA  length = 450
FEATURE                 Location/Qualifiers
REGION                  1..450
                        note = heavy chain for the OX40 agonist monoclonal antibody
                         18D8
source                  1..450
                        mol_type = protein
                        organism = synthetic construct
SEQUENCE: 107
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDQ STADYYFYYG MDVWGQGTTV  120
TVSSASTKGP SVFPLAPCSR STSESTAALG CLVKDYFPEP VTVSWNSGAL TSGVHTFPAV  180
LQSSGLYSLS SVVTVPSSNF GTQTYTCNVD HKPSNTKVDK TVERKCCVEC PPCPAPPVAG  240
PSVFLFPPKP KDTLMISRTP EVTCVVVDVS HEDPEVQFNW YVDGVEVHNA KTKPREEQFN  300
STFRVVSVLT VVHQDWLNGK EYKCKVSNKG LPAPIEKTIS KTKGQPREPQ VYTLPPSREE  360
MTKNQVSLTC LVKGFYPSDI AVEWESNGQP ENNYKTTPPM LDSDGSFFLY SKLTVDKSRW  420
QQGNVFSCSV MHEALHNHYT QKSLSLSPGK                                    450

SEQ ID NO: 108          moltype = AA  length = 213
FEATURE                 Location/Qualifiers
REGION                  1..213
                        note = light chain for the OX40 agonist monoclonal antibody
                         18D8
source                  1..213
                        mol_type = protein
                        organism = synthetic construct
SEQUENCE: 108
EIVVTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 109          moltype = AA  length = 124
FEATURE                 Location/Qualifiers
REGION                  1..124
                        note = heavy chain variable region (VH) for the OX40
                         agonist monoclonal antibody 18D8
source                  1..124
                        mol_type = protein
                        organism = synthetic construct
SEQUENCE: 109
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDQ STADYYFYYG MDVWGQGTTV  120
TVSS                                                                124

SEQ ID NO: 110          moltype = AA  length = 106
FEATURE                 Location/Qualifiers
REGION                  1..106
                        note = light chain variable region (VL) for the OX40
                         agonist monoclonal antibody 18D8
source                  1..106
                        mol_type = protein
                        organism = synthetic construct
SEQUENCE: 110
EIVVTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                  106

SEQ ID NO: 111          moltype = AA  length = 5
FEATURE                 Location/Qualifiers
```

```
REGION                  1..5
                        note = heavy chain CDR1 for the OX40 agonist monoclonal
                         antibody 18D8
source                  1..5
                        mol_type = protein
                        organism = synthetic construct
SEQUENCE: 111
DYAMH                                                                        5

SEQ ID NO: 112          moltype = AA  length = 17
FEATURE                 Location/Qualifiers
REGION                  1..17
                        note = heavy chain CDR2 for the OX40 agonist monoclonal
                         antibody 18D8
source                  1..17
                        mol_type = protein
                        organism = synthetic construct
SEQUENCE: 112
GISWNSGSIG YADSVKG                                                           17

SEQ ID NO: 113          moltype = AA  length = 15
FEATURE                 Location/Qualifiers
REGION                  1..15
                        note = heavy chain CDR3 for the OX40 agonist monoclonal
                         antibody 18D8
source                  1..15
                        mol_type = protein
                        organism = synthetic construct
SEQUENCE: 113
DQSTADYYFY YGMDV                                                             15

SEQ ID NO: 114          moltype = AA  length = 11
FEATURE                 Location/Qualifiers
REGION                  1..11
                        note = light chain CDR1 for the OX40 agonist monoclonal
                         antibody 18D8
source                  1..11
                        mol_type = protein
                        organism = synthetic construct
SEQUENCE: 114
RASQSVSSYL A                                                                 11

SEQ ID NO: 115          moltype = AA  length = 7
FEATURE                 Location/Qualifiers
REGION                  1..7
                        note = light chain CDR2 for the OX40 agonist monoclonal
                         antibody 18D8
source                  1..7
                        mol_type = protein
                        organism = synthetic construct
SEQUENCE: 115
DASNRAT                                                                      7

SEQ ID NO: 116          moltype = AA  length = 8
FEATURE                 Location/Qualifiers
REGION                  1..8
                        note = light chain CDR3 for the OX40 agonist monoclonal
                         antibody 18D8
source                  1..8
                        mol_type = protein
                        organism = synthetic construct
SEQUENCE: 116
QQRSNWPT                                                                     8

SEQ ID NO: 117          moltype = AA  length = 120
FEATURE                 Location/Qualifiers
REGION                  1..120
                        note = heavy chain variable region (VH) for the OX40
                         agonist monoclonal antibody Hu119-122
source                  1..120
                        mol_type = protein
                        organism = synthetic construct
SEQUENCE: 117
EVQLVESGGG LVQPGGSLRL SCAASEYEFP SHDMSWVRQA PGKGLELVAA INSDGGSTYY  60
PDTMERRFTI SRDNAKNSLY LQMNSLRAED TAVYYCARHY DDYYAWFAYW GQGTMVTVSS  120

SEQ ID NO: 118          moltype = AA  length = 111
FEATURE                 Location/Qualifiers
REGION                  1..111
```

```
                       note = light chain variable region (VL) for the OX40
                        agonist monoclonal antibody Hu119-122
source                 1..111
                       mol_type = protein
                       organism = synthetic construct
SEQUENCE: 118
EIVLTQSPAT LSLSPGERAT LSCRASKSVS TSGYSYMHWY QQKPGQAPRL LIYLASNLES  60
GVPARFSGSG SGTDFTLTIS SLEPEDFAVY YCQHSRELPL TFGGGTKVEI K           111

SEQ ID NO: 119         moltype = AA  length = 5
FEATURE                Location/Qualifiers
REGION                 1..5
                       note = heavy chain CDR1 for the OX40 agonist monoclonal
                        antibody Hu119-122
source                 1..5
                       mol_type = protein
                       organism = synthetic construct
SEQUENCE: 119
SHDMS                                                                5

SEQ ID NO: 120         moltype = AA  length = 17
FEATURE                Location/Qualifiers
REGION                 1..17
                       note = heavy chain CDR2 for the OX40 agonist monoclonal
                        antibody Hu119-122
source                 1..17
                       mol_type = protein
                       organism = synthetic construct
SEQUENCE: 120
AINSDGGSTY YPDTMER                                                   17

SEQ ID NO: 121         moltype = AA  length = 11
FEATURE                Location/Qualifiers
REGION                 1..11
                       note = heavy chain CDR3 for the OX40 agonist monoclonal
                        antibody Hu119-122
source                 1..11
                       mol_type = protein
                       organism = synthetic construct
SEQUENCE: 121
HYDDYYAWFA Y                                                         11

SEQ ID NO: 122         moltype = AA  length = 15
FEATURE                Location/Qualifiers
REGION                 1..15
                       note = light chain CDR1 for the OX40 agonist monoclonal
                        antibody Hu119-122
source                 1..15
                       mol_type = protein
                       organism = synthetic construct
SEQUENCE: 122
RASKSVSTSG YSYMH                                                     15

SEQ ID NO: 123         moltype = AA  length = 7
FEATURE                Location/Qualifiers
REGION                 1..7
                       note = light chain CDR2 for the OX40 agonist monoclonal
                        antibody Hu119-122
source                 1..7
                       mol_type = protein
                       organism = synthetic construct
SEQUENCE: 123
LASNLES                                                              7

SEQ ID NO: 124         moltype = AA  length = 9
FEATURE                Location/Qualifiers
REGION                 1..9
                       note = light chain CDR3 for the OX40 agonist monoclonal
                        antibody Hu119-122
source                 1..9
                       mol_type = protein
                       organism = synthetic construct
SEQUENCE: 124
QHSRELPLT                                                            9

SEQ ID NO: 125         moltype = AA  length = 122
FEATURE                Location/Qualifiers
REGION                 1..122
                       note = heavy chain variable region (VH) for the OX40
```

```
                        agonist monoclonal antibody Hu106-222
source                 1..122
                       mol_type = protein
                       organism = synthetic construct
SEQUENCE: 125
QVQLVQSGSE LKKPGASVKV SCKASGYTFT DYSMHWVRQA PGQGLKWMGW INTETGEPTY  60
ADDFKGRFVF SLDTSVSTAY LQISSLKAED TAVYYCANPY YDYVSYYAMD YWGQGTTVTV  120
SS                                                                122

SEQ ID NO: 126         moltype = AA  length = 107
FEATURE                Location/Qualifiers
REGION                 1..107
                       note = light chain variable region (VL) for the OX40
                        agonist monoclonal antibody Hu106-222
source                 1..107
                       mol_type = protein
                       organism = synthetic construct
SEQUENCE: 126
DIQMTQSPSS LSASVGDRVT ITCKASQDVS TAVAWYQQKP GKAPKLLIYS ASYLYTGVPS  60
RFSGSGSGTD FTFTISSLQP EDIATYYCQQ HYSTPRTFGQ GTKLEIK               107

SEQ ID NO: 127         moltype = AA  length = 5
FEATURE                Location/Qualifiers
REGION                 1..5
                       note = heavy chain CDR1 for the OX40 agonist monoclonal
                        antibody Hu106-222
source                 1..5
                       mol_type = protein
                       organism = synthetic construct
SEQUENCE: 127
DYSMH                                                             5

SEQ ID NO: 128         moltype = AA  length = 17
FEATURE                Location/Qualifiers
REGION                 1..17
                       note = heavy chain CDR2 for the OX40 agonist monoclonal
                        antibody Hu106-222
source                 1..17
                       mol_type = protein
                       organism = synthetic construct
SEQUENCE: 128
WINTETGEPT YADDFKG                                                17

SEQ ID NO: 129         moltype = AA  length = 13
FEATURE                Location/Qualifiers
REGION                 1..13
                       note = heavy chain CDR3 for the OX40 agonist monoclonal
                        antibody Hu106-222
source                 1..13
                       mol_type = protein
                       organism = synthetic construct
SEQUENCE: 129
PYYDYVSYYA MDY                                                    13

SEQ ID NO: 130         moltype = AA  length = 11
FEATURE                Location/Qualifiers
REGION                 1..11
                       note = light chain CDR1 for the OX40 agonist monoclonal
                        antibody Hu106-222
source                 1..11
                       mol_type = protein
                       organism = synthetic construct
SEQUENCE: 130
KASQDVSTAV A                                                      11

SEQ ID NO: 131         moltype = AA  length = 7
FEATURE                Location/Qualifiers
REGION                 1..7
                       note = light chain CDR2 for the OX40 agonist monoclonal
                        antibody Hu106-222
source                 1..7
                       mol_type = protein
                       organism = synthetic construct
SEQUENCE: 131
SASYLYT                                                           7

SEQ ID NO: 132         moltype = AA  length = 9
FEATURE                Location/Qualifiers
REGION                 1..9
```

```
                        note = light chain CDR3 for the OX40 agonist monoclonal
                         antibody Hu106-222
source                  1..9
                        mol_type = protein
                        organism = synthetic construct
SEQUENCE: 132
QQHYSTPRT                                                          9

SEQ ID NO: 133          moltype = AA  length = 183
FEATURE                 Location/Qualifiers
REGION                  1..183
                        note = OX40 ligand (OX40L) amino acid sequence
source                  1..183
                        mol_type = protein
                        organism = synthetic construct
SEQUENCE: 133
MERVQPLEEN VGNAARPRFE RNKLLLVASV IQGLGLLLCF TYICLHFSAL QVSHRYPRIQ  60
SIKVQFTEYK KEKGFILTSQ KEDEIMKVQN NSVIINCDGF YLISLKGYFS QEVNISLHYQ  120
KDEEPLFQLK KVRSVNSLMV ASLTYKDKVY LNVTTDNTSL DDFHVNGGEL ILIHQNPGEF  180
CVL                                                                183

SEQ ID NO: 134          moltype = AA  length = 131
FEATURE                 Location/Qualifiers
REGION                  1..131
                        note = soluble portion of OX40L polypeptide
source                  1..131
                        mol_type = protein
                        organism = synthetic construct
SEQUENCE: 134
SHRYPRIQSI KVQFTEYKKE KGFILTSQKE DEIMKVQNNS VIINCDGFYL ISLKGYFSQE  60
VNISLHYQKD EEPLFQLKKV RSVNSLMVAS LTYKDKVYLN VTTDNTSLDD FHVNGGELIL  120
IHQNPGEFCV L                                                       131

SEQ ID NO: 135          moltype = AA  length = 128
FEATURE                 Location/Qualifiers
REGION                  1..128
                        note = alternative soluble portion of OX40L polypeptide
source                  1..128
                        mol_type = protein
                        organism = synthetic construct
SEQUENCE: 135
YPRIQSIKVQ FTEYKKEKGF ILTSQKEDEI MKVQNNSVII NCDGFYLISL KGYFSQEVNI  60
SLHYQKDEEP LFQLKKVRSV NSLMVASLTY KDKVYLNVTT DNTSLDDFHV NGGELILIHQ  120
NPGEFCVL                                                           128

SEQ ID NO: 136          moltype = AA  length = 120
FEATURE                 Location/Qualifiers
REGION                  1..120
                        note = heavy chain variable region (VH) for the OX40
                         agonist monoclonal antibody 008
source                  1..120
                        mol_type = protein
                        organism = synthetic construct
SEQUENCE: 136
EVQLVESGGG LVQPGGSLRL SCAASGFTFS NYTMNWVRQA PGKGLEWVSA ISGSGGSTYY  60
ADSVKGRFTI SRDNSKNTLY LQMNSLRAED TAVYYCAKDR YSQVHYALDY WGQGTLVTVS  120

SEQ ID NO: 137          moltype = AA  length = 108
FEATURE                 Location/Qualifiers
REGION                  1..108
                        note = light chain variable region (VL) for the OX40
                         agonist monoclonal antibody 008
source                  1..108
                        mol_type = protein
                        organism = synthetic construct
SEQUENCE: 137
DIVMTQSPDS LPVTPGEPAS ISCRSSQSLL HSNGYNYLDW YLQKAGQSPQ LLIYLGSNRA  60
SGVPDRFSGS GSGTDFTLKI SRVEAEDVGV YYCQQYYNHP TTFGQGTK                108

SEQ ID NO: 138          moltype = AA  length = 120
FEATURE                 Location/Qualifiers
REGION                  1..120
                        note = heavy chain variable region (VH) for the OX40
                         agonist monoclonal antibody 011
source                  1..120
                        mol_type = protein
                        organism = synthetic construct
SEQUENCE: 138
EVQLVESGGG VVQPGRSLRL SCAASGFTFS DYTMNWVRQA PGKGLEWVSS ISGGSTYYAD  60
```

```
SRKGRFTISR DNSKNTLYLQ MNNLRAEDTA VYYCARDRYF RQQNAFDYWG QGTLVTVSSA  120

SEQ ID NO: 139          moltype = AA  length = 108
FEATURE                 Location/Qualifiers
REGION                  1..108
                        note = light chain variable region (VL) for the OX40
                         agonist monoclonal antibody 011
source                  1..108
                        mol_type = protein
                        organism = synthetic construct
SEQUENCE: 139
DIVMTQSPDS LPVTPGEPAS ISCRSSQSLL HSNGYNYLDW YLQKAGQSPQ LLIYLGSNRA  60
SGVPDRFSGS GSGTDFTLKI SRVEAEDVGV YYCQQYYNHP TTFGQGTK               108

SEQ ID NO: 140          moltype = AA  length = 120
FEATURE                 Location/Qualifiers
REGION                  1..120
                        note = heavy chain variable region (VH) for the OX40
                         agonist monoclonal antibody 021
source                  1..120
                        mol_type = protein
                        organism = synthetic construct
SEQUENCE: 140
EVQLVESGGG LVQPRGSLRL SCAASGFTFS SYAMNWVRQA PGKGLEWVAV ISYDGSNKYY  60
ADSVKGRFTI SRDNSKNTLY LQMNSLRAED TAVYYCAKDR YITLPNALDY WGQGTLVTVS  120

SEQ ID NO: 141          moltype = AA  length = 108
FEATURE                 Location/Qualifiers
REGION                  1..108
                        note = light chain variable region (VL) for the OX40
                         agonist monoclonal antibody 021
source                  1..108
                        mol_type = protein
                        organism = synthetic construct
SEQUENCE: 141
DIQMTQSPVS LPVTPGEPAS ISCRSSQSLL HSNGYNYLDW YLQKPGQSPQ LLIYLGSNRA  60
SGVPDRFSGS GSGTDFTLKI SRVEAEDVGV YYCQQYKSNP PTFGQGTK               108

SEQ ID NO: 142          moltype = AA  length = 120
FEATURE                 Location/Qualifiers
REGION                  1..120
                        note = heavy chain variable region (VH) for the OX40
                         agonist monoclonal antibody 023
source                  1..120
                        mol_type = protein
                        organism = synthetic construct
SEQUENCE: 142
EVQLVESGGG LVHPGGSLRL SCAGSGFTFS SYAMHWVRQA PGKGLEWVSA IGTGGGTYYA  60
DSVMGRFTIS RDNSKNTLYL QMNSLRAEDT AVYYCARYDN VMGLYWFDYW GQGTLVTVSS  120

SEQ ID NO: 143          moltype = AA  length = 108
FEATURE                 Location/Qualifiers
REGION                  1..108
                        note = light chain variable region (VL) for the OX40
                         agonist monoclonal antibody 023
source                  1..108
                        mol_type = protein
                        organism = synthetic construct
SEQUENCE: 143
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPAFGG GTKVEIKR               108

SEQ ID NO: 144          moltype = AA  length = 119
FEATURE                 Location/Qualifiers
REGION                  1..119
                        note = heavy chain variable region (VH) for an OX40 agonist
                         monoclonal antibody
source                  1..119
                        mol_type = protein
                        organism = synthetic construct
SEQUENCE: 144
EVQLQQSGPE LVKPGASVKM SCKASGYTFT SYVMHWVKQK PGQGLEWIGY INPYNDGTKY  60
NEKFKGKATL TSDKSSSTAY MELSSLTSED SAVYYCANYY GSSLSMDYWG QGTSVTVSS   119

SEQ ID NO: 145          moltype = AA  length = 108
FEATURE                 Location/Qualifiers
REGION                  1..108
                        note = light chain variable region (VL) for an OX40 agonist
                         monoclonal antibody
```

```
source                  1..108
                        mol_type = protein
                        organism = synthetic construct
SEQUENCE: 145
DIQMTQTTSS LSASLGDRVT ISCRASQDIS NYLNWYQQKP DGTVKLLIYY TSRLHSGVPS  60
RFSGSGSGTD YSLTISNLEQ EDIATYFCQQ GNTLPWTFGG GTKLEIKR              108

SEQ ID NO: 146          moltype = AA  length = 121
FEATURE                 Location/Qualifiers
REGION                  1..121
                        note = heavy chain variable region (VH) for an OX40 agonist
                         monoclonal antibody
source                  1..121
                        mol_type = protein
                        organism = synthetic construct
SEQUENCE: 146
EVQLQQSGPE LVKPGASVKI SCKTSGYTFK DYTMHWVKQS HGKSLEWIGG IYPNNGGSTY  60
NQNFKDKATL TVDKSSSTAY MEFRSLTSED SAVYYCARMG YHGPHLDFDV WGAGTTVTVS  120
P                                                                 121

SEQ ID NO: 147          moltype = AA  length = 108
FEATURE                 Location/Qualifiers
REGION                  1..108
                        note = light chain variable region (VL) for an OX40 agonist
                         monoclonal antibody
source                  1..108
                        mol_type = protein
                        organism = synthetic construct
SEQUENCE: 147
DIVMTQSHKF MSTSLGDRVS ITCKASQDVG AAVAWYQQKP GQSPKLLIYW ASTRHTGVPD  60
RFTGGGSGTD FTLTISNVQS EDLTDYFCQQ YINYPLTFGG GTKLEIKR              108

SEQ ID NO: 148          moltype = AA  length = 122
FEATURE                 Location/Qualifiers
REGION                  1..122
                        note = heavy chain variable region (VH) for a humanized
                         OX40 agonist monoclonal antibody
source                  1..122
                        mol_type = protein
                        organism = synthetic construct
SEQUENCE: 148
QIQLVQSGPE LKKPGETVKI SCKASGYTFT DYSMHWVKQA PGKGLKWMGW INTETGEPTY  60
ADDFKGRFAF SLETSASTAY LQINNLKNED TATYFCANPY YDYVSYYAMD YWGHGTSVTV  120
SS                                                                122

SEQ ID NO: 149          moltype = AA  length = 122
FEATURE                 Location/Qualifiers
REGION                  1..122
                        note = heavy chain variable region (VH) for a humanized
                         OX40 agonist monoclonal antibody
source                  1..122
                        mol_type = protein
                        organism = synthetic construct
SEQUENCE: 149
QVQLVQSGSE LKKPGASVKV SCKASGYTFT DYSMHWVRQA PGQGLKWMGW INTETGEPTY  60
ADDFKGRFVF SLDTSVSTAY LQISSLKAED TAVYYCANPY YDYVSYYAMD YWGQGTTVTV  120
SS                                                                122

SEQ ID NO: 150          moltype = AA  length = 107
FEATURE                 Location/Qualifiers
REGION                  1..107
                        note = light chain variable region (VL) for a humanized
                         OX40 agonist monoclonal antibody
source                  1..107
                        mol_type = protein
                        organism = synthetic construct
SEQUENCE: 150
DIVMTQSHKF MSTSVRDRVS ITCKASQDVS TAVAWYQQKP GQSPKLLIYS ASYLYTGVPD  60
RFTGSGSGTD FTFTISSVQA EDLAVYYCQQ HYSTPRTFGG GTKLEIK               107

SEQ ID NO: 151          moltype = AA  length = 107
FEATURE                 Location/Qualifiers
REGION                  1..107
                        note = light chain variable region (VL) for a humanized
                         OX40 agonist monoclonal antibody
source                  1..107
                        mol_type = protein
                        organism = synthetic construct
SEQUENCE: 151
```

```
DIVMTQSHKF MSTSVRDRVS ITCKASQDVS TAVAWYQQKP GQSPKLLIYS ASYLYTGVPD  60
RFTGSGSGTD FTFTISSVQA EDLAVYYCQQ HYSTPRTFGG GTKLEIK                107

SEQ ID NO: 152         moltype = AA  length = 120
FEATURE                Location/Qualifiers
REGION                 1..120
                       note = heavy chain variable region (VH) for a humanized
                        OX40 agonist monoclonal antibody
source                 1..120
                       mol_type = protein
                       organism = synthetic construct
SEQUENCE: 152
EVQLVESGGG LVQPGESLKL SCESNEYEFP SHDMSWVRKT PEKRLELVAA INSDGGSTYY  60
PDTMERRFII SRDNTKKTLY LQMSSLRSED TALYYCARHY DDYYAWFAYW GQGTLVTVSA  120

SEQ ID NO: 153         moltype = AA  length = 120
FEATURE                Location/Qualifiers
REGION                 1..120
                       note = heavy chain variable region (VH) for a humanized
                        OX40 agonist monoclonal antibody
source                 1..120
                       mol_type = protein
                       organism = synthetic construct
SEQUENCE: 153
EVQLVESGGG LVQPGGSLRL SCAASEYEFP SHDMSWVRQA PGKGLELVAA INSDGGSTYY  60
PDTMERRFTI SRDNAKNSLY LQMNSLRAED TAVYYCARHY DDYYAWFAYW GQGTMVTVSS  120

SEQ ID NO: 154         moltype = AA  length = 111
FEATURE                Location/Qualifiers
REGION                 1..111
                       note = light chain variable region (VL) for a humanized
                        OX40 agonist monoclonal antibody
source                 1..111
                       mol_type = protein
                       organism = synthetic construct
SEQUENCE: 154
DIVLTQSPAS LAVSLGQRAT ISCRASKSVS TSGYSYMHWY QQKPGQPPKL LIYLASNLES  60
GVPARFSGSG SGTDFTLNIH PVEEEDAATY YCQHSRELPL TFGAGTKLEL K           111

SEQ ID NO: 155         moltype = AA  length = 111
FEATURE                Location/Qualifiers
REGION                 1..111
                       note = light chain variable region (VL) for a humanized
                        OX40 agonist monoclonal antibody
source                 1..111
                       mol_type = protein
                       organism = synthetic construct
SEQUENCE: 155
EIVLTQSPAT LSLSPGERAT LSCRASKSVS TSGYSYMHWY QQKPGQAPRL LIYLASNLES  60
GVPARFSGSG SGTDFTLTIS SLEPEDFAVY YCQHSRELPL TFGGGTKVEI K           111

SEQ ID NO: 156         moltype = AA  length = 138
FEATURE                Location/Qualifiers
REGION                 1..138
                       note = heavy chain variable region (VH) for an OX40 agonist
                        monoclonal antibody
source                 1..138
                       mol_type = protein
                       organism = synthetic construct
SEQUENCE: 156
MYLGLNYVFI VFLLNGVQSE VKLEESGGGL VQPGGSMKLS CAASGFTFSD AWMDWVRQSP  60
EKGLEWVAEI RSKANNHATY YAESVNGRFT ISRDDSKSSV YLQMNSLRAE DTGIYYCTWG  120
EVFYFDYWGQ GTTLTVSS                                                138

SEQ ID NO: 157         moltype = AA  length = 126
FEATURE                Location/Qualifiers
REGION                 1..126
                       note = light chain variable region (VL) for an OX40 agonist
                        monoclonal antibody
source                 1..126
                       mol_type = protein
                       organism = synthetic construct
SEQUENCE: 157
MRPSIQFLGL LLFWLHGAQC DIQMTQSPSS LSASLGGKVT ITCKSSQDIN KYIAWYQHKP  60
GKGPRLLIHY TSTLQPGIPS RFSGSGSGRD YSFSISNLEP EDIATYYCLQ YDNLLTFGAG  120
TKLELK                                                             126

SEQ ID NO: 158         moltype = AA  length = 440
FEATURE                Location/Qualifiers
```

```
REGION                  1..440
                        note = heavy chain amino acid sequence of the PD-1
                         inhibitor nivolumab
source                  1..440
                        mol_type = protein
                        organism = synthetic construct
SEQUENCE: 158
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 159          moltype = AA  length = 214
FEATURE                 Location/Qualifiers
REGION                  1..214
                        note = light chain amino acid sequence of the PD-1
                         inhibitor nivolumab
source                  1..214
                        mol_type = protein
                        organism = synthetic construct
SEQUENCE: 159
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 160          moltype = AA  length = 113
FEATURE                 Location/Qualifiers
REGION                  1..113
                        note = heavy chain variable region (VH) amino acid sequence
                         of the PD-1 inhibitor nivolumab
source                  1..113
                        mol_type = protein
                        organism = synthetic construct
SEQUENCE: 160
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 161          moltype = AA  length = 107
FEATURE                 Location/Qualifiers
REGION                  1..107
                        note = light chain variable region (VL) amino acid sequence
                         of the PD-1 inhibitor nivolumab
source                  1..107
                        mol_type = protein
                        organism = synthetic construct
SEQUENCE: 161
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 162          moltype = AA  length = 5
FEATURE                 Location/Qualifiers
REGION                  1..5
                        note = heavy chain CDR1 amino acid sequence of the PD-1
                         inhibitor nivolumab
source                  1..5
                        mol_type = protein
                        organism = synthetic construct
SEQUENCE: 162
NSGMH                                                              5

SEQ ID NO: 163          moltype = AA  length = 17
FEATURE                 Location/Qualifiers
REGION                  1..17
                        note = heavy chain CDR2 amino acid sequence of the PD-1
                         inhibitor nivolumab
source                  1..17
                        mol_type = protein
                        organism = synthetic construct
SEQUENCE: 163
VIWYDGSKRY YADSVKG                                                 17

SEQ ID NO: 164          moltype = AA  length = 4
FEATURE                 Location/Qualifiers
REGION                  1..4
```

```
                         note = heavy chain CDR3 amino acid sequence of the PD-1
                          inhibitor nivolumab
source                   1..4
                         mol_type = protein
                         organism = synthetic construct
SEQUENCE: 164
NDDY                                                                        4

SEQ ID NO: 165           moltype = AA  length = 11
FEATURE                  Location/Qualifiers
REGION                   1..11
                         note = light chain CDR1 amino acid sequence of the PD-1
                          inhibitor nivolumab
source                   1..11
                         mol_type = protein
                         organism = synthetic construct
SEQUENCE: 165
RASQSVSSYL A                                                                11

SEQ ID NO: 166           moltype = AA  length = 7
FEATURE                  Location/Qualifiers
REGION                   1..7
                         note = light chain CDR2 amino acid sequence of the PD-1
                          inhibitor nivolumab
source                   1..7
                         mol_type = protein
                         organism = synthetic construct
SEQUENCE: 166
DASNRAT                                                                     7

SEQ ID NO: 167           moltype = AA  length = 9
FEATURE                  Location/Qualifiers
REGION                   1..9
                         note = light chain CDR3 amino acid sequence of the PD-1
                          inhibitor nivolumab
source                   1..9
                         mol_type = protein
                         organism = synthetic construct
SEQUENCE: 167
QQSSNWPRT                                                                   9

SEQ ID NO: 168           moltype = AA  length = 447
FEATURE                  Location/Qualifiers
REGION                   1..447
                         note = heavy chain amino acid sequence of the PD-1
                          inhibitor pembrolizumab
source                   1..447
                         mol_type = protein
                         organism = synthetic construct
SEQUENCE: 168
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 169           moltype = AA  length = 218
FEATURE                  Location/Qualifiers
REGION                   1..218
                         note = light chain amino acid sequence of the PD-1
                          inhibitor pembrolizumab
source                   1..218
                         mol_type = protein
                         organism = synthetic construct
SEQUENCE: 169
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 170           moltype = AA  length = 120
FEATURE                  Location/Qualifiers
REGION                   1..120
                         note = heavy chain variable region (VH) amino acid sequence
                          of the PD-1 inhibitor pembrolizumab
source                   1..120
```

```
                        mol_type = protein
                        organism = synthetic construct
SEQUENCE: 170
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 171          moltype = AA  length = 111
FEATURE                 Location/Qualifiers
REGION                  1..111
                        note = light chain variable region (VL) amino acid sequence
                         of the PD-1 inhibitor pembrolizumab
source                  1..111
                        mol_type = protein
                        organism = synthetic construct
SEQUENCE: 171
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI K           111

SEQ ID NO: 172          moltype = AA  length = 5
FEATURE                 Location/Qualifiers
REGION                  1..5
                        note = heavy chain CDR1 amino acid sequence of the PD-1
                         inhibitor pembrolizumab
source                  1..5
                        mol_type = protein
                        organism = synthetic construct
SEQUENCE: 172
NYYMY                                                              5

SEQ ID NO: 173          moltype = AA  length = 16
FEATURE                 Location/Qualifiers
REGION                  1..16
                        note = heavy chain CDR2 amino acid sequence of the PD-1
                         inhibitor pembrolizumab
source                  1..16
                        mol_type = protein
                        organism = synthetic construct
SEQUENCE: 173
GINPSNGGTN FNEKFK                                                  16

SEQ ID NO: 174          moltype = AA  length = 11
FEATURE                 Location/Qualifiers
REGION                  1..11
                        note = heavy chain CDR3 amino acid sequence of the PD-1
                         inhibitor pembrolizumab
source                  1..11
                        mol_type = protein
                        organism = synthetic construct
SEQUENCE: 174
RDYRFDMGFD Y                                                       11

SEQ ID NO: 175          moltype = AA  length = 15
FEATURE                 Location/Qualifiers
REGION                  1..15
                        note = light chain CDR1 amino acid sequence of the PD-1
                         inhibitor pembrolizumab
source                  1..15
                        mol_type = protein
                        organism = synthetic construct
SEQUENCE: 175
RASKGVSTSG YSYLH                                                   15

SEQ ID NO: 176          moltype = AA  length = 7
FEATURE                 Location/Qualifiers
REGION                  1..7
                        note = light chain CDR2 amino acid sequence of the PD-1
                         inhibitor pembrolizumab
source                  1..7
                        mol_type = protein
                        organism = synthetic construct
SEQUENCE: 176
LASYLES                                                            7

SEQ ID NO: 177          moltype = AA  length = 9
FEATURE                 Location/Qualifiers
REGION                  1..9
                        note = light chain CDR3 amino acid sequence of the PD-1
                         inhibitor pembrolizumab
source                  1..9
```

```
                         mol_type = protein
                         organism = synthetic construct
SEQUENCE: 177
QHSRDLPLT                                                           9

SEQ ID NO: 178           moltype = AA  length = 451
FEATURE                  Location/Qualifiers
REGION                   1..451
                         note = heavy chain amino acid sequence of the PD-L1
                          inhibitor durvalumab
source                   1..451
                         mol_type = protein
                         organism = synthetic construct
SEQUENCE: 178
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 179           moltype = AA  length = 265
FEATURE                  Location/Qualifiers
REGION                   1..265
                         note = light chain amino acid sequence of the PD-L1
                          inhibitor durvalumab
source                   1..265
                         mol_type = protein
                         organism = synthetic construct
SEQUENCE: 179
EVQLVESGGG LVQPGGSLRL SCAASGFTFS RYWMSWVRQA PGKGLEWVAN EIVLTQSPGT  60
LSLSPGERAT LSCRASQRVS SSYLAWYQQK PGQAPRLLIY DASSRATGIP DRFSGSGSGT  120
DFTLTISRLE PEDFAVYYCQ QYGSLPWTFG QGTKVEIKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                       265

SEQ ID NO: 180           moltype = AA  length = 121
FEATURE                  Location/Qualifiers
REGION                   1..121
                         note = heavy chain variable region (VH) amino acid sequence
                          of the PD-L1 inhibitor durvalumab
source                   1..121
                         mol_type = protein
                         organism = synthetic construct
SEQUENCE: 180
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                 121

SEQ ID NO: 181           moltype = AA  length = 108
FEATURE                  Location/Qualifiers
REGION                   1..108
                         note = light chain variable region (VL) amino acid sequence
                          of the PD-L1 inhibitor durvalumab
source                   1..108
                         mol_type = protein
                         organism = synthetic construct
SEQUENCE: 181
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 182           moltype = AA  length = 5
FEATURE                  Location/Qualifiers
REGION                   1..5
                         note = heavy chain CDR1 amino acid sequence of the PD-L1
                          inhibitor durvalumab
source                   1..5
                         mol_type = protein
                         organism = synthetic construct
SEQUENCE: 182
RYWMS                                                               5

SEQ ID NO: 183           moltype = AA  length = 17
FEATURE                  Location/Qualifiers
REGION                   1..17
                         note = heavy chain CDR2 amino acid sequence of the PD-L1
                          inhibitor durvalumab
```

```
source                  1..17
                        mol_type = protein
                        organism = synthetic construct
SEQUENCE: 183
NIKQDGSEKY YVDSVKG                                              17

SEQ ID NO: 184          moltype = AA  length = 12
FEATURE                 Location/Qualifiers
REGION                  1..12
                        note = heavy chain CDR3 amino acid sequence of the PD-L1
                         inhibitor durvalumab
source                  1..12
                        mol_type = protein
                        organism = synthetic construct
SEQUENCE: 184
EGGWFGELAF DY                                                   12

SEQ ID NO: 185          moltype = AA  length = 12
FEATURE                 Location/Qualifiers
REGION                  1..12
                        note = light chain CDR1 amino acid sequence of the PD-L1
                         inhibitor durvalumab
source                  1..12
                        mol_type = protein
                        organism = synthetic construct
SEQUENCE: 185
RASQRVSSSY LA                                                   12

SEQ ID NO: 186          moltype = AA  length = 7
FEATURE                 Location/Qualifiers
REGION                  1..7
                        note = light chain CDR2 amino acid sequence of the PD-L1
                         inhibitor durvalumab
source                  1..7
                        mol_type = protein
                        organism = synthetic construct
SEQUENCE: 186
DASSRAT                                                         7

SEQ ID NO: 187          moltype = AA  length = 9
FEATURE                 Location/Qualifiers
REGION                  1..9
                        note = light chain CDR3 amino acid sequence of the PD-L1
                         inhibitor durvalumab
source                  1..9
                        mol_type = protein
                        organism = synthetic construct
SEQUENCE: 187
QQYGSLPWT                                                       9

SEQ ID NO: 188          moltype = AA  length = 450
FEATURE                 Location/Qualifiers
REGION                  1..450
                        note = heavy chain amino acid sequence of the PD-L1
                         inhibitor avelumab
source                  1..450
                        mol_type = protein
                        organism = synthetic construct
SEQUENCE: 188
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                450

SEQ ID NO: 189          moltype = AA  length = 216
FEATURE                 Location/Qualifiers
REGION                  1..216
                        note = light chain amino acid sequence of the PD-L1
                         inhibitor avelumab
source                  1..216
                        mol_type = protein
                        organism = synthetic construct
SEQUENCE: 189
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
```

```
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 190          moltype = AA  length = 120
FEATURE                 Location/Qualifiers
REGION                  1..120
                        note = heavy chain variable region (VH) amino acid sequence
                         of the PD-L1 inhibitor avelumab
source                  1..120
                        mol_type = protein
                        organism = synthetic construct
SEQUENCE: 190
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120

SEQ ID NO: 191          moltype = AA  length = 110
FEATURE                 Location/Qualifiers
REGION                  1..110
                        note = light chain variable region (VL) amino acid sequence
                         of the PD-L1 inhibitor avelumab
source                  1..110
                        mol_type = protein
                        organism = synthetic construct
SEQUENCE: 191
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL             110

SEQ ID NO: 192          moltype = AA  length = 5
FEATURE                 Location/Qualifiers
REGION                  1..5
                        note = heavy chain CDR1 amino acid sequence of the PD-L1
                         inhibitor avelumab
source                  1..5
                        mol_type = protein
                        organism = synthetic construct
SEQUENCE: 192
SYIMM                                                              5

SEQ ID NO: 193          moltype = AA  length = 17
FEATURE                 Location/Qualifiers
REGION                  1..17
                        note = heavy chain CDR2 amino acid sequence of the PD-L1
                         inhibitor avelumab
source                  1..17
                        mol_type = protein
                        organism = synthetic construct
SEQUENCE: 193
SIYPSGGITF YADTVKG                                                 17

SEQ ID NO: 194          moltype = AA  length = 11
FEATURE                 Location/Qualifiers
REGION                  1..11
                        note = heavy chain CDR3 amino acid sequence of the PD-L1
                         inhibitor avelumab
source                  1..11
                        mol_type = protein
                        organism = synthetic construct
SEQUENCE: 194
IKLGTVTTVD Y                                                       11

SEQ ID NO: 195          moltype = AA  length = 14
FEATURE                 Location/Qualifiers
REGION                  1..14
                        note = light chain CDR1 amino acid sequence of the PD-L1
                         inhibitor avelumab
source                  1..14
                        mol_type = protein
                        organism = synthetic construct
SEQUENCE: 195
TGTSSDVGGY NYVS                                                    14

SEQ ID NO: 196          moltype = AA  length = 7
FEATURE                 Location/Qualifiers
REGION                  1..7
                        note = light chain CDR2 amino acid sequence of the PD-L1
                         inhibitor avelumab
source                  1..7
                        mol_type = protein
                        organism = synthetic construct
```

```
SEQUENCE: 196
DVSNRPS                                                     7

SEQ ID NO: 197         moltype = AA  length = 10
FEATURE                Location/Qualifiers
REGION                 1..10
                       note = light chain CDR3 amino acid sequence of the PD-L1
                        inhibitor avelumab
source                 1..10
                       mol_type = protein
                       organism = synthetic construct
SEQUENCE: 197
SSYTSSSTRV                                                  10

SEQ ID NO: 198         moltype = AA  length = 448
FEATURE                Location/Qualifiers
REGION                 1..448
                       note = heavy chain amino acid sequence of the PD-L1
                        inhibitor atezolizumab
source                 1..448
                       mol_type = protein
                       organism = synthetic construct
SEQUENCE: 198
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                  448

SEQ ID NO: 199         moltype = AA  length = 214
FEATURE                Location/Qualifiers
REGION                 1..214
                       note = light chain amino acid sequence of the PD-L1
                        inhibitor atezolizumab
source                 1..214
                       mol_type = protein
                       organism = synthetic construct
SEQUENCE: 199
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 200         moltype = AA  length = 118
FEATURE                Location/Qualifiers
REGION                 1..118
                       note = heavy chain variable region (VH) amino acid sequence
                        of the PD-L1 inhibitor atezolizumab
source                 1..118
                       mol_type = protein
                       organism = synthetic construct
SEQUENCE: 200
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 201         moltype = AA  length = 108
FEATURE                Location/Qualifiers
REGION                 1..108
                       note = light chain variable region (VL) amino acid sequence
                        of the PD-L1 inhibitor atezolizumab
source                 1..108
                       mol_type = protein
                       organism = synthetic construct
SEQUENCE: 201
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 202         moltype = AA  length = 10
FEATURE                Location/Qualifiers
REGION                 1..10
                       note = heavy chain CDR1 amino acid sequence of the PD-L1
                        inhibitor atezolizumab
source                 1..10
                       mol_type = protein
                       organism = synthetic construct
SEQUENCE: 202
```

```
GFTFSDSWIH                                                  10

SEQ ID NO: 203         moltype = AA  length = 18
FEATURE                Location/Qualifiers
REGION                 1..18
                       note = heavy chain CDR2 amino acid sequence of the PD-L1
                        inhibitor atezolizumab
source                 1..18
                       mol_type = protein
                       organism = synthetic construct
SEQUENCE: 203
AWISPYGGST YYADSVKG                                         18

SEQ ID NO: 204         moltype = AA  length = 9
FEATURE                Location/Qualifiers
REGION                 1..9
                       note = heavy chain CDR3 amino acid sequence of the PD-L1
                        inhibitor atezolizumab
source                 1..9
                       mol_type = protein
                       organism = synthetic construct
SEQUENCE: 204
RHWPGGFDY                                                   9

SEQ ID NO: 205         moltype = AA  length = 11
FEATURE                Location/Qualifiers
REGION                 1..11
                       note = light chain CDR1 amino acid sequence of the PD-L1
                        inhibitor atezolizumab
source                 1..11
                       mol_type = protein
                       organism = synthetic construct
SEQUENCE: 205
RASQDVSTAV A                                                11

SEQ ID NO: 206         moltype = AA  length = 7
FEATURE                Location/Qualifiers
REGION                 1..7
                       note = light chain CDR2 amino acid sequence of the PD-L1
                        inhibitor atezolizumab
source                 1..7
                       mol_type = protein
                       organism = synthetic construct
SEQUENCE: 206
SASFLYS                                                     7

SEQ ID NO: 207         moltype = AA  length = 9
FEATURE                Location/Qualifiers
REGION                 1..9
                       note = light chain CDR3 amino acid sequence of the PD-L1
                        inhibitor atezolizumab
source                 1..9
                       mol_type = protein
                       organism = synthetic construct
SEQUENCE: 207
QQYLYHPAT                                                   9

SEQ ID NO: 208         moltype = AA  length = 225
FEATURE                Location/Qualifiers
REGION                 1..225
                       note = heavy chain amino acid sequence of the CTLA-4
                        inhibitor ipilimumab
source                 1..225
                       mol_type = protein
                       organism = synthetic construct
SEQUENCE: 208
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTH                  225

SEQ ID NO: 209         moltype = AA  length = 215
FEATURE                Location/Qualifiers
REGION                 1..215
                       note = light chain amino acid sequence of the CTLA-4
                        inhibitor ipilimumab
source                 1..215
                       mol_type = protein
                       organism = synthetic construct
```

```
SEQUENCE: 209
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 210         moltype = AA  length = 118
FEATURE                Location/Qualifiers
REGION                 1..118
                       note = heavy chain variable region (VH) amino acid sequence
                        of the CTLA-4 inhibitor ipilimumab
source                 1..118
                       mol_type = protein
                       organism = synthetic construct
SEQUENCE: 210
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 211         moltype = AA  length = 108
FEATURE                Location/Qualifiers
REGION                 1..108
                       note = light chain variable region (VL) amino acid sequence
                        of the CTLA-4 inhibitor ipilimumab
source                 1..108
                       mol_type = protein
                       organism = synthetic construct
SEQUENCE: 211
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK               108

SEQ ID NO: 212         moltype = AA  length = 8
FEATURE                Location/Qualifiers
REGION                 1..8
                       note = heavy chain CDR1 amino acid sequence of the CTLA-4
                        inhibitor ipilimumab
source                 1..8
                       mol_type = protein
                       organism = synthetic construct
SEQUENCE: 212
GFTFSSYT                                                           8

SEQ ID NO: 213         moltype = AA  length = 10
FEATURE                Location/Qualifiers
REGION                 1..10
                       note = heavy chain CDR2 amino acid sequence of the CTLA-4
                        inhibitor ipilimumab
source                 1..10
                       mol_type = protein
                       organism = synthetic construct
SEQUENCE: 213
TFISYDGNNK                                                         10

SEQ ID NO: 214         moltype = AA  length = 11
FEATURE                Location/Qualifiers
REGION                 1..11
                       note = heavy chain CDR3 amino acid sequence of the CTLA-4
                        inhibitor ipilimumab
source                 1..11
                       mol_type = protein
                       organism = synthetic construct
SEQUENCE: 214
ARTGWLGPFD Y                                                       11

SEQ ID NO: 215         moltype = AA  length = 7
FEATURE                Location/Qualifiers
REGION                 1..7
                       note = light chain CDR1 amino acid sequence of the CTLA-4
                        inhibitor ipilimumab
source                 1..7
                       mol_type = protein
                       organism = synthetic construct
SEQUENCE: 215
QSVGSSY                                                            7

SEQ ID NO: 216         moltype =   length =
SEQUENCE: 216
000

SEQ ID NO: 217         moltype = AA  length = 9
```

```
FEATURE                 Location/Qualifiers
REGION                  1..9
                        note = light chain CDR3 amino acid sequence of the CTLA-4
                         inhibitor ipilimumab
source                  1..9
                        mol_type = protein
                        organism = synthetic construct
SEQUENCE: 217
QQYGSSPWT                                                                  9

SEQ ID NO: 218          moltype = AA  length = 451
FEATURE                 Location/Qualifiers
REGION                  1..451
                        note = heavy chain amino acid sequence of the CTLA-4
                         inhibitor tremelimumab
source                  1..451
                        mol_type = protein
                        organism = synthetic construct
SEQUENCE: 218
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCARDP RGATLYYYYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSN FGTQTYTCNV DHKPSNTKVD KTVERKCCVE CPPCPAPPVA  240
GPSVFLFPPK PKDTLMISRT PEVTCVVVDV SHEDPEVQFN WYVDGVEVHN AKTKPREEQF  300
NSTFRVVSVL TVVHQDWLNG KEYKCKVSNK GLPAPIEKTI SKTKGQPREP QVYTLPPSRE  360
EMTKNQVSLT CLVKGFYPSD IAVEWESNGQ PENNYKTTPP MLDSDGSFFL YSKLTVDKSR  420
WQQGNVFSCS VMHEALHNHY TQKSLSLSPG K                                 451

SEQ ID NO: 219          moltype = AA  length = 214
FEATURE                 Location/Qualifiers
REGION                  1..214
                        note = light chain amino acid sequence of the CTLA-4
                         inhibitor tremelimumab
source                  1..214
                        mol_type = protein
                        organism = synthetic construct
SEQUENCE: 219
DIQMTQSPSS LSASVGDRVT ITCRASQSIN SYLDWYQQKP GKAPKLLIYA ASSLQSGVPS  60
RFSGSGSGTD FTLTISSLQP EDFATYYCQQ YYSTPFTFGP GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 220          moltype = AA  length = 167
FEATURE                 Location/Qualifiers
REGION                  1..167
                        note = heavy chain variable region (VH) amino acid sequence
                         of the CTLA-4 inhibitor tremelimumab
source                  1..167
                        mol_type = protein
                        organism = synthetic construct
SEQUENCE: 220
GVVQPGRSLR LSCAASGFTF SSYGMHWVRQ APGKGLEWVA VIWYDGSNKY YADSVKGRFT  60
ISRDNSKNTL YLQMNSLRAE DTAVYYCARD PRGATLYYYY YGMDVWGQGT TVTVSSASTK  120
GPSVFPLAPC SRSTSESTAA LGCLVKDYFP EPVTVSWNSG ALTSGVH                167

SEQ ID NO: 221          moltype = AA  length = 139
FEATURE                 Location/Qualifiers
REGION                  1..139
                        note = light chain variable region (VL) amino acid sequence
                         of the CTLA-4 inhibitor tremelimumab
source                  1..139
                        mol_type = protein
                        organism = synthetic construct
SEQUENCE: 221
PSSLSASVGD RVTITCRASQ SINSYLDWYQ QKPGKAPKLL IYAASSLQSG VPSRFSGSGS  60
GTDFTLTISS LQPEDFATYY CQQYYSTPFT FGPGTKVEIK RTVAAPSVFI FPPSDEQLKS  120
GTASVVCLLN NFYPREAKV                                               139

SEQ ID NO: 222          moltype = AA  length = 10
FEATURE                 Location/Qualifiers
REGION                  1..10
                        note = heavy chain CDR1 amino acid sequence of the CTLA-4
                         inhibitor tremelimumab
source                  1..10
                        mol_type = protein
                        organism = synthetic construct
SEQUENCE: 222
GFTFSSYGMH                                                         10
```

```
SEQ ID NO: 223          moltype = AA  length = 15
FEATURE                 Location/Qualifiers
REGION                  1..15
                        note = heavy chain CDR2 amino acid sequence of the CTLA-4
                         inhibitor tremelimumab
source                  1..15
                        mol_type = protein
                        organism = synthetic construct
SEQUENCE: 223
VIWYDGSNKY YADSV                                                   15

SEQ ID NO: 224          moltype = AA  length = 16
FEATURE                 Location/Qualifiers
REGION                  1..16
                        note = heavy chain CDR3 amino acid sequence of the CTLA-4
                         inhibitor tremelimumab
source                  1..16
                        mol_type = protein
                        organism = synthetic construct
SEQUENCE: 224
DPRGATLYYY YYGMDV                                                  16

SEQ ID NO: 225          moltype = AA  length = 11
FEATURE                 Location/Qualifiers
REGION                  1..11
                        note = light chain CDR1 amino acid sequence of the CTLA-4
                         inhibitor tremelimumab
source                  1..11
                        mol_type = protein
                        organism = synthetic construct
SEQUENCE: 225
RASQSINSYL D                                                       11

SEQ ID NO: 226          moltype = AA  length = 7
FEATURE                 Location/Qualifiers
REGION                  1..7
                        note = light chain CDR2 amino acid sequence of the CTLA-4
                         inhibitor tremelimumab
source                  1..7
                        mol_type = protein
                        organism = synthetic construct
SEQUENCE: 226
AASSLQS                                                            7

SEQ ID NO: 227          moltype = AA  length = 9
FEATURE                 Location/Qualifiers
REGION                  1..9
                        note = light chain CDR3 amino acid sequence of the CTLA-4
                         inhibitor tremelimumab
source                  1..9
                        mol_type = protein
                        organism = synthetic construct
SEQUENCE: 227
QQYYSTPFT                                                          9

SEQ ID NO: 228          moltype = AA  length = 448
FEATURE                 Location/Qualifiers
REGION                  1..448
                        note = heavy chain amino acid sequence of the CTLA-4
                         inhibitor zalifrelimab
source                  1..448
                        mol_type = protein
                        organism = synthetic construct
SEQUENCE: 228
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVG LMGPFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 229          moltype = AA  length = 214
FEATURE                 Location/Qualifiers
REGION                  1..214
                        note = light chain amino acid sequence of the CTLA-4
                         inhibitor zalifrelimab
source                  1..214
```

```
                        mol_type = protein
                        organism = synthetic construct
SEQUENCE: 229
EIVLTQSPGT LSLSPGERAT LSCRASQSVS RYLGWYQQKP GQAPRLLIYG ASTRATGIPD  60
RFSGSGSGTD FTLTITRLEP EDFAVYYCQQ YGSSPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 230          moltype = AA  length = 118
FEATURE                 Location/Qualifiers
REGION                  1..118
                        note = heavy chain variable region (VH) amino acid sequence
                         of the CTLA-4 inhibitor zalifrelimab
source                  1..118
                        mol_type = protein
                        organism = synthetic construct
SEQUENCE: 230
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVG LMGPFDIWGQ GTMVTVSS    118

SEQ ID NO: 231          moltype = AA  length = 107
FEATURE                 Location/Qualifiers
REGION                  1..107
                        note = light chain variable region (VL) amino acid sequence
                         of the CTLA-4 inhibitor zalifrelimab
source                  1..107
                        mol_type = protein
                        organism = synthetic construct
SEQUENCE: 231
EIVLTQSPGT LSLSPGERAT LSCRASQSVS RYLGWYQQKP GQAPRLLIYG ASTRATGIPD  60
RFSGSGSGTD FTLTITRLEP EDFAVYYCQQ YGSSPWTFGQ GTKVEIK               107

SEQ ID NO: 232          moltype = AA  length = 8
FEATURE                 Location/Qualifiers
REGION                  1..8
                        note = heavy chain CDR1 amino acid sequence of the CTLA-4
                         inhibitor zalifrelimab
source                  1..8
                        mol_type = protein
                        organism = synthetic construct
SEQUENCE: 232
GFTFSSYS                                                          8

SEQ ID NO: 233          moltype = AA  length = 8
FEATURE                 Location/Qualifiers
REGION                  1..8
                        note = heavy chain CDR2 amino acid sequence of the CTLA-4
                         inhibitor zalifrelimab
source                  1..8
                        mol_type = protein
                        organism = synthetic construct
SEQUENCE: 233
ISSSSSYI                                                          8

SEQ ID NO: 234          moltype = AA  length = 11
FEATURE                 Location/Qualifiers
REGION                  1..11
                        note = heavy chain CDR3 amino acid sequence of the CTLA-4
                         inhibitor zalifrelimab
source                  1..11
                        mol_type = protein
                        organism = synthetic construct
SEQUENCE: 234
ARVGLMGPFD I                                                      11

SEQ ID NO: 235          moltype = AA  length = 6
FEATURE                 Location/Qualifiers
REGION                  1..6
                        note = light chain CDR1 amino acid sequence of the CTLA-4
                         inhibitor zalifrelimab
source                  1..6
                        mol_type = protein
                        organism = synthetic construct
SEQUENCE: 235
QSVSRY                                                            6

SEQ ID NO: 236          moltype =   length =
SEQUENCE: 236
000
```

```
SEQ ID NO: 237          moltype = AA  length = 9
FEATURE                 Location/Qualifiers
REGION                  1..9
                        note = light chain CDR3 amino acid sequence of the CTLA-4
                         inhibitor zalifrelimab
source                  1..9
                        mol_type = protein
                        organism = synthetic construct
SEQUENCE: 237
QQYGSSPWT                                                         9

SEQ ID NO: 238          moltype = AA  length = 453
FEATURE                 Location/Qualifiers
REGION                  1..453
                        note = bevacizumab heavy chain
source                  1..453
                        mol_type = protein
                        organism = synthetic construct
SEQUENCE: 238
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 239          moltype = AA  length = 214
FEATURE                 Location/Qualifiers
REGION                  1..214
                        note = bevacizumab light chain
source                  1..214
                        mol_type = protein
                        organism = synthetic construct
SEQUENCE: 239
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 240          moltype = AA  length = 123
FEATURE                 Location/Qualifiers
REGION                  1..123
                        note = bevacizumab variable heavy chain
source                  1..123
                        mol_type = protein
                        organism = synthetic construct
SEQUENCE: 240
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSS                                                                123

SEQ ID NO: 241          moltype = AA  length = 108
FEATURE                 Location/Qualifiers
REGION                  1..108
                        note = bevacizumab variable light chain
source                  1..108
                        mol_type = protein
                        organism = synthetic construct
SEQUENCE: 241
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKR               108

SEQ ID NO: 242          moltype = AA  length = 10
FEATURE                 Location/Qualifiers
REGION                  1..10
                        note = bevacizumab heavy chain CDR1
source                  1..10
                        mol_type = protein
                        organism = synthetic construct
SEQUENCE: 242
GYTFTNYGMN                                                         10

SEQ ID NO: 243          moltype = AA  length = 16
FEATURE                 Location/Qualifiers
REGION                  1..16
                        note = bevacizumab heavy chain CDR2
```

```
source                  1..16
                        mol_type = protein
                        organism = synthetic construct
SEQUENCE: 243
WINTYTGEPT YAADFK                                              16

SEQ ID NO: 244          moltype = AA  length = 14
FEATURE                 Location/Qualifiers
REGION                  1..14
                        note = bevacizumab heavy chain CDR3
source                  1..14
                        mol_type = protein
                        organism = synthetic construct
SEQUENCE: 244
YPHYYGSSHW YFDV                                                14

SEQ ID NO: 245          moltype = AA  length = 11
FEATURE                 Location/Qualifiers
REGION                  1..11
                        note = bevacizumab light chain CDR1
source                  1..11
                        mol_type = protein
                        organism = synthetic construct
SEQUENCE: 245
SASQDISNYL N                                                   11

SEQ ID NO: 246          moltype = AA  length = 7
FEATURE                 Location/Qualifiers
REGION                  1..7
                        note = bevacizumab light chain CDR2
source                  1..7
                        mol_type = protein
                        organism = synthetic construct
SEQUENCE: 246
FTSSLHS                                                        7

SEQ ID NO: 247          moltype = AA  length = 9
FEATURE                 Location/Qualifiers
REGION                  1..9
                        note = bevacizumab light chain CDR3
source                  1..9
                        mol_type = protein
                        organism = synthetic construct
SEQUENCE: 247
QQYSTVPWT                                                      9

SEQ ID NO: 248          moltype = AA  length = 231
FEATURE                 Location/Qualifiers
REGION                  1..231
                        note = ranibizumab heavy chain
source                  1..231
                        mol_type = protein
                        organism = synthetic construct
SEQUENCE: 248
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH L          231

SEQ ID NO: 249          moltype = AA  length = 214
FEATURE                 Location/Qualifiers
REGION                  1..214
                        note = ranibizumab light chain
source                  1..214
                        mol_type = protein
                        organism = synthetic construct
SEQUENCE: 249
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                          214

SEQ ID NO: 250          moltype = AA  length = 123
FEATURE                 Location/Qualifiers
REGION                  1..123
                        note = ranibizumab variable heavy chain
source                  1..123
                        mol_type = protein
                        organism = synthetic construct
```

```
SEQUENCE: 250
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSS                                                               123

SEQ ID NO: 251         moltype = AA  length = 108
FEATURE                Location/Qualifiers
REGION                 1..108
                       note = ranibizumab variable light chain
source                 1..108
                       mol_type = protein
                       organism = synthetic construct
SEQUENCE: 251
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKR              108

SEQ ID NO: 252         moltype = AA  length = 10
FEATURE                Location/Qualifiers
REGION                 1..10
                       note = ranibizumab heavy chain CDR1
source                 1..10
                       mol_type = protein
                       organism = synthetic construct
SEQUENCE: 252
GYDFTHYGMN                                                        10

SEQ ID NO: 253         moltype = AA  length = 17
FEATURE                Location/Qualifiers
REGION                 1..17
                       note = ranibizumab heavy chain
source                 1..17
                       mol_type = protein
                       organism = synthetic construct
SEQUENCE: 253
WINTYTGEPT YAADFKR                                                17

SEQ ID NO: 254         moltype = AA  length = 14
FEATURE                Location/Qualifiers
REGION                 1..14
                       note = ranibizumab heavy chain CDR3
source                 1..14
                       mol_type = protein
                       organism = synthetic construct
SEQUENCE: 254
YPYYYGTSHW YFDV                                                   14

SEQ ID NO: 255         moltype = AA  length = 11
FEATURE                Location/Qualifiers
REGION                 1..11
                       note = ranibizumab light chain CDR1
source                 1..11
                       mol_type = protein
                       organism = synthetic construct
SEQUENCE: 255
SASQDISNYL N                                                      11

SEQ ID NO: 256         moltype = AA  length = 7
FEATURE                Location/Qualifiers
REGION                 1..7
                       note = ranibizumab light chain CDR2
source                 1..7
                       mol_type = protein
                       organism = synthetic construct
SEQUENCE: 256
FTSSLHS                                                           7

SEQ ID NO: 257         moltype = AA  length = 9
FEATURE                Location/Qualifiers
REGION                 1..9
                       note = ranibizumab light chain CDR3
source                 1..9
                       mol_type = protein
                       organism = synthetic construct
SEQUENCE: 257
QQYSTVPWT                                                         9

SEQ ID NO: 258         moltype = AA  length = 456
FEATURE                Location/Qualifiers
REGION                 1..456
```

```
                        note = icrucumab heavy chain
source                  1..456
                        mol_type = protein
                        organism = synthetic construct
SEQUENCE: 258
QAQVVESGGG VVQSGRSLRL SCAASGFAFS SYGMHWVRQA PGKGLEWVAV IWYDGSNKYY  60
ADSVRGRFTI SRDNSENTLY LQMNSLRAED TAVYYCARDH YGSGVHHYFY YGLDVWGQGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKRVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 259          moltype = AA  length = 215
FEATURE                 Location/Qualifiers
REGION                  1..215
                        note = icrucumab light chain
source                  1..215
                        mol_type = protein
                        organism = synthetic construct
SEQUENCE: 259
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 260          moltype = AA  length = 125
FEATURE                 Location/Qualifiers
REGION                  1..125
                        note = icrucumab variable heavy chain
source                  1..125
                        mol_type = protein
                        organism = synthetic construct
SEQUENCE: 260
QAQWESGGGV VQSGRSLRLS CAASGFAFSS YGMHWVRQAP GKGLEWVAVI WYDGSNKYYA  60
DSVRGRFTIS RDNSENTLYL QMNSLRAEDT AVYYCARDHY GSGVHHYFYY GLDVWGQGTT  120
VTVSS                                                              125

SEQ ID NO: 261          moltype = AA  length = 108
FEATURE                 Location/Qualifiers
REGION                  1..108
                        note = icrucumab variable light chain
source                  1..108
                        mol_type = protein
                        organism = synthetic construct
SEQUENCE: 261
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG GGTKVEIK               108

SEQ ID NO: 262          moltype = AA  length = 7
FEATURE                 Location/Qualifiers
REGION                  1..7
                        note = icrucumab heavy chain CDR1
source                  1..7
                        mol_type = protein
                        organism = synthetic construct
SEQUENCE: 262
VVQSGRS                                                            7

SEQ ID NO: 263          moltype = AA  length = 9
FEATURE                 Location/Qualifiers
REGION                  1..9
                        note = icrucumab heavy chain CDR2
source                  1..9
                        mol_type = protein
                        organism = synthetic construct
SEQUENCE: 263
SGFAFSSYG                                                          9

SEQ ID NO: 264          moltype = AA  length = 17
FEATURE                 Location/Qualifiers
REGION                  1..17
                        note = icrucumab heavy chain CDR3
source                  1..17
                        mol_type = protein
                        organism = synthetic construct
SEQUENCE: 264
WVAVIWYDGS NKYYADS                                                 17
```

-continued

```
SEQ ID NO: 265          moltype = AA  length = 7
FEATURE                 Location/Qualifiers
REGION                  1..7
                        note = icrucumab light chain CDR1
source                  1..7
                        mol_type = protein
                        organism = synthetic construct
SEQUENCE: 265
LSPGERA                                                         7

SEQ ID NO: 266          moltype =   length =
SEQUENCE: 266
000

SEQ ID NO: 267          moltype = AA  length = 10
FEATURE                 Location/Qualifiers
REGION                  1..10
                        note = icrucumab light chain CDR3
source                  1..10
                        mol_type = protein
                        organism = synthetic construct
SEQUENCE: 267
APRLLIYGAS                                                      10
```

TREATMENT OF NSCLC PATIENTS WITH TUMOR INFILTRATING LYMPHOCYTE THERAPIES

CROSS-REFERENCE TO RELATED APPLICATIONS

This application is a continuation of U.S. application Ser. No. 18/247,877, filed Apr. 4, 2023, which is a national phase entry of PCT/US21/53841, filed Oct. 6, 2021, which claims priority to U.S. Provisional Application No. 63/088,282, filed Oct. 6, 2020; U.S. Provisional Application No. 63/127,027, filed Dec. 17, 2020; and U.S. Provisional Application No. 63/146,402, filed Feb. 5, 2021, all of which are herein incorporated by reference in their entireties.

SEQUENCE LISTING

The instant application contains a Sequence Listing, which has been submitted electronically in XML ST.26 format and is hereby incorporated by reference in its entirety. Said XML copy, created on May 23, 2024, is named 116983-5079-US Sequence Listing and is 364,771 bytes in size.

BACKGROUND OF THE INVENTION

A significant unmet need exists for new treatment options for patients with locally advanced or metastatic non-small-cell lung cancer (NSCLC); these patients comprise approximately 70% of newly diagnosed patients with NSCLC (Molina JR, Yang P, Cassivi SD, Schild SE, Adjei AA. Mayo Clin Proc. 2008; 83(5):584-94). Lung cancer is the leading cause of cancer deaths worldwide, with approximately 1.7 million deaths reported in 2015. Of the lung cancer deaths, >80% were attributed to non-small-cell lung cancer (NSCLC) (21). In 2020, there will be an estimated 228,820 new cases and 135,720 deaths attributed to lung and bronchus cancer in the United States (Siegel RL, 2015. CA Cancer J Clin. 2015; 65(1):5-29). Thus, despite the approval of checkpoint inhibitors (CPIs), which revolutionized NSCLC treatment and outcomes, there remains a significant unmet medical need in NSCLC.

Overall, in men and women, the lifetime risk of developing lung cancer regardless of smoking status is approximately 1 in 14 and 1 in 17, respectively. However, the risk of developing lung cancer is much higher in smokers vs. nonsmokers, e.g., men who smoke are 23 times more likely to develop cancer; likewise, women who smoke are 13 times more likely to develop lung cancer than those who do not (American Lung Association—Lung cancer fact sheet 2017 [American Lung Association—Lung cancer fact sheet]; available from: the World Wide Web at lung.org/lung-health-and-diseases/lung-disease-lookup/lung-cancer/resource-library/lung-cancer-fact-sheet.html).

Prior to checkpoint inhibitors, platinum doublet chemotherapy was utilized in the initial treatment of patients with incurable NSCLC (Schiller J. H. et al. 2002 *N Engl J Med* 346 (2):92-8.), and it produced an objective response rate (ORR) of 20% to 30% with limited durability. Pembrolizumab, alone or in combination with cytotoxic therapy, revolutionized the treatment, producing higher response rates that have proven more durable as well (Gandhi Leena et al. 2018 NEngl *J Med* 378 (22):2078-2092; Paz-Ares L. et al. 2018 NEngl *J Med* 379 (21):2040-2051; Viteri S. et al. 2020 Transl Lung *Cancer Res* 9 (3):828-832; Pacheco J. M. 2020 Transl Lung *Cancer Res* 9 (1):148-153; Mok T. S. K. et al. 2019 *Lancet* 393 (10183):1819-1830; Nosaki K. et al. 2019 Lung *Cancer* 135:188-195; Morgensztern D. 2019 J Thorac Dis 11 (Suppl 15):S1963-51965; Reck M. et al. 2016 NEngl *J Med* 375 (19):1823-1833). Other CPIs have demonstrated improved ORR and durability in combination with chemotherapy in the first-line setting for NSCLC (Socinski MA et al 2018 *New Engl J Med* 378:2288-301). Despite these impressive results, there are few complete responses; almost all patients either fail to respond or progress, thus necessitating subsequent therapy.

For NSCLC patients with identified driver mutations, the preferred option is treatment with targeted TKIs directed against the relevant mutation (e.g., osimertinib for epidermal growth factor receptor [EGFR] mutations, ceritinib for ALK mutations or crizotinib for ROS-1 mutations). For previously untreated patients with NSCLC whose tumors express PD-L1, the available treatment options include pembrolizumab monotherapy (commonly used only for patients with tumor proportion score (TPS) for PD-L1 expression of at least 50%) or pembrolizumab in combination with chemotherapy. For patients with NSCLC and PD-L1 expression <50%, the preferred option is the combination of pemetrexed, carboplatin or cisplatin, and pembrolizumab. Patients with TPS for PD-L1<1% and no actionable mutations have no viable treatment options and are not candidates for PD-1 or PD-L1 CPIs. The combination of platinum-based doublet chemotherapy, bevacizumab, and atezolizumab is another potential therapeutic alternative in patients with NSCLC, as is a combination of nivolumab, ipilimumab and cytotoxic therapy (Hellmann et al. 2019 *New Engl J Med* 381:2020-31).

Once a patient has disease progression on checkpoint inhibitor therapy plus chemotherapy, treatment options are limited and suffer from low efficacy, with objective response rate ~ 10% and short progression-free survival (PFS), as well as high toxicity. The most commonly used agent is docetaxol, though other single agent cytotoxics or cytotoxics combined with VEGF inhibitors are sometimes employed, but all have similar, poor, outcomes. Thus, there is an urgent need for better therapeutic options in the second line treatment following checkpoint inhibitor therapy plus chemotherapy.

Furthermore, current TIL manufacturing and treatment processes are limited by length, cost, sterility concerns, and other factors described herein such that the potential to treat patients which are refractory to anti-PD-1 and/or anit-PD-L1 and/or VEGF inhibitor treatments and as such have been severely limited. There is an urgent need to provide TIL manufacturing processes and therapies based on such processes that are appropriate for use in treating patients for whom very few or no viable treatment options remain. The present invention meets this need by providing a shortened manufacturing process for use in generating TILs which can then be employed in the treatment of non-small cell lung carcinoma (NSCLC) patients whom are refractory to anti-PD-1, anti-PD-L1, and/or VEGF inhibitor (including VEGF-A inhibitor) treatment.

BRIEF SUMMARY OF THE INVENTION

The present invention provides improved and/or shortened methods for expanding TILs and producing therapeutic populations of TILs for use in treatment of non-small cell lung carcinoma (NSCLC) patients whom are refractory to anti-PD-1 treatment.

In some embodiments, the present invention provides a method of treating non-small cell lung carcinoma (NSCLC)

by administering a population of tumor infiltrating lymphocytes (TILs) to a subject or patient in need thereof, wherein the subject or patient has at least one of.

i. a predetermined tumor proportion score (TPS) of PD-L1 of <1%,
ii. a TPS score of PD-L1 of 1%-49%, or
iii. a predetermined absence of one or more driver mutations.

In some embodiments, the present invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of PD-L1 of <1%,
ii. aTPS score ofPD-L1 of 1%-49%, or
iii. a predetermined absence of one or more driver mutations;

wherein the method comprises:

(a) obtaining and/or receiving a first population of TILs from a tumor resected from the subject or patient by processing a tumor sample obtained from the subject into multiple tumor fragments;
(b) adding the first population of TILs into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (b) to step (c) occurs without opening the system;
(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system;
(g) cryopreserving the infusion bag comprising the harvested TIL population from step (f) using a cryopreservation process; and
(h) administering a therapeutically effective dosage of the third population of TILs from the infusion bag in step (g) to the subject or patient.

In some embodiments, the present invention provides a method of treating non-small cell lung carcinoma (NSCLC), wherein the NSCLC is refractory or resistant to treatment with an anti-PD-1 and/or anti-PD-L1 antibody, by administering a population of tumor infiltrating lymphocytes (TILs) to a subject or patient in need thereof, wherein the subject or patient has at least one of:

i. a predetermined tumor proportion score (TPS) of PD-L1 of <1%,
ii. a TPS score of PD-L1 of 1%-49%, or
iii. a predetermined absence of one or more driver mutations;

wherein the method comprises:

(a) obtaining a first population of TILs from a tumor resected from a subject by processing a tumor sample obtained from the subject into multiple tumor fragments;
(b) adding the tumor fragments into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;
(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;
(e) harvesting the third population of TILs obtained from step (d), wherein the transition from step (d) to step (e) occurs without opening the system;
(f) transferring the harvested third TIL population from step (e) to an infusion bag, wherein the transfer from step (e) to (f) occurs without opening the system;
(g) cryopreserving the infusion bag comprising the harvested TIL population from step (f) using a cryopreservation process; and
(h) administering a therapeutically effective dosage of the third population of TILs from the infusion bag in step (g) to the subject.

In some embodiments, the present invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of PD-L1 of <1%,
ii. aTPS score ofPD-L1 of 1%-49%, or
iii. a predetermined absence of one or more driver mutations;

wherein the method comprises:

(a) obtaining and/or receiving a first population of TILs from surgical resection, needle biopsy, core biopsy, small biopsy, or other means for obtaining a sample that contains a mixture of tumor and TIL cells from a NSCLC tumor in the subject or patient,
(b) adding the first population of TILs into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the third population of TILs obtained from step (d), wherein the transition from step (d) to step (e) occurs without opening the system;

(f) transferring the harvested third TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject or patient.

In some embodiments, the present invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of PD-L1 of <1%, ii. aTPS score ofPD-L1 of 1%-49%, or iii. a predetermined absence of one or more driver mutations;

wherein the method comprises:

(a) resecting a NSCLC tumor from the subject or patient, the tumor comprising a first population of TILs, optionally from surgical resection, needle biopsy, core biopsy, small biopsy, or other means for obtaining a sample that contains a mixture of tumor and TIL cells from a NSCLC tumor;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the third population of TILs obtained from step (d), wherein the transition from step (d) to step (e) occurs without opening the system;

(f) transferring the harvested third TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject.

In some embodiments, the second population of TILs is at least 50-fold greater in number than the first population of TILs.

In some embodiments, the present invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of PD-L1 of <1%, ii. aTPS score ofPD-L1 of 1%-49%, or iii. a predetermined absence of one or more driver mutations;

wherein the method comprises:

(a) obtaining and/or receiving a first population of TILs from surgical resection, needle biopsy, core biopsy, small biopsy, or other means for obtaining a sample that contains a mixture of tumor and TIL cells from the subject or patient;

(c) contacting the first population of TILs with a first cell culture medium;

(d) performing an initial expansion (or priming first expansion) of the first population of TILs in the first cell culture medium to obtain a second population of TILs, wherein the second population of TILs is at least 5-fold greater in number than the first population of TILs, wherein the first cell culture medium comprises IL-2, optionally, where the priming first expansion occurs for a period of 1 to 8 days;

(e) performing a rapid expansion of the second population of TILs in a second cell culture medium to obtain a third population of TILs, wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less, optionally the rapid expansion can proceed for 1 day, 2 days, 3 days, 4, days, 5 days, 6 days, 7 days, 8 days, 9 days or 10 days after initiation of the rapid expansion;

(f) harvesting the third population of TILs; and (g) administering a therapeutically effective portion of the third population of TILs to the subject or patient with the NSCLC.

In some embodiments, the present invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of PD-L1 of <1%, ii. aTPS score ofPD-L1 of 1%-49%, or iii. a predetermined absence of one or more driver mutations;

wherein the method comprises:

(a) resecting a NSCLC tumor from the subject or patient, the tumor comprising a first population of TILs, optionally from surgical resection, needle biopsy, core biopsy, small biopsy, or other means for obtaining a sample that contains a mixture of tumor and TIL cells from a NSCLC tumor;

(b) fragmenting the tumor into tumor fragments;

(c) contacting the tumor fragments with a first cell culture medium;

(d) performing an initial expansion (or priming first expansion) of the first population of TILs in the first cell culture medium to obtain a second population of TILs, wherein the second population of TILs is at least 5-fold greater in number than the first population of TILs, wherein the first cell culture medium comprises IL-2, optionally, where the priming first expansion occurs for a period of 1 to 8 days;

(e) performing a rapid expansion of the second population of TILs in a second cell culture medium to obtain a third population of TILs, wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less, optionally the rapid expansion can proceed for 1 day, 2 days, 3 days, 4, days, 5 days, 6 days, 7 days, 8 days, 9 days or 10 days after initiation of the rapid expansion;

(f) harvesting the third population of TILs; and (g) administering a therapeutically effective portion of the third population of TILs to the subject or patient with the NSCLC.

A method of treating non-small cell lung carcinoma (NSCLC), wherein the NSCLC is refractory or resistant to treatment with an anti-PD-1 and/or anti-PD-L1 antibody, by administering a population of tumor infiltrating lymphocytes (TILs) to a subject or patient in need thereof, wherein the subject or patient has at least one of:

i. a predetermined tumor proportion score (TPS) of PD-L1 of <1%, ii. aTPS score ofPD-L1 of 1%-49%, or iii. a predetermined absence of one or more driver mutations;

wherein the method comprises:

(a) obtaining and/or receiving a first population of TILs from surgical resection, needle biopsy, core biopsy, small biopsy, or other means for obtaining a sample that contains a mixture of tumor and TIL cells from the subject or patient;

(c) contacting the first population of TILs with a first cell culture medium;

(d) performing an initial expansion (or priming first expansion) of the first population of TILs in the first cell culture medium to obtain a second population of TILs, wherein the second population of TILs is at least 5-fold greater in number than the first population of TILs, wherein the first cell culture medium comprises IL-2, optionally, where the priming first expansion occurs for a period of 1 to 8 days;

(e) performing a rapid expansion of the second population of TILs in a second cell culture medium to obtain a third population of TILs; wherein the second cell culture medium comprises IL-2, OKT-3 (anti-CD3 antibody), and optionally irradiated allogeneic peripheral blood mononuclear cells (PBMCs); and wherein the rapid expansion is performed over a period of 14 days or less, optionally the rapid expansion can proceed for 1 day, 2 days, 3 days, 4, days, 5 days, 6 days, 7 days, 8 days, 9 days or 10 days after initiation of the rapid expansion;

(f) harvesting the third population of TILs; and (g) administering a therapeutically effective portion of the third population of TILs to the subject or patient with the NSCLC.

In some embodiments, the third population of TILs is at least 50-fold greater in number than the second population of TILs after 7-8 days from the start of the rapid expansion.

In some embodiments, the patient or subject has a TPS of PD-L1 of <1%.

In some embodiments, the patient or subject has a TPS of PD-L1 of 1%-49%.

In some embodiments, the patient or subject has a NSCLC that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNAT1 inhibitor.

In some embodiments, the patient or subject has a predetermined absence of one or more driver mutations.

In some embodiments, the patient or subject has a TPS of PD-L1 of <1% and has a predetermined absence of one or more driver mutations.

In some embodiments, the one or more driver is selected from the group consisting of an EGFR mutation, an EGFR insertion, EGFR exon20, a KRAS mutation, a BRAF-mutation, a BRAF V600 mutation, an ALK-mutation, a c-ROS-mutation (ROS1-mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation.

In some embodiments, the patient or subject has a TPS of <1% and has a NSCLC that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNAT1 inhibitor.

In some embodiments, the NSCLC has low or no expression of PD-L1.

In some embodiments, the NSCLC is refractory or resistant to treatment with a chemotherapeutic agent.

In some embodiments, the NSCLC is refractory or resistant to treatment with a VEGF-A inhibitor.

In some embodiments, the NSCLC has been treated with a chemotherapeutic agent but is not being currently treated with a chemotherapeutic agent.

In some embodiments, the NSCLC has been treated with a chemotherapeutic agent but is not being currently treated with a chemotherapeutic agent and has a TPS of <1%.

In some embodiments, the NSCLC has been treated with a VEGF-A inhibitor but is not being currently treated with a VEGF-A inhibitor.

In some embodiments, the NSCLC has been treated with a VEGF-A inhibitor but is not being currently treated with a VEGF-A inhibitor and has a TPS of <1%.

In some embodiments, the NSCLC has been treated with a chemotherapeutic agent and/or a VEGF-A inhibitor, but is not being currently treated with a chemotherapeutic agent and/or a VEGF-A inhibitor.

In some embodiments, the NSCLC has been treated with a chemotherapeutic agent and/or a VEGF-A inhibitor but is not being currently treated with a chemotherapeutic agent and/or a VEGF-A inhibitor and has a TPS of <1%.

In some embodiments, the NSCLC has not been previously treated with an anti-PD-1 and/or anti-PD-L1 antibody.

In some embodiments, the NSCLC has not been previously treated with an anti-PD-1 and/or anti-PD-L1 antibody and has been previously treated a chemotherapeutic agent and/or a VEGF-A inhibitor.

In some embodiments, the NSCLC has not been previously treated with an anti-PD-1 and/or anti-PD-L1 antibody and has been previously treated a chemotherapeutic agent and/or a VEGF-A inhibitor but is not being currently treated with a chemotherapeutic agent and/or a VEGF-A inhibitor.

In some embodiments, the NSCLC has not been previously treated with an anti-PD-1 and/or anti-PD-L1 antibody and has been previously treated a VEGF-A inhibitor but is not being currently treated with a VEGF-A inhibitor.

In some embodiments, the NSCLC has not been previously treated with an anti-PD-1 and/or anti-PD-L1 antibody and has been previously treated a chemotherapeutic agent and/or a VEGF-A inhibitor but is not being currently treated with a chemotherapeutic agent and/or a VEGF-A inhibitor.

In some embodiments, the NSCLC has not been previously treated with an anti-PD-1 and/or anti-PD-L1 antibody and has low or no expression of PD-L1.

In some embodiments, the NSCLC has not been previously treated with an anti-PD-1 and/or anti-PD-L1 antibody and has been previously treated a chemotherapeutic agent and/or a VEGF-A inhibitor but is not being currently treated with a chemotherapeutic agent and/or a VEGF-A inhibitor and has a TPS of <1%.

In some embodiments, the NSCLC has been previously treated with an anti-PD-1 and/or anti-PD-L1 and/or anti-PD-L2 antibody.

In some embodiments, the NSCLC has been previously treated with an anti-PD-1 and/or anti-PD-L1 antibody and has been previously treated a chemotherapeutic agent and/or a VEGF-A inhibitor.

In some embodiments, the NSCLC is refractory or resistant to treatment with an anti-PD-1 and/or anti-PD-L1 antibody.

In some embodiments, the NSCLC has been previously treated with an anti-PD-1 and/or anti-PD-L1 antibody and the tumor proportion score was determined prior to the anti-PD-1 and/or anti-PD-L1 antibody treatment.

In some embodiments, the NSCLC has been previously treated with an anti-PD-L1 antibody and the tumor proportion score was determined prior to the anti-PD-L1 antibody treatment, or the NSCLC has been previously treated with an anti-PD-1 antibody and the tumor proportion score was determined prior to the anti-PD-1 antibody treatment.

In some embodiments, the NSCLC has been treated with a chemotherapeutic agent and/or a VEGF-A inhibitor.

In some embodiments, the NSCLC has not been previously treated with an anti-PD-1 and/or anti-PD-L1 antibody and has bulky disease at baseline.

In some embodiments, the NSCLC has been previously treated with an anti-PD-1 and/or anti-PD-L1 antibody and has bulky disease at baseline.

In some embodiments, the NSCLC has been treated with a chemotherapeutic agent and has bulky disease at baseline.

In some embodiments, the NSCLC has been treated with a chemotherapeutic agent and/or VEGF-A inhibitor but is not being currently treated with a chemotherapeutic agent and/or VEGF-A inhibitor and has bulky disease at baseline.

In some embodiments, bulky disease is indicated where the maximal tumor diameter is greater than 7 cm measured in either the transverse or coronal plane or swollen lymph nodes with a short-axis diameter of 20 mm or greater.

In some embodiments, the NSCLC is refractory or resistant to at least two prior systemic treatment courses, not including neo-adjuvant or adjuvant therapies.

In some embodiments, the NSCLC is refractory or resistant to an anti-PD-1 or an anti-PD-L1 antibody selected from the group consisting of nivolumab, pembrolizumab, JS001, TSR-042, pidilizumab, BGB-A317, SHR-1210, REGN2810, MDX-1106, PDR001, anti-PD-1 from clone: RMP1-14, anti-PD-1 antibodies disclosed in U.S. Pat. No. 8,008,449, durvalumab, atezolizumab, avelumab, and fragments, derivatives, variants, as well as biosimilars thereof.

In some embodiments, the NSCLC is refractory or resistant to pembrolizumab or a biosimilar thereof.

In some embodiments, the NSCLC is refractory or resistant to nivolumab or a biosimilar thereof.

In some embodiments, the NSCLC is refractory or resistant to an anti-CTLA-4 antibody.

In some embodiments, the NSCLC is refractory or resistant to an anti-CTLA-4 antibody and pembrolizumab or a biosimilar thereof.

In some embodiments, the NSCLC is refractory or resistant to an anti-CTLA-4 antibody, and nivolumab or a biosimilar thereof.

In some embodiments, the anti-CTLA-4 antibody is ipilimumab or a biosimilar thereof.

In some embodiments, the NSCLC is refractory or resistant to durvalumab or a biosimilar thereof.

In some embodiments, the NSCLC is refractory or resistant to atezolizumab or a biosimilar thereof.

In some embodiments, the NSCLC is refractory or resistant to avelumab or a biosimilar thereof.

In some embodiments, the chemotherapeutic agent is a platinum doublet chemotherapeutic agent(s).

In some embodiments, the platinum doublet chemotherapeutic agent therapy comprises:

i) a first chemotherapeutic agent selected from the group consisting of cisplatin and carboplatin, ii) and a second chemotherapeutic agent selected from the group consisting of vinorelbine, gemcitabine and a taxane (including for example, paclitaxel, docetaxel or nab-paclitaxel).

In some embodiments, the chemotherapeutic agent, including the first and/or second chemotherapeutic agent, is in combination with pemetrexed.

In some embodiments, the NSCLC is refractory or resistant to a combination therapy comprising carboplatin, paclitaxel, pemetrexed, and cisplatin.

In some embodiments, the NSCLC is refractory or resistant to a combination therapy comprising carboplatin, paclitaxel, pemetrexed, cisplatin, nivolumab, and ipilimumab.

In some embodiments, the NSCLC is refractory or resistant to a VEGF-A inhibitor.

In some embodiments, the NSCLC is refractory or resistant to a VEGF-A inhibitor selected from the group consisting of bevacizumab, ranibizumab, and icrucumab.

In some embodiments, the NSCLC is refractory or resistant to bevacizumab.

In some embodiments, the NSCLC has been analyzed for the absence or presence of one or more driver mutations.

In some embodiments, one or more driver mutations are not present.

In some embodiments, the NSCLC treatment is independent of the presence or absence of one or more driver mutations.

In some embodiments, the one or more driver mutations is selected from the group consisting of an EGFR mutation, an EGFR insertion, a KRAS mutation, a BRAF-mutation, an ALK-mutation, a c-ROS-mutation a c-ROS-mutation, EML4-ALK, and MET mutation.

In some embodiments, the EGFR mutation results in tumor transformation from NSCLC to small cell lung cancer (SCLC).

In some embodiments, the NSCLC treatment is independent of the presence or absence of high-tumor mutational burden (high-TMB) and/or microsatellite instability-high (MSI-high) status.

In some embodiments, the NSCLC exhibits high-TMB and/or MSI-high status.

In some embodiments, the IL-2 is present at an initial concentration of between 1000 IU/mL and 6000 IU/mL in the first cell culture medium, when present.

In some embodiments, the IL-2 is present at an initial concentration of between 1000 IU/mL and 6000 IU/mL and the OKT-3 antibody is present at an initial concentration of about 30 ng/mL in the second cell culture medium, when present.

In some embodiments, the initial expansion, when present, is performed using a gas permeable container.

In some embodiments, the rapid expansion, when present, is performed using a gas permeable container.

In some embodiments, the first cell culture medium, when present, further comprises a cytokine selected from the group consisting of IL-4, IL-7, IL-15, IL-21, and combinations thereof.

In some embodiments, the second cell culture medium, when present, further comprises a cytokine selected from the group consisting of IL-4, IL-7, IL-15, IL-21, and combinations thereof.

In some embodiments, the method further comprises the step of treating the patient with a non-myeloablative lymphodepletion regimen prior to administering the third population of TILs to the patient.

In some embodiments, the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In some embodiments, the non-myeloablative lymphodepletion regimen comprises the steps of administration of cyclophosphamide at a dose of 60 $mg/m^2$/day and fludarabine at a dose of 25 $mg/m^2$/day for two days followed by administration of fludarabine at a dose of 25 $mg/m^2$/day for three days.

In some embodiments, the cyclophosphamide is administered with mesna.

In some embodiments, the method further comprises the step of treating the patient with an IL-2 regimen starting on the day after administration of the third population of TILs to the patient.

In some embodiments, the method further comprises the step of treating the patient with an IL-2 regimen starting on the same day as administration of the third population of TILs to the patient.

In some embodiments, the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In some embodiments, a therapeutically effective population of TILs is administered and comprises from about $2.3\times10^{10}$ to about $13.7\times10^{10}$ TILs.

In some embodiments, the initial expansion is performed over a period of 21 days or less.

In some embodiments, the initial expansion is performed over a period of 7 days or less.

In some embodiments, the rapid expansion is performed over a period of 7 days or less.

In some embodiments, the first expansion in step (c) and the second expansion in step (d) are each individually performed within a period of 11 days.

In some embodiments, the steps (a) through (f) are performed in about 10 days to about 24 days.

In some embodiments, the steps (a) through (f) are performed in about 10 days to about 22 days.

BRIEF DESCRIPTION OF THE DRAWINGS

FIG. 1: Exemplary Gen 2 (Process 2A) type chart providing an overview of Steps A through F.

FIG. 5: Comparison table of Steps A through F from exemplary embodiments of process 1C and Gen 2.

FIG. 6: Detailed comparison of an embodiment of process 1C and an embodiment of Gen 2.

FIG. 8A-8D: A) Shows a comparison between the 2A process (approximately 22-day process) and an embodiment of the Gen 3 process for TIL manufacturing (approximately 14-days to 16-days process). B) Exemplary Process Gen 3 chart providing an overview of Steps A through F (approximately 14-days to 16-days process). C) Chart providing three exemplary Gen 3 processes with an overview of Steps A through F (approximately 14-days to 16-days process) for each of the three process variations. D) Exemplary Modified Gen 2-like process providing an overview of Steps A through F (approximately 22-days process).

FIG. 11: Table describing various features of embodiments of the Gen 2, Gen 2.1 and Gen 3.0 process.

FIG. 12: Overview of the media conditions for an embodiment of the Gen 3 process, referred to as Gen 3.1.

FIG. 13: Table describing various features of embodiments of the Gen 2, Gen 2.1 and Gen 3.0 process.

FIG. 14: Table comparing various features of embodiments of the Gen 2 and Gen 3.0 processes.

FIG. 15: Table providing media uses in the various embodiments of the described expansion processes.

FIG. 20: Provides a process overview for an exemplary embodiment of the Gen 3.1 process (a 16 day process).

FIG. 23A-23B: Comparison table for exemplary Gen 2 and exemplary Gen 3 processes.

FIG. 28: Comparison of Gen 2, Gen 2.1 and an embodiment of the Gen 3 process (a 16 day process).

FIG. 29: Comparison of Gen 2, Gen 2.1 and an embodiment of the Gen 3 process (a 16 day process).

FIG. 30: Gen 3 embodiment components.

FIG. 32: Shown are the components of an exemplary embodiment of the Gen 3 process (a 16-17 day process).

FIG. 33: Acceptance criteria table.

FIG. 37: Chart providing infomraiton regarding various FDA approved PD-L1 assays.

BRIEF DESCRIPTION OF THE SEQUENCE LISTING

Figure 2A:
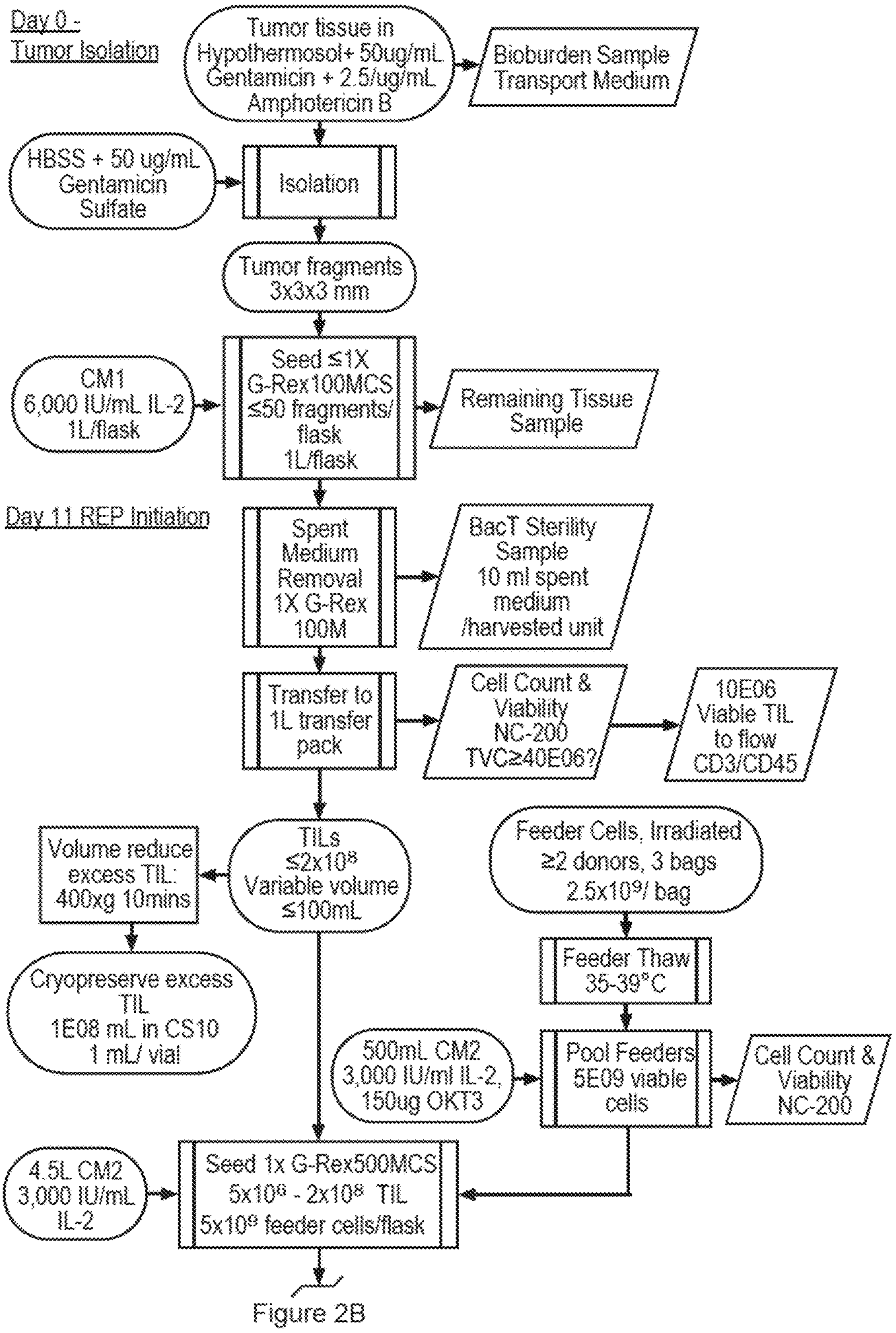
FIGS. 2A-2C: Exemplary process flow chart of Gen 2 (Process 2A) type process.

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is an IL-2 form.

SEQ ID NO:6 is the amino acid sequence of nemvaleukin alfa.

SEQ ID NO:7 is an IL-2 form.

SEQ ID NO:8 is a mucin domain polypeptide.

SEQ ID NO:9 is the amino acid sequence of a recombinant human IL-4 protein.

SEQ ID NO: 10 is the amino acid sequence of a recombinant human IL-7 protein.

SEQ ID NO: Iis the amino acid sequence of a recombinant human IL-15 protein.

SEQ ID NO: 12 is the amino acid sequence of a recombinant human IL-21 protein.

SEQ ID NO: 13 is an IL-2 sequence.

SEQ ID NO: 14 is an IL-2 mutein sequence.

SEQ ID NO:15 is an IL-2 mutein sequence.

SEQ ID NO:16 is the HCDR1_IL-2 for IgG.IL2R67A.H1.

SEQ ID NO: 17 is the HCDR2 for IgG.IL2R67A.H1.

SEQ ID NO: 18 is the HCDR3 for IgG.IL2R67A.H1.

SEQ ID NO: 19 is the HCDR1_IL-2 kabat for IgG.IL2R67A.H1.

SEQ ID NO:20 is the HCDR2 kabat for IgG.IL2R67A.H1.

SEQ ID NO:21 is the HCDR3 kabat for IgG.IL2R67A.H1.

SEQ ID NO:22 is the HCDR1_IL-2 clothia for IgG.IL2R67A.H1

SEQ ID NO:23 is the HCDR2 clothia for IgG.IL2R67A.H1.

SEQ ID NO:24 is the HCDR3 clothia for IgG.IL2R67A.H1.

SEQ ID NO:25 is the HCDR1_IL-2 IMGT for IgG.IL2R67A.H1.

SEQ ID NO:26 is the HCDR2 IMGT for IgG.IL2R67A.H1.

SEQ ID NO:27 is the HCDR3 IMGT for IgG.IL2R67A.H1.

SEQ ID NO:28 is the VH chain for IgG.IL2R67A.H1.

SEQ ID NO:29 is the heavy chain for IgG.IL2R67A.H1.

SEQ ID NO: 30 is the LCDR1 kabat for IgG.IL2R67A.H1.

SEQ ID NO:31 is the LCDR2 kabat for IgG.IL2R67A.H1.

SEQ ID NO: 32 is the LCDR3 kabat for IgG.IL2R67A.H1.

SEQ ID NO:33 is the LCDR1 chothia for IgG.IL2R67A.H1.

SEQ ID NO:34 is the LCDR2 chothia for IgG.IL2R67A.H1.

SEQ ID NO:35 is the LCDR3 chothia for IgG.IL2R67A.H1.

SEQ ID NO:36 is a VL chain.

SEQ ID NO:37 is a light chain.

SEQ ID NO:38 is a light chain.

SEQ ID NO:39 is a light chain.

SEQ ID NO:40 is the amino acid sequence of human 4-1BB.

SEQ ID NO:41 is the amino acid sequence of murine 4-1BB.

SEQ ID NO:42 is the heavy chain for the 4-1BB agonist monoclonal antibody utomilumab (PF-05082566).

SEQ ID NO:43 is the light chain for the 4-1BB agonist monoclonal antibody utomilumab (PF-05082566).

SEQ ID NO:44 is the heavy chain variable region ($V_H$) for the 4-1BB agonist monoclonal antibody utomilumab (PF-05082566).

SEQ ID NO:45 is the light chain variable region ($V_L$) for the 4-1BB agonist monoclonal antibody utomilumab (PF-05082566).

SEQ ID NO:46 is the heavy chain CDR1 for the 4-1BB agonist monoclonal antibody utomilumab (PF-05082566).

SEQ ID NO:47 is the heavy chain CDR2 for the 4-1BB agonist monoclonal antibody utomilumab (PF-05082566).

SEQ ID NO:48 is the heavy chain CDR3 for the 4-1BB agonist monoclonal antibody utomilumab (PF-05082566).

SEQ ID NO:49 is the light chain CDR1 for the 4-1BB agonist monoclonal antibody utomilumab (PF-05082566).

SEQ ID NO:50 is the light chain CDR2 for the 4-1BB agonist monoclonal antibody utomilumab (PF-05082566).

SEQ ID NO:51 is the light chain CDR3 for the 4-1BB agonist monoclonal antibody utomilumab (PF-05082566).

SEQ ID NO:52 is the heavy chain for the 4-1BB agonist monoclonal antibody urelumab (BMS-663513).

SEQ ID NO:53 is the light chain for the 4-1BB agonist monoclonal antibody urelumab (BMS-663513).

SEQ ID NO:54 is the heavy chain variable region ($V_H$) for the 4-1BB agonist monoclonal antibody urelumab (BMS-663513).

SEQ ID NO:55 is the light chain variable region ($V_L$) for the 4-1BB agonist monoclonal antibody urelumab (BMS-663513).

SEQ ID NO:56 is the heavy chain CDR1 for the 4-1BB agonist monoclonal antibody urelumab (BMS-663513).

SEQ ID NO:57 is the heavy chain CDR2 for the 4-1BB agonist monoclonal antibody urelumab (BMS-663513).

SEQ ID NO:58 is the heavy chain CDR3 for the 4-1BB agonist monoclonal antibody urelumab (BMS-663513).

SEQ ID NO:59 is the light chain CDR1 for the 4-1BB agonist monoclonal antibody urelumab (BMS-663513).

SEQ ID NO:60 is the light chain CDR2 for the 4-1BB agonist monoclonal antibody urelumab (BMS-663513).

SEQ ID NO:61 is the light chain CDR3 for the 4-1BB agonist monoclonal antibody urelumab (BMS-663513).

SEQ ID NO:62 is an Fc domain for a TNFRSF agonist fusion protein.

SEQ ID NO:63 is a linker for a TNFRSF agonist fusion protein.

SEQ ID NO: 64 is a linker for a TNFRSF agonist fusion protein.

SEQ ID NO: 65 is a linker for a TNFRSF agonist fusion protein.

SEQ ID NO: 66 is a linker for a TNFRSF agonist fusion protein.

SEQ ID NO: 67 is a linker for a TNFRSF agonist fusion protein.

SEQ ID NO: 68 is a linker for a TNFRSF agonist fusion protein.

SEQ ID NO: 69 is a linker for a TNFRSF agonist fusion protein.

SEQ ID NO: 70 is a linker for a TNFRSF agonist fusion protein.

SEQ ID NO:71 is a linker for a TNFRSF agonist fusion protein.

SEQ ID NO: 72 is a linker for a TNFRSF agonist fusion protein.

SEQ ID NO:73 is an Fc domain for a TNFRSF agonist fusion protein.

SEQ ID NO:74 is a linker for a TNFRSF agonist fusion protein.

SEQ ID NO: 75 is a linker for a TNFRSF agonist fusion protein.

SEQ ID NO: 76 is a linker for a TNFRSF agonist fusion protein.

SEQ ID NO:77 is a 4-1BB ligand (4-1BBL) amino acid sequence.

SEQ ID NO:78 is a soluble portion of 4-1BBL polypeptide.

SEQ ID NO:79 is a heavy chain variable region ($V_H$) for the 4-1BB agonist antibody 4B4-1-1 version 1.

SEQ ID NO:80 is a light chain variable region ($V_L$) for the 4-1BB agonist antibody 4B4-1-1 version 1.

SEQ ID NO:81 is a heavy chain variable region ($V_H$) for the 4-1BB agonist antibody 4B4-1-1 version 2.

SEQ ID NO:82 is a light chain variable region ($V_L$) for the 4-1BB agonist antibody 4B4-1-1 version 2.

SEQ ID NO:83 is a heavy chain variable region ($V_H$) for the 4-1BB agonist antibody H39E3-2.

SEQ ID NO:84 is a light chain variable region ($V_L$) for the 4-1BB agonist antibody H39E3-2.

SEQ ID NO:85 is the amino acid sequence of human OX40.

SEQ ID NO: 86 is the amino acid sequence of murine OX40.

SEQ ID NO:87 is the heavy chain for the OX40 agonist monoclonal antibody tavolixizumab (MEDI-0562).

SEQ ID NO:88 is the light chain for the OX40 agonist monoclonal antibody tavolixizumab (MEDI-0562).

SEQ ID NO:89 is the heavy chain variable region ($V_H$) for the OX40 agonist monoclonal antibody tavolixizumab (MEDI-0562).

SEQ ID NO:90 is the light chain variable region ($V_L$) for the OX40 agonist monoclonal antibody tavolixizumab (MEDI-0562).

SEQ ID NO:91 is the heavy chain CDR1 for the OX40 agonist monoclonal antibody tavolixizumab (MEDI-0562).

SEQ ID NO:92 is the heavy chain CDR2 for the OX40 agonist monoclonal antibody tavolixizumab (MEDI-0562).

SEQ ID NO:93 is the heavy chain CDR3 for the OX40 agonist monoclonal antibody tavolixizumab (MEDI-0562).

SEQ ID NO:94 is the light chain CDR1 for the OX40 agonist monoclonal antibody tavolixizumab (MEDI-0562).

SEQ ID NO:95 is the light chain CDR2 for the OX40 agonist monoclonal antibody tavolixizumab (MEDI-0562).

SEQ ID NO:96 is the light chain CDR3 for the OX40 agonist monoclonal antibody tavolixizumab (MEDI-0562).

SEQ ID NO:97 is the heavy chain for the OX40 agonist monoclonal antibody 11D4.

SEQ ID NO:98 is the light chain for the OX40 agonist monoclonal antibody 11D4.

SEQ ID NO:99 is the heavy chain variable region ($V_H$) for the OX40 agonist monoclonal antibody 11D4.

SEQ ID NO:100 is the light chain variable region ($V_L$) for the OX40 agonist monoclonal antibody 11D4.

SEQ ID NO:101 is the heavy chain CDR1 for the OX40 agonist monoclonal antibody 11D4.

SEQ ID NO:102 is the heavy chain CDR2 for the OX40 agonist monoclonal antibody 11D4.

SEQ ID NO: 103 is the heavy chain CDR3 for the OX40 agonist monoclonal antibody 11D4.

SEQ ID NO:104 is the light chain CDR1 for the OX40 agonist monoclonal antibody 11D4.

SEQ ID NO:105 is the light chain CDR2 for the OX40 agonist monoclonal antibody 11D4.

SEQ ID NO: 106 is the light chain CDR3 for the OX40 agonist monoclonal antibody 11D4.

SEQ ID NO: 107 is the heavy chain for the OX40 agonist monoclonal antibody 18D8.

SEQ ID NO: 108 is the light chain for the OX40 agonist monoclonal antibody 18D8.

SEQ ID NO:109 is the heavy chain variable region ($V_H$) for the OX40 agonist monoclonal antibody 18D8.

SEQ ID NO:110 is the light chain variable region ($V_L$) for the OX40 agonist monoclonal antibody 18D8.

SEQ ID NO:111 is the heavy chain CDR1 for the OX40 agonist monoclonal antibody 18D8.

SEQ ID NO:112 is the heavy chain CDR2 for the OX40 agonist monoclonal antibody 18D8.

SEQ ID NO:113 is the heavy chain CDR3 for the OX40 agonist monoclonal antibody 18D8.

SEQ ID NO:114 is the light chain CDR1 for the OX40 agonist monoclonal antibody 18D8.

SEQ ID NO:115 is the light chain CDR2 for the OX40 agonist monoclonal antibody 18D8.

SEQ ID NO:116 is the light chain CDR3 for the OX40 agonist monoclonal antibody 18D8.

SEQ ID NO: 117 is the heavy chain variable region ($V_H$) for the OX40 agonist monoclonal antibody Hu119-122.

SEQ ID NO:118 is the light chain variable region ($V_L$) for the OX40 agonist monoclonal antibody Hu119-122.

SEQ ID NO:119 is the heavy chain CDR1 for the OX40 agonist monoclonal antibody Hu119-122.

SEQ ID NO:120 is the heavy chain CDR2 for the OX40 agonist monoclonal antibody Hu119-122.

SEQ ID NO:121 is the heavy chain CDR3 for the OX40 agonist monoclonal antibody Hu119-122.

SEQ ID NO:122 is the light chain CDR1 for the OX40 agonist monoclonal antibody Hu119-122.

SEQ ID NO:123 is the light chain CDR2 for the OX40 agonist monoclonal antibody Hu119-122.

SEQ ID NO: 124 is the light chain CDR3 for the OX40 agonist monoclonal antibody Hu119-122.

SEQ ID NO:125 is the heavy chain variable region ($V_H$) for the OX40 agonist monoclonal antibody Hu106-222.

SEQ ID NO:126 is the light chain variable region ($V_L$) for the OX40 agonist monoclonal antibody Hu106-222.

SEQ ID NO:127 is the heavy chain CDR1 for the OX40 agonist monoclonal antibody Hu106-222.

SEQ ID NO:128 is the heavy chain CDR2 for the OX40 agonist monoclonal antibody Hu106-222.

SEQ ID NO:129 is the heavy chain CDR3 for the OX40 agonist monoclonal antibody Hu106-222.

SEQ ID NO:130 is the light chain CDR1 for the OX40 agonist monoclonal antibody Hu106-222.

SEQ ID NO:131 is the light chain CDR2 for the OX40 agonist monoclonal antibody Hu106-222.

SEQ ID NO:132 is the light chain CDR3 for the OX40 agonist monoclonal antibody Hu106-222.

SEQ ID NO:133 is an OX40 ligand (OX40L) amino acid sequence.

SEQ ID NO: 134 is a soluble portion of OX40L polypeptide.

SEQ ID NO:135 is an alternative soluble portion of OX40L polypeptide.

SEQ ID NO: 136 is the heavy chain variable region ($V_H$) for the OX40 agonist monoclonal antibody 008.

SEQ ID NO:137 is the light chain variable region ($V_L$) for the OX40 agonist monoclonal antibody 008.

SEQ ID NO:138 is the heavy chain variable region ($V_H$) for the OX40 agonist monoclonal antibody 011.

SEQ ID NO:139 is the light chain variable region ($V_L$) for the OX40 agonist monoclonal antibody 011.

SEQ ID NO: 140 is the heavy chain variable region ($V_H$) for the OX40 agonist monoclonal antibody 021.

SEQ ID NO:141 is the light chain variable region ($V_L$) for the OX40 agonist monoclonal antibody 021.

SEQ ID NO: 142 is the heavy chain variable region ($V_H$) for the OX40 agonist monoclonal antibody 023.

SEQ ID NO:143 is the light chain variable region ($V_L$) for the OX40 agonist monoclonal antibody 023.

SEQ ID NO: 144 is the heavy chain variable region ($V_H$) for an OX40 agonist monoclonal antibody.

SEQ ID NO:145 is the light chain variable region ($V_L$) for an OX40 agonist monoclonal antibody.

SEQ ID NO: 146 is the heavy chain variable region ($V_H$) for an OX40 agonist monoclonal antibody.

SEQ ID NO: 147 is the light chain variable region ($V_L$) for an OX40 agonist monoclonal antibody.

SEQ ID NO:148 is the heavy chain variable region ($V_H$) for a humanized OX40 agonist monoclonal antibody.

SEQ ID NO:149 is the heavy chain variable region ($V_H$) for a humanized OX40 agonist monoclonal antibody.

SEQ ID NO:150 is the light chain variable region ($V_L$) for a humanized OX40 agonist monoclonal antibody.

SEQ ID NO:151 is the light chain variable region ($V_L$) for a humanized OX40 agonist monoclonal antibody.

SEQ ID NO:152 is the heavy chain variable region ($V_H$) for a humanized OX40 agonist monoclonal antibody.

SEQ ID NO:153 is the heavy chain variable region ($V_H$) for a humanized OX40 agonist monoclonal antibody.

SEQ ID NO:154 is the light chain variable region ($V_L$) for a humanized OX40 agonist monoclonal antibody.

SEQ ID NO:155 is the light chain variable region ($V_L$) for a humanized OX40 agonist monoclonal antibody.

SEQ ID NO:156 is the heavy chain variable region ($V_H$) for an OX40 agonist monoclonal antibody.

SEQ ID NO:157 is the light chain variable region ($V_L$) for an OX40 agonist monoclonal antibody.

SEQ ID NO:158 is the heavy chain amino acid sequence of the PD-1 inhibitor nivolumab.

SEQ ID NO:159 is the light chain amino acid sequence of the PD-1 inhibitor nivolumab.

SEQ ID NO:160 is the heavy chain variable region ($V_H$) amino acid sequence of the PD-1 inhibitor nivolumab.

SEQ ID NO:161 is the light chain variable region ($V_L$) amino acid sequence of the PD-1 inhibitor nivolumab.

SEQ ID NO:162 is the heavy chain CDR1 amino acid sequence of the PD-1 inhibitor nivolumab.

SEQ ID NO:163 is the heavy chain CDR2 amino acid sequence of the PD-1 inhibitor nivolumab.

SEQ ID NO:164 is the heavy chain CDR3 amino acid sequence of the PD-1 inhibitor nivolumab.

SEQ ID NO:165 is the light chain CDR1 amino acid sequence of the PD-1 inhibitor nivolumab.

SEQ ID NO:166 is the light chain CDR2 amino acid sequence of the PD-1 inhibitor nivolumab.

SEQ ID NO:167 is the light chain CDR3 amino acid sequence of the PD-1 inhibitor nivolumab.

SEQ ID NO:168 is the heavy chain amino acid sequence of the PD-1 inhibitor pembrolizumab.

SEQ ID NO:169 is the light chain amino acid sequence of the PD-1 inhibitor pembrolizumab.

SEQ ID NO:170 is the heavy chain variable region ($V_H$) amino acid sequence of the PD-1 inhibitor pembrolizumab.

SEQ ID NO:171 is the light chain variable region ($V_L$) amino acid sequence of the PD-1 inhibitor pembrolizumab.

SEQ ID NO:172 is the heavy chain CDR1 amino acid sequence of the PD-1 inhibitor pembrolizumab.

SEQ ID NO:173 is the heavy chain CDR2 amino acid sequence of the PD-1 inhibitor pembrolizumab.

SEQ ID NO:174 is the heavy chain CDR3 amino acid sequence of the PD-1 inhibitor pembrolizumab.

SEQ ID NO:175 is the light chain CDR1 amino acid sequence of the PD-1 inhibitor pembrolizumab.

SEQ ID NO:176 is the light chain CDR2 amino acid sequence of the PD-1 inhibitor pembrolizumab.

SEQ ID NO: 177 is the light chain CDR3 amino acid sequence of the PD-1 inhibitor pembrolizumab.

SEQ ID NO:178 is the heavy chain amino acid sequence of the PD-L1 inhibitor durvalumab.

SEQ ID NO:179 is the light chain amino acid sequence of the PD-L1 inhibitor durvalumab.

SEQ ID NO:180 is the heavy chain variable region ($V_H$) amino acid sequence of the PD-L1 inhibitor durvalumab.

SEQ ID NO:181 is the light chain variable region ($V_L$) amino acid sequence of the PD-L1 inhibitor durvalumab.

SEQ ID NO:182 is the heavy chain CDR1 amino acid sequence of the PD-L1 inhibitor durvalumab.

SEQ ID NO:183 is the heavy chain CDR2 amino acid sequence of the PD-L1 inhibitor durvalumab.

SEQ ID NO:184 is the heavy chain CDR3 amino acid sequence of the PD-L1 inhibitor durvalumab.

SEQ ID NO:185 is the light chain CDR1 amino acid sequence of the PD-L1 inhibitor durvalumab.

SEQ ID NO:186 is the light chain CDR2 amino acid sequence of the PD-L1 inhibitor durvalumab.

SEQ ID NO:187 is the light chain CDR3 amino acid sequence of the PD-L1 inhibitor durvalumab.

SEQ ID NO:188 is the heavy chain amino acid sequence of the PD-L1 inhibitor avelumab.

SEQ ID NO:189 is the light chain amino acid sequence of the PD-L1 inhibitor avelumab.

SEQ ID NO:190 is the heavy chain variable region ($V_H$) amino acid sequence of the PD-L1 inhibitor avelumab.

SEQ ID NO:191 is the light chain variable region ($V_L$) amino acid sequence of the PD-L1 inhibitor avelumab.

SEQ ID NO:192 is the heavy chain CDR1 amino acid sequence of the PD-L1 inhibitor avelumab.

SEQ ID NO:193 is the heavy chain CDR2 amino acid sequence of the PD-L1 inhibitor avelumab.

SEQ ID NO:194 is the heavy chain CDR3 amino acid sequence of the PD-L1 inhibitor avelumab.

SEQ ID NO:195 is the light chain CDR1 amino acid sequence of the PD-L1 inhibitor avelumab.

SEQ ID NO:196 is the light chain CDR2 amino acid sequence of the PD-L1 inhibitor avelumab.

SEQ ID NO:197 is the light chain CDR3 amino acid sequence of the PD-L1 inhibitor avelumab.

SEQ ID NO:198 is the heavy chain amino acid sequence of the PD-L1 inhibitor atezolizumab.

SEQ ID NO:199 is the light chain amino acid sequence of the PD-L1 inhibitor atezolizumab.

SEQ ID NO:200 is the heavy chain variable region ($V_H$) amino acid sequence of the PD-L1 inhibitor atezolizumab.

SEQ ID NO:201 is the light chain variable region ($V_L$) amino acid sequence of the PD-L1 inhibitor atezolizumab.

SEQ ID NO:202 is the heavy chain CDR1 amino acid sequence of the PD-L1 inhibitor atezolizumab.

SEQ ID NO:203 is the heavy chain CDR2 amino acid sequence of the PD-L1 inhibitor atezolizumab.

SEQ ID NO:204 is the heavy chain CDR3 amino acid sequence of the PD-L1 inhibitor atezolizumab.

SEQ ID NO:205 is the light chain CDR1 amino acid sequence of the PD-L1 inhibitor atezolizumab.

SEQ ID NO:206 is the light chain CDR2 amino acid sequence of the PD-L1 inhibitor atezolizumab.

SEQ ID NO:207 is the light chain CDR3 amino acid sequence of the PD-L1 inhibitor atezolizumab.

SEQ ID NO:208 is the heavy chain amino acid sequence of the CTLA-4 inhibitor ipilimumab.

SEQ ID NO:209 is the light chain amino acid sequence of the CTLA-4 inhibitor ipilimumab.

SEQ ID NO:210 is the heavy chain variable region ($V_H$) amino acid sequence of the CTLA-4 inhibitor ipilimumab.

SEQ ID NO:211 is the light chain variable region ($V_L$) amino acid sequence of the CTLA-4 inhibitor ipilimumab.

SEQ ID NO:212 is the heavy chain CDR1 amino acid sequence of the CTLA-4 inhibitor ipilimumab.

SEQ ID NO:213 is the heavy chain CDR2 amino acid sequence of the CTLA-4 inhibitor ipilimumab.

SEQ ID NO:214 is the heavy chain CDR3 amino acid sequence of the CTLA-4 inhibitor ipilimumab.

SEQ ID NO:215 is the light chain CDR1 amino acid sequence of the CTLA-4 inhibitor ipilimumab.

SEQ ID NO:216 is the light chain CDR2 amino acid sequence of the CTLA-4 inhibitor ipilimumab.

SEQ ID NO:217 is the light chain CDR3 amino acid sequence of the CTLA-4 inhibitor ipilimumab.

SEQ ID NO:218 is the heavy chain amino acid sequence of the CTLA-4 inhibitor tremelimumab.

SEQ ID NO:219 is the light chain amino acid sequence of the CTLA-4 inhibitor tremelimumab.

SEQ ID NO:220 is the heavy chain variable region ($V_H$) amino acid sequence of the CTLA-4 inhibitor tremelimumab.

SEQ ID NO:221 is the light chain variable region ($V_L$) amino acid sequence of the CTLA-4 inhibitor tremelimumab.

SEQ ID NO:222 is the heavy chain CDR1 amino acid sequence of the CTLA-4 inhibitor tremelimumab.

SEQ ID NO:223 is the heavy chain CDR2 amino acid sequence of the CTLA-4 inhibitor tremelimumab.

SEQ ID NO:224 is the heavy chain CDR3 amino acid sequence of the CTLA-4 inhibitor tremelimumab.

SEQ ID NO:225 is the light chain CDR1 amino acid sequence of the CTLA-4 inhibitor tremelimumab.

SEQ ID NO:226 is the light chain CDR2 amino acid sequence of the CTLA-4 inhibitor tremelimumab.

SEQ ID NO:227 is the light chain CDR3 amino acid sequence of the CTLA-4 inhibitor tremelimumab.

SEQ ID NO:228 is the heavy chain amino acid sequence of the CTLA-4 inhibitor zalifrelimab.

SEQ ID NO:229 is the light chain amino acid sequence of the CTLA-4 inhibitor zalifrelimab.

SEQ ID NO:230 is the heavy chain variable region ($V_H$) amino acid sequence of the CTLA-4 inhibitor zalifrelimab.

SEQ ID NO:231 is the light chain variable region ($V_L$) amino acid sequence of the CTLA-4 inhibitor zalifrelimab.

SEQ ID NO:232 is the heavy chain CDR1 amino acid sequence of the CTLA-4 inhibitor zalifrelimab.

SEQ ID NO:233 is the heavy chain CDR2 amino acid sequence of the CTLA-4 inhibitor zalifrelimab.

SEQ ID NO:234 is the heavy chain CDR3 amino acid sequence of the CTLA-4 inhibitor zalifrelimab.

SEQ ID NO:235 is the light chain CDR1 amino acid sequence of the CTLA-4 inhibitor zalifrelimab.

SEQ ID NO:236 is the light chain CDR2 amino acid sequence of the CTLA-4 inhibitor zalifrelimab.

SEQ ID NO:237 is the light chain CDR3 amino acid sequence of the CTLA-4 inhibitor zalifrelimab.

DETAILED DESCRIPTION OF THE INVENTION

I. Introduction

Adoptive cell therapy utilizing TILs cultured ex vivo by the Rapid Expansion Protocol (REP) has produced successful adoptive cell therapy following host immunosuppression in patients with cancer such as melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naive to effector T cells (see Chang, et al., *Nat. Immunol.* 2016, 17, 364, hereby expressly incorporated in its entirety, and in particular for the discussion and markers of anaerobic and aerobic metabolism). For example, naive T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Current TIL manufacturing and treatment processes are limited by length, cost, sterility concerns, and other factors described herein such that the potential to treat patients which are refractory to anti-PD1 and as such have been severely limited. There is an urgent need to provide TIL manufacturing processes and therapies based on such processes that are appropriate for use in treating patients for whom very few or no viable treatment options remain. The present invention meets this need by providing a shortened manufacturing process for use in generating TILs which can then be employed in the treatment of non-small cell lung carcinoma (NSCLC) patients whom are refractory to anti-PD-1 treatment.

II. Definitions

Unless defined otherwise, all technical and scientific terms used herein have the same meaning as is commonly understood by one of skill in the art to which this invention belongs. All patents and publications referred to herein are incorporated by reference in their entireties.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

By "tumor infiltrating lymphocytes" or "TILs" herein is meant a population of cells originally obtained as white blood cells that have left the bloodstream of a subject and migrated into a tumor. TILs include, but are not limited to, CD8+cytotoxic T cells (lymphocytes), Th1 and Th17 CD4+ T cells, natural killer cells, dendritic cells and Ml macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR ap, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term “CS10” refers to a cryopreservation medium which is obtained from Stemcell Technologies or from Biolife Solutions. The CS10 medium may be referred to by the trade name “CryoStor® CS10”. The CS10 medium is a serum-free, animal component-free medium which comprises DMSO.

The term “central memory T cell” refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R.

Transcription factors for central memory T cells include BCL-6, BCL-6B, MBD2, and BMI1.

Central memory T cells primarily secret IL-2 and CD40L as effector molecules after TCR triggering. Central memory T cells are predominant in the CD4 compartment in blood, and in the human are proportionally enriched in lymph nodes and tonsils.

The term “effector memory T cell” refers to a subset of human or mammalian T cells that, like central memory T cells, are CD45R0+, but have lost the constitutive expression of CCR7 (CCR71°) and are heterogeneous or low for CD62L expression ($CD62L^{lo}$). The surface phenotype of central memory T cells also includes TCR, CD3, CD127 (IL-7R), and IL-15R. Transcription factors for central memory T cells include BLIMP1. Effector memory T cells rapidly secrete high levels of inflammatory cytokines following antigenic stimulation, including interferon-y, IL-4, and IL-5. Effector memory T cells are predominant in the CD8 compartment in blood, and in the human are proportionally enriched in the lung, liver, and gut. CD8+effector memory T cells carry large amounts of perform.

The term “closed system” refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms “fragmenting,” “fragment,” and “fragmented,” as used herein to describe processes for disrupting a tumor, includes mechanical fragmentation methods such as crushing, slicing, dividing, and morcellating tumor tissue as well as any other method for disrupting the physical structure of tumor tissue.

The terms “peripheral blood mononuclear cells” and “PBMCs” refers to a peripheral blood cell having a round nucleus, including lymphocytes (T cells, B cells, NK cells) and monocytes. When used as an antigen presenting cell (PBMCs are a type of antigen-presenting cell), the peripheral blood mononuclear cells are preferably irradiated allogeneic peripheral blood mononuclear cells.

The terms “peripheral blood lymphocytes” and “PBLs” refer to T cells expanded from peripheral blood. In some embodiments, PBLs are separated from whole blood or apheresis product from a donor. In some embodiments, PBLs are separated from whole blood or apheresis product from a donor by positive or negative selection of a T cell phenotype, such as the T cell phenotype of CD3+CD45+.

The term “anti-CD3 antibody” refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3c. Other anti-CD3 antibodies include, for example, otelixizumab, teplizumab, and visilizumab.

The term “OKT-3” (also referred to herein as “OKT3”) refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab (exemplary OKT-3 antibody).

| Identifier | Sequence (One-Letter Amino Acid Symbols) | |
|---|---|---|
| SEQ ID NO: 1 | QVQLQQSGAE LARPGASVKM SCKASGYTFT RYTMHWVKQR PGQGLEWIGY INPSRGYTNY | 60 |
| muromonab heavy | NQKFKDKATL TTDKSSSTAY MQLSSLTSED SAVYYCARYY DDHYCLDYWG QGTTLTVSSA | 120 |
| chain | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 | QIVLTQSPAI MSASPGEKVT MTCSASSSVS YMNWYQQKSG TSPKRWIYDT SKLASGVPAH | 60 |
| muromonab light | FRGSGSGTSY SLTISGMEAE DAATYYCQQW SSNPFTFGSG TKLEINRADT APTVSIFPPS | 120 |
| chain | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

The term “IL-2” (also referred to herein as “IL2”) refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, JI *Immunol.* 2004, 172, 3983-88 and Malek, Annu. Rev. *Immunol.* 2008, 26, 453-79, the disclosures of which are incorporated by reference herein. The amino acid sequence of recombinant human IL-2 suitable for use in the invention is given in Table 2 (SEQ ID NO: 3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug bempegaldesleukin (NKTR-214, pegylated human recombinant IL-2 as in SEQ ID NO:4 in which an average of 6 lysine residues are $N^6$ substituted with [(2,7-bis{[methylpoly(oxyethylene)]carbamoyl}-9H-fluoren-9-yl) methoxy]carbonyl), which is available from Nektar Therapeutics, South San Francisco, CA, USA, or which may be prepared by methods known in the art, such as the methods described in Example 19 of International Patent Application Publication No. WO 2018/132496 A1 or the method described in Example 1 of U.S. Patent Application Publication No. US 2019/0275133 A1, the disclosures of which are incorporated by reference herein. Bempegaldesleukin (NKTR-214) and other pegylated IL-2 molecules suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

In some embodiments, an IL-2 form suitable for use in the present invention is THOR-707, available from Synthorx, Inc. The preparation and properties of THOR-707 and additional alternative forms of IL-2 suitable for use in the invention are described in U.S. Patent Application Publication Nos. US 2020/0181220 A1 and US 2020/0330601 A1, the disclosures of which are incorporated by reference herein. In some embodiments, and IL-2 form suitable for use in the invention is an interleukin 2 (IL-2) conjugate comprising: an isolated and purified IL-2 polypeptide; and a conjugating moiety that binds to the isolated and purified IL-2 polypeptide at an amino acid position selected from K35, T37, R38, T41, F42, K43, F44, Y45, E61, E62, E68, K64, P65, V69, L72, and Y107, wherein the numbering of the amino acid residues corresponds to SEQ ID NO:5. In some embodiments, the amino acid position is selected from T37, R38, T41, F42, F44, Y45, E61, E62, E68, K64, P65, V69, L72, and Y107. In some embodiments, the amino acid position is selected from T37, R38, T41, F42, F44, Y45, E61, E62, E68, P65, V69, L72, and Y107. In some embodiments, the amino acid position is selected from T37, T41, F42, F44, Y45, P65, V69, L72, and Y107. In some embodiments, the amino acid position is selected from R38 and K64. In some embodiments, the amino acid position is selected from E61, E62, and E68. In some embodiments, the amino acid position is at E62. In some embodiments, the amino acid residue selected from K35, T37, R38, T41, F42, K43, F44, Y45, E61, E62, E68, K64, P65, V69, L72, and Y107 is further mutated to lysine, cysteine, or histidine. In some embodiments, the amino acid residue is mutated to cysteine. In some embodiments, the amino acid residue is mutated to lysine. In some embodiments, the amino acid residue selected from K35, T37, R38, T41, F42, K43, F44, Y45, E61, E62, E68, K64, P65, V69, L72, and Y107 is further mutated to an unnatural amino acid. In some embodiments, the unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl) selanyl)propanoic acid, 2-amino-3-(phenylselanyl)propanoic, or selenocysteine. In some embodiments, the IL-2 conjugate has a decreased affinity to IL-2 receptor a (IL-2Ra) subunit relative to a wild-type IL-2 polypeptide. In some embodiments, the decreased affinity is about 10%, 20%, 30%, 40%, 50%, 60%, 70%, 80%, 90%, 95%, 99%, or greater than 99% decrease in binding affinity to IL-2Ra relative to a wild-type IL-2 polypeptide. In some embodiments, the decreased affinity is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 500-fold, 1000-fold, or more relative to a wild-type IL-2 polypeptide. In some embodiments, the conjugating moiety impairs or blocks the binding of IL-2 with IL-2Ra. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(u-hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[D-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-a-methyl-a-(2-pyridyldithio)toluene (sMPT), sulfosuccinimidyl-6-[a-methyl-a-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(y-maleimidobutyryloxy)succinimide ester (GMBs), N-(y-maleimidobutyryloxy) sulfosuccinimide ester (sulfo-GMBs), succinimidyl 6-((iodoacetyl)amino) hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenyl amino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), 1-(p-azidosalicylamido)-4-(iodoacetamido)butane (AsIB), N-[4-(p-azidosalicylamido) butyl]-3'-(2'-pyridyldithio) propionamide (APDP), benzophenone-4-iodoacetamide, p-azidobenzoyl hydrazide (ABH), 4-(p-azidosalicylamido)butylamine (AsBA), or p-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate. In some embodiments, the IL-2 form suitable for use in the invention is a fragment of any of the IL-2 forms described herein. In some embodiments, the IL-2 form suitable for use in the invention is pegylated as disclosed in U.S. Patent Application Publication No. US 2020/0181220 A1 and U.S. Patent Application Publication No. US 2020/0330601 A1. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 80% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 polypeptide comprises an N-terminal deletion of one residue relative to SEQ ID NO:5. In some embodiments, the IL-2 form suitable for use in the invention lacks IL-2R alpha chain engagement but retains normal binding to the intermediate affinity IL-2R beta-gamma signaling complex. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 90% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 95% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 form suitable for use in the invention is an IL-2 conjugate comprising: an IL-2 polypeptide comprising an N6-azido-ethoxy-L-lysine (AzK) covalently attached to a conjugating moiety comprising a polyethylene glycol (PEG), wherein: the IL-2 polypeptide comprises an amino acid sequence having at least 98% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5.

In some embodiments, an IL-2 form suitable for use in the invention is nemvaleukin alfa, also known as ALKS-4230 (SEQ ID NO:6), which is available from Alkermes, Inc. Nemvaleukin alfa is also known as human interleukin 2 fragment (1-59), variant (Cys$^{125}$>Ser$^{51}$), fused via peptidyl linker ($^{60}$GG$^{61}$) to human interleukin 2 fragment (62-132), fused via peptidyl linker ($^{133}$GSGGGS$^{138}$) to human interleukin 2 receptor u-chain fragment (139-303), produced in Chinese hamster ovary (CHO) cells, glycosylated; human interleukin 2 (IL-2) (75-133)-peptide [Cys$^{125}$(51)>Ser]-mutant (1-59), fused via a G2 peptide linker (60-61) to human interleukin 2 (IL-2) (4-74)-peptide (62-132) and via a GSG3S peptide linker (133-138) to human interleukin 2 receptor u-chain (IL2R subunit alpha, IL2Ra, IL2RA) (1-165)-peptide (139-303), produced in Chinese hamster ovary (CHO) cells, glycoform alfa. The amino acid sequence of nemvaleukin alfa is given in SEQ ID NO:6. In some embodiments, nemvaleukin alfa exhibits the following post-translational modifications: disulfide bridges at positions: 31-116, 141-285, 184-242, 269-301, 166-197 or 166-199, 168-199 or 168-197 (using the numbering in SEQ ID NO:6), and glycosylation sites at positions: N187, N206, T212 using the numbering in SEQ ID NO:6. The preparation and properties of nemvaleukin alfa, as well as additional alternative forms of IL-2 suitable for use in the invention, is described in U.S. Patent Application Publication No. US 2021/0038684 A1 and U.S. Pat. No. 10,183,979, the disclosures of which are incorporated by reference herein. In some embodiments, an IL-2 form suitable for use in the invention is a protein having at least 80%, at least 90%, at least 95%, or at least 90% sequence identity to SEQ ID NO:6. In some embodiments, an IL-2 form suitable for use in the invention has the amino acid sequence given in SEQ ID NO:6 or conservative amino acid substitutions thereof. In some embodiments, an IL-2 form suitable for use in the invention is a fusion protein comprising amino acids 24-452 of SEQ ID NO:7, or variants, fragments, or derivatives thereof. In some embodiments, an IL-2 form suitable for use in the invention is a fusion protein comprising an amino acid sequence having at least 80%, at least 90%, at least 95%, or at least 90% sequence identity to amino acids 24-452 of SEQ ID NO:7, or variants, fragments, or derivatives thereof. Other IL-2 forms suitable for use in the present invention are described in U.S. Pat. No. 10,183,979, the disclosures of which are incorporated by reference herein. Optionally, in some embodiments, an IL-2 form suitable for use in the invention is a fusion protein comprising a first fusion partner that is linked to a second fusion partner by a mucin domain polypeptide linker, wherein the first fusion partner is IL-1Ra or a protein having at least 98% amino acid sequence identity to IL-1Ra and having the receptor antagonist activity of IL-Ra, and wherein the second fusion partner comprises all or a portion of an immunoglobulin comprising an Fc region, wherein the mucin domain polypeptide linker comprises SEQ ID NO:8 or an amino acid sequence having at least 90% sequence identity to SEQ ID NO:8 and wherein the half-life of the fusion protein is improved as compared to a fusion of the first fusion partner to the second fusion partner in the absence of the mucin domain polypeptide linker.

TABLE 2

Amino acid sequences of interleukins.

| Identifier | Sequence (One-Letter Amino Acid Symbols) | |
|---|---|---|
| SEQ ID NO: 3 | MAPTSSSTKK TQLQLEHLLL DLQMILNGIN NYKNPKLTRM LTFKFYMPKK ATELKHLQCL | 60 |
| recombinant | EEELKPLEEV LNLAQSKNFH LRPRDLISNI NVIVLELKGS ETTFMCEYAD ETATIVEFLN | 120 |
| human IL-2 | RWITFCQSII STLT | 134 |
| (rhIL-2) | | |
| SEQ ID NO: 4 | PTSSSTKKTQ LQLEHLLLDL QMILNGINNY KNPKLTRMLT FKFYMPKKAT ELKHLQCLEE | 60 |
| Aldesleukin | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 | APTSSSTKKT QLQLEHLLLD LQMILNGINN YKNPKLTRML TFKFYMPKKA TELKHLQCLE | 60 |
| IL-2 form | EELKPLEEVL NLAQSKNFHL RPRDLISNIN VIVLELKGSE TTFMCEYADE TATIVEFLNR | 120 |
| | WITFCQSIIS TLT | 133 |
| SEQ ID NO: 6 | SKNFHLRPRD LISNINVIVL ELKGSETTFM CEYADETATI VEFLNRWITF SQSIISTLTG | 60 |
| Nemvaleukin alfa | GSSSTKKTQL QLEHLLLDLQ MILNGINNYK NPKLTRMLTF KFYMPKKATE LKHLQCLEEE | 120 |
| | LKPLEEVLNL AQGSGGGSEL CDDDPPEIPH ATFKAMAYKE GTMLNCECKR GFRRIKSGSL | 180 |
| | YMLCTGNSSH SSWDNQCQCT SSATRNTTKQ VTPQPEEQKE RKTTEMQSPM QPVDQASLPG | 240 |
| | HCREPPPWEN EATERIYHFV VGQMVYYQCV QGYRALHRGP AESVCKMTHG KTRWTQPQLI | 300 |
| | CTG | 303 |

TABLE 2-continued

Amino acid sequences of interleukins.

| Identifier | Sequence (One-Letter Amino Acid Symbols) | |
|---|---|---|
| SEQ ID NO: 7 IL-2 form | MDAMKRGLCC VLLLCGAVFV SARRPSGRKS SKMQAFRIWD VNQKTFYLRN NQLVAGYLQG | 60 |
| | PNVNLEEKID VVPIEPHALF LGIHGGKMCL SCVKSGDETR LQLEAVNITD LSENRKQDKR | 120 |
| | FAFIRSDSGP TTSFESAACP GWFLCTAMEA DQPVSLTNMP DEGVMVTKFY FQEDESGSGG | 180 |
| | ASSESSASSD GPHPVITESR ASSESSASSD GPHPVITESR EPKSSDKTHT CPPCPAPELL | 240 |
| | GGPSVFLFPP KPKDTLMISR TPEVTCVVVD VSHEDPEVKF NWYVDGVEVH NAKTKPREEQ | 300 |
| | YNSTYRVVSV LTVLHQDWLN GKEYKCKVSN KALPAPIEKT ISKAKGQPRE PQVYTLPPSR | 360 |
| | EEMTKNQVSL TCLVKGFYPS DIAVEWESNG QPENNYKTTP PVLDSDGSFF LYSKLTVDKS | 420 |
| | RWQQGNVFSC SVMHEALHNH YTQKSLSLSP GK | 452 |
| SEQ ID NO: 8 mucin domain polypeptide | SESSASSDGP HPVITP | 16 |
| SEQ ID NO: 9 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 10 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 11 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LOSFVHIVQM FINTS | 115 |
| SEQ ID NO: 12 recombinant human IL-21 ( rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQKMIHQ | 120 |
| | HLSSRTHGSE DS | 132 |

In some embodiments, an IL-2 form suitable for use in the invention includes a antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the antibody cytokine engrafted protein preferentially expands T effector cells over regulatory T cells. In some embodiments, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, and wherein the antibody cytokine engrafted protein preferentially expands T effector cells over regulatory T cells. In some embodiments, the IL-2 regimen comprises administration of an antibody described in U.S. Patent Application Publication No. US 2020/0270334 A1, the disclosures of which are incorporated by reference herein. In some embodiments, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, wherein the antibody cytokine engrafted protein preferentially expands T effector cells over regulatory T cells, and wherein the antibody further comprises an IgG class heavy chain and an IgG class light chain selected from the group consisting of a IgG class light chain comprising SEQ ID NO:39 and a IgG class heavy chain comprising SEQ ID NO:38; a IgG class light chain comprising SEQ ID NO:37 and a IgG class heavy chain comprising SEQ ID NO:29; a IgG class light chain comprising SEQ ID NO:39 and a IgG class heavy chain comprising SEQ ID NO:29; and a IgG class light chain comprising SEQ ID NO:37 and a IgG class heavy chain comprising SEQ ID NO:38.

In some embodiments, an IL-2 molecule or a fragment thereof is engrafted into HCDR1 of the $V_H$, wherein the IL-2 molecule is a mutein. In some embodiments, an IL-2 molecule or a fragment thereof is engrafted into HCDR2 of the $V_H$, wherein the IL-2 molecule is a mutein. In some embodiments, an IL-2 molecule or a fragment thereof is engrafted into HCDR3 of the $V_H$, wherein the IL-2 molecule is a mutein. In some embodiments, an IL-2 molecule or a fragment thereof is engrafted into LCDR1 of the $V_L$, wherein the IL-2 molecule is a mutein. In some embodiments, an IL-2 molecule or a fragment thereof is engrafted into LCDR2 of the $V_L$, wherein the IL-2 molecule is a mutein.

In some embodiments, an IL-2 molecule or a fragment thereof is engrafted into LCDR3 of the $V_L$, wherein the IL-2 molecule is a mutein.

The insertion of the IL-2 molecule can be at or near the N-terminal region of the CDR, in the middle region of the CDR or at or near the C-terminal region of the CDR. In some embodiments, the antibody cytokine engrafted protein comprises an IL-2 molecule incorporated into a CDR, wherein the IL2 sequence does not frameshift the CDR sequence.

In some embodiments, the antibody cytokine engrafted protein comprises an IL-2 molecule incorporated into a CDR, wherein the IL-2 sequence replaces all or part of a CDR sequence.

The replacement by the IL-2 molecule can be the N-terminal region of the CDR, in the middle region of the CDR or at or near the C-terminal region the CDR. A replacement by the IL-2 molecule can be as few as one or two amino acids of a CDR sequence, or the entire CDR sequences.

In some embodiments, an IL-2 molecule is engrafted directly into a CDR without a peptide linker, with no additional amino acids between the CDR sequence and the IL-2 sequence. In some embodiments, an IL-2 molecule is engrafted indirectly into a CDR with a peptide linker, with one or more additional amino acids between the CDR sequence and the IL-2 sequence.

In some embodiments, the IL-2 molecule described herein is an IL-2 mutein. In some instances, the IL-2 mutein comprising an R67A substitution. In some embodiments, the IL-2 mutein comprises the amino acid sequence SEQ ID NO:14 or SEQ ID NO:15. In some embodiments, the IL-2 mutein comprises an amino acid sequence in Table 1 in U.S. Patent Application Publication No. US 2020/0270334 A1, the disclosure of which is incorporated by reference herein.

In some embodiments, the antibody cytokine engrafted protein comprises an HCDR1 selected from the group consisting of SEQ ID NO:16, SEQ ID NO:19, SEQ ID NO:22 and SEQ ID NO:25. In some embodiments, the antibody cytokine engrafted protein comprises an HCDR1 selected from the group consisting of SEQ ID NO:7, SEQ ID NO:10, SEQ ID NO:13 and SEQ ID NO:16. In some embodiments, the antibody cytokine engrafted protein comprises an HCDR1 selected from the group consisting of HCDR2 selected from the group consisting of SEQ ID NO:17, SEQ ID NO:20, SEQ ID NO:23, and SEQ ID NO:26.

In some embodiments, the antibody cytokine engrafted protein comprises an HCDR3 selected from the group consisting of SEQ ID NO:18, SEQ ID NO:21, SEQ ID NO:24, and SEQ ID NO:27. In some embodiments, the antibody cytokine engrafted protein comprises a $V_H$ region comprising the amino acid sequence of SEQ ID NO:28. In some embodiments, the antibody cytokine engrafted protein comprises a heavy chain comprising the amino acid sequence of SEQ ID NO:29. In some embodiments, the antibody cytokine engrafted protein comprises a $V_L$ region comprising the amino acid sequence of SEQ ID NO:36. In some embodiments, the antibody cytokine engrafted protein comprises a light chain comprising the amino acid sequence of SEQ ID NO:37. In some embodiments, the antibody cytokine engrafted protein comprises a $V_H$ region comprising the amino acid sequence of SEQ ID NO:28 and a $V_L$ region comprising the amino acid sequence of SEQ ID NO:36. In some embodiments, the antibody cytokine engrafted protein comprises a heavy chain region comprising the amino acid sequence of SEQ ID NO:29 and a light chain region comprising the amino acid sequence of SEQ ID NO:37. In some embodiments, the antibody cytokine engrafted protein comprises a heavy chain region comprising the amino acid sequence of SEQ ID NO:29 and a light chain region comprising the amino acid sequence of SEQ ID NO:39. In some embodiments, the antibody cytokine engrafted protein comprises a heavy chain region comprising the amino acid sequence of SEQ ID NO:38 and a light chain region comprising the amino acid sequence of SEQ ID NO:37. In some embodiments, the antibody cytokine engrafted protein comprises a heavy chain region comprising the amino acid sequence of SEQ ID NO:38 and a light chain region comprising the amino acid sequence of SEQ ID NO:39. In some embodiments, the antibody cytokine engrafted protein comprises IgG.IL2F71A.H1 or IgG.IL2R67A.H1 of U.S. Patent Application Publication No. 2020/0270334 A1, or variants, derivatives, or fragments thereof, or conservative amino acid substitutions thereof, or proteins with at least 80%, at least 90%, at least 95%, or at least 98% sequence identity thereto. In some embodiments, the antibody components of the antibody cytokine engrafted protein described herein comprise immunoglobulin sequences, framework sequences, or CDR sequences of palivizumab. In some embodiments, the antibody cytokine engrafted protein described herein has a longer serum half-life that a wild-type IL-2 molecule such as, but not limited to, aldesleukin or a comparable molecule. In some embodiments, the antibody cytokine engrafted protein described herein has a sequence as set forth in Table 3.

TABLE 3

Sequences of exemplary palivizumab antibody-IL-2 engrafted proteins

| Identifier | Sequence (One-Letter Amino Acid Symbols) | |
|---|---|---|
| SEQ ID NO: 13<br>IL-2 | MYRMQLLSCI ALSLALVTNS APTSSSTKKT QLQLEHLLLD LQMILNGINN YKNPKLTRML<br>TFKFYMPKKA TELKHLQCLE EELKPLEEVL NLAQSKNFHL RPRDLISNIN VIVLELKGSE<br>TTFMCEYADE TATIVEFLNR WITFCQSIIS TLT | 60<br>120<br>153 |
| SEQ ID NO: 14<br>IL-2 mutein | APTSSSTKKT QLQLEHLLLD LQMILNGINN YKNPKLTAML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 15<br>IL-2 mutein | APTSSSTKKT QLQLEHLLLD LQMILNGINN YKNPKLTRML TAKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 16<br>HCDR1_IL-2 | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GMSVG | 60<br>120<br>145 |
| SEQ ID NO: 17<br>HCDR2 | DIWWDDKKDY NPSLKS | 16 |
| SEQ ID NO: 18<br>HCDR3 | SMITNWYFDV | 10 |

TABLE 3-continued

Sequences of exemplary palivizumab antibody-IL-2 engrafted proteins

| Identifier | Sequence (One-Letter Amino Acid Symbols) | |
|---|---|---|
| SEQ ID NO: 19 HCDR1_IL-2 kabat | APTSSSTKKT QLQLEHLLLD LQMILNGINN YKNPKLTAML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLTSTSGMSV G | 60<br>120<br>141 |
| SEQ ID NO: 20 HCDR2 kabat | DIWWDDKKDY NPSLKS | 16 |
| SEQ ID NO: 21 HCDR3 kabat | SMITNWYFDV | 10 |
| SEQ ID NO: 22 HCDR1_IL-2 clothia | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GM | 60<br>120<br>142 |
| SEQ ID NO: 23 HCDR2 clothia | WWDDK | 5 |
| SEQ ID NO: 24 HCDR3 clothia | SMITNWYFDV | 10 |
| SEQ ID NO: 25 HCDR1_IL-2 IMGT | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GMS | 60<br>120<br>143 |
| SEQ ID NO: 26 HCDR2 IMGT | IWWDDKK | 7 |
| SEQ ID NO: 27 HCDR3 IMGT | ARSMITNWYF DV | 12 |
| SEQ ID NO: 28 $V_H$ | QVTLRESGPA LVKPTQTLTL TCTFSGFSLA PTSSSTKKTQ LQLEHLLLDL QMILNGINNY<br>KNPKLTAMLT FKFYMPKKAT ELKHLQCLEE ELKPLEEVLN LAQSKNFHLR PRDLISNINV<br>IVLELKGSET TFMCEYADET ATIVEFLNRW ITFCQSIIST LTSTSGMSVG WIRQPPGKAL<br>EWLADIWWDD KKDYNPSLKS RLTISKDTSK NQVVLKVTNM DPADTATYYC ARSMITNWYF<br>DVWGAGTTVT VSS | 60<br>120<br>180<br>240<br>253 |
| SEQ ID NO: 29 Heavy chain | QMILNGINNY KNPKLTAMLT FKFYMPKKAT ELKHLQCLEE ELKPLEEVLN LAQSKNFHLR<br>PRDLISNINV IVLELKGSET TFMCEYADET ATIVEFLNRW ITFCQSIIST LTSTSGMSVG<br>WIRQPPGKAL EWLADIWWDD KKDYNPSLKS RLTISKDTSK NQVVLKVTNM DPADTATYYC<br>ARSMITNWYF DVWGAGTTVT VSSASTKGPS VFPLAPSSKS TSGGTAALGC LVKDYFPEPV<br>TVSWNSGALT SGVHTFPAVL QSSGLYSLSS VVTVPSSSLG TQTYICNVNH KPSNTKVDKR<br>VEPKSCDKTH TCPPCPAPEL LGGPSVFLFP PKPKDTLMIS RTPEVTCVVV AVSHEDPEVK<br>FNWYVDGVEV HNAKTKPREE QYNSTYRVVS VLTVLHQDWL NGKEYKCKVS NKALAAPIEK<br>TISKAKGQPR EPQVYTLPPS REEMTKNQVS LTCLVKGFYP SDIAVEWESN GQPENNYKTT<br>PPVLDSDGSF FLYSKLTVDK SRWQQGNVFS CSVMHEALHN HYTQKSLSLS PGK | 60<br>120<br>180<br>240<br>300<br>360<br>420<br>480<br>533 |
| SEQ ID NO: 30 LCDR1 kabat | KAQLSVGYMH | 10 |
| SEQ ID NO: 31 LCDR2 kabat | DTSKLAS | 7 |
| SEQ ID NO: 32 LCDR3 kabat | FQGSGYPFT | 9 |
| SEQ ID NO: 33 LCDR1 chothia | QLSVGY | 6 |
| SEQ ID NO: 34 LCDR2 chothia | DTS | 3 |
| SEQ ID NO: 35 LCDR3 chothia | GSGYPF | 6 |
| SEQ ID NO: 36 $V_L$ | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIK | 60<br>106 |
| SEQ ID NO: 37 Light chain | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |

TABLE 3-continued

Sequences of exemplary palivizumab antibody-IL-2 engrafted proteins

| Identifier | Sequence (One-Letter Amino Acid Symbols) | |
|---|---|---|
| SEQ ID NO: 38 Light chain | QVTLRESGPA LVKPTQTLTL TCTFSGFSLA PTSSSTKKTQ LQLEHLLLDL QMILNGINNY | 60 |
| | KNPKLTRMLT AKFYMPKKAT ELKHLQCLEE ELKPLEEVLN LAQSKNFHLR PRDLISNINV | 120 |
| | IVLELKGSET TEMCEYADET ATIVEFLNRW ITFCQSIIST LTSTSGMSVG WIRQPPGKAL | 180 |
| | EWLADIWWDD KKDYNPSLKS RLTISKDTSK NQVVLKVTNM DPADTATYYC ARSMITNWYF | 240 |
| | DVWGAGTTVT VSSASTKGPS VFPLAPSSKS TSGGTAALGC LVKDYFPEPV TVSWNSGALT | 300 |
| | SGVHTFPAVL QSSGLYSLSS VVTVPSSSLG TQTYICNVNH KPSNTKVDKR VEPKSCDKTH | 360 |
| | TCPPCPAPEL LGGPSVFLFP PKPKDTLMIS RTPEVTCVVV AVSHEDPEVK FNWYVDGVEV | 420 |
| | HNAKTKPREE QYNSTYRVVS VLTVLHQDWL NGKEYKCKVS NKALAAPIEK TISKAKGQPR | 480 |
| | EPQVYTLPPS REEMTKNQVS LTCLVKGFYP SDIAVEWESN GQPENNYKTT PPVLDSDGSF | 540 |
| | FLYSKLTVDK SRWQQGNVFS CSVMHEALHN HYTQKSLSLS PGK | 583 |
| SEQ ID NO: 39 Light chain | DIQMTQSPST LSASVGDRVT ITCKAQLSVG YMHWYQQKPG KAPKLLIYDT SKLASGVPSR | 60 |
| | FSGSGSGTEF TLTISSLQPD DFATYYCFQG SGYPFTFGGG TKLEIKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |

The term "IL-4" (also referred to herein as "IL4") refers to the cytokine known as interleukin 4, which is produced by Th2 T cells and by eosinophils, basophils, and mast cells. IL-4 regulates the differentiation of naive helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgGi expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:9).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:10).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO: 11).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev Drug. Disc.* 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:12).

When "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g., secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$,$10^7$ to $10^{11}$, 107 to $10^{10}$, 108 to $10^{11}$, 108 to $10^{10}$, 109 to $10^{11}$, or 109 to $10^{10}$ cells/kg body weight), including all integer values within those ranges. TILs (including in some cases, genetically modified cytotoxic lymphocytes) compositions may also be administered multiple times at these dosages. The TILs (inlcuding in some cases, genetically) can be administered by using infusion techniques that are commonly known in immunotherapy (see, e.g., Rosenberg et al., *New Eng. J. ofMed.* 1988, 319: 1676). The optimal dosage and treatment regime for a particular patient can readily be determined by one skilled in the art of medicine by monitoring the patient for signs of disease and adjusting the treatment accordingly.

The term "hematological malignancy", "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), multiple myeloma, acute monocytic leukemia (AMoL), Hodgkin's lymphoma, and non-Hodgkin's lymphomas. The term "B cell hematological malignancy" refers to hematological malignancies that affect B cells.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment.

In some embodiments, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In some embodiments, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In some embodiments, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the TILs of the invention.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, CD8+cytotoxic T cells (lymphocytes), Th1 and Th17 CD4+ T cells, natural killer cells, dendritic cells and Ml macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 8, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILs may further be characterized by potency—for example, TILs may be considered potent if, for example, interferon (IFN) release is greater than about 50 μg/mL, greater than about 100 μg/mL, greater than about 150 μg/mL, or greater than about 200 μg/mL. TILs may be considered potent if, for example, interferon (IFNγ) release is greater than about 50 μg/mL, greater than about 100 μg/mL, greater than about 150 μg/mL, or greater than about 200 μg/mL, greater than about 300 μg/mL, greater than about 400 μg/mL, greater than about 500 μg/mL, greater than about 600 μg/mL, greater than about 700 μg/mL, greater than about 800 μg/mL, greater than about 900 μg/mL, greater than about 1000 μg/mL.

The term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

The term "RNA" defines a molecule comprising at least one ribonucleotide residue. The term "ribonucleotide" defines a nucleotide with a hydroxyl group at the 2' position of a b-D-ribofuranose moiety. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules described herein may also comprise non-standard nucleotides, such as non-naturally occurring nucleotides or chemically synthesized nucleotides or deoxynucleotides. These altered RNAs can be referred to as analogs or analogs of naturally-occurring RNA.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of"

The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (Clq) of the classical complement system.

The term "antigen" refers to a substance that induces an immune response. In some embodiments, an antigen is a molecule capable of being bound by an antibody or a TCR if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies specific to certain receptors can be made using knowledge and skill in the art of injecting test subjects with suitable antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion" or "fragment"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a domain antibody (dAb) fragment (Ward, et al., *Nature,* 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird, et al., *Science* 1988, 242, 423-426; and Huston, et al., Proc. *Natl. Acad. Sci. USA* 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies. In some embodiments, a scFv protein domain comprises a $V_H$ portion and a $V_L$ portion. A scFv molecule is denoted as either $V_L$-L-$V_H$ if the $V_L$ domain is the N-terminal part of the scFv molecule, or as $V_H$-L-$V_L$ if the $V_H$ domain is the N-terminal part of the scFv molecule. Methods for making scFv molecules and designing suitable peptide linkers are described in U.S. Pat. Nos. 4,704,692, 4,946,778, R. Raag and M. Whitlow, "Single Chain Fvs." FASEB Vol 9:73-80 (1995) and R. E. Bird and B. W. Walker, Single Chain Antibody Variable Regions, *TIBTECH*, Vol 9: 132-137 (1991), the disclosures of which are incorporated by reference herein.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In some embodiments, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgGI) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, including a conjugate of the antibody and another active pharmaceutical ingredient or antibody. The terms "conjugate," "antibody-drug conjugate", "ADC," or "immunoconjugate" refers to an antibody, or a fragment thereof, conjugated to another therapeutic moiety, which can be conjugated to antibodies described herein using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones, et al., *Nature* 1986, 321, 522-525; Riechmann, et al., *Nature* 1988, 332, 323-329; and Presta, *Curr. Op. Struct. Biol.* 1992, 2, 593-596. The antibodies described herein may also be modified to employ any Fc variant which is known to impart an improvement (e.g., reduction) in effector function and/or FcR binding. The Fc variants may include, for example, any one of the amino acid substitutions disclosed in International Patent Application Publication Nos. WO 1988/07089 A1, WO 1996/14339 A1, WO 1998/05787 A1, WO 1998/23289 A1, WO 1999/51642 A1, WO 99/58572 A1, WO 2000/09560 A2, WO 2000/32767 A1, WO 2000/42072 A2, WO 2002/44215 A2, WO 2002/060919 A2, WO 2003/074569 A2, WO 2004/016750 A2, WO 2004/029207 A2, WO 2004/035752 A2, WO 2004/063351 A2, WO 2004/074455 A2, WO 2004/099249 A2, WO 2005/040217 A2, WO 2005/070963 A1, WO 2005/077981 A2, WO 2005/092925 A2, WO 2005/123780 A2, WO 2006/019447 A1, WO 2006/047350 A2, and WO 2006/085967 A2; and U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784; the disclosures of which are incorporated by reference herein.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger, et al., *Proc. Nat. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see e.g. U.S. Patent Publication No. 2004/0110704 or Yamane-Ohnuki, et al., *Biotechnol. Bioeng.,* 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$)alkoxy-or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384 and U.S. Pat. No. 5,824,778, the disclosures of each of which are incorporated by reference herein.

The term "biosimilar" means a biological product, including a monoclonal antibody or protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

III. Gen 2 TIL Manufacturing Processes

Figure 2B:
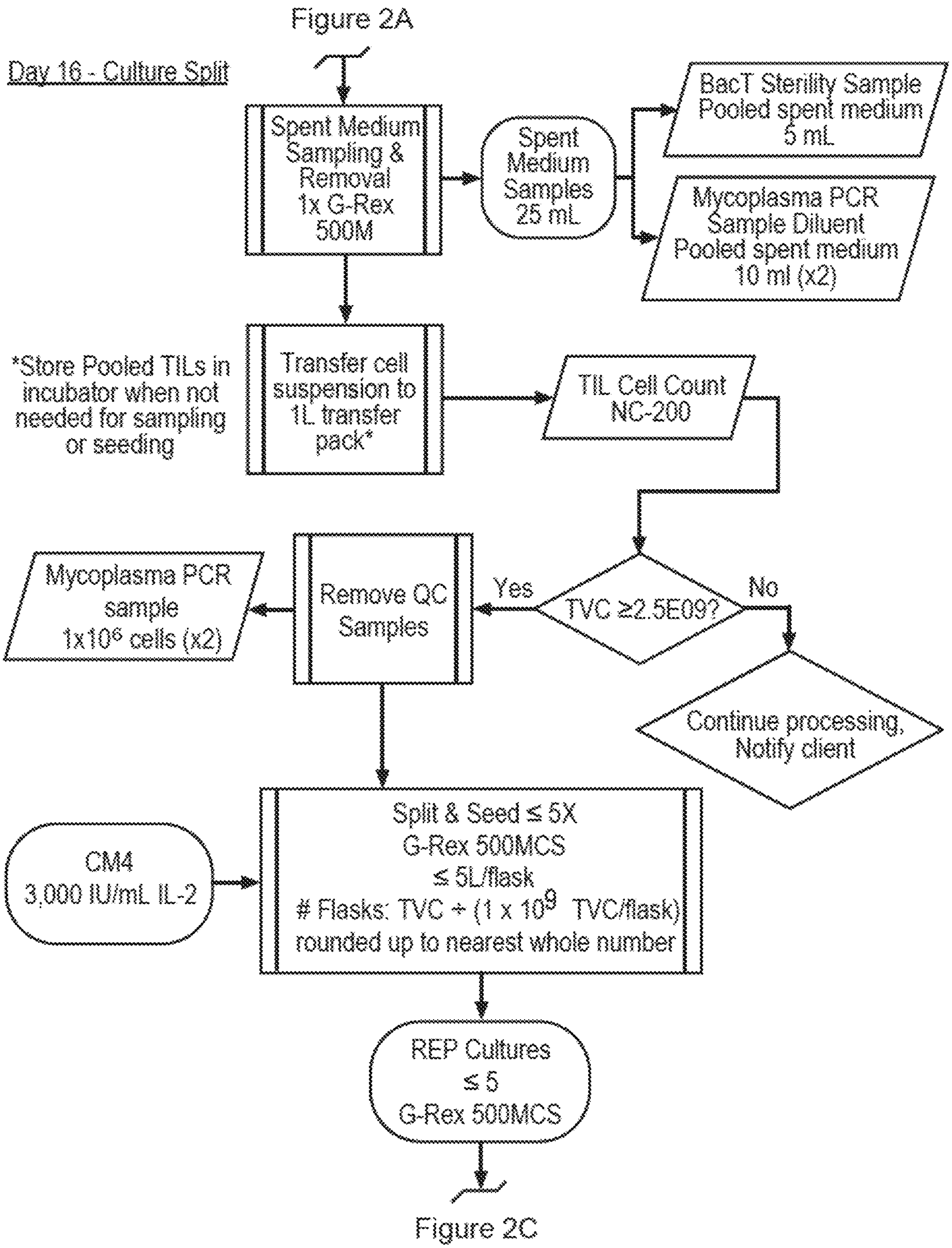
Figure 2C:
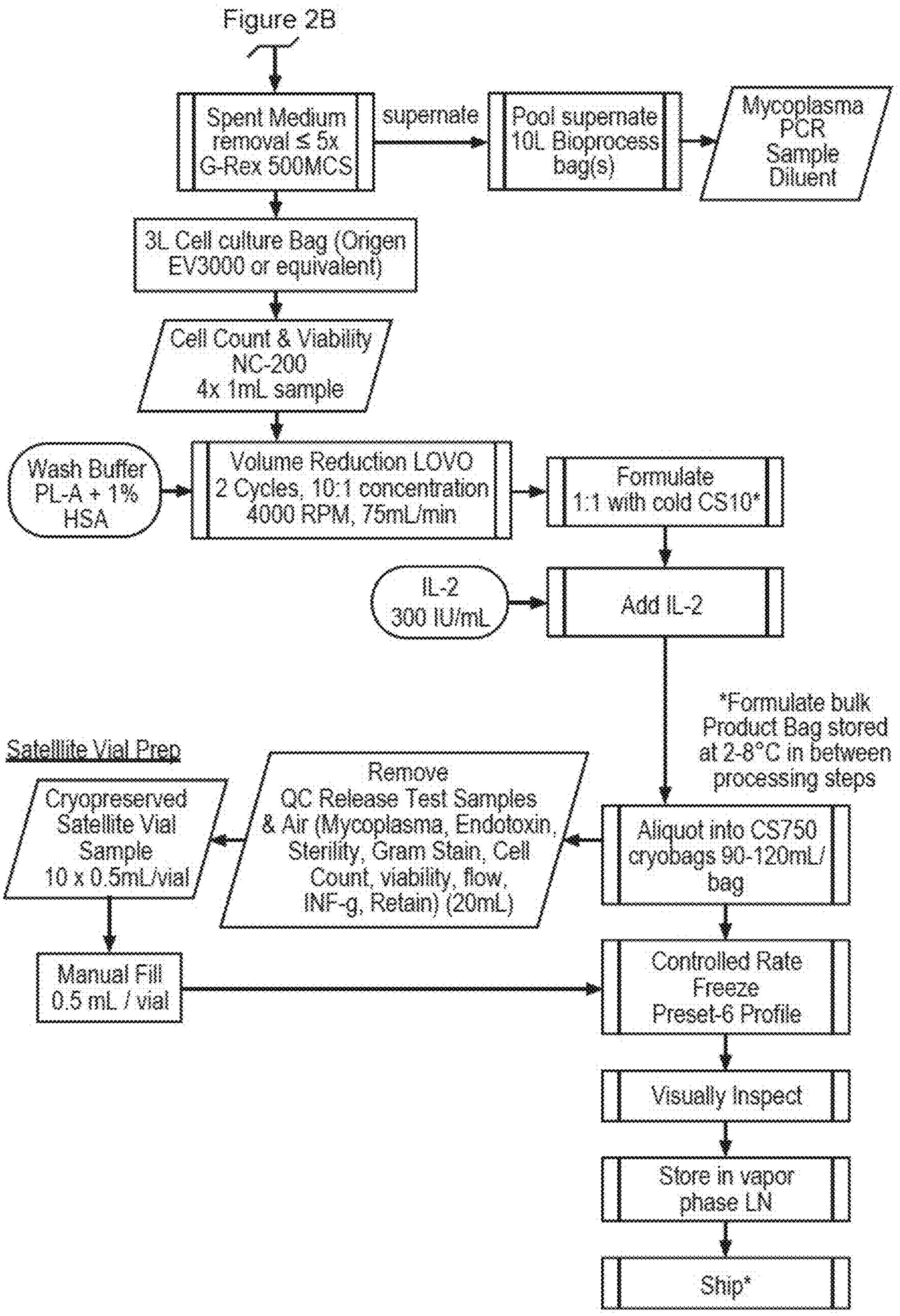
Figure 3:
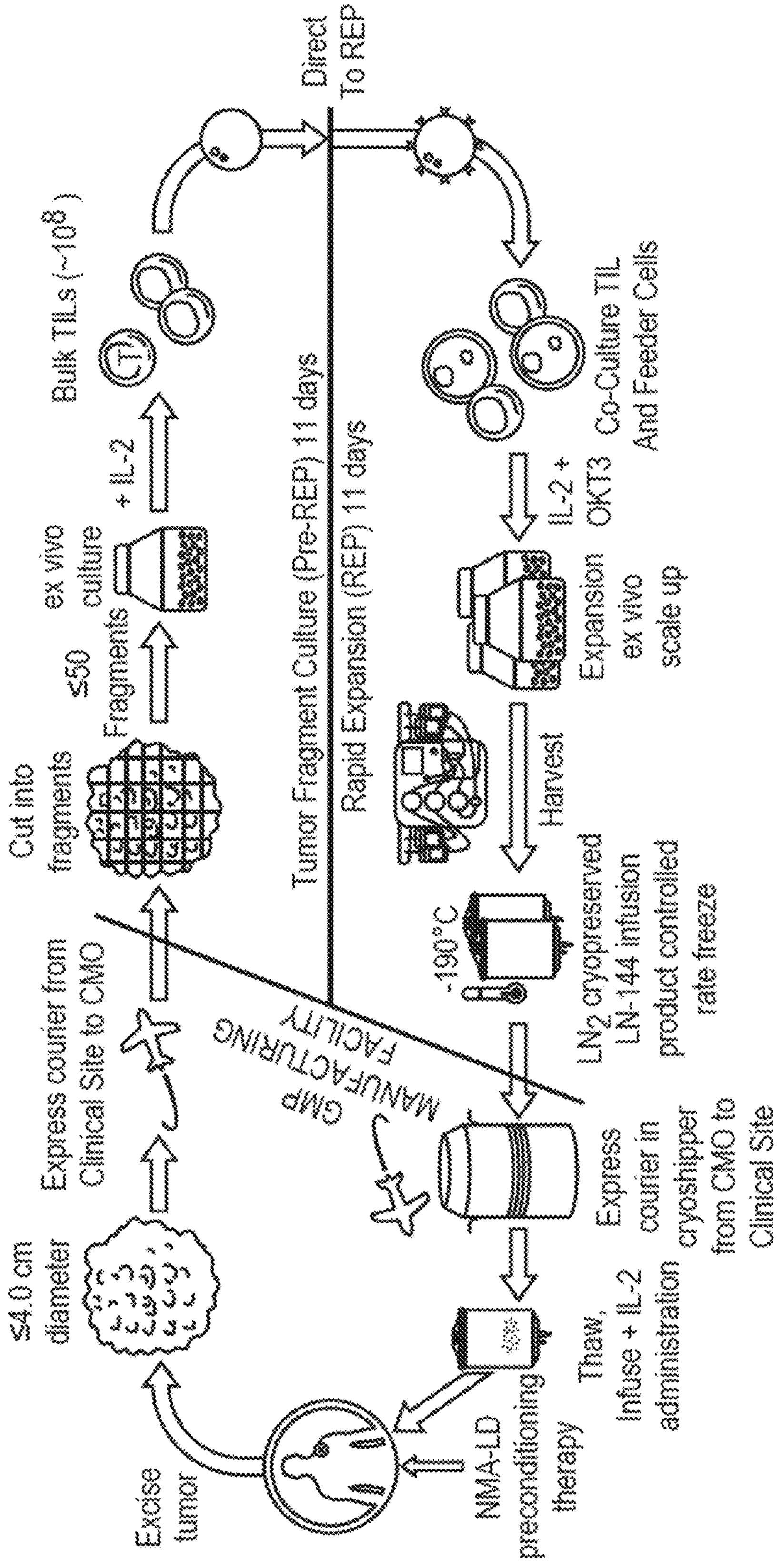
FIG. 3: Shows a diagram of an embodiment of a cryopreserved TIL exemplary manufacturing process (~22 days).

An exemplary family of TIL processes known as Gen 2 (also known as process 2A) containing some of these features is depicted in FIGS. 1 and 2. An embodiment of Gen 2 is shown in FIG. 2.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 1 as Step A) is shortened to 3 to 14 days and the second expansion (including processes referred to as the REP as well as processes shown in FIG. 1 as Step B) is shorted to 7 to 14 days, as discussed in detail below as well as in the examples and figures. In some embodiments, the first expansion (for example, an expansion described as Step B in FIG. 1) is shortened to 11 days and the second expansion (for example, an expansion as described in Step D in FIG. 1) is shortened to 11 days. In some embodiments, the combination of the first expansion and second expansion (for example, expansions described as Step B and Step D in FIG. 1) is shortened to 22 days, as discussed in detail below and in the examples and figures.

The "Step" Designations A, B, C, etc., below are in reference to FIG. 1 and in reference to certain embodiments described herein. The ordering of the Steps below and in FIG. 1 is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy, core biopsy, small biopsy, or other means for obtaining a sample that contains a mixture of tumor and TIL cells. In some embodiments, multilesional sampling is used. In some embodiments, surgical resection, needle biopsy, core biopsy, small biopsy, or other means for obtaining a sample that contains a mixture of tumor and TIL cells includes multilesional sampling (i.e., obtaining samples from one or more tumor sites and/or locations in the patient, as well as one or more tumors in the same location or in close proximity). In general, the tumor sample may be from any solid tumor, including primary tumors, invasive tumors or metastatic tumors. The tumor sample may also be a liquid tumor, such as a tumor obtained from a hematological malignancy. The solid tumor may be of lung tissue. In some embodiments, useful TILs are obtained from non-small cell lung carcinoma (NSCLC). The solid tumor may be of skin tissue. In some embodiments, useful TILs are obtained from a melanoma.

Once obtained, the tumor sample is generally fragmented using sharp dissection into small pieces of between 1 to about 8 $mm^3$, with from about 2-3 $mm^3$ being particularly useful. In some embodiments, the TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

Tumor dissociating enzyme mixtures can include one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof.

In some embodiments, the dissociating enzymes are reconstituted from lyophilized enzymes. In some embodiments, lyophilized enzymes are reconstituted in an amount of sterile buffer such as HBSS.

In some instances, collagenase (such as animal free-type 1 collagenase) is reconstitued in 10 mL of sterile HBSS or another buffer. The lyophilized stock enzyme may be at a concentration of 2892 PZ U/vial. In some embodiments, collagenase is reconstituted in 5 mL to 15 mL buffer. In some embodiment, after reconstitution the collagenase stock ranges from about 100 PZ U/mL-about 400 PZ U/mL, e.g., about 100 PZ U/mL-about 400 PZ U/mL, about 100 PZ U/mL-about 350 PZ U/mL, about 100 PZ U/mL-about 300 PZ U/mL, about 150 PZ U/mL-about 400 PZ U/mL, about 100 PZ U/mL, about 150 PZ U/mL, about 200 PZ U/mL, about 210 PZ U/mL, about 220 PZ U/mL, about 230 PZ U/mL, about 240 PZ U/mL, about 250 PZ U/mL, about 260 PZ U/mL, about 270 PZ U/mL, about 280 PZ U/mL, about 289.2 PZ U/mL, about 300 PZ U/mL, about 350 PZ U/mL, or about 400 PZ U/mL.

In some embodiments, neutral protease is reconstituted in 1-ml of sterile HBSS or another buffer. The lyophilized stock enzyme may be at a concentration of 175 DMC U/vial. In some embodiments, after reconstitution the neutral protease stock ranges from about 100 DMC/mL-about 400 DMC/mL, e.g., about 100 DMC/mL-about 400 DMC/mL, about 100 DMC/mL-about 350 DMC/mL, about 100 DMC/mL-about 300 DMC/mL, about 150 DMC/mL-about 400 DMC/mL, about 100 DMC/mL, about 110 DMC/mL, about 120 DMC/mL, about 130 DMC/mL, about 140 DMC/mL, about 150 DMC/mL, about 160 DMC/mL, about 170 DMC/mL, about 175 DMC/mL, about 180 DMC/mL, about 190 DMC/mL, about 200 DMC/mL, about 250 DMC/mL, about 300 DMC/mL, about 350 DMC/mL, or about 400 DMC/mL.

In some embodiments, DNAse I is reconstituted in 1-ml of sterile HBSS or another buffer. The lyophilized stock enzyme was at a concentration of 4 KU/vial. In some embodiments, after reconstitution the DNase I stock ranges from about 1 KU/mL-10 KU/mL, e.g., about 1 KU/mL, about 2 KU/mL, about 3 KU/mL, about 4 KU/mL, about 5 KU/mL, about 6 KU/mL, about 7 KU/mL, about 8 KU/mL, about 9 KU/mL, or about 10 KU/mL.

In some embodiments, the stock of enzymes is variable and the concentrations may need to be determined. In some embodiments, the concentration of the lyophilized stock can be verified. In some embodiments, the final amount of enzyme added to the digest cocktail is adjusted based on the determined stock concentration.

In some embodiment, the enzyme mixture includes about 10.2-ul of neutral protease (0.36 DMC U/mL), 21.3-ul of collagenase (1.2 PZ/mL) and 250-ul of DNAse I (200 U/mL) in about 4.7-ml of sterile HBSS.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/mL 10× working stock.

In some embodiments, the enzyme mixture comprises DNAse. In some embodiments, the working stock for the DNAse is a 10,000IU/mL 10× working stock.

In some embodiments, the enzyme mixture comprises hyaluronidase. In some embodiments, the working stock for the hyaluronidase is a 10-mg/mL 10× working stock.

In some embodiments, the enzyme mixture comprises 10 mg/mL collagenase, 1000 IU/mL DNAse, and 1 mg/mL hyaluronidase.

In some embodiments, the enzyme mixture comprises 10 mg/mL collagenase, 500 IU/mL DNAse, and 1 mg/mL hyaluronidase.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from digesting or fragmenting a tumor sample obtained from a patient.

In some embodiments, where the tumor is a solid tumor, the tumor undergoes physical fragmentation after the tumor sample is obtained in, for example, Step A (as provided in FIG. 1). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 1, as well as FIG. 8.

1. Pleural Effusion T-Cells or TILs

In some embodiments, the sample is a pleural fluid sample. In some embodiments, the source of the T-cells or TILs for expansion according to the processes described herein is a pleural fluid sample. In some embodiments, the sample is a pleural effusion derived sample. In some embodiments, the source of the T-cells or TILs for expansion according to the processes described herein is a pleural effusion derived sample. See, for example, methods described in U.S. Patent Publication US 2014/0295426, incorporated herein by reference in its entirety for all purposes.

In some embodiments, any pleural fluid or pleural effusion suspected of and/or containing TILs can be employed. Such a sample may be derived from a primary or metastatic lung cancer, such as NSCLC or SCLC. In some embodiments, the sample may be secondary metastatic cancer cells which originated from another organ, e.g., breast, ovary, colon or prostate. In some embodiments, the sample for use in the expansion methods described herein is a pleural exudate. In some embodiments, the sample for use in the expansion methods described herein is a pleural transudate. Other biological samples may include other serous fluids containing TILs, including, e.g., ascites fluid from the abdomen or pancreatic cyst fluid. Ascites fluid and pleural fluids involve very similar chemical systems; both the abdomen and lung have mesothelial lines and fluid forms in the pleural space and abdominal spaces in the same matter in malignancies and such fluids in some embodiments contain TILs. In some embodiments, wherein the disclosure exemplifies pleural fluid, the same methods may be performed with similar results using ascites or other cyst fluids containing TILs.

In some embodiments, the pleural fluid is in unprocessed form, directly as removed from the patient. In some embodiments, the unprocessed pleural fluid is placed in a standard blood collection tube, such as an EDTA or Heparin tube, prior to the contacting step. In some embodiments, the unprocessed pleural fluid is placed in a standard CellSave® tube (Veridex) prior to the contacting step. In some embodiments, the sample is placed in the CellSave tube immediately after collection from the patient to avoid a decrease in the number of viable TILs. The number of viable TILs can decrease to a significant extent within 24 hours, if left in the untreated pleural fluid, even at 4° C. In some embodiments, the sample is placed in the appropriate collection tube within 1 hour, 5 hours, 10 hours, 15 hours, or up to 24 hours after removal from the patient. In some embodiments, the sample is placed in the appropriate collection tube within 1 hour, 5 hours, 10 hours, 15 hours, or up to 24 hours after removal from the patient at 4° C.

In some embodiments, the pleural fluid sample from the chosen subject may be diluted. In one embodiment, the dilution is 1:10 pleural fluid to diluent. In some embodiments, the dilution is 1:9 pleural fluid to diluent. In some embodiments, the dilution is 1:8 pleural fluid to diluent. In some embodiments, the dilution is 1:5 pleural fluid to diluent. In some embodiments, the dilution is 1:2 pleural fluid to diluent. In some embodiments, the dilution is 1:1 pleural fluid to diluent. In some embodiments, diluents include saline, phosphate buffered saline, another buffer or a physiologically acceptable diluent. In some embodiments, the sample is placed in the CellSave tube immediately after collection from the patient and dilution to avoid a decrease in the viable TILs, which may occur to a significant extent within 24-48 hours, if left in the untreated pleural fluid, even at 4° C. In some embodiments, the pleural fluid sample is placed in the appropriate collection tube within 1 hour, 5 hours, 10 hours, 15 hours, 24 hours, 36 hours, up to 48 hours after removal from the patient, and dilution. In some embodiments, the pleural fluid sample is placed in the appropriate collection tube within 1 hour, 5 hours, 10 hours, 15 hours, 24 hours, 36 hours, up to 48 hours after removal from the patient, and dilution at 4° C.

In still another embodiment, pleural fluid samples are concentrated by conventional means prior further processing steps. In some embodiments, this pre-treatment of the pleural fluid is preferable in circumstances in which the pleural fluid must be cryopreserved for shipment to a laboratory performing the method or for later analysis (e.g., later than 24-48 hours post-collection). In some embodiments, the pleural fluid sample is prepared by centrifuging the pleural fluid sample after its withdrawal from the subject and resuspending the centrifugate or pellet in buffer. In some embodiments, the pleural fluid sample is subjected to multiple centrifugations and resuspensions, before it is cryopreserved for transport or later analysis and/or processing.

In some embodiments, pleural fluid samples are concentrated prior to further processing steps by using a filtration method. In some embodiments, the pleural fluid sample used in the contacting step is prepared by filtering the fluid through a filter containing a known and essentially uniform pore size that allows for passage of the pleural fluid through the membrane but retains the tumor cells. In some embodiments, the diameter of the pores in the membrane may be at least 4 μM. In some embodiments the pore diameter may be 5 μM or more, and in other embodiment, any of 6, 7, 8, 9, or 10 μM. After filtration, the cells, including TILs, retained by the membrane may be rinsed off the membrane into a suitable physiologically acceptable buffer. Cells, including TILs, concentrated in this way may then be used in the contacting step of the method.

In some embodiment, pleural fluid sample (including, for example, the untreated pleural fluid), diluted pleural fluid, or the resuspended cell pellet, is contacted with a lytic reagent that differentially lyses non-nucleated red blood cells present in the sample. In some embodiments, this step is performed prior to further processing steps in circumstances in which the pleural fluid contains substantial numbers of RBCs. Suitable lysing reagents include a single lytic reagent or a lytic reagent and a quench reagent, or a lytic agent, a quench reagent and a fixation reagent. Suitable lytic systems are marketed commercially and include the BD Pharm Lyse™ system (Becton Dickenson). Other lytic systems include the Versalyse™ system, the FACSlyse™ system (Becton Dickenson), the Immunoprep™ system or Erythrolyse II system (Beckman Coulter, Inc.), or an ammonium chloride system. In some embodiments, the lytic reagent can vary with the primary requirements being efficient lysis of the red blood cells, and the conservation of the TILs and phenotypic properties of the TILs in the pleural fluid. In addition to employing a single reagent for lysis, the lytic systems useful in methods described herein can include a second reagent, e.g., one that quenches or retards the effect of the lytic reagent during the remaining steps of the method, e.g., Stabilyse™ reagent (Beckman Coulter, Inc.). A conventional fixation reagent may also be employed depending upon the choice of lytic reagents or the preferred implementation of the method.

In some embodiments, the pleural fluid sample, unprocessed, diluted or multiply centrifuged or processed as described herein above is cryopreserved at a temperature of about −140° C. prior to being further processed and/or expanded as provided herein.

B. STEP B: First Expansion

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, et al., *Scand. J. Immunol.* 2012, 75, 157-167; Dudley, et al., *Clin. Cancer Res.* 2010, 16, 6122-6131; Huang, et al., *J Immunother.* 2005, 28, 258-267; Besser, et al., *Clin. Cancer Res.* 2013, 19, OF1-OF9; Besser, et al., *J Immunother.* 2009, 32:415-423; Robbins, et al., *J Immunol.* 2004, 173, 7125-7130; Shen, et al., *J. Immunother.,* 2007, 30, 123-129; Zhou, et al., *J Immunother.* 2005, 28, 53-62; and Tran, et al., *J Immunother.,* 2008, 31, 742-751, each of which is incorporated herein by reference.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 1. In some embodiments, the TILs obtained by the present method exhibit an increase in the T-cell repertoire diversity as compared to freshly harvested TILs and/or TILs prepared using methods referred to as process 1C, as exemplified in FIG. 5 and/or FIG. 6. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 1, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In some embodiments, expansion of TILs may be performed using an initial bulk TIL expansion step (for example such as those described in Step B of FIG. 1, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Coming Incorporated, Coming, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-REX10; Wilson Wolf Manufacturing, New Brighton, MN), each flask was loaded with $10\text{-}40\times10^6$ viable tumor digest cells or 5-30 tumor fragments in 10-40 mL of CM with IL-2. Both the G-REX10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $S^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2.

In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more ammo acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine. L-threonine, L-tryptophan, L-tyrosine, L-valine, thiamine, reduced glutathione, L-ascorbic acid-2-phosphate, iron saturated transferrin, insulin, and compounds containing, the trace element moieties Ag, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640. F-10, F-12, Minimal Essential Medium (.MEM), Glasgow's Minimal Essential Medium (G-MEM), RPM1 growh medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e. g, AlbuMAX®1I) is about 5000-50,000 mg/L.

In some embodiments, the non-trace element moiety ingredients in the defined medium are present in the concentration ranges listed in the column under the heading "Concentration Range in TX Medium" in Table 4. In other embodiments, the non-trace element moiety ingredients in the defined medium are present in the final concentrations listed in the column under the heading "A Preferred Embodiment of the TX Medium" in Table 4. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table 4 below.

TABLE 4

Concentrations of Non-Trace Element Moiety Ingredients

| Ingredient | A preferred embodiment in supplement (mg/L) (About) | Concentration range in 1× medium (mg/L) (About) | A preferred embodiment in 1× medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ® I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In some embodiments, the cell medium in the first and/or second gas permeable container is unfiltered. The use of unfiltered cell medium may simplify the procedures necessary to expand the number of cells. In some embodiments, the cell medium in the first and/or second gas permeable container lacks beta-mercaptoethanol (BME or PME; also known as 2-mercaptoethanol, CAS 60-24-2).

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of an APC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 5. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In some embodiments, the cell culture medium further comprises IL-2. In some embodiments, the cell culture medium comprises about 3000 IU/mL of IL-2. In some embodiments, the cell culture medium further comprises IL-2. In some embodiments, the cell culture medium comprises about 3000 IU/mL of IL-2. In some embodiments, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In some embodiments, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In some embodiments, the cell culture medium further comprises IL-15. In some embodiments, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In some embodiments, the cell culture medium further comprises IL-21. In some embodiments, the cell culture medium comprises about 1 IU/mL of IL-21.

In some embodiments, the cell culture medium comprises an anti-CD3 agonist antibody, e.g., OKT-3 antibody. In some embodiments, the cell culture medium comprises about 30 ng/mL of OKT-3 antibody. In some embodiments, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In some embodiments, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab. See, for example, Table 1.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-REX10; Wilson Wolf Manufacturing, New Brighton, MN), each flask was loaded with 10-40×$10^6$ viable tumor digest cells or 5-30 tumor fragments in 10-40 mL of CM with IL-2. Both the G-REX10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 1. In some embodiments, the first expansion occurs in an initial cell culture medium or a first cell culture medium. In some embodiments, the initial cell culture medium or the first cell culture medium comprises IL-2.

Figure 4:
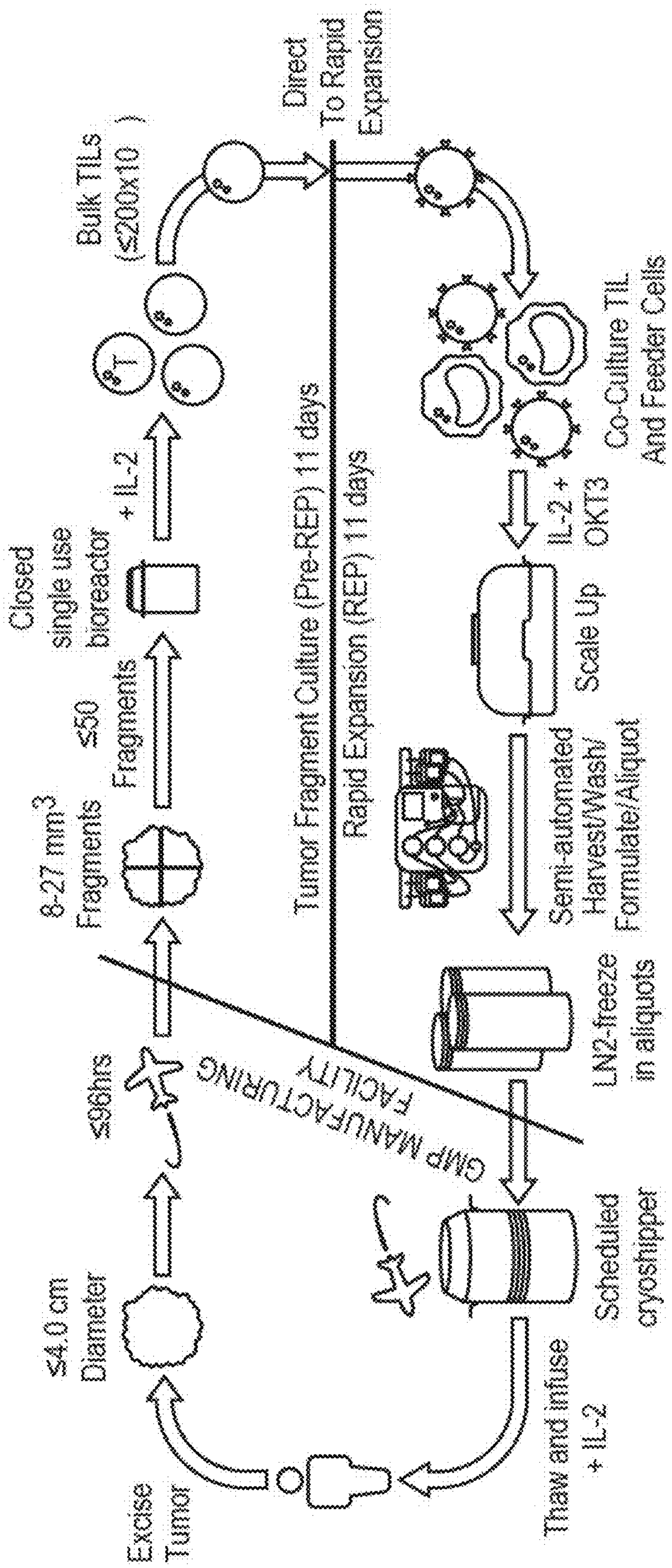
FIG. 4: Shows a diagram of an embodiment of Gen 2, a 22-day process for TIL manufacturing.

In some embodiments, the first expansion (including processes such as for example those described in Step B of FIG. 1, which can include those sometimes referred to as the pre-REP) process is shortened to 3-14 days, as discussed in the examples and figures. In some embodiments, the first expansion (including processes such as for example those described in Step B of FIG. 1, which can include those sometimes referred to as the pre-REP) is shortened to 7 to 14 days, as discussed in the Examples and shown in FIGS. 4 and 5, as well as including for example, an expansion as described in Step B of FIG. 1. In some embodiments, the first expansion of Step B is shortened to 10-14 days. In some embodiments, the first expansion is shortened to 11 days, as discussed in, for example, an expansion as described in Step B of FIG. 1.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 1, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 1 and as described herein.

In some embodiments, the first expansion (including processes referred to as the pre-REP; for example, Step B according to FIG. 1) process is shortened to 3 to 14 days, as discussed in the examples and figures. In some embodiments, the first expansion of Step B is shortened to 7 to 14 days. In some embodiments, the first expansion of Step B is shortened to 10 to 14 days. In some embodiments, the first expansion is shortened to 11 days.

In some embodiments, the first expansion, for example, Step B according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Cytokines and Other Additives

The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is described in U.S. Patent Application Publication No. US 2017/0107490 A1, the disclosure of which is incorporated by reference herein. Thus, possible combinations include IL-2 and IL-15, IL-2 and IL-21, IL-15 and IL-21 and IL-2, or IL-15 and IL-21, with the latter finding particular use in many embodiments. The use of combinations of cytokines specifically favors the generation of lymphocytes, and in particular T-cells as described therein.

In some embodiments, Step B may also include the addition of OKT-3 antibody or muromonab to the culture media, as described elsewhere herein. In some embodiments, Step B may also include the addition of a 4-1BB agonist to the culture media, as described elsewhere herein. In some embodiments, Step B may also include the addition of an OX-40 agonist to the culture media, as described elsewhere herein. In other embodiments, additives such as peroxisome proliferator-activated receptor gamma coactivator I-alpha agonists, including proliferator-activated receptor (PPAR)-gamma agonists such as a thiazolidinedione compound, may be used in the culture media during Step B, as described in U.S. Patent Application Publication No. US 2019/0307796 A1, the disclosure of which is incorporated by reference herein.

C. STEP C: First Expansion to Second Expansion Transition

In some cases, the bulk TIL population obtained from the first expansion, including for example the TIL population obtained from for example, Step B as indicated in FIG. 1, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 1) are stored until phenotyped for selection. In some embodiments, the TILs obtained from the first expansion (for example, from Step B as indicated in FIG. 1) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 1). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

D. STEP D: Second Expansion

In some embodiments, the TIL cell population is expanded in number after harvest and initial bulk processing for example, after Step A and Step B, and the transition referred to as Step C, as indicated in FIG. 1). This further expansion is referred to herein as the second expansion, which can include expansion processes generally referred to in the art as a rapid expansion process (REP; as well as processes as indicated in Step D of FIG. 1). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 1) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In some embodiments, the second expansion can be performed in a gas permeable container using the methods of the present disclosure (including for example, expansions referred to as REP; as well as processes as indicated in Step D of FIG. 1). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/mL of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+allogeneic lymphocytes and IL-2.

In some embodiments, the cell culture medium further comprises IL-2. In some embodiments, the cell culture medium comprises about 3000 IU/mL of IL-2. In some embodiments, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In some embodiments, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In some embodiments, the cell culture medium comprises OKT-3 antibody. In some embodiments, the cell culture medium comprises about 30 ng/mL of OKT-3 antibody. In some embodiments, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In some embodiments, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 1, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15.

In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In some embodiments, the cell culture medium further comprises IL-15. In some embodiments, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In some embodiments, the cell culture medium further comprises IL-21. In some embodiments, the cell culture medium comprises about 1 IU/mL of IL-21.

In some embodiments the antigen-presenting feeder cells (APCs) are PBMCs. In some embodiments, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In some embodiments, the ratio of TILs to PBMCs in the rapid expansion and/or the second expansion is between 1 to 50 and 1 to 300. In some embodiments, the ratio of TILs to PBMCs in the rapid expansion and/or the second expansion is between 1 to 100 and 1 to 200.

In some embodiments, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 mL media. Media replacement is done (generally 2/3 media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In some embodiments, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-REX flasks). In some embodiments, the second expansion (including expansions referred to as rapid expansions) is performed in T-175 flasks, and about $1\times10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per mL of anti-CD3. The T-175 flasks may be incubated at 370 C in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 mL of TIL suspension. The number of cells in each bag was counted every day or two and fresh media was added to keep the cell count between 0.5 and $2.0\times10^6$ cells/mL.

In some embodiments, the second expansion (which can include expansions referred to as REP, as well as those referred to in Step D of FIG. 1) may be performed in 500 mL capacity gas permeable flasks with 100 cm gas-permeable silicon bottoms (G-REX 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per mL of anti-CD3 (OKT3). The G-REX 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-REX 100 flasks. When TIL are expanded serially in G-REX 100 flasks, on day 7 the TIL in each G-REX 100 may be suspended in the 300 mL of media present in each flask and the cell suspension may be divided into 3 100 mL aliquots that may be used to seed 3 G-REX 100 flasks. Then 150 mL of AIM-V with 5% human AB serum and 3000 IU per mL of IL-2 may be added to each flask. The G-REX 100 flasks may be incubated at 370 C in 5% $CO_2$ and after 4 days 150 mL of AIM-V with 3000 IU per mL of IL-2 may be added to each G-REX 100 flask. The cells may be harvested on day 14 of culture.

In some embodiments, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 mL media. In some embodiments, media replacement is done until the cells are transferred to an alternative growth chamber. In some embodiments, 2/3 of the media is replaced by respiration with fresh media. In some embodiments, alternative growth chambers include G-REX flasks and gas permeable containers as more fully discussed below.

In some embodiments, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

In some embodiments, the second expansion (including expansions referred to as REP) of TIL can be performed using T-175 flasks and gas-permeable bags as previously described (Tran, et al., 2008, *JImmunother.*, 31:742-751, and Dudley, et al., 2003, *J Immunother.*, 26:332-342) or gas-permeable G-REX flasks. In some embodiments, the second expansion is performed using flasks. In some embodiments, the second expansion is performed using gas-permeable G-REX flasks. In some embodiments, the second expansion is performed in T-175 flasks, and about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 $cm^2$ gas-permeable silicon bottoms (G-REX 100, Wilson Wolf), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-REX 100 flasks are incubated at 37° C. in 5% $CO_2$. In some embodiments, on day 5, 250 mL of supernatant is removed and placed into centrifuge bottles and centrifuged at 1500 rpm (491g) for 10 minutes. The TIL pellets can then be resuspended with 150 mL of fresh 50/50 medium with 3000 IU/mL of IL-2 and added back to the original G-REX 100 flasks. In embodiments where TILs are expanded serially in G-REX 100 flasks, on day 7 the TIL in each G-REX 100 are suspended in the 300 mL of media present in each flask and the cell suspension was divided into three 100 mL aliquots that are used to seed 3 G-REX 100 flasks. Then 150 mL of AIM-V with 5% human AB serum and 3000 IU/mL of IL-2 is added to each flask. The G-REX 100 flasks are incubated at 37° C. in 5% $CO_2$ and after 4 days 150 mL of AIM-V with 3000 IU/mL of IL-2 is added to each G-REX 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one Or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine. L-threonine, L-tryptophan, L-tyrosine, L-valine, thiamine, reduced glutathione, L-ascorbic acid-2-phosphate, iron saturated transferrin insulin and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 16-40 F-10, F-12, Minimal Essential Medium (αMEM), Glasgow's Minimal Essential Medium (C-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table 4. In other embodiments, the non-trace element moiety ingredients in the defined medium are present in the final concentrations listed in the column under the heading "A Preferred Embodiment of the 1× Medium" in Table 4. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table 4.

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In some embodiments, the cell medium in the first and/or second gas permeable container is unfiltered. The use of unfiltered cell medium may simplify the procedures necessary to expand the number of cells. In some embodiments, the cell medium in the first and/or second gas permeable container lacks beta-mercaptoethanol (BME or PME; also known as 2-mercaptoethanol, CAS 60-24-2).

In some embodiments, the second expansion, for example, Step D according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, the step of rapid or second expansion is split into a plurality of steps to achieve a scaling up of the culture by: (a) performing the rapid or second expansion by culturing TILs in a small scale culture in a first container, e.g., a G-REX-100 MCS container, for a period of about 3 to 7 days, and then (b) effecting the transfer of the TILs in the small scale culture to a second container larger than the first container, e.g., a G-REX-500-MCS container, and culturing the TILs from the small scale culture in a larger scale culture in the second container for a period of about 4 to 7 days.

In some embodiments, the step of rapid or second expansion is split into a plurality of steps to achieve a scaling out of the culture by: (a) performing the rapid or second expansion by culturing TILs in a first small scale culture in a first container, e.g., a G-REX-100 MCS container, for a period of about 3 to 7 days, and then (b) effecting the transfer and apportioning of the TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the TILs from first small scale culture transferred to such second container is cultured in a second small scale culture for a period of about 4 to 7 days.

In some embodiments, the first small scale TIL culture is apportioned into a plurality of about 2 to 5 subpopulations of TILs.

In some embodiments, the step of rapid or second expansion is split into a plurality of steps to achieve a scaling out and scaling up of the culture by: (a) performing the rapid or second expansion by culturing TILs in a small scale culture in a first container, e.g., a G-REX-100 MCS container, for a period of about 3 to 7 days, and then (b) effecting the transfer and apportioning of the TILs from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX-500MCS containers, wherein in each second container the portion of the TILs from the small scale culture transferred to such second container is cultured in a larger scale culture for a period of about 4 to 7 days.

In some embodiments, the step of rapid or second expansion is split into a plurality of steps to achieve a scaling out and scaling up of the culture by: (a) performing the rapid or second expansion by culturing TILs in a small scale culture in a first container, e.g., a G-REX-100 MCS container, for a period of about 5 days, and then (b) effecting the transfer and apportioning of the TILs from the small scale culture into and amongst 2, 3 or 4 second containers that are larger in size than the first container, e.g., G-REX-500 MCS containers, wherein in each second container the portion of the TILs from the small scale culture transferred to such second container is cultured in a larger scale culture for a period of about 6 days.

In some embodiments, upon the splitting of the rapid or second expansion, each second container comprises at least $10^8$ TILs. In some embodiments, upon the splitting of the rapid or second expansion, each second container comprises at least $10^8$ TILs, at least $10^9$ TILs, or at least $10^{10}$ TILs. In one exemplary embodiment, each second container comprises at least $10^{10}$ TILs.

In some embodiments, the first small scale TIL culture is apportioned into a plurality of subpopulations. In some embodiments, the first small scale TIL culture is apportioned into a plurality of about 2 to 5 subpopulations. In some embodiments, the first small scale TIL culture is apportioned into a plurality of about 2, 3, 4, or 5 subpopulations.

In some embodiments, after the completion of the rapid or second expansion, the plurality of subpopulations comprises a therapeutically effective amount of TILs. In some embodiments, after the completion of the rapid or second expansion, one or more subpopulations of TILs are pooled together to produce a therapeutically effective amount of TILs. In some embodiments, after the completion of the rapid expansion, each subpopulation of TILs comprises a therapeutically effective amount of TILs.

In some embodiments, the rapid or second expansion is performed for a period of about 3 to 7 days before being split into a plurality of steps. In some embodiments, the splitting of the rapid or second expansion occurs at about day 3, day 4, day 5, day 6, or day 7 after the initiation of the rapid or second expansion.

In some embodiments, the splitting of the rapid or second expansion occurs at about day 7, day 8, day 9, day 10, day 11, day 12, day 13, day 14, day 15, or day 16 day 17, or day 18 after the initiation of the first expansion (i.e., pre-REP expansion). In one exemplary embodiment, the splitting of the rapid or second expansion occurs at about day 16 after the initiation of the first expansion.

In some embodiments, the rapid or second expansion is further performed for a period of about 7 to 11 days after the splitting. In some embodiments, the rapid or second expansion is further performed for a period of about 5 days, 6 days, 7 days, 8 days, 9 days, 10 days, or 11 days after the splitting.

In some embodiments, the cell culture medium used for the rapid or second expansion before the splitting comprises the same components as the cell culture medium used for the rapid or second expansion after the splitting. In some embodiments, the cell culture medium used for the rapid or second expansion before the splitting comprises different components from the cell culture medium used for the rapid or second expansion after the splitting.

In some embodiments, the cell culture medium used for the rapid or second expansion before the splitting comprises IL-2, optionally OKT-3 and further optionally APCs. In some embodiments, the cell culture medium used for the rapid or second expansion before the splitting comprises IL-2, OKT-3, and further optionally APCs. In some embodiments, the cell culture medium used for the rapid or second expansion before the splitting comprises IL-2, OKT-3 and APCs.

In some embodiments, the cell culture medium used for the rapid or second expansion before the splitting is generated by supplementing the cell culture medium in the first expansion with fresh culture medium comprising IL-2, optionally OKT-3 and further optionally APCs. In some embodiments, the cell culture medium used for the rapid or second expansion before the splitting is generated by supplementing the cell culture medium in the first expansion with fresh culture medium comprising IL-2, OKT-3 and APCs. In some embodiments, the cell culture medium used for the rapid or second expansion before the splitting is generated by replacing the cell culture medium in the first expansion with fresh cell culture medium comprising IL-2, optionally OKT-3 and further optionally APCs. In some embodiments, the cell culture medium used for the rapid or second expansion before the splitting is generated by replacing the cell culture medium in the first expansion with fresh cell culture medium comprising IL-2, OKT-3 and APCs.

In some embodiments, the cell culture medium used for the rapid or second expansion after the splitting comprises IL-2, and optionally OKT-3. In some embodiments, the cell culture medium used for the rapid or second expansion after the splitting comprises IL-2, and OKT-3. In some embodiments, the cell culture medium used for the rapid or second expansion after the splitting is generated by replacing the cell culture medium used for the rapid or second expansion before the splitting with fresh culture medium comprising IL-2 and optionally OKT-3. In some embodiments, the cell culture medium used for the rapid or second expansion after the splitting is generated by replacing the cell culture medium used for the rapid or second expansion before the splitting with fresh culture medium comprising IL-2 and OKT-3.

In some embodiments, the splitting of the rapid expansion occurs in a closed system.

In some embodiments, the scaling up of the TIL culture during the rapid or second expansion comprises adding fresh cell culture medium to the TIL culture (also referred to as feeding the TILs). In some embodiments, the feeding comprises adding fresh cell culture medium to the TIL culture frequently. In some embodiments, the feeding comprises adding fresh cell culture medium to the TIL culture at a regular interval. In some embodiments, the fresh cell culture medium is supplied to the TILs via a constant flow. In some embodiments, an automated cell expansion system such as Xuri W25 is used for the rapid expansion and feeding.

1. Feeder Cells and Antigen Presenting Cells

In some embodiments, the second expansion procedures described herein (for example including expansion such as those described in Step D from FIG. 1, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/mL OKT3 antibody and 3000 IU/mL IL-2.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/mL OKT3 antibody and 1000-6000 IU/mL IL-2. In some embodiments, the PBMCs are cultured in the presence of 10-50 ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2.

In some embodiments, the antigen-presenting feeder cells are PBMCs. In some embodiments, the antigen-presenting feeder cells are artificial antigen-presenting feeder cells. In some embodiments, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In some embodiments, the ratio of TILs to antigen-presenting feeder cells in the second expansion is between 1 to 50 and 1 to 300. In some embodiments, the ratio of TIL to antigen-presenting feeder cells in the second expansion is between 1 to 100 and 1 to 200.

In some embodiments, the second expansion procedures described herein require a ratio of about $2.5\times10^9$ feeder cells to about $100\times10^6$ TIL. In some embodiments, the second expansion procedures described herein require a ratio of about $2.5\times10^9$ feeder cells to about $50\times10^6$ TIL. In yet another embodiment, the second expansion procedures described herein require about $2.5\times10^9$ feeder cells to about $25\times10^6$ TIL.

In some embodiments, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In some embodiments, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In some embodiments, artificial antigen presenting cells are used in the second expansion as a replacement for, or in combination with, PBMCs. 2. Cytokines The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is described in U.S. Patent Application US 2017/0107490 A1, the disclosure of which is incorporated by reference herein. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

In some embodiments, Step D may also include the addition of OKT-3 antibody or muromonab to the culture media, as described elsewhere herein. In some embodiments, Step D may also include the addition of a 4-1BB agonist to the culture media, as described elsewhere herein. In some embodiments, Step D may also include the addition of an OX-40 agonist to the culture media, as described elsewhere herein. In addition, additives such as peroxisome proliferator-activated receptor gamma coactivator I-alpha agonists, including proliferator-activated receptor (PPAR)-gamma agonists such as a thiazolidinedione compound, may be used in the culture media during Step D, as described in U.S. Patent Application Publication No. US 2019/0307796 A1, the disclosure of which is incorporated by reference herein.

E. STEP E: Harvest TILs

After the second expansion step, cells can be harvested. In some embodiments the TILs are harvested after one, two, three, four or more expansion steps, for example as provided in FIG. 1. In some embodiments the TILs are harvested after two expansion steps, for example as provided in FIG. 1.

TILs can be harvested in any appropriate and sterile manner, including for example by centrifugation. Methods for TIL harvesting are well known in the art and any such know methods can be employed with the present process. In some embodiments, TILs are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 1, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, Step E according to FIG. 1, is performed according to the processes described herein. In some embodiments, the closed system is accessed via syringes under sterile conditions in order to maintain the sterility and closed nature of the system. In some embodiments, a closed system as described in the Examples is employed.

In some embodiments, TILs are harvested according to the methods described in the Examples. In some embodiments, TILs between days 1 and 11 are harvested using the methods as described in the steps referred herein, such as in the day 11 TIL harvest in the Examples. In some embodiments, TILs between days 12 and 24 are harvested using the methods as described in the steps referred herein, such as in the Day 22 TIL harvest in the Examples. In some embodiments, TILs between days 12 and 22 are harvested using the methods as described in the steps referred herein, such as in the Day 22 TIL harvest in the Examples.

F. STEP F: Final Formulation and Transfer to Infusion Container

After Steps A through E as provided in an exemplary order in FIG. 1 and as outlined in detailed above and herein are complete, cells are transferred to a container for use in administration to a patient, such as an infusion bag or sterile vial. In some embodiments, once a therapeutically sufficient number of TILs are obtained using the expansion methods described above, they are transferred to a container for use in administration to a patient.

In some embodiments, TILs expanded using APCs of the present disclosure are administered to a patient as a pharmaceutical composition. In some embodiments, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

IV. Gen 3 TIL Manufacturing Processes

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells. In some embodiments, the step of rapid second expansion is split into a plurality of steps to achieve a scaling up of the culture by: (a) performing the rapid second expansion by culturing T cells in a small scale culture in a first container, e.g., a G-REX 100MCS container, for a period of about 3 to 4 days, and then (b) effecting the transfer of the T cells in the small scale culture to a second container larger than the first container, e.g., a G-REX 500MCS container, and culturing the T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T cells in a first small scale culture in a first container, e.g., a G-REX TOOMCS container, for a period of about 3 to 4 days, and then (b) effecting the transfer and apportioning of the T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX TOOMCS container, for a period of about 3 to 4 days, and then (b) effecting the transfer and apportioning of the T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100MCS container, for a period of about 4 days, and then (b) effecting the transfer and apportioning of the T cells from the small scale culture into and amongst 2, 3 or 4 second containers that are larger in size than the first container, e.g., G-REX 500MCS containers, wherein in each second container the portion of the T cells from the small scale culture transferred to such second container is cultured in a larger scale culture for a period of about 5 days.

In some embodiments, upon the splitting of the rapid expansion, each second container comprises at least $10^8$ TILs. In some embodiments, upon the splitting of the rapid expansion, each second container comprises at least $10^8$ TILs, at least 109 TILs, or at least $10^{10}$ TILs. In one exemplary embodiment, each second container comprises at least $10^{10}$ TILs.

In some embodiments, the first small scale TIL culture is apportioned into a plurality of subpopulations. In some embodiments, the first small scale TIL culture is apportioned into a plurality of about 2 to 5 subpopulations. In some embodiments, the first small scale TIL culture is apportioned into a plurality of about 2, 3, 4, or 5 subpopulations.

In some embodiments, after the completion of the rapid expansion, the plurality of subpopulations comprises a therapeutically effective amount of TILs. In some embodiments, after the completion of the rapid expansion, one or more subpopulations of TILs are pooled together to produce a therapeutically effective amount of TILs. In some embodiments, after the completion of the rapid expansion, each subpopulation of TILs comprises a therapeutically effective amount of TILs.

In some embodiments, the rapid expansion is performed for a period of about 1 to 5 days before being split into a plurality of steps. In some embodiments, the splitting of the rapid expansion occurs at about day 1, day 2, day 3, day 4, or day 5 after the initiation of the rapid expansion.

In some embodiments, the splitting of the rapid expansion occurs at about day 8, day 9, day 10, day 11, day 12, or day 13 after the initiation of the first expansion (i.e., pre-REP expansion). In one exemplary embodiment, the splitting of the rapid expansion occurs at about day 10 after the initiation of the priming first expansion. In another exemplary embodiment, the splitting of the rapid expansion occurs at about day 11 after the initiation of the priming first expansion.

In some embodiments, the rapid expansion is further performed for a period of about 4 to 11 days after the splitting. In some embodiments, the rapid expansion is further performed for a period of about 3 days, 4 days, 5 days, 6 days, 7 days, 8 days, 9 days, 10 days, or 11 days after the splitting.

In some embodiments, the cell culture medium used for the rapid expansion before the splitting comprises the same components as the cell culture medium used for the rapid expansion after the splitting. In some embodiments, the cell culture medium used for the rapid expansion before the splitting comprises different components from the cell culture medium used for the rapid expansion after the splitting.

In some embodiments, the cell culture medium used for the rapid expansion before the splitting comprises IL-2, optionally OKT-3 and further optionally APCs. In some embodiments, the cell culture medium used for the rapid expansion before the splitting comprises IL-2, OKT-3, and further optionally APCs. In some embodiments, the cell culture medium used for the rapid expansion before the splitting comprises IL-2, OKT-3 and APCs.

In some embodiments, the cell culture medium used for the rapid expansion before the splitting is generated by supplementing the cell culture medium in the first expansion with fresh culture medium comprising IL-2, optionally OKT-3 and further optionally APCs. In some embodiments, the cell culture medium used for the rapid expansion before the splitting is generated by supplementing the cell culture medium in the first expansion with fresh culture medium comprising IL-2, OKT-3 and APCs. In some embodiments, the cell culture medium used for the rapid expansion before the splitting is generated by replacing the cell culture medium in the first expansion with fresh cell culture medium comprising IL-2, optionally OKT-3 and further optionally APCs. In some embodiments, the cell culture medium used for the rapid expansion before the splitting is generated by replacing the cell culture medium in the first expansion with fresh cell culture medium comprising IL-2, OKT-3 and APCs.

In some embodiments, the cell culture medium used for the rapid expansion after the splitting comprises IL-2, and optionally OKT-3. In some embodiments, the cell culture medium used for the rapid expansion after the splitting comprises IL-2, and OKT-3. In some embodiments, the cell culture medium used for the rapid expansion after the splitting is generated by replacing the cell culture medium used for the rapid expansion before the splitting with fresh culture medium comprising IL-2 and optionally OKT-3. In some embodiments, the cell culture medium used for the rapid expansion after the splitting is generated by replacing the cell culture medium used for the rapid expansion before the splitting with fresh culture medium comprising IL-2 and OKT-3.

In some embodiments, the splitting of the rapid expansion occurs in a closed system.

In some embodiments, the scaling up of the TIL culture during the rapid expansion comprises adding fresh cell culture medium to the TIL culture (also referred to as feeding the TILs). In some embodiments, the feeding comprises adding fresh cell culture medium to the TIL culture frequently. In some embodiments, the feeding comprises adding fresh cell culture medium to the TIL culture at a regular interval. In some embodiments, the fresh cell culture medium is supplied to the TILs via a constant flow. In some embodiments, an automated cell expansion system such as Xuri W25 is used for the rapid expansion and feeding.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days or about 8 days.

In some embodiments, the priming first expansion of T cells is performed during a period of up to at or about 1 day, 2 days, 3 days, 4 days, 5 days, 6 days, 7 days, or 8 days.

In some embodiments, the priming first expansion of T cells is performed during a period of 1 day, 2 days, 3 days, 4 days, 5 days, 6 days, 7 days, or 8 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, 7 days, or 8 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 8 days and the rapid second expansion of T cells is performed during a period of from at or about 1 day to at or about 9 days.

In some embodiments, the priming first expansion of T cells is performed during a period of 8 days and the rapid second expansion of T cells is performed during a period of 9 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the cancer is the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+CD45+, for T cell phenotype, or removing non-T cell phenotype cells, leaving PBLs.

In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1\times10^7$ PBLs) in the priming first expansion culture according to the priming first expansion step of any of the methods described herein.

An exemplary TIL process known as process 3 (also referred to herein as Gen 3) containing some of these features is depicted in FIG. 8 (in particular, e.g., FIG. 8A and/or FIG. 8B and/or FIG. 8C and/or FIG. 8D), and some of the advantages of this embodiment of the present invention over Gen 2 are described in FIGS. 1, 2, 8, 30, and 31 (in particular, e.g., FIG. 8A and/or FIG. 8B and/or FIG. 8C and/or FIG. 8D). Embodiments of Gen 3 are shown in FIGS. 1, 8, and 30 (in particular, e.g., FIG. 8A and/or FIG. 8B and/or FIG. 8C and/or FIG. 8D). Process 2A or Gen 2 or Gen 2A is also described in U.S. Patent Publication No. 2018/0280436, incorporated by reference herein in its entirety. The Gen 3 process is also described in International Patent Publication WO 2020/096988.

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 8 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 8 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 7 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 1B and/or FIG. 8C) as Step B) is 1 to 7 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is 1 to 10 days, as discussed in detail below as well as in the examples and figures. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 8 days and the rapid second expansion (for example, an expansion as described in Step D in FIG. 8 (in particular, e.g., FIG. 8A and/or FIG. 8B and/or FIG. 8C and/or FIG. 8D)) is 7 to 9 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 8 to 9 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 7 days and the rapid second expansion (for example, an expansion as described in Step D in FIG. 8 (in particular, e.g., FIG. 8A and/or FIG. 8B and/or FIG. 8C and/or FIG. 8D)) is 7 to 8 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 8 days and the rapid second expansion (for example, an expansion as described in Step D in FIG. 8 (in particular, e.g., FIG. 8A and/or FIG. 8B and/or FIG. 8C and/or FIG. 8D)) is 8 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 9 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 7 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 8 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 9 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 7 days and the rapid second expansion (for example, an expansion as described in Step D in FIG. 8 (in particular, e.g., FIG. 8A and/or FIG. 8B and/or FIG. 8C and/or FIG. 8D)) is 7 to 9 days. In some embodiments, the combination of the priming first expansion and rapid second expansion (for example, expansions described as Step B and Step D in FIG. 8 (in particular, e.g., FIG. 1B and/or FIG. 8C)) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e., which are a primary cell population.

The "Step" Designations A, B, C, etc., below are in reference to the non-limiting example in FIG. 8 (in particular, e.g., FIG. 8A and/or FIG. 8B and/or FIG. 8C and/or FIG. 8D) and in reference to certain non-limiting embodiments described herein. The ordering of the Steps below and in FIG. 8 (in particular, e.g., FIG. 8A and/or FIG. 8B and/or FIG. 8C and/or FIG. 8D) is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") or from circulating lymphocytes, such as peripheral blood lymphocytes, including peripheral blood lymphocytes having TIL-like characteristics, and are then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma. In some embodiments, the cancer is melanoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g. using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/mL 10× working stock.

In some embodiments, the enzyme mixture comprises DNAse. In some embodiments, the working stock for the DNAse is a 10,000IU/mL 10× working stock.

In some embodiments, the enzyme mixture comprises hyaluronidase. In some embodiments, the working stock for the hyaluronidase is a 10-mg/mL 10× working stock.

In some embodiments, the enzyme mixture comprises 10 mg/mL collagenase, 1000 IU/mL DNAse, and 1 mg/mL hyaluronidase.

In some embodiments, the enzyme mixture comprises 10 mg/mL collagenase, 500 IU/mL DNAse, and 1 mg/mL hyaluronidase.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including, for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In some embodiments, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 8 (in particular, e.g., FIG. 8A and/or FIG. 8B and/or FIG. 8C and/or FIG. 8D)). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm. In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece.

In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without performing a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contains a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g. after obtaining the tumor sample and/or after obtaining the cell suspension from the tumor sample) and stored frozen prior to entry into the expansion described in Step B, which is described in further detail below, as well as exemplified in FIG. 8 (in particular, e.g., FIG. 8B).

1. Core/Small Biopsy Derived TILs

In some embodiments, TILs are initially obtained from a patient tumor sample ("primary TILs") obtained by a core biopsy or similar procedure and then expanded into a larger population for further manipulation as described herein, optionally cryopreserved, and optionally evaluated for phenotype and metabolic parameters.

In some embodiments, a patient tumor sample may be obtained using methods known in the art, generally via small biopsy, core biopsy, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. In some embodiments, the sample can be from multiple small tumor samples or biopsies. In some embodiments, the sample can comprise multiple tumor samples from a single tumor from the same patient. In some embodiments, the sample can comprise multiple tumor samples from one, two, three, or four tumors from the same patient. In some embodiments, the sample can comprise multiple tumor samples from multiple tumors from the same patient. The solid tumor may of lung and/or non-small cell lung carcinoma (NSCLC).

In general, the cell suspension obtained from the tumor core or fragment is called a "primary cell population" or a "freshly obtained" or a "freshly isolated" cell population. In certain embodiments, the freshly obtained cell population of TILs is exposed to a cell culture medium comprising antigen presenting cells, IL-2 and OKT-3.

In some embodiments, if the tumor is metastatic and the primary lesion has been efficiently treated/removed in the past, removal of one of the metastatic lesions may be needed. In some embodiments, the least invasive approach is to remove a skin lesion, or a lymph node on the neck or axillary area when available. In some embodiments, a skin lesion is removed or small biopsy thereof is removed. In some embodiments, a lymph node or small biopsy thereof is removed. In some embodiments, a lung or liver metastatic lesion, or an intra-abdominal or thoracic lymph node or small biopsy is removed. In some embodiments, the tumor is a melanoma. In some embodiments, the small biopsy for a melanoma comprises a mole or portion thereof.

In some embodiments, the small biopsy is a punch biopsy. In some embodiments, the punch biopsy is obtained with a circular blade pressed into the skin. In some embodiments, the punch biopsy is obtained with a circular blade pressed into the skin. around a suspicious mole. In some embodiments, the punch biopsy is obtained with a circular blade pressed into the skin, and a round piece of skin is removed. In some embodiments, the small biopsy is a punch biopsy and round portion of the tumor is removed.

In some embodiments, the small biopsy is an excisional biopsy. In some embodiments, the small biopsy is an excisional biopsy and the entire mole or growth is removed. In some embodiments, the small biopsy is an excisional biopsy and the entire mole or growth is removed along with a small border of normal-appearing skin.

In some embodiments, the small biopsy is an incisional biopsy. In some embodiments, the small biopsy is an incisional biopsy and only the most irregular part of a mole or growth is taken. In some embodiments, the small biopsy is an incisional biopsy and the incisional biopsy is used when other techniques can't be completed, such as if a suspicious mole is very large.

In some embodiments, the small biopsy is a lung biopsy. In some embodiments, the small biopsy is obtained by bronchoscopy. Generally, bronchoscopy, the patient is put under anesthesia, and a small tool goes through the nose or mouth, down the throat, and into the bronchial passages, where small tools are used to remove some tissue. In some embodiments, where the tumor or growth cannot be reached via bronchoscopy, a transthoracic needle biopsy can be employed. Generally, for a transthoracic needle biopsy, the patient is also under anesthesia and a needle is inserted through the skin directly into the suspicious spot to remove a small sample of tissue. In some embodiments, a transthoracic needle biopsy may require interventional radiology (for example, the use of x-rays or CT scan to guide the needle). In some embodiments, the small biopsy is obtained by needle biopsy. In some embodiments, the small biopsy is obtained endoscopic ultrasound (for example, an endoscope with a light and is placed through the mouth into the esophagus). In some embodiments, the small biopsy is obtained surgically.

In some embodiments, the small biopsy is a head and neck biopsy. In some embodiments, the small biopsy is an incisional biopsy. In some embodiments, the small biopsy is an incisional biopsy, wherein a small piece of tissue is cut from an abnormal-looking area. In some embodiments, if the abnormal region is easily accessed, the sample may be taken without hospitalization. In some embodiments, if the tumor is deeper inside the mouth or throat, the biopsy may need to be done in an operating room, with general anesthesia. In some embodiments, the small biopsy is an excisional biopsy. In some embodiments, the small biopsy is an excisional biopsy, wherein the whole area is removed. In some embodiments, the small biopsy is a fine needle aspiration (FNA). In some embodiments, the small biopsy is a fine needle aspiration (FNA), wherein a very thin needle attached to a syringe is used to extract (aspirate) cells from a tumor or lump. In some embodiments, the small biopsy is a punch biopsy. In some embodiments, the small biopsy is a punch biopsy, wherein punch forceps are used to remove a piece of the suspicious area.

In some embodiments, the small biopsy is a cervical biopsy. In some embodiments, the small biopsy is obtained via colposcopy. Generally, colposcopy methods employ the use of a lighted magnifying instrument attached to magnifying binoculars (a colposcope) which is then used to biopsy a small section of the surface of the cervix. In some embodiments, the small biopsy is a conization/cone biopsy. In some embodiments, the small biopsy is a conization/cone biopsy, wherein an outpatient surgery may be needed to remove a larger piece of tissue from the cervix. In some embodiments, the cone biopsy, in addition to helping to confirm a diagnosis, a cone biopsy can serve as an initial treatment.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include cancers of the lung. In some embodiments, the cancer is melanoma. In some embodiments,the cancer is non-small cell lung carcinoma (NSCLC). The tissue structure of solid tumors includes interdependent tissue compartments including the parenchyma (cancer cells) and the supporting stromal cells in which the cancer cells are dispersed and which may provide a supporting microenvironment.

In some embodiments, the sample from the tumor is obtained as a fine needle aspirate (FNA), a core biopsy, a small biopsy (including, for example, a punch biopsy). In some embodiments, sample is placed first into a G-REX 10. In some embodiments, sample is placed first into a G-REX 10 when there are 1 or 2 core biopsy and/or small biopsy samples. In some embodiments, sample is placed first into a G-REX 100 when there are 3, 4, 5, 6, 8, 9, or 10 or more core biopsy and/or small biopsy samples. In some embodiments, sample is placed first into a G-REX 500 when there are 3, 4, 5, 6, 8, 9, or 10 or more core biopsy and/or small biopsy samples.

The FNA can be obtained from a skin tumor, including, for example, a melanoma. In some embodiments, the FNA is obtained from a skin tumor, such as a skin tumor from a patient with metastatic melanoma. In some cases, the patient with melanoma has previously undergone a surgical treatment.

The FNA can be obtained from a lung tumor, including, for example, an NSCLC. In some embodiments, the FNA is obtained from a lung tumor, such as a lung tumor from a patient with non-small cell lung cancer (NSCLC). In some cases, the patient with NSCLC has previously undergone a surgical treatment.

TILs described herein can be obtained from an FNA sample. In some cases, the FNA sample is obtained or isolated from the patient using a fine gauge needle ranging from an 18 gauge needle to a 25 gauge needle. The fine gauge needle can be 18 gauge, 19 gauge, 20 gauge, 21 gauge, 22 gauge, 23 gauge, 24 gauge, or 25 gauge. In some embodiments, the FNA sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In some cases, the TILs described herein are obtained from a core biopsy sample. In some cases, the core biopsy sample is obtained or isolated from the patient using a surgical or medical needle ranging from an 11 gauge needle to a 16 gauge needle. The needle can be 11 gauge, 12 gauge, 13 gauge, 14 gauge, 15 gauge, or 16 gauge. In some embodiments, the core biopsy sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In general, the harvested cell suspension is called a "primary cell population" or a "freshly harvested" cell population.

In some embodiments, the TILs are not obtained from tumor digests. In some embodiments, the solid tumor cores are not fragmented.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, obtaining the first population of TILs comprises a multilesional sampling method.

Tumor dissociating enzyme mixtures can include one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof.

In some embodiments, the dissociating enzymes are reconstituted from lyophilized enzymes. In some embodiments, lyophilized enzymes are reconstituted in an amount of sterile buffer such as Hank's balance salt solution (HBSS).

In some instances, collagenase (such as animal free-type 1 collagenase) is reconstituted in 10 mL of sterile HBSS or another buffer. The lyophilized stock enzyme may be at a concentration of 2892 PZ U/vial. In some embodiments, collagenase is reconstituted in 5 mL to 15 mL buffer. In some embodiment, after reconstitution the collagenase stock ranges from about 100 PZ U/mL-about 400 PZ U/mL, e.g., about 100 PZ U/mL-about 400 PZ U/mL, about 100 PZ U/mL-about 350 PZ U/mL, about 100 PZ U/mL-about 300 PZ U/mL, about 150 PZ U/mL-about 400 PZ U/mL, about 100 PZ U/mL, about 150 PZ U/mL, about 200 PZ U/mL, about 210 PZ U/mL, about 220 PZ U/mL, about 230 PZ U/mL, about 240 PZ U/mL, about 250 PZ U/mL, about 260 PZ U/mL, about 270 PZ U/mL, about 280 PZ U/mL, about 289.2 PZ U/mL, about 300 PZ U/mL, about 350 PZ U/mL, or about 400 PZ U/mL.

In some embodiments neutral protease is reconstituted in 1-ml of sterile HBSS or another buffer. The lyophilized stock enzyme may be at a concentration of 175 DMC U/vial. In some embodiments, after reconstitution the neutral protease stock ranges from about 100 DMC/mL-about 400 DMC/mL, e.g., about 100 DMC/mL-about 400 DMC/mL, about 100 DMC/mL-about 350 DMC/mL, about 100 DMC/mL-about 300 DMC/mL, about 150 DMC/mL-about 400 DMC/mL, about 100 DMC/mL, about 110 DMC/mL, about 120 DMC/mL, about 130 DMC/mL, about 140 DMC/mL, about 150 DMC/mL, about 160 DMC/mL, about 170 DMC/mL, about 175 DMC/mL, about 180 DMC/mL, about 190 DMC/mL, about 200 DMC/mL, about 250 DMC/mL, about 300 DMC/mL, about 350 DMC/mL, or about 400 DMC/mL.

In some embodiments, DNAse I is reconstituted in 1-ml of sterile HBSS or another buffer. The lyophilized stock enzyme was at a concentration of 4 KU/vial. In some embodiments, after reconstitution the DNase I stock ranges from about 1 KU/mL-10 KU/mL, e.g., about 1 KU/mL, about 2 KU/mL, about 3 KU/mL, about 4 KU/mL, about 5 KU/mL, about 6 KU/mL, about 7 KU/mL, about 8 KU/mL, about 9 KU/mL, or about 10 KU/mL.

In some embodiments, the stock of enzymes could change so verify the concentration of the lyophilized stock and amend the final amount of enzyme added to the digest cocktail accordingly.

In some embodiments, the enzyme mixture includes about 10.2-ul of neutral protease (0.36 DMC U/mL), 21.3-ul of collagenase (1.2 PZ/mL) and 250-ul of DNAse I (200 U/mL) in about 4.7-ml of sterile HBSS.

2. Pleural effusion T-cells and TILs

In some embodiments, the sample is a pleural fluid sample. In some embodiments, the source of the T-cells or TILs for expansion according to the processes described herein is a pleural fluid sample. In some embodiments, the sample is a pleural effusion derived sample.

In some embodiments, the source of the T-cells or TILs for expansion according to the processes described herein is a pleural effusion derived sample. See, for example, methods described in U.S. Patent Publication US 2014/0295426, incorporated herein by reference in its entirety for all purposes.

In some embodiments, any pleural fluid or pleural effusion suspected of and/or containing TILs can be employed. Such a sample may be derived from a primary or metastatic lung cancer, such as NSCLC or SCLC. In some embodiments, the sample may be derived from secondary metastatic cancer cells which originated from another organ, e.g., breast, ovary, colon or prostate. In some embodiments, the sample for use in the expansion methods described herein is a pleural exudate. In some embodiments, the sample for use in the expansion methods described herein is a pleural transudate. Other biological samples may include other serous fluids containing TILs, including, e.g., ascites fluid from the abdomen or pancreatic cyst fluid. Ascites fluid and pleural fluids involve very similar chemical systems; both the abdomen and lung have mesothelial lines and fluid forms in the pleural space and abdominal spaces in the same matter in malignancies and such fluids in some embodiments contain TILs. In some embodiments, wherein the disclosed methods utilize pleural fluid, the same methods may be performed with similar results using ascites or other cyst fluids containing TILs.

In some embodiments, the pleural fluid is in unprocessed form, directly as removed from the patient. In some embodiments, the unprocessed pleural fluid is placed in a standard blood collection tube, such as an EDTA or Heparin tube, prior to further processing steps. In some embodiments, the unprocessed pleural fluid is placed in a standard CellSave® tube (Veridex) prior to the further processing steps. In some embodiments, the sample is placed in the CellSave tube immediately after collection from the patient to avoid a decrease in the number of viable TILs. The number of viable TILs can decrease to a significant extent within 24 hours, if left in the untreated pleural fluid, even at 4° C. In some embodiments, the sample is placed in the appropriate collection tube within 1 hour, 5 hours, 10 hours, 15 hours, or up to 24 hours after removal from the patient. In some embodiments, the sample is placed in the appropriate collection tube within 1 hour, 5 hours, 10 hours, 15 hours, or up to 24 hours after removal from the patient at 4° C.

In some embodiments, the pleural fluid sample from the chosen subject may be diluted. In one embodiment, the dilution is 1:10 pleural fluid to diluent. In some embodiments, the dilution is 1:9 pleural fluid to diluent. In some embodiments, the dilution is 1:8 pleural fluid to diluent. In some embodiments, the dilution is 1:5 pleural fluid to diluent. In some embodiments, the dilution is 1:2 pleural fluid to diluent. In some embodiments, the dilution is 1:1 pleural fluid to diluent. In some embodiments, diluents include saline, phosphate buffered saline, another buffer or a physiologically acceptable diluent. In some embodiments, the sample is placed in the CellSave tube immediately after collection from the patient and dilution to avoid a decrease in the viable TILs, which may occur to a significant extent within 24-48 hours, if left in the untreated pleural fluid, even at 4° C. In some embodiments, the pleural fluid sample is placed in the appropriate collection tube within 1 hour, 5 hours, 10 hours, 15 hours, 24 hours, 36 hours, up to 48 hours after removal from the patient, and dilution. In some embodiments, the pleural fluid sample is placed in the appropriate collection tube within 1 hour, 5 hours, 10 hours, 15 hours, 24 hours, 36 hours, up to 48 hours after removal from the patient, and dilution at 4° C.

In still another embodiment, pleural fluid samples are concentrated by conventional means prior to further processing steps. In some embodiments, this pre-treatment of the pleural fluid is preferable in circumstances in which the pleural fluid must be cryopreserved for shipment to a laboratory performing the method or for later analysis (e.g., later than 24-48 hours post-collection). In some embodiments, the pleural fluid sample is prepared by centrifuging the pleural fluid sample after its withdrawal from the subject and resuspending the centrifugate or pellet in buffer. In some embodiments, the pleural fluid sample is subjected to multiple centrifugations and resuspensions, before it is cryopreserved for transport or later analysis and/or processing.

In some embodiments, pleural fluid samples are concentrated prior to further processing steps by using a filtration method. In some embodiments, the pleural fluid sample used in the further processing, is prepared by filtering the fluid through a filter containing a known and essentially uniform pore size that allows for passage of the pleural fluid through the membrane but retains the tumor cells. In some embodiments, the diameter of the pores in the membrane may be at least 4 μM. In some embodiments, the pore diameter may be 5 μM or more, and in other embodiment, any of 6, 7, 8, 9, or 10 μM. After filtration, the cells, including TILs, retained by the membrane may be rinsed off the membrane into a suitable physiologically acceptable buffer. Cells, including TILs, concentrated in this way may then be used in the further processing steps of the method.

In some embodiment, pleural fluid sample (including, for example, the untreated pleural fluid), diluted pleural fluid, or the resuspended cell pellet, is contacted with a lytic reagent that differentially lyses non-nucleated red blood cells present in the sample. In some embodiments, this step is performed prior to further processing steps in circumstances in which the pleural fluid contains substantial numbers of RBCs. Suitable lysing reagents include a single lytic reagent or a lytic reagent and a quench reagent, or a lytic agent, a quench reagent and a fixation reagent. Suitable lytic systems are marketed commercially and include the BD Pharm Lyse™ system (Becton Dickenson). Other lytic systems include the Versalyse™ system, the FACSlyse™ system (Becton Dickenson), the Immunoprep™ system or Erythrolyse II system (Beckman Coulter, Inc.), or an ammonium chloride system. In some embodiments, the lytic reagent can vary with the primary requirements being efficient lysis of the red blood cells, and the conservation of the TILs and phenotypic properties of the TILs in the pleural fluid. In addition to employing a single reagent for lysis, the lytic systems useful in methods described herein can include a second reagent, e.g., one that quenches or retards the effect of the lytic reagent during the remaining steps of the method, e.g., Stabilyse™ reagent (Beckman Coulter, Inc.). A conventional fixation reagent may also be employed depending upon the choice of lytic reagents or the preferred implementation of the method.

In some embodiments, the pleural fluid sample, unprocessed, diluted or multiply centrifuged or processed as described herein above is cryopreserved at a temperature of about −140° C. prior to being further processed and/or expanded as provided herein.

1. Methods of Expanding Peripheral Blood Lymphocytes (PBLs) from Peripheral Blood PBL Method 1. In some embodiments of the invention, PBLs are expanded using the processes described herein. In some embodiments of the invention, the method comprises obtaining a PBMC sample from whole blood. In some embodiments, the method comprises enriching T-cells by isolating pure T-cells from PBMCs using negative selection of a non-CD19+fraction. In some embodiments, the method comprises enriching T-cells by isolating pure T-cells from PBMCs using magnetic bead-based negative selection of a non-CD19+fraction.

In some embodiments of the invention, PBL Method 1 is performed as follows: On Day 0, a cryopreserved PBMC sample is thawed and PBMCs are counted. T-cells are isolated using a Human Pan T-Cell Isolation Kit and LS columns (Miltenyi Biotec).

PBL Method 2. In some embodiments of the invention, PBLs are expanded using PBL Method 2, which comprises obtaining a PBMC sample from whole blood. The T-cells from the PBMCs are enriched by incubating the PBMCs for at least three hours at 37° C. and then isolating the non-adherent cells.

In some embodiments of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In some embodiments of the invention, PBLs are expanded using PBL Method 3, which comprises obtaining a PBMC sample from peripheral blood. B-cells are isolated using a CD19+selection and T-cells are selected using negative selection of the non-CD19+fraction of the PBMC sample.

In some embodiments of the invention, PBL Method 3 is performed as follows: On Day 0, cryopreserved PBMCs derived from peripheral blood are thawed and counted. CD19+B-cells are sorted using a CD19 Multisort Kit, Human (Miltenyi Biotec). Of the non-CD19+cell fraction, T-cells are purified using the Human Pan T-cell Isolation Kit and LS Columns (Miltenyi Biotec).

In some embodiments, PBMCs are isolated from a whole blood sample. In some embodiments, the PBMC sample is used as the starting material to expand the PBLs. In some embodiments, the sample is cryopreserved prior to the expansion process. In other embodiments, a fresh sample is used as the starting material to expand the PBLs. In some embodiments of the invention, T-cells are isolated from PBMCs using methods known in the art. In some embodiments, the T-cells are isolated using a Human Pan T-cell isolation kit and LS columns. In some embodiments of the invention, T-cells are isolated from PBMCs using antibody selection methods known in the art, for example, CD19 negative selection.

In some embodiments of the invention, the PBMC sample is incubated for a period of time at a desired temperature effective to identify the non-adherent cells. In some embodiments of the invention, the incubation time is about 3 hours. In some embodiments of the invention, the temperature is about 37° Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In other embodiments, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In other embodiments, the PBMCs are derived from a patient who has prior exposure to an ITK inhibitor, but has not been treated in at least 3 months, at least 6 months, at least 9 months, or at least 1 year.

In some embodiments of the invention, at Day 0, cells are selected for CD19+ and sorted accordingly. In some embodiments of the invention, the selection is made using antibody binding beads. In some embodiments of the invention, pure T-cells are isolated on Day 0 from the PBMCs.

In some embodiments of the invention, for patients that are not pre-treated with ibrutinib or other ITK inhibitor, 10-15 mL of Buffy Coat will yield about $5\times10^{9}$ PBMC, which, in turn, will yield about $5.5\times10^{7}$ PBLs.

In some embodiments of the invention, for patients that are pre-treated with ibrutinib or other ITK inhibitor, the expansion process will yield about $20\times10^{9}$ PBLs. In some embodiments of the invention, $40.3\times10^{6}$ PBMCs will yield about $4.7\times10^{5}$ PBLs.

In any of the foregoing embodiments, PBMCs may be derived from a whole blood sample, by apheresis, from the buffy coat, or from any other method known in the art for obtaining PBMCs.

In some embodiments, PBLs are prepared using the methods described in U.S. Patent Application Publication No. US 2020/0347350 A1, the disclosures of which are incorporated by reference herein.

2. Methods of Expanding Marrow Infiltrating Lymphocytes (MILs) from PBMCs Derived from Bone Marrow MIL Method 3. In some embodiments of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+cell fraction is sonicated and a portion of the sonicated cell fraction is added back to the selected cell fraction.

In some embodiments of the invention, MIL Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions —an immune cell fraction (or the MIL fraction) (CD3+CD33+CD20+CD14+) and an AML blast cell fraction (non-CD3+CD33+CD20+CD14+).

In some embodiments of the invention, PBMCs are obtained from bone marrow. In some embodiments, the PBMCs are obtained from the bone marrow through apheresis, aspiration, needle biopsy, or other similar means known in the art. In some embodiments, the PBMCs are fresh. In other embodiments, the PBMCs are cryopreserved.

In some embodiments of the invention, MILs are expanded from 10-50 mL of bone marrow aspirate. In some embodiments of the invention, 10 mL of bone marrow aspirate is obtained from the patient. In other embodiments, 20 mL of bone marrow aspirate is obtained from the patient. In other embodiments, 30 mL of bone marrow aspirate is obtained from the patient. In other embodiments, 40 mL of bone marrow aspirate is obtained from the patient. In other embodiments, 50 mL of bone marrow aspirate is obtained from the patient.

In some embodiments of the invention, the number of PBMCs yielded from about 10-50 mL of bone marrow aspirate is about $5\times10^{7}$ to about $10\times10^{7}$ PBMCs. In other embodiments, the number of PMBCs yielded is about $7\times10^{7}$ PBMCs.

In some embodiments of the invention, about $5\times10^{7}$ to about $10\times10^{7}$ PBMCs, yields about $0.5\times10^{6}$ to about $1.5\times10^{6}$ MILs. In some embodiments of the invention, about $1\times10^{6}$ MILs is yielded.

In some embodiments of the invention, $12\times10^{6}$ PBMC derived from bone marrow aspirate yields approximately $1.4\times10^{5}$ MILs.

In any of the foregoing embodiments, PBMCs may be derived from a whole blood sample, from bone marrow, by apheresis, from the buffy coat, or from any other method known in the art for obtaining PBMCs.

In some embodiments, MILs are prepared using the methods described in U.S. Patent Application Publication No. US 2020/0347350 A1, the disclosures of which are incorporated by reference herein.

B. STEP B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, et al., *Scand. J Immunol.* 2012, 75, 157-167; Dudley, et al., *Clin. Cancer Res.* 2010, 16, 6122-6131; Huang, et al., *J Immunother.* 2005, 28, 258-267; Besser, et al., *Clin. Cancer Res.* 2013, 19, OF1-OF9; Besser, et al., *J. Immunother.* 2009, 32:415-423; Robbins, et al., *J. Immunol.* 2004, 173, 7125-7130; Shen, et al., *J. Immunother.*, 2007, 30, 123-129; Zhou, et al., *J. Immunother.* 2005, 28, 53-62; and Tran, et al., *J. Immunother.*, 2008, 31, 742-751, each of which is incorporated herein by reference.

After dissection or digestion of tumor fragments and/or tumor fragments, for example such as described in Step A of FIG. 8 (in particular, e.g., FIG. 8A and/or FIG. 8B and/or FIG. 8C and/or FIG. 8D), the resulting cells are cultured in serum containing IL-2, OKT-3, and feeder cells (e.g., antigen-presenting feeder cells), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments per container and with 6000 IU/mL of IL-2. In some embodiments, this primary cell population is cultured for a period of days, generally from 1 to 8 days, resulting in a bulk TIL population, generally about $1\times10^8$ bulk TIL cells. In some embodiments, this primary cell population is cultured for a period of days, generally from 1 to 7 days, resulting in a bulk TIL population, generally about $1\times10^8$ bulk TIL cells. In some embodiments, priming first expansion occurs for a period of 1 to 8 days, resulting in a bulk TIL population, generally about $1\times10^8$ bulk TIL cells. In some embodiments, priming first expansion occurs for a period of 1 to 7 days, resulting in a bulk TIL population, generally about $1\times10^8$ bulk TIL cells. In some embodiments, this priming first expansion occurs for a period of 5 to 8 days, resulting in a bulk TIL population, generally about $1\times10^8$ bulk TIL cells. In some embodiments, this priming first expansion occurs for a period of 5 to 7 days, resulting in a bulk TIL population, generally about $1\times10^8$ bulk TIL cells. In some embodiments, this priming first expansion occurs for a period of about 6 to 8 days, resulting in a bulk TIL population, generally about $1\times10^8$ bulk TIL cells. In some embodiments, this priming first expansion occurs for a period of about 6 to 7 days, resulting in a bulk TIL population, generally about $1\times10^8$ bulk TIL cells. In some embodiments, this priming first expansion occurs for a period of about 7 to 8 days, resulting in a bulk TIL population, generally about $1\times10^8$ bulk TIL cells. In some embodiments, this priming first expansion occurs for a period of about 7 days, resulting in a bulk TIL population, generally about $1\times10^8$ bulk TIL cells. In some embodiments, this priming first expansion occurs for a period of about 8 days, resulting in a bulk TIL population, generally about $1\times10^8$ bulk TIL cells.

In some embodiments, expansion of TILs may be performed using a priming first expansion step (for example such as those described in Step B of FIG. 8 (in particular, e.g., FIG. 8A and/or FIG. 8B and/or FIG. 8C and/or FIG. 8D), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin.

In some embodiments, there are less than or equal to 240 tumor fragments. In some embodiments, there are less than or equal to 240 tumor fragments placed in less than or equal to 4 containers. In some embodiments, the containers are G-REX100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5\times10^8$ antigen-presenting feeder cells per container. In some embodiments, the media comprises OKT-3. In some embodiments, the media comprises 30 ng/mL of OKT-3 per container. In some embodiments, the container is a G-REX100 MCS flask. In some embodiments, the media comprises 6000 IU/mL of IL-2, 30 ng of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container.

After preparation of the tumor fragments, the resulting cells (i.e., fragments which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 8 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, this primary cell population is cultured for a period of days, generally from 1 to 7 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of 20-$30\times10^6$ IU/mg for a 1 mg vial. In some embodiments the IL-2 stock solution has a specific activity of 20×106 IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of 4-$8\times10^6$ IU/mg of IL-2. In some embodiments, the IL-2 stock solution has a final concentration of 5-$7\times10^6$ IU/mg of IL-2. In some embodiments, the IL-2 stock solution has a final concentration of $6\times10^6$ IU/mg of IL-2. In some embodiments, the IL-2 stock solution is prepare as described in Example C. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In some embodiments, the cell culture medium further comprises IL-2. In some embodiments, the priming first expansion cell culture medium comprises about 3000 IU/mL of IL-2. In some embodiments, the priming first expansion cell culture medium further comprises IL-2. In some embodiments, the priming first expansion cell culture medium comprises about 3000 IU/mL of IL-2. In some embodiments, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In some embodiments, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In some embodiments, the priming first expansion cell culture medium further comprises IL-15. In some embodiments, the priming first expansion cell culture medium comprises about 180 IU/mL of IL-15.

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10 IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In some embodiments, the cell culture medium further comprises IL-21. In some embodiments, the priming first expansion cell culture medium comprises about 1 IU/mL of IL-21.

In some embodiments, the priming first expansion cell culture medium comprises OKT-3 antibody. In some embodiments, the priming first expansion cell culture medium comprises about 30 ng/mL of OKT-3 antibody. In some embodiments, the priming first expansion cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In some embodiments, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium comprises between 15 ng/mL and 30 ng/mL of OKT-3 antibody. In some embodiments, the cell culture medium comprises 30 ng/mL of OKT-3 antibody. In some embodiments, the OKT-3 antibody is muromonab. See, Table 1.

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/mL, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In some embodiments, the CM is the CM1 described in the Examples, see, Example A. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (aMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum free supplement capable of supporting the growth of cells in serum-free culture. The serum-free eukaryotic cell culture medium supplement comprises or is obtained by combining one or more ingredients selected from the group consisting of one or more albumins or albumin substitutes. one or more amino acids, one or more vitamins, one or more transferrins or transferrin substitutes, one or more antioxidants, one or more insulins or insulin substitutes, one or more collagen precursors, one or more trace element. and one or more antibiotics. In some embodiments, the defined medium further comprises L-glutamine. sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes. one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline L-serine, L-threonine. L-tryptophan L-tyrosine, L-valine, thiamine, reduced glutathione, L-ascorbic acid-2-phosphate, iron saturated transferrin. insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM) Basal Medium Eagle (BiME), RPMI 1640, F-10, F-12, Minimal Essential Medium (αMEM), Glasgow's Minimal Essential Medium (G-MEM), RPMI growth medium, and Iscove's Modified Dulbecco's Medium In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table 4. In other embodiments, the non-trace element moiety ingredients in the defined medium are present in the final concentrations listed in the column under the heading "A Preferred Embodiment of the 1× Medium" in Table 4. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table 4.

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In some embodiments, the cell medium in the first and/or second gas permeable container is unfiltered. The use of unfiltered cell medium may simplify the procedures necessary to expand the number of cells. In some embodiments, the cell medium in the first and/or second gas permeable container lacks beta-mercaptoethanol (BME or PME; also known as 2-mercaptoethanol, CAS 60-24-2).

In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 1 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 2 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 3 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 4 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 5 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 6 to 8 days, as discussed in the examples and figures. In some embodiments, the priming first expansion (including processes such as for example those provided in Step B of FIG. 1 (in particular, e.g., FIG. 8A and/or FIG. 8B and/or FIG. 8C and/or FIG. 8D), which can include those sometimes referred to as the pre-REP or priming REP) process is 7 to 8 days, as discussed in the examples and figures. In some embodiments, the priming first expansion (including processes such as for example those provided in Step B of FIG. 8 (in particular, e.g., FIG. 8A and/or FIG. 8B and/or FIG. 8C and/or FIG. 8D), which can include those sometimes referred to as the pre-REP or priming REP) process is 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 1 to 7 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 2 to 7 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 3 to 7 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 4 to 7 days, as discussed in the examples and figures. In some embodiments, the priming first expansion (including processes such as for example those described in Step B of FIG. 8 (in particular, e.g., FIG. 8B and/or FIG. 8C), which can include those sometimes referred to as the pre-REP or priming REP) process is 5 to 7 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 6 to 7 days, as discussed in the examples and figures. In some embodiments, the priming first expansion (including processes such as for example those provided in Step B of FIG. 8 (in particular, e.g., FIG. 8A and/or FIG. 8B and/or FIG. 8C and/or FIG. 8D), which can include those sometimes referred to as the pre-REP or priming REP) process is 7 days, as discussed in the examples and figures.

In some embodiments, the priming first TIL expansion can proceed for 1 days to 8 days from when fragmentation occurs and/or when the first priming expansion step is initiated. In some embodiments, the priming first TIL expansion can proceed for 1 days to 7 days from when fragmentation occurs and/or when the first priming expansion step is initiated. In some embodiments, the priming first TIL expansion can proceed for 2 days to 8 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 8 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 8 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 8 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 8 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 to 8 days from when fragmentation occurs and/or when the first priming expansion step is initiated. In some embodiments, the priming first TIL expansion can proceed for 8 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, 7 days, or 8 days. In some embodiments, the first TIL expansion can proceed for 1 day to 8 days. In some embodiments, the first TIL expansion can proceed for 1 day to 7 days. In some embodiments, the first TIL expansion can proceed for 2 days to 8 days. In some embodiments, the first TIL expansion can proceed for 2 days to 7 days. In some embodiments, the first TIL expansion can proceed for 3 days to 8 days. In some embodiments, the first TIL expansion can proceed for 3 days to 7 days. In some embodiments, the first TIL expansion can proceed for 4 days to 8 days. In some embodiments, the first TIL expansion can proceed for 4 days to 7 days. In some embodiments, the first TIL expansion can proceed for 5 days to 8 days. In some embodiments, the first TIL expansion can proceed for 5 days to 7 days. In some embodiments, the first TIL expansion can proceed for 6 days to 8 days. In some embodiments, the first TIL expansion can proceed for 6 days to 7 days. In some embodiments, the first TIL expansion can proceed for 7 to 8 days. In some embodiments, the first TIL expansion can proceed for 8 days. In some embodiments, the first TIL expansion can proceed for 7 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including, for example during Step B processes according to FIG. 8 (in particular, e.g., FIG. 8A and/or FIG. 8B and/or FIG. 8C and/or FIG. 8D), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 8 (in particular, e.g., FIG. 8A and/or FIG. 8B and/or FIG. 8C and/or FIG. 8D) and as described herein.

In some embodiments, the priming first expansion, for example, Step B according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-10 or a G-REX-100. In some embodiments, the bioreactor employed is a G-REX-100. In some embodiments, the bioreactor employed is a G-REX-10.

1. Feeder Cells and Antigen Presenting Cells

In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 4-8. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 4-7. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 5-8. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 5-7. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 6-8. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 6-7. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 7 or 8. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 7. In some embodiments, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 8

In some embodiments, the priming first expansion procedures described herein (for example including expansion such as those described in Step B from FIG. 8 (in particular, e.g., FIG. 8B), as well as those referred to as pre-REP or priming REP) require feeder cells (also referred to herein as "antigen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5\times10^8$ feeder cells are used during the priming first expansion. In some embodiments, $2.5\times10^8$ feeder cells per container are used during the priming first expansion. In some embodiments, $2.5\times10^8$ feeder cells per GREX-10 are used during the priming first expansion. In some embodiments, $2.5\times10^8$ feeder cells per GREX-100 are used during the priming first expansion.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/mL OKT3 antibody and 3000 IU/mL IL-2. In some embodiments, the PBMCs are cultured in the presence of 30 ng/mL OKT3 antibody and 6000 IU/mL IL-2.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/mL OKT3 antibody and 1000-6000 IU/mL IL-2. In some embodiments, the PBMCs are cultured in the presence of 10-50 ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/mL OKT3 antibody and 6000 IU/mL IL-2. In some embodiments, the PBMCs are cultured in the presence of 15 ng/mL OKT3 antibody and 3000 IU/mL IL-2. In some embodiments, the PBMCs are cultured in the presence of 15 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells.

In some embodiments, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In some embodiments, the ratio of TILs to antigen-presenting feeder cells in the second expansion is between 1 to 50 and 1 to 300. In some embodiments, the ratio of TILs to antigen-presenting feeder cells in the second expansion is between 1 to 100 and 1 to 200.

In some embodiments, the priming first expansion procedures described herein require a ratio of about $2.5\times10^8$ feeder cells to about $100\times10^6$ TILs. In some embodiments, the priming first expansion procedures described herein require a ratio of about $2.5\times10^8$ feeder cells to about $50\times10^6$ TILs. In yet another embodiment, the priming first expansion described herein require about $2.5\times10^8$ feeder cells to about $25\times10^6$ TILs. In yet another embodiment, the priming first expansion described herein require about $2.5\times10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5\times10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng/mL of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container. In some embodiments, the media comprises 500 mL of culture medium and 15 μg of OKT-3 per container. In some embodiments, the container is a GREX100 MCS flask. In some embodiments, the media comprises 500 mL of culture medium, 6000 IU/mL of IL-2, 30 ng/mL of OKT-3, and $2.5\times10^8$ antigen-presenting feeder cells. In some embodiments, the media comprises 500 mL of culture medium, 6000 IU/mL of IL-2, 15 μg of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container.

In some embodiments, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In some embodiments, artificial antigen presenting cells are used in the priming first expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein. See, Table 2.

In some embodiments, Step B may also include the addition of OKT-3 antibody or muromonab to the culture media, as described elsewhere herein. In some embodiments, Step B may also include the addition of a 4-1BB agonist to the culture media, as described elsewhere herein. In some embodiments, Step B may also include the addition of an OX-40 agonist to the culture media, as described elsewhere herein. In addition, additives such as peroxisome proliferator-activated receptor gamma coactivator I-alpha agonists, including proliferator-activated receptor (PPAR)-gamma agonists such as a thiazolidinedione compound, may be used in the culture media during Step B, as described in U.S. Patent Application Publication No. US 2019/0307796 A1, the disclosure of which is incorporated by reference herein.

C. STEP C: Priming First Expansion to Rapid Second Expansion Transition

In some cases, the bulk TIL population obtained from the priming first expansion (which can include expansions sometimes referred to as pre-REP), including, for example the TIL population obtained from for example, Step B as indicated in FIG. 8 (in particular, e.g. FIG. 8A and/or FIG. 8B and/or FIG. 8C and/or FIG. 8D), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic modifications for suitable treatments prior to the expansion step or after the priming first expansion and prior to the rapid second expansion.

In some embodiments, the TILs obtained from the priming first expansion (for example, from Step B as indicated in FIG. 8 (in particular, e.g., FIG. 8A and/or FIG. 8B and/or FIG. 8C and/or FIG. 8D)) are stored until phenotyped for selection. In some embodiments, the TILs obtained from the priming first expansion (for example, from Step B as indicated in FIG. 8 (in particular, e.g., FIG. 8A and/or FIG. 8B and/or FIG. 8C and/or FIG. 8D)) are not stored and proceed directly to the rapid second expansion. In some embodiments, the TILs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, 7 days, or 8 days from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition from the priming first expansion to the rapid second expansion occurs at about 3 days to 8 days from when fragmentation occurs and/or when the first priming expansion step is initiated. In some embodiments, the transition from the priming first expansion to the second expansion occurs at about 4 days to 7 days from when fragmentation occurs and/or when the first priming expansion step is initiated. In some embodiments, the transition from the priming first expansion to the second expansion occurs at about 4 days to 8 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 5 days to 8 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 6 days to 8 days from when fragmentation occurs and/or when the first priming expansion step is initiated. In some embodiments, the transition from the priming first expansion to the second expansion occurs at about 7 days to 8 days from when fragmentation occurs and/or when the first priming expansion step is initiated. In some embodiments, the transition from the priming first expansion to the second expansion occurs at about 7 days from when fragmentation occurs and/or when the first priming expansion step is initiated. In some embodiments, the transition from the priming first expansion to the second expansion occurs at about 8 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, 7 days, or 8 days from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the rapid second expansion occurs 1 day to 8 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 2 days to 8 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the second expansion occurs 3 days to 8 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 4 days to 8 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 5 days to 8 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated.. In some embodiments, the transition from the priming first expansion to the rapid second expansion occurs 6 days to 8 days from when fragmentation occurs and/or when the first priming expansion step is initiated. In some embodiments, the transition from the priming first expansion to the rapid second expansion occurs 7 days to 8 days from when fragmentation occurs and/or when the first priming expansion step is initiated. In some embodiments, the transition from the priming first expansion to the rapid second expansion occurs 7 days from when fragmentation occurs and/or when the first priming expansion step is initiated. In some embodiments, the transition from the priming first expansion to the rapid second expansion occurs 8 days from when fragmentation occurs and/or when the first priming expansion step is initiated In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 8 (in particular, e.g., FIG. 8A and/or FIG. 8B and/or FIG. 8C and/or FIG. 8D)). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

D. STEP D: Rapid Second Expansion

In some embodiments, the TIL cell population is further expanded in number after harvest and the priming first expansion, after Step A and Step B, and the transition referred to as Step C, as indicated in FIG. 8 (in particular, e.g., FIG. 8A and/or FIG. 8B and/or FIG. 8C and/or FIG. 8D)). This further expansion is referred to herein as the rapid second expansion or a rapid expansion, which can include expansion processes generally referred to in the art as a rapid expansion process (Rapid Expansion Protocol or REP; as well as processes as indicated in Step D of FIG. 8 (in particular, e.g., FIG. 8A and/or FIG. 8B and/or FIG. 8C and/or FIG. 8D). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, the rapid second expansion (which can include expansions sometimes referred to as REP; as well as processes as indicated in Step D of FIG. 8 (in particular, e.g., FIG. 8A and/or FIG. 8B and/or FIG. 8C and/or FIG. 8D)) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, 9 days or 10 days after initiation of the rapid second expansion. In some embodiments, the second TIL expansion can proceed for about 1 days to about 9 days after initiation of the rapid second expansion. In some embodiments, the second TIL expansion can proceed for about 1 days to about 10 days after initiation of the rapid second expansion. In some embodiments, the second TIL expansion can proceed for about 2 days to about 9 days after initiation of the rapid second expansion. In some embodiments, the second TIL expansion can proceed for about 2 days to about 10 days after initiation of the rapid second expansion. In some embodiments, the second TIL expansion can proceed for about 3 days to about 9 days after initiation of the rapid second expansion. In some embodiments, the second TIL expansion can proceed for about 3 days to about 10 days after initiation of the rapid second expansion. In some embodiments, the second TIL expansion can proceed for about 4 days to about 9 days after initiation of the rapid second expansion. In some embodiments, the second TIL expansion can proceed for about 4 days to about 10 days after initiation of the rapid second expansion. In some embodiments, the second TIL expansion can proceed for about 5 days to about 9 days after initiation of the rapid second expansion. In some embodiments, the second TIL expansion can proceed for about 5 days to about 10 days after initiation of the rapid second expansion. In some embodiments, the second TIL expansion can proceed for about 6 days to about 9 days after initiation of the rapid second expansion. In some embodiments, the second TIL expansion can proceed for about 6 days to about 10 days after initiation of the rapid second expansion. In some embodiments, the second TIL expansion can proceed for about 7 days to about 9 days after initiation of the rapid second expansion. In some embodiments, the second TIL expansion can proceed for about 7 days to about 10 days after initiation of the rapid second expansion. In some embodiments, the second TIL expansion can proceed for about 8 days to about 9 days after initiation of the rapid second expansion. In some embodiments, the second TIL expansion can proceed for about 8 days to about 10 days after initiation of the rapid second expansion. In some embodiments, the second TIL expansion can proceed for about 9 days to about 10 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion. In some embodiments, the second TIL expansion can proceed for about 10 days after initiation of the rapid second expansion.

In some embodiments, the rapid second expansion can be performed in a gas permeable container using the methods of the present disclosure (including, for example, expansions referred to as REP; as well as processes as indicated in Step D of FIG. 8 (in particular, e.g., FIG. 8A and/or FIG. 8B and/or FIG. 8C and/or FIG. 8D). In some embodiments, the TILs are expanded in the rapid second expansion in the presence of IL-2, OKT-3, and feeder cells (also referred herein as “antigen-presenting cells”). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/mL of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+allogeneic lymphocytes and IL-2.

In some embodiments, the cell culture medium further comprises IL-2. In some embodiments, the cell culture medium comprises about 3000 IU/mL of IL-2. In some embodiments, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In some embodiments, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In some embodiments, the cell culture medium comprises OKT-3 antibody. In some embodiments, the cell culture medium comprises about 30 ng/mL of OKT-3 antibody. In some embodiments, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In some embodiments, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium comprises between 15 ng/mL and 30 ng/mL of OKT-3 antibody. In some embodiments, the cell culture medium comprises between 30 ng/mL and 60 ng/mL of OKT-3 antibody. In some embodiments, the cell culture medium comprises about 30 ng/mL OKT-3. In some embodiments, the cell culture medium comprises about 60 ng/mL OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5\times10^8$ antigen-presenting feeder cells per container. In some embodiments, the media in the rapid second expansion comprises OKT-3. In some embodiments, the in the rapid second expansion media comprises 500 mL of culture medium and 30 μg of OKT-3 per container. In some embodiments, the container is a GREX100 MCS flask. In some embodiments, the in the rapid second expansion media comprises 6000 IU/mL of IL-2, 60 ng/mL of OKT-3, and $7.5\times10^8$ antigen-presenting feeder cells. In some embodiments, the media comprises 500 mL of culture medium and 6000 IU/mL of IL-2, 30 μg of OKT-3, and $7.5\times10^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between $5\times10^8$ and $7.5\times10^8$ antigen-presenting feeder cells per container. In some embodiments, the media in the rapid second expansion comprises OKT-3. In some embodiments, the media in the rapid second expansion comprises 500 mL of culture medium and 30 μg of OKT-3 per container. In some embodiments, the container is a GREX100 MCS flask. In some embodiments, the media in the rapid second expansion comprises 6000 IU/mL of IL-2, 60 ng/mL of OKT-3, and between $5\times10^8$ and $7.5\times10^8$ antigen-presenting feeder cells. In some embodiments, the media in the rapid second expansion comprises 500 mL of culture medium and 6000 IU/mL of IL-2, 30 μg of OKT-3, and between $5\times10^8$ and $7.5\times10^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including, for example during a Step D processes according to FIG. 8 (in particular, e.g., FIG. 8A and/or FIG. 8B and/or FIG. 8C and/or FIG. 8D), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 8 (in particular, e.g., FIG. 8A and/or FIG. 8B and/or FIG. 8C and/or FIG. 8D) and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15.

In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In some embodiments, the cell culture medium further comprises IL-15. In some embodiments, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In some embodiments, the cell culture medium further comprises IL-21. In some embodiments, the cell culture medium comprises about 1 IU/mL of IL-21.

In some embodiments, the antigen-presenting feeder cells (APCs) are PBMCs. In some embodiments, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In some embodiments, the ratio of TILs to PBMCs in the rapid expansion and/or the second expansion is between 1 to 50 and 1 to 300. In some embodiments, the ratio of TILs to PBMCs in the rapid expansion and/or the second expansion is between 1 to 100 and 1 to 200.

In some embodiments, REP and/or the rapid second expansion is performed in flasks with the bulk TILs being mixed with a 100- or 200-fold excess of inactivated feeder cells, wherein the feeder cell concentration is at least 1.1 times (1.1X), 1.2X, 1.3X, 1.4X, 1.5X, 1.6X, 1.7X, 1.8X, 1.8X, 2X, 2.1×2.2X, 2.3X, 2.4X, 2.5X, 2.6X, 2.7X, 2.8X, 2.9X, 3.OX, 3.1X, 3.2X, 3.3X, 3.4X, 3.5X, 3.6X, 3.7X, 3.8X, 3.9X or 4.0X the feeder cell concentration in the priming first expansion, 30 ng/mL OKT3 anti-CD3 antibody and 6000 IU/mL IL-2 in 150 mL media. Media replacement is done (generally 2/3 media replacement via aspiration of 2/3 of spent media and replacement with an equal volume of fresh media) until the cells are transferred to an alternative growth chamber. Alternative growth chambers include G-REX flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In some embodiments, the second expansion (which can include expansions referred to as REP, as well as those referred to in Step D of FIG. 8 (in particular, e.g., FIG. 8A and/or FIG. 8B and/or FIG. 8C and/or FIG. 8D) may be performed in 500 mL capacity gas permeable flasks with 100 cm gas-permeable silicon bottoms (G-REX 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per mL of anti-CD3 (OKT3).

The G-REX 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, 2/3 of the media is replaced by aspiration of spent media and replacement with an equal volume of fresh media. In some embodiments, alternative growth chambers include GREX flasks and gas permeable containers as more fully discussed below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International Patent Application Publication No. WO/1998/030679 and U.S. Patent Application Publication No. US 2002/0076747 A1, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table 4. In other embodiments, the non-trace element moiety ingredients in the defined medium are present in the final concentrations listed in the column under the heading "A Preferred Embodiment of the 1× Medium" in Table 4. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table 4.

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In some embodiments, the cell medium in the first and/or second gas permeable container is unfiltered. The use of unfiltered cell medium may simplify the procedures necessary to expand the number of cells. In some embodiments, the cell medium in the first and/or second gas permeable container lacks beta-mercaptoethanol (BME or PME; also known as 2-mercaptoethanol, CAS 60-24-2).

In some embodiments, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $7.5\times10^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $5\times10^8$ antigen-presenting feeder cells (APCs), as discussed in more detail below.

In some embodiments, the rapid second expansion, for example, Step D according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, the step of rapid second expansion is split into a plurality of steps to achieve a scaling up of the culture by: (a) performing the rapid second expansion by culturing TILs in a small scale culture in a first container, e.g., a G-REX-100 MCS container, for a period of about 3 to 7 days, and then (b) effecting the transfer of the TILs in the small scale culture to a second container larger than the first container, e.g., a G-REX-500-MCS container, and culturing the TILs from the small scale culture in a larger scale culture in the second container for a period of about 4 to 7 days.

In some embodiments, the step of rapid second expansion is split into a plurality of steps to achieve a scaling out of the culture by: (a) performing the rapid second expansion by culturing TILs in a first small scale culture in a first container, e.g., a G-REX-100 MCS container, for a period of about 3 to 7 days, and then (b) effecting the transfer and apportioning of the TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the TILs from first small scale culture transferred to such second container is cultured in a second small scale culture for a period of about 4 to 7 days.

In some embodiments, the first small scale TIL culture is apportioned into a plurality of about 2 to 5 subpopulations of TILs.

In some embodiments, the step of rapid second expansion is split into a plurality of steps to achieve a scaling out and scaling up of the culture by: (a) performing the rapid second expansion by culturing TILs in a small scale culture in a first container, e.g., a G-REX-100 MCS container, for a period of about 3 to 7 days, and then (b) effecting the transfer and apportioning of the TILs from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX-500MCS containers, wherein in each second container the portion of the TILs from the small scale culture transferred to such second container is cultured in a larger scale culture for a period of about 4 to 7 days.

In some embodiments, the step of rapid second expansion is split into a plurality of steps to achieve a scaling out and scaling up of the culture by: (a) performing the rapid or second expansion by culturing TILs in a small scale culture in a first container, e.g., a G-REX-100 MCS container, for a period of about 5 days, and then (b) effecting the transfer and apportioning of the TILs from the small scale culture into and amongst 2, 3 or 4 second containers that are larger in size than the first container, e.g., G-REX-500 MCS containers, wherein in each second container the portion of the TILs from the small scale culture transferred to such second container is cultured in a larger scale culture for a period of about 6 days.

In some embodiments, upon the splitting of the rapid second expansion, each second container comprises at least $10^8$ TILs. In some embodiments, upon the splitting of the rapid or second expansion, each second container comprises at least $10^8$ TILs, at least 109 TILs, or at least $10^{10}$ TILs. In one exemplary embodiment, each second container comprises at least $10^{10}$ TILs.

In some embodiments, the first small scale TIL culture is apportioned into a plurality of subpopulations. In some embodiments, the first small scale TIL culture is apportioned into a plurality of about 2 to 5 subpopulations. In some embodiments, the first small scale TIL culture is apportioned into a plurality of about 2, 3, 4, or 5 subpopulations.

In some embodiments, after the completion of the rapid second expansion, the plurality of subpopulations comprises a therapeutically effective amount of TILs. In some embodiments, after the completion of the rapid or second expansion, one or more subpopulations of TILs are pooled together to produce a therapeutically effective amount of TILs. In some embodiments, after the completion of the rapid expansion, each subpopulation of TILs comprises a therapeutically effective amount of TILs.

In some embodiments, the rapid second expansion is performed for a period of about 3 to 7 days before being split into a plurality of steps. In some embodiments, the splitting of the rapid second expansion occurs at about day 3, day 4, day 5, day 6, or day 7 after the initiation of the rapid or second expansion.

In some embodiments, the splitting of the rapid second expansion occurs at about day 7, day 8, day 9, day 10, day 11, day 12, day 13, day 14, day 15, or day 16 day 17, or day 18 after the initiation of the first expansion (i.e., pre-REP expansion). In one exemplary embodiment, the splitting of the rapid or second expansion occurs at about day 16 after the initiation of the first expansion.

In some embodiments, the rapid second expansion is further performed for a period of about 7 to 11 days after the splitting. In some embodiments, the rapid second expansion is further performed for a period of about 5 days, 6 days, 7 days, 8 days, 9 days, 10 days, or 11 days after the splitting.

In some embodiments, the cell culture medium used for the rapid second expansion before the splitting comprises the same components as the cell culture medium used for the rapid second expansion after the splitting. In some embodiments, the cell culture medium used for the rapid second expansion before the splitting comprises different components from the cell culture medium used for the rapid second expansion after the splitting.

In some embodiments, the cell culture medium used for the rapid second expansion before the splitting comprises IL-2, optionally OKT-3 and further optionally APCs. In some embodiments, the cell culture medium used for the rapid second expansion before the splitting comprises IL-2, OKT-3, and further optionally APCs. In some embodiments, the cell culture medium used for the rapid second expansion before the splitting comprises IL-2, OKT-3 and APCs.

In some embodiments, the cell culture medium used for the rapid second expansion before the splitting is generated by supplementing the cell culture medium in the first expansion with fresh culture medium comprising IL-2, optionally OKT-3 and further optionally APCs. In some embodiments, the cell culture medium used for the rapid second expansion before the splitting is generated by supplementing the cell culture medium in the first expansion with fresh culture medium comprising IL-2, OKT-3 and APCs. In some embodiments, the cell culture medium used for the rapid second expansion before the splitting is generated by replacing the cell culture medium in the first expansion with fresh cell culture medium comprising IL-2, optionally OKT-3 and further optionally APCs. In some embodiments, the cell culture medium used for the rapid second expansion before the splitting is generated by replacing the cell culture medium in the first expansion with fresh cell culture medium comprising IL-2, OKT-3 and APCs.

In some embodiments, the cell culture medium used for the rapid second expansion after the splitting comprises IL-2, and optionally OKT-3. In some embodiments, the cell culture medium used for the rapid second expansion after the splitting comprises IL-2, and OKT-3. In some embodiments, the cell culture medium used for the rapid second expansion after the splitting is generated by replacing the cell culture medium used for the rapid second expansion before the splitting with fresh culture medium comprising IL-2 and optionally OKT-3. In some embodiments, the cell culture medium used for the rapid second expansion after the splitting is generated by replacing the cell culture medium used for the rapid second expansion before the splitting with fresh culture medium comprising IL-2 and OKT-3.

1. Feeder Cells and Antigen Presenting Cells

In some embodiments, the rapid second expansion procedures described herein (for example including expansion such as those described in Step D from FIG. 8 (in particular, e.g., FIG. 8A and/or FIG. 8B and/or FIG. 8C and/or FIG. 8D), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/mL OKT3 antibody and 3000 IU/mL IL-2.

In some embodiments, the PBMCs are cultured in the presence of 60 ng/mL OKT3 antibody and 6000 IU/mL IL-2. In some embodiments, the PBMCs are cultured in the presence of 60 ng/mL OKT3 antibody and 3000 IU/mL IL-2. In some embodiments, the PBMCs are cultured in the presence of 30 ng/mL OKT3 antibody and 6000 IU/mL IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30-60 ng/mL OKT3 antibody and 1000-6000 IU/mL IL-2. In some embodiments, the PBMCs are cultured in the presence of 30-60 ng/mL OKT3 antibody and 2000-5000 IU/mL IL-2. In some embodiments, the PBMCs are cultured in the presence of 30-60 ng/mL OKT3 antibody and 2000-4000 IU/mL IL-2. In some embodiments, the PBMCs are cultured in the presence of 30-60 ng/mL OKT3 antibody and 2500-3500 IU/mL IL-2. In some embodiments, the PBMCs are cultured in the presence of 30-60 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells. In some embodiments, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In some embodiments, the ratio of TILs to antigen-presenting feeder cells in the second expansion is between 1 to 50 and 1 to 300. In some embodiments, the ratio of TILs to antigen-presenting feeder cells in the second expansion is between 1 to 100 and 1 to 200.

In some embodiments, the second expansion procedures described herein require a ratio of about $5\times10^8$ feeder cells to about $100\times10^6$ TILs. In some embodiments, the second expansion procedures described herein require a ratio of about $7.5\times10^8$ feeder cells to about $100\times10^6$ TILs. In some embodiments, the second expansion procedures described herein require a ratio of about $5\times10^8$ feeder cells to about $50\times10^6$ TILs. In some embodiments, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires twice the number of feeder cells as the rapid second expansion. In yet another embodiment, when the priming first expansion described herein requires about $2.5\times10^8$ feeder cells, the rapid second expansion requires about $5\times10^8$ feeder cells. In yet another embodiment, when the priming first expansion described herein requires about $2.5\times10^8$ feeder cells, the rapid second expansion requires about $7.5\times10^8$ feeder cells. In yet another embodiment, the rapid second expansion requires two times (2.0×), 2.5×, 3.0×, 3.5× or 4.0× the number of feeder cells as the priming first expansion.

In some embodiments, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, artificial antigen-presenting (aAPC) cells are used in place of PBMCs. In some embodiments, the PBMCs are added to the rapid second expansion at twice the concentration of PBMCs that were added to the priming first expansion.

In general, the allogenic PBMCs are inactivated, either via irradiation or heat treatment, and used in the TIL expansion procedures described herein, including the exemplary procedures described in the figures and examples.

In some embodiments, artificial antigen presenting cells are used in the rapid second expansion as a replacement for, or in combination with, PBMCs.

2. Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

In some embodiments, Step D (from in particular, e.g., FIG. 8A and/or FIG. 8B and/or FIG. 8C and/or FIG. 8D) may also include the addition of OKT-3 antibody or muromonab to the culture media, as described elsewhere herein. In some embodiments, Step D may also include the addition of a 4-1BB agonist to the culture media, as described elsewhere herein. In some embodiments, Step D (from, in particular, e.g., FIG. 8A and/or FIG. 8B and/or FIG. 8C and/or FIG. 8D) may also include the addition of an OX-40 agonist to the culture media, as described elsewhere herein. In addition, additives such as peroxisome proliferator-activated receptor gamma coactivator I-alpha agonists, including proliferator-activated receptor (PPAR)-gamma agonists such as a thiazolidinedione compound, may be used in the culture media during Step D (from, in particular, e.g., FIG. 8A and/or FIG. 8B and/or FIG. 8C and/or FIG. 8D), as described in U.S. Patent Application Publication No. US 2019/0307796 A1, the disclosure of which is incorporated by reference herein.

E. STEP E: Harvest TILs

After the rapid second expansion step, cells can be harvested. In some embodiments the TILs are harvested after one, two, three, four or more expansion steps, for example as provided in FIG. 8 (in particular, e.g., FIG. 8A and/or FIG. 8B and/or FIG. 8C and/or FIG. 8D). In some embodiments the TILs are harvested after two expansion steps, for example as provided in FIG. 8 (in particular, e.g., FIG. 8A and/or FIG. 8B and/or FIG. 8C and/or FIG. 8D). In some embodiments the TILs are harvested after two expansion steps, one priming first expansion and one rapid second expansion, for example as provided in FIG. 8 (in particular, e.g., FIG. 8A and/or FIG. 8B and/or FIG. 8C and/or FIG. 8D).

TILs can be harvested in any appropriate and sterile manner, including, for example by centrifugation. Methods for TIL harvesting are well known in the art and any such known methods can be employed with the present process. In some embodiments, TILs are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, Step E according to FIG. 8 (in particular, e.g., FIG. 8A and/or FIG. 8B and/or FIG. 8C and/or FIG. 8D), is performed according to the processes described herein. In some embodiments, the closed system is accessed via syringes under sterile conditions in order to maintain the sterility and closed nature of the system. In some embodiments, a closed system as described herein is employed.

In some embodiments, TILs are harvested according to the methods described in herein. In some embodiments, TILs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

F. STEP F: Final Formulation and Transfer to Infusion Container

After Steps A through E as provided in an exemplary order in FIG. 8 (in particular, e.g., FIG. 8A and/or FIG. 8B and/or FIG. 8C and/or FIG. 8D) and as outlined in detailed above and herein are complete, cells are transferred to a container for use in administration to a patient, such as an infusion bag or sterile vial. In some embodiments, once a therapeutically sufficient number of TILs are obtained using the expansion methods described above, they are transferred to a container for use in administration to a patient.

In some embodiments, TILs expanded using the methods of the present disclosure are administered to a patient as a pharmaceutical composition. In some embodiments, the pharmaceutical composition is a suspension of TILs in a sterile buffer. TILs expanded as disclosed herein may be administered by any suitable route as known in the art. In some embodiments, the TILs are administered as a single intra-arterial or intravenous infusion, which preferably lasts approximately 30 to 60 minutes. Other suitable routes of administration include intraperitoneal, intrathecal, and intralymphatic.

V. Further Gen 2, Gen 3, and Other TIL Manufacturing Process Embodiments

A. PBMC Feeder Cell Ratios

In some embodiments, the culture media used in expansion methods described herein (see for example, FIG. 8 (in particular, e.g., FIG. 8A and/or FIG. 8B and/or FIG. 8C and/or FIG. 8D)) include an anti-CD3 antibody e.g. OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In some embodiments, the number of PBMC feeder layers is calculated as follows:

A. Volume of a T-cell (10 μm diameter): $V=(4/3)\pi r^3=523.6\ \mu m^3$

B. Column of G-REX 100 (M) with a 40 μm (4 cells) height: $V=(4/3)\pi r^3=4\times10^{12}\ \mu m^3$ C. Number cell required to fill column B: $4\times10^{12}\ \mu m^3/523.6\ \mu m^3=7.6\times10^8\ m^3*0.64=4.86\times10^8$ D. Number cells that can be optimally activated in 4D space: $4.86\times10^8/24=20.25\times10^6$ E. Number of feeders and TIL extrapolated to G-REX 500: TIL: $100\times10^6$ and Feeder: $2.5\times10^9$ In this calculation, an approximation of the number of mononuclear cells required to provide an icosahedral geometry for activation of TIL in a cylinder with a 100 $cm^2$ base is used. The calculation derives the experimental result of $\sim5\times10^8$ for threshold activation of T-cells which closely mirrors NCI experimental data, as described in Jin, et.al., *J. Immunother.* 2012, 35, 283-292. In (C), the multiplier (0.64) is the random packing density for equivalent spheres as calculated by Jaeger and Nagel, *Science,* 1992, 255, 1523-3. In (D), the divisor 24 is the number of equivalent spheres that could contact a similar object in 4-dimensional space or "the Newton number" as described in Musin, Russ. Math. Surv, 2003, 58, 794-795.

In other embodiments, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In other embodiments, the number of antigen-presenting feeder cells (APCs) exogenously supplied during the rapid second expansion is greater than the number of APCs exogenously supplied during the priming first expansion.

In other embodiments, the ratio of the number of APCs exogenously supplied during the rapid second expansion to the number of APCs exogenously supplied during the priming first expansion is selected from a range of from at or about 1.1:1 to at or about 20:1.

In other embodiments, the ratio of the number of APCs exogenously supplied during the rapid second expansion to the number of APCs exogenously supplied during the priming first expansion is selected from a range of from at or about 1.1:1 to at or about 10:1.

In other embodiments, the ratio of the number of APCs exogenously supplied during the rapid second expansion to the number of APCs exogenously supplied during the priming first expansion is selected from a range of from at or about 1.1:1 to at or about 9:1.

In other embodiments, the ratio of the number of APCs exogenously supplied during the rapid second expansion to the number of APCs exogenously supplied during the priming first expansion is selected from a range of from at or about 1.1:1 to at or about 8:1.

In other embodiments, the ratio of the number of APCs exogenously supplied during the rapid second expansion to the number of APCs exogenously supplied during the priming first expansion is selected from a range of from at or about 1.1:1 to at or about 7:1.

In other embodiments, the ratio of the number of APCs exogenously supplied during the rapid second expansion to the number of APCs exogenously supplied during the priming first expansion is selected from a range of from at or about 1.1:1 to at or about 6:1.

In other embodiments, the ratio of the number of APCs exogenously supplied during the rapid second expansion to the number of APCs exogenously supplied during the priming first expansion is selected from a range of from at or about 1.1:1 to at or about 5:1.

In other embodiments, the ratio of the number of APCs exogenously supplied during the rapid second expansion to the number of APCs exogenously supplied during the priming first expansion is selected from a range of from at or about 1.1:1 to at or about 4:1.

In other embodiments, the ratio of the number of APCs exogenously supplied during the rapid second expansion to the number of APCs exogenously supplied during the priming first expansion) is selected from a range of from at or about 1.1:1 to at or about 3:1.

In other embodiments, the ratio of the number of APCs exogenously supplied during the rapid second expansion to the number of APCs exogenously supplied during the priming first expansion is selected from a range of from at or about 1.1:1 to at or about 2.9:1.

In other embodiments, the ratio of the number of APCs exogenously supplied during the rapid second expansion to the number of APCs exogenously supplied during the priming first expansion is selected from a range of from at or about 1.1:1 to at or about 2.8:1.

In other embodiments, the ratio of the number of APCs exogenously supplied during the rapid second expansion to the number of APCs exogenously supplied during the priming first expansion is selected from a range of from at or about 1.1:1 to at or about 2.7:1.

In other embodiments, the ratio of the number of APCs exogenously supplied during the rapid second expansion to the number of APCs exogenously supplied during the priming first expansion is selected from a range of from at or about 1.1:1 to at or about 2.6:1.

In other embodiments, the ratio of the number of APCs exogenously supplied during the rapid second expansion to the number of APCs exogenously supplied during the priming first expansion is selected from a range of from at or about 1.1:1 to at or about 2.5:1.

In other embodiments, the ratio of the number of APCs exogenously supplied during the rapid second expansion to the number of APCs exogenously supplied during the priming first expansion is selected from a range of from at or about 1.1:1 to at or about 2.4:1.

In other embodiments, the ratio of the number of APCs exogenously supplied during the rapid second expansion to the number of APCs exogenously supplied during the priming first expansion is selected from a range of from at or about 1.1:1 to at or about 2.3:1.

In other embodiments, the ratio of the number of APCs exogenously supplied during the rapid second expansion to the number of APCs exogenously supplied during the priming first expansion is selected from a range of from at or about 1.1:1 to at or about 2.2:1.

In other embodiments, the ratio of the number of APCs exogenously supplied during the rapid second expansion to the number of APCs exogenously supplied during the priming first expansion is selected from a range of from at or about 1.1:1 to at or about 2.1:1.

In other embodiments, the ratio of the number of APCs exogenously supplied during the rapid second expansion to the number of APCs exogenously supplied during the priming first expansion is selected from a range of from at or about 1.1:1 to at or about 2:1.

In other embodiments, the ratio of the number of APCs exogenously supplied during the rapid second expansion to the number of APCs exogenously supplied during the priming first expansion is selected from a range of from at or about 2:1 to at or about 10:1.

In other embodiments, the ratio of the number of APCs exogenously supplied during the rapid second expansion to the number of APCs exogenously supplied during the priming first expansion is selected from a range of from at or about 2:1 to at or about 5:1.

In other embodiments, the ratio of the number of APCs exogenously supplied during the rapid second expansion to the number of APCs exogenously supplied during the priming first expansion is selected from a range of from at or about 2:1 to at or about 4:1.

In other embodiments, the ratio of the number of APCs exogenously supplied during the rapid second expansion to the number of APCs exogenously supplied during the priming first expansion is selected from a range of from at or about 2:1 to at or about 3:1.

In other embodiments, the ratio of the number of APCs exogenously supplied during the rapid second expansion to the number of APCs exogenously supplied during the priming first expansion is selected from a range of from at or about 2:1 to at or about 2.9:1.

In other embodiments, the ratio of the number of APCs exogenously supplied during the rapid second expansion to the number of APCs exogenously supplied during the priming first expansion is selected from a range of from at or about 2:1 to at or about 2.8:1.

In other embodiments, the ratio of the number of APCs exogenously supplied during the rapid second expansion to the number of APCs exogenously supplied during the priming first expansion is selected from a range of from at or about 2:1 to at or about 2.7:1.

In other embodiments, the ratio of the number of APCs exogenously supplied during the rapid second expansion to the number of APCs exogenously supplied during the priming first expansion is selected from a range of from at or about 2:1 to at or about 2.6:1.

In other embodiments, the ratio of the number of APCs exogenously supplied during the rapid second expansion to the number of APCs exogenously supplied during the priming first expansion is selected from a range of from at or about 2:1 to at or about 2.5:1.

In other embodiments, the ratio of the number of APCs exogenously supplied during the rapid second expansion to the number of APCs exogenously supplied during the priming first expansion is selected from a range of from at or about 2:1 to at or about 2.4:1.

In other embodiments, the ratio of the number of APCs exogenously supplied during the rapid second expansion to the number of APCs exogenously supplied during the priming first expansion is selected from a range of from at or about 2:1 to at or about 2.3:1.

In other embodiments, the ratio of the number of APCs exogenously supplied during the rapid second expansion to the number of APCs exogenously supplied during the priming first expansion is selected from a range of from at or about about 2:1 to at or about 2.2:1.

In other embodiments, the ratio of the number of APCs exogenously supplied during the rapid second expansion to the number of APCs exogenously supplied during the priming first expansion is selected from a range of from at or about 2:1 to at or about 2.1:1.

In other embodiments, the ratio of the number of APCs exogenously supplied during the rapid second expansion to the number of APCs exogenously supplied during the priming first expansion is at or about 2:1.

In other embodiments, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In other embodiments, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$APCs.

In other embodiments, the number of APCs exogenously supplied during the priming first expansion is selected from the range of at or about $1.5\times10^8$ APCs to at or about $3\times10^8$ APCs, and the number of APCs exogenously supplied during the rapid second expansion is selected from the range of at or about $4\times10^8$ APCs to at or about $7.5\times10^8$ APCs.

In other embodiments, the number of APCs exogenously supplied during the priming first expansion is selected from the range of at or about $2\times10^8$ APCs to at or about $2.5\times10^8$ APCs, and the number of APCs exogenously supplied during the rapid second expansion is selected from the range of at or about $4.5\times10^8$ APCs to at or about $5.5\times10^8$ APCs.

In other embodiments, the number of APCs exogenously supplied during the priming first expansion is at or about $2.5\times10^8$ APCs, and the number of APCs exogenously supplied during the rapid second expansion is at or about $5\times10^8$ APCs.

In other embodiments, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In other embodiments, the number of APCs (including, for example, PBMCs) exogenously supplied at day 7 of the rapid second expansion is greater than the number of PBMCs exogenously supplied at day 0 of the priming first expansion.

In other embodiments, the APCs exogenously supplied in the priming first expansion are seeded in the culture flask at a density selected from a range of at or about $1.0\times10^6$ APCs/cm$^2$ to at or about $4.5\times10^6$ APCs/cm$^2$.

In other embodiments, the APCs exogenously supplied in the priming first expansion are seeded in the culture flask at a density selected from a range of at or about $1.5\times10^6$ APCs/cm$^2$ to at or about $3.5\times10^6$ APCs/cm$^2$.

In other embodiments, the APCs exogenously supplied in the priming first expansion are seeded in the culture flask at a density selected from a range of at or about $2\times10^6$ APCs/cm$^2$ to at or about $3\times10^6$ APCs/cm$^2$.

In other embodiments, the APCs exogenously supplied in the priming first expansion are seeded in the culture flask at a density of at or about $2\times10^6$ APCs/cm$^2$.

In other embodiments, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$.

In other embodiments, the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In other embodiments, the APCs exogenously supplied in the rapid second expansion are seeded in the culture flask at a density selected from a range of at or about $3.5\times10^6$ APCs/cm$^2$ to about $6.0\times10^6$ APCs/cm$^2$.

In other embodiments, the APCs exogenously supplied in the rapid second expansion are seeded in the culture flask at a density selected from a range of at or about $4.0\times10^6$ APCs/cm$^2$ to about 5.5×106 APCs/cm$^2$.

In other embodiments, the APCs exogenously supplied in the rapid second expansion are seeded in the culture flask at a density selected from a range of at or about $4.0\times10^6$ APCs/cm$^2$.

In other embodiments, the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times$ $10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In other embodiments, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$ and the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In other embodiments, the APCs exogenously supplied in the priming first expansion are seeded in the culture flask at a density selected from a range of at or about $1.0\times10^6$ APCs/cm$^2$ to at or about $4.5\times10^6$ APCs/cm$^2$, and the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In other embodiments, the APCs exogenously supplied in the priming first expansion are seeded in the culture flask at a density selected from a range of at or about $1.5\times10^6$ APCs/cm$^2$ to at or about $3.5\times10^6$ APCs/cm$^2$, and the APCs exogenously supplied in the rapid second expansion are seeded in the culture flask at a density selected from a range of at or about $3.5\times10^6$ APCs/cm$^2$ to at or about $6\times10^6$ APCs/cm$^2$.

In other embodiments, the APCs exogenously supplied in the priming first expansion are seeded in the culture flask at a density selected from a range of at or about $2\times10^6$ APCs/cm$^2$ to at or about $3\times10^6$ APCs/cm$^2$, and the APCs exogenously supplied in the rapid second expansion are seeded in the culture flask at a density selected from a range of at or about $4\times10^6$ APCs/cm$^2$ to at or about $5.5\times10^6$ APCs/cm$^2$.

In other embodiments, the APCs exogenously supplied in the priming first expansion are seeded in the culture flask at a density at or about $2\times10^6$ APCs/cm$^2$ and the APCs exogenously supplied in the rapid second expansion are seeded in the culture flask at a density of at or about $4\times10^6$ APCs/cm$^2$.

In other embodiments, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 20:1.

In other embodiments, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 10:1.

In other embodiments, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 9:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 8:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 7:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 6:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 5:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 4:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 3:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.9:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.8:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.7:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.6:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.5:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.4:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.3:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.2:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.1:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 10:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 5:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 4:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 3:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.9:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.8:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.7:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.6:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.5:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.4:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.3:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.2:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.1:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In other embodiments, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In other embodiments, the number of APCs (including, for example, PBMCs) exogenously supplied at day 0 of the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs (including, for example, PBMCs), and the number of APCs (including, for example, PBMCs) exogenously supplied at day 7 of the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$APCs (including, for example, PBMCs).

In other embodiments, the number of APCs (including, for example, PBMCs) exogenously supplied at day 0 of the priming first expansion is selected from the range of at or about $1\times10^8$ APCs (including, for example, PBMCs) to at or about $3.5\times10^8$ APCs (including, for example, PBMCs), and the number of APCs (including, for example, PBMCs) exogenously supplied at day 7 of the rapid second expansion is selected from the range of at or about $3.5\times10^8$ APCs (including, for example, PBMCs) to at or about $1\times10^9$ APCs (including, for example, PBMCs).

In other embodiments, the number of APCs (including, for example, PBMCs) exogenously supplied at day 0 of the priming first expansion is selected from the range of at or about $1.5\times10^8$ APCs to at or about $3\times10^8$ APCs (including, for example, PBMCs), and the number of APCs (including, for example, PBMCs) exogenously supplied at day 7 of the rapid second expansion is selected from the range of at or about $4\times10^8$ APCs (including, for example, PBMCs) to at or about $7.5\times10^8$ APCs (including, for example, PBMCs).

In other embodiments, the number of APCs (including, for example, PBMCs) exogenously supplied at day 0 of the priming first expansion is selected from the range of at or about $2\times10^8$ APCs (including, for example, PBMCs) to at or about $2.5\times10^8$ APCs (including, for example, PBMCs), and the number of APCs (including, for example, PBMCs) exogenously supplied at day 7 of the rapid second expansion is selected from the range of at or about $4.5\times10^8$ APCs (including, for example, PBMCs) to at or about $5.5\times10^8$ APCs (including, for example, PBMCs).

In other embodiments, the number of APCs (including, for example, PBMCs) exogenously supplied at day 0 of the priming first expansion is at or about $2.5\times10^8$ APCs (including, for example, PBMCs) and the number of APCs (including, for example, PBMCs) exogenously supplied at day 7 of the rapid second expansion is at or about $5\times10^8$ APCs (including, for example, PBMCs)

In other embodiments, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In other embodiments, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In other embodiments, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In other embodiments, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In other embodiments, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In other embodiments, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In other embodiments, day 0 of the priming first expansion occurs in the presence of layered APCs (including, for example, PBMCs) with an average thickness of of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In other embodiments, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In other embodiments, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In other embodiments, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In other embodiments, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:10.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:8.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:7.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:6.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:5.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:4.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:3.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:2.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.2 to at or about 1:8.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.3 to at or about 1:7.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.4 to at or about 1:6.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.5 to at or about 1:5.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.6 to at or about 1:4.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.7 to at or about 1:3.5.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.8 to at or about 1:3.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.9 to at or about 1:2.5.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In other embodiments, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is selected from the range of about $1.0\times10^6$ APCs/$cm^2$ to about $4.5\times10^6$ APCs/$cm^2$, and the number of APCs in the rapid second expansion is selected from the range of about $2.5\times10^6$ APCs/$cm^2$ to about $7.5\times10^6$ APCs/$cm^2$.

In some embodiments, the number of APCs in the priming first expansion is selected from the range of about $1.5\times10^6$ APCs/$cm^2$ to about $3.5\times10^6$ APCs/$cm^2$, and the number of APCs in the rapid second expansion is selected from the range of about $3.5\times10^6$ APCs/$cm^2$ to about $6.0\times10^6$ APCs/$cm^2$.

In some embodiments, the number of APCs in the priming first expansion is selected from the range of about $2.0\times10^6$ APCs/$cm^2$ to about $3.0\times10^6$ APCs/$cm^2$, and the number of APCs in the rapid second expansion is selected from the range of about 4.Ox $10^6$ APCs/$cm^2$ to about $5.5\times10^6$ APCs/$cm^2$.

B. Optional Cell Medium Components

1. Anti-CD3 Antibodies

In some embodiments, the culture media used in expansion methods described herein (including those referred to as REP, see for example, FIGS. 1 and 8 (in particular, e.g., FIG. 8B)) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody muromonab is used (commercially available from Ortho-McNeil, Raritan, NJ or Miltenyi Biotech, Auburn, CA). See, Table 1.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In some embodiments, the OKT3 anti-CD3 antibody muromonab is used (commercially available from Ortho-McNeil, Raritan, NJ or Miltenyi Biotech, Auburn, CA).

2. 4-1BB (CD137) Agonists

In some embodiments, the cell culture medium of the priming first expansion and/or the rapid second expansion comprises a TNFRSF agonist. In some embodiments, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g. IgG, IgE, IgM, IgD, IgA, and IgY), class (e.g., IgGI, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In some embodiments, the 4-1BB agonist is an antigen binding protein that is a fully human antibody. In some embodiments, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In some embodiments, the 4-1BB agonist is an agonistic, anti-4-1BB humanized or fully human monoclonal antibody (i.e., an antibody derived from a single cell line). In some embodiments, the 4-1BB agonist is EU-101 (Eutilex Co. Ltd.), utomilumab, or urelumab, or a fragment, derivative, conjugate, variant, or biosimilar thereof. In some embodiments, the 4-1BB agonist is utomilumab or urelumab, or a fragment, derivative, conjugate, variant, or biosimilar thereof.

In some embodiments, the 4-1BB agonist or 4-1BB binding molecule may also be a fusion protein. In some embodiments, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In some embodiments, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In some embodiments, the 4-1BB agonist is a binding molecule that binds to human 4-1BB (SEQ ID NO:40). In some embodiments, the 4-1BB agonist is a binding molecule that binds to murine 4-1BB (SEQ ID NO:41). The amino acid sequences of 4-1BB antigen to which a 4-1BB agonist or binding molecule binds are summarized in Table 5.

TABLE 5

Amino acid sequences of 4-1BB antigens.

| Identifier | Sequence (One-Letter Amino Acid Symbols) | |
|---|---|---|
| SEQ ID NO: 40 human 4-1BB, Tumor necrosis factor receptor superfamily, member 9 (*Homo sapiens*) | MGNSCYNIVA TLLLVLNFER TRSLQDPCSN CPAGTFCDNN RNQICSPCPP NSFSSAGGQR | 60 |
| | TCDICRQCKG VFRTRKECSS TSNAECDCTP GFHCLGAGCS MCEQDCKQGQ ELTKKGCKDC | 120 |
| | CFGTFNDQKR GICRPWTNCS LDGKSVLVNG TKERDVVCGP SPADLSPGAS SVTPPAPARE | 180 |
| | PGHSPQIISF FLALTSTALL FLLFFLTLRF SVVKRGRKKL LYIFKQPFMR PVQTTQEEDG | 240 |
| | CSCRFPEEEE GGCEL | 255 |
| SEQ ID NO: 41 murine 4-1BB, Tumor necrosis factor receptor superfamily, member 9 (*Mus musculus*) | MGNNCYNVVV IVLLLVGCEK VGAVQNSCDN CQPGTFCRKY NPVCKSCPPS TFSSIGGQPN | 60 |
| | CNICRVCAGY FRFKKFCSST HNAECECIEG FHCLGPQCTR CEKDCRPGQE LTKQGCKTCS | 120 |
| | LGTFNDQNGT GVCRPWTNCS LDGRSVLKTG TTEKDVVCGP PVVSFSPSTT ISVTPEGGPG | 180 |
| | GHSLQVLTLF LALTSALLLA LIFITLLFSV LKWIRKKFPH IFKQPFKKTT GAAQEEDACS | 240 |
| | CRCPQEEEGG GGGYEL | 256 |

In some embodiments, the compositions, processes and methods described include a 4-1BB agonist that binds human or murine 4-1BB with a $K_D$ of about 100 µM or lower, binds human or murine 4-1BB with a $K_D$ of about 90 µM or lower, binds human or murine 4-1BB with a $K_D$ of about 80 µM or lower, binds human or murine 4-1BB with a $K_D$ of about 70 µM or lower, binds human or murine 4-1BB with a $K_D$ of about 60 µM or lower, binds human or murine 4-1BB with a $K_D$ of about 50 µM or lower, binds human or murine 4-1BB with a $K_D$ of about 40 µM or lower, or binds human or murine 4-1BB with a $K_D$ of about 30 µM or lower.

In some embodiments, the compositions, processes and methods described include a 4-1BB agonist that binds to human or murine 4-1BB with a $k_{assoc}$ of about $7.5\times10^5$ 1/M s or faster, binds to human or murine 4-1BB with a $k_{assoc}$ of about $7.5\times10^5$ 1/M s or faster, binds to human or murine 4-1BB with a $k_{assoc}$ of about $8\times10^5$ 1/M s or faster, binds to human or murine 4-1BB with a $k_{assoc}$ of about $8.5\times10^5$ 1/M s or faster, binds to human or murine 4-1BB with a $k_{assoc}$ of about $9\times10^5$ 1/M s or faster, binds to human or murine 4-1BB with a $k_{assoc}$ of about $9.5\times10^5$ 1/M s or faster, or binds to human or murine 4-1BB with a $k_{assoc}$ of about $1\times10^6$ 1/M s or faster.

In some embodiments, the compositions, processes and methods described include a 4-1BB agonist that binds to human or murine 4-1BB with a $k_{dissoc}$ of about $2\times10^{-5}$ 1/s or slower, binds to human or murine 4-1BB with a $k_{dissoc}$ of about $2.1\times10^{-5}$ 1/s or slower, binds to human or murine 4-1BB with a $k_{dissoc}$ of about $2.2\times10^{-5}$ 1/s or slower, binds to human or murine 4-1BB with a $k_{dissoc}$ of about $2.3\times10^{-5}$ 1/s or slower, binds to human or murine 4-1BB with a $k_{dissoc}$ of about $2.4\times10^{-5}$ 1/s or slower, binds to human or murine 4-1BB with a $k_{dissoc}$ of about $2.5\times10^{-5}$ 1/s or slower, binds to human or murine 4-1BB with a $k_{dissoc}$ of about $2.6\times10^{-5}$ 1/s or slower or binds to human or murine 4-1BB with a $k_{dissoc}$ of about $2.7\times10^{-5}$ 1/s or slower, binds to human or murine 4-1BB with a $k_{dissoc}$ of about $2.8\times10^{-5}$ 1/s or slower, binds to human or murine 4-1BB with a $k_{dissoc}$ of about $2.9\times10^{-5}$ 1/s or slower, or binds to human or murine 4-1BB with a $k_{dissoc}$ of about $3\times10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In some embodiments, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 6. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In some embodiments, a 4-1BB agonist comprises a heavy chain given by SEQ ID NO:42 and a light chain given by SEQ ID NO:43. In some embodiments, a 4-1BB agonist comprises heavy and light chains having the sequences shown in SEQ ID NO:42 and SEQ ID NO:43, respectively, or antigen binding fragments, Fab fragments, single-chain variable fragments (scFv), variants, or conjugates thereof. In some embodiments, a 4-1BB agonist comprises heavy and light chains that are each at least 99% identical to the sequences shown in SEQ ID NO:42 and SEQ ID NO:43, respectively. In some embodiments, a 4-1BB agonist comprises heavy and light chains that are each at least 98% identical to the sequences shown in SEQ ID NO:42 and SEQ ID NO:43, respectively. In some embodiments, a 4-1BB agonist comprises heavy and light chains that are each at least 97% identical to the sequences shown in SEQ ID NO:42 and SEQ ID NO:43, respectively. In some embodiments, a 4-1BB agonist comprises heavy and light chains that are each at least 96% identical to the sequences shown in SEQ ID NO:42 and SEQ ID NO:43, respectively. In some embodiments, a 4-1BB agonist comprises heavy and light chains that are each at least 95% identical to the sequences shown in SEQ ID NO:42 and SEQ ID NO:43, respectively.

In some embodiments, the 4-1BB agonist comprises the heavy and light chain CDRs or variable regions (VRs) of utomilumab. In some embodiments, the 4-1BB agonist heavy chain variable region ($V_H$) comprises the sequence shown in SEQ ID NO:44, and the 4-1BB agonist light chain variable region ($V_L$) comprises the sequence shown in SEQ ID NO:45, and conservative amino acid substitutions thereof. In some embodiments, a 4-1BB agonist comprises $V_H$ and $V_L$ regions that are each at least 99% identical to the sequences shown in SEQ ID NO:44 and SEQ ID NO:45, respectively. In some embodiments, a 4-1BB agonist comprises $V_H$ and $V_L$ regions that are each at least 98% identical to the sequences shown in SEQ ID NO:44 and SEQ ID NO:45, respectively. In some embodiments, a 4-1BB agonist comprises $V_H$ and $V_L$ regions that are each at least 97% identical to the sequences shown in SEQ ID NO:44 and SEQ ID NO:45, respectively. In some embodiments, a 4-1BB agonist comprises $V_H$ and $V_L$ regions that are each at least 96% identical to the sequences shown in SEQ ID NO:44 and SEQ ID NO:45, respectively. In some embodiments, a 4-1BB agonist comprises $V_H$ and $V_L$ regions that are each at least 95% identical to the sequences shown in SEQ ID NO:44 and SEQ ID NO:45, respectively. In some embodiments, a 4-1BB agonist comprises an scFv antibody comprising $V_H$ and $V_L$ regions that are each at least 99% identical to the sequences shown in SEQ ID NO:44 and SEQ ID NO:45.

In some embodiments, a 4-1BB agonist comprises heavy chain CDR1, CDR2 and CDR3 domains having the sequences set forth in SEQ ID NO:46, SEQ ID NO:47, and SEQ ID NO:48, respectively, and conservative amino acid substitutions thereof, and light chain CDR1, CDR2 and CDR3 domains having the sequences set forth in SEQ ID NO:49, SEQ ID NO:50, and SEQ ID NO:51, respectively, and conservative amino acid substitutions thereof..

In some embodiments, the 4-1BB agonist is a 4-1BB agonist biosimilar monoclonal antibody approved by drug regulatory authorities with reference to utomilumab. In some embodiments, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 6

Amino acid sequences for 4-1BB agonist antibodies related to utomilumab.

| Identifier | Sequence (One-Letter Amino Acid Symbols) | |
|---|---|---|
| SEQ ID NO: 42 heavy chain for utomilumab | EVQLVQSGAE VKKPGESLRI SCKGSGYSFS TYWISWVRQM PGKGLEWMGK IYPGDSYTNY | 60 |
| | SPSFQGQVTI SADKSISTAY LQWSSLKASD TAMYYCARGY GIFDYWGQGT LVTVSSASTK | 120 |
| | GPSVFPLAPC SRSTSESTAA LGCLVKDYFP EPVTVSWNSG ALTSGVHTFP AVLQSSGLYS | 180 |
| | LSSVVTVPSS NFGTQTYTCN VDHKPSNTKV DKTVERKCCV ECPPCPAPPV AGPSVFLFPP | 240 |
| | KPKDTLMISR TPEVTCVVVD VSHEDPEVQF NWYVDGVEVH NAKTKPREEQ FNSTFRVVSV | 300 |
| | LTVVHQDWLN GKEYKCKVSN KGLPAPIEKT ISKTKGQPRE PQVYTLPPSR EEMTKNQVSL | 360 |
| | TCLVKGFYPS DIAVEWESNG QPENNYKTTP PMLDSDGSFF LYSKLTVDKS RWQQGNVFSC | 420 |
| | SVMHEALHNH YTQKSLSLSP G | 441 |
| SEQ ID NO: 43 light chain for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVLGQ PKAAPSVTLF | 120 |
| | PPSSEELQAN KATLVCLISD FYPGAVTVAW KADSSPVKAG VETTTPSKQS NNKYAASSYL | 180 |
| | SLTPEQWKSH RSYSCQVTHE GSTVEKTVAP TECS | 214 |
| SEQ ID NO: 44 heavy chain variable region for utomilumab | EVQLVQSGAE VKKPGESLRI SCKGSGYSFS TYWISWVRQM PGKGLEWMG KIYPGDSYTN | 60 |
| | YSPSFQGQVT ISADKSISTA YLQWSSLKAS DTAMYYCARG YGIFDYWGQ GTLVTVSS | 118 |
| SEQ ID NO: 45 light chain variable region for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVL | 108 |
| SEQ ID NO: 46 heavy chain CDR1 for utomilumab | STYWIS | 6 |
| SEQ ID NO: 47 heavy chain CDR2 for utomilumab | KIYPGDSYTN YSPSFQG | 17 |
| SEQ ID NO: 48 heavy chain CDR3 for utomilumab | RGYGIFDY | 8 |
| SEQ ID NO: 49 light chain CDR1 for utomilumab | SGDNIGDQYA H | 11 |
| SEQ ID NO: 50 light chain CDR2 for utomilumab | QDKNRPS | 7 |

TABLE 6-continued

| Amino acid sequences for 4-1BB agonist antibodies related to utomilumab. | | |
|---|---|---|
| Identifier | Sequence (One-Letter Amino Acid Symbols) | |
| SEQ ID NO: 51 light chain CDR3 for utomilumab | ATYTGFGSLA V | 11 |

In some embodiments, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD 137)], *Homo sapiens* (fully human) monoclonal antibody. The amino acid sequences of urelumab are set forth in Table 7. Urelumab comprises N-glycosylation sites at positions 298 (and 298"); heavy chain intrachain disulfide bridges at positions 22-95 ($V_H$-$V_L$), 148-204 (CHI-$C_L$), 262-322 ($C_H2$) and 368-426 ($C_H3$) (and at positions 22"-95", 148"-204", 262"-322", and 368"-426"); light chain intrachain disulfide bridges at positions 23'-88' ($V_H$-$V_L$) and 136'-196' ($C_H1$-$C_L$) (and at positions 23'"-88'" and 136'"-196'"); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http://dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In some embodiments, a 4-1BB agonist comprises a heavy chain given by SEQ ID NO:52 and a light chain given by SEQ ID NO:53. In some embodiments, a 4-1BB agonist comprises heavy and light chains having the sequences shown in SEQ ID NO:52 and SEQ ID NO:53, respectively, or antigen binding fragments, Fab fragments, single-chain variable fragments (scFv), variants, or conjugates thereof. In some embodiments, a 4-1BB agonist comprises heavy and light chains that are each at least 99% identical to the sequences shown in SEQ ID NO:52 and SEQ ID NO:53, respectively. In some embodiments, a 4-1BB agonist comprises heavy and light chains that are each at least 98% identical to the sequences shown in SEQ ID NO:52 and SEQ ID NO:53, respectively. In some embodiments, a 4-1BB agonist comprises heavy and light chains that are each at least 97% identical to the sequences shown in SEQ ID NO:52 and SEQ ID NO:53, respectively. In some embodiments, a 4-1BB agonist comprises heavy and light chains that are each at least 96% identical to the sequences shown in SEQ ID NO:52 and SEQ ID NO:53, respectively. In some embodiments, a 4-1BB agonist comprises heavy and light chains that are each at least 95% identical to the sequences shown in SEQ ID NO:52 and SEQ ID NO:53, respectively.

In some embodiments, the 4-1BB agonist comprises the heavy and light chain CDRs or variable regions (VRs) of urelumab. In some embodiments, the 4-1BB agonist heavy chain variable region ($V_H$) comprises the sequence shown in SEQ ID NO:54, and the 4-1BB agonist light chain variable region ($V_L$) comprises the sequence shown in SEQ ID NO:55, and conservative amino acid substitutions thereof. In some embodiments, a 4-1BB agonist comprises $V_H$ and $V_L$ regions that are each at least 99% identical to the sequences shown in SEQ ID NO:54 and SEQ ID NO:55, respectively. In some embodiments, a 4-1BB agonist comprises $V_H$ and $V_L$ regions that are each at least 98% identical to the sequences shown in SEQ ID NO:54 and SEQ ID NO:55, respectively. In some embodiments, a 4-1BB agonist comprises $V_H$ and $V_L$ regions that are each at least 97% identical to the sequences shown in SEQ ID NO:54 and SEQ ID NO:55, respectively. In some embodiments, a 4-1BB agonist comprises $V_H$ and $V_L$ regions that are each at least 96% identical to the sequences shown in SEQ ID NO:54 and SEQ ID NO:55, respectively. In some embodiments, a 4-1BB agonist comprises $V_H$ and $V_L$ regions that are each at least 95% identical to the sequences shown in SEQ ID NO:54 and SEQ ID NO:55, respectively. In some embodiments, a 4-1BB agonist comprises an scFv antibody comprising $V_H$ and $V_L$ regions that are each at least 99% identical to the sequences shown in SEQ ID NO:54 and SEQ ID NO:55.

In some embodiments, a 4-1BB agonist comprises heavy chain CDR1, CDR2 and CDR3 domains having the sequences set forth in SEQ ID NO:56, SEQ ID NO:57, and SEQ ID NO:58, respectively, and conservative amino acid substitutions thereof, and light chain CDR1, CDR2 and CDR3 domains having the sequences set forth in SEQ ID NO:59, SEQ ID NO:60, and SEQ ID NO:61, respectively, and conservative amino acid substitutions thereof.

In some embodiments, the 4-1BB agonist is a 4-1BB agonist biosimilar monoclonal antibody approved by drug regulatory authorities with reference to urelumab. In some embodiments, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

In some embodiments, the biosinmilar is provided as a composition which further comprises one or more excipients, wherein the one or more excipients are the same or different to the excipients comprised in a reference medicinal product or reference biological product, wherein the reference medicinal product or reference biological product is urelumab.

(such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in

TABLE 7

Amino acid sequences for 4-1BB agonist antibodies related to urelumab.

| Identifier | Sequence (One-Letter Amino Acid Symbols) | |
|---|---|---|
| SEQ ID NO: 52 heavy chain for urelumab | QVQLQQWGAG LLKPSETLSL TCAVYGGSFS GYYWSWIRQS PEKGLEWIGE INHGGYVTYN | 60 |
| | PSLESRVTIS VDTSKNQFSL KLSSVTAADT AVYYCARDYG PGNYDWYFDL WGRGTLVTVS | 120 |
| | SASTKGPSVF PLAPCSRSTS ESTAALGCLV KDYFPEPVTV SWNSGALTSG VHTFPAVLQS | 180 |
| | SGLYSLSSVV TVPSSSLGTK TYTCNVDHKP SNTKVDKRVE SKYGPPCPPC PAPEFLGGPS | 240 |
| | VFLFPPKPKD TLMISRTPEV TCVVVDVSQE DPEVQFNWYV DGVEVHNAKT KPREEQFNST | 300 |
| | YRVVSVLTVL HQDWLNGKEY KCKVSNKGLP SSIEKTISKA KGQPREPQVY TLPPSQEEMT | 360 |
| | KNQVSLTCLV KGFYPSDIAV EWESNGQPEN NYKTTPPVLD SDGSFFLYSR LTVDKSRWQE | 420 |
| | GNVFSCSVMH EALHNHYTQK SLSLSLGK | 448 |
| SEQ ID NO: 53 light chain for urelumab | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPALTF CGGTKVEIKR TVAAPSVFIF | 120 |
| | PPSDEQLKSG TASVVCLLNN FYPREAKVQW KVDNALQSGN SQESVTEQDS KDSTYSLSST | 180 |
| | LTLSKADYEK HKVYACEVTH QGLSSPVTKS FNRGEC | 216 |
| SEQ ID NO: 54 variable heavy chain for urelumab | MKHLWFFLLL VAAPRWVLSQ VQLQQWGAGL LKPSETLSLT CAVYGGSFSG YYWSWIRQSP | 60 |
| | EKGLEWIGEI NHGGYVTYNP SLESRVTISV DTSKNQFSLK LSSVTAADTA VYYCARDYGP | 120 |
| SEQ ID NO: 55 variable light chain for urelumab | MEAPAQLLFL LLLWLPDTTG EIVLTQSPAT LSLSPGERAT LSCRASQSVS SYLAWYQQKP | 60 |
| | GQAPRLLIYD ASNRATGIPA RFSGSGSGTD FTLTISSLEP EDFAVYYCQQ | 110 |
| SEQ ID NO: 56 heavy chain CDR1 for urelumab | GYYWS | 5 |
| SEQ ID NO: 57 heavy chain CDR2 for urelumab | EINHGGYVTY NPSLES | 16 |
| SEQ ID NO: 58 heavy chain CDR3 for urelumab | DYGPGNYDWY FDL | 13 |
| SEQ ID NO: 59 light chain CDR1 for urelumab | RASQSVSSYL A | 11 |
| SEQ ID NO: 60 light chain CDR2 for urelumab | DASNRAT | 7 |
| SEQ ID NO: 61 light chain CDR3 for urelumab | QQRSDWPPAL T | 11 |

In some embodiments, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In some embodiments, the 4-1BB agonist is a 4-1BB agonistic fusion protein described in International Patent Application Publication Nos. WO 2008/025516 A1, WO 2009/007120 A1, WO 2010/003766 A1, WO 2010/010051

A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

Figure 18:
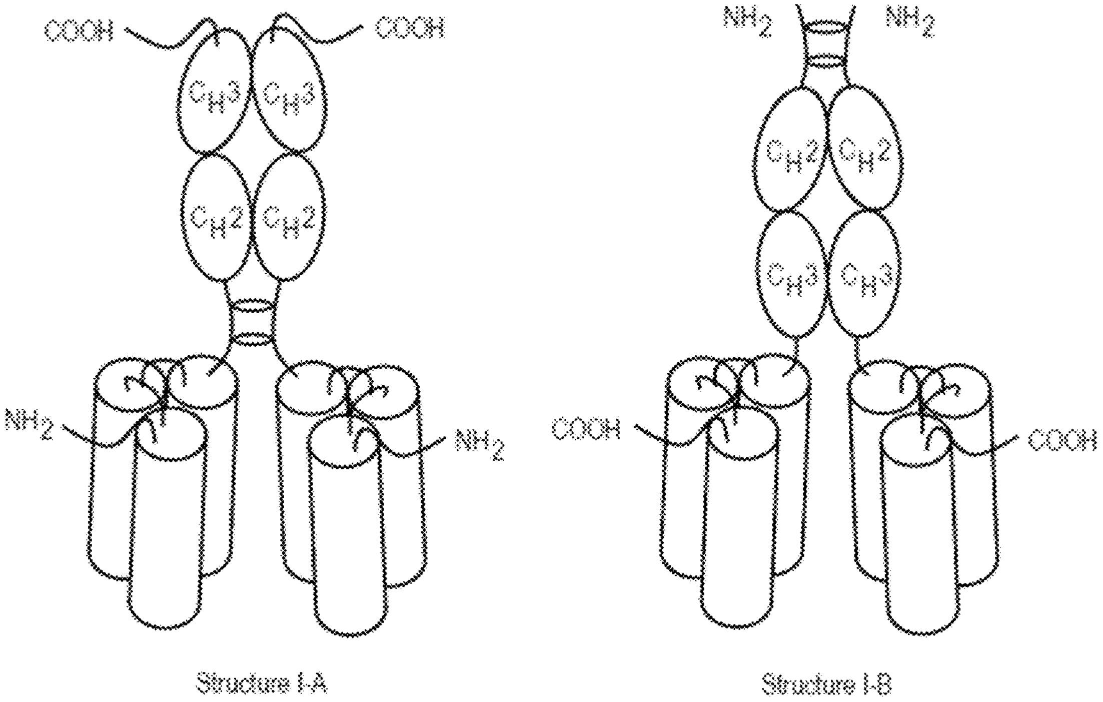
FIG. 18: Provides the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.
Figure 19:
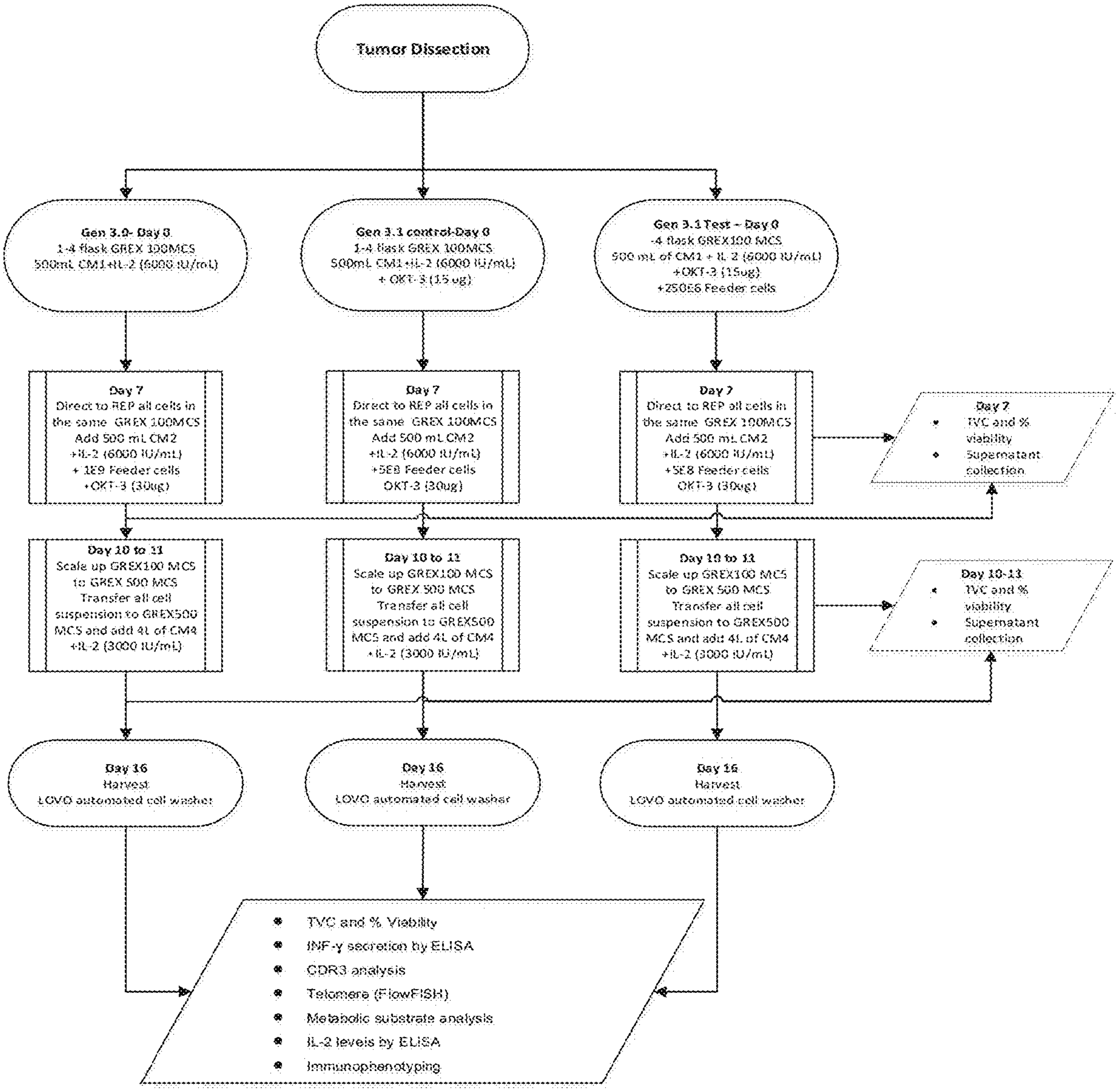
FIG. 19: Schematic of an exemplary embodiment of the Gen 3 process (a 16-day process).
Figure 21:
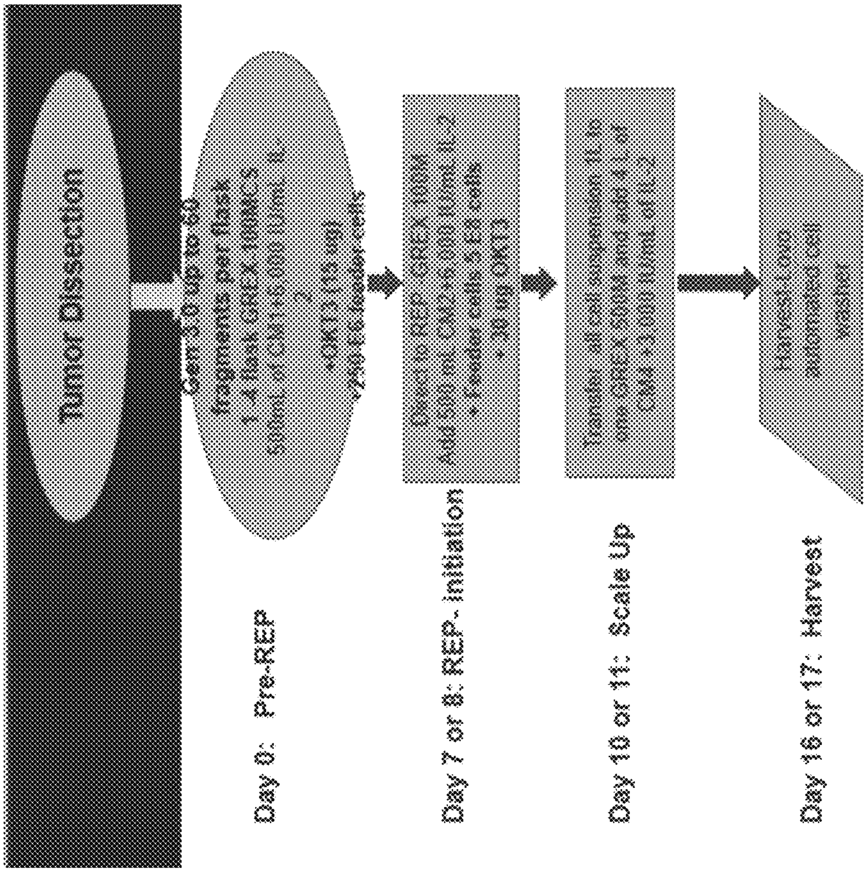
FIG. 21: Schematic of an exemplary embodiment of the Gen 3.1 Test process (a 16-17 day process).
Figure 22:
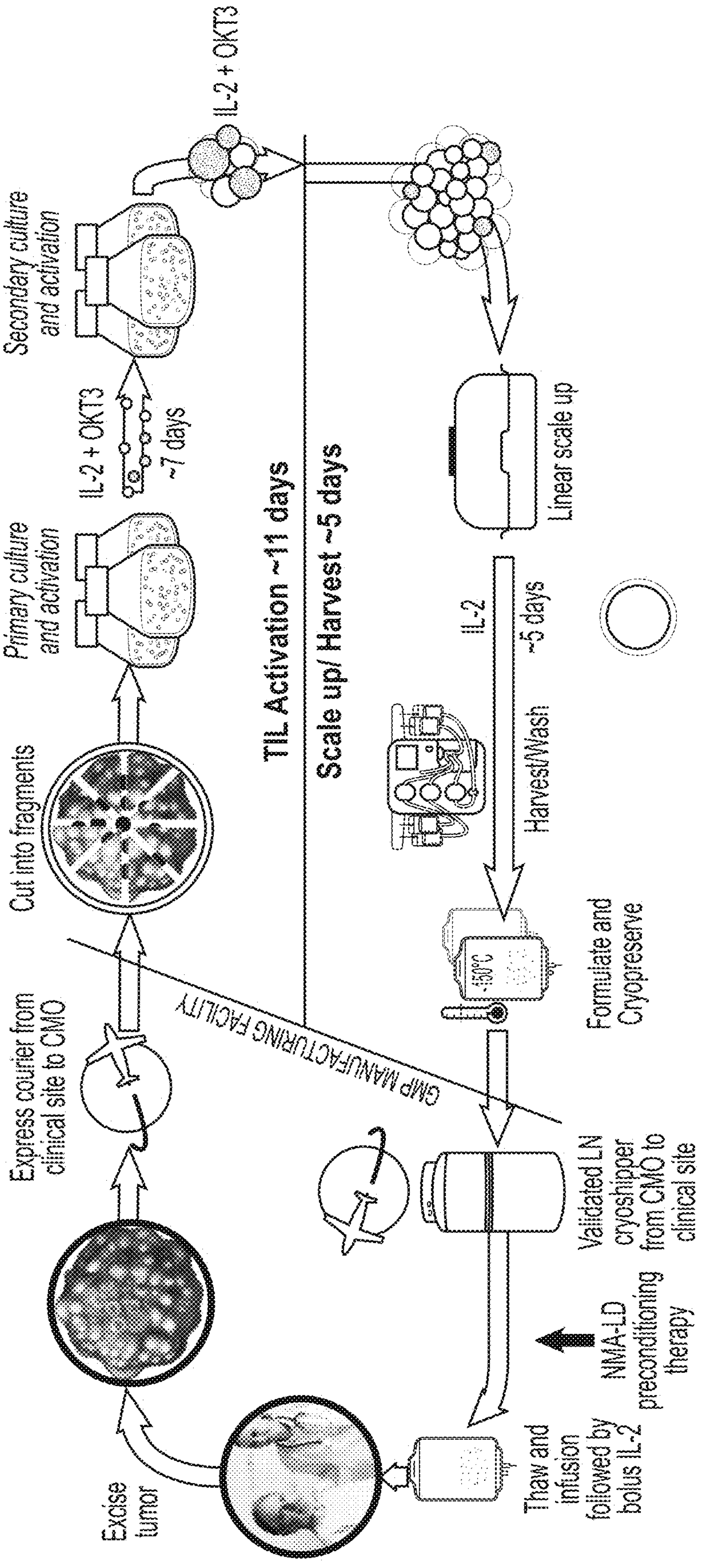
FIG. 22: Schematic of an exemplary embodiment of the Gen 3 process (a 16-day process).
Figure 24:
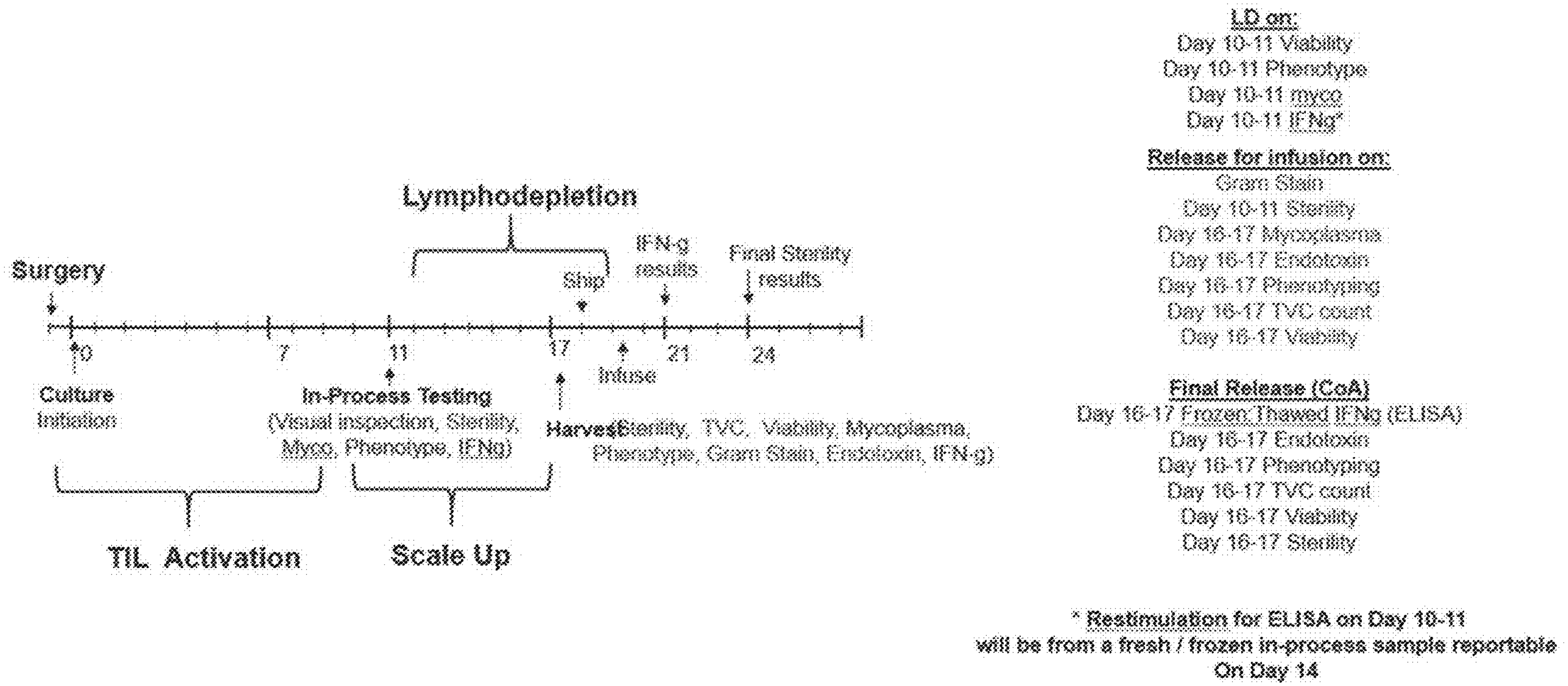
FIG. 24: Schematic of an exemplary embodiment of the Gen 3 process (a 16/17 day process) preparation timeline.
Figure 25:
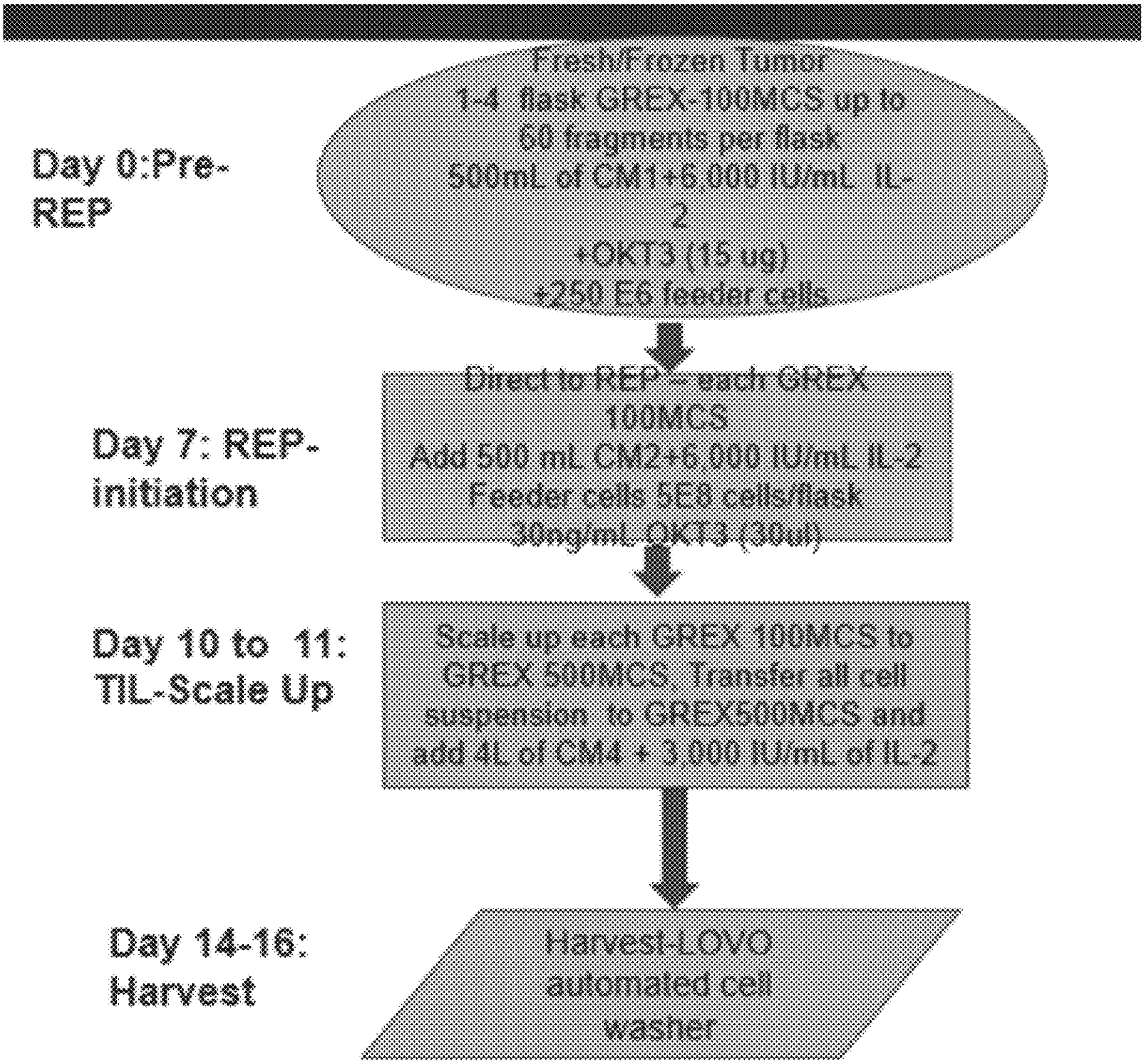
FIG. 25: Schematic of an exemplary embodiment of the Gen 3 process (a 14-16 day process).
Figure 26A:
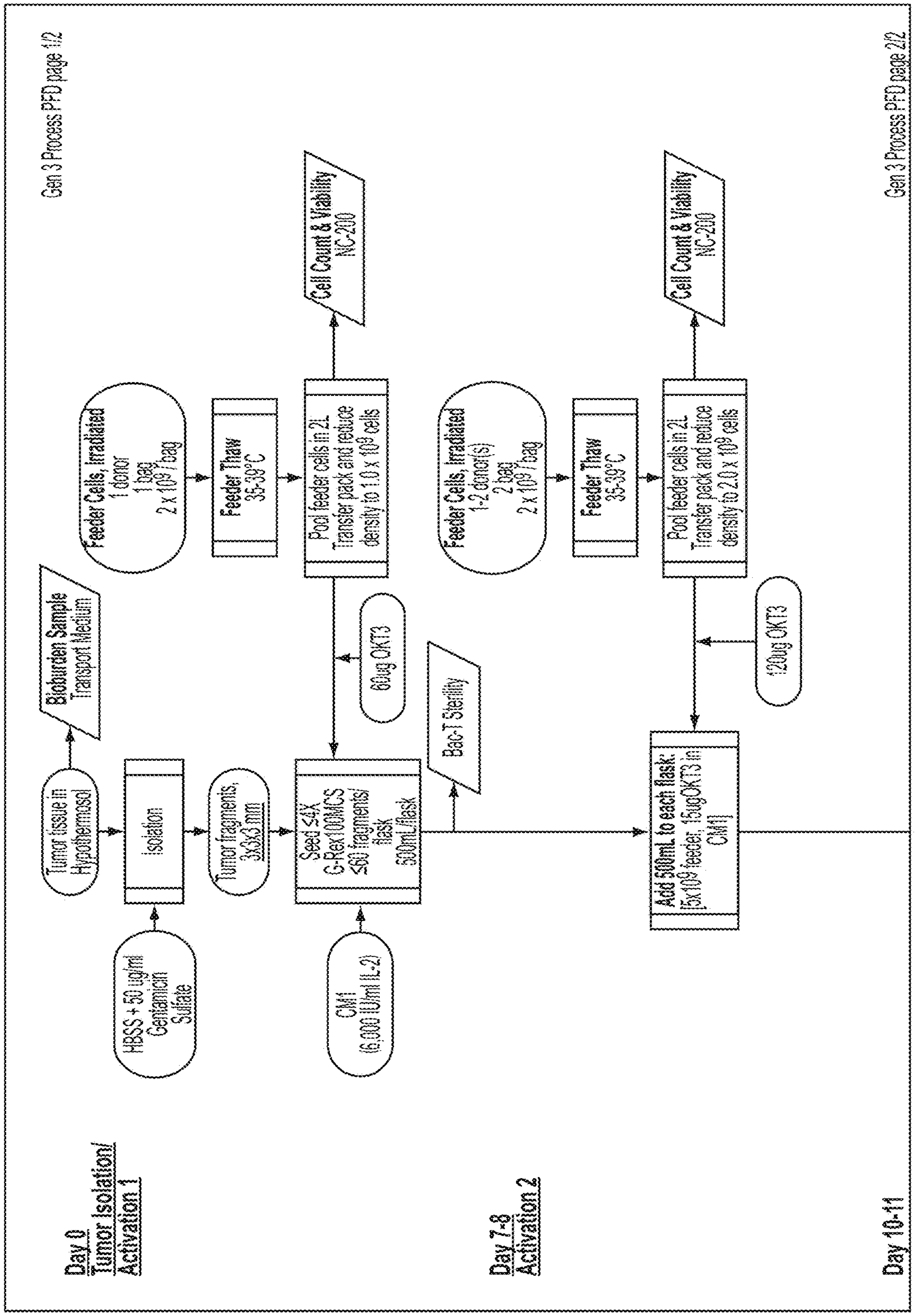
FIG. 26A-26B: Schematic of an exemplary embodiment of the Gen 3 process (a 16 day process).
Figure 26B:
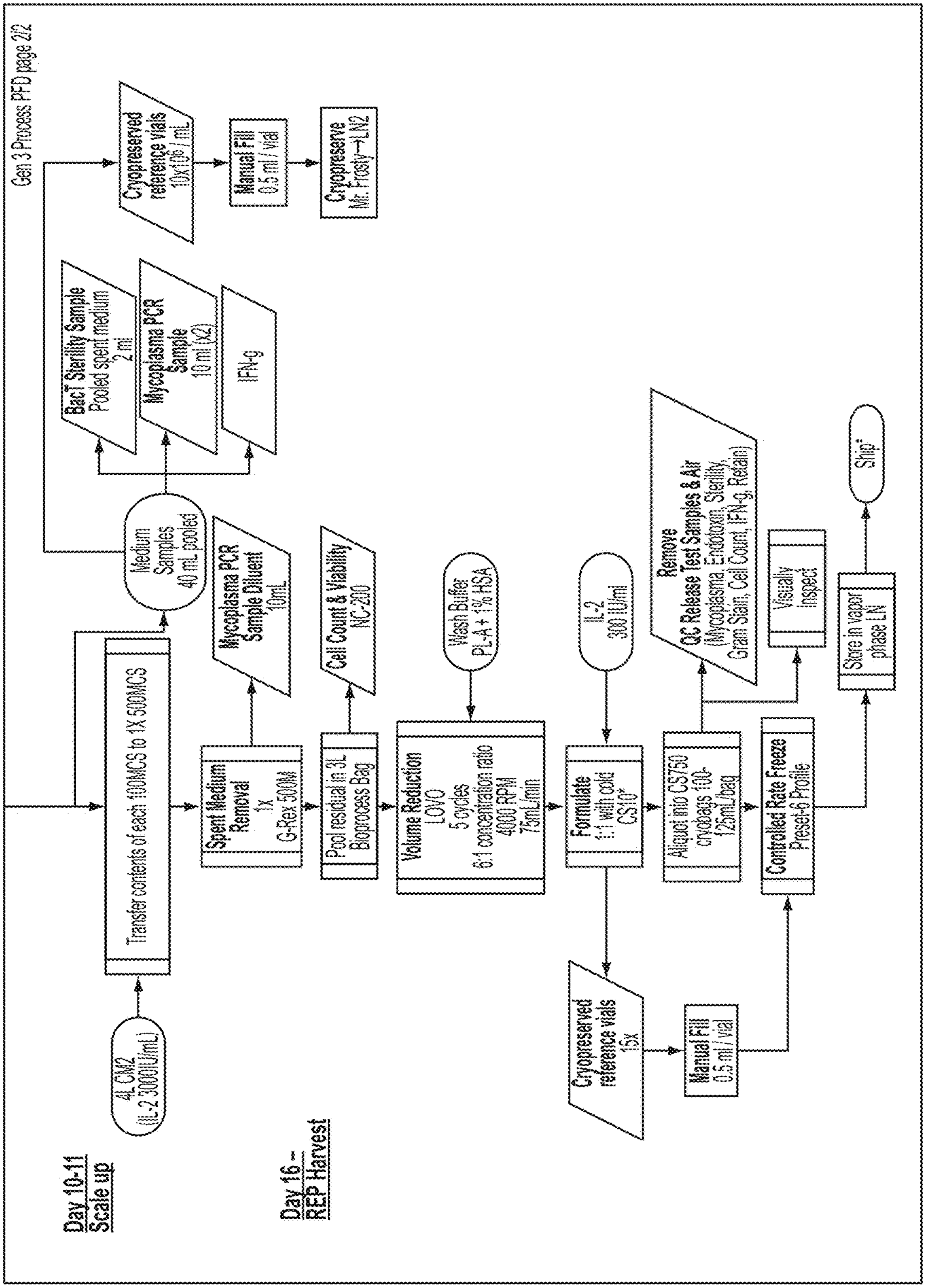

In some embodiments, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof (see, FIG. 18). In structures I-A and I-B, the cylinders refer to individual polypeptide binding domains. Structures I-A and I-B comprise three linearly-linked TNFRSF binding domains derived from e.g., 4-1BBL (4-1BB ligand, CD137 ligand (CD137L), or tumor necrosis factor superfamily member 9 (TNFSF9)) or an antibody that binds 4-1BB, which fold to form a trivalent protein, which is then linked to a second triavelent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, Microbial Cell Factories, 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A given in FIG. 18 are found in Table 8. The Fc domain preferably comprises a complete constant domain (amino acids 17-230 of SEQ ID NO:62) the complete hinge domain (amino acids 1-16 of SEQ ID NO:62) or a portion of the hinge domain (e.g., amino acids 4-16 of SEQ ID NO:62). Preferred linkers for connecting a C-terminal Fc-antibody may be selected from the embodiments given in SEQ ID NO:63 to SEQ ID NO:72, including linkers suitable for fusion of additional polypeptides.

TABLE 8

Amino acid sequences for TNFRSF agonist fusion proteins, including 4-1BB agonist fusion proteins, with C-terminal Fc-antibody fragment fusion protein design (structure I-A).

| Identifier | Sequence (One-Letter Amino Acid Symbols) | |
|---|---|---|
| SEQ ID NO: 62<br>Fc domain | KSCDKTHTCP PCPAPELLGG PSVFLFPPKP KDTLMISRTP EVTCVVVDVS HEDPEVKFNW<br>YVDGVEVHNA KTKPREEQYN STYRVVSVLT VLHQDWLNGK EYKCKVSNKA LPAPIEKTIS<br>KAKGQPREPQ VYTLPPSREE MTKNQVSLTC LVKGFYPSDI AVEWESNGQP ENNYKTTPPV<br>LDSDGSFFLY SKLTVDKSRW QQGNVFSCSV MHEALHNHYT QKSLSLSPGK | 60<br>120<br>180<br>230 |
| SEQ ID NO: 63<br>linker | GGPGSSKSCD KTHTCPPCPA PE | 22 |
| SEQ ID NO: 64<br>linker | GGSGSSKSCD KTHTCPPCPA PE | 22 |
| SEQ ID NO: 65<br>linker | GGPGSSSSSS SKSCDKTHTC PPCPAPE | 27 |
| SEQ ID NO: 66<br>linker | GGSGSSSSSS SKSCDKTHTC PPCPAPE | 27 |
| SEQ ID NO: 67<br>linker | GGPGSSSSSS SSSKSCDKTH TCPPCPAPE | 29 |
| SEQ ID NO: 68<br>linker | GGSGSSSSSS SSSKSCDKTH TCPPCPAPE | 29 |
| SEQ ID NO: 69<br>linker | GGPGSSGSGS SDKTHTCPPC PAPE | 24 |
| SEQ ID NO: 70<br>linker | GGPGSSGSGS DKTHTCPPCP APE | 23 |
| SEQ ID NO: 71<br>linker | GGPSSSGSDK THTCPPCPAP E | 21 |
| SEQ ID NO: 72<br>linker | GGSSSSSSSS GSDKTHTCPP CPAPE | 25 |

Amino acid sequences for the other polypeptide domains of structure I-B given in FIG. 18 are found in Table 9. If an Fc antibody fragment is fused to the N-terminus of an TNRFSF fusion protein as in structure I-B, the sequence of the Fc module is preferably that shown in SEQ ID NO: 73, and the linker sequences are preferably selected from those embodiments set forth in SED ID NO: 74 to SEQ ID NO: 76.

TABLE 9

Amino acid sequences for TNFRSF agonist fusion proteins, including 4-1BB agonist fusion proteins, with N-terminal Fc-antibody fragment fusion protein design (structure I-B).

| Identifier | Sequence (One-Letter Amino Acid Symbols) | |
|---|---|---|
| SEQ ID NO: 73 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 74 linker | SGSGSGSGSG S | 11 |
| SEQ ID NO: 75 linker | SSSSSSGSGS GS | 12 |
| SEQ ID NO: 76 linker | SSSSSSGSGS GSGSGS | 16 |

In some embodiments, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 5, any combination of a variable heavy chain and variable light chain of the foregoing, and fragments, derivatives, conjugates, variants, and biosimilars thereof.

In some embodiments, a 4-1BB agonist fusion protein according to structures I-A or I-B comprises one or more 4-1BB binding domains comprising a 4-1BBL sequence. In some embodiments, a 4-1BB agonist fusion protein according to structures I-A or I-B comprises one or more 4-1BB binding domains comprising a sequence according to SEQ ID NO:77. In some embodiments, a 4-1BB agonist fusion protein according to structures I-A or I-B comprises one or more 4-1BB binding domains comprising a soluble 4-1BBL sequence. In some embodiments, a 4-1BB agonist fusion protein according to structures I-A or I-B comprises one or more 4-1BB binding domains comprising a sequence according to SEQ ID NO:78.

In some embodiments, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:43 and SEQ ID NO:44, respectively, wherein the $V_H$ and $V_L$ domains are connected by a linker. In some embodiments, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:54 and SEQ ID NO:55, respectively, wherein the $V_H$ and $V_L$ domains are connected by a linker. In some embodiments, a 4-1BB agonist fusion protein according to structures I-A or I-B comprises one or more 4-1BB binding domains that is a scFv domain comprising $V_H$ and $V_L$ regions that are each at least 95% o identical to the $V_H$ and $V_L$ sequences given in Table 10, wherein the $V_H$ and $V_L$ domains are connected by a linker.

TABLE 10

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 77 4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 78 4-1BBL soluble domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 79 variable heavy chain for 4B4-1-1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 80 variable light chain for 4B4-1-1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |

TABLE 10-continued

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 81 variable heavy chain for 4B4-1-1 version 2 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVSA | 60<br>119 |
| SEQ ID NO: 82 variable light chain for 4B4-1-1 version 2 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIKR | 60<br>108 |
| SEQ ID NO: 83 variable heavy chain for H39E3-2 | MDWTWRILFL VAAATGAHSE VQLVESGGGL VQPGGSLRLS CAASGFTFSD YWMSWVRQAP<br>GKGLEWVADI KNDGSYTNYA PSLTNRFTIS RDNAKNSLYL QMNSLRAEDT AVYYCARELT | 60<br>120 |
| SEQ ID NO: 84 variable light chain for H39E3-2 | MEAPAQLLFL LLLWLPDTTG DIVMTQSPDS LAVSLGERAT INCKSSQSLL SSGNQKNYL<br>WYQQKPGQPP KLLIYYASTR QSGVPDRFSG SGSGTDFTLT ISSLQAEDVA | 60<br>110 |

In some embodiments, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In some embodiments, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In some embodiments, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In some embodiments, the 4-1BB agonist is a 4-1BB agonistic scFv antibody comprising any of the foregoing $V_H$ domains linked to any of the foregoing $V_L$ domains.

In some embodiments, the 4-1BB agonist is BPS Bioscience 4-1BB agonist antibody catalog no. 79097-2, commercially available from BPS Bioscience, San Diego, CA, USA. In some embodiments, the 4-1BB agonist is Creative Biolabs 4-1BB agonist antibody catalog no. MOM-18179, commercially available from Creative Biolabs, Shirley, NY, USA.

3. OX40 (CD134) Agonists

In some embodiments, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgGI, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In some embodiments, the OX40 agonist is an antigen binding protein that is a fully human antibody. In some embodiments, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In some embodiments, the OX40 agonist is an agonistic, anti-OX40 humanized or fully human monoclonal antibody (i.e., an antibody derived from a single cell line).

In some embodiments, the OX40 agonist or OX40 binding molecule may also be a fusion protein. OX40 fusion proteins comprising an Fc domain fused to OX40L are described, for example, in Sadun, et al., *J Immunother.* 2009, 182, 1481-89. In some embodiments, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In some embodiments, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:85) with high affinity and agonistic activity. In some embodiments, the OX40 agonist is a binding molecule that binds to human OX40 (SEQ ID NO:85). In some embodiments, the OX40 agonist is a binding molecule that binds to murine OX40 (SEQ ID NO:86). The amino acid sequences of OX40 antigen to which an OX40 agonist or binding molecule binds are summarized in Table 11.

TABLE 11

Amino acid sequences of OX40 antigens.

| Identifier | Sequence (One-Letter Amino Acid Symbols) |
|---|---|
| SEQ ID NO: 85 | MCVGARRLGR GPCAALLLLG LGLSTVTGLH CVGDTYPSND RCCHECRPGN GMVSRCSRSQ 60 |
| human OX40 | NTVCRPCGPG FYNDVVSSKP CKPCTWCNLR SGSERKQLCT ATQDTVCRCR AGTQPLDSYK 120 |
| (*Homo sapiens*) | PGVDCAPCPP GHFSPGDNQA CKPWTNCTLA GKHTLQPASN SSDAICEDRD PPATQPQETQ 180 |
| | GPPARPITVQ PTEAWPRTSQ GPSTRPVEVP GGRAVAAILG LGLVLGLLGP LAILLALYLL 240 |
| | RRDQRLPPDA HKPPGGGSFR TPIQEEQADA HSTLAKI 277 |
| SEQ ID NO: 86 | MYVWVQQPTA LLLLGLTLGV TARRLNCVKH TYPSGHKCCR ECQPGHGMVS RCDHTRDTLC 60 |
| murine OX40 | HPCETGFYNE AVNYDTCKQC TQCNHRSGSE LKQNCTPTQD TVCRCRPGTQ PRQDSGYKLG 120 |
| (*Mus musculus*) | VDCVPCPPGH FSPGNNQACK PWTNCTLSGK QTRHPASDSL DAVCEDRSLL ATLLWETQRP 180 |
| | TFRPTTVQST TVWPRTSELP SPPTLVTPEG PAFAVLLGLG LGLLAPLTVL LALYLLRKAW 240 |
| | RLPNTPKPCW GNSFRTPIQE EHTDAHFTLA KI 272 |

In some embodiments, the compositions, processes and methods described include a OX40 agonist that binds human or murine OX40 with a $K_D$ of about 100 μM or lower, binds human or murine OX40 with a $K_D$ of about 90 μM or lower, binds human or murine OX40 with a $K_D$ of about 80 μM or lower, binds human or murine OX40 with a $K_D$ of about 70 μM or lower, binds human or murine OX40 with a $K_D$ of about 60 μM or lower, binds human or murine OX40 with a $K_D$ of about 50 μM or lower, binds human or murine OX40 with a $K_D$ of about 40 μM or lower, or binds human or murine OX40 with a $K_D$ of about 30 μM or lower.

In some embodiments, the compositions, processes and methods described include a OX40 agonist that binds to human or murine OX40 with a $k_{assoc}$ of about $7.5\times10^5$ 1/M s or faster, binds to human or murine OX40 with a $k_{assoc}$ of about $7.5\times10^5$ 1/M s or faster, binds to human or murine OX40 with a $k_{assoc}$ of about $8\times10^5$ 1/M s or faster, binds to human or murine OX40 with a $k_{assoc}$ of about $8.5\times10^5$ 1/M s or faster, binds to human or murine OX40 with a $k_{assoc}$ of about $9\times10^5$ 1/M s or faster, binds to human or murine OX40 with a $k_{assoc}$ of about $9.5\times10^5$ 1/M s or faster, or binds to human or murine OX40 with a $k_{assoc}$ of about $1\times10^6$ 1/M s or faster.

In some embodiments, the compositions, processes and methods described include a OX40 agonist that binds to human or murine OX40 with a $k_{dissoc}$ of about $2\times10^{-5}$ 1/s or slower, binds to human or murine OX40 with a $k_{dissoc}$ of about $2.1\times10^{-5}$ 1/s or slower, binds to human or murine OX40 with a $k_{dissoc}$ of about $2.2\times10^{-5}$ 1/s or slower, binds to human or murine OX40 with a $k_{dissoc}$ of about $2.3\times10^{-5}$ 1/s or slower, binds to human or murine OX40 with a $k_{dissoc}$ of about $2.4\times10^{-5}$ 1/s or slower, binds to human or murine OX40 with a $k_{dissoc}$ of about $2.5\times10^{-5}$ 1/s or slower, binds to human or murine OX40 with a $k_{dissoc}$ of about $2.6\times10^{-5}$ 1/s or slower or binds to human or murine OX40 with a $k_{dissoc}$ of about $2.7\times10^{-5}$ 1/s or slower, binds to human or murine OX40 with a $k_{dissoc}$ of about $2.8\times10^{-5}$ 1/s or slower, binds to human or murine OX40 with a $k_{dissoc}$ of about $2.9\times10^{-5}$ 1/s or slower, or binds to human or murine OX40 with a $k_{dissoc}$ of about $3\times10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MED10562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 12. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'"-88'" and 134'"-194'"); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials.gov identifiers NCT02318394 and NCT02705482.

In some embodiments, a OX40 agonist comprises a heavy chain given by SEQ ID NO:87 and a light chain given by SEQ ID NO:88. In some embodiments, a OX40 agonist comprises heavy and light chains having the sequences shown in SEQ ID NO:87 and SEQ ID NO:88, respectively, or antigen binding fragments, Fab fragments, single-chain variable fragments (scFv), variants, or conjugates thereof. In some embodiments, a OX40 agonist comprises heavy and light chains that are each at least 99% identical to the sequences shown in SEQ ID NO:87 and SEQ ID NO:88, respectively. In some embodiments, a OX40 agonist comprises heavy and light chains that are each at least 98% identical to the sequences shown in SEQ ID NO:87 and SEQ ID NO:88, respectively. In some embodiments, a OX40 agonist comprises heavy and light chains that are each at least 97% identical to the sequences shown in SEQ ID NO:87 and SEQ ID NO:88, respectively. In some embodiments, a OX40 agonist comprises heavy and light chains that are each at least 96% identical to the sequences shown in SEQ ID NO:87 and SEQ ID NO:88, respectively. In some embodiments, a OX40 agonist comprises heavy and light chains that are each at least 95% identical to the sequences shown in SEQ ID NO:87 and SEQ ID NO:88, respectively.

In some embodiments, the OX40 agonist comprises the heavy and light chain CDRs or variable regions (VRs) of tavolixizumab. In some embodiments, the OX40 agonist heavy chain variable region ($V_H$) comprises the sequence shown in SEQ ID NO:89, and the OX40 agonist light chain variable region ($V_L$) comprises the sequence shown in SEQ ID NO:90, and conservative amino acid substitutions thereof. In some embodiments, a OX40 agonist comprises $V_H$ and $V_L$ regions that are each at least 99% identical to the sequences shown in SEQ ID NO:89 and SEQ ID NO:90, respectively. In some embodiments, a OX40 agonist comprises $V_H$ and $V_L$ regions that are each at least 98% identical to the sequences shown in SEQ ID NO:89 and SEQ ID NO:90, respectively. In some embodiments, a OX40 agonist comprises $V_H$ and $V_L$ regions that are each at least 97% identical to the sequences shown in SEQ ID NO:89 and SEQ ID NO:90, respectively. In some embodiments, a OX40 agonist comprises $V_H$ and $V_L$ regions that are each at least 96% identical to the sequences shown in SEQ ID NO:89 and SEQ ID NO:90, respectively. In some embodiments, a OX40 agonist comprises $V_H$ and $V_L$ regions that are each at least 95% identical to the sequences shown in SEQ ID NO:89 and SEQ ID NO:90, respectively. In some embodiments, an OX40 agonist comprises an scFv antibody comprising $V_H$ and $V_L$ regions that are each at least 99% identical to the sequences shown in SEQ ID NO:89 and SEQ ID NO:90.

In some embodiments, a OX40 agonist comprises heavy chain CDR1, CDR2 and CDR3 domains having the sequences set forth in SEQ ID NO:91, SEQ ID NO:92, and SEQ ID NO:93, respectively, and conservative amino acid substitutions thereof, and light chain CDR1, CDR2 and CDR3 domains having the sequences set forth in SEQ ID NO:94, SEQ ID NO:95, and SEQ ID NO:96, respectively, and conservative amino acid substitutions thereof.

In an embodiment, the OX40 agonist is a OX40 agonist biosimilar monoclonal antibody approved by drug regulatory authorities with reference to tavolixizumab. In an embodiment. In some embodiments, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab.

The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 12

Amino acid sequences for OX40 agonist antibodies related to tavolixizumab.

| Identifier | Sequence (One-Letter Amino Acid Symbols) | |
|---|---|---|
| SEQ ID NO: 87 heavy chain for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRE | 360 |
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |

TABLE 12-continued

Amino acid sequences for OX40 agonist antibodies related to tavolixizumab.

| Identifier | Sequence (One-Letter Amino Acid Symbols) | |
|---|---|---|
| SEQ ID NO: 88 light chain for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQP EDFATYYCQQ GSALPWTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 89 heavy chain variable region for tavolixizumab | QVQLQESGPG LVKPSQTLSL TCAVYGGSFS SGYWNWIRKH PGKGLEYIGY ISYNGITYHN | 60 |
| | PSLKSRITIN RDTSKNQYSL QLNSVTPEDT AVYYCARYKY DYDGGHAMDY WGQGTLVT | 118 |
| SEQ ID NO: 90 light chain variable region for tavolixizumab | DIQMTQSPSS LSASVGDRVT ITCRASQDIS NYLNWYQQKP GKAPKLLIYY TSKLHSGVPS | 60 |
| | RFSGSGSGTD YTLTISSLQP EDFATYYCQQ GSALPWTFGQ GTKVEIKR | 108 |
| SEQ ID NO: 91 heavy chain CDR1 for tavolixizumab | GSFSSGYWN | 9 |
| SEQ ID NO: 92 heavy chain CDR2 for tavolixizumab | YIGYISYNGI TYH | 13 |
| SEQ ID NO: 93 heavy chain CDR3 for tavolixizumab | RYKYDYDGGH AMDY | 14 |
| SEQ ID NO: 94 light chain CDR1 for tavolixizumab | QDISNYLN | 8 |
| SEQ ID NO: 95 light chain CDR2 for tavolixizumab | LLIYYTSKLH S | 11 |
| SEQ ID NO: 96 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Patent Nos. 7,960,515; 8,236,930; and 9,028,824, the disclosures of which are incorporated by reference herein. The amino acid sequences of 11D4 are set forth in Table 13.

In some embodiments, a OX40 agonist comprises a heavy chain given by SEQ ID NO: 97 and a light chain given by SEQ ID NO: 98. In some embodiments, a OX40 agonist comprises heavy and light chains having the sequences shown in SEQ ID NO:97 and SEQ ID NO: 98, respectively, or antigen binding fragments, Fab fragments, single-chain variable fragments (scFv), variants, or conjugates thereof. In some embodiments, a OX40 agonist comprises heavy and light chains that are each at least 99% o identical to the sequences shown in SEQ ID NO: 97 and SEQ ID NO: 98, respectively. In some embodiments, a OX40 agonist comprises heavy and light chains that are each at least 98% identical to the sequences shown in SEQ ID NO:97 and SEQ ID NO:98, respectively. In some embodiments, a OX40 agonist comprises heavy and light chains that are each at least 97% identical to the sequences shown in SEQ ID NO:97 and SEQ ID NO:98, respectively. In some embodiments, a OX40 agonist comprises heavy and light chains that are each at least 96% identical to the sequences shown in SEQ ID NO:97 and SEQ ID NO:98, respectively. In some embodiments, a OX40 agonist comprises heavy and light chains that are each at least 95% identical to the sequences shown in SEQ ID NO:97 and SEQ ID NO:98, respectively.

In some embodiments, the OX40 agonist comprises the heavy and light chain CDRs or variable regions (VRs) of 11D4. In some embodiments, the OX40 agonist heavy chain variable region ($V_H$) comprises the sequence shown in SEQ ID NO:99, and the OX40 agonist light chain variable region ($V_L$) comprises the sequence shown in SEQ ID NO:100, and conservative amino acid substitutions thereof. In some embodiments, a OX40 agonist comprises $V_H$ and $V_L$ regions that are each at least 99% identical to the sequences shown in SEQ ID NO:99 and SEQ ID NO:100, respectively. In some embodiments, a OX40 agonist comprises $V_H$ and $V_L$ regions that are each at least 98% identical to the sequences shown in SEQ ID NO:99 and SEQ ID NO:100, respectively. In some embodiments, a OX40 agonist comprises $V_H$ and $V_L$ regions that are each at least 97% identical to the sequences shown in SEQ ID NO:99 and SEQ ID NO:100, respectively. In some embodiments, a OX40 agonist comprises $V_H$ and $V_L$ regions that are each at least 96% identical to the sequences shown in SEQ ID NO:99 and SEQ ID NO:100, respectively. In some embodiments, a OX40 agonist comprises $V_H$ and $V_L$ regions that are each at least 95% identical to the sequences shown in SEQ ID NO:99 and SEQ ID NO:100, respectively.

In some embodiments, a OX40 agonist comprises heavy chain CDR1, CDR2 and CDR3 domains having the sequences set forth in SEQ ID NO:101, SEQ ID NO:102, and SEQ ID NO:103, respectively, and conservative amino acid substitutions thereof, and light chain CDR1, CDR2 and CDR3 domains having the sequences set forth in SEQ ID NO:104, SEQ ID NO:10[5], and SEQ ID NO:106, respectively, and conservative amino acid substitutions thereof.

In some embodiments, the OX40 agonist is a OX40 agonist biosimilar monoclonal antibody approved by drug regulatory authorities with reference to 11D4. In some embodiments, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 13

Amino acid sequences for OX40 agonist antibodies related to 11D4.

| Identifier | Sequence (One-Letter Amino Acid Symbols) | |
|---|---|---|
| SEQ ID NO: 97 heavy chain for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSSAS | 120 |
| | TKGPSVFPLA PCSRSTSEST AALGCLVKDY FPEPVTVSWN SGALTSGVHT FPAVLQSSGL | 180 |
| | YSLSSVVTVP SSNFGTQTYT CNVDHKPSNT KVDKTVERKC CVECPPCPAP PVAGPSVFLF | 240 |
| | PPKPKDTLMI SRTPEVTCVV VDVSHEDPEV QFNWYVDGVE VHNAKTKPRE EQFNSTFRVV | 300 |
| | SVLTVVHQDW LNGKEYKCKV SNKGLPAPIE KTISKTKGQP REPQVYTLPP SREEMTKNQV | 360 |
| | SLTCLVKGFY PSDIAVEWES NGQPENNYKT TPPMLDSDGS FFLYSKLTVD KSRWQQGNVF | 420 |
| | SCSVMHEALH NHYTQKSLSL SPGK | 444 |
| SEQ ID NO: 98 light chain for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 99 heavy chain variable region for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSS | 118 |
| SEQ ID NO: 100 light chain variable region for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIK | 107 |
| SEQ ID NO: 101 heavy chain CDR1 for 11D4 | SYSMN | 5 |
| SEQ ID NO: 102 heavy chain CDR2 for 11D4 | YISSSSSTID YADSVKG | 17 |
| SEQ ID NO: 103 heavy chain CDR3 for 11D4 | ESGWYLFDY | 9 |
| SEQ ID NO: 104 light chain CDR1 for 11D4 | RASQGISSWL A | 11 |

TABLE 13-continued

| Amino acid sequences for OX40 agonist antibodies related to 11D4. | | |
|---|---|---|
| Identifier | Sequence (One-Letter Amino Acid Symbols) | |
| SEQ ID NO: 105 light chain CDR2 for 11D4 | AASSLQS | 7 |
| SEQ ID NO: 106 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 14.

In some embodiments, a OX40 agonist comprises a heavy chain given by SEQ ID NO: 107 and a light chain given by SEQ ID NO: 108. In some embodiments, a OX40 agonist comprises heavy and light chains having the sequences shown in SEQ ID NO: 107 and SEQ ID NO: 108, respectively, or antigen binding fragments, Fab fragments, single-chain variable fragments (scFv), variants, or conjugates thereof. In some embodiments, a OX40 agonist comprises heavy and light chains that are each at least 99% o identical to the sequences shown in SEQ ID NO:107 and SEQ ID NO:108, respectively. In some embodiments, a OX40 agonist comprises heavy and light chains that are each at least 98% identical to the sequences shown in SEQ ID NO:107 and SEQ ID NO:108, respectively. In some embodiments, a OX40 agonist comprises heavy and light chains that are each at least 97% identical to the sequences shown in SEQ ID NO:107 and SEQ ID NO:108, respectively. In some embodiments, a OX40 agonist comprises heavy and light chains that are each at least 96% identical to the sequences shown in SEQ ID NO:107 and SEQ ID NO:108, respectively. In some embodiments, a OX40 agonist comprises heavy and light chains that are each at least 95% identical to the sequences shown in SEQ ID NO:107 and SEQ ID NO:108, respectively.

In some embodiments, the OX40 agonist comprises the heavy and light chain CDRs or variable regions (VRs) of 18D8. In some embodiments, the OX40 agonist heavy chain variable region ($V_H$) comprises the sequence shown in SEQ ID NO:109, and the OX40 agonist light chain variable region ($V_L$) comprises the sequence shown in SEQ ID NO:110, and conservative amino acid substitutions thereof. In some embodiments, a OX40 agonist comprises $V_H$ and $V_L$ regions that are each at least 99% identical to the sequences shown in SEQ ID NO:109 and SEQ ID NO:110, respectively. In some embodiments, a OX40 agonist comprises $V_H$ and $V_L$ regions that are each at least 98% identical to the sequences shown in SEQ ID NO:109 and SEQ ID NO:110, respectively. In some embodiments, a OX40 agonist comprises $V_H$ and $V_L$ regions that are each at least 97% identical to the sequences shown in SEQ ID NO:109 and SEQ ID NO:110, respectively. In some embodiments, a OX40 agonist comprises $V_H$ and $V_L$ regions that are each at least 96% identical to the sequences shown in SEQ ID NO:109 and SEQ ID NO:110, respectively. In some embodiments, a OX40 agonist comprises $V_H$ and $V_L$ regions that are each at least 95% identical to the sequences shown in SEQ ID NO:109 and SEQ ID NO:110, respectively.

In some embodiments, a OX40 agonist comprises heavy chain CDR1, CDR2 and CDR3 domains having the sequences set forth in SEQ ID NO:111, SEQ ID NO:112, and SEQ ID NO:113, respectively, and conservative amino acid substitutions thereof, and light chain CDR1, CDR2 and CDR3 domains having the sequences set forth in SEQ ID NO:114, SEQ ID NO:115, and SEQ ID NO:116, respectively, and conservative amino acid substitutions thereof.

In some embodiments, the OX40 agonist is a OX40 agonist biosimilar monoclonal antibody approved by drug regulatory authorities with reference to 18D8. In some embodiments, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 14

Amino acid sequences for OX40 agonist antibodies related to 18D8.

| Identifier | Sequence (One-Letter Amino Acid Symbols) | |
|---|---|---|
| SEQ ID NO: 107 heavy chain for 18D8 | EVQLVESGGG LVQPGRSLRL SCAASGFTFD DYAMHWVRQA PGKGLEWVSG ISWNSGSIGY | 60 |
| | ADSVKGRFTI SRDNAKNSLY LQMNSLRAED TALYYCAKDQ STADYYFYYG MDVWGQGTTV | 120 |
| | TVSSASTKGP SVFPLAPCSR STSESTAALG CLVKDYFPEP VTVSWNSGAL TSGVHTFPAV | 180 |
| | LQSSGLYSLS SVVTVPSSNF GTQTYTCNVD HKPSNTKVDK TVERKCCVEC PPCPAPPVAG | 240 |
| | PSVFLFPPKP KDTLMISRTP EVTCVVVDVS HEDPEVQFNW YVDGVEVHNA KTKPREEQFN | 300 |
| | STFRVVSVLT VVHQDWLNGK EYKCKVSNKG LPAPIEKTIS KTKGQPREPQ VYTLPPSREE | 360 |
| | MTKNQVSLTC LVKGFYPSDI AVEWESNGQP ENNYKTTPPM LDSDGSFFLY SKLTVDKSRW | 420 |
| | QQGNVFSCSV MHEALHNHYT QKSLSLSPGK | 450 |
| SEQ ID NO: 108 light chain for 18D8 | EIVVTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPTFGQG TKVEIKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |
| SEQ ID NO: 109 heavy chain variable region for 18D8 | EVQLVESGGG LVQPGRSLRL SCAASGFTFD DYAMHWVRQA PGKGLEWVSG ISWNSGSIGY | 60 |
| | ADSVKGRFTI SRDNAKNSLY LQMNSLRAED TALYYCAKDQ STADYYFYYG MDVWGQGTTV | 120 |
| | TVSS | 124 |
| SEQ ID NO: 110 light chain variable region for 18D8 | EIVVTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPTFGQG TKVEIK | 106 |
| SEQ ID NO: 111 heavy chain CDR1 for 18D8 | DYAMH | 5 |
| SEQ ID NO: 112 heavy chain CDR2 for 18D8 | GISWNSGSIG YADSVKG | 17 |
| SEQ ID NO: 113 heavy chain CDR3 for 18D8 | DQSTADYYFY YGMDV | 15 |
| SEQ ID NO: 114 light chain CDR1 for 18D8 | RASQSVSSYL A | 11 |
| SEQ ID NO: 115 light chain CDR2 for 18D8 | DASNRAT | 7 |
| SEQ ID NO: 116 light chain CDR3 for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 15.

In some embodiments, the OX40 agonist comprises the heavy and light chain CDRs or variable regions (VRs) of Hu119-122. In some embodiments, the OX40 agonist heavy chain variable region ($V_H$) comprises the sequence shown in SEQ ID NO: 117, and the OX40 agonist light chain variable region ($V_L$) comprises the sequence shown in SEQ ID NO:118, and conservative amino acid substitutions thereof. In some embodiments, a OX40 agonist comprises $V_H$ and $V_L$ regions that are each at least 99% identical to the sequences shown in SEQ ID NO:117 and SEQ ID NO:118, respectively. In some embodiments, a OX40 agonist comprises $V_H$ and $V_L$ regions that are each at least 98% identical to the sequences shown in SEQ ID NO:117 and SEQ ID NO:118, respectively. In some embodiments, a OX40 agonist comprises $V_H$ and $V_L$ regions that are each at least 97% identical to the sequences shown in SEQ ID NO:117 and SEQ ID NO:118, respectively. In some embodiments, a OX40 agonist comprises $V_H$ and $V_L$ regions that are each at least 96% identical to the sequences shown in SEQ ID NO:117 and SEQ ID NO:118, respectively. In some embodiments, a OX40 agonist comprises $V_H$ and $V_L$ regions that are each at least 95% identical to the sequences shown in SEQ ID NO:117 and SEQ ID NO:118, respectively.

In some embodiments, a OX40 agonist comprises heavy chain CDR1, CDR2 and CDR3 domains having the sequences set forth in SEQ ID NO:119, SEQ ID NO: 120, and SEQ ID NO:121, respectively, and conservative amino acid substitutions thereof, and light chain CDR1, CDR2 and CDR3 domains having the sequences set forth in SEQ ID NO:122, SEQ ID NO:123, and SEQ ID NO:124, respectively, and conservative amino acid substitutions thereof.

In some embodiments, the OX40 agonist is a OX40 agonist biosimilar monoclonal antibody approved by drug regulatory authorities with reference to Hu119-122. In some embodiments, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 16.

In some embodiments, the OX40 agonist comprises the heavy and light chain CDRs or variable regions (VRs) of Hu106-222. In some embodiments, the OX40 agonist heavy chain variable region ($V_H$) comprises the sequence shown in SEQ ID NO:125, and the OX40 agonist light chain variable region ($V_L$) comprises the sequence shown in SEQ ID NO:126, and conservative amino acid substitutions thereof. In some embodiments, a OX40 agonist comprises $V_H$ and $V_L$ regions that are each at least 99% identical to the sequences shown in SEQ ID NO:125 and SEQ ID NO:126, respectively. In some embodiments, a OX40 agonist comprises $V_H$ and $V_L$ regions that are each at least 98% identical to the sequences shown in SEQ ID NO:125 and SEQ ID NO:126, respectively. In some embodiments, a OX40 agonist comprises $V_H$ and $V_L$ regions that are each at least 97% identical to the sequences shown in SEQ ID NO:125 and SEQ ID NO:126, respectively. In some embodiments, a OX40 agonist comprises $V_H$ and $V_L$ regions that are each at least 96% identical to the sequences shown in SEQ ID NO:125 and SEQ ID NO:126, respectively. In some embodiments, a OX40 agonist comprises $V_H$ and $V_L$ regions that are each at least 95% identical to the sequences shown in SEQ ID NO:125 and SEQ ID NO:126, respectively.

TABLE 15

Amino acid sequences for OX40 agonist antibodies related to Hu119-122.

| Identifier | Sequence (One-Letter Amino Acid Symbols) | |
|---|---|---|
| SEQ ID NO: 117 heavy chain variable region for Hu119-122 | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 118 light chain variable region for Hu119-122 | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 119 heavy chain CDR1 for Hu119-122 | SHDMS | 5 |
| SEQ ID NO: 120 heavy chain CDR2 for Hu119-122 | AINSDGGSTY YPDTMER | 17 |
| SEQ ID NO: 121 heavy chain CDR3 for Hu119-122 | HYDDYYAWFA Y | 11 |
| SEQ ID NO: 122 light chain CDR1 for Hu119-122 | RASKSVSTSG YSYMH | 15 |
| SEQ ID NO: 123 light chain CDR2 for Hu119-122 | LASNLES | 7 |
| SEQ ID NO: 124 light chain CDR3 for Hu119-122 | QHSRELPLT | 9 |

In some embodiments, a OX40 agonist comprises heavy chain CDR1, CDR2 and CDR3 domains having the sequences set forth in SEQ ID NO:127, SEQ ID NO:128, and SEQ ID NO:129, respectively, and conservative amino acid substitutions thereof, and light chain CDR1, CDR2 and CDR3 domains having the sequences set forth in SEQ ID NO:130, SEQ ID NO:131, and SEQ ID NO:132, respectively, and conservative amino acid substitutions thereof.

In some embodiments, the OX40 agonist is a OX40 agonist biosimilar monoclonal antibody approved by drug regulatory authorities with reference to Hu106-222. In some embodiments, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 16

Amino acid sequences for OX40 agonist antibodies related to Hu106-222.

| Identifier | Sequence (One-Letter Amino Acid Symbols) | |
|---|---|---|
| SEQ ID NO: 125 heavy chain variable region for Hu106-222 | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 126 light chain variable region for Hu106-222 | DIQMTQSPSS LSASVGDRVT ITCKASQDVS TAVAWYQQKP GKAPKLLIYS ASYLYTGVPS<br>RFSGSGSGTD FTFTISSLQP EDIATYYCQQ HYSTPRTFGQ GTKLEIK | 60<br>107 |
| SEQ ID NO: 127 heavy chain CDR1 for Hu106-222 | DYSMH | 5 |
| SEQ ID NO: 128 heavy chain CDR2 for Hu106-222 | WINTETGEPT YADDFKG | 17 |
| SEQ ID NO: 129 heavy chain CDR3 for Hu106-222 | PYYDYVSYYA MDY | 13 |
| SEQ ID NO: 130 light chain CDR1 for Hu106-222 | KASQDVSTAV A | 11 |
| SEQ ID NO: 131 light chain CDR2 for Hu106-222 | SASYLYT | 7 |
| SEQ ID NO: 132 light chain CDR3 for Hu106-222 | QQHYSTPRT | 9 |

In some embodiments, the OX40 agonist antibody is MED16469 (also referred to as 9B12). MED16469 is a murine monoclonal antibody. Weinberg, et al., *J Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MED16469. In some embodiments, the antibody comprises a heavy chain variable region sequence and/or a light chain variable region sequence of MED16469.

In some embodiments, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In some embodiments, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In some embodiments, the OX40 agonist is the murine monoclonal antibody anti-mCD134/mOX40 (clone OX86), commercially available from InVivoMAb, BioXcell Inc, West Lebanon, NH.

In some embodiments, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In some embodiments, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A given in FIG. 18 are found in Table 9. The Fc domain preferably comprises a complete constant domain (amino acids 17-230 of SEQ ID NO:62) the complete hinge domain (amino acids 1-16 of SEQ ID NO:62) or a portion of the hinge domain (e.g., amino acids 4-16 of SEQ ID NO:62). Preferred linkers for connecting a C-terminal Fc-antibody may be selected from the embodiments given in SEQ ID NO:63 to SEQ ID NO:72, including linkers suitable for fusion of additional polypeptides. Likewise, amino acid sequences for the polypeptide domains of structure I-B given in FIG. 18 are found in Table 9. If an Fc antibody fragment is fused to the N-terminus of an TNRFSF fusion protein as in structure I-B, the sequence of the Fc module is preferably that shown in SEQ ID NO:73, and the linker sequences are preferably selected from those embodiments set forth in SED ID NO:74 to SEQ ID NO:76.

In some embodiments, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In some embodiments, an OX40 agonist fusion protein according to structures I-A or I-B comprises one or more OX40 binding domains comprising an OX40L sequence. In some embodiments, an OX40 agonist fusion protein according to structures I-A or I-B comprises one or more OX40 binding domains comprising a sequence according to SEQ ID NO:133. In some embodiments, an OX40 agonist fusion protein according to structures I-A or I-B comprises one or more OX40 binding domains comprising a soluble OX40L sequence. In some embodiments, a OX40 agonist fusion protein according to structures I-A or I-B comprises one or more OX40 binding domains comprising a sequence according to SEQ ID NO:134. In some embodiments, a OX40 agonist fusion protein according to structures I-A or I-B comprises one or more OX40 binding domains comprising a sequence according to SEQ ID NO:135.

In some embodiments, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:89 and SEQ ID NO:90, respectively, wherein the $V_H$ and $V_L$ domains are connected by a linker. In some embodiments, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:99 and SEQ ID NO:100, respectively, wherein the $V_H$ and $V_L$ domains are connected by a linker. In some embodiments, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:109 and SEQ ID NO:110, respectively, wherein the $V_H$ and $V_L$ domains are connected by a linker. In some embodiments, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:127 and SEQ ID NO:128, respectively, wherein the $V_H$ and $V_L$ domains are connected by a linker. In some embodiments, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:125 and SEQ ID NO:126, respectively, wherein the $V_H$ and $V_L$ domains are connected by a linker. In some embodiments, an OX40 agonist fusion protein according to structures I-A or I-B comprises one or more OX40 binding domains that is a scFv domain comprising $V_H$ and $V_L$ regions that are each at least 95% o identical to the $V_H$ and $V_L$ sequences given in Table 17, wherein the $V_H$ and $V_L$ domains are connected by a linker.

TABLE 17

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 133 | MERVQPLEEN VGNAARPRFE RNKLLLVASV IQGLGLLLCF TYICLHFSAL QVSHRYPRIQ | 60 |
| OX40L | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |

TABLE 17-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 134 OX40L soluble domain | SHRYPRIQSI KVQFTEYKKE KGFILTSQKE DEIMKVQNNS VIINCDGFYL ISLKGYFSQE<br>VNISLHYQKD EEPLFQLKKV RSVNSLMVAS LTYKDKVYLN VTTDNTSLDD FHVNGGELIL<br>IHQNPGEFCV L | 60<br>120<br>131 |
| SEQ ID NO: 135 OX40L soluble domain (alternative) | YPRIQSIKVQ FTEYKKEKGF ILTSQKEDEI MKVQNNSVII NCDGFYLISL KGYFSQEVNI<br>SLHYQKDEEP LFQLKKVRSV NSLMVASLTY KDKVYLNVTT DNTSLDDFHV NGGELILIHQ<br>NPGEFCVL | 60<br>120<br>128 |
| SEQ ID NO: 136 variable heavy chain for 008 | EVQLVESGGG LVQPGGSLRL SCAASGFTFS NYTMNWVRQA PGKGLEWVSA ISGSGGSTYY<br>ADSVKGRFTI SRDNSKNTLY LQMNSLRAED TAVYYCAKDR YSQVHYALDY WGQGTLVTVS | 60<br>120 |
| SEQ ID NO: 137 variable light chain for 008 | DIVMTQSPDS LPVTPGEPAS ISCRSSQSLL HSNGYNYLDW YLQKAGQSPQ LLIYLGSNRA<br>SGVPDRFSGS GSGTDFTLKI SRVEAEDVGV YYCQQYYNHP TTFGQGTK | 60<br>108 |
| SEQ ID NO: 138 variable heavy chain for 011 | EVQLVESGGG VVQPGRSLRL SCAASGFTFS DYTMNWVRQA PGKGLEWVSS ISGGSTYYAD<br>SRKGRFTISR DNSKNTLYLQ MNNLRAEDTA VYYCARDRYF RQQNAFDYWG QGTLVTVSSA | 60<br>120 |
| SEQ ID NO: 139 variable light chain for 011 | DIVMTQSPDS LPVTPGEPAS ISCRSSQSLL HSNGYNYLDW YLQKAGQSPQ LLIYLGSNRA<br>SGVPDRFSGS GSGTDFTLKI SRVEAEDVGV YYCQQYYNHP TTFGQGTK | 60<br>108 |
| SEQ ID NO: 140 variable heavy chain for 021 | EVQLVESGGG LVQPRGSLRL SCAASGFTFS SYAMNWVRQA PGKGLEWVAV ISYDGSNKYY<br>ADSVKGRFTI SRDNSKNTLY LQMNSLRAED TAVYYCAKDR YITLPNALDY WGQGTLVTVS | 60<br>120 |
| SEQ ID NO: 141 variable light chain for 021 | DIQMTQSPVS LPVTPGEPAS ISCRSSQSLL HSNGYNYLDW YLQKPGQSPQ LLIYLGSNRA<br>SGVPDRFSGS GSGTDFTLKI SRVEAEDVGV YYCQQYKSNP PTFGQGTK | 60<br>108 |
| SEQ ID NO: 142 variable heavy chain for 023 | EVQLVESGGG LVHPGGSLRL SCAGSGFTFS SYAMHWVRQA PGKGLEWVSA IGTGGGTYYA<br>DSVMGRFTIS RDNSKNTLYL QMNSLRAEDT AVYYCARYDN VMGLYWFDYW GQGTLVTVSS | 60<br>120 |
| SEQ ID NO: 143 variable light chain for 023 | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPPAFGG GTKVEIKR | 60<br>108 |
| SEQ ID NO: 144 heavy chain variable region | EVQLQQSGPE LVKPGASVKM SCKASGYTFT SYVMHWVKQK PGQGLEWIGY INPYNDGTKY<br>NEKFKGKATL TSDKSSSTAY MELSSLTSED SAVYYCANYY GSSLSMDYWG QGTSVTVSS | 60<br>119 |
| SEQ ID NO: 145 light chain variable region | DIQMTQTTSS LSASLGDRVT ISCRASQDIS NYLNWYQQKP DGTVKLLIYY TSRLHSGVPS<br>RFSGSGSGTD YSLTISNLEQ EDIATYFCQQ GNTLPWTFGG GTKLEIKR | 60<br>108 |
| SEQ ID NO: 146 heavy chain variable region | EVQLQQSGPE LVKPGASVKI SCKTSGYTFK DYTMHWVKQS HGKSLEWIGG IYPNNGGSTY<br>NQNFKDKATL TVDKSSSTAY MEFRSLTSED SAVYYCARMG YHGPHLDFDV WGAGTTVTVS<br>P | 60<br>120<br>121 |
| SEQ ID NO: 147 light chain variable region | DIVMTQSHKF MSTSLGDRVS ITCKASQDVG AAVAWYQQKP GQSPKLLIYW ASTRHTGVPD<br>RFTGGGSGTD FTLTISNVQS EDLTDYFCQQ YINYPLTFGG GTKLEIKR | 60<br>108 |
| SEQ ID NO: 148 heavy chain variable region of humanized antibody | QIQLVQSGPE LKKPGETVKI SCKASGYTFT DYSMHWVKQA PGKGLKWMGW INTETGEPTY<br>ADDFKGRFAF SLETSASTAY LQINNLKNED TATYFCANPY YDYVSYYAMD YWGHGTSVTV<br>SS | 60<br>120<br>122 |
| SEQ ID NO: 149 heavy chain variable region of humanized antibody | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 150 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |

TABLE 17-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 151 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 152 heavy chain variable region of humanized antibody | EVQLVESGGG LVQPGESLKL SCESNEYEFP SHDMSWVRKT PEKRLELVAA INSDGGSTYY | 60 |
| | PDTMERRFII SRDNTKKTLY LQMSSLRSED TALYYCARHY DDYYAWFAYW GQGTLVTVSA | 120 |
| SEQ ID NO: 153 heavy chain variable region of humanized antibody | EVQLVESGGG LVQPGGSLRL SCAASEYEFP SHDMSWVRQA PGKGLELVAA INSDGGSTYY | 60 |
| | PDTMERRFTI SRDNAKNSLY LQMNSLRAED TAVYYCARHY DDYYAWFAYW GQGTMVTVSS | 120 |
| SEQ ID NO: 154 light chain variable region of humanized antibody | DIVLTQSPAS LAVSLGQRAT ISCRASKSVS TSGYSYMHWY QQKPGQPPKL LIYLASNLES | 60 |
| | GVPARFSGSG SGTDFTLNIH PVEEEDAATY YCQHSRELPL TFGAGTKLEL K | 111 |
| SEQ ID NO: 155 light chain variable region of humanized antibody | EIVLTQSPAT LSLSPGERAT LSCRASKSVS TSGYSYMHWY QQKPGQAPRL LIYLASNLES | 60 |
| | GVPARFSGSG SGTDFTLTIS SLEPEDFAVY YCQHSRELPL TFGGGTKVEI K | 111 |
| SEQ ID NO: 156 heavy chain variable region | MYLGLNYVFI VFLLNGVQSE VKLEESGGGL VQPGGSMKLS CAASGFTFSD AWMDWVRQSP | 60 |
| | EKGLEWVAEI RSKANNHATY YAESVNGRFT ISRDDSKSSV YLQMNSLRAE DTGIYYCTWG | 120 |
| | EVFYFDYWGQ GTTLTVSS | 138 |
| SEQ ID NO: 157 light chain variable region | MRPSIQFLGL LLFWLHGAQC DIQMTQSPSS LSASLGGKVT ITCKSSQDIN KYIAWYQHKP | 60 |
| | GKGPRLLIHY TSTLQPGIPS RFSGSGSGRD YSFSISNLEP EDIATYYCLQ YDNLLTFGAG | 120 |
| | TKLELK | 126 |

In some embodiments, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In some embodiments, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In some embodiments, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In some embodiments, the OX40 agonist is an OX40 agonistic scFv antibody comprising any of the foregoing $V_H$ domains linked to any of the foregoing $V_L$ domains.

In some embodiments, the OX40 agonist is Creative Biolabs OX40 agonist monoclonal antibody MOM-18455, commercially available from Creative Biolabs, Inc., Shirley, NY, USA.

In some embodiments, the OX40 agonist is OX40 agonistic antibody clone Ber-ACT35 commercially available from BioLegend, Inc., San Diego, CA, USA.

C. Optional Cell Viability Analyses

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Patent Application Publication No. 2018/0282694, incorporated by reference herein in its entirety. Cell viability can also be assayed based on U.S. Patent Application Publication No. 2018/0280436 or International Patent Application Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In some embodiments, a method for expanding TILs, including those discussed above as well as exemplified in FIGS. 1 and 8, in particular, e.g., FIG. 8A and/or FIG. 8B and/or FIG. 8C and/or FIG. 8D, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion) are both serum free. In some embodiments, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In some embodiments, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In some embodiments, the cell culture medium in the first and/or second gas permeable container is unfiltered. The use of unfiltered cell medium may simplify the procedures necessary to expand the number of cells. In some embodiments, the cell medium in the first and/or second gas permeable container lacks beta-mercaptoethanol (BME).

In some embodiments, the duration of the method comprising obtaining a tumor tissue sample from the mammal; culturing the tumor tissue sample in a first gas permeable container containing cell medium including IL-2, 1X antigen-presenting feeder cells, and OKT-3 for a duration of about 1 to 8 days, e.g., about 7 days as a priming first expansion, or about 8 days as a priming first expansion; transferring the TILs to a second gas permeable container and expanding the number of TILs in the second gas permeable container containing cell medium including IL-2, 2X antigen-presenting feeder cells, and OKT-3 for a duration of about 7 to 9 days, e.g., about 7 days, about 8 days, or about 9 days.

In some embodiments, the duration of the method comprising obtaining a tumor tissue sample from the mammal; culturing the tumor tissue sample in a first gas permeable container containing cell medium including IL-2, 1X antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2X antigen-presenting feeder cells, and OKT-3 for a duration of about 7 to 14 days, or about 7 to 9 days, e.g., about 7 days, about 8 days, or about 9 days, about 10 days, or about 11 days.

In some embodiments, the duration of the method comprising obtaining a tumor tissue sample from the mammal; culturing the tumor tissue sample in a first gas permeable container containing cell medium including IL-2, 1X antigen-presenting feeder cells, and OKT-3 for a duration of about 1 to 7 days, e.g., about 7 days, as a priming first expansion; transferring the TILs to a second gas permeable container and expanding the number of TILs in the second gas permeable container containing cell medium including IL-2, 2X antigen-presenting feeder cells, and OKT-3 for a duration of about 7 to 11 days, e.g., about 7 days, about 8 days, about 9 days, about 10, or about 11 days.

In some embodiments, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In some embodiments, TILs are expanded in gas-permeable bags. In some embodiments, TILs are expanded using a cell expansion system that expands TILs in gas permeable bags, such as the Xuri Cell Expansion System W25 (GE Healthcare). In some embodiments, TILs are expanded using a cell expansion system that expands TILs in gas permeable bags, such as the WAVE Bioreactor System, also known as the Xuri Cell Expansion System W5 (GE Healthcare). In some embodiments, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In some embodiments, TILs can be expanded in G-REX flasks (commercially available from Wilson Wolf Manufacturing). Such embodiments allow for cell populations to expand from about 5,i10$^5$ cells/cm$^2$ to between 10×10$^6$ and 30x. 10$^6$ cells/cm$^2$. In some embodiments this is without feeding. In some embodiments, this is without feeding so long as medium resides at a height of about 10 cm in the G-REX flask. In some embodiments this is without feeding but with the addition of one or more cytokines. In some embodiments, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy,* 2012, 35:283-292.

D. Optional Knockdown or Knockout of Genes in TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 8 (particularly FIG. 8A and/or FIG. 8B and/or FIG. 8C and/or FIG. 8D). In some embodiments, the transient alteration of protein expression occurs during the first expansion, including, for example in the TIL population expanded in for example, Step B as indicated in FIG. 8 (for example FIG. 8A and/or FIG. 8B and/or FIG. 8C and/or FIG. 8D). In some embodiments, the transient alteration of protein expression occurs after the first expansion, including, for example in the TIL population in transition between the first and second expansion (e.g., the second population of TILs as described herein), the TIL population obtained from for example, Step B and included in Step C as indicated in FIG. 8. In some embodiments, the transient alteration of protein expression occurs in the bulk TIL population prior to second expansion, including, for example in the TIL population obtained from for example, Step C and prior to its expansion in Step D as indicated in FIG. 8. In some embodiments, the transient alteration of protein expression occurs during the second expansion, including, for example in the TIL population expanded in for example, Step D as indicated in FIG. 8 (e.g., the third population of TILs). In some embodiments, the transient alteration of protein expression occurs after the second expansion, including, for example in the TIL population obtained from the expansion in for example, Step D as indicated in FIG. 8.

In some embodiments, a method of transiently altering protein expression in a population of TILs includes the step of electroporation. Electroporation methods are known in the art and are described, e.g., in Tsong, *Biophys. J* 1991, 60, 297-306, and U.S. Patent Application Publication No. 2014/0227237 A1, the disclosures of each of which are incorporated by reference herein. In some embodiments, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, Virology 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In some embodiments, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In some embodiments, a method of transiently altering protein expression in a population of TILs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer. In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH 1/2 ICD, CTLA-4, TIM3, LAG3, TIGIT, TET2, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, thymocyte selection associated high mobility group (HMG) box (TOX), ankyrin repeat domain 11 (ANKRD11), BCL6 co-repressor (BCOR), and/or cAMP protein kinase A (PKA). In some embodiments, the transient alteration of protein expression targets a gene selected from the group consisting of PD-1, TGFBR2, CCR4/5, CTLA-4, CBLB (CBL-B), CISH, CCRs (chimeric co-stimulatory receptors), IL-2, IL-12, IL-15, IL-21, NOTCH 1/2 ICD, TIM3, LAG3, TIGIT, TET2, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, thymocyte selection associated high mobility group (HMG) box (TOX), ankyrin repeat domain 11 (ANKRD11), BCL6 co-repressor (BCOR), and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CTLA-4. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TET2. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets thymocyte selection associated high mobility group (HMG) box (TOX). In some embodiments, the transient alteration of protein expression targets ankyrin repeat domain 11 (ANKRD11). In some embodiments, the transient alteration of protein expression targets BCL6 co-repressor (BCOR). In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-la), CCL4 (MIP1-0), CCL5 (RANTES), CXCL1, CXCL8, CCL22, and/or CCLT7.

In some embodiments, the transient alteration of protein expression results in a decrease and/or reduced expression of PD-1, CTLA-4, CBLB, CISH, TIM-3, LAG-3, TIGIT, TET2, TGFβR2, and/or TGFβ (including resulting in, for example, TGFβ pathway blockade). In some embodiments, the transient alteration of protein expression results in a decrease and/or reduced expression of PD-1. In some embodiments, the transient alteration of protein expression results in a decrease and/or reduced expression of CBLB (CBL-B). In some embodiments, the transient alteration of protein expression results in a decrease and/or reduced expression of CISH. In some embodiments, the transient alteration of protein expression results in a decrease and/or reduced expression of TIM-3. In some embodiments, the transient alteration of protein expression results in a decrease and/or reduced expression of LAG-3. In some embodiments, the transient alteration of protein expression results in a decrease and/or reduced expression of TIGIT. In some embodiments, the transient alteration of protein expression results in a decrease and/or reduced expression of TET2. In some embodiments, the transient alteration of protein expression results in a decrease and/or reduced expression of TGFβR2. In some embodiments, the transient alteration of protein expression results in a decrease and/or reduced expression of TGFβ.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH 1/2 ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, TET2, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, TET2, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, TET2, CISH, TGFβR2, PKA, CBLB, BAFF (BR3), and combinations thereof. In some embodiments, the transient alteration of protein expression results in decreased and/or reduced expression of PD-1, CTLA-4, LAG-3, CISH, CBLB, TIM3, TIGIT and combinations thereof. In some embodiments, the transient alteration of protein expression results in decreased and/or reduced expression of PD-1 and one of CTLA-4, LAG3, CISH, CBLB, TIM3, TIGIT, TET2 and combinations thereof. In some embodiments, the transient alteration of protein expression results in decreased and/or reduced expression of PD-1 and CTLA-4. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of PD-1 and TIM3. In some embodiments, the transient alteration of protein expression results in decreased and/or reduced expression of PD-1 and TIGIT. In some embodiments, the transient alteration of protein expression results in decreased and/or reduced expression of PD-1 and TET2. In some embodiments, the transient alteration of protein expression results in decreased and/or reduced expression of CTLA-4 and LAG3. In some embodiments, the transient alteration of protein expression results in decreased and/or reduced expression of CTLA-4 and CISH. In some embodiments, the transient alteration of protein expression results in decreased and/or reduced expression of CTLA-4 and CBLB. In some embodiments, the transient alteration of protein expression results in decreased and/or reduced expression of CTLA-4 and TIM3. In some embodiments, the transient alteration of protein expression results in decreased and/or reduced expression of CTLA-4 and TIGIT. In some embodiments, the transient alteration of protein expression results in decreased and/or reduced expression of CTLA-4 and TET2. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of LAG3 and TIM3. In some embodiments, the transient alteration of protein expression results in decreased and/or reduced expression of LAG3 and TIGIT. In some embodiments, the transient alteration of protein expression results in decreased and/or reduced expression of LAG3 and TET2. In some embodiments, the transient alteration of protein expression results in decreased and/or reduced expression of CISH and CBLB. In some embodiments, the transient alteration of protein expression results in decreased and/or reduced expression of CISH and TIM3. In some embodiments, the transient alteration of protein expression results in decreased and/or reduced expression of CISH and TIGIT. In some embodiments, the transient alteration of protein expression results in decreased and/or reduced expression of CISH and TET2. In some embodiments, the transient alteration of protein expression results in decreased and/or reduced expression of CBLB and TIM3. In some embodiments, the transient alteration of protein expression results in decreased and/or reduced expression of CBLB and TIGIT. In some embodiments, the transient alteration of protein expression results in decreased and/or reduced expression of CBLB and TET2. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB. In some embodiments, the transient alteration of protein expression results in decreased and/or reduced expression of TIM3 and TIGIT. In some embodiments, the transient alteration of protein expression results in decreased and/or reduced expression of TIM3 and TET2.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, TET2, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, CTLA-4, LAG3, TIM3, CISH, CBLB, TIGIT, TET2 and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (which have been described in U.S. Patent Application Publication Nos. US 2019/0093073 A1, US 2018/0201889 A1, and US 2019/0017072 A1, the disclosures of each of which are incorporated herein by reference). Such method can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In some embodiments, a method of genetically modifying a population of TILs includes the step of retroviral transduction. In some embodiments, a method of genetically modifying a population of TILs includes the step of lentiviral transduction. Lentiviral transduction systems are known in the art and are described, e.g., in Levine, et al., Proc. Nat'l *Acad. Sci.* 2006, 103, 17372-77; Zufferey, et al., *Nat. Biotechnol.* 1997, 15, 871-75; Dull, et al., *J Virology* 1998, 72, 8463-71, and U.S. Pat. No. 6,627,442, the disclosures of each of which are incorporated by reference herein. In some embodiments, a method of genetically modifying a population of TILs includes the step of gamma-retroviral transduction. Gamma-retroviral transduction systems are known in the art and are described, e.g., Cepko and Pear, Cur. Prot. *Mol. Biol.* 1996, 9.9.1-9.9.16, the disclosure of which is incorporated by reference herein. In some embodiments, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some embodiments, transient alteration of protein expression in TILs is induced by small interfering RNA (siRNA), sometimes known as short interfering RNA or silencing RNA, which is a double stranded RNA molecule, generally 19-25 base pairs in length. siRNA is used in RNA interference (RNAi), where it interferes with expression of specific genes with complementary nucleotide sequences. In some embodiments, transient alteration of protein expression is a reduction in expression. In some embodiments, transient alteration of protein expression in TILs is induced by self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences. sdRNA are covalently and hydrophobically modified RNAi compounds that do not require a delivery vehicle to enter cells. sdRNAs are generally asymmetric chemically modified nucleic acid molecules with minimal double stranded regions. sdRNA molecules typically contain single stranded regions and double stranded regions and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, U.S. Patent Application Publication Nos. US 2016/0304873 A1, US 2019/0211337 A1, US 2009/0131360 A1, and US 2019/0048341 A1, and U.S. Pat. Nos. 10,633,654 and 10,913,948B2, the disclosures of each of which are incorporated by reference herein. To optimize sdRNA structure, chemistry, targeting position, sequence preferences, and the like, an algorithm has been developed and utilized for sdRNA potency prediction. Based on these analyses, functional sdRNA sequences have been generally defined as having over 70% reduction in expression at 1 μM concentration, with a probability over 40%.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

In some embodiments, the method comprises transient alteration of protein expression in a population of TILs, including TILs modified to express a CCR, comprising the use of self-delivering RNA interference (sdRNA), which is for example, a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. Methods of using siRNA and sdRNA have been described in Khvorova and Watts, *Nat. Biotechnol.* 2017, 35, 238-248; Byrne, et al., *J Ocul. Pharmacol.* Ther. 2013, 29, 855-864; and Ligtenberg, et al., *Mol. Therapy,* 2018, 26, 1482-93, the disclosures of which are incorporated by reference herein. In some embodiments, delivery of siRNA is accomplished using electroporation or cell membrane disruption (such as the squeeze or SQZ method). In some embodiments, delivery of sdRNA to a TIL population is accomplished without use of electroporation, SQZ, or other methods, instead using a 1 to 3 day period in which a TIL population is exposed to sdRNA at a concentration of 1 μM/10,000 TILs in medium. In certain embodiments, the method comprises delivery or siRNA or sdRNA to a TILs population comprising exposing the TILs population to sdRNA at a concentration of 1 μM/10,000 TILs in medium for a period of between 1 to 3 days. In some embodiments, delivery of sdRNA to a TIL population is accomplished using a 1 to 3 day period in which a TIL population is exposed to sdRNA at a concentration of 10 μM/10,000 TILs in medium. In some embodiments, delivery of sdRNA to a TIL population is accomplished using a 1 to 3 day period in which a TIL population is exposed to sdRNA at a concentration of 50 μM/10,000 TILs in medium. In some embodiments, delivery of sdRNA to a TIL population is accomplished using a 1 to 3 day period in which a TIL population is exposed to sdRNA at a concentration of between 0.1 μM/10,000 TILs and 50 μM/10,000 TILs in medium. In some embodiments, delivery of sdRNA to a TIL population is accomplished using a 1 to 3 day period in which a TIL population is exposed to sdRNA at a concentration of between 0.1 μM/10,000 TILs and 50 μM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, siRNA or sdRNA is inserted into a population of TILs during manufacturing. In some embodiments, the sdRNA encodes RNA that interferes with NOTCH 1/2 ICD, PD-1, CTLA-4 TIM-3, LAG-3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., *Mol. Therapy,* 2018, 26, 1482-93 and U.S. Patent Application Publication No. 2016/0304873 A1, the disclosures of which are incorporated by reference herein) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific siRNAs or sdRNAs occurs. In some embodiments, siRNAs or sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post siRNAs or sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by siRNAs or sdRNA results in an increase TIL proliferation.

In some embodiments, the sdRNA sequences used in the invention exhibit a 70% reduction in expression of the target gene. In some embodiments, the sdRNA sequences used in the invention exhibit a 75% reduction in expression of the target gene. In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 μM to about 4 μM. In some embodiments, the sdRNA sequences used in the invention exhibit a reduction in expression of the target gene when delivered at a concentration of about 0.25 μM. In some embodiments, the sdRNA sequences used in the invention exhibit a reduction in expression of the target gene when delivered at a concentration of about 0.5 μM. In some embodiments, the sdRNA sequences used in the invention exhibit a reduction in expression of the target gene when delivered at a concentration of about 0.75 μM. In some embodiments, the sdRNA sequences used in the invention exhibit a reduction in expression of the target gene when delivered at a concentration of about 1.0 μM. In some embodiments, the sdRNA sequences used in the invention exhibit a reduction in expression of the target gene when delivered at a concentration of about 1.25 μM. In some embodiments, the sdRNA sequences used in the invention exhibit a reduction in expression of the target gene when delivered at a concentration of about 1.5 μM. In some embodiments, the sdRNA sequences used in the invention exhibit a reduction in expression of the target gene when delivered at a concentration of about 1.75 μM. In some embodiments, the sdRNA sequences used in the invention exhibit a reduction in expression of the target gene when delivered at a concentration of about 2.0 μM. In some embodiments, the sdRNA sequences used in the invention exhibit a reduction in expression of the target gene when delivered at a concentration of about 2.25 μM. In some embodiments, the sdRNA sequences used in the invention exhibit a reduction in expression of the target gene when delivered at a concentration of about 2.5 μM. In some embodiments, the sdRNA sequences used in the invention exhibit a reduction in expression of the target gene when delivered at a concentration of about 2.75 μM. In some embodiments, the sdRNA sequences used in the invention exhibit a reduction in expression of the target gene when delivered at a concentration of about 3.0 μM. In some embodiments, the sdRNA sequences used in the invention exhibit a reduction in expression of the target gene when delivered at a concentration of about 3.25 μM. In some embodiments, the sdRNA sequences used in the invention exhibit a reduction in expression of the target gene when delivered at a concentration of about 3.5 μM. In some embodiments, the sdRNA sequences used in the invention exhibit a reduction in expression of the target gene when delivered at a concentration of about 3.75 μM. In some embodiments, the sdRNA sequences used in the invention exhibit a reduction in expression of the target gene when delivered at a concentration of about 4.0 μM.

In some embodiments, the siRNA or sdRNA oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-fluro modification, a diphosphorothioate modification, 2' F modified nucleotide, a2'-O-methyl modified and/or a 2'deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In some embodiments, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-O-ethyl), i.e., 2'-alkoxy, 2'-amino, 2'-S-alkyl, 2'-halo (including 2'-fluoro), T-methoxyethoxy, 2'-allyloxy (—$OCH_2C_H$=$C_H$2), 2'-propargyl, 2'-propyl, ethynyl, ethenyl, propenyl, and cyano and the like. In some embodiments, the sugar moiety can be a hexose and incorporated into an oligonucleotide as described in Augustyns, et al., *Nucl*. Acids. Res. 1992, 18, 4711, the disclosure of which is incorporated by reference herein.

In some embodiments, the double-stranded siRNA or sdRNA oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded siRNA or sdRNA oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded siRNA or sdRNA oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In other embodiments, a double-stranded siRNA or sdRNA oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded siRNA or sdRNA oligonucleotide of the invention contains at least or up to 1, 2, 3, 4, 5, 6, 7, 8, 9, 10, 11, 12, 13, 14, or 15 mismatches.

In some embodiments, the siRNA or sdRNA oligonucleotide can be substantially protected from nucleases e.g., by modifying the 3' or 5' linkages, as described in U.S. Pat. No. 5,849,902, the disclosure of which is incorporated by reference herein). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($C_H$2-$C_H$2-$C_H$3), glycol (—O—$C_H$2-$C_H$2-O-) phosphate ($PO_3^{2-}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the siRNA or sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, or 500 percent in cellular uptake of an siRNA or sdRNA. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the siRNA or sdRNA molecules exhibit enhanced endosomal release through the incorporation of protonatable amines. In some embodiments, protonatable amines are incorporated in the sense strand (in the part of the molecule which is discarded after RISC loading). In some embodiments, the siRNA or sdRNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the siRNA or sdRNA comprises 2-12 phosphorothioate internucleotide linkages (referred to as phosphorothioate modifications). In some embodiments, 6-8 phosphorothioate internucleotide linkages are employed. In some embodiments, the siRNA or sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the siRNA or sdRNA ae modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the siRNA or sdRNA are modified. In some embodiments, 100% of the nucleotides in the siRNA or sdRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the siRNA or sdRNA molecules have increased stability. In some instances, a chemically modified siRNA or sdRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the siRNA or sdRNA has a half-life in media that is longer than 12 hours.

In some embodiments, the siRNA or sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the siRNA or sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent (whether siRNA, sdRNA, or other RNAi agents), without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNA method allows direct delivery of chemically synthesized compounds to a wide range of primary cells and tissues, both ex-vivo and in vivo. The sdRNAs described in some embodiments of the invention herein are commercially available from Advima LLC, Worcester, MA, USA.

The siRNA or sdRNA may be formed as hydrophobically-modified siRNA-antisense oligonucleotide hybrid structures, and are disclosed, for example in Byrne, et al., *J Ocular Pharmacol. Therapeut.*, 2013, 29, 855-864, the disclosure of which is incorporated by reference herein.

In some embodiments, the siRNA or sdRNA oligonucleotides can be delivered to the TILs described herein using sterile electroporation. In certain embodiments, the method comprises sterile electroporation of a population of TILs to deliver siRNA or sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver siRNA or sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In some embodiments, one or more sdRNAs targeting genes as described herein, including PD-1, LAG-3, TIM-3, CISH, CTLA-4, TIGIT, TET2 and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In some embodiments, one or more sdRNAs targeting genes as described herein, including PD-1, LAG-3, TIM-3, CISH, CTLA-4, TIGIT, TET2 and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs /100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In some embodiments, one or more sdRNAs targeting genes as described herein, including PD-1, LAG-3, TIM-3, CISH, CTLA-4, TIGIT, TET2 and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art, such as those methods described in U.S. Pat. Nos. 4,897,355; 5,459,127; 5,631,237; 5,955,365; 5,976,567; 10,087,464; and 10,155,945; and Bergan, et al., *Nucl. Acids Res.* 1993, 21, 3567, the disclosures of each of which are incorporated by reference herein.

In some embodiments, more than one siRNA or sdRNA is used to reduce expression of a target gene. In some embodiments, one or more of PD-1, TIM-3, CBLB, LAG3, CTLA-4, TIGIT, TET2 and/or CISH targeting siRNA or sdRNAs are used together. In some embodiments, a PD-1 siRNA or sdRNA is used with one or more of TIM-3, CBLB, LAG3, CTLA-4, TIGIT, TET2 and/or CISH in order to reduce expression of more than one gene target. In some embodiments, a LAG3 siRNA or sdRNA is used in combination with a CISH targeting siRNA or sdRNA to reduce gene expression of both targets. In some embodiments, the siRNA or sdRNAs targeting one or more of PD-1, TIM-3, CBLB, LAG3, CTLA-4, TIGIT, TET2 and/or CISH herein are commercially available from Advirna LLC, Worcester, MA, USA.

In some embodiments, the siRNA or sdRNA targets a gene selected from the group consisting of PD-1, LAG3, TIM3, CTLA-4, TIGIT, TET2, CISH, TGFβR2, PKA, CBLB, BAFF (BR3), and combinations thereof. In some embodiments, the siRNA or sdRNA targets a gene selected from the group consisting of PD-1, LAG3, TIM3, CTLA-4, TIGIT, TET2, CISH, TGFβR2, PKA, CBLB, BAFF (BR3), and combinations thereof. In some embodiments, one siRNA or sdRNA targets PD-1 and another siRNA or sdRNA targets a gene selected from the group consisting of LAG3, TIM3, CTLA-4, TIGIT, TET2, CISH, TGFβR2, PKA, CBLB, BAFF (BR3), and combinations thereof. In some embodiments, the siRNA or sdRNA targets a gene selected from PD-1, LAG-3, CISH, CBLB, TIM3, CTLA-4, TIGIT, TET2 and combinations thereof. In some embodiments, the siRNA or sdRNA targets a gene selected from PD-1 and one of LAG3, CISH, CBLB, TIM3, CTLA-4, TIGIT, TET2 and combinations thereof. In some embodiments, one siRNA or sdRNA targets PD-1 and one siRNA or sdRNA targets LAG3. In some embodiments, one siRNA or sdRNA targets PD-1 and one siRNA or sdRNA targets CISH. In some embodiments, one siRNA or sdRNA targets PD-1 and one siRNA or sdRNA targets CBLB. In some embodiments, one siRNA or sdRNA targets PD-1 and one siRNA or sdRNA targets TIM3. In some embodiments, one siRNA or sdRNA targets PD-1 and one siRNA or sdRNA targets CTLA-4. In some embodiments, one siRNA or sdRNA targets PD-1 and one siRNA or sdRNA targets TIGIT. In some embodiments, one siRNA or sdRNA targets PD-1 and one siRNA or sdRNA targets TET2. In some embodiments, one siRNA or sdRNA targets LAG3 and one siRNA or sdRNA targets CISH. In some embodiments, one siRNA or sdRNA targets LAG3 and one siRNA or sdRNA targets CBLB. In some embodiments, one siRNA or sdRNA targets LAG3 and one siRNA or sdRNA targets TIM3. In some embodiments, one siRNA or sdRNA targets LAG3 and one siRNA or sdRNA targets CTLA-4. In some embodiments, one siRNA or sdRNA targets LAG3 and one siRNA or sdRNA targets TIGIT. In some embodiments, one siRNA or sdRNA targets LAG3 and one siRNA or sdRNA targets TET2. In some embodiments, one siRNA or sdRNA targets CISH and one siRNA or sdRNA targets CBLB. In some embodiments, one siRNA or sdRNA targets CISH and one siRNA or sdRNA targets TIM3. In some embodiments, one siRNA or sdRNA targets CISH and one siRNA or sdRNA targets CTLA-4.

In some embodiments, one siRNA or sdRNA targets CISH and one siRNA or sdRNA targets TIGIT. In some embodiments, one siRNA or sdRNA targets CISH and one siRNA or sdRNA targets TET2. In some embodiments, one siRNA or sdRNA targets CBLB and one siRNA or sdRNA targets TIM3. In some embodiments, one siRNA or sdRNA targets CBLB and one siRNA or sdRNA targets CTLA-4. In some embodiments, one siRNA or sdRNA targets CBLB and one siRNA or sdRNA targets TIGIT. In some embodiments, one siRNA or sdRNA targets CBLB and one siRNA or sdRNA targets TET2. In some embodiments, one siRNA or sdRNA targets TIM3 and one siRNA or sdRNA targets PD-1. In some embodiments, one siRNA or sdRNA targets TIM3 and one siRNA or sdRNA targets LAG3. In some embodiments, one siRNA or sdRNA targets TIM3 and one siRNA or sdRNA targets CISH. In some embodiments, one siRNA or sdRNA targets TIM3 and one siRNA or sdRNA targets CBLB. In some embodiments, one siRNA or sdRNA targets TIM3 and one siRNA or sdRNA targets CTLA-4. In some embodiments, one siRNA or sdRNA targets TIM3 and one siRNA or sdRNA targets TIGIT. In some embodiments, one siRNA or sdRNA targets TIM3 and one siRNA or sdRNA targets TET2. In some embodiments, one siRNA or sdRNA targets CTLA-4 and one siRNA or sdRNA targets TIGIT. In some embodiments, one siRNA or sdRNA targets CTLA-4 and one siRNA or sdRNA targets TET2. In some embodiments, one siRNA or sdRNA targets TIGIT and one siRNA or sdRNA targets TET2.

As discussed herein, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs in a first population, a second population and/or a third population as described herein. In some embodiments, a method of genetically modifying a population of TILs includes the step of stable incorporation of genes for production or inhibition (e.g., silencing) of one ore more proteins. In some embodiments, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In some embodiments, the electroporation method is a sterile electroporation method. In some embodiments, the electroporation method is a pulsed electroporation method. In some embodiments, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In some embodiments, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In some embodiments, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In some embodiments, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In some embodiments, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In some embodiments, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, Virology 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In some embodiments, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In some embodiments, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., Gen 3) or as described in U.S. Patent Application Publication Nos. US 2020/0299644 A1 and US 2020/0121719 A1 and U.S. Pat. No. 10,925,900, the disclosures of which are incorporated by reference herein, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TILs in vitro, e.g., by evaluating in vitro effector function, cytokine profiles, etc. compared to unmodified TILs. In certain embodiments, the method comprises gene editing a population of TILs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., Gen 3) or as described in U.S. Patent Application Publication Nos. US 2020/0299644 A1 and US 2020/0121719 A1 and U.S. Pat. No. 10,925,900, the disclosures of which are incorporated by reference herein, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "clustered regularly interspaced short palindromic repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endo-nuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, TET2, CD96, CRTAM, LAIRI, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAGI, SIT1, FOXP3, PRDM1, BATF, GUCY1A2, GUCY1A3, GUCYIB2, GUCYIB3, TOX, SOCS1, ANKRD11, and BCOR.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, the disclosures of each of which are incorporated by reference herein. Resources for carrying out CRISPR methods, such as plasmids for expressing CRISPR/Cas9 and CRISPR/Cpf1, are commercially available from companies such as GenScript.

In some embodiments, genetic modifications of populations of TILs, as described herein, may be performed using the CRISPR/Cpf1 system as described in U.S. Pat. No. 9,790,490, the disclosure of which is incorporated by reference herein.

A method for expanding TILs into a therapeutic population may be carried out in accordance with any embodiment of the methods described herein (e.g., Gen 2) or as described in U.S. Patent Application Publication Nos. US 2020/0299644 A1 and US 2020/0121719 A1 and U.S. Pat. No. 10,925,900, the disclosures of which are incorporated by reference herein, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for transcription activator-like effector " " proteins, which include transcription activator-like effector nucleases (TALENs" "). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of each of which are incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGF0, PKA, CBL-B, PPP2CA, PPP2CB, PTPN6, PTPN22, PDCD1, BTLA, CD160, TIGIT, TET2, CD96, CRTAM, LAIRI, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAGI, SITI, FOXP3, PRDM1, BATF, GUCY1A2, GUCY1A3, GUCYlB2, GUCYlB3, TOX, SOCS1, ANKRD11, and BCOR.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein or as described in U.S. Patent Application Publication Nos. US 2020/0299644 A1 and US 2020/0121719 A1 and U.S. Pat. No. 10,925,900, the disclosures of which are incorporated by reference herein, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved 00a configuration. Several amino acids on the surface of the a-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site.

Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially from Sangamo Biosciences (Richmond, CA, USA) and Sigma-Aldrich (St. Louis, MO, USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, TET2, CD96, CRTAM, LAIRI, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAGI, SIT1, FOXP3, PRDM1, BATF, GUCY1A2, GUCY1A3, GUCYlB2, GUCYlB3, TOX, SOCS1, ANKRD11, and BCOR.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S.

Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, each of which are incorporated by reference herein.

Other examples of systems, methods, and compositions for altering the expression of a target gene sequence by a zinc finger method, which may be used in accordance with embodiments of the present invention, are described in Beane, et al., *Mol. Therapy,* 2015, 23, 1380-1390, the disclosure of which is incorporated by reference herein.

In some embodiments, the TILs are optionally genetically engineered to include additional functionalities, including, but not limited to, a high-affinity TCR, e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). In some embodiments, the method comprises genetically engineering a population of TILs to include a high-affinity TCR, e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). Aptly, the population of TILs may be a first population, a second population and/or a third population as described herein.

E. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in the Examples. In some embodiments, the closed system is accessed via syringes under sterile conditions in order to maintain the sterility and closed nature of the system. In some embodiments, a closed system as described in Example 21 is employed. In some embodiments, the TILs are formulated into a final product formulation container according to the methods described herein in the Examples" ".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

F. Optional Cryopreservation of TILs

Either the bulk TIL population (for example the second population of TILs) or the expanded population of TILs (for example the third population of TILs) can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIGS. 1 and/or 8 (in particular, e.g., FIG. 8A and/or FIG. 8B and/or FIG. 8C and/or FIG. 8D). In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some embodiments, a population of TILs is cryopreserved using CS10 cryopreservation media (CryoStor 10, BioLife Solutions). In some embodiments, a population of TILs is cryopreserved using a cryopreservation media containing dimethylsulfoxide (DMSO). In some embodiments, a population of TILs is cryopreserved using a 1:1 (vol:vol) ratio of CS10 and cell culture media. In some embodiments, a population of TILs is cryopreserved using about a 1:1 (vol:vol) ratio of CS10 and cell culture media, further comprising additional IL-2.

As discussed above, and exemplified in Steps A through E as provided in FIGS. 1 and/or 8 (in particular, e.g., FIG. 8A and/or FIG. 8B and/or FIG. 8C and/or FIG. 8D), cryopreservation can occur at numerous points throughout the TIL expansion process. In some embodiments, the expanded population of TILs after the first expansion (as provided for example, according to Step B or the expanded population of TILs after the one or more second expansions according to Step D of FIGS. 1 or 8 (in particular, e.g., FIG. 8A and/or FIG. 8B and/or FIG. 8C and/or FIG. 8D) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example 6.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B from FIGS. 1 or 8, (in particular, e.g., FIG. 8A and/or FIG. 8B and/or FIG. 8C and/or FIG. 8D) TIL population can be cryopreserved immediately, using the protocols discussed below. Alternatively, the bulk TIL population can be subjected to Step C and Step D from FIGS. 1 or 8, (in particular, e.g., FIG. 8A and/or FIG. 8B and/or FIG. 8C and/or FIG. 8D) and then cryopreserved after Step D from FIGS. 1 or 8, (in particular, e.g., FIG. 8A and/or FIG. 8B and/or FIG. 8C and/or FIG. 8D). Similarly, in the case where genetically modified TILs will be used in therapy, the Step B or Step D from FIGS. 1 or 8, (in particular, e.g., FIG. 8A and/or FIG. 8B and/or FIG. 8C and/or FIG. 8D) TIL populations can be subjected to genetic modifications for suitable treatments.

G. Phenotypic Characteristics of Expanded TILs

In some embodiment, the TILs are analyzed for expression of numerous phenotype markers after expansion, including those described herein and in the Examples. In some embodiments, expression of one or more phenotypic markers is examined. In some embodiments, the phenotypic characteristics of the TILs are analyzed after the first expansion in Step B from FIGS. 1 or 8, (in particular, e.g., FIG. 8A and/or FIG. 8B and/or FIG. 8C and/or FIG. 8D). In some embodiments, the phenotypic characteristics of the TILs are analyzed during the transition in Step C from FIGS. 1 or 8, (in particular, e.g., FIG. 8A and/or FIG. 8B and/or FIG. 8C and/or FIG. 8D). In some embodiments, the phenotypic characteristics of the TILs are analyzed during the transition according to Step C from FIGS. 1 or 8, (in particular, e.g., FIG. 8A and/or FIG. 8B and/or FIG. 8C and/or FIG. 8D) and after cryopreservation. In some embodiments, the phenotypic characteristics of the TILs are analyzed after the second expansion according to Step D from FIGS. 1 or 8, (in particular, e.g., FIG. 8A and/or FIG. 8B and/or FIG. 8C and/or FIG. 8D). In some embodiments, the phenotypic characteristics of the TILs are analyzed after two or more expansions according to Step D from FIGS. 1 or 8, (in particular, e.g., FIG. 8A and/or FIG. 8B and/or FIG. 8C and/or FIG. 8D).

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 8 (in particular, e.g., FIG. 8A and/or FIG. 8B and/or FIG. 8C and/or FIG. 8D), as compared to the 2A process as provided for example in FIG. 8 (in particular, e.g., FIG. 8A and/or FIG. 8B and/or FIG. 8C and/or FIG. 8D). In some embodiments, the expression of CD8 is higher on TILs produced according the current invention process, as compared to other processes (e.g., the Gen 3 process as provided for example in FIG. 8 (in particular, e.g., FIG. 8B), as compared to the 2A process as provided for example in FIG. 8 (in particular, e.g., FIG. 8A and/or FIG. 8B and/or FIG. 8C and/or FIG. 8D). In some embodiments, the expression of CD28 is higher on TILs produced according the current invention process, as compared to other processes (e.g., the Gen 3 process as provided for example in FIG. 8 (in particular, e.g., FIG. 8A and/or FIG. 8B and/or FIG. 8C and/or FIG. 8D), as compared to the 2A process as provided for example in FIG. 8 (in particular, e.g., FIG. 8A)). In some embodiments, high CD28 expression is indicative of a younger, more presisitent TIL phenotype. In some embodiments, expression of one or more regulatory markers is measured.

In some embodiments, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 8 (in particular, e.g., FIG. 8A and/or FIG. 8B and/or FIG. 8C and/or FIG. 8D), as compared to the 2A process as provided for example in FIG. 8 (in particular, e.g., FIG. 8A)). In some embodiments the memory marker for central memory cells is selected from the group consisting of CCR7 and CD62L.

In some embodiments, the CD4+ and/or CD8+TIL Memory subsets can be divided into different memory subsets. In some embodiments, the CD4+ and/or CD8+TILs comprise the naive (CD45RA+CD62L+) TILs. In some embodiments, the CD4+ and/or CD8+TILs comprise the central memory (CM; CD45RA-CD62L+) TILs. In some embodiments, the CD4+ and/or CD8+TILs comprise the effector memory (EM; CD45RA-CD62L-) TILs. In some embodiments, the CD4+ and/or CD8+TILs comprise the, RA+effector memory/effector (TEMRA/TEFF; CD45RA+ CD62L+) TILs.

In some embodiments, the TILs express one more markers selected from the group consisting of granzyme B, perform, and granulysin. In some embodiments, the TILs express granzyme B. In some embodiments, the TILs express perform. In some embodiments, the TILs express granulysin.

In some embodiments, restimulated TILs can also be evaluated for cytokine release, using cytokine release assays. In some embodiments, TILs can be evaluated for interferon-y (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 8 (in particular, e.g., FIG. 8A and/or FIG. 8B and/or FIG. 8C and/or FIG. 8D). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 8 (in particular, e.g., FIG. 8A and/or FIG. 8B and/or FIG. 8C and/or FIG. 8D) TILs as compared to for example Step D in the 2A process as provided in FIG. 8 (in particular, e.g., FIG. 8A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including, for example FIG. 8B methods.

In some embodiments, TILs capable of at least one-fold, two-fold, three-fold, four-fold, or five-fold or more IFN-γ secretion are TILs produced by the expansion methods of the present invention, including, for example FIG. 8A and/or FIG. 8B and/or FIG. 8C and/or FIG. 8D methods. In some embodiments, TILs capable of at least one-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least two-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least three-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least four-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least five-fold more IFN-γ secretion are TILs produced by the expansion methods of the present invention, including, for example FIG. 8A and/or FIG. 8B and/or FIG. 8C and/or FIG. 8D methods.

In some embodiments, TILs capable of at least 100 μg/mL to about 1000 μg/mL or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 μg/mL, at least 250 μg/mL, at least 300 μg/mL, at least 350 μg/mL, at least 400 μg/mL, at least 450 μg/mL, at least 500 μg/mL, at least 550 μg/mL, at least 600 μg/mL, at least 650 μg/mL, at least 700 μg/mL, at least 750 μg/mL, at least 800 μg/mL, at least 850 μg/mL, at least 900 μg/mL, at least 950 μg/mL, or at least 1000 μg/mL or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 300 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 400 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 500 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 600 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 700 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 800 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 900 μg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 1000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 2000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 3000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 4000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 5000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 6000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 7000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 8000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 9000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 10,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 15,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 20,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 25,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 30,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 35,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 40,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 45,000 µg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 50,000 µg/mL IFN-γ secretion are TILs produced by the expansion methods of the present invention, including, for example FIG. 8A and/or FIG. 8B and/or FIG. 8C and/or FIG. 8D methods.

In some embodiments, TILs capable of at least 100 µg/mL/5e5 cells to about 1000 µg/mL/5e5 cells or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 µg/mL/5e5 cells, at least 250 µg/mL/5e5 cells, at least 300 µg/mL/5e5 cells, at least 350 µg/mL/5e5 cells, at least 400 µg/mL/5e5 cells, at least 450 µg/mL/5e5 cells, at least 500 µg/mL/5e5 cells, at least 550 µg/mL/5e5 cells, at least 600 µg/mL/5e5 cells, at least 650 µg/mL/5e5 cells, at least 700 µg/mL/5e5 cells, at least 750 µg/mL/5e5 cells, at least 800 µg/mL/5e5 cells, at least 850 µg/mL/5e5 cells, at least 900 µg/mL/5e5 cells, at least 950 µg/mL/5e5 cells, or at least 1000 µg/mL/5e5 cells or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 300 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 400 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 500 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 600 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 700 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 800 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 900 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 1000 µg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 2000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 3000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 4000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 5000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 6000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 7000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 8000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 9000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 10,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 15,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 20,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 25,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 30,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 35,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 40,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 45,000 μg/mL/5e5 cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 50,000 μg/mL/5e5 cells IFN-γ secretion are TILs produced by the expansion methods of the present invention, including, for example FIG. 8A and/or FIG. 8B and/or FIG. 8C and/or FIG. 8D methods.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, the TILs obtained by the present method exhibit an increase in the T-cell repertoire diversity as compared to freshly harvested TILs and/or TILs prepared using methods referred to as Gen 2, as exemplified in FIG. 8 (in particular, e.g., FIG. 8A). In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRαβ (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample.

In some embodiments, the activation and exhaustion of TILs can be determined by examining one or more markers. In some embodiments, the activation and exhaustion can be determined using multicolor flow cytometry. In some embodiments, the activation and exhaustion of markers include but not limited to one or more markers selected from the group consisting of CD3, PD-1, 2B4/CD244, CD8, CD25, BTLA, KLRG, TIM-3, CD194/CCR4, CD4, TIGIT, CD183, CD69, CD95, CD127, CD103, and/or LAG-3). In some embodiments, the activation and exhaustion of markers include but not limited to one or more markers selected from the group consisting of BTLA, CTLA-4, ICOS, Ki67, LAG-3, PD-1, TIGIT, and/or TIM-3. In some embodiments, the activation and exhaustion of markers include but not limited to one or more markers selected from the group consisting of BTLA, CTLA-4, ICOS, Ki67, LAG-3, CD103+/CD69+, CD103+/CD69-, PD-1, TIGIT, and/or TIM-3. In some embodiments, the T-cell markers (including activation and exhaustion markers) can be determined and/ or analyzed to examine T-cell activation, inhibition, or function. In some embodiments, the T-cell markers can include but are not limited to one or more markers selected from the group consisting of TIGIT, CD3, FoxP3, Tim-3, PD-1, CD103, CTLA-4, LAG-3, BTLA-4, ICOS, Ki67, CD8, CD25, CD45, CD4, and/or CD59.

In some embodiments, TILs that exhibit greater than 3000 μg/$10^6$ TILs to 300000 μg/$10^6$ TILs or more Granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 μg/$10^6$ TILs greater than 5000 μg/$10^6$ TILs, greater than 7000 μg/$10^6$ TILs, greater than 9000 μg/$10^6$ TILs, greater than 11000 μg/$10^6$ TILs, greater than 13000 μg/$10^6$ TILs, greater than 15000 μg/106 TILs, greater than 17000 μg/$10^6$ TILs, greater than 19000 μg/$10^6$ TILs, greater than 20000 μg/$10^6$ TILs, greater than 40000 μg/$10^6$ TILs, greater than 60000 μg/$10^6$ TILs, greater than 80000 μg/$10^6$ TILs, greater than 100000 μg/$10^6$ TILs, greater than 120000 μg/$10^6$ TILs, greater than 140000 μg/$10^6$ TILs, greater than 160000 μg/$10^6$ TILs, greater than 180000 μg/$10^6$ TILs, greater than 200000 μg/$10^6$ TILs, greater than 220000 μg/$10^6$ TILs, greater than 240000 μg/$10^6$ TILs, greater than 260000 μg/$10^6$ TILs, greater than 280000 μg/$10^6$ TILs, greater than 300000 μg/$10^6$ TILs or more Granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 5000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 7000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 9000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 11000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 13000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 15000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 17000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 19000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 20000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 40000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 60000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 80000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 100000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 120000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 μg/$10^6$ TILs to 300000 μg/$10^6$ TILs or more Granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 μg/$10^6$ TILs greater than 5000 μg/$10^6$ TILs, greater than 7000 μg/$10^6$ TILs, greater than 9000 μg/$10^6$ TILs, greater than 11000 μg/$10^6$ TILs, greater than 13000 μg/106 TILs, greater than 15000 μg/$10^6$ TILs, greater than 17000 μg/$10^6$ TILs, greater than 19000 μg/$10^6$ TILs, greater than 20000 μg/$10^6$ TILs, greater than 40000 μg/$10^6$ TILs, greater than 60000 μg/$10^6$ TILs, greater than 80000 μg/$10^6$ TILs, greater than 100000 μg/$10^6$ TILs, greater than 120000 μg/$10^6$ TILs, greater than 140000 μg/$10^6$ TILs, greater than 160000 μg/$10^6$ TILs, greater than 180000 μg/$10^6$ TILs, greater than 200000 μg/$10^6$ TILs, greater than 220000 μg/$10^6$ TILs, greater than 240000 μg/$10^6$ TILs, greater than 260000 μg/$10^6$ TILs, greater than 280000 μg/$10^6$ TILs, greater than 300000 μg/$10^6$ TILsor more Granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 5000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 7000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 9000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 11000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 13000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 15000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 17000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 19000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 20000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 40000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 60000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 80000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 100000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 120000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 μg/$10^6$ TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 μg/$10^6$ TILs Granzyme B secretion are TILs produced by the expansion methods of the present invention, including for example FIG. 8A and/or FIG. 8B and/or FIG. 8C and/or FIG. 8D.

In some embodiments, TILs that exhibit greater than 1000 μg/mL to 300000 μg/mL or more Granzyme B secretion are TILs produced by the expansion methods of the present invention, including for example FIG. 8A and/or FIG. 8B and/or FIG. 8C and/or FIG. 8D. In some embodiments, TILs that exhibit greater than 1000 μg/mL, greater than 2000 μg/mL, greater than 3000 μg/mL, greater than 4000 μg/mL, greater than 5000 μg/mL, greater than 6000 μg/mL, greater than 7000 μg/mL, greater than 8000 μg/mL, greater than 9000 μg/mL, greater than 10000 μg/mL, greater than 20000 μg/mL, greater than 30000 μg/mL, greater than 40000 μg/mL, greater than 50000 μg/mL, greater than 60000 μg/mL, greater than 70000 μg/mL, greater than 80000 μg/mL, greater than 90000 μg/mL, greater than 100000 μg/mL or more Granzyme B secretion are TILs produced by the expansion methods of the present invention, including for example FIG. 8A and/or FIG. 8B and/or FIG. 8C and/or FIG. 8D. In some embodiments, TILs that exhibit greater than 1000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 2000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 3000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 4000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 5000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 6000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 7000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 8000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 9000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 10000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 20000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 30000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 40000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 50000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 60000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 70000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 80000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 90000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 100000 μg/mL Granzyme B are TILs produced by the expansion methods of the present invention, including for example FIG. 8A and/or FIG. 8B and/or FIG. 8C and/or FIG. 8D. In some embodiments, TILs that exhibit greater than 120000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 μg/mL Granzyme B are TILs Granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 μg/mL Granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 μg/mL Granzyme B secretion are TILs produced by the expansion methods of the present invention, including for example FIG. 8A and/or FIG. 8B and/or FIG. 8C and/or FIG. 8D.

In some embodiments, the expansion methods of the present invention produce an expanded population of TILs that exhibits increased Granzyme B secretion in vitro including for example TILs as provided in FIG. 8A and/or FIG. 8B and/or FIG. 8C and/or FIG. 8D, as compared to non-expanded population of TILs. In some embodiments, Granzyme B secretion of the expanded population of TILs of the present invention is increased by at least one-fold to fifty-fold or more as compared to non-expanded population of TILs. In some embodiments, IFN-γ secretion is increased by at least one-fold, at least two-fold, at least three-fold, at least four-fold, at least five-fold, at least six-fold, at least seven-fold, at least eight-fold, at least nine-fold, at least ten-fold, at least twenty-fold, at least thirty-fold, at least forty-fold, at least fifty-fold or more as compared to non-expanded population of TILs. In some embodiments, Granzyme B secretion of the expanded population of TILs of the present invention is increased by at least one-fold as compared to non-expanded population of TILs. In some embodiments, Granzyme B secretion of the expanded population of TILs of the present invention is increased by at least two-fold as compared to non-expanded population of TILs. In some embodiments, Granzyme B secretion of the expanded population of TILs of the present invention is increased by at least three-fold as compared to non-expanded population of TILs. In some embodiments, Granzyme B secretion of the expanded population of TILs of the present invention is increased by at least four-fold as compared to non-expanded population of TILs. In some embodiments, Granzyme B secretion of the expanded population of TILs of the present invention is increased by at least five-fold as compared to non-expanded population of TILs. In some embodiments, Granzyme B secretion of the expanded population of TILs of the present invention is increased by at least six-fold as compared to non-expanded population of TILs. In some embodiments, Granzyme B secretion of the expanded population of TILs of the present invention is increased by at least seven-fold as compared to non-expanded population of TILs. In some embodiments, Granzyme B secretion of the expanded population of TILs of the present invention is increased by at least eight-fold as compared to non-expanded population of TILs. In some embodiments, Granzyme B secretion of the expanded population of TILs of the present invention is increased by at least nine-fold as compared to non-expanded population of TILs.

In some embodiments, Granzyme B secretion of the expanded population of TILs of the present invention is increased by at least ten-fold as compared to non-expanded population of TILs. In some embodiments, Granzyme B secretion of the expanded population of TILs of the present invention is increased by at least twenty-fold as compared to non-expanded population of TILs. In some embodiments, Granzyme B secretion of the expanded population of TILs of the present invention is increased by at least thirty-fold as compared to non-expanded population of TILs. In some embodiments, Granzyme B secretion of the expanded population of TILs of the present invention is increased by at least forty-fold as compared to non-expanded population of TILs. In some embodiments, Granzyme B secretion of the expanded population of TILs of the present invention is increased by at least fifty-fold as compared to non-expanded population of TILs.

In some embodiments, TILs capable of at least one-fold, two-fold, three-fold, four-fold, or five-fold or more lower levels of TNF-u (i.e., TNF-alpha) secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least one-fold lower levels of TNF-u secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least two-fold lower levels of TNF-u secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least three-fold lower levels of TNF-u secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least four-fold lower levels of TNF-u secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least five-fold lower levels of TNF-u secretion as compared to IFN-γ secretion are TILs produced by the expansion methods of the present invention, including, for example FIG. 8A and/or FIG. 8B and/or FIG. 8C and/or FIG. 8D methods.

In some embodiments, TILs capable of at least 200 μg/mL/5e5 cells to about 10,000 μg/mL/5e5 cells or more TNF-u (i.e., TNF-alpha) secretion are TILs produced by the expansion methods of the present invention, including, for example FIG. 8A and/or FIG. 8B and/or FIG. 8C and/or FIG. 8D methods. In some embodiments, TILs capable of at least 500 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 1000 μg/mL/5e5 cells to about 10,000 μg/mL/5e5 cells or more TNF-a secretion are TILs produced by the expansion methods of the present invention, including, for example FIG. 8A and/or FIG. 8B and/or FIG. 8C and/or FIG. 8D methods. In some embodiments, TILs capable of at least 2000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 3000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 4000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 5000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 6000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 7000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 8000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods. In some embodiments, TILs capable of at least 9000 μg/mL/5e5 cells to about 10,000 μg/mL/5e5 cells or more TNF-u secretion are TILs produced by the expansion methods of the present invention, including, for example FIG. 8A and/or FIG. 8B and/or FIG. 8C and/or FIG. 8D methods.

In some embodiments, IFN-γ and granzyme B levels are measured to determine the phenotypic characteristics of the TILs produced by the expansion methods of the present invention, including, for example FIG. 8A and/or FIG. 8B and/or FIG. 8C and/or FIG. 8D methods. In some embodiments, IFN-γ and TNF-u levels are measured to determine the phenotypic characteristics of the TILs produced by the expansion methods of the present invention, including, for example FIG. 8A and/or FIG. 8B and/or FIG. 8C and/or FIG. 8D methods. In some embodiments, granzyme B and TNF-u levels are measured to determine the phenotypic characteristics of the TILs produced by the expansion methods of the present invention, including, for example FIG. 8A and/or FIG. 8B and/or FIG. 8C and/or FIG. 8D methods. In some embodiments, IFN-γ, granzyme B and TNF-u levels are measured to determine the phenotypic characteristics of the TILs produced by the expansion methods of the present invention, including, for example FIG. 8A and/or FIG. 8B and/or FIG. 8C and/or FIG. 8D methods.

In some embodiments, the phenotypic characterization is examined after cryopreservation.

H. Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days or about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days or about 1 to 10 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, or about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days, or about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, or about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX TOOMCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 to 7 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 8 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX TOOMCS container, for a period of about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX TOOMCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX TOOMCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX TOOMCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 4 to 5 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 days.

In other embodiments, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In other embodiments, the invention provides the method described in any of the preceding paragraphs as applicable above modified such that in step (c) the culture medium is supplemented with additional exogenous APCs.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 20:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 10:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 9:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 8:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 7:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 6:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 5:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 4:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 3:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.9:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.8:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.7:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.6:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.5:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.4:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.3:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.2:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2.1:1.

In other embodiments, the invention provides the method described in any of the preceding paragraphs as applicable above modified such that the ratio of number of APCs added in the rapid second expansion to the number of APCs added in step (b) is selected from a range of from at or about 1.1:1 to at or about 2:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 10:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 5:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 4:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 3:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.9:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.8:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.7:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.6:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.5:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.4:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.3:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.2:1.

In other embodiments, the invention provides the method described in any of the preceding paragraphs as applicable above modified such that the ratio of number of APCs added in the rapid second expansion to the number of APCs added in step (b) is selected from a range of from at or about 2:1 to at or about 2.1:1.

In other embodiments, the invention provides the method described in any of the preceding paragraphs as applicable above modified such that the ratio of number of APCs added in the rapid second expansion to the number of APCs added in step (b) is at or about 2:1.

In other embodiments, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In other embodiments, the invention provides the method described in any of the preceding paragraphs as applicable above modified such that the number of APCs added in the primary first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and such that the number of APCs added in the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$APCs.

In other embodiments, the invention provides the method described in any of the preceding paragraphs as applicable above modified such that the number of APCs added in the primary first expansion is selected from the range of at or about $1\times10^8$ APCs to at or about $3.5\times10^8$ APCs, and wherein the number of APCs added in the rapid second expansion is selected from the range of at or about $3.5\times10^8$ APCs to at or about $1\times10^9$ APCs.

In other embodiments, the invention provides the method described in any of the preceding paragraphs as applicable above modified such that the number of APCs added in the primary first expansion is selected from the range of at or about $1.5\times10^8$ APCs to at or about $3\times10^8$ APCs, and wherein the number of APCs added in the rapid second expansion is selected from the range of at or about $4\times10^8$ APCs to at or about $7.5\times10^8$ APCs.

In other embodiments, the invention provides the method described in any of the preceding paragraphs as applicable above modified such that the number of APCs added in the primary first expansion is selected from the range of at or about $2\times10^8$ APCs to at or about $2.5\times10^8$ APCs, and wherein the number of APCs added in the rapid second expansion is selected from the range of at or about $4.5\times10^8$ APCs to at or about $5.5\times10^8$ APCs.

In other embodiments, the invention provides the method described in any of the preceding paragraphs as applicable above modified such that at or about $2.5\times10^8$ APCs are added to the primary first expansion and at or about $5\times10^8$ APCs are added to the rapid second expansion.

In other embodiments, the invention provides the method described in any of the preceding paragraphs as applicable above modified such that the antigen-presenting cells are peripheral blood mononuclear cells (PBMCs).

In other embodiments, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In other embodiments, the invention provides the method described in any of the preceding paragraphs as applicable above modified such that the multiple tumors are evenly distributed into the plurality of separate containers.

In other embodiments, the invention provides the method described in any of the preceding paragraphs as applicable above modified such that the plurality of separate containers comprises at least two separate containers.

In other embodiments, the invention provides the method described in any of the preceding paragraphs as applicable above modified such that the plurality of separate containers comprises from two to twenty separate containers.

In other embodiments, the invention provides the method described in any of the preceding paragraphs as applicable above modified such that the plurality of separate containers comprises from two to fifteen separate containers.

In other embodiments, the invention provides the method described in any of the preceding paragraphs as applicable above modified such that the plurality of separate containers comprises from two to ten separate containers.

In other embodiments, the invention provides the method described in any of the preceding paragraphs as applicable above modified such that the plurality of separate containers comprises from two to five separate containers.

In other embodiments, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In other embodiments, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TILs.

In other embodiments, the invention provides the method described in any of the preceding paragraphs as applicable above modified such that each of the separate containers comprises a first gas-permeable surface area.

In other embodiments, the invention provides the method described in any of the preceding paragraphs as applicable above modified such that the multiple tumor fragments are distributed in a single container.

In other embodiments, the invention provides the method described in any of the preceding paragraphs as applicable above modified such that the single container comprises a first gas-permeable surface area.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In other embodiments, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In other embodiments, the invention provides the method described in any of the preceding paragraphs as applicable above modified such that in step (b) the APCs are layered onto the first gas-permeable surface area at an average thickness of at or about 2 cell layers.

In other embodiments, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In other embodiments, the invention provides the method described in any of the preceding paragraphs as applicable above modified such that in step (c) the APCs are layered onto the first gas-permeable surface area at an average thickness of at or about 3 cell layers to at or about 10 cell layers.

In other embodiments, the invention provides the method described in any of the preceding paragraphs as applicable above modified such that in step (c) the APCs are layered onto the first gas-permeable surface area at an average thickness of at or about 4 cell layers to at or about 8 cell layers.

In other embodiments, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In other embodiments, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In other embodiments, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In other embodiments, the invention provides the method described in any of the preceding paragraphs as applicable above modified such that the second container is larger than the first container.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In other embodiments, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In other embodiments, the invention provides the method described in any of the preceding paragraphs as applicable above modified such that in step (b) the APCs are layered onto the first gas-permeable surface area at an average thickness of at or about 2 cell layers.

In other embodiments, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In other embodiments, the invention provides the method described in any of the preceding paragraphs as applicable above modified such that in step (c) the APCs are layered onto the second gas-permeable surface area at an average thickness of at or about 3 cell layers to at or about 10 cell layers.

In other embodiments, the invention provides the method described in any of the preceding paragraphs as applicable above modified such that in step (c) the APCs are layered onto the second gas-permeable surface area at an average thickness of at or about 4 cell layers to at or about 8 cell layers.

In other embodiments, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In other embodiments, the invention provides the method described in any of the preceding paragraphs as applicable modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In other embodiments, the invention provides the method described in any of the preceding paragraphs as applicable above modified such that in step (b) the priming first expansion is performed in a first container comprising a first gas-permeable surface area and in step (c) the rapid second expansion is performed in the first container.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In other embodiments, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In other embodiments, the invention provides the method described in any of the preceding paragraphs as applicable above modified such that in step (b) the APCs are layered onto the first gas-permeable surface area at an average thickness of at or about 2 cell layers.

In other embodiments, the invention provides the method described any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In other embodiments, the invention provides the method described in any of the preceding paragraphs as applicable above modified such that in step (c) the APCs are layered onto the first gas-permeable surface area at an average thickness of at or about 3 cell layers to at or about 10 cell layers.

In other embodiments, the invention provides the method described in any of the preceding paragraphs as applicable above modified such that in step (c) the APCs are layered onto the first gas-permeable surface area at an average thickness of at or about 4 cell layers to at or about 8 cell layers.

In other embodiments, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In other embodiments, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:10.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:9.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:8.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:7.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:6.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:5.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:4.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:3.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:2.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.2 to at or about 1:8.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.3 to at or about 1:7.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.4 to at or about 1:6.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.5 to at or about 1:5.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.6 to at or about 1:4.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.7 to at or about 1:3.5.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.8 to at or about 1:3.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.9 to at or about 1:2.5.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:2.

In other embodiments, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In other embodiments, the invention provides the method described in any of the preceding paragraphs as applicable above modified such that the ratio of the number of TILs in the second population of TILs to the number of TILs in the first population of TILs is at or about 1.5:1 to at or about 100:1.

In other embodiments, the invention provides the method described in any of the preceding paragraphs as applicable above modified such that the ratio of the number of TILs in the second population of TILs to the number of TILs in the first population of TILs is at or about 50:1.

In other embodiments, the invention provides the method described in any of the preceding paragraphs as applicable above modified such that the ratio of the number of TILs in the second population of TILs to the number of TILs in the first population of TILs is at or about 25:1.

In other embodiments, the invention provides the method described in any of the preceding paragraphs as applicable above modified such that the ratio of the number of TILs in the second population of TILs to the number of TILs in the first population of TILs is at or about 20:1.

In other embodiments, the invention provides the method described in any of the preceding paragraphs as applicable above modified such that the ratio of the number of TILs in the second population of TILs to the number of TILs in the first population of TILs is at or about 10:1.

In other embodiments, the invention provides the method described in any of the preceding paragraphs as applicable above modified such that the second population of TILs is at least at or about 50-fold greater in number than the first population of TILs.

In other embodiments, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TILs.

In other embodiments, the invention provides the method described in any of the preceding paragraphs as applicable above modified such that at or about 2 days or at or about 3 days after the commencement of the second period in step (c), the cell culture medium is supplemented with additional IL-2.

In other embodiments, the invention provides the method described in any of the preceding paragraphs as applicable above modified to further comprise the step of cryopreserving the harvested TIL population in step (d) using a cryopreservation process.

In other embodiments, the invention provides the method described in any of the preceding paragraphs as applicable above modified to comprise performing after step (d) the additional step of (e) transferring the harvested TIL population from step (d) to an infusion bag that optionally contains HypoThermosol.

In other embodiments, the invention provides the method described in any of the preceding paragraphs as applicable above modified to comprise the step of cryopreserving the infusion bag comprising the harvested TIL population in step (e) using a cryopreservation process.

In other embodiments, the invention provides the method described in any of the preceding paragraphs as applicable above modified such that the cryopreservation process is performed using a 1:1 ratio of harvested TIL population to cryopreservation media.

In other embodiments, the invention provides the method described in any of the preceding paragraphs as applicable above modified such that the antigen-presenting cells are peripheral blood mononuclear cells (PBMCs).

In other embodiments, the invention provides the method described in any of the preceding paragraphs as applicable above modified such that the PBMCs are irradiated and allogeneic.

In other embodiments, the invention provides the method described in any of the preceding paragraphs as applicable above modified such that the total number of APCs added to the cell culture in step (b) is $2.5\times10^8$.

In other embodiments, the invention provides the method described in any of the preceding paragraphs as applicable above modified such that the total number of APCs added to the cell culture in step (c) is $5\times10^8$.

In other embodiments, the invention provides the method described in any of the preceding paragraphs as applicable above modified such that the APCs are PBMCs.

In other embodiments, the invention provides the method described in any of the preceding paragraphs as applicable above modified such that the PBMCs are irradiated and allogeneic.

In other embodiments, the invention provides the method described in any of the preceding paragraphs as applicable above modified such that the antigen-presenting cells are artificial antigen-presenting cells.

In other embodiments, the invention provides the method described in any of the preceding paragraphs as applicable above modified such that the harvesting in step (d) is performed using a membrane-based cell processing system.

In other embodiments, the invention provides the method described in any of the preceding paragraphs as applicable above modified such that the harvesting in step (d) is performed using a LOVO cell processing system.

In other embodiments, the invention provides the method described in any of the preceding paragraphs as applicable above modified such that the multiple fragments comprise at or about 5 to at or about 60 fragments per container in step (b).

In other embodiments, the invention provides the method described in any of the preceding paragraphs as applicable above modified such that the multiple fragments comprise at or about 10 to at or about 60 fragments per container in step (b).

In other embodiments, the invention provides the method described in any of the preceding paragraphs as applicable above modified such that the multiple fragments comprise at or about 15 to at or about 60 fragments per container in step (b).

In other embodiments, the invention provides the method described in any of the preceding paragraphs as applicable above modified such that the multiple fragments comprise at or about 20 to at or about 60 fragments per container in step (b).

In other embodiments, the invention provides the method described in any of the preceding paragraphs as applicable above modified such that the multiple fragments comprise at or about 25 to at or about 60 fragments per container in step (b).

In other embodiments, the invention provides the method described in any of the preceding paragraphs as applicable above modified such that the multiple fragments comprise at or about 30 to at or about 60 fragments per container in step (b).

In other embodiments, the invention provides the method described in any of the preceding paragraphs as applicable above modified such that the multiple fragments comprise at or about 35 to at or about 60 fragments per container in step (b).

In other embodiments, the invention provides the method described in any of the preceding paragraphs as applicable above modified such that the multiple fragments comprise at or about 40 to at or about 60 fragments per container in step (b).

In other embodiments, the invention provides the method described in any of the preceding paragraphs as applicable above modified such that the multiple fragments comprise at or about 45 to at or about 60 fragments per container in step (b).

In other embodiments, the invention provides the method described in any of the preceding paragraphs as applicable above modified such that the multiple fragments comprise at or about 50 to at or about 60 fragments per container in step (b).

In other embodiments, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In other embodiments, the invention provides the method described in any of the preceding paragraphs as applicable above modified such that each fragment has a volume of at or about 27 $mm^3$.

In other embodiments, the invention provides the method described in any of the preceding paragraphs as applicable above modified such that each fragment has a volume of at or about 20 $mm^3$ to at or about 50 $mm^3$.

In other embodiments, the invention provides the method described in any of the preceding paragraphs as applicable above modified such that each fragment has a volume of at or about 21 $mm^3$ to at or about 30 $mm^3$.

In other embodiments, the invention provides the method described in any of the preceding paragraphs as applicable above modified such that each fragment has a volume of at or about 22 $mm^3$ to at or about 29.5 $mm^3$.

In other embodiments, the invention provides the method described in any of the preceding paragraphs as applicable above modified such that each fragment has a volume of at or about 23 $mm^3$ to at or about 29 $mm^3$.

In other embodiments, the invention provides the method described in any of the preceding paragraphs as applicable above modified such that each fragment has a volume of at or about 24 $mm^3$ to at or about 28.5 $mm^3$.

In other embodiments, the invention provides the method described in any of the preceding paragraphs as applicable above modified such that each fragment has a volume of at or about 25 $mm^3$ to at or about 28 $mm^3$.

In other embodiments, the invention provides the method described in any of the preceding paragraphs as applicable above modified such that each fragment has a volume of at or about 26.5 $mm^3$ to at or about 27.5 $mm^3$.

In other embodiments, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $mm^3$.

In other embodiments, the invention provides the method described in any of the preceding paragraphs as applicable above modified such that the multiple fragments comprise at or about 30 to at or about 60 fragments with a total volume of at or about 1300 $mm^3$ to at or about 1500 $mm^3$.

In other embodiments, the invention provides the method described in any of the preceding paragraphs as applicable above modified such that the multiple fragments comprise at or about 50 fragments with a total volume of at or about 1350 $mm^3$.

In other embodiments, the invention provides the method described in any of the preceding paragraphs as applicable above modified such that the multiple fragments comprise at or about 50 fragments with a total mass of at or about 1 gram to at or about 1.5 grams.

In other embodiments, the invention provides the method described in any of the preceding paragraphs as applicable above modified such that the cell culture medium is provided in a container that is a G-container or a Xuri cellbag.

In other embodiments, the invention provides the method described in any of the preceding paragraphs as applicable above modified such that the IL-2 concentration in the cell culture medium is about 10,000 IU/mL to about 5,000 IU/mL.

In other embodiments, the invention provides the method described in any of the preceding paragraphs as applicable above modified such that the IL-2 concentration in the cell culture medium is about 6,000 IU/mL.

In other embodiments, the invention provides the method described in any of the preceding paragraphs as applicable above modified such that the cryopreservation media comprises dimethlysulfoxide (DMSO).

In other embodiments, the invention provides the method described in any of the preceding paragraphs as applicable above modified such that the cryopreservation media comprises 7% to 10% DMSO.

In other embodiments, the invention provides the method described in any of the preceding paragraphs as applicable above modified such that the first period in step (b) is performed within a period of at or about 1 day, 2 days, 3 days, 4 days, 5 days, 6 days, or 7 days.

In other embodiments, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In other embodiments, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In other embodiments, the invention provides the method described in any of the preceding paragraphs as applicable above modified such that the first period in step (b) and the second period in step (c) are each individually performed within a period of at or about 5 days, 6 days, or 7 days.

In other embodiments, the invention provides the method described in any of the preceding paragraphs as applicable above modified such that the first period in step (b) and the second period in step (c) are each individually performed within a period of at or about 7 days.

In other embodiments, the invention provides the method described in any of the preceding paragraphs as applicable above modified such that steps (a) through (d) are performed in a total of at or about 14 days to at or about 18 days.

In other embodiments, the invention provides the method described in any of the preceding paragraphs as applicable above modified such that steps (a) through (d) are performed in a total of at or about 15 days to at or about 18 days.

In other embodiments, the invention provides the method described in any of the preceding paragraphs as applicable above modified such that steps (a) through (d) are performed in a total of at or about 16 days to at or about 18 days.

In other embodiments, the invention provides the method described in any of the preceding paragraphs as applicable above modified such that steps (a) through (d) are performed in a total of at or about 17 days to at or about 18 days.

In other embodiments, the invention provides the method described in any of the preceding paragraphs as applicable above modified such that steps (a) through (d) are performed in a total of at or about 14 days to at or about 17 days.

In other embodiments, the invention provides the method described in any of the preceding paragraphs as applicable above modified such that steps (a) through (d) are performed in a total of at or about 15 days to at or about 17 days.

In other embodiments, the invention provides the method described in any of the preceding paragraphs as applicable above modified such that steps (a) through (d) are performed in a total of at or about 16 days to at or about 17 days.

In other embodiments, the invention provides the method described in any of the preceding paragraphs as applicable above modified such that steps (a) through (d) are performed in a total of at or about 14 days to at or about 16 days.

In other embodiments, the invention provides the method described in any of the preceding paragraphs as applicable above modified such that steps (a) through (d) are performed in a total of at or about 15 days to at or about 16 days.

In other embodiments, the invention provides the method described in any of the preceding paragraphs as applicable above modified such that steps (a) through (d) are performed in a total of at or about 14 days.

In other embodiments, the invention provides the method described in any of the preceding paragraphs as applicable above modified such that steps (a) through (d) are performed in a total of at or about 15 days.

In other embodiments, the invention provides the method described in any of the preceding paragraphs as applicable above modified such that steps (a) through (d) are performed in a total of at or about 16 days.

In other embodiments, the invention provides the method described in any of the preceding paragraphs as applicable above modified such that steps (a) through (d) are performed in a total of at or about 17 days.

In other embodiments, the invention provides the method described in any of the preceding paragraphs as applicable above modified such that steps (a) through (d) are performed in a total of at or about 18 days.

In other embodiments, the invention provides the method described in any of the preceding paragraphs as applicable above modified such that steps (a) through (d) are performed in a total of at or about 14 days or less.

In other embodiments, the invention provides the method described in any of the preceding paragraphs as applicable above modified such that steps (a) through (d) are performed in a total of at or about 15 days or less.

In other embodiments, the invention provides the method described in any of the preceding paragraphs as applicable above modified such that steps (a) through (d) are performed in a total of at or about 16 days or less.

In other embodiments, the invention provides the method described in any of the preceding paragraphs as applicable above modified such that steps (a) through (d) are performed in a total of at or about 18 days or less.

In other embodiments, the invention provides the method described in any of the preceding paragraphs as applicable above modified such that the therapeutic population of TILs harvested in step (d) comprises sufficient TILs for a therapeutically effective dosage of the TILs.

In other embodiments, the invention provides the method described in any of the preceding paragraphs as applicable above modified such that the number of TILs sufficient for a therapeutically effective dosage is from at or about $2.3\times10^{10}$ to at or about $13.7\times10^{10}$.

In other embodiments, the invention provides the method described in any of the preceding paragraphs as applicable above modified such that the third population of TILs in step (c) provides for increased efficacy, increased interferon-gamma production, and/or increased polyclonality.

In other embodiments, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In other embodiments, the invention provides the method described in any of the preceding paragraphs as applicable above modified such that the third population of TILs in step (c) provides for at least a one-fold to five-fold or more interferon-gamma production as compared to TILs prepared by a process longer than 17 days.

In other embodiments, the invention provides the method described in any of the preceding paragraphs as applicable above modified such that the third population of TILs in step (c) provides for at least a one-fold to five-fold or more interferon-gamma production as compared to TILs prepared by a process longer than 18 days.

In other embodiments, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In other embodiments, the invention provides the method described in any of the preceding paragraphs as applicable above modified such that each container recited in the method is a closed container.

In other embodiments, the invention provides the method described in any of the preceding paragraphs as applicable above modified such that each container recited in the method is a G-container.

In other embodiments, the invention provides the method described in any of the preceding paragraphs as applicable above modified such that each container recited in the method is a GREX-10.

In other embodiments, the invention provides the method described in any of the preceding paragraphs as applicable above modified such that each container recited in the method is a GREX-100.

In other embodiments, the invention provides the method described in any of the preceding paragraphs as applicable above modified such that each container recited in the method is a GREX-500.

In other embodiments, the invention provides the therapeutic population of tumor infiltrating lymphocytes (TILs) made by the method described in any of the preceding paragraphs as applicable above.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 17 days.

In other embodiments, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 18 days.

In other embodiments, the invention provides for the therapeutic population of TILs described in any of the preceding paragraphs as applicable above that provides for increased interferon-gamma production.

In other embodiments, the invention provides for the therapeutic population of TILs described in any of the preceding paragraphs as applicable above that provides for increased polyclonality.

In other embodiments, the invention provides for the therapeutic population of TILs described in any of the preceding paragraphs as applicable above that provides for increased efficacy.

In other embodiments, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days. In other embodiments, the invention provides for the therapeutic population of TILs described in any of the preceding paragraphs as applicable above modified such that the therapeutic population of TILs is capable of at least one-fold more interferon-gamma production as compared to TILs prepared by a process longer than 17 days. In other embodiments, the invention provides for the therapeutic population of TILs described in any of the preceding paragraphs as applicable above modified such that the therapeutic population of TILs is capable of at least one-fold more interferon-gamma production as compared to TILs prepared by a process longer than 18 days. In other embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days. In other embodiments, the invention provides for the therapeutic population of TILs described in any of the preceding paragraphs as applicable above modified such that the therapeutic population of TILs is capable of at least two-fold more interferon-gamma production as compared to TILs prepared by a process longer than 17 days. In other embodiments, the invention provides for the therapeutic population of TILs described in any of the preceding paragraphs as applicable above modified such that the therapeutic population of TILs is capable of at least two-fold more interferon-gamma production as compared to TILs prepared by a process longer than 18 days. In other embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days. In other embodiments, the invention provides for the therapeutic population of TILs described in any of the preceding paragraphs as applicable above modified such that the therapeutic population of TILs is capable of at least three-fold more interferon-gamma production as compared to TILs prepared by a process longer than 17 days. In other embodiments, the invention provides for the therapeutic population of TILs described in any of the preceding paragraphs as applicable above modified such that the therapeutic population of TILs is capable of at least three-fold more interferon-gamma production as compared to TILs prepared by a process longer than 18 days. In other embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs). In other embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of tumor infiltrating lymphocytes (TILs) that is capable of at least one-fold more interferon-gamma production as compared to TILs prepared by a process in which the first expansion of TILs is performed without any added OKT3. In other embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of TILs that is capable of at least two-fold more interferon-gamma production as compared to TILs prepared by a process in which the first expansion of TILs is performed without any added APCs. In other embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of TILs that is capable of at least two-fold more interferon-gamma production as compared to TILs prepared by a process in which the first expansion of TILs is performed without any added OKT3. In other embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of TILs that is capable of at least three-fold more interferon-gamma production as compared to TILs prepared by a process in which the first expansion of TILs is performed without any added APCs. In other embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides for a therapeutic population of TILs that is capable of at least three-fold more interferon-gamma production as compared to TILs prepared by a process in which the first expansion of TILs is performed without any added OKT3. In other embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8A and/or FIG. 8B and/or FIG. 8C and/or FIG. 8D).

In other embodiments, the invention provides the method described in any of the preceding paragraphs as applicable above modified such that the tumor fragments are small biopsies (including, for example, a punch biopsy), core biopsies, core needle biopsies or fine needle aspirates.

In other embodiments, the invention provides the method described in any of the preceding paragraphs as applicable above modified such that the tumor fragments are core biopsies.

In other embodiments, the invention provides the method described in any of the preceding paragraphs as applicable above modified such that the tumor fragments are fine needle aspirates.

In other embodiments, the invention provides the method described in any of the preceding paragraphs as applicable above modified such that the tumor fragments are small biopsies (including, for example, a punch biopsy).

In other embodiments, the invention provides the method described in any of the preceding paragraphs as applicable above modified such that the tumor fragments are core needle biopsies.

In other embodiments, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion for a period of about 11 days. In some of the foregoing embodiments, the steps of the method are completed in about 22 days.

In other embodiments, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion by culturing the culture of the second population of TILs for about 5 days, splitting the culture into up to 5 subcultures and culturing the subcultures for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In other embodiments, the invention provides the method described in any of the preceding paragraphs as applicable above modified such that the first population of TILs is obtained from 1 to about 20 small biopsies (including, for example, a punch biopsy), core biopsies, core needle biopsies or fine needle aspirates of tumor tissue from the subject.

In other embodiments, the invention provides the method described in any of the preceding paragraphs as applicable above modified such that the first population of TILs is obtained from 1 to about 10 small biopsies (including, for example, a punch biopsy), core biopsies, core needle biopsies or fine needle aspirates of tumor tissue from the subject.

In other embodiments, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the subject.

In other embodiments, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy), core biopsies, core needle biopsies or fine needle aspirates of tumor tissue from the subject.

In other embodiments, the invention provides the method described in any of the preceding paragraphs as applicable above modified such that the first population of TILs is obtained from 1 to about 20 core biopsies of tumor tissue from the subject.

In other embodiments, the invention provides the method described in any of the preceding paragraphs as applicable above modified such that the first population of TILs is obtained from 1 to about 10 core biopsies of tumor tissue from the subject.

In other embodiments, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core biopsies of tumor tissue from the subject.

In other embodiments, the invention provides the method described in any of the preceding paragraphs as applicable above modified such that the first population of TILs is obtained from 1, 2, 3, 4, 5, 6, 7, 8, 9 or 10 core biopsies of tumor tissue from the subject.

In other embodiments, the invention provides the method described in any of the preceding paragraphs as applicable above modified such that the first population of TILs is obtained from 1 to about 20 fine needle aspirates of tumor tissue from the subject.

In other embodiments, the invention provides the method described in any of the preceding paragraphs as applicable above modified such that the first population of TILs is obtained from 1 to about 10 fine needle aspirates of tumor tissue from the subject.

In other embodiments, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 fine needle aspirates of tumor tissue from the subject.

In other embodiments, the invention provides the method described in any of the preceding paragraphs as applicable above modified such that the first population of TILs is obtained from 1, 2, 3, 4, 5, 6, 7, 8, 9 or 10 fine needle aspirates of tumor tissue from the subject.

In other embodiments, the invention provides the method described in any of the preceding paragraphs as applicable above modified such that the first population of TILs is obtained from 1 to about 20 core needle biopsies of tumor tissue from the subject.

In other embodiments, the invention provides the method described in any of the preceding paragraphs as applicable above modified such that the first population of TILs is obtained from 1 to about 10 core needle biopsies of tumor tissue from the subject.

In other embodiments, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core needle biopsies of tumor tissue from the subject.

In other embodiments, the invention provides the method described in any of the preceding paragraphs as applicable above modified such that the first population of TILs is obtained from 1, 2, 3, 4, 5, 6, 7, 8, 9 or 10 core needle biopsies of tumor tissue from the subject.

In other embodiments, the invention provides the method described in any of the preceding paragraphs as applicable above modified such that the first population of TILs is obtained from 1 to about 20 small biopsies (including, for example, a punch biopsy) of tumor tissue from the subject.

In other embodiments, the invention provides the method described in any of the preceding paragraphs as applicable above modified such that the first population of TILs is obtained from 1 to about 10 small biopsies (including, for example, a punch biopsy) of tumor tissue from the subject.

In other embodiments, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the subject.

In other embodiments, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy) of tumor tissue from the subject.

In some embodiments, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion step by culturing the second population of TILs in a culture medium comprising IL-2, OKT-3 and APCs for a period of about 11 days. In some of the foregoing embodiments, the steps of the method are completed in about 22 days.

In some embodiments, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion by culturing the culture of the second population of TILs in a culture medium comprising IL-2, OKT-3 and APCs for about 5 days, splitting the culture into up to 5 subcultures and culturing each of the subcultures in a culture medium comprising IL-2 for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In some embodiments, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising 6000 IU IL-2/mL in 0.5 L of CM1 culture medium in a G-REX 100 M flask for a period of about 3 days prior to performing the step of the priming first expansion, (iii) the method comprises performing the priming first expansion by adding 0.5 L of CM1 culture medium containing 6000 IU/mL IL-2, 30 ng/mL OKT-3, and about 108 feeder cells and culturing for a period of about 8 days, and (iv) the method comprises performing the rapid second expansion by (a) transferring the second population of TILs to a G-REX 500MCS flask containing 5 L of CM2 culture medium with 3000 IU/mL IL-2, 30 ng/mL OKT-3, and $5\times10^9$ feeder cells and culturing for about 5 days (b) splitting the culture into up to 5 subcultures by transferring $10^9$ TILs into each of up to 5 G-REX 500MCS flasks containing 5 L of AIM-V medium with 3000 IU/mL IL-2, and culturing the subcultures for about 6 days. In some of the foregoing embodiments, the steps of the method are completed in about 22 days.

In some embodiments, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In some embodiments, the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 3 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing the first population of T cells in a first small scale culture in a first container, e.g., a G-REX TOOMCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing the first population of T cells in a small scale culture in a first container, e.g., a G-REX TOOMCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing the first population of T cells in a small scale culture in a first container, e.g., a G-REX TOOMCS container, for a period of about 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In some embodiments, the invention provides the method described in any of the preceding paragraphs as applicable above modified such that the step of rapid second expansion is split into a plurality of steps to achieve a scaling up of the culture by: (a) performing the rapid second expansion by culturing the first population of T cells in a small scale culture in a first container, e.g., a G-REX TOOMCS container, for a period of about 2 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 5 to 7 days.

In some embodiments, the invention provides the method described in any of the preceding paragraphs as applicable above modified such that the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 2 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 5 to 7 days.

In some embodiments, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX TOOMCS container, for a period of about 2 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 5 to 7 days.

In some embodiments, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 to 6 days.

In some embodiments, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In some embodiments, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX TOOMCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 6 days.

In some embodiments, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX TOOMCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 7 days.

In some embodiments, the invention provides the method described in any of the preceding paragraphs as applicable above modified such that the priming first expansion of step (a) is performed during a period of up to 7 days.

In some embodiments, the invention provides the method described in any of the preceding paragraphs as applicable above modified such that the rapid second expansion of step (b) is performed during a period of up to 8 days.

In some embodiments, the invention provides the method described in any of the preceding paragraphs as applicable above modified such that the rapid second expansion of step (b) is performed during a period of up to 9 days.

In some embodiments, the invention provides the method described in any of the preceding paragraphs as applicable above modified such that the rapid second expansion of step (b) is performed during a period of up to 10 days.

In some embodiments, the invention provides the method described in any of the preceding paragraphs as applicable above modified such that the rapid second expansion of step (b) is performed during a period of up to 11 days.

In some embodiments, the invention provides the method described in any of the preceding paragraphs as applicable above modified such that the priming first expansion in step (a) is performed during a period of 7 days and the rapid second expansion of step (b) is performed during a period of up to 9 days.

In some embodiments, the invention provides the method described in any of the preceding paragraphs as applicable above modified such that the priming first expansion in step (a) is performed during a period of 7 days and the rapid second expansion of step (b) is performed during a period of up to 10 days.

In some embodiments, the invention provides the method described in any of the preceding paragraphs as applicable above modified such that the priming first expansion in step (a) is performed during a period of 7 days or 8 days and the rapid second expansion of step (b) is performed during a period of up to 9 days.

In some embodiments, the invention provides the method described in any of the preceding paragraphs as applicable above modified such that the priming first expansion in step (a) is performed during a period of 7 days or 8 days and the rapid second expansion of step (b) is performed during a period of up to 10 days.

In some embodiments, the invention provides the method described in any of the preceding paragraphs as applicable above modified such that the priming first expansion in step (a) is performed during a period of 8 days and the rapid second expansion of step (b) is performed during a period of up to 9 days.

In some embodiments, the invention provides the method described in any of the preceding paragraphs as applicable above modified such that the priming first expansion in step (a) is performed during a period of 8 days and the rapid second expansion of step (b) is performed during a period of up to 8 days.

In some embodiments, the invention provides the method described in any of the preceding paragraphs as applicable above modified such that in step (a) the first population of T cells is cultured in a first culture medium comprising OKT-3 and IL-2.

In some embodiments, the invention provides the method described in any of the preceding paragraphs as applicable above modified such that the first culture medium comprises 4-1BB agonist, OKT-3 and IL-2.

In some embodiments, the invention provides the method described in any of the preceding paragraphs as applicable above modified such that the first culture medium comprises OKT-3, IL-2 and antigen-presenting cells (APCs).

In some embodiments, the invention provides the method described in any of the preceding paragraphs as applicable above modified such that the first culture medium comprises 4-1BB agonist, OKT-3, IL-2 and antigen-presenting cells (APCs).

In some embodiments, the invention provides the method described in any of the preceding paragraphs as applicable above modified such that in step (b) the first population of T cells is cultured in a second culture medium comprising OKT-3, IL-2 and antigen-presenting cells (APCs).

In some embodiments, the invention provides the method described in any of the preceding paragraphs as applicable above modified such that the second culture medium comprises 4-1BB agonist, OKT-3, IL-2 and antigen-presenting cells (APCs).

In some embodiments, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In some embodiments, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In some embodiments, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In some embodiments, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In some embodiments, the invention provides the method described in any of the preceding paragraphs as applicable above modified such that the ratio of the number of APCs in the second population of APCs to the number of APCs in the first population of APCs is about 2:1.

In some embodiments, the invention provides the method described in any of the preceding paragraphs as applicable above modified such that the number of APCs in the first population of APCs is about $2.5\times10^8$ and the number of APCs in the second population of APCs is about $5\times10^8$.

In some embodiments, the invention provides the method described in any of the preceding paragraphs as applicable above modified such that in step (a) the first population of APCs is layered onto the first gas-permeable surface at an average thickness of 2 layers of APCs.

In some embodiments, the invention provides the method described in any of the preceding paragraphs as applicable above modified such that in step (b) the second population of APCs is layered onto the first gas-permeable surface at an average thickness selected from the range of 4 to 8 layers of APCs.

In some embodiments, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In some embodiments, the invention provides the method described in any of the preceding paragraphs as applicable above modified such that in step (a) the first population of APCs is seeded on the first gas permeable surface at a density selected from the range of at or about 1. Ox $10^6$ APCs/cm$^2$ to at or about $4.5\times10^6$ APCs/cm$^2$.

In some embodiments, the invention provides the method described in any of the preceding paragraphs as applicable above modified such that in step (a) the first population of APCs is seeded on the first gas permeable surface at a density selected from the range of at or about $1.5\times10^6$ APCs/cm$^2$ to at or about $3.5\times10^6$ APCs/cm$^2$.

In some embodiments, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$.

In some embodiments, the invention provides the method described in any of the preceding paragraphs as applicable above modified such that in step (a) the first population of APCs is seeded on the first gas permeable surface at a density of at or about $2.0\times10^6$ APCs/cm$^2$.

In some embodiments, the invention provides the method described in any of the preceding paragraphs as applicable above modified such that in step (b) the second population of APCs is seeded on the first gas permeable surface at a density selected from the range of at or about $2.5\times10^6$ APCs/cm$^2$ to at or about $7.5\times10^6$ APCs/cm$^2$.

In some embodiments, the invention provides the method described in any of the preceding paragraphs as applicable above modified such that in step (b) the second population of APCs is seeded on the first gas permeable surface at a density selected from the range of at or about $3.5\times10^6$ APCs/cm$^2$ to at or about $6.0\times10^6$ APCs/cm$^2$.

In some embodiments, the invention provides the method described in any of the preceding paragraphs as applicable above modified such that in step (b) the second population of APCs is seeded on the first gas permeable surface at a density selected from the range of at or about $4.0\times10^6$ APCs/cm$^2$ to at or about $5.5\times10^6$ APCs/cm$^2$.

In some embodiments, the invention provides the method described in any of the preceding paragraphs as applicable above modified such that in step (b) the second population of APCs is seeded on the first gas permeable surface at a density of at or about $4.0\times10^6$ APCs/cm$^2$.

In some embodiments, the invention provides the method described in any of the preceding paragraphs as applicable above modified such that in step (a) the first population of APCs is seeded on the first gas permeable surface at a density selected from the range of at or about 1. Ox $10^6$ APCs/cm$^2$ to at or about $4.5\times10^6$ APCs/cm$^2$ and in step (b) the second population of APCs is seeded on the first gas permeable surface at a density selected from the range of at or about $2.5\times10^6$ APCs/cm$^2$ to at or about 7.5x106 APCs/cm$^2$.

In some embodiments, the invention provides the method described in any of the preceding paragraphs as applicable modified such that in step (a) the first population of APCs is seeded on the first gas permeable surface at a density selected from the range of at or about $1.5\times10^6$ APCs/cm$^2$ to at or about $3.5\times10^6$ APCs/cm$^2$ and in step (b) the second population of APCs is seeded on the first gas permeable surface at a density selected from the range of at or about $3.5\times10^6$ APCs/cm$^2$ to at or about $6.0\times10^6$ APCs/cm$^2$.

In some embodiments, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$ and in step (b) the second population of APCs is seeded on the first gas permeable surface at a density selected from the range of at or about $4.0\times10^6$ APCs/cm$^2$ to at or about $5.5\times10^6$ APCs/cm$^2$.

In some embodiments, the invention provides the method described in any of the preceding paragraphs as applicable above modified such that in step (a) the first population of APCs is seeded on the first gas permeable surface at a density of at or about 2.Ox $10^6$ APCs/cm$^2$ and in step (b) the second population of APCs is seeded on the first gas permeable surface at a density of at or about $4.0\times10^6$ APCs/cm$^2$.

In some embodiments, the invention provides the method described in any of the preceding paragraphs as applicable above modified such that the APCs are peripheral blood mononuclear cells (PBMCs).

In some embodiments, the invention provides the method described in any of the preceding paragraphs as applicable above modified such that the PBMCs are irradiated and exogenous to the donor of the first population of T cells.

In some embodiments, the invention provides the method described in any of the preceding paragraphs as applicable above modified such that the T cells are tumor infiltrating lymphocytes (TILs).

In some embodiments, the invention provides the method described in any of the preceding paragraphs as applicable above modified such that the T cells are marrow infiltrating lymphocytes (MILs).

In some embodiments, the invention provides the method described in any of the preceding paragraphs as applicable above modified such that the T cells are peripheral blood lymphocytes (PBLs).

In some embodiments, the invention provides the method described in any of the preceding paragraphs as applicable above modified such that the first population of T cells is obtained by separation from the whole blood of the donor.

In some embodiments, the invention provides the method described in any of the preceding paragraphs as applicable above modified such that the first population of T cells is obtained by separation from the apheresis product of the donor.

In some embodiments, the invention provides the method described in any of the preceding paragraphs as applicable above modified such that the first population of T cells is separated from the whole blood or apheresis product of the donor by positive or negative selection of a T cell phenotype.

In some embodiments, the invention provides the method described in any of the preceding paragraphs as applicable above modified such that the T cell phenotype is CD3+ and CD45+.

In some embodiments, the invention provides the method described in any of the preceding paragraphs as applicable above modified such that before performing the priming first expansion of the first population of T cells the T cells are separated from NK cells. In some embodiments, the T cells are separated from NK cells in the first population of T cells by removal of CD3-CD56+cells from the first population of T cells. In some embodiments, the CD3-CD56+cells are removed from the first population of T cells by subjecting the first population of T cells to cell sorting using a gating strategy that removes the CD3-CD56+cell fraction and recovers the negative fraction. In some embodiments, the foregoing method is utilized for the expansion of T cells in a first population of T cells characterized by a high percentage of NK cells. In some embodiments, the foregoing method is utilized for the expansion of T cells in a first population of T cells characterized by a high percentage of CD3-CD56+cells. In some embodiments, the foregoing method is utilized for the expansion of T cells in tumor tissue characterized by the present of a high number of NK cells. In some embodiments, the foregoing method is utilized for the expansion of T cells in tumor tissue characterized by a high number of CD3-CD56+cells. In some embodiments, the foregoing method is utilized for the expansion of T cells in tumor tissue obtained from a patient suffering from a tumor characterized by the presence of a high number of NK cells. In some embodiments, the foregoing method is utilized for the expansion of T cells in tumor tissue obtained from a patient suffering from a tumor characterized by the presence of a high number of CD3-CD56+cells. In some embodiments, the foregoing method is utilized for the expansion of T cells in tumor tissue obtained from a patient suffering from ovarian cancer.

In some embodiments, the invention provides the method described in any of the preceding paragraphs as applicable above modified such that at or about $1\times10^7$ T cells from the first population of T cells are seeded in a container to initiate the primary first expansion culture in such container.

In some embodiments, the invention provides the method described in any of the preceding paragraphs as applicable above modified such that the first population of T cells is distributed into a plurality of containers, and in each container at or about $1\times10^7$ T cells from the first population of T cells are seeded to initiate the primary first expansion culture in such container.

In some embodiments, the invention provides the method described in any of the preceding paragraphs as applicable above modified such that the second population of T cells harvested in step (c) is a therapeutic population of TILs.

In some embodiments, the invention provides the method described in any of the preceding paragraphs as applicable above modified such that the first population of T cells is obtained from one or more small biopsies (including, for example, a punch biopsy), core biopsies, core needle biopsies or fine needle aspirates of tumor tissue from the donor.

In some embodiments, the invention provides the method described in any of the preceding paragraphs as applicable above modified such that the first population of T cells is obtained from 1 to 20 small biopsies (including, for example, a punch biopsy), core biopsies, core needle biopsies or fine needle aspirates of tumor tissue from the donor.

In some embodiments, the invention provides the method described in any of the preceding paragraphs as applicable above modified such that the first population of T cells is obtained from 1 to 10 small biopsies (including, for example, a punch biopsy), core biopsies, core needle biopsies or fine needle aspirates of tumor tissue from the donor.

In some embodiments, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the donor.

In some embodiments, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy), core biopsies, core needle biopsies or fine needle aspirates of tumor tissue from the donor.

In some embodiments, the invention provides the method described in any of the preceding paragraphs as applicable above modified such that the first population of T cells is obtained from one or more core biopsies of tumor tissue from the donor.

In some embodiments, the invention provides the method described in any of the preceding paragraphs as applicable above modified such that the first population of T cells is obtained from 1 to 20 core biopsies of tumor tissue from the donor.

In some embodiments, the invention provides the method described in any of the preceding paragraphs as applicable above modified such that the first population of T cells is obtained from 1 to 10 core biopsies of tumor tissue from the donor.

In some embodiments, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core biopsies of tumor tissue from the donor.

In some embodiments, the invention provides the method described in any of the preceding paragraphs as applicable above modified such that the first population of T cells is obtained from 1, 2, 3, 4, 5, 6, 7, 8, 9, or 10 core biopsies of tumor tissue from the donor.

In some embodiments, the invention provides the method described in any of the preceding paragraphs as applicable above modified such that the first population of T cells is obtained from one or more fine needle aspirates of tumor tissue from the donor.

In some embodiments, the invention provides the method described in any of the preceding paragraphs as applicable above modified such that the first population of T cells is obtained from 1 to 20 fine needle aspirates of tumor tissue from the donor.

In some embodiments, the invention provides the method described in any of the preceding paragraphs as applicable above modified such that the first population of T cells is obtained from 1 to 10 fine needle aspirates of tumor tissue from the donor.

In some embodiments, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 fine needle aspirates of tumor tissue from the donor.

In some embodiments, the invention provides the method described in any of the preceding paragraphs as applicable above modified such that the first population of T cells is obtained from 1, 2, 3, 4, 5, 6, 7, 8, 9, or 10 fine needle aspirates of tumor tissue from the donor.

In some embodiments, the invention provides the method described in any of the preceding paragraphs as applicable above modified such that the first population of T cells is obtained from one or more small biopsies (including, for example, a punch biopsy) of tumor tissue from the donor.

In some embodiments, the invention provides the method described in any of the preceding paragraphs as applicable above modified such that the first population of T cells is obtained from 1 to 20 small biopsies (including, for example, a punch biopsy) of tumor tissue from the donor.

In some embodiments, the invention provides the method described in any of the preceding paragraphs as applicable above modified such that the first population of T cells is obtained from 1 to 10 small biopsies (including, for example, a punch biopsy) of tumor tissue from the donor.

In some embodiments, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the donor.

In some embodiments, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy) of tumor tissue from the donor.

In some embodiments, the invention provides the method described in any of the preceding paragraphs as applicable above modified such that the first population of T cells is obtained from one or more core needle biopsies of tumor tissue from the donor.

In some embodiments, the invention provides the method described in any of the preceding paragraphs as applicable above modified such that the first population of T cells is obtained from 1 to 20 core needle biopsies of tumor tissue from the donor.

In some embodiments, the invention provides the method described in any of the preceding paragraphs as applicable above modified such that the first population of T cells is obtained from 1 to 10 core needle biopsies of tumor tissue from the donor.

In some embodiments, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core needle biopsies of tumor tissue from the donor.

In some embodiments, the invention provides the method described in any of the preceding paragraphs as applicable above modified such that the first population of T cells is obtained from 1, 2, 3, 4, 5, 6, 7, 8, 9, or 10 core needle biopsies of tumor tissue from the donor.

In some embodiments, the invention provides a method for expanding tumor infiltrating lymphocytes (TILs) into a therapeutic population of TILs comprising: i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 7 or 8 days to obtain the second population of TILs, wherein the second population of TILs is greater in number than the first population of TILs; (iii) performing a rapid second expansion by supplementing the second cell culture medium of the second population of TILs with additional IL-2, OKT-3, and APCs, to produce a third population of TILs, wherein the number of APCs added in the rapid second expansion is at least twice the number of APCs added in step (ii), wherein the rapid second expansion is performed for a second period of about 11 days to obtain the third population of TILs, wherein the third population of TILs is a therapeutic population of TILs, wherein the rapid second expansion is performed in a container comprising a second gas-permeable surface area; (iv) harvesting the therapeutic population of TILs obtained from step (iii); and (v) transferring the harvested TIL population from step (iv) to an infusion bag.

In some embodiments, the invention provides a method for expanding tumor infiltrating lymphocytes (TILs) into a therapeutic population of TILs comprising: (i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed for first period of about 7 or 8 days to obtain the second population of TILs, wherein the second population of TILs is greater in number than the first population of TILs; (iii) performing a rapid second expansion by contacting the second population of TILs with a third cell culture medium comprising IL-2, OKT-3, and APCs, to produce a third population of TILs, wherein the rapid second expansion is performed for a second period of about 11 days to obtain the third population of TILs, wherein the third population of TILs is a therapeutic population of TILs; and (iv) harvesting the therapeutic population of TILs obtained from step (iii).

In some embodiments, the invention provides the method described in any of the preceding paragraphs as applicable above modified such that after day 5 of the second period the culture is split into 2 or more subcultures, and each subculture is supplemented with an additional quantity of the third culture medium and cultured for about 6 days.

In some embodiments, the invention provides the method described in any of the preceding paragraphs as applicable above modified such that after day 5 of the second period the culture is split into 2 or more subcultures, and each subculture is supplemented with a fourth culture medium comprising IL-2 and cultured for about 6 days.

In some embodiments, the invention provides the method described in any of the preceding paragraphs as applicable above modified such that after day 5 of the second period the culture is split into up to 5 subcultures.

In some embodiments, the invention provides the method described in any of the preceding paragraphs as applicable above modified such that all steps in the method are completed in about 24 days. In some embodiments, the invention provides the method described in any of the preceding paragraphs as applicable above modified such that all steps in the method are completed in about 22 days.

In some embodiments, the invention provides a method of expanding T cells comprising: (i) performing a priming first expansion of a first population of T cells from a tumor sample obtained from one or more small biopsies, core biopsies, or needle biopsies of a tumor in a donor by culturing the first population of T cells to effect growth and to prime an activation of the first population of T cells; (ii) after the activation of the first population of T cells primed in step (a) begins to decay, performing a rapid second expansion of the first population of T cells by culturing the first population of T cells to effect growth and to boost the activation of the first population of T cells to obtain a second population of T cells; and (iv) harvesting the second population of T cells. In some embodiments, the tumor sample is obtained from a plurality of core biopsies. In some embodiments, the plurality of core biopsies is selected from the group consisting of 2, 3, 4, 5, 6, 7, 8, 9 and 10 core biopsies.

In some embodiments, the invention the method described in any of the preceding paragraphs as applicable above modified such that T cells or TILs are obtained from tumor digests. In some embodiments, tumor digests are generated by incubating the tumor in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). In some embodiments, the tumor is placed in a tumor dissociating enzyme mixture including one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof. In other embodiments, the tumor is placed in a tumor dissociating enzyme mixture including collagenase (including any blend or type of collagenase), neutral protease (dispase) and deoxyribonuclease I (DNase).

VI. Pharmaceutical Compositions, Dosages, and Dosing Regimens

In some embodiments, TILs, MILs, or PBLs expanded and/or genetically modified (including TILs, MILs, or PBLs genetically-modified to express a CCR) using the methods of the present disclosure are administered to a patient as a pharmaceutical composition. In some embodiments, the pharmaceutical composition is a suspension of TILs in a sterile buffer.

TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration. [001326]Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is NSCLC or melanoma. In some embodiments, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered.

In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$to $5\times10^{12}$, and $5\times10^{12}$to $1\times10^{13}$ In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.00010% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.10% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, 9×107, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^{6}$ to $5\times10^{6}$, $5\times10^{6}$ to $1\times10^{7}$, 1×107 to $5\times10^{7}$, $5\times10^{7}$ to $1\times10^{8}$, 1×108 to $5\times10^{8}$, $5\times10^{8}$ to Ix $10^{9}$, 1×109 to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$to $5\times10^{12}$, and $5\times10^{12}$to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

In some embodiments, the invention provides an infusion bag comprising the therapeutic population of TILs described in any of the preceding paragraphs above.

In some embodiments, the invention provides a tumor infiltrating lymphocyte (TIL) composition comprising the therapeutic population of TILs described in any of the preceding paragraphs above and a pharmaceutically acceptable carrier.

In some embodiments, the invention provides an infusion bag comprising the TIL composition described in any of the preceding paragraphs above.

In some embodiments, the invention provides a cryopreserved preparation of the therapeutic population of TILs described in any of the preceding paragraphs above.

In some embodiments, the invention provides a tumor infiltrating lymphocyte (TIL) composition comprising the therapeutic population of TILs described in any of the preceding paragraphs above and a cryopreservation media.

In some embodiments, the invention provides the TIL composition described in any of the preceding paragraphs above modified such that the cryopreservation media contains DMSO.

In some embodiments, the invention provides the TIL composition described in any of the preceding paragraphs above modified such that the cryopreservation media contains 7-10% DMSO.

In some embodiments, the invention provides a cryopreserved preparation of the TIL composition described in any of the preceding paragraphs above.

In some embodiments, TILs expanded using the methods of the present disclosure are administered to a patient as a pharmaceutical composition. In some embodiments, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is NSCLC. In some embodiments, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, therapeutically effective dosage is about $2.3\times10^{10}$to about $13.7\times10^{10}$. In some embodiments, therapeutically effective dosage is about $7.8\times10^{10}$ TILs, particularly of the cancer is NSCLC. In some embodiments, therapeutically effective dosage is about $1.2\times10^{10}$to about $4.3\times10^{10}$ of TILs. In some embodiments, therapeutically effective dosage is about $3\times10^{10}$ to about $12\times10^{10}$ TILs.

In some embodiments, therapeutically effective dosage is about $4\times10^{10}$ to about $10\times10^{10}$ TILs. In some embodiments, therapeutically effective dosage is about $5\times10^{10}$ to about $8\times10^{10}$ TILs. In some embodiments, therapeutically effective dosage is about $6\times10^{10}$ to about $8\times10^{10}$ TILs. In some embodiments, therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$to $5\times10^{12}$, and $5\times10^{12}$to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.0010% to about 10%, about 0.010% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, 1×107 to $5\times10^7$, $5\times10^7$ to $1\times10^8$, 1×108 to $5\times10^8$, $5\times10^8$ to $1\times10^9$, 1×109 to $5\times10^9$, 5×109 to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$to $5\times10^{12}$, and $5\times10^{12}$to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

VII. Methods of Treating Patients

Methods of treatment begin with the initial TIL collection and culture of TILs. Such methods have been both described in the art by, for example, Jin et al., *J. Immunotherapy,* 2012, 35(3):283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 1 and/or FIG. 8) find particular use in the treatment of patients with cancer (for example, as described in Goff, et al., *J Clinical Oncol-*

*ogy,* 2016, 34(20):2389-239, as well as the supplemental content; incorporated by reference herein in its entirety. In some embodiments, TIL were grown from resected deposits of metastatic melanoma as previously described (see, Dudley, et al., *J Immunother.,* 2003, 26:332-342; incorporated by reference herein in its entirety). Fresh tumor can be dissected under sterile conditions. A representative sample can be collected for formal pathologic analysis. Single fragments of 2 $mm^3$ to 3 $mm^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 μg/mL and twice background. (Goff, et al., *J Immunother.,* 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 1 and/or FIG. 8), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 1 and/or FIG. 8), are selected for an additional second expansion according to Step D of FIG. 1 and/or FIG. 8.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 μg/mL and greater than 4 3 baseline levels.

In some embodiments, the TILs produced by the methods provided herein, for example those exemplified in FIG. 1 and/or FIG. 8, provide for a surprising improvement in clinical efficacy of the TILs. In some embodiments, the TILs produced by the methods provided herein, for example those exemplified in FIG. 1 and/or FIG. 8, exhibit increased clinical efficacy as compared to TILs produced by methods other than those described herein, including for example, methods other than those exemplified in FIG. 1 and/or FIG. 8. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILs produced by the methods provided herein, for example those exemplified in FIG. 1, exhibit a similar time to response and safety profile compared to TILs produced by methods other than those described herein, including for example, methods other than those exemplified in FIG. 1 and/or FIG. 8.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1 and/or FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1 and/or FIG. 8. In some embodiments, IFN-γ secretion is increased one-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased two-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased three-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased four-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased five-fold as compared to an untreated patient and/or as compared to a patient treated with TILs prepared using other methods than those provide herein including for example, methods other than those embodied in FIG. 1 and/or FIG. 8. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 1 and/or FIG. 8. In some embodiments, IFN-γ is measured in blood of a subject treated with TILs prepared by the methods of the present invention, including those as described for example in FIG. 1 and/or FIG. 8. In some embodiments, IFN-γ is measured in TILs serum of a subject treated with TILs prepared by the methods of the present invention, including those as described for example in FIG. 1 and/or FIG. 8. In some embodiments, IFN-gamma (IFN-γ) is indicative of treatment efficacy and/or increased clinical efficacy in the treatment of cancer In some embodiments, in the TILs prepared by the methods of the present invention, including those as described for example in FIG. 1 and/or FIG. 8 IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1 and/or FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more IFN-γ as compared to an untreated patient and/or as compared to a patient treated with TILs prepared using other methods than those provide herein including for example, methods other than those embodied in FIG. 1 and/or FIG. 8.

In some embodiments, the TILs prepared by the methods of the present invention, including those as described for example in FIG. 1 and/or FIG. 8, exhibit increased polyclonality as compared to TILs produced by other methods, including those not exemplified in FIG. 1 and/or FIG. 8, including for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1 and/or FIG. 8. In some embodiments, polyclonality is increased one-fold as compared to an untreated patient and/or as compared to a patient treated with TILs prepared using other methods than those provide herein including for example, methods other than those embodied in FIG. 1 and/or FIG. 8. In some embodiments, polyclonality is increased two-fold as compared to an untreated patient and/or as compared to a patient treated with TILs prepared using other methods than those provide herein including for example, methods other than those embodied in FIG. 1 and/or FIG. 8. In some embodiments, polyclonality is increased ten-fold as compared to an untreated patient and/or as compared to a patient treated with TILs prepared using other methods than those provide herein including for example, methods other than those embodied in FIG. 1 and/or FIG. 8. In some embodiments, polyclonality is increased 100-fold as compared to an untreated patient and/or as compared to a patient treated with TILs prepared using other methods than those provide herein including for example, methods other than those embodied in FIG. 1 and/or FIG. 8. In some embodiments, polyclonality is increased 500-fold as compared to an untreated patient and/or as compared to a patient treated with TILs prepared using other methods than those provide herein including for example, methods other than those embodied in FIG. 1 and/or FIG. 8. In some embodiments, polyclonality is increased 1000-fold as compared to an untreated patient and/or as compared to a patient treated with TILs prepared using other methods than those provide herein including for example, methods other than those embodied in FIG. 1 and/or FIG. 8.

Measures of efficacy can include the disease control rate (DCR) as well as overall response rate (ORR), as known in the art as well as described herein.

In some embodiments, the invention includes a method of treating NSCLC with a population of TILs, wherein a patient is pre-treated with non-myeloablative chemotherapy prior to an infusion of TILs according to the present disclosure. In some embodiments, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In some embodiments, the non-myeloablative chemotherapy is cyclophosphamide 60 mg/kg/d for 2 days (days 27 and 26 prior to TIL infusion) and fludarabine 25 mg/m$^2$/d for 3 days (days 27 to 25 prior to TIL infusion). In some embodiments, the non-myeloablative chemotherapy is cyclophosphamide 60 mg/kg/d for 2 days (days 27 and 26 prior to TIL infusion) followed by fludarabine 25 mg/m$^2$/d for 3 days (days 25 to 23 prior to TIL infusion). In some embodiments, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp.* Otorhinolaryngol. 2009, 2, 55-60; and Sano, Head Neck Oncol. 2009, 1, 32.

In some embodiments, IFN-gamma (IFN-γ) is indicative of treatment efficacy for NSCLC treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 8 (in particular, e.g., FIG. 8A and/or FIG. 8B and/or FIG. 8C and/or FIG. 8D). In some embodiments, the TILs obtained by the present method provide for increased IFN-γ in the blood of subjects treated with the TILs of the present method as compared subjects treated with TILs prepared using methods referred to as the Gen 3 process, as exemplified FIG. 8 (in particular, e.g., FIG. 8A and/or FIG. 8B and/or FIG. 8C and/or FIG. 8D) and throughout this application. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased one-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-y secretion is increased two-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased three-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased four-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased five-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-y is measured in blood in a patient treated with the TILs produced by the methods of the present invention. In some embodiments, IFN-γ is measured in serum in a patient treated with the TILs produced by the methods of the present invention.

In some embodiments, the TILs prepared by the methods of the present invention, including those as described for example in FIG. 8 (in particular, e.g., FIG. 8A and/or FIG. 8B and/or FIG. 8C and/or FIG. 8D and/or FIG. 8E and/or FIG. 8F and/or FIG. 8G), exhibit increased polyclonality as compared to TILs produced by other methods, including those not exemplified in FIG. 8 (in particular, e.g., FIG. 8A and/or FIG. 8B and/or FIG. 8C and/or FIG. 8D), such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased one-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased two-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased ten-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 100-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 500-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 1000-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D).

1. Methods of Treating NSCLC

The compositions and methods described herein can be used in a method for treating non-small-cell lung cancer (NSCLC), wherein the NSCLC is refractory to treatment with an anti-PD-1 or anti-PD-L1 antibody. In some embodiments the NSCLC is metastatic NSCLC. In some embodiments the anti-PD-1 antibody includes, e.g., but is not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat A)-BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immu2740274ne response, are include. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are included.

In some embodiments, the NSCLC is refractory to the anti-CTLA-4 and/or anti-PD-1 and a chemotherapeutic agent. In some embodiments, the NSCLC is refractory to the anti-CTLA-4 and/or anti-PD-1 and chemotherapy, wherein the chemotherapeutic agent is carboplatin, paclitaxel, pemetrexed, cisplatin. In some embodiments, the NSCLS is refractory to an anti-CTLA-4 antibody, such as ipilimumab (Yervoy®).

In some embodiments, the NSCLC is refractory to treatment with combined PD-1 (including for example pembrolizumab) and a chemotherapeutic agent. In some embodiments, the chemotherapeutic agent(s) is a platinum doublet chemotherapeutic agent. In some embodiments, the platinum doublet therapy comprises a first chemotherapeutic agent selected from the group consisting of cisplatin and carboplatin and a second chemotherapeutic agent selected from the group consisting of vinorelbine, gemcitabine and a taxane (including for example, paclitaxel, docetaxel or nab-paclitaxel). In some embodiments, the platinum doublet chemotherapeutic agent is in combination with pemetrexed.

In some embodiments, the NSCLC is refractory to a combination treatment or combination therapy comprising an anti-PD-1 and a chemotherapeutic agent. In some embodiments, the anti-PD-1 or the anti-PD-L1 antibody is selected from the group consisting of nivolumab, pembrolizumab, JS001, TSR-042, pidilizumab, (BGB-A317, SHR-1210, REGN2810, MDX-1106, PDR001, anti-PD-1 from clone: RMP1-14, an anti-PD-1 antibodies disclosed in U.S. Pat. No. 8,008,449, durvalumab, atezolizumab, avelumab, and fragments, derivatives, variants, as well as biosimilars thereof. In some embodiments, the anti-PD-1 is pembrolizumab. In some embodiments, the chemotherapeutic agent is a platinum doublet chemotherapeutic agent. In some embodiments, the chemotherapeutic agent is in combination with pemetrexed. In some embodiments, the NSCLC is refractory to a combination therapy comprising carboplatin, paclitaxel, pemetrexed, and cisplatin. In some embodiments, the NSCLC is refractory to a combination therapy comprising carboplatin, paclitaxel, pemetrexed, cisplatin, nivolumab, and ipilimumab.

In some embodiments, the NSCLS has undergone no prior therapy.

In some embodiments, the NSCLC is PD-1 negative and/or is from a subject that is PD-1.

In some embodiments, the NSCLC is refractory to a combination therapy comprising the anti-PD-1 or the anti-PD-L1 and a platinum doublet therapy, wherein the platinum doublet therapy comprises:

i) a first chemotherapeutic agent selected from the group consisting of cisplatin and carboplatin,
ii) and a second chemotherapeutic agent selected from the group consisting of vinorelbine, gemcitabine and a taxane (including for example, paclitaxel, docetaxel or nab-paclitaxel).

In some embodiments, the NSCLC is refractory to a combination therapy comprising the anti-PD-1 or the anti-PD-L1, pemetrexed, and a platinum doublet therapy, wherein the platinum doublet therapy comprises:

i) a first chemotherapeutic agent selected from the group consisting of cisplatin and carboplatin,
ii) and a second chemotherapeutic agent selected from the group consisting of vinorelbine, gemcitabine and a taxane (including for example, paclitaxel, docetaxel or nab-paclitaxel).

In some embodiments, the NSCLC has been treated with an anti-PD-1 antibody. In some embodiments, the NSCLC has been treated with an anti-PD-L1 antibody. In some embodiments, the NSCLC subject is treatment naive. In some embodiments, the NSCLC has not been treated with an anti-PD-1 antibody. In some embodiments, the NSCLC has not been treated with an anti-PD-L1 antibody. In some embodiments, the NSCLC has been previously treated with a chemotherapeutic agent. In some embodiments, the NSCLC has been previously treated with a chemotherapeutic agent but is not longer being treated with the chemotherapeutic agent. In some embodiments, the NSCLC patient is anti-PD-1/PD-L1 naive. In some embodiments, the NSCLC subject has low expression of PD-L1. In some embodiments, the NSCLC subject has treatment naive NSCLC or is post-chemotherapeutic treatment but anti-PD-1/PD-L1 naive. In some embodiments, the NSCLC subject is treatment naive NSCLC or post-chemotherapeutic treatment but anti-PD-1/PD-L1 naive and has low expression of PD-L1. In some embodiments, the NSCLC subject has bulky disease at baseline. In some embodiments, the subject has bulky disease at baseline and has low expression of PD-L1. In some embodiments, the NSCLC subject has no detectable expression of PD-L1. In some embodiments, the NSCLC subject is treatment naive NSCLC or post-chemotherapeutic treatment but anti-PD-1/PD-L1 naive and has no detectable expression of PD-L1. In some embodiments, the subject has bulky disease at baseline and has no detectable expression of PD-L1. In some embodiments, the NSCLC subject has treatment naive NSCLC or post chemotherapy (e.g., post chemotherapeutic agent) but anti-PD-1/PD-L1 naive who have low expression of PD-L1 and/or have bulky disease at baseline. In some embodiments, bulky disease is indicated where the maximal tumor diameter is greater than 7 cm measured in either the transverse or coronal plane. In some embodiments, bulky disease is indicated when there are swollen lymph nodes with a short-axis diameter of 20 mm or greater. In some embodiments, the chemotherapeutic includes a standard of care therapeutic for NSCLC.

In some embodiments, PD-L1 expression is determined by the tumor proportion score. In some embodiments, the subject with a refractory NSCLC tumor has a<1% tumor proportion score (TPS). In some embodiments, the subject with a refractory NSCLC tumor has a≥1% TPS. In some embodiments, subject with the refractory NSCLC has been previously treated with an anti-PD-1 and/or anti-PD-L1 antibody and the tumor proportion score was determined prior to said anti-PD-1 and/or anti-PD-L1 antibody treatment. In some embodiments, subject with the refractory NSCLC has been previously treated with an anti-PD-L1 antibody and the tumor proportion score was determined prior to said anti-PD-L1 antibody treatment.

In some embodiments, the TILs prepared by the methods of the present invention, including those as described for example in FIG. 1 and/or FIG. 8, exhibit increased polyclonality as compared to TILs produced by other methods, including those not exemplified in FIG. 1 and/or FIG. 8, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TILs prepared using other methods than those provide herein including for example, methods other than those embodied in FIG. 1. In some embodiments, polyclonality is increased ten-fold as compared to an untreated patient and/or as compared to a patient treated with TILs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

a. Exemplary PD-L1 Testing Methods

In some embodiments, PD-L1 expression is determined by the tumor proportion score using one more testing methods as described herein. In some embodiments, the subject or patient with a NSCLC tumor has a<1% tumor proportion score (TPS). In some embodiments, the NSCLC tumor has a≥1% TPS. In some embodiments, the subject or patient with the NSCLC has been previously treated with an anti-PD-1 and/or anti-PD-L1 antibody and the tumor proportion score was determined prior to the anti-PD-1 and/or anti-PD-L1 antibody treatment. In some embodiments, the subject or patient with the NSCLC has been previously treated with an anti-PD-L1 antibody and the tumor proportion score was determined prior to the anti-PD-L1 antibody treatment. In some embodiments, the subject or patient with a refractory or resistant NSCLC tumor has a<1% tumor proportion score (TPS). In some embodiments, the subject or patient with a refractory or resistant NSCLC tumor has a≥i % TPS. In some embodiments, the subject or patient with the refractory or resistant NSCLC has been previously treated with an anti-PD-1 and/or anti-PD-L1 antibody and the tumor proportion score was determined prior to the anti-PD-1 and/or anti-PD-L1 antibody treatment. In some embodiments, the subject or patient with the refractory or resistant NSCLC has been previously treated with an anti-PD-L1 antibody and the tumor proportion score was determined prior to the anti-PD-L1 antibody treatment.

In some embodiments, the NSCLC is an NSCLC that exhibits a tumor proportion score (TPS), or the percentage of viable tumor cells from a patient taken prior to anti-PD-1 or anti-PD-L1 therapy, showing partial or complete membrane staining at any intensity, for the PD-L1 protein that is less than 1% (TPS <1%). In some embodiments, the NSCLC is an NSCLC that exhibits a TPS selected from the group consisting of <50%, <45%, <40%, <35%, <30%, <25%, <20%, <15%, <10%, <9%, <8%, <7%, <6%, <5%, <4%, <3%, <2%, <1%, <0.9%, <0.8%, <0.7%, <0.6%, <0.5%, <0.4%, <0.3%, <0.2%, <0.1%, <0.09%, <0.08%, <0.07%, <0.06%, <0.05%, <0.04%, <0.03%, <0.02%, and <0.01%. In some embodiments, the NSCLC is an NSCLC that exhibits a TPS selected from the group consisting of about 50%, about 45%, about 40%, about 35%, about 30%, about 25%, about 20%, about 15%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, and about 0.01%. In some embodiments, the NSCLC is an NSCLC that exhibits a TPS between 0% and 1%. In some embodiments, the NSCLC is an NSCLC that exhibits a TPS between 0% and 0.9%. In some embodiments, the NSCLC is an NSCLC that exhibits a TPS between 0% and 0.8%. In some embodiments, the NSCLC is an NSCLC that exhibits a TPS between 0% and 0.7%. In some embodiments, the NSCLC is an NSCLC that exhibits a TPS between 0% and 0.6%. In some embodiments, the NSCLC is an NSCLC that exhibits a TPS between 0% and 0.5%. In some embodiments, the NSCLC is an NSCLC that exhibits a TPS between 0% and 0.4%. In some embodiments, the NSCLC is an NSCLC that exhibits a TPS between 0% and 0.3%. In some embodiments, the NSCLC is an NSCLC that exhibits a TPS between 0% and 0.2%. In some embodiments, the NSCLC is an NSCLC that exhibits a TPS between 0% and 0.1%. TPS may be measured by methods known in the art, such as those described in Hirsch, et al. *J. Thorac. Oncol.* 2017:12, 208-222 or those used for the determination of TPS prior to treatment with pembrolizumab or other anti-PD-1 or anti-PD-L1 therapies. Methods for measurement of TPS that have been approved by the U.S. Food and Drug Administration may also be used. In some embodiments, the PD-L1 is exosomal PD-L1. In some embodiments, the PD-L1 is found on circulating tumor cells.

In some embodiments, the partial membrane staining includes 1%, 5%, 10%, 15%, 20%, 25%, 30%, 35%, 40%, 45%, 50%, 55%, 60%, 65%, 70%, 75%, 80%, 85%, 90%, 95%, 97%, 99%, or more. In some embodiments, the completed membrane staining includes approximately 100% membrane staining.

In some embodiments, testing for PD-L1 can involve measuring levels of PD-L1 in patient serum. In these embodiments, measurement of PD-L1 in patient serum removes the uncertainty of tumor heterogeneity and the patient discomfort of serial biopsies.

In some embodiments, elevated soluble PD-L1 as compared to a baseline or standard level correlates with worsened prognosis in NSCLC. See, for example, Okuma, Y et al., 2018, *Clinical Lung Cancer,* 19(5): 410-417; Vecchiarelli, S., et al., 2018, *Oncotarget,* 9(25):17554-17563. In some embodiments, the PD-L1 is exosomal PD-L1. In some embodiments, the PD-L1 is expressed on circulating tumor cells.

2. Driver Mutations

As used herein, the phrases "driver mutation" and/or "actionable mutation" and/or "oncogenic driver mutation" refer to mutations that are typically considered oncogenic drivers (i.e., cancer drivers or cancer inducers). The presence of one or more of these mutations has traditionally been the utilized as the target for a targeted therapy. Often driver mutations are examined and/or analyzed for treatment with targeted therapeutic moieties, including for example tyrosine kinase inhibitors (TKIs). Such driver mutations can, in some embodiments, impact or affect response to a first line therapeutic treatment. TIL therapy methods and compositions described herein are effective for treatment whether such driver mutations are present or absent in the patient or subject. Such driver mutations can be tested and determined by any method known in the art, including whole exome sequencing or methods targeted to the detection of a specific driver mutation.

In some embodiments, the NSCLC is an NSCLC that exhibits the presence or absence of one or more driver mutations. In some embodiments, the NSCLC is an NSCLC that exhibits the presence of one or more driver mutations.

In some embodiments, the NSCLC is an NSCLC that exhibits the absence of one or more driver mutations. In some embodiments, the NSCLC has been analyzed for the absence or presence of one or more driver mutations. In some embodiments, the one or more driver mutations are not present. In some embodiments, the NSCLC treatment is independent of the presence or absence of one or more driver mutations. In some embodiments, the one or more driver mutations is selected from the group consisting of an EGFR mutation, an EGFR insertion, EGFR exon20, a KRAS mutation, a BRAF-mutation, a BRAF V600E mutation, a BRAF V600K mutation, a BRAF V600 mutation, an ALK mutation, a c-ROS mutation (ROS1-mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARIDIA mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNAT1 mutation. In some embodiments, the NSCLC exhibits a TPS of <1% and has a predetermined absence of one or more driver mutations.

In some embodiments, the NSCLC is an NSCLC that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNA11 inhibitor.

In some embodiments, the NSCLC exhibits a TPS of <1% and is a NSCLC that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNA11 inhibitor In some embodiments, the EGFR mutation results in tumor transformation from NSCLC to small cell lung cancer (SCLC).

In some embodiments, the NSCLC (or a biopsy thereof) exhibits high-tumor mutational burden (high-TMB; >10 mut/kb) and/or microsatellite instability high (MSI-high). In some embodiments, the NSCLC (or a biopsy thereof) exhibits high-tumor mutational burden (high-TMB; >10 mut/kb). In some embodiments, the NSCLC (or a biopsy thereof) exhibits microsatellite instability high (MSI-high). Methods and systems for evaluating tumor mutational burden are known in the art. Exemplary disclosures of such methods and systems can be found in U.S. Pat. No. 9,792,403, US Application Publication No. US20180363066A1, International Application publication Nos. WO2013070634 and WO2018106884, as well as Metzker, M. (2010) *Nature Biotechnology Reviews* 11:31-46, incorporated herein by reference, all of which are incorporated by reference in their entireties.

In some embodiments, the NSCLC (or a biopsy thereof) exhibits high-tumor mutational burden (high-TMB; >10 mut/kb) and/or microsatellite instability high (MSI-high). In some embodiments, the NSCLC (or a biopsy thereof) exhibits high-tumor mutational burden (high-TMB; >10 mut/kb). In some embodiments, the NSCLC (or a biopsy thereof) exhibits microsatellite instability high (MSI-high). Methods and systems for evaluating tumor mutational burden are known in the art. Exemplary disclosures of such methods and systems can be found in U.S. Pat. No. 9,792,403, US Application Publication No. US20180363066A1, International Application publication Nos. WO2013070634 and WO2018106884, as well as Metzker, M. (2010) *Nature Biotechnology Reviews* 11:31-46, incorporated herein by reference, all of which are incorporated by reference in their entireties.

In some embodiments, the EGFR mutation includes, for example, but is not limited to T790M, Ex19Del, L858R, Exon 20 insertion, delE709-T710insD, 1744_K745insKIPVAI, K745_E746insTPVAIK, E709X, E709K, E709A, Exon 18 deletion, G719X, G719A, G719S, L861Q, S7681, L747P, A763_764insFQEA, D770_N771insNPG, A763_764insFQEA, P772_H773insDNP exon 20 insertion, H773_V774insNPH exon 20 insertion, S7681, D770_N771insSVD, V769_D770InsASV, p.K745_E746insIPVAIK, p.K745_E746insTPVAIK, p.I744_K745insKIPVAI, D770_N771insNPG, P772_H773insPNP, A763_Y764insFQEA, and/or EGFR kinase domain duplication (EGFR-KDD). In some embodiments, the EGFR mutation is selected from the group consisting of T790M, Ex19Del, L858R, Exon 20 insertion, delE709-T710insD, 1744_K745insKIPVAI, K745_E746insTPVAIK, E709X, E709K, E709A, Exon 18 deletion, G719X, G719A, G719S, L861Q, S7681, L747P, A763_764insFQEA, D770_N771insNPG, A763_764insFQEA, P772_H773insDNP exon 20 insertion, H773_V774insNPH exon 20 insertion, S7681, D770_N771insSVD, V769_D770InsASV, p.K745_E746insIPVAIK, p.K745_E746insTPVAIK, p.1744_K745insKIPVAI, D770_N771insNPG, P772_H773insPNP, A763_Y764insFQEA, and EGFR kinase domain duplication (EGFR-KDD).

In some embodiments, the EGFR mutation is a double mutation including for example, but not limited to, L858R/T790M, Ex19Del/T790M, G719X/L861Q, G719X/57681 (or S768I/G719X), S768I/L858R, L858R/E709A, and/or E746_T751delinsA+T790M. In some embodiments, the EGFR mutation is a double mutation selected from group consisting of L858R/T790M, Ex19Del/T790M, G719X/L861Q, G719X/S768I (or S768I/G719X), 57681/L858R, L858R/E709A, and E746_T751delinsA+T790M.

Additional disclosures of the EGFR mutation are provided in International Application Publication No. WO2010020618, which is incorporated by referenced herein in its entirety.

In some embodiments, the ALK mutation includes, but not limited to, EML4-ALK Variant 1 (AB274722.1; BAF73611.1), EML4-ALK Variant 2 (AB275889.1; BAF73612.1), EML4-ALK Variant 3a (AB374361.1; BAG55003.1), EML4-ALK Variant 3b (AB374362.1; BAG55004.1), EML4-ALK Variant 4 (AB374363.1;

BAG75147.1), EML4-ALK Variant 5a (AB374364.1; BAG75148.1), EML4-ALK Variant 5b (AB374365.1; BAG75149.1), EML4-ALK Variant 6 (AB462411.1; BAH57335.1), EML4-ALK Variant 7 (AB462412.1; BAH57336.1), KIF5B-ALK (AB462413.1; BAH57337.1), NPM-ALK, TPM3-ALK, TFGXL-ALK, TEGL-ALK, TFGS-ALK, AT1C-ALK, CLTC-ALK, MSN-ALK, TPM4-ALK, MYH9-ALK, RANBP2-ALK, AL017-ALK, and CARS-ALK (see, for example. Pulford et al., (2004) *J. Cell. Physiol.* 199:330-358). In addition, a skilled artisan will understand that ALK kinase variants can arise depending upon the particular fusion event between an ALK kinase and its fusion partner (e.g., EML4 can fuse at least exon 2, 6a, 6b, 13, 14, and/or 15, as described, for example, in Horn and Pao, (2009) *J. Clin. Oncol.* 27:4247-4253) (incorporated by reference in its entirety).

Additional examples of ALK mutations are described in U.S. Pat. Nos. 9,018,230 and 9,458,508, the disclosures of which are incorporated by reference herein.

In some embodiments, the ROS1 mutation of the present invention is a ROS1 fusion, where a portion of the ROS1 polypeptide that includes the kinase domain of the ROS1 protein (or polynucleotide encoding the same) fused to all or a portion of another polypeptide (or polynucleotide encoding the same) and where the name of that second polypeptide or polynucleotide is named in the fusion. In some embodiments, the ROS1 mutation is determined as ROS1-fusion protein (e.g. by IHC) and/or ROS-fusion gene (e.g. by FISH), and/or ROS1 mRNA (e.g. by qRT-PCR), preferably indicative of a ROS1-fusion protein selected from the group consisting of SLC34A2-ROS1 (SLC34A2 exons 13de12046 and 4 fused to ROS1 exons 32 and 34), CD74-ROS1 (CD74 exon 6 fused to ROS1 exons 32 and 34), EZR-ROS1 (EZR exon 10 fused to ROS1 exon 34), TPM3-ROS1 (TPM3 exon 8 fused to ROS1 exon 35), LRIG3-ROS1 (LRIG3 exon 16 fused to ROS1 exon 35), SDC4-ROS1 (SDC4 exon 2 and 4 fused to ROS1 exon 32 and SDC4 exon 4 fused to ROS1 exon 34), GOPC-ROS1, also known as FIG-ROS1, (GOPC exon 8 fused to ROS1 exon 35 and GOPC exon 4 fused to ROS1 exon 36), and G2032R, i.e. ROS1 $^{G2032R}$.

Additional disclosures of the ROS1 mutations and the ROS fusion have been provided in U.S. Patent Publication Nos. 20100221737, 20150056193, and 20100143918, and PCT Publication No, WO2010/093928, all of which are hereby incorporated by reference in their entirety. In some embodiments, the RET mutation is a RET fusion or point mutation.

In some embodiments, the RET point mutation includes but is not limited to H6650, K666E, K666M, S686N, G691S, R694Q, M700L, V706M, V706A, E713K, G736R, G748C, A750P, S765P, P766S, E768Q, E768D, L769L, R770Q, D771N, N777S, V7781, Q781R, L790F, Y791F, Y791N, V804L, V804M, V804E, E805K, E806C, Y806E, Y806F, Y806S, Y806GY806C E818K S8191 G823E Y826M R833C P841L P841P E843D R844W, R844Q, R844L, M848T, 1852M A866W R873W A876V L881V A883F A883S A883T E884K R886W, S891A, R8970, D898V, E901K 5904F S904C2 K907E K907M R908K G911D R912P R912Q M918T, M918V, M918L6, A919V, E921K, S922P S922Y T930M F961L R972G R982C M1009V D1017N V10416, and M1064T.

In some embodiments, the RET fusion is a fusion between RET and a fusion partner that is selected from the group consisting of BCR, BCR, CLIP 1, KIFSB, CCDC6, PTClex9, NCOA4, TRIM33, ERC1, FGFRIOP, MBD1, RAB61P2, PRKARIA, TRIM24, KTN1, GOLGA5, HOOK3, KIAA1468, TRIM27, AKAP13, FKBP15, SPECCIL, TBL1XR1, CEP55, CUX1, ACBD5, MYH13, PIBF1, KIAA1217, and MPRIP.

Additional disclosures of the RET mutations has been provided in U.S. patent Ser. No. 10/035,789, which is hereby incorporated by reference in their entirety.

In some embodiments, the BRAF mutation is BRAF V600E/K mutation. In other embodiments, the BRAF mutation is a non-V600E/K mutation.

In some embodiments, the non-V600E/K BRAF mutation is a kinase-activated mutation, a kinase-impaired mutation, or a kinase-unknown mutation, and combinations thereof. In some embodiments, the kinase-activated mutation is selected from the group consisting of R4621, 1463S, G464E, G464R, G464V, G466A, G469A, N58 is, E586K, F595L, L597Q, L597R, L5975, L597V, A598V, T599E, V600R, K601E, 5602D, A728V, and combinations thereof. In some embodiments, the kinase-impaired mutation is selected from the group consisting of G466E, G466R, G466V, Y472C, K483M, D594A, D594E, D594G, D594H, D594N, D594V, G596R, T599A, 5602A, and combinations thereof. In some embodiments, the kinase-unknown mutation is selected from the group consisting of T4401, 5467L, G469E, G469R, G4695, G469V, L584F, L588F, V600 K6OldelinsE, 56051, Q609L, E611Q, and combinations thereof. In some embodiments, the non-V600E/K BRAF mutation is selected from the group consisting of D594, G469, K601E, L597, T599 duplication, L485W, F247L, G466V, BRAF fusion, BRAF-AGAP3 rearrangement, BRAF exon 15 slice variant, and combinations thereof.

In some embodiments, the Met mutation includes point mutation, deletion mutation, insertion mutation, inversion, aberrant splicing, missense mutation, or gene magnification that causes the increase of at least one bioactivity of c-Met protein, the tyrosine kinase activity such as improved, receptor homolog dimerization Ligand binding of formation, enhancing of body and heterodimer etc. The Met mutation can be located at any part of c-Met genes. In one embodiment, the mutation is in the kinase domain of c-Met protein encoded by the c-MET gene. In some embodiments, the c-Met mutations are point mutation at N375, V13, V923, R175, V136, L229, S323, R988, S1058/T10[10] and E168.

In some embodiments, the ERBB2 mutation is a point mutation in the amino acid sequence of ERBB2. In some embodiments, the point mutation of ERBB2 is one that causes amino acid substitutions, causes mRNA splicing, or is a point mutation in the upstream region. Wherein the mutation comprises a nucleotide mutation causing at least one amino acid substitution selected from the group consisting of Q568E, P601R, 1628M, P885S, R143Q, R434Q, and E874K.

In some embodiments, the ERBB2 mutation is ERBB2 amplification. In some embodiments, the ERBB2 amplification includes point mutation selected from the group consisting ofV659E, G309A, G309E, S310F, D769H, D769Y, V777L, P780ins, P780-Y781insGSP, V8421, R896C, K753E, and L755S and can be detected by Polymerase Chain Reaction or any sequencing technique (Bose et al. *Cancer Discov.* 2013, 3(2), 224-237; Zuo et al. *Clin Cancer Res* 2016, 22(19), 4859-4869).

In some embodiments, the BRCA mutation is a mutation in BRCA1 and/or BRCA2, preferably BRCA1, and/or in one or more other genes of which the protein product associates with BRCA1 and/or BRCA2 at DNA damage sites, including ATM, ATR, Chk2, H2AX, 53BP1, NFBD1, Mrell, Rad50, Nibrin, BRCA1-associated RING domain (BARDI), Abraxas, and MSH2. A mutation in one or more of these genes may result in a gene expression pattern that mimics a mutation in BRCA1 and/or BRCA2.

In certain embodiments the BRCA mutation comprises a non-synonymous mutation. In some embodiments, the BRCA mutation comprises a nonsense mutation. In some embodiments, the BRCA mutation comprises a frameshift mutation. In some embodiments, the BRCA mutation comprises a splicing mutation. In some embodiments, the BRCA mutation is expressed as a mutant mRNA and ultimately a mutant protein. In some embodiments, the BRCA1/2 protein is functional. In other embodiments, the BRCA1/2 protein has reduced activity. In other embodiments, the BRCA1/2 protein is non-functional.

As used herein with regard to susbtitions, the "=" sign with regard to mutaitons generally refers to synonymous substitutions, silent codons, and/or silent substitutions. In particular, a synonymous substitution (also called a silent substitution or silent codon) refers to the substitution of one nucleotide base for another in an exon of a gene encoding a protein, wherein the produced amino acid sequence is not modified. This is due to the fact that the genetic code is "degenerate", i.e., that some amino acids are coded for by more than one three-base-pair codon. Because some of the codons for a given amino acid vary by just one base pair from others coding for the same amino acid, a point mutation that replaces the wild-type base by one of the alternatives will result in incorporation of the same amino acid into the elongating polypeptide chain during translation of the gene. In some embodiments, synonymous substitutions and mutations affecting noncoding DNA are often considered silent mutations; however, it is not always the case that the mutation is silent and without any impact. For example, a synonymous mutation can affect transcription, splicing, mRNA transport, and translation, any of which could alter the resulting phenotype, rendering the synonymous mutation non-silent. The substrate specificity of the tRNA to the rare codon can affect the timing of translation, and in turn the co-translational folding of the protein. This is manifested in the codon usage bias that has been observed in many species. A nonsynonymous substitution/mutation results in a change in amino acid that may be arbitrarily classified as conservative (a change to an amino acid with similar physiochemical properties), semi-conservative (e.g. negatively to positively charged amino acid), or radical (vastly different amino acid).In some embodiments, the BRCA mutation is a BRCA1 mutation that includes, but is not limited to P871L, K1183R, D693N, 51634G, E1038G, 51040N, S694=(=: silience codon), M1673I, Q356R, 51436=, L771=, K654Sfs*47, S198N, R496H, R841W, R1347G, H619N, S15331, L30=, A622V, Y655Vfs*18, R496C, E597K, R1443*, E23Vfs*17, L30F, E111Gfs*3, K339Rfs*2, L512F, D693N, P871S, 51140G, Q1240*, P1770S, R7=, L52F, T176M, A224S,L347=, S561F, E597*, K820E, K893Rfs*107, E962K, M10141, R1028H, E1258D, E1346K, R1347T, L1439F, H1472R, Q1488*, 51572C, E1602K, R1610C, L1621=, Q1625*, Q1625=, D1754N, R1772Q, R1856*, and any combination thereof.

In some embodiments, the BRCA mutation is a BRCA2 mutation that includes, but is not limited to V2466A, N289H, N991D, S455=(=: silience codon), N372H, H743=, V1269=, S2414=, V2171=, L1521=, T3033Nfs*11, K1132=, T3033Lfs*29, R2842C, N1784Tfs*7, K3326*, K3326*, D1420Y, I605Yfs*9, I3412V, A2951T, T3085Nfs*26, R2645Nfs*3, 51013*, T1915M, F3090=, V32441, A1393V, R2034C, L1356=, E2981Rfs*37, N1784Kfs*3, K3416Nfs*11, K1691Nfs*15, 51982Rfs*22, and any combination thereof.

In some embodiments, the NRAS mutation of the present invention includes but is not limited to E63K, Q61R, Q61K, G12D, G13D, Q61R, Q61L, Q61K, G12S, G12C, G13R, Q61H, G12V, G12A, Q61L, G13V, Q61H, Q61H, G12R, G13C, Q61P, G13S, G12D, G13A, G13D, A18T, Q61X, G60E, G12S, Q61=(=: silience codon), Q61E, Q61R, A146T, A59T, A59D, Q61=, R68T, A146T, G12A, E62Q, G75=, A91V, and any combination thereof.

E132K In some embodiments, the PIK3CA mutation includes substitution mutations, deletion mutations, and insertion mutations. In some embodiments, mutations occur in PIK3CA's helical domain and in its kinase. In other embodiments, in PIK3CA's P85BD domain. In some embodiments, the PIK3CA mutation is in exon 1, 2, 4, 5, 7, 9, 13, 18, and 20. In some embodiments, the PIK3CA mutation is in exons 9 and 20. In yet other embodiments, the PIK3CA mutation is a combination of the any mutations listed above. Any combination of these exons can be tested, optionally in conjunction with testing other exons. Testing for mutations can be done along the whole coding sequence or can be focused in the areas where mutations have been found to cluster. Particular hotspots of mutations occur at nucleotide positions 1624, 1633, 1636, and 3140 of PIK3CA coding sequence.

In some embodiments, the size of the PIK3CA mutation is small, ranging from 1 to 3 nucleotides. In some embodiments, the PIK3CA mutations include, but are not limited to G1624A, G1633A, C1636A, A3140G, G113A, T1258C, G3129T, C3139T, E542K, E545K, Q546R, H1047L, H1047R and G2702T.

In some embodiments, the MAP2K1 mutation is a somatic MAP2K1 mutation, optionally a MAP2K1 mutation that upregulates MEKI levels. In some embodiments, the MAP2K1 mutation is a mutation in one or more genes associated with the RAS/MAPK pathway, comprising: HRAS, KRAS, NRAS, ARAF, BRAF, RAFI, MAP2K2, MAPKI, MAPK3, MAP3K3. In certain embodiments, the MAP2K1 mutation is in one or more genes selected from the group consisting of RASA, PTEN, ENG, ACVRL1, SMAD4, GDF2 or combinations thereof.

In some embodiments, the MAP2K1 mutation includes, but is not limited to, P124S, Q56P, K57N, E203K, G237*, P124L, G128D, D67N, K57E, E102_I103del, C121S, K57T, K57N, Q56P, P124L, K57N, G128V, Q58_E62del, F53L, 1126=, 1103_K104del, and any combination thereof.

In certain embodiments the KRAS mutation comprises a non-synonymous mutation. In some embodiments, the KRAS mutation comprises a nonsense mutation. In some embodiments, the KRAS mutation comprises a frameshift mutation. In some embodiments, the KRAS mutation comprises a splicing mutation. In some embodiments, the KRAS mutation is expressed as a mutant mRNA and ultimately a mutant protein. In some embodiments, the mutated KRAS protein is functional. In other embodiments, the mutated KRAS protein has reduced activity. In other embodiments, the mutated KRAS protein is non-functional.

In some embodiments, the KRAS mutation includes but is not limited to GT2D, G12V, G13D, G12C, G12A, G12S, G12R, G13C, Q61H, A146T, Q61R, Q61H, Q61L, G13S, A146V, Q61K, G13R, G12F, K117N, G13A, G13V, A59T, V14I, K117N, Q22K, Q61P, A146P, G13D, L19F, L19F, Q61K, G12V, G60=, G12=, G13=, A18D, T58I, Q61E, E63K, G12L, G13V, A59G, G60D, G10R, G10dup, D57N, A59E, V14G, D33E, G12I, G13dup, and any combination thereof, wherein=is indiciative of silence coding.

In some embodiments, the NF1 mutation includes substitution mutations, deletion mutations, missense mutations, aberrant splicing mutations, and insertion mutations. In some embodiments, the NF1 mutation is a loss of function (LOF) mutation. In some embodiments, the NF1 mutation is selected from the group consisting of R1947X (C5839T), R304X, exon 37 mutation, exon 4b mutation, exon 7 mutation, exon 10b mutation, and exon 10c mutation (e.g., 1570G-4T, E524X).

In some embodiments, the CDKN2A mutation includes but is not limited to R24P, D108G, D108N, D108Y, G125R, P114L, R80*, R58*, H83Y, W110*, P114L, E88*, W110*, E120*, D108Y, D84Y, D84N, E69*, P81L, Q50*, L78Hfs*41, D108N, S12*, P48L, E61*, Y44*, E88K, R80*, D84G, L16Pfs*9, Y129*, D108H,A148T, A36G, A102V, W15*, H83R, A57V, E33*, D74Y, A76V, E153K, D74N, H83D, V82M, R58*, Y129*, E119*, Y44*, D74A, T18_A19dup, Y44Lfs*76, L32_L37del, V28_E33del, D14_L16del, A68T, or any combination thereof.

In certain embodiments the PTEN mutation comprises a non-synonymous mutation. In some embodiments, the PTEN mutation comprises a nonsense mutation. In some embodiments, the PTEN mutation comprises a frameshift mutation. In some embodiments, the PTEN mutation comprises a splicing mutation. In some embodiments, the mutated PTEN is expressed as an mRNA and ultimately a protein. In some embodiments, the mutated PTEN protein is functional. In other embodiments, the mutated PTEN protein has reduced activity. In other embodiments, the mutated PTEN protein is non-functional. In some embodiments, the PTEN mutation includes, but is not limited to, R130Q, R130G, T319*, R233*, R130*, K267Rfs*9, N323Mfs*21, N323Kfs*2, R173C, R173H, R335*, Q171*, Q245*, E7*, D268Gfs*30, R130Q, Q214*, R130L, C136R, Q298*, Q17*, H93R, P248Tfs*5, I33del, R233*, E299*, G132D, Y68H, T319Kfs*24, N329Kfs*14, V166Sfs*14, V290*, T319Nfs*6, R142W, P38S, A126T, H61R, F278L, S229*, R130P, G129R, R130Qfs*4, P246L, R130*, G165R, C136Y, R173C, I101T, Y155C, D92E, K164Rfs*3, N184Efs*6, G129E,R130G, G36R, F341V, H123Y, C124S, M35VG127E, G165E and any combination thereof.

In some embodiments, the TP53 mutation includes, but is not limited to, R175H, G245S, R248Q, R248W, R249S, R273C, R273H, R282W, C135Y, C141Y, P151S, V157F, R158L, Y163C, V173L, V173M, C176F, H179R, H179Y, H179Q, Y205C, Y220C, Y234C, M2371, C238Y, S241F, G245D, G245C, R248L, R249M, V272M, R273L, P278L, R280T, E285K, E286K, R158H, C176Y, 1195T, G214R, G245V, G266R, G266E, P278S, R280K, or any combination thereof. In some further embodiments, the TP53 mutation is selected from the group consisting of: G245S; R249S; R273C; R273H; C141Y, V157F, R158L, Y163C, V173L, V173M, Y205C, Y220C, G245C, R249M, V272M, R273L, and E286K. In some embodiments, the TP53 mutation includes one or more of the mutations above.

In some embodiments, the CREBBP mutation includes, but is not limited to, R1446C, R1446H, 51680del, I1084Sfs*15, P1948L, I1084Nfs*3, ?R386*, S893L, R1341*, P1423Lfs*36, P1488L, Y1503H, R1664C, A1824T, R1173*, R1360*, Y1450C, H2228D, S71L, P928=, D1435N, W1502C, Y1503D, R483*, R601Q, S945L, R1103*, R1288W, R1392*, C1408Y, D1435G, R1446L, H1485Y, Q1491K, Q96*, L361M, L524Wfs*6, Q540*, Q1073*, A1100V, R1169C, C1237Y, R1347W, G1411E, W1472C, I1483F, P1488T, R1498*, Y1503F, Q1856*, R1985C, R2104C, 52328L, V2349=, 52377L, and any combination thereof.

In some embodiments, the KMT2C mutation includes, but is not limited to, D348N, P350=, R380L, C391*, P309S, C988F, Y987H, S990G, K2797Rfs*26, V346=, R894Q, R284Q, S806=, R1690=, P986=, A1685S, G315S, Q755*, R909K, T316S, S772L, G838S, L291F, P335=, C988F, Q2680=, E765G, K339N, Y816*, R526P, N729D, G845E, I817Nfs*11, G892R, C1103*, 53660L, F4496Lfs*21, G315C, R886C, D348N, S793=, V919L, R2481S, R2884*, R4549C, M305Dfs*28, T316S, P377=, 1455M, T8201, S965=, S730Y, P860S, Q873Hfs*40, R904*, R2610Q, R4478*, and any combination thereof.

In some embodiments, the KMT2D mutation includes, but is not limited to, L1419P, E640D, E541D, E455D, T2131P, K1420R. P2354Lfs*30, G2493=, Q3612=, I942=, T1195Hfs*17, P4170=, P1194H, G1235Vfs*95, P4563=, P647Hfs*283, L449_P457del, P3557=, Q3603=, R1702*, P648Tfs*2, R5501*, R4198*, R4484*, R83Q, R1903*, R2685*, R4282*, L5326=, R5432W, R2734*, Q2800*, R2830*, Q3745dup, 54010P, R4904*, G5182Afs*61, R5214H, R1615*, Q2380*, R2687*, R2771*, V3089Wfs*30, Q3799Gfs*212, R4536*, R5030C, R5048C, R5432Q, A221Lfs*40, A476T, A2119Lfs*25,P2557L, R2801*, Q3913*, R4420W, G4641=, R5097*, and any combination thereof.

In some embodiments, the ARID1A mutation includes, but is not limited to, For example, subject has a mutation ofARID1A selected from the group consisting of a C884* (*: nonsense mutation), E966K, Q1411*, F1720fs (fs: frameshift), G1847fs, C1874fs, D1957E, Q1430, R1721fs, G1255E, G284fs, R1722*, M274fs, G1847fs, P559fs, R1276*, Q2176fs, H203fs, A591fs, Q1322*, S2264*, Q586*, Q548fs, and N756fs.

In some embodiments, the RB1 mutation includes, but is not limited to, R320X, R467X, R579X, R455X, R358X, R251X, R787X, R552X, R255X, R556X, Y790X, Q575X, E323X, R661W, R579*, R455*, R556*. R787*, R661W, R445*, R467*, Q217*, Q471*, W195*, Q395*, 1680T, E137*, R255*, Q344*, Q62*, E440K, A488V, P777Lfs*33, E322K, R656W, G617Rfs*36, C221*, E440*,Q93*, Q504*, E125*, S834*, E323*, Q685*, S829*, W516*, G435*, Q257*, E79*, S567L, V654M, V654Sfs*14,G100Efs*11, K715*, and any combination thereof.

In some embodiments, the ATM mutation is a mutation in the ATM gene sequence including, but is not limited to, 10744A>G;10744A>G; 11482G>A; IVS3-558A>T; 146C>G; 381delA; IVS8-3delGT; 1028delAAAA; 1120C>T; 1930ins16; IVS16+2T>C; 2572T>C; IVS21+1G>A; 3085delA; 3381delTGAC; 3602delTT; 4052delT; 4396C>T; 5188C>T; 5290delC; 5546delT; 5791G>CCT; 6047A>G; IVS44-1G>T; 6672de1GC/6677de1TACG; 6736dell 1/6749del7; 7159insAGCC; 7671delGTTT; 7705de114; 7865C>T; 7979delTGT; 8177C>T; 8545C>T; 8565T>A; IVS64+1G>T; and 9010del28.

In some embodiments of the present invention, the SETD2 mutation is an alteration in the gene sequence encoding the SETD2 protein, when the transcription initiation codon position of the mRNA sequence of NCBI accession number NM_014159 is set to 1. In some embodiments, the 7558th G (guanine) is substituted with T (thymine), 4774 th C (cytosine) is substituted by T, 1210 th A (adenine) is substituted by T, 4883 th is substituted by G, 5290 th C is replaced by T, 7072 th C is replaced by T, 4144 th G Is substituted by T, 1297 is replaced by T, 755 is replaced by G, 7261 is substituted by G, 6700 is replaced by T, 2536 is substituted by T, 7438 is replaced by T Substitution, insertion of A at position 3866, insertion of T at position 6712, insertion of T at position 7572, deletion of 913th A, deletion of 5619th C, deletion of bases 4603-4604, 894-897 Deletion of the 1st base, deletion of the 1936th C, deletion of the 3094-3118 base, insertion of A in the 5289th position, and deletion of the 6323-6333 base One or more mutations selected from the group true luer included.

In one embodiment of the present invention, the mutation of the SETD2 protein is stopped after 2520 glutamic acid, stop after 1592 arginine, stop after 404 arginine, stop after 1764 glutamine, 1032 of SETD2 amino acid sequence corresponding to NCBI accession number NP_054878 Frameshift after the first serine, Frameshift after the 646 histidine, Frameshift after the 2108th valine, Frameshift after the 1764 glutamine, Frameshift after the 298th isoleucine, Frameshift after the 1289th asparagine, Frameshift since the 289th serine Frameshift after, stop after 2525 lysine, frame shift after 305 threonine, frame shift after 1873 proline, frame shift after 1535 asparagine, stop after 2234 glutamic acid, replace 2536 alanine with threonine, 7438 Glutamine stopped, 1628 Group consisting of spargine substituted by serine, 2358 th proline by serine, 1382 alanine by serine, 433 th arginine by cytosine, 252nd alanine by glycine, and 2421 threonine by alanine One or more mutations selected from.

In some embodiments, the FLT3 mutation includes, but is not limited to, (Q569_E648)ins, D835X, (Q569_E648)delins, (D835 1836), D835Y, D835V, D835Y, D835H, T227M, 1836del, N676K, D835E, Y597_E598insDYVDFREY, D835E, D835del, F594_D600dup, A680V, D839G, D96=, D835H, V491L, D835E, Q989*, D835V, L561=, 1836del, P986Afs*27, D7G, D324N, S45IF, D835N, L576P, Y597 E598insDVDFREY, V491L, N841T, D324N, Y572C, R595_L601dup, K663R, N676K,F691L, D835A, 1836H, N841K, S993L, L832F, 1836M, A66V, and any combination thereof.

In some embodiments, the PTPN11 mutation includes, but is not limited to, c E76K, A72V, A72T, D61Y, D61V, G60V, E69K, E76G, G507V, S506L, G507A, T731, E76A, E76Q, S506P, D61N, F71L, E76V, F71L, A72D, V432M, T472M, P495L, N58Y, F285S, S506A, S189A, A465T, R502W, G507R, T511K, D61H, D61G, G507E, G60R, G60A, Q514L, E139D, Y197*, N308D, Q514H, Q514H, N58S, E123D, L206=, A465G, P495S, G507R, and any combination thereof.

In some embodiments, the FGFR1 mutation includes, but is not limited to, N577K, K687E, N577K, D166del, T371M, R476W, T350=, E498K, N577D, D683G, R87C, A154D, N303=, A374V, D550=, S633=, V695L, G728=, R765W, P803S, W19C, P56=, R113C, V1491, S158L, D166dupR220C, N224Kfs*8, D249N, R281W, R281Q, A299S, S424L, S461F, S467F, R506Q, and any combination thereof.

In some embodiments, the EP300 mutation includes, but is not limited to, D1399N, Y1414C, M1470Cfs*26, Y1111*, H2324Pfs*55, R1627W, N2209_Q2213delinsK, Q2268del, L415P, M1470Nfs*3, E1514K, C1201Y, P1452L, S952*, C1164Y, D1399Y, S507G, Q824*, D1507N, H2324Tfs*29, P925T, P1440L, W1466C, P1502L, A1629V, R1645*, N1700Tfs*9, P1869L, Q65*, A171V, R202*, R580Q, A627V, Q1082*, N1236Kfs*2, N1286S, R1312*, R1356*, C1385F, H1451L, R1462*, Y1467N, Y1467H, R1478H, R1627Q, R86*, R370H, R397*, R754C, P842S, 1997V, E1014*,and any combination thereof.

In some embodiments, the MYC mutation includes, but is limited to, E61T, E681, R74Q, R75N, W135E, W136E, V394D, L420P, W96E, V325D, L351P, a MYC protein with 41 amino acid deleted at the N-terminus (dN2MYC), N26S, S161L, P74L, V7M, F153S, E54D, P246, L164V, P74S, A59V, T731, P72T,T73A, H374R, P17S, T73N, S264N, P72S, Q52del, S21T, P74A, S107N, P75S, S77P, P261S, P74Q, S190R, A59T, F153C, P75H, T731, S77F, N11S, S21N, P78L, P72L, N9K, S190N, S267F, T73P, P78S, G105D, S187C, L71M, Q10H, L191x, Q50x, L191F, R25K, F130L, Y27S, D195N, D2G, V20A, V6G, V201, D2H, P75A, G152D, P74T, C40Y, E8K, Q48x, and any combination thereof.

In some embodiments, the EZH2 mutation is associated with altered histone methylation patterns. In some embodiments, the EZH2 mutation leads to the conversion of amino acid Y641 (equivalent to Y646, catalytic domain), to either F, N, H, S or C resulting in hypertrimethylation of H3K27 and drives lymphomagenesis. In some embodiments, the EZH2 mutation includes EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

In some embodiments, the EZH2 mutation includes, but is not limited to, Y646F, Y646N, D185H, Y646F, Y646S, Y646H, R690H, Y646X, E745K, Y646C, V626M, V679M, R690H, R684H, A682G, E249K, G159R, R288Q, N322S, A692V, R690C, D730* (insertion frameshift), S695L, R684C, M667T, R288*, S644*, D192N, K550T,Q653E, D664G, R347Q,Y646C,G660R, R213C, A255T, S538L, N693K, I55M, R561H, A692V, K515R,Y733*, R63*, Q570*, Q328*, R25Q, T467P A656V, T573I, C571Y, E725K, R16W, P577L, F145S, V680M, G686D, G135R, K634E, S652F, R298C, G648E, R566H, L149R, R502Q, Y731D, R313W, N675K, S652C, T374Hfs*3, N152Ifs*15, E401Kfs*22, K406Mfs*17, E246*, S624C, 1146T, V626M, L674S, H694R, A581S, and any combination thereof.

In some embodiments, the JAK2 mutation is a mutation in the JAK2 gene includes, but is not limited to, T1923C mutation in combination with a G1920T mutation, a G1920T/C1922T mutation, or a G1920A mutation. In some embodiments, the JAK2 mutation is a mutant JAK2 protein comprising one or more substitutions include, but are not limited to, V617F, V617I, R683G, N542 E543del, E543 D544del, R683S, R683X, F537 K539delinsL (deletion in frame), K539L, N1108S, R1113H, R1063H, R487C, I540Mfs*3 (deletion-frameshift), R867Q, K539L, G571S, R1113C, R938Q, R228Q, L830*, E1080*, K539L, C618R, R564Q, D1036H, L1088S, H538Nfs*4, D873N, V392M, I682F, L393V, M535I, C618R, T875N, L611V, D319N, L611S, G921S, H538Y, 51035L, and any combination thereof.

In some embodiments, the FBXW7 mutation is a point mutation selected from the group consisting of W244* (*:stop codon), R222*, R278*, E192A, S282*, E113D, R465H/C, 726+1 G>A splice, R505C, R479Q, R465C, R367*, R499Vfs*25 (fs*: frameshift), R658*, D600Y, D520N, D520Y, and any combination thereof. In further embodiments, the FBXW7 mutation is double- or triple-mutation includes, but is not limited to, R479Q and S582L, R465H and S582L, D520N, D520Y and R14Q, and R367* and S582L.

In some embodiments, the CCND3 mutation includes, but is not limited to, S259A, R271Pfs*53 (insertion-caused frameshift), E51*, Q260*, P199S, T283A, T283P, V287D, D286_T288del, R271Gfs*33, Q276*, R241Q, D238G, R33P, 1290K, 1290T, 1290R, P267fs, P284S, P284L, P100S, E253D, S2621, R14W, R114L, D238N, A266E, R167W, and any combination thereof.

In some embodiments, the GNAI1 mutation includes, but is not limited to, Q209L, R183C, T257=, R183C, G208Afs*16, Q209H, R183C, Q209P, Q209R, Q209H, ?T96=, R210W, R256Q, T334=, G48D, S53G, Q209P, R213Q, and any combination thereof. In some embodiments, the GNAI1 mutation has two mutations in exon 4, eg, a mutation in V182 and a mutation in T175, or one or more mutation in exon 5.

3. Combinations with PD-1 and PD-L1 Inhibitors

Programmed death 1 (PD-1) is a 288-amino acid transmembrane immuno checkpoint receptor protein expressed by T cells, B cells, natural killer (NK) T cells, activated monocytes, and dendritic cells. PD-1, which is also known as CD279, belongs to the CD28 family, and in humans is encoded by the Pdcd1 gene on chromosome 2. PD-1 consists of one immunoglobulin (Ig) superfamily domain, a transmembrane region, and an intracellular domain containing an immunoreceptor tyrosine-based inhibitory motif (ITIM) and an immunoreceptor tyrosine-based switch motif (ITSM). PD-1 and its ligands (PD-L1 and PD-L2) are known to play a key role in immune tolerance, as described in Keir, et al., *Annu. Rev. Immunol.* 2008, 26, 677-704. PD-1 provides inhibitory signals that negatively regulate T cell immune responses. PD-L1 (also known as B7-H1 or CD274) and PD-L2 (also known as B7-DC or CD273) are expressed on tumor cells and stromal cells, which may be encountered by activated T cells expressing PD-1, leading to immunosuppression of the T cells. PD-L1 is a 290 amino acid transmembrane protein encoded by the Cd274 gene on human chromosome 9. Blocking the interaction between PD-1 and its ligands PD-L1 and PD-L2 by use of a PD-1 inhibitor, a PD-L1 inhibitor, and/or a PD-L2 inhibitor can overcome immune resistance, as demonstrated in recent clinical studies, such as that described in Topalian, et al., *N. Eng. J Med.* 2012, 366, 2443-54. PD-L1 is expressed on many tumor cell lines, while PD-L2 is expressed is expressed mostly on dendritic cells and a few tumor lines. In addition to T cells (which inducibly express PD-1 after activation), PD-1 is also expressed on B cells, natural killer cells, macrophages, activated monocytes, and dendritic cells.

In some embodiments, TILs and a PD-1 inhibitor are administered as a combination therapy or co-therapy for the treatment of NSCLC.

In some embodiments, the NSCLC has undergone no prior therapy. In some embodiments, a PD-1 inhibitor is administered as a front-line therapy or initial therapy. In some embodiments, a PD-1 inhibitor is administered as a front-line therapy or initial therapy in combination with the TILs as described herein.

In some embodiments, the PD-1 inhibitor may be any PD-1 inhibitor or PD-1 blocker known in the art. In particular, it is one of the PD-1 inhibitors or blockers described in more detail in the following paragraphs. The terms "inhibitor," "antagonist," and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a small molecule compound or a pharmaceutically acceptable salt, ester, solvate, hydrate, cocrystal, or prodrug thereof.

In some embodiments, the PD-1 inhibitor is an antibody (i.e., an anti-PD-1 antibody), a fragment thereof, including Fab fragments, or a single-chain variable fragment (scFv) thereof. In some embodiments the PD-1 inhibitor is a polyclonal antibody. In some embodiments, the PD-1 inhibitor is a monoclonal antibody. In some embodiments, the PD-1 inhibitor competes for binding with PD-1, and/or binds to an epitope on PD-1. In some embodiments, the antibody competes for binding with PD-1, and/or binds to an epitope on PD-1.

In some embodiments, the PD-1 inhibitor is one that binds human PD-1 with a $K_D$ of about 100 μM or lower, binds human PD-1 with a $K_D$ of about 90 μM or lower, binds human PD-1 with a $K_D$ of about 80 μM or lower, binds human PD-1 with a $K_D$ of about 70 μM or lower, binds human PD-1 with a $K_D$ of about 60 μM or lower, binds human PD-1 with a $K_D$ of about 50 μM or lower, binds human PD-1 with a $K_D$ of about 40 μM or lower, binds human PD-1 with a $K_D$ of about 30 μM or lower, binds human PD-1 with a $K_D$ of about 20 μM or lower, binds human PD-1 with a $K_D$ of about 10 μM or lower, or binds human PD-1 with a $K_D$ of about 1 μM or lower.

In some embodiments, the PD-1 inhibitor is one that binds to human PD-1 with a $k_{assoc}$ of about $7.5\times10^5$ 1/M s or faster, binds to human PD-1 with a $k_{assoc}$ of about $7.5\times10^5$ 1/M s or faster, binds to human PD-1 with a $k_{assoc}$ of about $8\times10^5$ 1/M s or faster, binds to human PD-1 with a $k_{assoc}$ of about $8.5\times10^5$ 1/M s or faster, binds to human PD-1 with a $k_{assoc}$ of about $9\times10^5$ 1/M s or faster, binds to human PD-1 with a $k_{assoc}$ of about $9.5\times10^5$ 1/M s or faster, or binds to human PD-1 with a $k_{assoc}$ of about $1\times10^6$ 1/M s or faster.

In some embodiments, the PD-1 inhibitor is one that binds to human PD-1 with a $k_{dissoc}$ of about $2\times10^{-5}$ 1/s or slower, binds to human PD-1 with a $k_{dissoc}$ of about $2.1\times10^{-5}$ 1/s or slower, binds to human PD-1 with a $k_{dissoc}$ of about $2.2\times10^{-5}$ 1/s or slower, binds to human PD-1 with a $k_{dissoc}$ of about $2.3\times10^{-5}$ 1/s or slower, binds to human PD-1 with a $k_{dissoc}$ of about $2.4\times10^{-5}$ 1/s or slower, binds to human PD-1 with a $k_{dissoc}$ of about $2.5\times10^{-5}$ 1/s or slower, binds to human PD-1 with a $k_{dissoc}$ of about $2.6\times10^{-5}$ 1/s or slower or binds to human PD-1 with a $k_{dissoc}$ of about $2.7\times10^{-5}$ 1/s or slower, binds to human PD-1 with a $k_{dissoc}$ of about $2.8\times10^{-5}$ 1/s or slower, binds to human PD-1 with a $k_{dissoc}$ of about $2.9\times10^{-5}$ 1/s or slower, or binds to human PD-1 with a $k_{dissoc}$ of about $3\times10^{-5}$ 1/s or slower.

In some embodiments, the PD-1 inhibitor is one that blocks or inhibits binding of human PD-L1 or human PD-L2 to human PD-1 with an $IC_{50}$ of about 10 nM or lower, blocks or inhibits binding of human PD-L1 or human PD-L2 to human PD-1 with an $IC_{50}$ of about 9 nM or lower, blocks or inhibits binding of human PD-L1 or human PD-L2 to human PD-1 with an $IC_{50}$ of about 8 nM or lower, blocks or inhibits binding of human PD-L1 or human PD-L2 to human PD-1 with an $IC_{50}$ of about 7 nM or lower, blocks or inhibits binding of human PD-L1 or human PD-L2 to human PD-1 with an $IC_{50}$ of about 6 nM or lower, blocks or inhibits binding of human PD-L1 or human PD-L2 to human PD-1 with an $IC_{50}$ of about 5 nM or lower, blocks or inhibits binding of human PD-L1 or human PD-L2 to human PD-1 with an $IC_{50}$ of about 4 nM or lower, blocks or inhibits binding of human PD-L1 or human PD-L2 to human PD-1 with an $IC_{50}$ of about 3 nM or lower, blocks or inhibits binding of human PD-L1 or human PD-L2 to human PD-1 with an $IC_{50}$ of about 2 nM or lower, or blocks or inhibits binding of human PD-L1 or human PD-L2 to human PD-1 with an $IC_{50}$ of about 1 nM or lower.

In some embodiments, the PD-1 inhibitor is nivolumab (commercially available as OPDIVO from Bristol-Myers Squibb Co.), or biosimilars, antigen-binding fragments, conjugates, or variants thereof. Nivolumab is a fully human IgG4 antibody blocking the PD-1 receptor. In some embodiments, the anti-PD-1 antibody is an immunoglobulin G4 kappa, anti-(human CD274) antibody. Nivolumab is assigned Chemical Abstracts Service (CAS) registry number 946414-94-4 and is also known as 5C4, BMS-936558, MDX-1106, and ONO-4538. The preparation and properties of nivolumab are described in U.S. Pat. No. 8,008,449 and International Patent Publication No. WO 2006/121168, the disclosures of which are incorporated by reference herein. The clinical safety and efficacy of nivolumab in various forms of cancer has been described in Wang, et al., *Cancer Immunol Res.* 2014, 2, 846-56; Page, et al., *Ann. Rev Med.,* 2014, 65, 185-202; and Weber, et al., *J Clin. Oncology,* 2013, 31, 4311-4318, the disclosures of which are incorporated by reference herein. The amino acid sequences of nivolumab are set forth in Table 18. Nivolumab has intra-heavy chain disulfide linkages at 22-96,140-196, 254-314, 360-418, 22"-96", 140"-196", 254"-314", and 360"-418"; intra-light chain disulfide linkages at 23'-88', 134'-194', 23'"-88'", and 134'"-194'"; inter-heavy-light chain disulfide linkages at 127-214', 127"-214'", inter-heavy-heavy chain disulfide linkages at 219-219" and 222-222"; and N-glycosylation sites (H $C_H2$ 84.4) at 290, 290".

In some embodiments, a PD-1 inhibitor comprises a heavy chain given by SEQ ID NO:158 and a light chain given by SEQ ID NO:159. In some embodiments, a PD-1 inhibitor comprises heavy and light chains having the sequences shown in SEQ ID NO:158 and SEQ ID NO:159, respectively, or antigen binding fragments, Fab fragments, single-chain variable fragments (scFv), variants, or conjugates thereof. In some embodiments, a PD-1 inhibitor comprises heavy and light chains that are each at least 99% identical to the sequences shown in SEQ ID NO:158 and SEQ ID NO:159, respectively. In some embodiments, a PD-1 inhibitor comprises heavy and light chains that are each at least 98% identical to the sequences shown in SEQ ID NO:158 and SEQ ID NO:159, respectively. In some embodiments, a PD-1 inhibitor comprises heavy and light chains that are each at least 97% identical to the sequences shown in SEQ ID NO:158 and SEQ ID NO:159, respectively. In some embodiments, a PD-1 inhibitor comprises heavy and light chains that are each at least 96% identical to the sequences shown in SEQ ID NO: 158 and SEQ ID NO:159, respectively. In some embodiments, a PD-1 inhibitor comprises heavy and light chains that are each at least 95% identical to the sequences shown in SEQ ID NO:158 and SEQ ID NO:159, respectively.

In some embodiments, the PD-1 inhibitor comprises the heavy and light chain CDRs or variable regions (VRs) of nivolumab. In some embodiments, the PD-1 inhibitor heavy chain variable region ($V_H$) comprises the sequence shown in SEQ ID NO:160, and the PD-1 inhibitor light chain variable region ($V_L$) comprises the sequence shown in SEQ ID NO:161, and conservative amino acid substitutions thereof. In some embodiments, a PD-1 inhibitor comprises $V_H$ and $V_L$ regions that are each at least 99% identical to the sequences shown in SEQ ID NO:160 and SEQ ID NO:161, respectively. In some embodiments, a PD-1 inhibitor comprises $V_H$ and $V_L$ regions that are each at least 98% identical to the sequences shown in SEQ ID NO:160 and SEQ ID NO:161, respectively. In some embodiments, a PD-1 inhibitor comprises $V_H$ and $V_L$ regions that are each at least 97% identical to the sequences shown in SEQ ID NO:160 and SEQ ID NO:161, respectively. In some embodiments, a PD-1 inhibitor comprises $V_H$ and $V_L$ regions that are each at least 96% identical to the sequences shown in SEQ ID NO:160 and SEQ ID NO:161, respectively. In some embodiments, a PD-1 inhibitor comprises $V_H$ and $V_L$ regions that are each at least 95% identical to the sequences shown in SEQ ID NO:160 and SEQ ID NO:161, respectively.

In some embodiments, a PD-1 inhibitor comprises heavy chain CDR1, CDR2 and CDR3 domains having the sequences set forth in SEQ ID NO:162, SEQ ID NO:163, and SEQ ID NO:164, respectively, or conservative amino acid substitutions thereof, and light chain CDR1, CDR2 and CDR3 domains having the sequences set forth in SEQ ID NO:165, SEQ ID NO:166, and SEQ ID NO:167, respectively, or conservative amino acid substitutions thereof. In some embodiments, the antibody competes for binding with, and/or binds to the same epitope on PD-1 as any of the aforementioned antibodies.

In some embodiments, the PD-1 inhibitor is an anti-PD-1 biosimilar monoclonal antibody approved by drug regulatory authorities with reference to nivolumab. In some embodiments, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

TABLE 18

Amino acid sequences for PD-1 inhibitors related to nivolumab.

| Identifier | Sequence (One-Letter Amino Acid Symbols) | |
|---|---|---|
| SEQ ID NO: 158 | QVQLVESGGG VVQPGRSLRL DCKASGITFS NSGMHWVRQA PGKGLEWVAV IWYDGSKRYY | 60 |
| nivolumab | ADSVKGRFTI SRDNSKNTLF LQMNSLRAED TAVYYCATND DYWGQGTLVT VSSASTKGPS | 120 |
| heavy chain | VFPLAPCSRS TSESTAALGC LVKDYFPEPV TVSWNSGALT SGVHTFPAVL QSSGLYSLSS | 180 |

TABLE 18-continued

Amino acid sequences for PD-1 inhibitors related to nivolumab.

| Identifier | Sequence (One-Letter Amino Acid Symbols) | |
|---|---|---|
| | VVTVPSSSLG TKTYTCNVDH KPSNTKVDKR VESKYGPPCP PCPAPEFLGG PSVFLFPPKP | 240 |
| | KDTLMISRTP EVTCVVVDVS QEDPEVQFNW YVDGVEVHNA KTKPREEQFN STYRVVSVLT | 300 |
| | VLHQDWLNGK EYKCKVSNKG LPSSIEKTIS KAKGQPREPQ VYTLPPSQEE MTKNQVSLTC | 360 |
| | LVKGFYPSDI AVEWESNGQP ENNYKTTPPV LDSDGSFFLY SRLTVDKSRW QEGNVFSCSV | 420 |
| | MHEALHNHYT QKSLSLSLGK | 440 |
| SEQ ID NO: 159 nivolumab light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ SSNWPRTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 160 nivolumab variable heavy chain | QVQLVESGGG VVQPGRSLRL DCKASGITFS NSGMHWVRQA PGKGLEWVAV IWYDGSKRYY | 60 |
| | ADSVKGRFTI SRDNSKNTLF LQMNSLRAED TAVYYCATND DYWGQGTLVT VSS | 113 |
| SEQ ID NO: 161 nivolumab variable light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ SSNWPRTFGQ GTKVEIK | 107 |
| SEQ ID NO: 162 nivolumab heavy chain CDR1 | NSGMH | 5 |
| SEQ ID NO: 163 nivolumab heavy chain CDR2 | VIWYDGSKRY YADSVKG | 17 |
| SEQ ID NO: 164 nivolumab heavy chain CDR3 | NDDY | 4 |
| SEQ ID NO: 165 nivolumab light chain CDR1 | RASQSVSSYL A | 11 |
| SEQ ID NO: 166 nivolumab light chain CDR2 | DASNRAT | 7 |
| SEQ ID NO: 167 nivolumab light chain CDR3 | QQSSNWPRT | 9 |

In some embodiments, the PD-i inhibitor is nivolumab or a biosimilar thereof, and the nivolumab is administered at a dose of about 0.5 mg/kg to about 10 mg/kg. In some PP3,N, embodiments, the PD-i inhibitor is nivolumab or a biosimilar thereof, and the nivolumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg.

In some embodiments, the PD-i inhibitor is nivolumab or a biosimilar thereof, and the nivolumab is administered at a dose of about 200 mg to about 500 mg. In some embodiments, the PD-i inhibitor is nivolumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the nivolumab is administered to treat metastatic non-small cell lung cancer. In some embodiments, the nivolumab is administered to treat metastatic non-small cell lung cancer at about 3 mg/kg every 2 weeks along with ipilimumab at about 1 mg/kg every 6 weeks. In some embodiments, the nivolumab is administered to treat metastatic non-small cell lung cancer at about 360 mg every 3 weeks with ipilimumab 1 mg/kg every 6 weeks and 2 cycles of platinum-doublet chemotherapy. In some embodiments, the nivolumab is administered to treat metastatic non-small cell lung cancer at about 240 mg every 2 weeks or 480 mg every 4 weeks.

In some embodiments, the PD-1 inhibitor comprises pembrolizumab (commercially available as KEYTRUDA from Merck & Co., Inc., Kenilworth, NJ, USA), or antigen-binding fragments, conjugates, or variants thereof. Pembrolizumab is assigned CAS registry number 1374853-91-4 and is also known as lambrolizumab, MK-3475, and SCH-900475. Pembrolizumab has an immunoglobulin G4, anti- (human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline(H10-S>P)]γ4 heavy chain (134-218')-disulfide with humanized mouse monoclonal x light chain dimer (226-226":229-229")-bisdisulfide. The properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. The clinical safety and efficacy of pembrolizumab in various forms of cancer is described in Fuerst, Oncology Times, 2014, 36, 35-36; Robert, et al., *Lancet,* 2014, 384, 1109-17; and Thomas, et al., *Exp. Opin. Biol. Ther.,* 2014, 14, 1061-1064. The amino acid sequences of pembrolizumab are set forth in Table 19. Pembrolizumab includes the following disulfide bridges: 22-96, 22"-96", 23'-92', 23'"-92'", 134-218', 134"-218'", 138'-198', 138'-198'", 147-203, 147"-203", 226-226", 229-229", 261-321, 261"-321", 367-425, and 367"-425", and the following glycosylation sites (N): Asn-297 and Asn-297". Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (GOF).

In some embodiments, a PD-1 inhibitor comprises a heavy chain given by SEQ ID NO:168 and a light chain given by SEQ ID NO:169. In some embodiments, a PD-1 inhibitor comprises heavy and light chains having the sequences shown in SEQ ID NO:168 and SEQ ID NO:169, respectively, or antigen binding fragments, Fab fragments, single-chain variable fragments (scFv), variants, or conjugates thereof. In some embodiments, a PD-1 inhibitor comprises heavy and light chains that are each at least 99% identical to the sequences shown in SEQ ID NO:168 and SEQ ID NO:169, respectively. In some embodiments, a PD-1 inhibitor comprises heavy and light chains that are each at least 98% identical to the sequences shown in SEQ ID NO:168 and SEQ ID NO:169, respectively. In some embodiments, a PD-1 inhibitor comprises heavy and light chains that are each at least 97% identical to the sequences shown in SEQ ID NO:168 and SEQ ID NO:169, respectively. In some embodiments, a PD-1 inhibitor comprises heavy and light chains that are each at least 96% identical to the sequences shown in SEQ ID NO: 168 and SEQ ID NO:169, respectively. In some embodiments, a PD-1 inhibitor comprises heavy and light chains that are each at least 95% identical to the sequences shown in SEQ ID NO:168 and SEQ ID NO:169, respectively.

In some embodiments, the PD-1 inhibitor comprises the heavy and light chain CDRs or variable regions (VRs) of pembrolizumab. In some embodiments, the PD-1 inhibitor heavy chain variable region ($V_H$) comprises the sequence shown in SEQ ID NO:170, and the PD-1 inhibitor light chain variable region ($V_L$) comprises the sequence shown in SEQ ID NO:171, or conservative amino acid substitutions thereof. In some embodiments, a PD-1 inhibitor comprises $V_H$ and $V_L$ regions that are each at least 99% identical to the sequences shown in SEQ ID NO:170 and SEQ ID NO:171, respectively. In some embodiments, a PD-1 inhibitor comprises $V_H$ and $V_L$ regions that are each at least 98% identical to the sequences shown in SEQ ID NO:170 and SEQ ID NO:171, respectively. In some embodiments, a PD-1 inhibitor comprises $V_H$ and $V_L$ regions that are each at least 97% identical to the sequences shown in SEQ ID NO:170 and SEQ ID NO:171, respectively. In some embodiments, a PD-1 inhibitor comprises $V_H$ and $V_L$ regions that are each at least 96% identical to the sequences shown in SEQ ID NO:170 and SEQ ID NO:171, respectively. In some embodiments, a PD-1 inhibitor comprises $V_H$ and $V_L$ regions that are each at least 95% identical to the sequences shown in SEQ ID NO:170 and SEQ ID NO:171, respectively.

In some embodiments, a PD-1 inhibitor comprises the heavy chain CDR1, CDR2 and CDR3 domains having the sequences set forth in SEQ ID NO:172, SEQ ID NO:173, and SEQ ID NO:174, respectively, or conservative amino acid substitutions thereof, and light chain CDR1, CDR2 and CDR3 domains having the sequences set forth in SEQ ID NO:175, SEQ ID NO:176, and SEQ ID NO:177, respectively, or conservative amino acid substitutions thereof. In some embodiments, the antibody competes for binding with, and/or binds to the same epitope on PD-1 as any of the aforementioned antibodies.

In some embodiments, the PD-1 inhibitor is an anti-PD-1 biosimilar monoclonal antibody approved by drug regulatory authorities with reference to pembrolizumab. In some embodiments, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

TABLE 19

Amino acid sequences for PD-1 inhibitors related to pembrolizumab.

| Identifier | Sequence (One-Letter Amino Acid Symbols) | |
|---|---|---|
| SEQ ID NO: 168 pembrolizumab heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| | ASTKGPSVFP LAPCSRSTSE STAALGCLVK DYFPEPVTVS WNSGALTSGV HTFPAVLQSS | 180 |
| | GLYSLSSVVT VPSSSLGTKT YTCNVDHKPS NTKVDKRVES KYGPPCPPCP APEFLGGPSV | 240 |
| | FLFPPKPKDT LMISRTPEVT CVVVDVSQED PEVQFNWYVD GVEVHNAKTK PREEQFNSTY | 300 |
| | RVVSVLTVLH QDWLNGKEYK CKVSNKGLPS SIEKTISKAK GQPREPQVYT LPPSQEEMTK | 360 |
| | NQVSLTCLVK GFYPSDIAVE WESNGQPENN YKTTPPVLDS DGSFFLYSRL TVDKSRWQEG | 420 |
| | NVFSCSVMHE ALHNHYTQKS LSLSLGK | 447 |
| SEQ ID NO: 169 pembrolizumab light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI KRTVAAPSVF | 120 |
| | IFPPSDEQLK SGTASVVCLL NNFYPREAKV QWKVDNALQS GNSQESVTEQ DSKDSTYSLS | 180 |
| | STLTLSKADY EKHKVYACEV THQGLSSPVT KSFNRGEC | 218 |
| SEQ ID NO: 170 pembrolizumab variable heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| SEQ ID NO: 171 pembrolizumab variable light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI K | 111 |
| SEQ ID NO: 172 pembrolizumab heavy chain CDR1 | NYYMY | 5 |
| SEQ ID NO: 173 pembrolizumab heavy chain CDR2 | GINPSNGGTN FNEKFK | 16 |
| SEQ ID NO: 174 pembrolizumab heavy chain CDR3 | RDYRFDMGFD Y | 11 |
| SEQ ID NO: 175 pembrolizumab light chain CDR1 | RASKGVSTSG YSYLH | 15 |
| SEQ ID NO: 176 pembrolizumab light chain CDR2 | LASYLES | 7 |
| SEQ ID NO: 177 pembrolizumab light chain CDR3 | QHSRDLPLT | 9 |

In some embodiments, the PD-i inhibitor is pembrolizumab or a biosimilar thereof, and the pembrolizumab is administered at a dose of about 0.5 mg/kg to about 10 mg/kg. In some embodiments, the PD-i inhibitor is pembrolizumab or a biosimilar thereof, and the pembrolizumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg.

In some embodiments, the PD-i inhibitor is pembrolizumab or a biosimilar thereof, wherein the pembrolizumab is administered at a dose of about 200 mg to about 500 mg. In some embodiments, the PD-i inhibitor is pembrolizumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the PD-1 inhibitor is pembrolizumab or a biosimilar thereof, wherein the pembrolizumab is administered every 2 weeks, every 3 weeks, every 4 weeks, every 5 weeks, or every 6 weeks.

In some embodiments, the pembrolizumab is administered to treat NSCLC. In some embodiments, the pembrolizumab is administered to treat NSCLC at about 200 mg every 3 weeks. In some embodiments, the pembrolizumab is administered to treat NSCLC at about 400 mg every 6 weeks.

In some embodiments, if the patient or subject is an adult, i.e., treatment of adult indications, and additional dosing regimen of 400 mg every 6 weeks can be employed.

In some embodiments, the PD-1 inhibitor is a commercially-available anti-PD-1 monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

In some embodiments, the PD-1 inhibitor is an antibody disclosed in U.S. Pat. No. 8,354,509 or U.S. Patent Application Publication Nos. 2010/0266617 A1, 2013/0108651 A1, 2013/0109843 A2, the disclosures of which are incorporated by reference herein. In some embodiments, the PD-1 inhibitor is an anti-PD-1 antibody described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In some embodiments, the PD-1 inhibitor is an anti-PD-1 antibody disclosed in U.S. Pat. No. 8,735,553 B1, the disclosure of which is incorporated herein by reference. In some embodiments, the PD-1 inhibitor is pidilizumab, also known as CT-011, which is described in U.S. Pat. No. 8,686,119, the disclosure of which is incorporated by reference herein.

In some embodiments, the PD-1 inhibitor may be a small molecule or a peptide, or a peptide derivative, such as those described in U.S. Pat. Nos. 8,907,053; 9,096,642; and 9,044,442 and U.S. Patent Application Publication No. US 2015/0087581; 1,2,4-oxadiazole compounds and derivatives such as those described in U.S. Patent Application Publication No. 2015/0073024; cyclic peptidomimetic compounds and derivatives such as those described in U.S. Patent Application Publication No. US 2015/0073042; cyclic compounds and derivatives such as those described in U.S. Patent Application Publication No. US 2015/0125491; 1,3,4-oxadiazole and 1,3,4-thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. US 2014/0294898; the disclosures of each of which are hereby incorporated by reference in their entireties.

In some embodiments, TILs and a PD-L1 inhibitor or a PD-L2 inhibitor are administered as a combination therapy or co-therapy for the treatment of NSCLC.

In some embodiments, the NSCLC has undergone no prior therapy. In some embodiments, a PD-L1 inhibitor or a PD-L2 inhibitor is administered as a front-line therapy or initial therapy. In some embodiments, a PD-L1 inhibitor or a PD-L2 inhibitor is administered as a front-line therapy or initial therapy in combination with the TILs as described herein.

In some embodiments, the PD-L1 or PD-L2 inhibitor may be any PD-L1 or PD-L2 inhibitor, antagonist, or blocker known in the art. In particular, it is one of the PD-L1 or PD-L2 inhibitors, antagonist, or blockers described in more detail in the following paragraphs. The terms "inhibitor,". "antagonist," and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions, processes and methods described herein include a PD-L1 or PD-L2 inhibitor. In some embodiments, the PD-L1 or PD-L2 inhibitor is a small molecule. In some embodiments, the PD-L1 or PD-L2 inhibitor is an antibody (i.e., an anti-PD-1 antibody), a fragment thereof, including Fab fragments, or a single-chain variable fragment (scFv) thereof. In some embodiments the PD-L1 or PD-L2 inhibitor is a polyclonal antibody. In some embodiments, the PD-L1 or PD-L2 inhibitor is a monoclonal antibody. In some embodiments, the PD-L1 or PD-L2 inhibitor competes for binding with PD-L1 or PD-L2, and/or binds to an epitope on PD-L1 or PD-L2. In some embodiments, the antibody competes for binding with PD-L1 or PD-L2, and/or binds to an epitope on PD-L1 or PD-L2.

In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L1 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L2 receptor.

In some embodiments, the PD-L2 inhibitors provided herein are selective for PD-L2, in that the compounds bind or interact with PD-L2 at substantially lower concentrations than they bind or interact with other receptors, including the PD-L1 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In some embodiments, the tumor cells express PD-L1. In some embodiments, the tumor cells do not express PD-L1. In some embodiments, the methods can include a combination of a PD-1 and a PD-L1 antibody, such as those described herein, in combination with a TIL. The administration of a combination of a PD-1 and a PD-L1 antibody and a TIL may be simultaneous or sequential.

In some embodiments, the PD-L1 and/or PD-L2 inhibitor is one that binds human PD-L1 and/or PD-L2 with a $K_D$ of about 100 μM or lower, binds human PD-L1 and/or PD-L2 with a $K_D$ of about 90 μM or lower, binds human PD-L1 and/or PD-L2 with a $K_D$ of about 80 μM or lower, binds human PD-L1 and/or PD-L2 with a $K_D$ of about 70 μM or lower, binds human PD-L1 and/or PD-L2 with a $K_D$ of about 60 μM or lower, a $K_D$ of about 50 μM or lower, binds human PD-L1 and/or PD-L2 with a $K_D$ of about 40 μM or lower, or binds human PD-L1 and/or PD-L2 with a $K_D$ of about 30 μM or lower, In some embodiments, the PD-L1 and/or PD-L2 inhibitor is one that binds to human PD-L1 and/or PD-L2 with a $k_{assoc}$ of about $7.5\times10^5$ 1/M s or faster, binds to human PD-L1 and/or PD-L2 with a $k_{assoc}$ of about $8\times10^5$ 1/M s or faster, binds to human PD-L1 and/or PD-L2 with a $k_{assoc}$ of about $8.5\times10^5$ 1/M s or faster, binds to human PD-L1 and/or PD-L2 with a $k_{assoc}$ of about $9\times10^5$ 1/M s or faster, binds to human PD-L1 and/or PD-L2 with a $k_{assoc}$ of about $9.5\times10^5$ 1/M s and/or faster, or binds to human PD-L1 and/or PD-L2 with a $k_{assoc}$ of about $1\times10^6$ 1/M s or faster.

In some embodiments, the PD-L1 and/or PD-L2 inhibitor is one that binds to human PD-L1 or PD-L2 with a $k_{dissoc}$ of about $2\times10^{-5}$ 1/s or slower, binds to human PD-1 with a $k_{dissoc}$ of about $2.1\times10^{-5}$ 1/s or slower, binds to human PD-1 with a $k_{dissoc}$ of about $2.2\times10^{-5}$ 1/s or slower, binds to human PD-1 with a $k_{dissoc}$ of about $2.3\times10^{-5}$ 1/s or slower, binds to human PD-1 with a $k_{dissoc}$ of about $2.4\times10^{-5}$ 1/s or slower, binds to human PD-1 with a $k_{dissoc}$ of about $2.5\times10^{-5}$ 1/s or slower, binds to human PD-1 with a $k_{dissoc}$ of about $2.6\times10^{-5}$ 1/s or slower, binds to human PD-L1 or PD-L2 with a $k_{dissoc}$ of about $2.7\times10^{-5}$ 1/s or slower, or binds to human PD-L1 or PD-L2 with a $k_{dissoc}$ of about $3\times10^{-5}$ 1/s or slower.

In some embodiments, the PD-L1 and/or PD-L2 inhibitor is one that blocks or inhibits binding of human PD-L1 or human PD-L2 to human PD-1 with an $IC_{50}$ of about 10 nM or lower; blocks or inhibits binding of human PD-L1 or human PD-L2 to human PD-1 with an $IC_{50}$ of about 9 nM or lower; blocks or inhibits binding of human PD-L1 or human PD-L2 to human PD-1 with an $IC_{50}$ of about 8 nM or lower; blocks or inhibits binding of human PD-L1 or human PD-L2 to human PD-1 with an $IC_{50}$ of about 7 nM or lower; blocks or inhibits binding of human PD-L1 or human PD-L2 to human PD-1 with an $IC_{50}$ of about 6 nM or lower; blocks or inhibits binding of human PD-L1 or human PD-L2 to human PD-1 with an $IC_{50}$ of about 5 nM or lower; blocks or inhibits binding of human PD-L1 or human PD-L2 to human PD-1 with an $IC_{50}$ of about 4 nM or lower; blocks or inhibits binding of human PD-L1 or human PD-L2 to human PD-1 with an $IC_{50}$ of about 3 nM or lower; blocks or inhibits binding of human PD-L1 or human PD-L2 to human PD-1 with an $IC_{50}$ of about 2 nM or lower; or blocks human PD-1, or blocks binding of human PD-L1 or human PD-L2 to human PD-1 with an $IC_{50}$ of about 1 nM or lower.

In some embodiments, the PD-L1 inhibitor is durvalumab, also known as MED14736 (which is commercially available from Medimmune, LLC, Gaithersburg, Maryland, a subsidiary of AstraZeneca plc.), or antigen-binding fragments, conjugates, or variants thereof. In some embodiments, the PD-L1 inhibitor is an antibody disclosed in U.S. Pat. No. 8,779,108 or U.S. Patent Application Publication No. 2013/0034559, the disclosures of which are incorporated by reference herein. The clinical efficacy of durvalumab has been described in Page, et al., *Ann. Rev Med.*, 2014, 65, 185-202; Brahmer, et al., *J Clin. Oncol.* 2014, 32, 5s (supplement, abstract 8021); and McDermott, et al., *Cancer Treatment Rev*, 2014, 40, 1056-64. The preparation and properties of durvalumab are described in U.S. Pat. No. 8,779,108, the disclosure of which is incorporated by reference herein. The amino acid sequences of durvalumab are set forth in Table 20. The durvalumab monoclonal antibody includes disulfide linkages at 22-96, 22"-96", 23'-89', 23'"-89'", 135'-195', 135'-195'", 148-204, 148"-204", 215'-224, 215'"-224", 230-230", 233-233", 265-325, 265"-325", 371-429, and 371"-429'; and N-glycosylation sites at Asn-301 and Asn-301".

In some embodiments, a PD-L1 inhibitor comprises a heavy chain given by SEQ ID NO:178 and a light chain given by SEQ ID NO:179. In some embodiments, a PD-L1 inhibitor comprises heavy and light chains having the sequences shown in SEQ ID NO:178 and SEQ ID NO:179, respectively, or antigen binding fragments, Fab fragments, single-chain variable fragments (scFv), variants, or conjugates thereof. In some embodiments, a PD-L1 inhibitor comprises heavy and light chains that are each at least 99% identical to the sequences shown in SEQ ID NO:178 and SEQ ID NO:179, respectively. In some embodiments, a PD-L1 inhibitor comprises heavy and light chains that are each at least 98% identical to the sequences shown in SEQ ID NO:178 and SEQ ID NO:179, respectively. In some embodiments, a PD-L1 inhibitor comprises heavy and light chains that are each at least 97% identical to the sequences shown in SEQ ID NO: 178 and SEQ ID NO:179, respectively.

In some embodiments, a PD-L1 inhibitor comprises heavy and light chains that are each at least 96% identical to the sequences shown in SEQ ID NO:178 and SEQ ID NO:179, respectively. In some embodiments, a PD-L1 inhibitor comprises heavy and light chains that are each at least 95% identical to the sequences shown in SEQ ID NO:178 and SEQ ID NO:179, respectively.

In some embodiments, the PD-L1 inhibitor comprises the heavy and light chain CDRs or variable regions (VRs) of durvalumab. In some embodiments, the PD-L1 inhibitor heavy chain variable region ($V_H$) comprises the sequence shown in SEQ ID NO:180, and the PD-L1 inhibitor light chain variable region ($V_L$) comprises the sequence shown in SEQ ID NO:181, or conservative amino acid substitutions thereof. In some embodiments, a PD-L1 inhibitor comprises $V_H$ and $V_L$ regions that are each at least 99% identical to the sequences shown in SEQ ID NO:180 and SEQ ID NO:181, respectively. In some embodiments, a PD-L1 inhibitor comprises $V_H$ and $V_L$ regions that are each at least 98% identical to the sequences shown in SEQ ID NO:180 and SEQ ID NO:181, respectively. In some embodiments, a PD-L1 inhibitor comprises $V_H$ and $V_L$ regions that are each at least 97% identical to the sequences shown in SEQ ID NO:180 and SEQ ID NO:181, respectively. In some embodiments, a PD-L1 inhibitor comprises $V_H$ and $V_L$ regions that are each at least 96% identical to the sequences shown in SEQ ID NO:180 and SEQ ID NO:181, respectively. In some embodiments, a PD-L1 inhibitor comprises $V_H$ and $V_L$ regions that are each at least 95% identical to the sequences shown in SEQ ID NO:180 and SEQ ID NO:181, respectively.

In some embodiments, a PD-L1 inhibitor comprises heavy chain CDR1, CDR2 and CDR3 domains having the sequences set forth in SEQ ID NO:182, SEQ ID NO:183, and SEQ ID NO:184, respectively, or conservative amino acid substitutions thereof, and light chain CDR1, CDR2 and CDR3 domains having the sequences set forth in SEQ ID NO:185, SEQ ID NO:186, and SEQ ID NO:187, respectively, or conservative amino acid substitutions thereof. In some embodiments, the antibody competes for binding with, and/or binds to the same epitope on PD-L1 as any of the aforementioned antibodies.

In some embodiments, the PD-L1 inhibitor is an anti-PD-L1 biosimilar monoclonal antibody approved by drug regulatory authorities with reference to durvalumab. In some embodiments, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

TABLE 20

Amino acid sequences for PD-L1 inhibitors related to durvalumab.

| Identifier | Sequence (One-Letter Amino Acid Symbols) | |
|---|---|---|
| SEQ ID NO: 178<br>durvalumab<br>heavy chain | EVQLVESGGG LVQPGGSLRL SCAASGFTFS RYWMSWVRQA PGKGLEWVAN IKQDGSEKYY<br>VDSVKGRFTI SRDNAKNSLY LQMNSLRAED TAVYYCAREG GWFGELAFDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPEFEG<br>GPSVFLFPPK PKDTLMISRT PEVTCVVVDV SHEDPEVKEN WYVDGVEVHN AKTKPREEQY<br>NSTYRVVSVL TVLHQDWLNG KEYKCKVSNK ALPASIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 179<br>durvalumab<br>light chain | EVQLVESGGG LVQPGGSLRL SCAASGFTFS RYWMSWVRQA PGKGLEWVAN EIVLTQSPGT<br>LSLSPGERAT LSCRASQRVS SSYLAWYQQK PGQAPRLLIY DASSRATGIP DRFSGSGSGT<br>DFTLTISRLE PEDFAVYYCQ QYGSLPWTFG QGTKVEIKRT VAAPSVFIFP PSDEQLKSGT<br>ASVVCLLNNF YPREAKVQWK VDNALQSGNS QESVTEQDSK DSTYSLSSTL TLSKADYEKH<br>KVYACEVTHQ GLSSPVTKSF NRGEC | 60<br>120<br>180<br>240<br>265 |
| SEQ ID NO: 180<br>durvalumab<br>variable<br>heavy chain | EVQLVESGGG LVQPGGSLRL SCAASGFTFS RYWMSWVRQA PGKGLEWVAN IKQDGSEKYY<br>VDSVKGRFTI SRDNAKNSLY LQMNSLRAED TAVYYCAREG GWFGELAFDY WGQGTLVTVS<br>S | 60<br>120<br>121 |
| SEQ ID NO: 181<br>durvalumab<br>variable<br>light chain | EIVLTQSPGT LSLSPGERAT LSCRASQRVS SSYLAWYQQK PGQAPRLLIY DASSRATGIP<br>DRFSGSGSGT DFTLTISRLE PEDFAVYYCQ QYGSLPWTFG QGTKVEIK | 60<br>108 |
| SEQ ID NO: 182<br>durvalumab<br>heavy chain<br>CDR1 | RYWMS | 5 |
| SEQ ID NO: 183<br>durvalumab<br>heavy chain<br>CDR2 | NIKQDGSEKY YVDSVKG | 17 |
| SEQ ID NO: 184<br>durvalumab<br>heavy chain<br>CDR3 | EGGWFGELAF DY | 12 |
| SEQ ID NO: 185<br>durvalumab<br>light chain<br>CDR1 | RASQRVSSSY LA | 12 |
| SEQ ID NO: 186<br>durvalumab<br>light chain<br>CDR2 | DASSRAT | 7 |
| SEQ ID NO: 187<br>durvalumab<br>light chain<br>CDR3 | QQYGSLPWT | 9 |

In some embodiments, the PD-Li inhibitor is avelumab, also known as MSB0010718C (commercially available from Merck KGaA/EMD Serono), or antigen-binding fragments, conjugates, or variants thereof. The preparation and properties of avelumab are described in U.S. Patent Application Publication No. US 2014/0341917 A1, the disclosure of which is specifically incorporated by reference herein. The amino acid sequences of avelumab are set forth in Table 21. Avelumab has intra-heavy chain disulfide linkages (C23-C104) at 22-96, 147-203, 264-324, 370-428, 22"-96", 147"-203", 264"-324", and 370"-428"; intra-light chain disulfide linkages (C23-C104) at 22'-90', 138'-197', 22"-90"', and 138'-197"'; intra-heavy-light chain disulfide linkages (h 5-$C_L$ 126) at 223-215' and 223"-215"'; intra-heavy-heavy chain disulfide linkages (h 11, h 14) at 229-229" and 232-232"; N-glycosylation sites (H $C_H$2 N84.4) at 300, 300"; fucosylated complex bi-antennary CHO-type glycans; and H CHS K2 C-terminal lysine clipping at 450 and 450'.

In some embodiments, a PD-L1 inhibitor comprises a heavy chain given by SEQ ID NO:188 and a light chain given by SEQ ID NO:189. In some embodiments, a PD-L1 inhibitor comprises heavy and light chains having the sequences shown in SEQ ID NO:188 and SEQ ID NO:189, respectively, or antigen binding fragments, Fab fragments, single-chain variable fragments (scFv), variants, or conjugates thereof. In some embodiments, a PD-L1 inhibitor comprises heavy and light chains that are each at least 99% identical to the sequences shown in SEQ ID NO:188 and SEQ ID NO:189, respectively. In some embodiments, a PD-L1 inhibitor comprises heavy and light chains that are each at least 98% identical to the sequences shown in SEQ ID NO:188 and SEQ ID NO:189, respectively. In some embodiments, a PD-L1 inhibitor comprises heavy and light chains that are each at least 97% identical to the sequences shown in SEQ ID NO: 188 and SEQ ID NO:189, respectively. In some embodiments, a PD-L1 inhibitor comprises heavy and light chains that are each at least 96% identical to the sequences shown in SEQ ID NO:188 and SEQ ID NO:189, respectively. In some embodiments, a PD-L1 inhibitor comprises heavy and light chains that are each at least 95% identical to the sequences shown in SEQ ID NO:188 and SEQ ID NO:189, respectively.

In some embodiments, the PD-L1 inhibitor comprises the heavy and light chain CDRs or variable regions (VRs) of avelumab. In some embodiments, the PD-L1 inhibitor heavy chain variable region ($V_H$) comprises the sequence shown in SEQ ID NO:190, and the PD-L1 inhibitor light chain variable region ($V_L$) comprises the sequence shown in SEQ ID NO:191, or conservative amino acid substitutions thereof. In some embodiments, a PD-L1 inhibitor comprises $V_H$ and $V_L$ regions that are each at least 99% identical to the sequences shown in SEQ ID NO:190 and SEQ ID NO:191, respectively. In some embodiments, a PD-L1 inhibitor comprises $V_H$ and $V_L$ regions that are each at least 98% identical to the sequences shown in SEQ ID NO:190 and SEQ ID NO:191, respectively. In some embodiments, a PD-L1 inhibitor comprises $V_H$ and $V_L$ regions that are each at least 97% identical to the sequences shown in SEQ ID NO:190 and SEQ ID NO:191, respectively. In some embodiments, a PD-L1 inhibitor comprises $V_H$ and $V_L$ regions that are each at least 96% identical to the sequences shown in SEQ ID NO: 190 and SEQ ID NO:191, respectively. In some embodiments, a PD-L1 inhibitor comprises $V_H$ and $V_L$ regions that are each at least 95% identical to the sequences shown in SEQ ID NO: 190 and SEQ ID NO:191, respectively.

In some embodiments, a PD-L1 inhibitor comprises heavy chain CDR1, CDR2 and CDR3 domains having the sequences set forth in SEQ ID NO:192, SEQ ID NO:193, and SEQ ID NO:194, respectively, or conservative amino acid substitutions thereof, and light chain CDR1, CDR2 and CDR3 domains having the sequences set forth in SEQ ID NO:195, SEQ ID NO:196, and SEQ ID NO:197, respectively, or conservative amino acid substitutions thereof. In some embodiments, the antibody competes for binding with, and/or binds to the same epitope on PD-L1 as any of the aforementioned antibodies.

In some embodiments, the PD-L1 inhibitor is an anti-PD-L1 biosimilar monoclonal antibody approved by drug regulatory authorities with reference to avelumab. In some embodiments, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

TABLE 21

Amino acid sequences for PD-L1 inhibitors related to avelumab.

| Identifier | Sequence (One-Letter Amino Acid Symbols) | |
|---|---|---|
| SEQ ID NO: 188 avelumab heavy chain | EVQLLESGGG LVQPGGSLRL SCAASGFTFS SYIMMWVRQA PGKGLEWVSS IYPSGGITFY | 60 |
| | ADTVKGRFTI SRDNSKNTLY LQMNSLRAED TAVYYCARIK LGTVTTVDYW GQGTLVTVSS | 120 |
| | ASTKGPSVFP LAPSSKSTSG GTAALGCLVK DYFPEPVTVS WNSGALTSGV HTFPAVLQSS | 180 |
| | GLYSLSSVVT VPSSSLGTQT YICNVNHKPS NTKVDKKVEP KSCDKTHTCP PCPAPELLGG | 240 |

TABLE 21-continued

Amino acid sequences for PD-L1 inhibitors related to avelumab.

| Identifier | Sequence (One-Letter Amino Acid Symbols) | |
|---|---|---|
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 189 avelumab light chain | QSALTQPASV SGSPGQSITI SCTGTSSDVG GYNYVSWYQQ HPGKAPKLMI YDVSNRPSGV | 60 |
| | SNRFSGSKSG NTASLTISGL QAEDEADYYC SSYTSSSTRV FGTGTKVTVL GQPKANPTVT | 120 |
| | LFPPSSEELQ ANKATLVCLI SDFYPGAVTV AWKADGSPVK AGVETTKPSK QSNNKYAASS | 180 |
| | YLSLTPEQWK SHRSYSCQVT HEGSTVEKTV APTECS | 216 |
| SEQ ID NO: 190 avelumab variable heavy chain | EVQLLESGGG LVQPGGSLRL SCAASGFTFS SYIMMWVRQA PGKGLEWVSS IYPSGGITFY | 60 |
| | ADTVKGRFTI SRDNSKNTLY LQMNSLRAED TAVYYCARIK LGTVTTVDYW GQGTLVTVSS | 120 |
| SEQ ID NO: 191 avelumab variable light chain | QSALTQPASV SGSPGQSITI SCTGTSSDVG GYNYVSWYQQ HPGKAPKLMI YDVSNRPSGV | 60 |
| | SNRFSGSKSG NTASLTISGL QAEDEADYYC SSYTSSSTRV FGTGTKVTVL | 110 |
| SEQ ID NO: 192 avelumab heavy chain CDR1 | SYIMM | 5 |
| SEQ ID NO: 193 avelumab heavy chain CDR2 | SIYPSGGITF YADTVKG | 17 |
| SEQ ID NO: 194 avelumab heavy chain CDR3 | IKLGTVTTVD Y | 11 |
| SEQ ID NO: 195 avelumab light chain CDR1 | TGTSSDVGGY NYVS | 14 |
| SEQ ID NO: 196 avelumab light chain CDR2 | DVSNRPS | 7 |
| SEQ ID NO: 197 avelumab light chain CDR3 | SSYTSSSTRV | 10 |

In some embodiments, the PD-Li inhibitor is atezolizumab, also known as MPDL3280A or RG7446 (commercially available as TECENTRIQ from Genentech, Inc., a subsidiary of Roche Holding AG, Basel, Switzerland), or antigen-binding fragments, conjugates, or variants thereof. In some embodiments, the PD-Li inhibitor is an antibody disclosed in U.S. Pat. No. 8,217,149, the disclosure of which is specifically incorporated by reference herein. In some embodiments, the PD-Li inhibitor is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The preparation and properties of atezolizumab are described in U.S. Pat. No. 8,217,149, the disclosure of which is incorporated by reference herein. The amino acid sequences of atezolizumab are set forth in Table 22. Atezolizumab has intra-heavy chain disulfide linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'"-88'", and 134"-194'"; intra-heavy-light chain disulfide linkages (h 5-$C_L$ 126) at 221-214' and 221"-214'"; intra-heavy-heavy chain disulfide linkages (h 11, h 14) at 227-227" and 230-230"; and N-glycosylation sites (H $C_H$2 N84.4>A) at 298 and 298'.

In some embodiments, a PD-L1 inhibitor comprises a heavy chain given by SEQ ID NO:198 and a light chain given by SEQ ID NO:199. In some embodiments, a PD-L1 inhibitor comprises heavy and light chains having the sequences shown in SEQ ID NO:198 and SEQ ID NO:199, respectively, or antigen binding fragments, Fab fragments, single-chain variable fragments (scFv), variants, or conjugates thereof. In some embodiments, a PD-L1 inhibitor comprises heavy and light chains that are each at least 99% identical to the sequences shown in SEQ ID NO:198 and SEQ ID NO:199, respectively. In some embodiments, a PD-L1 inhibitor comprises heavy and light chains that are each at least 98% identical to the sequences shown in SEQ ID NO:198 and SEQ ID NO:199, respectively. In some embodiments, a PD-L1 inhibitor comprises heavy and light chains that are each at least 97% identical to the sequences shown in SEQ ID NO: 198 and SEQ ID NO:199, respectively. In some embodiments, a PD-L1 inhibitor comprises heavy and light chains that are each at least 96% identical to the sequences shown in SEQ ID NO:198 and SEQ ID NO:199, respectively. In some embodiments, a PD-L1 inhibitor comprises heavy and light chains that are each at least 95% identical to the sequences shown in SEQ ID NO:198 and SEQ ID NO:199, respectively.

In some embodiments, the PD-L1 inhibitor comprises the heavy and light chain CDRs or variable regions (VRs) of atezolizumab. In some embodiments, the PD-L1 inhibitor heavy chain variable region ($V_H$) comprises the sequence shown in SEQ ID NO:200, and the PD-L1 inhibitor light chain variable region ($V_L$) comprises the sequence shown in SEQ ID NO:201, or conservative amino acid substitutions thereof. In some embodiments, a PD-L1 inhibitor comprises $V_H$ and $V_L$ regions that are each at least 99% identical to the sequences shown in SEQ ID NO:200 and SEQ ID NO:201, respectively. In some embodiments, a PD-L1 inhibitor comprises $V_H$ and $V_L$ regions that are each at least 98% identical to the sequences shown in SEQ ID NO:200 and SEQ ID NO:201, respectively. In some embodiments, a PD-L1 inhibitor comprises $V_H$ and $V_L$ regions that are each at least 97% identical to the sequences shown in SEQ ID NO:200 and SEQ ID NO:201, respectively. In some embodiments, a PD-L1 inhibitor comprises $V_H$ and $V_L$ regions that are each at least 96% identical to the sequences shown in SEQ ID NO:200 and SEQ ID NO:201, respectively. In some embodiments, a PD-L1 inhibitor comprises $V_H$ and $V_L$ regions that are each at least 95% identical to the sequences shown in SEQ ID NO:200 and SEQ ID NO:201, respectively.

In some embodiments, a PD-L1 inhibitor comprises heavy chain CDR1, CDR2 and CDR3 domains having the sequences set forth in SEQ ID NO:202, SEQ ID NO:203, and SEQ ID NO:204, respectively, or conservative amino acid substitutions thereof, and light chain CDR1, CDR2 and CDR3 domains having the sequences set forth in SEQ ID NO:205, SEQ ID NO:206, and SEQ ID NO:207, respectively, or conservative amino acid substitutions thereof. In some embodiments, the antibody competes for binding with, and/or binds to the same epitope on PD-L1 as any of the aforementioned antibodies.

In some embodiments, the anti-PD-L1 antibody is an anti-PD-L1 biosimilar monoclonal antibody approved by drug regulatory authorities with reference to atezolizumab. In some embodiments, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab.

TABLE 22. Amino acid sequences for PD-L1 inhibitors related to atezolizumab.

TABLE 22

Amino acid sequences for PD-L1 inhibitors related to atezolizumab.

| Identifier | Sequence (One-Letter Amino Acid Symbols) | |
|---|---|---|
| SEQ ID NO: 198 atezolizumab heavy chain | EVQLVESGGG LVQPGGSLRL SCAASGFTFS DSWIHWVRQA PGKGLEWVAW ISPYGGSTYY | 60 |
| | ADSVKGRFTI SADTSKNTAY LQMNSLRAED TAVYYCARRH WPGGFDYWGQ GTLVTVSSAS | 120 |
| | TKGPSVFPLA PSSKSTSGGT AALGCLVKDY FPEPVTVSWN SGALTSGVHT FPAVLQSSGL | 180 |
| | YSLSSVVTVP SSSLGTQTYI CNVNHKPSNT KVDKKVEPKS CDKTHTCPPC PAPELLGGPS | 240 |
| | VFLFPPKPKD TLMISRTPEV TCVVVDVSHE DPEVKFNWYV DGVEVHNAKT KPREEQYAST | 300 |
| | YRVVSVLTVL HQDWLNGKEY KCKVSNKALP APIEKTISKA KGQPREPQVY TLPPSREEMT | 360 |
| | KNQVSLTCLV KGFYPSDIAV EWESNGQPEN NYKTTPPVLD SDGSFFLYSK LTVDKSRWQQ | 420 |
| | GNVFSCSVMH EALHNHYTQK SLSLSPGK | 448 |
| SEQ ID NO: 199 atezolizumab light chain | DIQMTQSPSS LSASVGDRVT ITCRASQDVS TAVAWYQQKP GKAPKLLIYS ASFLYSGVPS | 60 |
| | RFSGSGSGTD FTLTISSLQP EDFATYYCQQ YLYHPATFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 200 atezolizumab variable heavy chain | EVQLVESGGG LVQPGGSLRL SCAASGFTFS DSWIHWVRQA PGKGLEWVAW ISPYGGSTYY | 60 |
| | ADSVKGRFTI SADTSKNTAY LQMNSLRAED TAVYYCARRH WPGGFDYWGQ GTLVTVSA | 118 |
| SEQ ID NO: 201 atezolizumab variable light chain | DIQMTQSPSS LSASVGDRVT ITCRASQDVS TAVAWYQQKP GKAPKLLIYS ASFLYSGVPS | 60 |
| | RFSGSGSGTD FTLTISSLQP EDFATYYCQQ YLYHPATFGQ GTKVEIKR | 108 |

TABLE 22-continued

| Amino acid sequences for PD-L1 inhibitors related to atezolizumab. | | |
|---|---|---|
| Identifier | Sequence (One-Letter Amino Acid Symbols) | |
| SEQ ID NO: 202 atezolizumab heavy chain CDR1 | GFTFSDSWIH | 10 |
| SEQ ID NO: 203 atezolizumab heavy chain CDR2 | AWISPYGGST YYADSVKG | 18 |
| SEQ ID NO: 204 atezolizumab heavy chain CDR3 | RHWPGGFDY | 9 |
| SEQ ID NO: 205 atezolizumab light chain CDR1 | RASQDVSTAV A | 11 |
| SEQ ID NO: 206 atezolizumab light chain CDR2 | SASFLYS | 7 |
| SEQ ID NO: 207 atezolizumab light chain CDR3 | QQYLYHPAT | 9 |

In some embodiments, PD-L1 inhibitors include those antibodies described in U.S. Patent Application Publication No. US 2014/0341917 A1, the disclosure of which is incorporated by reference herein. In some embodiments, antibodies that compete with any of these antibodies for binding to PD-L1 are also included. In some embodiments, the anti-PD-L1 antibody is MDX-1105, also known as BMS-935559, which is disclosed in U.S. Pat. No. 7,943,743, the disclosures of which are incorporated by reference herein. In some embodiments, the anti-PD-L1 antibody is selected from the anti-PD-L1 antibodies disclosed in U.S. Pat. No. 7,943,743, which are incorporated by reference herein.

In some embodiments, the PD-L1 inhibitor is a commercially-available monoclonal antibody, such as INVIVOMAB anti-m-PD-L1 clone IOF.9G2 (Catalog #BE0101, Bio X Cell, Inc., West Lebanon, NH, USA). In some embodiments, the anti-PD-L1 antibody is a commercially-available monoclonal antibody, such as AFFYMETRIX EBIOSCIENCE (MIH1). Anumber of commercially-available anti-PD-L1 antibodies are known to one of ordinary skill in the art.

In some embodiments, the PD-L2 inhibitor is a commercially-available monoclonal antibody, such as BIOLEGEND 24F.10C12 Mouse IgG2a, x isotype (catalog #329602 Biolegend, Inc., San Diego, CA), SIGMA anti-PD-L2 antibody (catalog #SAB3500395, Sigma-Aldrich Co., St. Louis, MO), or other commercially-available anti-PD-L2 antibodies known to one of ordinary skill in the art.

4. Combinations with CTLA-4 Inhibitors

In some embodiments, TILs and a CTLA-4 inhibitor are administered as a combination therapy or co-therapy for the treatment of NSCLC.

In some embodiments, the NSCLC has undergone no prior therapy. In some embodiments, the CTLA-4 inhibitor is administered as a front-line therapy or initial therapy. In some embodiments, the CTLA-4 inhibitor is administered as a front-line therapy or initial therapy in combination with the TILs as described herein.

Cytotoxic T lymphocyte antigen 4 (CTLA-4) is a member of the immunoglobulin superfamily and is expressed on the surface of helper T cells. CTLA-4 is a negative regulator of CD28-dependent T cell activation and acts as a checkpoint for adaptive immune responses. Similar to the T cell costimulatory protein CD28, the CTLA-4 binding antigen presents CD80 and CD86 on the cells. CTLA-4 delivers a suppressor signal to T cells, while CD28 delivers a stimulus signal. Human antibodies against human CTLA-4 have been described as immunostimulatory modulators in many disease conditions, such as treating or preventing viral and bacterial infections and for treating cancer (WO 01/14424 and WO 00/37504). Various preclinical studies have shown that CTLA-4 blockade by CTLA-4 inhibitors such as monoclonal antibodies enhances host immune responses against immunogenic tumors and can even rule out established tumors. A number of fully human anti-human CTLA-4 monoclonal antibodies (mAbs) have been studied in clinical trials for the treatment of various types of solid tumors, including, but limited to, ipilimumab (MDX-010) and tremelimumab (CP-675,206).

In some embodiments, a CTLA-4 inhibitor may be any CTLA-4 inhibitor or CTLA-4 blocker known in the art. In particular, it is one of the CTLA-4 inhibitors or blockers described in more detail in the following paragraphs. The terms "inhibitor," "antagonist," and "blocker" are used interchangeably herein in reference to CTLA-4 inhibitors. For avoidance of doubt, references herein to a CTLA-4 inhibitor that is an antibody may refer to a compound or antigen-binding fragments, variants, conjugates, or biosimilars thereof. For avoidance of doubt, references herein to a CTLA-4 inhibitor may also refer to a small molecule compound or a pharmaceutically acceptable salt, ester, solvate, hydrate, cocrystal, or prodrug thereof.

Suitable CTLA-4 inhibitors for use in the methods of the invention, include, without limitation, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, MDX-010 (ipilimumab), tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1, the disclosures of each of which are incorporated herein by reference. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014, the disclosures of each of which are incorporated herein by reference. Other anti-CTLA-4 antibodies that can be used in a method of the present invention include, for example, those disclosed in: WO 98/42752; U.S. Pat. Nos. 6,682,736 and 6,207,156; Hurwitz et al., *Proc. Natl. Acad. Sci. USA,* 95(17):10067-10071 (1998); Camacho et al., *J. Clin.* Oncology, 22(145): Abstract No. 2505 (2004) (antibody CP-675206); Mokyr et al., *Cancer Res.,* 58:5301-5304 (1998), and U.S. Pat. Nos. 5,977,318, 6,682,736, $7{,}10^{9}$,003, and 7,132,281, the disclosures of each of which are incorporated herein by reference the non-myeloablative lymphodepletion regimen.

Additional CTLA-4 inhibitors include, but are not limited to, the following: any inhibitor that is capable of disrupting the ability of CD28 antigen to bind to its cognate ligand, to inhibit the ability of CTLA-4 to bind to its cognate ligand, to augment T cell responses via the co-stimulatory pathway, to disrupt the ability of B7 to bind to CD28 and/or CTLA-4, to disrupt the ability of B7 to activate the co-stimulatory pathway, to disrupt the ability of CD80 to bind to CD28 and/or CTLA-4, to disrupt the ability of CD80 to activate the co-stimulatory pathway, to disrupt the ability of CD86 to bind to CD28 and/or CTLA-4, to disrupt the ability of CD86 to activate the co-stimulatory pathway, and to disrupt the co-stimulatory pathway, in general from being activated. This necessarily includes small molecule inhibitors of CD28, CD80, CD86, CTLA-4, among other members of the co-stimulatory pathway; antibodies directed to CD28, CD80, CD86, CTLA-4, among other members of the co-stimulatory pathway; antisense molecules directed against CD28, CD80, CD86, CTLA-4, among other members of the co-stimulatory pathway; adnectins directed against CD28, CD80, CD86, CTLA-4, among other members of the co-stimulatory pathway, RNAi inhibitors (both single and double stranded) of CD28, CD80, CD86, CTLA-4, among other members of the co-stimulatory pathway, among other CTLA-4 inhibitors.

In some embodiments a CTLA-4 inhibitor binds to CTLA-4 with a Kd of about $10^{-6}$ M or less, $10^{-7}$M or less, $10^{-8}$ M or less, $10^{-9}$ M or less, $10^{-10}$ M or less, $10^{-11}$ M or less, $10^{-12}$ M or less, e.g., between $10^{-13}$ M and $10^{-16}$ M, or within any range having any two of the afore-mentioned values as endpoints. In some embodiments a CTLA-4 inhibitor binds to CTLA-4 with a Kd of no more than 10-fold that of ipilimumab, when compared using the same assay. In some embodiments a CTLA-4 inhibitor binds to CTLA-4 with a Kd of about the same as, or less (e.g., up to 10-fold lower, or up to 100-fold lower) than that of ipilimumab, when compared using the same assay. In some embodiments, the $IC_{50}$ values for inhibition by a CTLA-4 inhibitor of CTLA-4 binding to CD80 or CD86 is no more than 10-fold greater than that of ipilimumab-mediated inhibition of CTLA-4 binding to CD80 or CD86, respectively, when compared using the same assay. In some embodiments, the $IC_{50}$ values for inhibition by a CTLA-4 inhibitor of CTLA-4 binding to CD80 or CD86 is about the same or less (e.g., up to 10-fold lower, or up to 100-fold lower) than that of ipilimumab-mediated inhibition of CTLA-4 binding to CD80 or CD86, respectively, when compared using the same assay.

In some embodiments a CTLA-4 inhibitor is used in an amount sufficient to inhibit expression and/or decrease biological activity of CTLA-4 by at least 20%, 30%, 40%, 50%, 60%, 70%, 80%, 90%, 95%, or 100% relative to a suitable control, e.g., between 50% and 75%, 75% and 90%, or 90% and 100%. In some embodiments a CTLA-4 pathway inhibitor is used in an amount sufficient to decrease the biological activity of CTLA-4 by reducing binding of CTLA-4 to CD80, CD86, or both by at least 20%, 30%, 40%, 50%, 60%, 70%, 80%, 90%, 95%, or 100% relative to a suitable control, e.g., between 50% and 75%, 75% and 90%, or 90% and 100% relative to a suitable control. A suitable control in the context of assessing or quantifying the effect of an agent of interest is typically a comparable biological system (e.g., cells or a subject) that has not been exposed to or treated with the agent of interest, e.g., CTLA-4 pathway inhibitor (or has been exposed to or treated with a negligible amount). In some embodiments a biological system may serve as its own control (e.g., the biological system may be assessed before exposure to or treatment with the agent and compared with the state after exposure or treatment has started or finished. In some embodiments a historical control may be used.

In some embodiments, the CTLA-4 inhibitor is ipilimumab (commercially available as Yervoy from Bristol-Myers Squibb Co.), or biosimilars, antigen-binding fragments, conjugates, or variants thereof. As is known in the art, ipilimumab refers to an anti-CTLA-4 antibody, a fully human IgG 1x antibody derived from a transgenic mouse with human genes encoding heavy and light chains to generate a functional human repertoire. is there. Ipilimumab can also be referred to by its CAS Registry Number 477202-00-9, and in PCT Publication Number WO 01/14424, which is incorporated herein by reference in its entirety for all purposes. It is disclosed as antibody 10DI. Specifically, ipilimumab contains a light chain variable region and a heavy chain variable region (having a light chain variable region comprising SEQ ID NO: 516 and having a heavy chain variable region comprising SEQ ID NO: 515). Represents a human monoclonal antibody or its antigen binding site that specifically binds to CTLA-4. A pharmaceutical composition of ipilimumab includes all pharmaceutically acceptable compositions containing ipilimumab and one or more diluents, vehicles and/or excipients. An example of a pharmaceutical composition containing ipilimumab is described in PCT Publication No. WO 2007/67959. Impilimumab can be administered intravenously (IV).

In some embodiments, a CTLA-4 inhibitor comprises a heavy chain given by SEQ ID NO:208 and a light chain given by SEQ ID NO:209. In some embodiments, a CTLA-4 inhibitor comprises heavy and light chains having the sequences shown in SEQ ID NO:208 and SEQ ID NO:209, respectively, or antigen binding fragments, Fab fragments, single-chain variable fragments (scFv), variants, or conjugates thereof. In some embodiments, a CTLA-4 inhibitor comprises heavy and light chains that are each at least 99% identical to the sequences shown in SEQ ID NO:208 and SEQ ID NO:209, respectively. In some embodiments, a CTLA-4 inhibitor comprises heavy and light chains that are each at least 98% identical to the sequences shown in SEQ ID NO:208 and SEQ ID NO:209, respectively. In some embodiments, a CTLA-4 inhibitor comprises heavy and light chains that are each at least 97% identical to the sequences shown in SEQ ID NO:208 and SEQ ID NO:209, respectively. In some embodiments, a CTLA-4 inhibitor comprises heavy and light chains that are each at least 96% identical to the sequences shown in SEQ ID NO:208 and SEQ ID NO:209, respectively. In some embodiments, a CTLA-4 inhibitor comprises heavy and light chains that are each at least 95% identical to the sequences shown in SEQ ID NO:208 and SEQ ID NO:209, respectively.

In some embodiments, the CTLA-4 inhibitor comprises the heavy and light chain CDRs or variable regions (VRs) of ipilimumab. In some embodiments, the CTLA-4 inhibitor heavy chain variable region ($V_H$) comprises the sequence shown in SEQ ID NO:210, and the CTLA-4 inhibitor light chain variable region ($V_L$) comprises the sequence shown in SEQ ID NO:211, or conservative amino acid substitutions thereof. In some embodiments, a CTLA-4 inhibitor comprises $V_H$ and $V_L$ regions that are each at least 99% identical to the sequences shown in SEQ ID NO:210 and SEQ ID NO:211, respectively. In some embodiments, a CTLA-4 inhibitor comprises $V_H$ and $V_L$ regions that are each at least 98% identical to the sequences shown in SEQ ID NO:210 and SEQ ID NO:211, respectively. In some embodiments, a CTLA-4 inhibitor comprises $V_H$ and $V_L$ regions that are each at least 97% identical to the sequences shown in SEQ ID NO:210 and SEQ ID NO:211, respectively. In some embodiments, a CTLA-4 inhibitor comprises $V_H$ and $V_L$ regions that are each at least 96% identical to the sequences shown in SEQ ID NO:210 and SEQ ID NO:211, respectively. In some embodiments, a CTLA-4 inhibitor comprises $V_H$ and $V_L$ regions that are each at least 95% identical to the sequences shown in SEQ ID NO:210 and SEQ ID NO:211, respectively.

In some embodiments, a CTLA-4 inhibitor comprises the heavy chain CDR1, CDR2 and CDR3 domains having the sequences set forth in SEQ ID NO:212, SEQ ID NO:213, and SEQ ID NO:214, respectively, or conservative amino acid substitutions thereof, and light chain CDR1, CDR2 and CDR3 domains having the sequences set forth in SEQ ID NO:215, SEQ ID NO:216, and SEQ ID NO:217, respectively, or conservative amino acid substitutions thereof. In some embodiments, the antibody competes for binding with, and/or binds to the same epitope on CTLA-4 as any of the aforementioned antibodies.

In some embodiments, the CTLA-4 inhibitor is a CTLA-4 biosimilar monoclonal antibody approved by drug regulatory authorities with reference to ipilimumab. In some embodiments, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is ipilimumab. In some embodiments, the one or more post-translational modifications are selected from one or more of: glycosylation, oxidation, deamidation, and truncation. The amino acid sequences of ipilimumab are set forth in Table 23. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is ipilimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab.

TABLE 23

Amino acid sequences for ipilimumab.

| Identifier | | Sequence (One-Letter Amino Acid Symbols) |
|---|---|---|
| SEQ ID NO: 208 | 1 | QVQLVESGGG VVQPGRSLRL SCAASGFTFS SYTMHWVRQA PGKGLEWVTF ISYDGNNKYY |
| ipilimumab | 61 | ADSVKGRFTI SRDNSKNTLY LQMNSLRAED TAIYYCARTG WLGPFDYWGQ GTLVTVSSAS |
| heavy chain | 121 | TKGPSVFPLA PSSKSTSGGT AALGCLVKDY FPEPVTVSWN SGALTSGVHT FPAVLQSSGL |
| | 181 | YSLSSVVTVP SSSLGTQTYI CNVNHKPSNT KVDKRVEPKS CDKTH |
| SEQ ID NO: 209 | 1 | EIVLTQSPGT LSLSPGERAT LSCRASQSVG SSYLAWYQQK PGQAPRLLIY GAFSRATGIP |
| ipilimumab | 61 | DRFSGSGSGT DFTLTISRLE PEDFAVYYCQ QYGSSPWTFG QGTKVEIKRT VAAPSVFIFP |
| light chain | 121 | PSDEQLKSGT ASVVCLLNNF YPREAKVQWK VDNALQSGNS QESVTEQDSK DSTYSLSSTL |
| | 181 | TLSKADYEKH KVYACEVTHQ GLSSPVTKSF NRGEC |
| SEQ ID NO: 210 | 1 | QVQLVESGGG VVQPGRSLRL SCAASGFTFS SYTMHWVRQA PGKGLEWVTF ISYDGNNKYY |
| ipilimumab variable heavy chain | 61 | ADSVKGRFTI SRDNSKNTLY LQMNSLRAED TAIYYCARTG WLGPFDYWGQ GTLVTVSS |

TABLE 23-continued

| Amino acid sequences for ipilimumab. | | |
|---|---|---|
| Identifier | Sequence (One-Letter Amino Acid Symbols) | |
| SEQ ID NO: 211 ipilimumab variable light chain | 1 EIVLTQSPGT LSLSPGERAT LSCRASQSVG SSYLAWYQQK PGQAPRLLIY GAFSRATGIP<br>61 DRFSGSGSGT DFTLTISRLE PEDFAVYYCQ QYGSSPWTFG QGTKVEIK | |
| SEQ ID NO: 212 ipilimumab heavy chain CDR1 | GFTFSSYT | 8 |
| SEQ ID NO: 213 ipilimumab heavy chain CDR2 | TFISYDGNNK | 10 |
| SEQ ID NO: 214 ipilimumab heavy chain CDR3 | ARTGWLGPFD Y | 11 |
| SEQ ID NO: 215 ipilimumab light chain CDR1 | QSVGSSY | 7 |
| SEQ ID NO: 216 ipilimumab light chain CDR2 | GAF | 3 |
| SEQ ID NO: 217 ipilimumab light chain CDR3 | QQYGSSPWT | 9 |

In some embodiments, the CTLA-4 inhibitor is ipilimumab or a biosimilar thereof, and the ipilimumab is administered at a dose of about 0.5 mg/kg to about 10 mg/kg. In some embodiments, the CTLA-4 inhibitor is ipilimumab or a biosimilar thereof, and the ipilimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg.

In some embodiments, the CTLA-4 inhibitor is ipilimumab or a biosimilar thereof, and the ipilimumab is administered at a dose of about 200 mg to about 500 mg. In some embodiments, the CTLA-4 inhibitor is ipilimumab or a biosimilar thereof, and the ipilimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the CTLA-4 inhibitor is ipilimumab or a biosimilar thereof, and the ipilimumab is administered every 2 weeks, every 3 weeks, every 4 weeks, every 5 weeks, or every 6 weeks.

In some embodiments, the ipilimumab is administered to treat metastatic non-small cell lung cancer. In some embodiments, the ipilimumab is administered to treat metastatic non-small cell lung cancer at about 1 mg/kg every 6 weeks with nivolumab 3 mg/kg every 2 weeks. In some embodiments, the ipilimumab is administered to treat metastatic non-small cell lung cancer at about 1 mg/kg every 6 weeks with nivolumab 360 mg every 3 weeks and 2 cycles of platinum-doublet chemotherapy.

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736 (incorporated herein by reference). The amino acid sequences of the heavy chain and light chain of tremelimumab are set forth in Table 24, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, tremelimumab is administered locally, particularly intradermally or subcutaneously. The effective amount of tremelimumab administered intradermally or subcutaneously is typically in the range of 5-200 mg/dose per person. In some embodiments, the effective amount of tremelimumab is in the range of 10-150 mg/dose per person per dose. In some particular embodiments, the effective amount of tremelimumab is about 10, 25, 37.5, 40, 50, 75, 100, 125, 150, 175, or 200 mg/dose per person.

In some embodiments, a CTLA-4 inhibitor comprises a heavy chain given by SEQ ID NO:218 and a light chain given by SEQ ID NO:219. In some embodiments, a CTLA-4 inhibitor comprises heavy and light chains having the sequences shown in SEQ ID NO:218 and SEQ ID NO:219, respectively, or antigen binding fragments, Fab fragments, single-chain variable fragments (scFv), variants, or conjugates thereof. In some embodiments, a CTLA-4 inhibitor comprises heavy and light chains that are each at least 99% identical to the sequences shown in SEQ ID NO:218 and SEQ ID NO:219, respectively. In some embodiments, a CTLA-4 inhibitor comprises heavy and light chains that are each at least 98% identical to the sequences shown in SEQ ID NO:218 and SEQ ID NO:219, respectively. In some embodiments, a CTLA-4 inhibitor comprises heavy and light chains that are each at least 97% identical to the sequences shown in SEQ ID NO:218 and SEQ ID NO:219, respectively. In some embodiments, a CTLA-4 inhibitor comprises heavy and light chains that are each at least 96% identical to the sequences shown in SEQ ID NO:218 and SEQ ID NO:219, respectively. In some embodiments, a CTLA-4 inhibitor comprises heavy and light chains that are each at least 95% identical to the sequences shown in SEQ ID NO:218 and SEQ ID NO:219, respectively.

In some embodiments, the CTLA-4 inhibitor comprises the heavy and light chain CDRs or variable regions (VRs) of tremelimumab. In some embodiments, the CTLA-4 inhibitor heavy chain variable region ($V_H$) comprises the sequence shown in SEQ ID NO:220, and the CTLA-4 inhibitor light chain variable region ($V_L$) comprises the sequence shown in SEQ ID NO:221, or conservative amino acid substitutions thereof. In some embodiments, a CTLA-4 inhibitor comprises $V_H$ and $V_L$ regions that are each at least 99% identical to the sequences shown in SEQ ID NO:220 and SEQ ID NO:221, respectively. In some embodiments, a CTLA-4 inhibitor comprises $V_H$ and $V_L$ regions that are each at least 98% identical to the sequences shown in SEQ ID NO:220 and SEQ ID NO:221, respectively. In some embodiments, a CTLA-4 inhibitor comprises $V_H$ and $V_L$ regions that are each at least 97% identical to the sequences shown in SEQ ID NO:220 and SEQ ID NO:221, respectively. In some embodiments, a CTLA-4 inhibitor comprises $V_H$ and $V_L$ regions that are each at least 96% identical to the sequences shown in SEQ ID NO:220 and SEQ ID NO:221, respectively. In some embodiments, a CTLA-4 inhibitor comprises $V_H$ and $V_L$ regions that are each at least 95% identical to the sequences shown in SEQ ID NO:220 and SEQ ID NO:221, respectively.

In some embodiments, a CTLA-4 inhibitor comprises the heavy chain CDR1, CDR2 and CDR3 domains having the sequences set forth in SEQ ID NO:222, SEQ ID NO:223, and SEQ ID NO:224, respectively, or conservative amino acid substitutions thereof, and light chain CDR1, CDR2 and CDR3 domains having the sequences set forth in SEQ ID NO:225, SEQ ID NO:226, and SEQ ID NO:227, respectively, or conservative amino acid substitutions thereof. In some embodiments, the antibody competes for binding with, and/or binds to the same epitope on CTLA-4 as any of the aforementioned antibodies.

In some embodiments, the CTLA-4 inhibitor is an anti-CTLA-4 biosimilar monoclonal antibody approved by drug regulatory authorities with reference to tremelimumab. In some embodiments, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tremelimumab. In some embodiments, the one or more post-translational modifications are selected from one or more of: glycosylation, oxidation, deamidation, and truncation. The amino acid sequences of tremelimumab are set forth in Table 24. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is tremelimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab.

TABLE 24. Amino acid sequences for tremelimumab.

Identifier Sequence (One-Letter Amino Acid Symbols) SEQ ID 1 QVQLVESGGG VVQPGRSLRL SCAASGFTFS SYGMHWVRQA NO:218 PGKGLEWVAV IWYDGSNKYY tremelimumab 61 ADSVKGRFTI SRDNSKNTLY LQMNSLRAED TAVYYCARDP heavy chain RGATLYYYYY GMDVWGQGTT

TABLE 24

Amino acid sequences for tremelimumab.

| Identifier | | Sequence (One-Letter Amino Acid Symbols) |
|---|---|---|
| SEQ ID NO: 218 | 1 | QVQLVESGGG VVQPGRSLRL SCAASGFTFS SYGMHWVRQA PGKGLEWVAV IWYDGSNKYY |
| tremelimumab | 61 | ADSVKGRFTI SRDNSKNTLY LQMNSLRAED TAVYYCARDP RGATLYYYYY GMDVWGQGTT |
| heavy chain | 121 | VTVSSASTKG PSVFPLAPCS RSTSESTAAL GCLVKDYFPE PVTVSWNSGA LTSGVHTFPA |
| | 181 | VLQSSGLYSL SSVVTVPSSN FGTQTYTCNV DHKPSNTKVD KTVERKCCVE CPPCPAPPVA |
| | 241 | GPSVFLFPPK PKDTLMISRT PEVTCVVVDV SHEDPEVQFN WYVDGVEVHN AKTKPREEQF |
| | 301 | NSTFRVVSVL TVVHQDWLNG KEYKCKVSNK GLPAPIEKTI SKTKGQPREP QVYTLPPSRE |
| | 361 | EMTKNQVSLT CLVKGFYPSD IAVEWESNGQ PENNYKTTPP MLDSDGSFFL YSKLTVDKSR |
| | 421 | WQQGNVFSCS VMHEALHNHY TQKSLSLSPG K |
| SEQ ID NO: 219 | 1 | DIQMTQSPSS LSASVGDRVT ITCRASQSIN SYLDWYQQKP GKAPKLLIYA ASSLQSGVPS |
| tremelimumab | 61 | RFSGSGSGTD FTLTISSLQP EDFATYYCQQ YYSTPFTFGP GTKVEIKRTV AAPSVFIFPP |
| light chain | 121 | SDEQLKSGTA SVVCLLNNFY PREAKVQWKV DNALQSGNSQ ESVTEQDSKD STYSLSSTLT |
| | 181 | LSKADYEKHK VYACEVTHQG LSSPVTKSFN RGEC |

TABLE 24-continued

| Amino acid sequences for tremelimumab. | | |
|---|---|---|
| Identifier | Sequence (One-Letter Amino Acid Symbols) | |
| SEQ ID NO: 220 tremelimumab variable heavy chain | 1 GVVQPGRSLR LSCAASGFTF SSYGMHWVRQ APGKGLEWVA VIWYDGSNKY YADSVKGRFT<br>61 ISRDNSKNTL YLQMNSLRAE DTAVYYCARD PRGATLYYYY YGMDVWGQGT TVTVSSASTK<br>121 GPSVFPLAPC SRSTSESTAA LGCLVKDYFP EPVTVSWNSG ALTSGVH | |
| SEQ ID NO: 221 tremelimumab variable light chain | 1 PSSLSASVGD RVTITCRASQ SINSYLDWYQ QKPGKAPKLL IYAASSLQSG VPSRFSGSGS<br>61 GTDFTLTISS LQPEDFATYY CQQYYSTPFT FGPGTKVEIK RTVAAPSVFI FPPSDEQLKS<br>121 GTASVVCLLN NFYPREAKV | |
| SEQ ID NO: 222 tremelimumab heavy chain CDR1 | GFTFSSYGMH | 10 |
| SEQ ID NO: 223 tremelimumab heavy chain CDR2 | VIWYDGSNKY YADSV | 15 |
| SEQ ID NO: 224 tremelimumab heavy chain CDR3 | DPRGATLYYY YYGMDV | 16 |
| SEQ ID NO: 225 tremelimumab light chain CDR1 | RASQSINSYL D | 11 |
| SEQ ID NO: 226 tremelimumab light chain CDR2 | AASSLQS | 7 |
| SEQ ID NO: 227 tremelimumab light chain CDR3 | QQYYSTPFT | 9 |

In some embodiments, the CTLA-4 inhibitor is tremelimumab or a biosimilar thereof, and the tremelimumab is administered at a dose of about 0.5 mg/kg to about 10 mg/kg. In some embodiments, the CTLA-4 inhibitor is tremelimumab or a biosimilar thereof, and the tremelimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg.

In some embodiments, the CTLA-4 inhibitor is tremelimumab or a biosimilar thereof, and the tremelimumab is administered at a dose of about 200 mg to about 500 mg. In some embodiments, the CTLA-4 inhibitor is tremelimumab or a biosimilar thereof, and the tremelimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the CTLA-4 inhibitor is tremelimumab or a biosimilar thereof, and the tremelimumab is administered every 2 weeks, every 3 weeks, every 4 weeks, every 5 weeks, or every 6 weeks.

In some embodiments, the CTLA-4 inhibitor is zalifrelimab from Agenus, or biosimilars, antigen-binding fragments, conjugates, or variants thereof. Zalifrelimab is a fully human monoclonal antibody. Zalifrelimab is assigned Chemical Abstracts Service (CAS) registry number 2148321-69-9 and is also known as also known as AGEN1884. The preparation and properties of zalifrelimab are described in U.S. Pat. No. 10,144,779 and US Patent Application Publication No. US2020/0024350 A1, the disclosures of which are incorporated by reference herein.

In some embodiments, a CTLA-4 inhibitor comprises a heavy chain given by SEQ ID NO:228 and a light chain given by SEQ ID NO:229. In some embodiments, a CTLA-4 inhibitor comprises heavy and light chains having the sequences shown in SEQ ID NO:228 and SEQ ID NO:229, respectively, or antigen binding fragments, Fab fragments, single-chain variable fragments (scFv), variants, or conjugates thereof. In some embodiments, a CTLA-4 inhibitor comprises heavy and light chains that are each at least 99% identical to the sequences shown in SEQ ID NO:228 and SEQ ID NO:229, respectively. In some embodiments, a CTLA-4 inhibitor comprises heavy and light chains that are each at least 98% identical to the sequences shown in SEQ ID NO:228 and SEQ ID NO:229, respectively. In some embodiments, a CTLA-4 inhibitor comprises heavy and light chains that are each at least 97% identical to the sequences shown in SEQ ID NO:228 and SEQ ID NO:229, respectively. In some embodiments, a CTLA-4 inhibitor comprises heavy and light chains that are each at least 96% identical to the sequences shown in SEQ ID NO:228 and SEQ ID NO:229, respectively. In some embodiments, a CTLA-4 inhibitor comprises heavy and light chains that are each at least 95% identical to the sequences shown in SEQ ID NO:228 and SEQ ID NO:229, respectively.

In some embodiments, the CTLA-4 inhibitor comprises the heavy and light chain CDRs or variable regions (VRs) of zalifrelimab. In some embodiments, the CTLA-4 inhibitor heavy chain variable region ($V_H$) comprises the sequence shown in SEQ ID NO:230, and the CTLA-4 inhibitor light chain variable region ($V_L$) comprises the sequence shown in SEQ ID NO:231, or conservative amino acid substitutions thereof. In some embodiments, a CTLA-4 inhibitor comprises $V_H$ and $V_L$ regions that are each at least 99% identical to the sequences shown in SEQ ID NO:230 and SEQ ID NO:231, respectively. In some embodiments, a CTLA-4 inhibitor comprises $V_H$ and $V_L$ regions that are each at least 98% identical to the sequences shown in SEQ ID NO:230 and SEQ ID NO:231, respectively. In some embodiments, a CTLA-4 inhibitor comprises $V_H$ and $V_L$ regions that are each at least 97% identical to the sequences shown in SEQ ID NO:230 and SEQ ID NO:231, respectively. In some embodiments, a CTLA-4 inhibitor comprises $V_H$ and $V_L$ regions that are each at least 96% identical to the sequences shown in SEQ ID NO:230 and SEQ ID NO:231, respectively. In some embodiments, a CTLA-4 inhibitor comprises $V_H$ and $V_L$ regions that are each at least 95% identical to the sequences shown in SEQ ID NO:230 and SEQ ID NO:231, respectively.

In some embodiments, a CTLA-4 inhibitor comprises the heavy chain CDR1, CDR2 and CDR3 domains having the sequences set forth in SEQ ID NO:231, SEQ ID NO:233, and SEQ ID NO:234, respectively, or conservative amino acid substitutions thereof, and light chain CDR1, CDR2 and CDR3 domains having the sequences set forth in SEQ ID NO:235, SEQ ID NO:236, and SEQ ID NO:237, respectively, or conservative amino acid substitutions thereof. In some embodiments, the antibody competes for binding with, and/or binds to the same epitope on CTLA-4 as any of the aforementioned antibodies.

In some embodiments, the CTLA-4 inhibitor is a CTLA-4 biosimilar monoclonal antibody approved by drug regulatory authorities with reference to zalifrelimab. In some embodiments, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is zalifrelimab. In some embodiments, the one or more post-translational modifications are selected from one or more of: glycosylation, oxidation, deamidation, and truncation. The amino acid sequences of zalifrelimab are set forth in Table 25. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is zalifrelimab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab.

TABLE 25

Amino acid sequences for zalifrelimab.

| Identifier | | Sequence (One-Letter Amino Acid Symbols) | |
|---|---|---|---|
| SEQ ID NO: 228 zalifrelimab heavy chain | 1 | EVQLVESGGG LVKPGGSLRL SCAASGFTFS SYSMNWVRQA PGKGLEWVSS ISSSSSYIYY | |
| | 61 | ADSVKGRFTI SRDNAKNSLY LQMNSLRAED TAVYYCARVG LMGPFDIWGQ GTMVTVSSAS | |
| | 121 | TKGPSVFPLA PSSKSTSGGT AALGCLVKDY FPEPVTVSWN SGALTSGVHT FPAVLQSSGL | |
| | 181 | YSLSSVVTVP SSSLGTQTYI CNVNHKPSNT KVDKRVEPKS CDKTHTCPPC PAPELLGGPS | |
| | 241 | VFLFPPKPKD TLMISRTPEV TCVVVDVSHE DPEVKFNWYV DGVEVHNAKT KPREEQYNST | |
| | 301 | YRVVSVLTVL HQDWLNGKEY KCKVSNKALP APIEKTISKA KGQPREPQVY TLPPSREEMT | |
| | 361 | KNQVSLTCLV KGFYPSDIAV EWESNGQPEN NYKTTPPVLD SDGSFFLYSK LTVDKSRWQQ | |
| | 421 | GNVFSCSVMH EALHNHYTQK SLSLSPGK | |
| SEQ ID NO: 229 zalifrelimab light chain | 1 | EIVLTQSPGT LSLSPGERAT LSCRASQSVS RYLGWYQQKP GQAPRLLIYG ASTRATGIPD | |
| | 61 | RFSGSGSGTD FTLTITRLEP EDFAVYYCQQ YGSSPWTFGQ GTKVEIKRTV AAPSVFIFPP | |
| | 121 | SDEQLKSGTA SVVCLLNNFY PREAKVQWKV DNALQSGNSQ ESVTEQDSKD STYSLSSTLT | |
| | 181 | LSKADYEKHK VYACEVTHQG LSSPVTKSFN RGEC | |
| SEQ ID NO: 230 zalifrelimab variable heavy chain | 1 | EVQLVESGGG LVKPGGSLRL SCAASGFTFS SYSMNWVRQA PGKGLEWVSS ISSSSSYIYY | |
| | 61 | ADSVKGRFTI SRDNAKNSLY LQMNSLRAED TAVYYCARVG LMGPFDIWGQ GTMVTVSS | |
| SEQ ID NO: 231 zalifrelimab variable light chain | 1 | EIVLTQSPGT LSLSPGERAT LSCRASQSVS RYLGWYQQKP GQAPRLLIYG ASTRATGIPD | |
| | 61 | RFSGSGSGTD FTLTITRLEP EDFAVYYCQQ YGSSPWTFGQ GTKVEIK | |
| SEQ ID NO: 232 zalifrelimab heavy chain CDR1 | GFTFSSYS | | 8 |

TABLE 25-continued

| Amino acid sequences for zalifrelimab. | | |
|---|---|---|
| Identifier | Sequence (One-Letter Amino Acid Symbols) | |
| SEQ ID NO: 233 zalifrelimab heavy chain CDR2 | ISSSSSYI | 8 |
| SEQ ID NO: 234 zalifrelimab heavy chain CDR3 | ARVGLMGPFD I | 11 |
| SEQ ID NO: 235 zalifrelimab light chain CDR1 | QSVSRY | 6 |
| SEQ ID NO: 236 zalifrelimab light chain CDR2 | GAS | 3 |
| SEQ ID NO: 237 zalifrelimab light chain CDR3 | QQYGSSPWT | 9 |

Examples of additional anti-CTLA-4 antibodies includes, but are not limited to: AGEN1181, BMS-986218, BCD-145, ONC-392, CS1002, REGN4659, and ADG116, which are known to one of ordinary skill in the art.

In some embodiments, the anti-CTLA-4 antibody is an anti-CTLA-4 antibody disclosed in any of the following patent publications (incorporated herein by reference): US2019/0048096A1; US2020/0223907; US2019/0201334; US2019/0201334; US2005/0201994; EP 1212422 B1; WO2018204760; WO2018204760; WO2001014424; WO2004035607; WO2003086459; WO2012120125; WO2000037504; WO2009100140; W0200609649; WO2005092380; WO2007123737; WO2006029219; WO20100979597; W0200612168; and WO1997020574. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, incorporated herein by reference). In some embodiments, the anti-CTLA-4 antibody is an, for example, those disclosed in: WO 98/42752; U.S. Pat. Nos. 6,682,736 and 6,207,156; Hurwitz et al., Proc. *Natl. Acad. Sci. USA,* 95(17): 10067-10071 (1998); Camacho et al., *J. Clin. Oncol.,* 22(145): Abstract No. 2505 (2004) (antibody CP-675206); Mokyr et al., *Cancer Res.,* 58:5301-5304 (1998) (incorporated herein by reference).

In some embodiments, the CTLA-4 inhibitor is a CTLA-4 ligand as disclosed in WO1996040915 (incorporated herein by reference).

In some embodiments, the CTLA-4 inhibitor is a nucleic acid inhibitor of CTLA-4 expression. For example, anti-CTLA-4 RNAi molecules may take the form of the molecules described by Mello and Fire in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA-4 RNAi molecules take the form of double stranded RNAi molecules described by Tuschl in European Patent No. EP 1309726 (incorporated herein by reference). In some instances, the anti-CTLA-4 RNAi molecules take the form of double stranded RNAi molecules described by Tuschl in U.S. Pat. Nos. 7,056,704 and 7,078,196 (incorporated herein by reference). In some embodiments, the CTLA-4 inhibitor is an aptamer described in PCT Publication No. WO2004081021 (incorporated herein by reference).

In other embodiments, the anti-CTLA-4 RNAi molecules of the present invention are RNA molecules described by Crooke in U.S. Pat. Nos. 5,898,031, 6,107,094, 7,432,249, and 7,432,250, and European Application No. EP 0928290 (incorporated herein by reference).

5. Combinations with VEGF-A Inhibitors

In some embodiments, TILs and a VEGF-A inhibitor are administered as a combination therapy or co-therapy for the treatment of NSCLC.

In some embodiments, the NSCLC has undergone no prior therapy. In some embodiments, the VEGF-A inhibitor is administered as a front-line therapy or initial therapy. In some embodiments, the VEGF-A inhibitor is administered as a front-line therapy or initial therapy in combination with the TILs as described herein.

VEGF-A (polynucleotide and polypeptide sequences shown in SEQ ID NOs: 1 and 2, respectively) is a secreted, disulfide-linked homodimeric glycoprotein belonging to the VEGF/PDGF (platelet-derived growth factor) group of the cystine-knot superfamily of hormones and extracellular signaling molecules (see Vitt et al., *Mol. Endocrinol.,* 15:681-694, 2001), which are all characterized by the presence of eight conserved cysteine residues forming the typical cystine-knot structure (named after cystine, a dimer of two cysteines linked by a disulfide bond). Five human VEGF-A isoforms of 121, 145, 165, 189 or 206 amino acids in length (VEGF-A121-206), encoded by distinct mRNA splice variants, have been described, all of which are capable of stimulating mitogenesis in endothelial cells. These isoforms differ in biological activity, receptor specificity, and affinity for cell surface- and extracellular matrix-associated heparan-sulfate proteoglycans, which behave as low affinity receptors for VEGF-A: VEGF-A121 does not bind to either heparin or heparan-sulfate; VEGF-A145 and VEGF-A165 (GenBank Acc. No. M32977) are both capable of binding to heparin; and VEGF-A189 and VEGF-A206 show the strongest affinity for heparin and heparan-sulfates. VEGF-A121, VEGF-A145, and VEGF-A165 are secreted in a soluble form, although most of VEGF-A165 is confined to cell surface and extracellular matrix proteoglycans, whereas VEGF-A189 and VEGF-A206 remain associated with extracellular matrix. Both VEGF-A189 and VEGF-A206 can be released by treatment with heparin or heparinase, indicating that these isoforms are bound to extracellular matrix via proteoglycans. Cell-bound VEGF-A180 can also be cleaved by proteases such as plasmin, resulting in release of an active soluble VEGF-A110.

VEGF-A-driven angiogenesis has a major role in the pathogenesis of diverse human diseases, including cancer, eye disorders, and rheumatoid arthritis. See Carmeliet et al., *Nature* 407:249-257, 2000. Recognition of the importance of VEGF-A for the development of several important classes of cancer recently culminated in the approval of AVASTIN™, a humanized monoclonal antibody to VEGF-A, for the treatment of metastatic colorectal cancer. See Ferrara et al., *Nat. Rev. Drug Discov.* 2004, 3:391-400, 2004. Similarly, the importance ofVEGF-A in the pathogenesis of neovascular ocular disorders is reflected in the recent approval of LUCENTIS™, a humanized monoclonal antibody fragment, for the treatment of neovascular (wet) age-related macular degeneration (AMD).

VEGF-A inhibitors for use within the present invention include molecules that bind to VEGF-A or a VEGF-A receptor and thereby reduce the activity of VEGF-A on cells that express the receptor such as, e.g., VEGFR-1, VEGFR-2, neuropilin-1, and/or neuropilin-2. In particular, VEGF-A inhibitors include anti-VEGF-A antibodies. Other suitable VEGF-A inhibitors include soluble VEGF-A receptors comprising a VEGFR extracellular domain, as well as small molecule antagonists capable of inhibiting the interaction of VEGF-A with its receptor or otherwise capable in inhibiting VEGF-A-induced intracellular signaling through a VEGF-A receptor. In addition, binding proteins based on non-antibody scaffolds may be employed. (See, e.g., Koide et al., *J. Mol. Biol.* 284:1141-1151, 1998; Hosse et al. *Protein Sci.* 15:14-27, 2006, and references therein.) Preferred VEGF-A inhibitors for use within the invention include antibodies that specifically bind to VEGF-A, including bispecific antibodies that also comprise a binding site for PDGFRO. Antibodies that are specific for VEGF-A bind at least the soluble secreted forms of VEGF-A, and preferably also bind cell surface-associated forms.

In some embodiments, the VEGF-A inhibitor may be any VEGF-A inhibitor or VEGF-A blocker known in the art. In particular, it is one of the VEGF-A inhibitors or blockers described in more detail in the following paragraphs. The terms "inhibitor," "antagonist," and "blocker" are used interchangeably herein in reference to VEGF-A inhibitors. For avoidance of doubt, references herein to a VEGF-A inhibitor that is an antibody may refer to a compound or antigen-binding fragments, variants, conjugates, or biosimilars thereof. For avoidance of doubt, references herein to a VEGF-A inhibitor may also refer to a small molecule compound or a pharmaceutically acceptable salt, ester, solvate, hydrate, cocrystal, or prodrug thereof.

In some embodiments, the VEGF-A inhibitor may be any VEGF-A inhibitor or VEGF-A blocker known in the art. In particular, it is one of the VEGF-A inhibitors or blockers described in more detail in the following paragraphs. The terms "inhibitor," "antagonist," and "blocker" are used interchangeably herein in reference to VEGF-A inhibitors. For avoidance of doubt, references herein to a VEGF-A inhibitor that is an antibody may refer to a compound or antigen-binding fragments, variants, conjugates, or biosimilars thereof. For avoidance of doubt, references herein to a VEGF-A inhibitor may also refer to a small molecule compound or a pharmaceutically acceptable salt, ester, solvate, hydrate, cocrystal, or prodrug thereof.

In some embodiments, the VEGF-A inhibitor is an antibody (i.e., an anti-VEGF-A antibody), a fragment thereof, including Fab fragments, or a single-chain variable fragment (scFv) thereof. In some embodiments the VEGF-A inhibitor is a polyclonal antibody. In some embodiments, the VEGF-A inhibitor is a monoclonal antibody. In some embodiments, the VEGF-A inhibitor competes for binding with VEGF-A, and/or binds to an epitope on VEGF-A. In some embodiments, the antibody competes for binding with VEGF-A, and/or binds to an epitope on VEGF-A.

In some embodiments, the VEGF-A inhibitor is one that binds human VEGF-A with a $K_D$ of about 100 μM or lower, binds human VEGF-A with a $K_D$ of about 90 μM or lower, binds human VEGF-A with a $K_D$ of about 80 μM or lower, binds human VEGF-A with a $K_D$ of about 70 μM or lower, binds human VEGF-A with a $K_D$ of about 60 μM or lower, binds human VEGF-A with a $K_D$ of about 50 μM or lower, binds human VEGF-A with a $K_D$ of about 40 μM or lower, binds human VEGF-A with a $K_D$ of about 30 μM or lower, binds human VEGF-A with a $K_D$ of about 20 μM or lower, binds human VEGF-A with a $K_D$ of about 10 μM or lower, or binds human VEGF-A with a $K_D$ of about 1 μM or lower.

In some embodiments, the VEGF-A inhibitor is one that binds to human VEGF-A with a $k_{assoc}$ of about $7.5\times10^5$ 1/M s or faster, binds to human VEGF-A with a $k_{assoc}$ of about $7.5\times10^5$ 1/M s or faster, binds to human VEGF-A with a $k_{assoc}$ of about $8\times10^5$ 1/M s or faster, binds to human VEGF-A with a $k_{assoc}$ of about $8.5\times10^5$ 1/M s or faster, binds to human VEGF-A with a $k_{assoc}$ of about $9\times10^5$ 1/M s or faster, binds to human VEGF-A with a $k_{assoc}$ of about $9.5\times10^5$ 1/M s or faster, or binds to human VEGF-A with a $k_{assoc}$ of about $1\times10^6$ 1/M s or faster.

In some embodiments, the VEGF-A inhibitor is one that binds to human VEGF-A with a $k_{dissoc}$ of about $2\times10^{-5}$ 1/s or slower, binds to human VEGF-A with a $k_{dissoc}$ of about $2.1\times10^{-5}$ 1/s or slower, binds to human VEGF-A with a $k_{dissoc}$ of about $2.2\times10^{-5}$ 1/s or slower, binds to human VEGF-A with a $k_{dissoc}$ of about $2.3\times10^{-5}$ 1/s or slower, binds to human VEGF-A with a $k_{dissoc}$ of about $2.4\times10^{-5}$ 1/s or slower, binds to human VEGF-A with a $k_{dissoc}$ of about $2.5\times10^{-5}$ 1/s or slower, binds to human VEGF-A with a $k_{dissoc}$ of about $2.6\times10^{-5}$ 1/s or slower or binds to human VEGF-A with a $k_{dissoc}$ of about $2.7\times10^{-5}$ 1/s or slower, binds to human VEGF-A with a $k_{dissoc}$ of about $2.8\times10^{-5}$ 1/s or slower, binds to human VEGF-A with a $k_{dissoc}$ of about $2.9\times10^{-5}$ 1/s or slower, or binds to human VEGF-A with a $k_{dissoc}$ of about $3\times10^{-5}$ 1/s or slower.

In some embodiments, the VEGF-A inhibitor is one that blocks or inhibits binding of human VEGFR-1 receptor or human VEGFR-2 receptor to human VEGF-A with an $IC_{50}$ of about 10 nM or lower, blocks or inhibits binding of human VEGFR-1 receptor or human VEGFR-2 receptor to human VEGF-A with an $IC_{50}$ of about 9 nM or lower, blocks or inhibits binding of human VEGFR-1 receptor or human VEGFR-2 receptor to human VEGF-A with an $IC_{50}$ of about 8 nM or lower, blocks or inhibits binding of human VEGFR-1 receptor or human VEGFR-2 receptor to human VEGF-A with an $IC_{50}$ of about 7 nM or lower, blocks or inhibits binding of human VEGFR-1 receptor or human VEGFR-2 receptor to human VEGF-A with an $IC_{50}$ of about 6 nM or lower, blocks or inhibits binding of human VEGFR-1 receptor or human VEGFR-2 receptor to human VEGF-A with an $IC_{50}$ of about 5 nM or lower, blocks or inhibits binding of human VEGFR-1 receptor or human VEGFR-2 receptor to human VEGF-A with an $IC_{50}$ of about 4 nM or lower, blocks or inhibits binding of human VEGFR-1 receptor or human VEGFR-2 receptor to human VEGF-A with an $IC_{50}$ of about 3 nM or lower, blocks or inhibits binding of human VEGFR-1 receptor or human VEGFR-2 receptor to human VEGF-A with an $IC_{50}$ of about 2 nM or lower, or blocks or inhibits binding of human VEGFR-1 receptor or human VEGFR-2 receptor to human VEGF-A with an $IC_{50}$ of about 1 nM or lower.

In some embodiments, the VEGF-A inhibitor is bevacizumab, or biosimilars, antigen-binding fragments, conjugates, or variants thereof. Bevacizumab (CAS registry number 216974-75-3, AVASTIN®, Genentech) is an anti-VEGF monoclonal antibody against vascular endothelial growth factor used in cancer treatment (U.S. Pat. Nos. 7,227,004; 6,884,879; 7,060,269; 7,169,901; 7,297,334), which inhibits tumor growth by blocking neovascularization. Bevacizumab is the first clinically available angiogenesis inhibitor in the United States. It was approved by the FDA in 2004 in combination with standard chemotherapy for the treatment of metastatic colon cancer and most forms of metastatic non-small cell lung cancer. Several post-clinical studies are underway to determine its safety and effectiveness in patients with the following diseases: auxiliary/non-metastatic colon cancer, metastatic breast cancer, metastatic renal cell carcinoma, metastatic polymorphic glioblastoma Neoplasms, metastatic ovarian cancer, metastatic hormone refractory prostate cancer and metastasis Metastatic pancreatic cancer or unresectable locally advanced pancreatic cancer.

Figure 27:
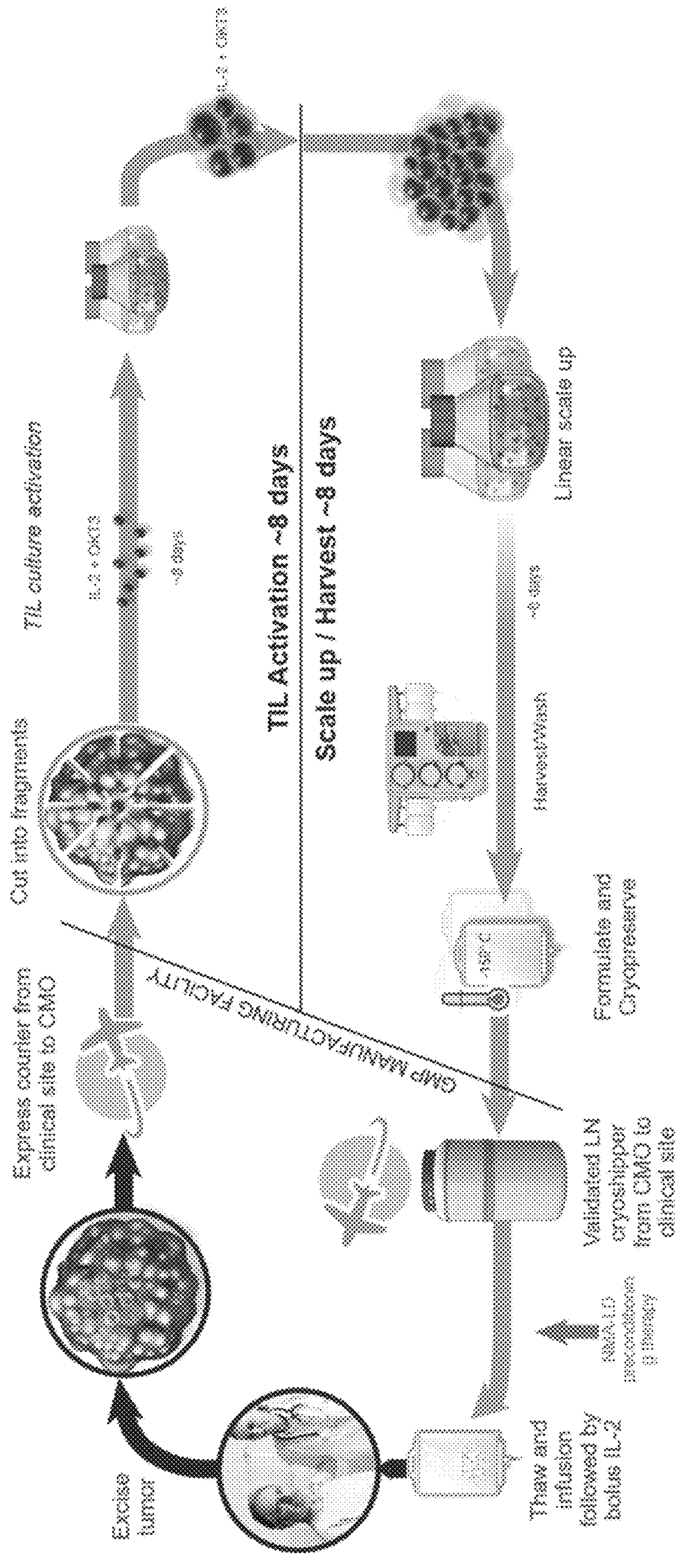
FIG. 27: Schematic of an exemplary embodiment of the Gen 3 process (a 16 day process).
Figure 31:
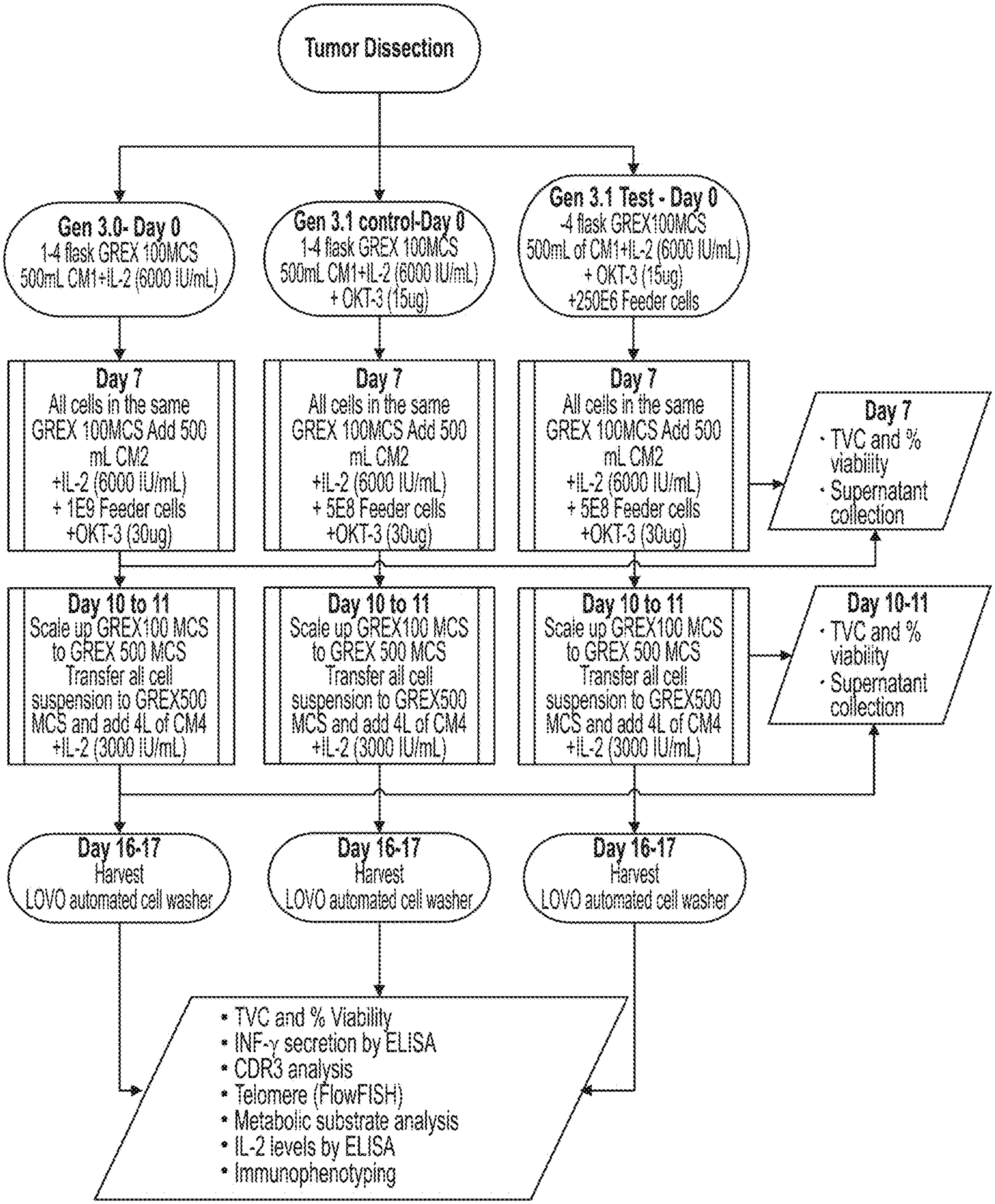
FIG. 31: Gen 3 embodiment flow chart comparison (Gen 3.0, Gen 3.1 control, Gen 3.1 Test).

Bevacizumab includes a mutant human IgGI framework region and an antigen-binding complementarity determining region from a murine anti-hVEGF monoclonal antibody A.4.6.1 that blocks the binding of human VEGF to its receptor. About 93% of the bevacizumab amino acid sequences (including most framework regions) are derived from human IgGI and about 7% of the sequences are derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879. Additional anti-VEGF antibodies include G6 or B20 series antibodies (eg G6-31, B20-4.1) as described in any of FIGS. 27-29 of International Patent Publication No. WO 2005/012359. In one embodiment, the B20 series antibodies bind to functional epitopes on human VEGF containing residues F17, M18, D19, Y21, Y25, Q89, 191, K101, E103, and C104. Additional VEGF antibodies are in are described in International Patent Publication No. WO2010148223.

In some embodiments, a VEGF-A inhibitor comprises a heavy chain given by SEQ ID NO:207 and a light chain given by SEQ ID NO:208. In some embodiments, a VEGF-A inhibitor comprises heavy and light chains having the sequences shown in SEQ ID NO:207 and SEQ ID NO:208, respectively, or antigen binding fragments, Fab fragments, single-chain variable fragments (scFv), variants, or conjugates thereof. In some embodiments, a VEGF-A inhibitor comprises heavy and light chains that are each at least 99% identical to the sequences shown in SEQ ID NO:207 and SEQ ID NO:208, respectively. In some embodiments, a VEGF-A inhibitor comprises heavy and light chains that are each at least 98% identical to the sequences shown in SEQ ID NO:207 and SEQ ID NO:208, respectively. In some embodiments, a VEGF-A inhibitor comprises heavy and light chains that are each at least 97% identical to the sequences shown in SEQ ID NO:207 and SEQ ID NO:208, respectively. In some embodiments, a VEGF-A inhibitor comprises heavy and light chains that are each at least 96% identical to the sequences shown in SEQ ID NO:207 and SEQ ID NO:208, respectively. In some embodiments, a VEGF-A inhibitor comprises heavy and light chains that are each at least 95% identical to the sequences shown in SEQ ID NO:207 and SEQ ID NO:208, respectively.

In some embodiments, the VEGF-A inhibitor comprises the heavy and light chain CDRs or variable regions (VRs) of bevacizumab. In some embodiments, the VEGF-A inhibitor heavy chain variable region ($V_H$) comprises the sequence shown in SEQ ID NO:209, and the VEGF-A inhibitor light chain variable region ($V_L$) comprises the sequence shown in SEQ ID NO:210, and conservative amino acid substitutions thereof. In some embodiments, a VEGF-A inhibitor comprises $V_H$ and $V_L$ regions that are each at least 99% identical to the sequences shown in SEQ ID NO:209 and SEQ ID NO:210, respectively. In some embodiments, a VEGF-A inhibitor comprises $V_H$ and $V_L$ regions that are each at least 98% identical to the sequences shown in SEQ ID NO:209 and SEQ ID NO:210, respectively. In some embodiments, a VEGF-A inhibitor comprises $V_H$ and $V_L$ regions that are each at least 97% identical to the sequences shown in SEQ ID NO:209 and SEQ ID NO:210, respectively. In some embodiments, a VEGF-A inhibitor comprises $V_H$ and $V_L$ regions that are each at least 96% identical to the sequences shown in SEQ ID NO:209 and SEQ ID NO:210, respectively. In some embodiments, a VEGF-A inhibitor comprises $V_H$ and $V_L$ regions that are each at least 95% identical to the sequences shown in SEQ ID NO:209 and SEQ ID NO:210, respectively.

In some embodiments, a VEGF-A inhibitor comprises the heavy chain CDR1, CDR2 and CDR3 domains having the sequences set forth in SEQ ID NO:211, SEQ ID NO:212, and SEQ ID NO:213, respectively, and conservative amino acid substitutions thereof, and light chain CDR1, CDR2 and CDR3 domains having the sequences set forth in SEQ ID NO:214, SEQ ID NO:215, and SEQ ID NO:216, respectively, and conservative amino acid substitutions thereof. In some embodiments, the antibody competes for binding with, and/or binds to the same epitope on VEGF-A as any of the aforementioned antibodies.

In some embodiments, the VEGF-A inhibitor is a VEGF-A biosimilar monoclonal antibody approved by drug regulatory authorities with reference to bevacizumab. In some embodiments, the biosimilar comprises an anti-VEGF-A antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is bevacizumab. In some embodiments, the one or more post-translational modifications are selected from one or more of: glycosylation, oxidation, deamidation, and truncation. In some embodiments, the biosimilar is an anti-VEGF-A antibody authorized or submitted for authorization, wherein the anti-VEGF-A antibody is provided in a formulation which differs from the formulations of a reference medicinal product or reference biological product, wherein the reference medicinal product or reference biological product is bevacizumab. The anti-VEGF-A antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is bevacizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is bevacizumab.

TABLE 26

Amino acid sequences for bevacizumab.

| Identifier | Sequence (One-Letter Amino Acid Symbols) | |
|---|---|---|
| SEQ ID NO: 207 bevacizumab heavy chain | 1 EVQLVESGGG LVQPGGSLRL SCAASGYTFT NYGMNWVRQA PGKGLEWVGW INTYTGEPTY<br>61 AADFKRRFTF SLDTSKSTAY LQMNSLRAED TAVYYCAKYP HYYGSSHWYF DVWGQGTLVT<br>121 VSSASTKGPS VFPLAPSSKS TSGGTAALGC LVKDYFPEPV TVSWNSGALT SGVHTFPAVL<br>181 QSSGLYSLSS VVTVPSSSLG TQTYICNVNH KPSNTKVDKK VEPKSCDKTH TCPPCPAPEL<br>241 LGGPSVFLFP PKPKDTLMIS RTPEVTCVVV DVSHEDPEVK FNWYVDGVEV HNAKTKPREE<br>301 QYNSTYRVVS VLTVLHQDWL NGKEYKCKVS NKALPAPIEK TISKAKGQPR EPQVYTLPPS<br>361 REEMTKNQVS LTCLVKGFYP SDIAVEWESN GQPENNYKTT PPVLDSDGSF FLYSKLTVDK<br>421 SRWQQGNVFS CSVMHEALHN HYTQKSLSLS PGK | |
| SEQ ID NO: 208 bevacizumab light chain | 1 DIQMTQSPSS LSASVGDRVT ITCSASQDIS NYLNWYQQKP GKAPKVLIYF TSSLHSGVPS<br>61 RFSGSGSGTD FTLTISSLQP EDFATYYCQQ YSTVPWTFGQ GTKVEIKRTV AAPSVFIFPP<br>121 SDEQLKSGTA SVVCLLNNFY PREAKVQWKV DNALQSGNSQ ESVTEQDSKD STYSLSSTLT<br>181 LSKADYEKHK VYACEVTHQG LSSPVTKSEN RGEC | |
| SEQ ID NO: 209 bevacizumab variable heavy chain | 1 EVQLVESGGG LVQPGGSLRL SCAASGYTFT NYGMNWVRQA PGKGLEWVGW INTYTGEPTY<br>61 AADFKRRFTF SLDTSKSTAY LQMNSLRAED TAVYYCAKYP HYYGSSHWYF DVWGQGTLVT<br>121 VSS | |
| SEQ ID NO: 210 bevacizumab variable light chain | 1 DIQMTQSPSS LSASVGDRVT ITCSASQDIS NYLNWYQQKP GKAPKVLIYF TSSLHSGVPS<br>61 RFSGSGSGTD FTLTISSLQP EDFATYYCQQ YSTVPWTFGQ GTKVEIKR | |
| SEQ ID NO: 211 bevacizumab heavy chain CDR1 | GYTFTNYGMN | 10 |
| SEQ ID NO: 212 bevacizumab heavy chain CDR2 | WINTYTGEPT YAADFK | 16 |
| SEQ ID NO: 213 bevacizumab heavy chain CDR3 | YPHYYGSSHW YFDV | 14 |
| SEQ ID NO: 214 bevacizumab light chain CDR1 | SASQDISNYL N | 11 |
| SEQ ID NO: 215 bevacizumab light chain CDR2 | FTSSLHS | 7 |
| SEQ ID NO: 216 bevacizumab light chain CDR3 | QQYSTVPWT | 9 |

In some embodiments, the VEGF-A inhibitor is ranibizumab, or biosimilars, antigen-binding fragments, conjugates, or variants thereof. Ranibizumab (CAS registry number 347396-82-1, Lucentis@) is a monoclonal antibody fragment (Fab) created from the same parent mouse antibody as bevacizumab. It is an anti-angiogenic that has been approved to treat age-related macular degeneration (AMD, also ARMD), a common form of age-related vision loss. Its rates of side effects is similar to that of bevacizumab. However, ranibizumab typically costs $2,000 a dose, while the equivalent dose of bevacizumab typically costs $50.

In some embodiments, a VEGF-A inhibitor comprises a heavy chain given by SEQ ID NO:217 and a light chain given by SEQ ID NO:218. In some embodiments, a VEGF-A inhibitor comprises heavy and light chains having the sequences shown in SEQ ID NO:217 and SEQ ID NO:218, respectively, or antigen binding fragments, Fab fragments, single-chain variable fragments (scFv), variants, or conjugates thereof. In some embodiments, a VEGF-A inhibitor comprises heavy and light chains that are each at least 99% identical to the sequences shown in SEQ ID NO:217 and SEQ ID NO:218, respectively. In some embodiments, a VEGF-A inhibitor comprises heavy and light chains that are each at least 98% identical to the sequences shown in SEQ ID NO:217 and SEQ ID NO:218, respectively. In some embodiments, a VEGF-A inhibitor comprises heavy and light chains that are each at least 97% identical to the sequences shown in SEQ ID NO:217 and SEQ ID NO:218, respectively. In some embodiments, a VEGF-A inhibitor comprises heavy and light chains that are each at least 96% identical to the sequences shown in SEQ ID NO:217 and SEQ ID NO:218, respectively. In some embodiments, a VEGF-A inhibitor comprises heavy and light chains that are each at least 95% identical to the sequences shown in SEQ ID NO:217 and SEQ ID NO:218, respectively.

In some embodiments, the VEGF-A inhibitor comprises the heavy and light chain CDRs or variable regions (VRs) of ranibizumab. In some embodiments, the VEGF-A inhibitor heavy chain variable region ($V_H$) comprises the sequence shown in SEQ ID NO:219, and the VEGF-A inhibitor light chain variable region ($V_L$) comprises the sequence shown in SEQ ID NO:220, and conservative amino acid substitutions thereof. In some embodiments, a VEGF-A inhibitor comprises $V_H$ and $V_L$ regions that are each at least 99% identical to the sequences shown in SEQ ID NO:219 and SEQ ID NO:220, respectively. In some embodiments, a VEGF-A inhibitor comprises $V_H$ and $V_L$ regions that are each at least 98% identical to the sequences shown in SEQ ID NO:219 and SEQ ID NO:220, respectively. In some embodiments, a VEGF-A inhibitor comprises $V_H$ and $V_L$ regions that are each at least 97% identical to the sequences shown in SEQ ID NO:219 and SEQ ID NO:220, respectively. In some embodiments, a VEGF-A inhibitor comprises $V_H$ and $V_L$ regions that are each at least 96% identical to the sequences shown in SEQ ID NO:219 and SEQ ID NO:220, respectively. In some embodiments, a VEGF-A inhibitor comprises $V_H$ and $V_L$ regions that are each at least 95% identical to the sequences shown in SEQ ID NO:219 and SEQ ID NO:220, respectively.

In some embodiments, a VEGF-A inhibitor comprises the heavy chain CDR1, CDR2 and CDR3 domains having the sequences set forth in SEQ ID NO:221, SEQ ID NO:222, and SEQ ID NO:223, respectively, and conservative amino acid substitutions thereof, and light chain CDR1, CDR2 and CDR3 domains having the sequences set forth in SEQ ID NO:224, SEQ ID NO:225, and SEQ ID NO:226, respectively, and conservative amino acid substitutions thereof. In some embodiments, the antibody competes for binding with, and/or binds to the same epitope on VEGF-A as any of the aforementioned antibodies.

In some embodiments, the VEGF-A inhibitor is a VEGF-A biosimilar monoclonal antibody approved by drug regulatory authorities with reference to ranibizumab. In some embodiments, the biosimilar comprises an anti-VEGF-A antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is ranibizumab. In some embodiments, the one or more post-translational modifications are selected from one or more of. glycosylation, oxidation, deamidation, and truncation. In some embodiments, the biosimilar is an anti-VEGF-A antibody authorized or submitted for authorization, wherein the anti-VEGF-A antibody is provided in a formulation which differs from the formulations of a reference medicinal product or reference biological product, wherein the reference medicinal product or reference biological product is ranibizumab. The anti-VEGF-A antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ranibizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ranibizumab.

TABLE 27

Amino acid sequences for ranibizumab.

| Identifier | | Sequence (One-Letter Amino Acid Symbols) |
|---|---|---|
| SEQ ID NO: 217 | 1 | EVQLVESGGG LVQPGGSLRL SCAASGYDFT HYGMNWVRQA PGKGLEWVGW INTYTGEPTY |
| ranibizumab | 61 | AADFKRRFTF SLDTSKSTAY LQMNSLRAED TAVYYCAKYP YYYGTSHWYF DVWGQGTLVT |
| heavy chain | 121 | VSSASTKGPS VFPLAPSSKS TSGGTAALGC LVKDYFPEPV TVSWNSGALT SGVHTFPAVL |
| | 181 | QSSGLYSLSS VVTVPSSSLG TQTYICNVNH KPSNTKVDKK VEPKSCDKTH L |
| SEQ ID NO: 218 | 1 | DIQLTQSPSS LSASVGDRVT ITCSASQDIS NYLNWYQQKP GKAPKVLIYF TSSLHSGVPS |
| ranibizumab | 61 | RFSGSGSGTD FTLTISSLQP EDFATYYCQQ YSTVPWTFGQ GTKVEIKRTV AAPSVFIFPP |
| light chain | 121 | SDEQLKSGTA SVVCLLNNFY PREAKVQWKV DNALQSGNSQ ESVTEQDSKD STYSLSSTLT |
| | 181 | LSKADYEKHK VYACEVTHQG LSSPVTKSFN RGEC |

TABLE 27-continued

Amino acid sequences for ranibizumab.

| Identifier | | Sequence (One-Letter Amino Acid Symbols) | |
|---|---|---|---|
| SEQ ID NO: 219 ranibizumab variable heavy chain | 1<br>61<br>121 | EVQLVESGGG LVQPGGSLRL SCAASGYDFT HYGMNWVRQA PGKGLEWVGW INTYTGEPTY<br>AADFKRRFTF SLDTSKSTAY LQMNSLRAED TAVYYCAKYP YYYGTSHWYF DVWGQGTLVT<br>VSS | |
| SEQ ID NO: 220 ranibizumab variable light chain | 1<br>61 | DIQLTQSPSS LSASVGDRVT ITCSASQDIS NYLNWYQQKP GKAPKVLIYF TSSLHSGVPS<br>RFSGSGSGTD FTLTISSLQP EDFATYYCQQ YSTVPWTFGQ GTKVEIKR | |
| SEQ ID NO: 221 ranibizumab heavy chain CDR1 | | GYDFTHYGMN | 10 |
| SEQ ID NO: 222 ranibizumab heavy chain CDR2 | | WINTYTGEPT YAADFKR | 17 |
| SEQ ID NO: 223 ranibizumab heavy chain CDR3 | | YPYYYGTSHW YFDV | 14 |
| SEQ ID NO: 224 ranibizumab light chain CDR1 | | SASQDISNYL N | 11 |
| SEQ ID NO: 225 ranibizumab light chain CDR2 | | FTSSLHS | 7 |
| SEQ ID NO: 226 ranibizumab light chain CDR3 | | QQYSTVPWT | 9 |

In some embodiments, the VEGF-A inhibitor is icrucumab, or biosimilars, antigen-binding fragments, conjugates, or variants thereof. Icrucumab (CAS registry number 1024603-92-6, also known as IMC-18F1) is a human monoclonal antibody designed for the treatment of solid tumors. A fully human IgGI monoclonal antibody directed against human vascular endothelial growth factor receptor 1 (VEGFR-1/FLT-1) with potential antiangiogenesis and antineoplastic activities. Icrucumab specifically binds to and inhibits the activity of VEGFR-1, which may prevent the activation of downstream signaling pathways and so inhibit tumor angiogenesis; the subsequent reduction in tumor nutrient supply may inhibit tumor cell proliferation. Tumor cell overexpression of VEGFR-1 may be associated with tumor angiogenesis and tumor cell proliferation and invasion; VEGFR-1 may modulate VEGFR-2 signaling.

In some embodiments, a VEGF-A inhibitor comprises a heavy chain given by SEQ ID NO:227 and a light chain given by SEQ ID NO:228. In some embodiments, a VEGF-A inhibitor comprises heavy and light chains having the sequences shown in SEQ ID NO:227 and SEQ ID NO: 564, respectively, or antigen binding fragments, Fab fragments, single-chain variable fragments (scFv), variants, or conjugates thereof. In some embodiments, a VEGF-A inhibitor comprises heavy and light chains that are each at least 99% identical to the sequences shown in SEQ ID NO:227 and SEQ ID NO:228, respectively. In some embodiments, a VEGF-A inhibitor comprises heavy and light chains that are each at least 98% identical to the sequences shown in SEQ ID NO:227 and SEQ ID NO:228, respectively. In some embodiments, a VEGF-A inhibitor comprises heavy and light chains that are each at least 97% identical to the sequences shown in SEQ ID NO:227 and SEQ ID NO:228, respectively. In some embodiments, a VEGF-A inhibitor comprises heavy and light chains that are each at least 96% identical to the sequences shown in SEQ ID NO:227 and SEQ ID NO:228, respectively. In some embodiments, a VEGF-A inhibitor comprises heavy and light chains that are each at least 95% identical to the sequences shown in SEQ ID NO:227 and SEQ ID NO:228, respectively.

In some embodiments, the VEGF-A inhibitor comprises the heavy and light chain CDRs or variable regions (VRs) of icrucumab. In some embodiments, the VEGF-A inhibitor heavy chain variable region ($V_H$) comprises the sequence shown in SEQ ID NO:229, and the VEGF-A inhibitor light chain variable region ($V_L$) comprises the sequence shown in SEQ ID NO:230, and conservative amino acid substitutions thereof. In some embodiments, a VEGF-A inhibitor comprises $V_H$ and $V_L$ regions that are each at least 99% identical to the sequences shown in SEQ ID NO:229 and SEQ ID NO:230, respectively. In some embodiments, a VEGF-A inhibitor comprises $V_H$ and $V_L$ regions that are each at least 98% identical to the sequences shown in SEQ ID NO:229 and SEQ ID NO:230, respectively. In some embodiments, a VEGF-A inhibitor comprises $V_H$ and $V_L$ regions that are each at least 97% identical to the sequences shown in SEQ ID NO:229 and SEQ ID NO:230, respectively. In some embodiments, a VEGF-A inhibitor comprises $V_H$ and $V_L$ regions that are each at least 96% identical to the sequences shown in SEQ ID NO:229 and SEQ ID NO:230, respectively. In some embodiments, a VEGF-A inhibitor comprises $V_H$ and $V_L$ regions that are each at least 95% identical to the sequences shown in SEQ ID NO:229 and SEQ ID NO:230, respectively.

In some embodiments, a VEGF-A inhibitor comprises the heavy chain CDR1, CDR2 and CDR3 domains having the sequences set forth in SEQ ID NO:231, SEQ ID NO:232, and SEQ ID NO:233, respectively, and conservative amino acid substitutions thereof, and light chain CDR1, CDR2 and CDR3 domains having the sequences set forth in SEQ ID NO:234, SEQ ID NO:235, and SEQ ID NO:236, respectively, and conservative amino acid substitutions thereof. In some embodiments, the antibody competes for binding with, and/or binds to the same epitope on VEGF-A as any of the aforementioned antibodies.

In some embodiments, the VEGF-A inhibitor is a VEGF-A biosimilar monoclonal antibody approved by drug regulatory authorities with reference to icrucumab. In some embodiments, the biosimilar comprises an anti-VEGF-A antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is icrucumab. In some embodiments, the one or more post-translational modifications are selected from one or more of: glycosylation, oxidation, deamidation, and truncation. In some embodiments, the biosimilar is an anti-VEGF-A antibody authorized or submitted for authorization, wherein the anti-VEGF-A antibody is provided in a formulation which differs from the formulations of a reference medicinal product or reference biological product, wherein the reference medicinal product or reference biological product is icrucumab. The anti-VEGF-A antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is icrucumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is icrucumab.

TABLE 28

Amino acid sequences for icrucumab.

| Identifier | | Sequence (One-Letter Amino Acid Symbols) |
|---|---|---|
| SEQ ID NO: 227<br>icrucumab<br>heavy chain | 1<br>61<br>121<br>181 | QAQVVESGGG VVOSGRSLRL SCAASGFAFS SYGMHWVRQA PGKGLEWVAV IWYDGSNKYY<br>ADSVRGRFTI SRDNSENTLY LOMNSLRAED TAVYYCARDH YGSGVHHYFY YGLDVWGOGT<br>TVTVSSASTK GPSVFPLAPS SKSTSGGTAA LGCLVKDYFP EPVTVSWNSG ALTSGVHTFP<br>AVLOSSGLYS LSSVVTVPSS SLGTQTYICN VNHKPSNTKV DKRVEPKSCD KTHTCPPCPA<br>PELLGGPSVF LFPPKPKDTL MISRTPEVTC VVVDVSHEDP EVKFNWYVDG VEVHNAKTKP<br>REEQYNSTYR VVSVLTVLHQ DWLNGKEYKC KVSNKALPAP IEKTISKAKG QPREPQVYTL<br>PPSREEMTKN QVSLTCLVKG FYPSDIAVEW ESNGQPENNY KTTPPVLDSD GSFFLYSKLT<br>VDKSRWQQGN VFSCSVMHEA LHNHYTQKSL SLSPGK |
| SEQ ID NO: 228<br>icrucumab<br>light chain | 1<br>61<br>121<br>181 | EIVLTQSPGT LSLSPGERAT LSCRASQSVS SSYLAWYQQK PGQAPRLLIY GASSRATGIP<br>DRESGSGSGT DFTLTISRLE PEDFAVYYCQ QYGSSPLTFG GGTKVEIKRT VAAPSVFIFP<br>PSDEQLKSGT ASVVCLLNNF YPREAKVOWK VDNALQSGNS QESVTEQDSK DSTYSLSSTL<br>TLSKADYEKH KVYACEVTHQ GLSSPVTKSF NRGEC |
| SEQ ID NO: 229<br>icrucumab<br>variable<br>heavy chain | | QAQWESGGGVVQSGRSLRLSCAASGFAFSSYGMHWVRQAPGKGLEWVAVIWYDGSNKYYADSVRGRFTISRDNSEN<br>TLYLQMNSLRAEDTAVYYCARDHYGSGVHHYFYYGLDVWGQGTTVTVSS |
| SEQ ID NO: 230<br>icrucumab<br>variable<br>light chain | | EIVLTQSPGTLSLSPGERATLSCRASQSVSSSYLAWYQQKPGQAPRLLIYGASSRATGIPDRFSGSGSGTDFTLTI<br>SRLEPEDFAVYYCQQYGSSPLTFGGGTKVEIK |
| SEQ ID NO: 231<br>icrucumab heavy<br>chain CDR1 | | VVQSGRS |
| SEQ ID NO: 232<br>icrucumab heavy<br>chain CDR2 | | SGFAFSSYG |
| SEQ ID NO: 233<br>icrucumab heavy<br>chain CDR3 | | WVAVIWYDGSNKYYADS |
| SEQ ID NO: 234<br>icrucumab light<br>chain CDR1 | | LSPGERA |

TABLE 28-continued

| Amino acid sequences for icrucumab. | |
|---|---|
| Identifier | Sequence (One-Letter Amino Acid Symbols) |
| SEQ ID NO: 235 icrucumab light chain CDR2 | QSV |
| SEQ ID NO: 236 icrucumab light chain CDR3 | APRLLIYGAS |

In some embodiments, the VEGF-A inhibitor is a decoy VEGF receptor (also known as VEGF trap), such as Aflibercept (Eylea, Zaltrap), which is disclosed in US Patent Application Publication No. US2019/0298801 and International Patent Application Publication No. WO2014006113A1 (disclosure incorporated herein by reference) or Conbercept, which is disclosed in US Patent Application Publication Nos. US2019/0002546 and US2019/0343918 (disclosure incorporated herein by reference). Additional disclosure and examples of decoy VEGF receptor is provided in U.S. Pat. Nos. 6,383,486, 6,375,929, 6,348,333, 6,100,071, and 9,777,261, the disclosure of which are incorporated herein by reference in their entireties.

In some embodiments, the VEGF-A inhibitor is a small molecule tyrosine kinases inhibitor. Small molecule tyrosine kinases are known to those of ordinary skill in the art. Examples of small molecule tyrosine kinases inhibitor include, but are not limited to, Pegaptanib, Pazopanib, lapatinib, Sunitinib, sorafenib, regorafenib, Ponatinib, lenvatinib, axitinib (AG-013736), Cediranib (AZD2171), vatalanib, and/or Lucitanib.

In some embodiments, the VEGF-A inhibitor is an anti-VEGFR ribozyme, an anti-VEGFR antisense, and an siRNA that inhibits a VEGFR that are disclosed in U.S. Pat. No. 7,148,342 and International Patent Application No. WO2010058426 (disclosure incorporated herein by reference in their entireties).

6. Lymphodepletion Preconditioning of Patients

In some embodiments, the invention includes a method of treating a cancer with a population of TILs, wherein a patient is pre-treated with non-myeloablative chemotherapy prior to an infusion of TILs according to the present disclosure. In some embodiments, the invention includes a population of TILs for use in the treatment of cancer in a patient which has been pre-treated with non-myeloablative chemotherapy. In some embodiments, the population of TILs is for administration by infusion. In some embodiments, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In some embodiments, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. C/in. Pract. Oncol.*, 2006, 3, 668-681, Dudley, et al., *J Clin. Oncol.* 2008, 26, 5233-5239, and Dudley, et al., *J C/in. Oncol.* 2005, 23, 2346-2357, all of which are incorporated by reference herein in their entireties.

In some embodiments, the fludarabine is administered at a concentration of 0.5 μg/mL to 10 μg/mL fludarabine. In some embodiments, the fludarabine is administered at a concentration of 1 μg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 μg/mL to 10 μg/mL by administration of cyclophosphamide. In some embodiments, mafosfamide, the active form of cyclophosphamide, is obtained at a concentration of 1 μg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.). In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In some embodiments, the lymphodepletion is performed by administration of cyclophosphamide at a dose of 60 mg/m$^2$/day for two days followed by administration of fludarabine at a dose of 25 mg/m$^2$/day for five days.

In some embodiments, the lymphodepletion is performed by administration of cyclophosphamide at a dose of 60 mg/m$^2$/day for two days and administration of fludarabine at a dose of 25 mg/m$^2$/day for five days, wherein cyclophosphamide and fludarabine are both administered on the first two days, and wherein the lymphodepletion is performed in five days in total.

In some embodiments, the lymphodepletion is performed by administration of cyclophosphamide at a dose of about 50 mg/m$^2$/day for two days and administration of fludarabine at a dose of about 25 mg/m$^2$/day for five days, wherein cyclophosphamide and fludarabine are both administered on the first two days, and wherein the lymphodepletion is performed in five days in total.

In some embodiments, the lymphodepletion is performed by administration of cyclophosphamide at a dose of about 50 mg/m$^2$/day for two days and administration of fludarabine at a dose of about 20 mg/m$^2$/day for five days, wherein cyclophosphamide and fludarabine are both administered on the first two days, and wherein the lymphodepletion is performed in five days in total.

In some embodiments, the lymphodepletion is performed by administration of cyclophosphamide at a dose of about 40 mg/m$^2$/day for two days and administration of fludarabine at a dose of about 20 mg/m$^2$/day for five days, wherein cyclophosphamide and fludarabine are both administered on the first two days, and wherein the lymphodepletion is performed in five days in total.

In some embodiments, the lymphodepletion is performed by administration of cyclophosphamide at a dose of about 40 mg/m$^2$/day for two days and administration of fludarabine at a dose of about 15 mg/m$^2$/day for five days, wherein cyclophosphamide and fludarabine are both administered on the first two days, and wherein the lymphodepletion is performed in five days in total.

In some embodiments, the lymphodepletion is performed by administration of cyclophosphamide at a dose of 60 mg/m$^2$/day and fludarabine at a dose of 25 mg/m$^2$/day for two days followed by administration of fludarabine at a dose of 25 mg/m$^2$/day for three days.

In some embodiments, the cyclophosphamide is administered with mesna. In some embodiments, mesna is administered at 15 mg/kg. In some embodiments where mesna is infused, and if infused continuously, mesna can be infused over approximately 2 hours with cyclophosphamide (on Days −5 and/or −4), then at a rate of 3 mg/kg/hour for the remaining 22 hours over the 24 hours starting concomitantly with each cyclophosphamide dose.

In some embodiments, the lymphodepletion comprises the step of treating the patient with an IL-2 regimen starting on the day after administration of the third population of TILs to the patient.

In some embodiments, the lymphodepletion comprises the step of treating the patient with an IL-2 regimen starting on the same day as administration of the third population of TILs to the patient.

In some embodiments, the lymphodeplete comprises 5 days of preconditioning treatment. In some embodiments, the days are indicated as days −5 through −1, or Day 0 through Day 4. In some embodiments, the regimen comprises cyclophosphamide on days −5 and −4 (i.e., days 0 and 1). In some embodiments, the regimen comprises intravenous cyclophosphamide on days −5 and −4 (i.e., days 0 and 1). In some embodiments, the regimen comprises 60 mg/kg intravenous cyclophosphamide on days −5 and −4 (i.e., days 0 and 1). In some embodiments, the cyclophosphamide is administered with mesna. In some embodiments, the regimen further comprises fludarabine. In some embodiments, the regimen further comprises intravenous fludarabine. In some embodiments, the regimen further comprises 25 mg/m$^2$ intravenous fludarabine. In some embodiments, the regimen further comprises 25 mg/m$^2$ intravenous fludarabine on days −5 and −1 (i.e., days 0 through 4). In some embodiments, the regimen further comprises 25 mg/m$^2$ intravenous fludarabine on days −5 and −1 (i.e., days 0 through 4).

In some embodiments, the non-myeloablative lymphodepletion regimen comprises the steps of administration of cyclophosphamide at a dose of 60 mg/m$^2$/day and fludarabine at a dose of 25 mg/m$^2$/day for two days followed by administration of fludarabine at a dose of 25 mg/m$^2$/day for five days.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for three days.

In some embodiments, the non-myeloablative lymphodepletion regimen comprises the steps of administration of cyclophosphamide at a dose of 60 mg/m$^2$/day and fludarabine at a dose of 25 mg/m$^2$/day for two days followed by administration of fludarabine at a dose of 25 mg/m$^2$/day for three days.

In some embodiments, the non-myeloablative lymphodepletion regimen comprises the steps of administration of cyclophosphamide at a dose of 60 mg/m$^2$/day and fludarabine at a dose of 25 mg/m$^2$/day for two days followed by administration of fludarabine at a dose of 25 mg/m$^2$/day for one day.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for three days.

In some embodiments, the non-myeloablative lymphodepletion regimen comprises the steps of administration of cyclophosphamide at a dose of 60 mg/m$^2$/day and fludarabine at a dose of 25 mg/m$^2$/day for two days followed by administration of fludarabine at a dose of 25 mg/m$^2$/day for three days.

In some embodiments, the non-myeloablative lymphodepletion regimen is administered according to Table 29.

TABLE 29

Exemplary lymphodepletion and treatment regimen.

| Day | −5 | −4 | −3 | −2 | −1 | 0 | 1 | 2 | 3 | 4 |
|---|---|---|---|---|---|---|---|---|---|---|
| Cyclophosphamide 60 mg/kg | X | X | | | | | | | | |
| Mesna (as needed) | X | X | | | | | | | | |
| Fludarabine 25 mg/m$^2$/day | X | X | X | X | X | | | | | |
| TIL infusion | | | | | | X | | | | |

In some embodiments, the non-myeloablative lymphodepletion regimen is administered according to Table 30.

TABLE 30

Exemplary lymphodepletion and treatment regimen.

| Day | −4 | −3 | −2 | 1 | 0 | 1 | 2 | 3 | 4 |
|---|---|---|---|---|---|---|---|---|---|
| Cyclophosphamide 60 mg/kg | X | X | | | | | | | |
| Mesna (as needed) | X | X | | | | | | | |
| Fludarabine 25 mg/m$^2$/day | X | X | X | X | | | | | |
| TIL infusion | | | | | X | | | | |

In some embodiments, the non-myeloablative lymphodepletion regimen is administered according to Table 31.

TABLE 31

Exemplary lymphodepletion and treatment regimen.

| Day | −3 | −2 | −1 | 0 | 1 | 2 | 3 | 4 |
|---|---|---|---|---|---|---|---|---|
| Cyclophosphamide 60 mg/kg | X | X | | | | | | |
| Mesna (as needed) | X | X | | | | | | |
| Fludarabine 25 mg/m$^2$/day | X | X | X | | | | | |
| TIL infusion | | | | X | | | | |

In some embodiments, the non-myeloablative lymphodepletion regimen is administered according to Table 32.

TABLE 32

Exemplary lymphodepletion and treatment regimen.

| Day | −5 | −4 | −3 | −2 | −1 | 0 | 1 | 2 | 3 | 4 |
|---|---|---|---|---|---|---|---|---|---|---|
| Cyclophosphamide 60 mg/kg | X | X | | | | | | | | |
| Mesna (as needed) | X | X | | | | | | | | |
| Fludarabine 25 mg/m$^2$/day | | | X | X | X | | | | | |
| TIL infusion | | | | | | X | | | | |

In some embodiments, the non-myeloablative lymphodepletion regimen is administered according to Table 33.

TABLE 33

Exemplary lymphodepletion and treatment regimen.

| Day | −5 | −4 | −3 | −2 | −1 | 0 | 1 | 2 | 3 | 4 |
|---|---|---|---|---|---|---|---|---|---|---|
| Cyclophosphamide 300 mg/kg | X | X | | | | | | | | |
| Mesna (as needed) | X | X | | | | | | | | |
| Fludarabine 30 mg/m$^2$/day | X | X | X | X | X | | | | | |
| TIL infusion | | | | | | X | | | | |

In some embodiments, the non-myeloablative lymphodepletion regimen is administered according to Table 34.

TABLE 34

Exemplary lymphodepletion and treatment regimen.

| Day | −4 | −3 | −2 | −1 | 0 | 1 | 2 | 3 | 4 |
|---|---|---|---|---|---|---|---|---|---|
| Cyclophosphamide 300 mg/kg | X | X | | | | | | | |
| Mesna (as needed) | X | X | | | | | | | |
| Fludarabine 30 mg/m$^2$/day | X | X | X | X | | | | | |
| TIL infusion | | | | | X | | | | |

In some embodiments, the non-myeloablative lymphodepletion regimen is administered according to Table 35.

TABLE 35

Exemplary lymphodepletion and treatment regimen.

| Day | −3 | −2 | −1 | 0 | 1 | 2 | 3 | 4 |
|---|---|---|---|---|---|---|---|---|
| Cyclophosphamide 300 mg/kg | X | X | | | | | | |
| Mesna (as needed) | X | X | | | | | | |
| Fludarabine 30 mg/m$^2$/day | X | X | X | | | | | |
| TIL infusion | | | | X | | | | |

In some embodiments, the non-myeloablative lymphodepletion regimen is administered according to Table 36.

TABLE 36

Exemplary lymphodepletion and treatment regimen.

| Day | −5 | −4 | −3 | −2 | −1 | 0 | 1 | 2 | 3 | 4 |
|---|---|---|---|---|---|---|---|---|---|---|
| Cyclophosphamide 300 mg/kg | X | X | | | | | | | | |
| Mesna (as needed) | X | X | | | | | | | | |
| Fludarabine 30 mg/m$^2$/day | | | X | X | X | | | | | |
| TIL infusion | | | | | | X | | | | |

In some embodiments, the TIL infusion used with the foregoing embodiments of myeloablative lymphodepletion regimens may be any TIL composition described herein, as well as the addition of IL-2 regimens and administration of co-therapies (such as PD-1 and PD-L1 inhibitors) as described herein.

7. IL-2 Regimens

In some embodiments, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total. In some embodiments, IL-2 is administered in 1, 2, 3, 4, 5, or 6 doses. In some embodiments, IL-2 is administered at a maximum dosage of up to 6 doses.

In some embodiments, the IL-2 regimen comprises a decrescendo IL-2 regimen. Decrescendo IL-2 regimens have been described in O'Day, et al., *J Clin. Oncol.* 1999, 17, 2752-61 and Eton, et al., *Cancer* 2000, 88, 1703-9, the disclosures of which are incorporated herein by reference. In some embodiments, a decrescendo IL-2 regimen comprises $18\times10^6$ IU/m$^2$ aldesleukin, or a biosimilar or variant thereof, administered intravenously over 6 hours, followed by $18\times10^6$ IU/m$^2$ administered intravenously over 12 hours, followed by $18\times10^6$ IU/m$^2$ administered intravenously over 24 hours, followed by $4.5\times10^6$ IU/m$^2$ administered intravenously over 72 hours. This treatment cycle may be repeated every 28 days for a maximum of four cycles. In some embodiments, a decrescendo IL-2 regimen comprises 18,000,000 IU/m$^2$ on day 1, 9,000,000 IU/m$^2$ on day 2, and 4,500,000 IU/m$^2$ on days 3 and 4.

In some embodiments, the IL-2 regimen comprises a low-dose IL-2 regimen. Any low-dose IL-2 regimen known in the art may be used, including the low-dose IL-2 regimens described in Dominguez-Villar and Hafler, Nat. Immunology 2000, 19, 665-673; Hartemann, et al., *Lancet Diabetes Endocrinol.* 2013, 1, 295-305; and Rosenzwaig, et al., *Ann. Rheum*. Dis. 2019, 78, 209-217, the disclosures of which are incorporated herein by reference. In some embodiments, a low-dose IL-2 regimen comprises $18\times10^6$ IU per $m^2$ of aldesleukin, or a biosimilar or variant thereof, per 24 hours, administered as a continuous infusion for 5 days, followed by 2-6 days without IL-2 therapy, optionally followed by an an additional 5 days of intravenous aldesleukin or a biosimilar or variant thereof, as a continuous infusion of $18\times10^6$ IU per $m^2$ per 24 hours, optionally followed by 3 weeks without IL-2 therapy, after which additional cycles may be administered.

In some embodiments, IL-2 is administered at a maximum dosage of up to 6 doses. In some embodiments, the high-dose IL-2 regimen is adapted for pediatric use. In some embodiments, a dose of 600,000 international units (IU)/kg of aldesleukin every 8-12 hours for up to a maximum of 6 doses is used. In some embodiments, a dose of 500,000 international units (IU)/kg of aldesleukin every 8-12 hours for up to a maximum of 6 doses is used. In some embodiments, a dose of 400,000 international units (IU)/kg of aldesleukin every 8-12 hours for up to a maximum of 6 doses is used. In some embodiments, a dose of 500,000 international units (IU)/kg of aldesleukin every 8-12 hours for up to a maximum of 6 doses is used. In some embodiments, a dose of 300,000 international units (IU)/kg of aldesleukin every 8-12 hours for up to a maximum of 6 doses is used. In some embodiments, a dose of 200,000 international units (IU)/kg of aldesleukin every 8-12 hours for up to a maximum of 6 doses is used. In some embodiments, a dose of 100,000 international units (IU)/kg of aldesleukin every 8-12 hours for up to a maximum of 6 doses is used.

In some embodiments, the IL-2 regimen comprises administration of pegylated IL-2 every 1, 2, 4, 6, 7, 14 or 21 days at a dose of 0.10 mg/day to 50 mg/day. In some embodiments, the IL-2 regimen comprises administration of bempegaldesleukin, or a fragment, variant, or biosimilar thereof, every 1, 2, 4, 6, 7, 14 or 21 days at a dose of 0.10 mg/day to 50 mg/day.

In some embodiments, the IL-2 regimen comprises administration of THOR-707, or a fragment, variant, or biosimilar thereof, every 1, 2, 4, 6, 7, 14 or 21 days at a dose of 0.10 mg/day to 50 mg/day.

In some embodiments, the IL-2 regimen comprises administration of nemvaleukin alfa, or a fragment, variant, or biosimilar thereof, following administration of TIL. In certain embodiments, the patient the nemvaleukin is administered every 1, 2, 4, 6, 7, 14 or 21 days at a dose of 0.10 mg/day to 50 mg/day.

In some embodiments, the IL-2 regimen comprises administration of an IL-2 fragment engrafted onto an antibody backbone. In some embodiments, the IL-2 regimen comprises administration of an antibody-cytokine engrafted protein that binds the IL-2 low affinity receptor. In some embodiments, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the antibody cytokine engrafted protein preferentially expands T effector cells over regulatory T cells. In some embodiments, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, and wherein the antibody cytokine engrafted protein preferentially expands T effector cells over regulatory T cells. In some embodiments, the IL-2 regimen comprises administration of an antibody comprising a heavy chain selected from the group consisting of SEQ ID NO:29 and SEQ ID NO:38 and a light chain selected from the group consisting of SEQ ID NO:37 and SEQ ID NO:39, or a fragment, variant, or biosimilar thereof, every 1, 2, 4, 6, 7, 14 or 21 days at a dose of 0.10 mg/day to 50 mg/day.

In some embodiments, the antibody cytokine engrafted protein described herein has a longer serum half-life that a wild-type IL-2 molecule such as, but not limited to, aldesleukin (Proleukin®) or a comparable molecule.

In some embodiments, the TIL infusion used with the foregoing embodiments of myeloablative lymphodepletion regimens may be any TIL composition described herein and may also include infusions of MILs and PBLs in place of the TIL infusion, as well as the addition of IL-2 regimens and administration of co-therapies (such as PD-1 and/or PD-L1 inhibitors and/or CTLA-4 inhibitors) as described herein.

8. Additional Methods of Treatment

In some embodiments, the invention provides a method of treating non-small cell lung carcinoma (NSCLC) by administering a population of tumor infiltrating lymphocytes (TILs) to a subject or patient in need thereof, wherein the subject or patient has at least one of:

i. a predetermined tumor proportion score (TPS) of of PD-L1<1%,
ii. a TPS score of of PD-L1 of 1%-49%, or
iii. a predetermined absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation,a MET mutation, a MET splice and/or altered MET signaling, a TP53 mutation, a CREBBP mutation, a KMT2C mutation, a KMT2D mutation, an ARIDIA mutation, a RBi mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation, and wherein the method comprises:

(a) obtaining and/or receiving a first population of TILs from a tumor resected from the subject or patient by processing a tumor sample obtained from the subject into multiple tumor fragments;
(b) adding the first population of TILs into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject or patient.

In some embodiments, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation,a MET mutation, a MET splice and/or altered MET signaling, a TP53 mutation, a CREBBP mutation, a KMT2C mutation, a KMT2D mutation, an ARID1A mutation, a RBT mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNAT1 mutation, (c) determining that the patient has a TPS score for PD-L1 of about 1% to about 49% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;

(h) harvesting therapeutic population of TILs obtained from step (d), wherein the transition from step (d) to step (e) occurs without opening the system; and (i) transferring the harvested TIL population from step (e) to an infusion bag, wherein the transfer from step (e) to (f) occurs without opening the system;

(j) cryopreserving the infusion bag comprising the harvested TIL population from step (f) using a cryopreservation process; and (k) administering a therapeutically effective dosage of the third population of TILs from the infusion bag in step (g) to the subject or patient.

In some embodiments, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RBT mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation, (c) determining that the patient has a TPS score for PD-L1 of less than about 1% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;

(h) harvesting therapeutic population of TILs obtained from step (d), wherein the transition from step (d) to step (e) occurs without opening the system; and (i) transferring the harvested TIL population from step (e) to an infusion bag, wherein the transfer from step (e) to (f) occurs without opening the system;

(j) cryopreserving the infusion bag comprising the harvested TIL population from step (f) using a cryopreservation process; and (k) administering a therapeutically effective dosage of the third population of TILs from the infusion bag in step (g) to the subject or patient.

In some embodiments, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, a KRAS mutation, a BRAF mutation, an ALK mutation, a c-ROS mutation (ROS1 mutation), a ROS1 fusion, a RET mutation, or a RET fusion, (c) determining that the patient has a TPS score for PD-L1 of about 1% to about 49% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;

(h) harvesting therapeutic population of TILs obtained from step (d), wherein the transition from step (d) to step (e) occurs without opening the system; and (i) transferring the harvested TIL population from step (e) to an infusion bag, wherein the transfer from step (e) to (f) occurs without opening the system;

(j) cryopreserving the infusion bag comprising the harvested TIL population from step (f) using a cryopreservation process; and (k) administering a therapeutically effective dosage of the third population of TILs from the infusion bag in step (g) to the subject or patient.

In some embodiments, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, a KRAS mutation, a BRAF mutation, an ALK mutation, a c-ROS mutation (ROS1 mutation), a ROS1 fusion, a RET mutation, or a RET fusion, (c) determining that the patient has a TPS score for PD-L1 of less than about 1% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;

(h) harvesting therapeutic population of TILs obtained from step (d), wherein the transition from step (d) to step (e) occurs without opening the system; and (i) transferring the harvested TIL population from step (e) to an infusion bag, wherein the transfer from step (e) to (f) occurs without opening the system;

(j) cryopreserving the infusion bag comprising the harvested TIL population from step (f) using a cryopreservation process; and (k) administering a therapeutically effective dosage of the third population of TILs from the infusion bag in step (g) to the subject or patient.

In some embodiments, the second population of TILs is at least 50-fold greater in number than the first population of TILs, In some embodiments, the invention provides a method for treating a subject with cancer comprising administering to the subject a therapeutically effective dosage of the therapeutic TIL population described in any of the preceding paragraphs above.

In some embodiments, the invention provides a method for treating a subject with cancer comprising administering to the subject a therapeutically effective dosage of the TIL composition described in any of the preceding paragraphs above.

In some embodiments, the invention provides the method for treating a subject with cancer described in any of the preceding paragraphs above modified such that prior to administering the therapeutically effective dosage of the therapeutic TIL population and the TIL composition described in any of the preceding paragraphs above, respectively, a non-myeloablative lymphodepletion regimen has been administered to the subject.

In some embodiments, the invention provides the method for treating a subject with cancer described in any of the preceding paragraphs above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In some embodiments, the invention provides the method for treating a subject with cancer described in any of the preceding paragraphs above modified to further comprise the step of treating the subject with a high-dose IL-2 regimen starting on the day after administration of the TIL cells to the subject.

In some embodiments, the invention provides the method for treating a subject with cancer described in any of the preceding paragraphs above modified such that the high-dose IL-2 regimen comprises 600,000 or 720,000 IU/kg administered as a 15-minute bolus intravenous infusion every eight hours until tolerance.

In some embodiments, the invention provides the method for treating a subject with cancer described in any of the preceding paragraphs above modified such that the cancer is a solid tumor.

In some embodiments, the invention provides the method for treating a subject with cancer described in any of the preceding paragraphs above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In some embodiments, the invention provides the method for treating a subject with cancer described in any of the preceding paragraphs above modified such that the cancer is melanoma, HNSCC, cervical cancers, NSCLC, glioblastoma (including GBM), and gastrointestinal cancer.

In some embodiments, the invention provides the method for treating a subject with cancer described in any of the preceding paragraphs above modified such that the cancer is melanoma.

In some embodiments, the invention provides the method for treating a subject with cancer described in any of the preceding paragraphs above modified such that the cancer is HNSCC.

In some embodiments, the invention provides the method for treating a subject with cancer described in any of the preceding paragraphs above modified such that the cancer is a cervical cancer.

In some embodiments, the invention provides the method for treating a subject with cancer described in any of the preceding paragraphs above modified such that the cancer is NSCLC.

In some embodiments, the invention provides the method for treating a subject with cancer described in any of the preceding paragraphs above modified such that the cancer is glioblastoma (including GBM).

In some embodiments, the invention provides the method for treating a subject with cancer described in any of the preceding paragraphs above modified such that the cancer is gastrointestinal cancer.

In some embodiments, the invention provides the method for treating a subject with cancer described in any of the preceding paragraphs above modified such that the cancer is a hypermutated cancer.

In some embodiments, the invention provides the method for treating a subject with cancer described in any of the preceding paragraphs above modified such that the cancer is a pediatric hypermutated cancer.

In some embodiments, the invention provides the therapeutic TIL population described in any of the preceding paragraphs above for use in a method for treating a subject with cancer comprising administering to the subject a therapeutically effective dosage of the therapeutic TIL population.

In some embodiments, the invention provides the TIL composition described in any of the preceding paragraphs above for use in a method for treating a subject with cancer comprising administering to the subject a therapeutically effective dosage of the TIL composition.

In some embodiments, the invention provides the therapeutic TIL population described in any of the preceding paragraphs above or the TIL composition described in any of the preceding paragraphs above modified such that prior to administering to the subject the therapeutically effective dosage of the therapeutic TIL population described in any of the preceding paragraphs above or the TIL composition described in any of the preceding paragraphs above, a non-myeloablative lymphodepletion regimen has been administered to the subject.

In some embodiments, the invention provides the therapeutic TIL population or the TIL composition described in any of the preceding paragraphs above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In some embodiments, the invention provides the therapeutic TIL population or the TIL composition described in any of the preceding paragraphs above modified to further comprise the step of treating patient with a high-dose IL-2 regimen starting on the day after administration of the TIL cells to the patient.

In some embodiments, the invention provides the therapeutic TIL population or the TIL composition described in any of the preceding paragraphs above modified such that the high-dose IL-2 regimen comprises 600,000 or 720,000 IU/kg administered as a 15-minute bolus intravenous infusion every eight hours until tolerance.

In some embodiments, the invention provides the therapeutic TIL population or the TIL composition described in any of the preceding paragraphs above modified such that the cancer is a solid tumor.

In some embodiments, the invention provides the therapeutic TIL population or the TIL composition described in any of the preceding paragraphs above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In some embodiments, the invention provides the therapeutic TIL population or the TIL composition described in any of the preceding paragraphs above modified such that the cancer is melanoma, HNSCC, cervical cancers, NSCLC, glioblastoma (including GBM), and gastrointestinal cancer.

In some embodiments, the invention provides the therapeutic TIL population or the TIL composition described in any of the preceding paragraphs above modified such that the cancer is melanoma.

In some embodiments, the invention provides the therapeutic TIL population or the TIL composition described in any of the preceding paragraphs above modified such that the cancer is HNSCC.

In some embodiments, the invention provides the therapeutic TIL population or the TIL composition described in any of the preceding paragraphs above modified such that the cancer is a cervical cancer.

In some embodiments, the invention provides the therapeutic TIL population or the TIL composition described in any of the preceding paragraphs above modified such that the cancer is NSCLC.

In some embodiments, the invention provides the therapeutic TIL population or the TIL composition described in any of the preceding paragraphs above modified such that the cancer is glioblastoma (including GBM).

In some embodiments, the invention provides the therapeutic TIL population or the TIL composition described in any of the preceding paragraphs above modified such that the cancer is gastrointestinal cancer.

In some embodiments, the invention provides the therapeutic TIL population or the TIL composition described in any of the preceding paragraphs above modified such that the cancer is a hypermutated cancer.

In some embodiments, the invention provides the therapeutic TIL population or the TIL composition described in any of the preceding paragraphs above modified such that the cancer is a pediatric hypermutated cancer.

In some embodiments, the invention provides the use of the therapeutic TIL population described in any of any of the preceding paragraphs above in a method of treating cancer in a subject comprising administering to the subject a therapeutically effective dosage of the therapeutic TIL population.

In some embodiments, the invention provides the use of the TIL composition described in any of the preceding paragraphs above in a method of treating cancer in a subject comprising administering to the subject a therapeutically effective dosage of the TIL composition.

In some embodiments, the invention provides the use of the therapeutic TIL population described in any of the preceding paragraphs above or the TIL composition described in any of the preceding paragraphs above in a method of treating cancer in a subject comprising administering to the subject a non-myeloablative lymphodepletion regimen and then administering to the subject the therapeutically effective dosage of the therapeutic TIL population described in any of the preceding paragraphs above or the therapeutically effective dosage of the TIL composition described in any of the preceding paragraphs above.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Preparation of Media for Pre-Rep and Rep Processes

This Example describes the procedure for the preparation of tissue culture media for use in protocols involving the culture of tumor infiltrating lymphocytes (TIL) derived from various tumor types including non-small cell lung carcinoma (NSCLC). This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 37 below by adding each of the ingredients into the top section of a 0.2 μm filter unit appropriate to the volume to be filtered. Store at 4° C.

TABLE 37

Preparation of CM1

| Ingredient | Final concentration | Final Volume 500 ml | Final Volume IL |
|---|---|---|---|
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 μM | 0.5ml | 1 ml |
| 50 mg/mL gentamicin sulfate | 50 μg/mL | 0.5ml | 1 ml |

On the day of use, prewarmed required amount of CM1 in 37° C. water bath and add 6000 IU/ml IL-2.

Additional supplementation—as needed according to Table 38.

TABLE 38

Additional supplementation of CM1, as needed.

| Supplement | Stock concentration | Dilution | Final concentration |
|---|---|---|---|
| GlutaMAX™ | 200 mM | 1:100 | 2 mM |
| Penicillin/streptomycin | 10,000 U/mL penicillin 10,000 μg/mL streptomycin | 1:100 | 100 U/mL penicillin 100 μg/mL streptomycin |
| Amphotericin B | 250 μg/mL | 1:100 | 2.5 μg/mL |

Preparation of CM2

Removed prepared CM1 from refrigerator or prepare fresh CM1 as per Section 7.3 above. Removed AIM-V® from refrigerator and prepared the amount of CM2 needed by mixing prepared CM1 with an equal volume of AIM-VR in a sterile media bottle. Added 3000 IU/mL IL-2 to CM2 medium on the day of usage. Made sufficient amount of CM2 with 3000 IU/mL IL-2 on the day of usage. Labeled the CM2 media bottle with its name, the initials of the preparer, the date it was filtered/prepared, the two-week expiration date and store at 4° C. until needed for tissue culture.

Preparation of CM3

Prepared CM3 on the day it was required for use. CM3 was the same as AIM-V®medium, supplemented with 3000 IU/mL IL-2 on the day of use. Prepared an amount of CM3 sufficient to experimental needs by adding IL-2 stock solution directly to the bottle or bag of AIM-V. Mixed well by gentle shaking. Label bottle with “3000 IU/mL IL-2” immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with “3000 IL/nil IL-2 and GlutaMAX” immediately after adding to the AIM-V. If there was excess CM4, stored it in bottles at 4° C. labeled with the media name, “GlutaMAX”, and its expiration date (7 days after preparation). Discarded media supplemented with IL-2 after 7-days storage at 4° C.

Example 2: Use of IL-2, IL-15, and IL-21 Cytokine Cocktail

This example describes the use of IL-2, IL-15, and IL-21 cytokines, which serve as additional T cell growth factors, in combination with the TIL process of Examples A to G.

Using the processes described herein, TILs can be grown from non-small cell lung carcinoma (NSCLC) tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vp repertoire. IL-15 and IL-21 are described elsewhere herein and in Gruijl, et al., IL-21 promotes the expansion of CD27+ CD28+tumor infiltrating lymphocytes with high cytotoxic potential and low collateral expansion of regulatory T cells, *Santegoets, S. J, J Transl Med.,* 2013, 11:37 (https://www.ncbi.nlm.nih.gov/pmc/articles/PMC3626797/).

The results can show that enhanced TIL expansion (>20%), in both CD4+ and CD8+cells in the IL-2, IL-15, and IL-21 treated conditions can observed relative to the IL-2 only conditions. There was a skewing towards a predominantly CD8+population with a skewed TCR Vp repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 3: Qualifying Individual Lots of Gamma-Irradiated Peripheral Mononuclear Cells This Example describes an abbreviated procedure for qualifying individual lots of gamma-irradiated peripheral mononuclear cells (PBMCs, also known as mononuclear cells or MNCs) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL to verify that the received dose of gamma radiation was sufficient to render them replication incompetent.

Gamma-irradiated, growth-arrested MNC feeder cells are required for REP of TILs. Membrane receptors on the feeder MNCs bind to anti-CD3 (clone OKT3) antibody and crosslink to TILs in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable feeder cells as this can result in graft-versus-host disease (GVHD). Feeder cells are therefore growth-arrested by dosing the cells with gamma-irradiation, resulting in double strand DNA breaks and the loss of cell viability of the MNC cells upon re-culture.

Feeder lots were evaluated on two criteria: (1) their ability to expand TILs in co-culture >100-fold and (2) their replication incompetency.

Feeder lots were tested in mini-REP format utilizing two primary pre-REP TIL lines grown in upright T25 tissue culture flasks. Feeder lots were tested against two distinct TIL lines, as each TIL line is unique in its ability to proliferate in response to activation in a REP. As a control, a lot of irradiated MNC feeder cells which has historically been shown to meet the criteria above was run alongside the test lots.

To ensure that all lots tested in a single experiment receive equivalent testing, sufficient stocks of the same pre-REP TIL lines were available to test all conditions and all feeder lots.

For each lot of feeder cells tested, there was a total of six T25 flasks: Pre-REP TIL line #1 (2 flasks); Pre-REP TIL line #2 (2 flasks); and feeder control (2 flasks). Flasks containing TIL lines #1 and #2 evaluated the ability of the feeder lot to expand TIL. The feeder control flasks evaluated the replication incompetence of the feeder lot.

A. Experimental Protocol

Day −2/3, Thaw of TIL lines. Prepare CM2 medium and warm CM2 in 37° C. water bath. Prepare 40 mL of CM2 supplemented with 3000 IU/mL IL-2. Keep warm until use. Place 20 mL of pre-warmed CM2 without IL-2 into each of two 50 mL conical tubes labeled with names of the TIL lines used. Removed the two designated pre-REP TIL lines from LN2 storage and transferred the vials to the tissue culture room. Thawed vials by placing them inside a sealed zipper storage bag in a 37° C. water bath until a small amount of ice remains.

Using a sterile transfer pipet, the contents of each vial were immediately transferred into the 20 mL of CM2 in the prepared, labeled 50 mL conical tube. QS to 40 mL using CM2 without IL-2 to wash cells and centrifuged at 400×CF for 5 minutes. Aspirated the supernatant and resuspend in 5 mL warm CM2 supplemented with 3000 IU/mL IL-2.

A small aliquot (20 μL) was removed in duplicate for cell counting using an automated cell counter. The counts were recorded. While counting, the 50 mL conical tube with TIL cells was placed into a humidified 37° C., 5% $CO_2$ incubator, with the cap loosened to allow for gas exchange. The cell concentration was determined, and the TILs were diluted to $1\times10^6$ cells/mL in CM2 supplemented with IL-2 at 3000 IU/mL.

Cultured in 2 mL/well of a 24-well tissue culture plate in as many wells as needed in a humidified 37° C. incubator until Day 0 of the mini-REP. The different TIL lines were cultured in separate 24-well tissue culture plates to avoid confusion and potential cross-contamination.

Day 0, initiate Mini-REP. Prepared enough CM2 medium for the number of feeder lots to be tested. (e.g., for testing 4 feeder lots at one time, prepared 800 mL of CM2 medium). Aliquoted a portion of the CM2 prepared above and supplemented it with 3000 IU/mL IL-2 for the culturing of the cells. (e.g., for testing 4 feeder lots at one time, prepare 500 mL of CM2 medium with 3000 IU/mL IL-2).

Working with each TIL line separately to prevent cross-contamination, the 24-well plate with TIL culture was removed from the incubator and transferred to the BSC.

Using a sterile transfer pipet or 100-1000 μL pipettor and tip, about 1 mL of medium was removed from each well of TILs to be used and placed in an unused well of the 24-well tissue culture plate.

Using a fresh sterile transfer pipet or 100-1000 μL pipettor and tip, the remaining medium was mixed with TILs in wells to resuspend the cells and then transferred the cell suspension to a 50 mL conical tube labeled with the TIL lot name and recorded the volume.

Washed the wells with the reserved media and transferred that volume to the same 50 mL conical tube. Spun the cells at 400×CF to collect the cell pellet. Aspirated off the media supernatant and resuspend the cell pellet in 2-5 mL of CM2 medium containing 3000 IU/mL IL-2, volume to be used based on the number of wells harvested and the size of the pellet—volume should be sufficient to ensure a concentration of $>1.3\times10^6$ cells/mL.

Using a serological pipet, the cell suspension was mixed thoroughly and the volume was recorded. Removed 200 μL for a cell count using an automated cell counter.

While counting, placed the 50 mL conical tube with TIL cells into a humidified, 5% $CO_2$, 37° C. incubator, with the cap loosened to allow gas exchange. Recorded the counts.

Removed the 50 mL conical tube containing the TIL cells from the incubator and resuspend them cells at a concentration of $1.3\times10^6$ cells/mL in warm CM2 supplemented with 3000 IU/mL IL-2. Returned the 50 mL conical tube to the incubator with a loosened cap.

The steps above were repeated for the second TIL line.

Just prior to plating the TIL into the T25 flasks for the experiment, TIL were diluted 1:10 for a final concentration of $1.3\times10^5$ cells/mL as per below.

Prepare MACS GMP CD3 pure (OKT3) working solution. Took out stock solution of OKT3 (1 mg/mL) from 4° C. refrigerator and placed in BSC. A final concentration of 30 ng/mL OKT3 was used in the media of the mini-REP.

600 ng of OKT3 were needed for 20 mL in each T25 flask of the experiment; this was the equivalent of 60 μL of a 10 μg/mL solution for each 20 mL, or 360 μL for all 6 flasks tested for each feeder lot.

For each feeder lot tested, made 400 μL of a 1:100 dilution of 1 mg/mL OKT3 for a working concentration of 10 μg/mL (e.g., for testing 4 feeder lots at one time, make 1600 μL of a 1:100 dilution of 1 mg/mL OKT3:16 μL of 1 mg/mL OKT3+1.584 mL of CM2 medium with 3000 IU/mL IL-2.)

Prepare T25 flasks. Labeled each flask and filled flask with the CM2 medium prior to preparing the feeder cells. Placed flasks into 37° C. humidified 5% $CO_2$ incubator to keep media warm while waiting to add the remaining components. Once feeder cells were prepared, the components will be added to the CM2 in each flask.

Further information is provided in Table 39.

TABLE 39

Solution information.

| Component | Volume in co-culture flasks | Volume in control (feeder only) flasks |
|---|---|---|
| CM2 + 3000 IU/mL IL-2 | 18 mL | 19 mL |
| MNC: $1.3\times10^7$/mL in CM2 + 3000 IU IL-2 (final concentration $1.3\times10^7$/flask) | 1 mL | 1 mL |
| OKT3: 10 μL/mL in CM2 = 3000 IU IL-2 | 60 μL | 60 μL |
| TIL: $1.3\times10^5$/mL in CM2 with 3000 IU of IL-2 (final concentration $1.3\times10^5$/flask) | 1 mL | 0 |

Prepare Feeder Cells. A minimum of $78\times10^6$ feeder cells were needed per lot tested for this protocol. Each 1 mL vial frozen by SDBB had $100\times10^6$ viable cells upon freezing. Assuming a 50% recovery upon thaw from liquid N2 storage, it was recommended to thaw at least two 1 mL vials of feeder cells per lot giving an estimated $100\times10^6$ viable cells for each REP. Alternately, if supplied in 1.8 mL vials, only one vial provided enough feeder cells.

Before thawing feeder cells, approximately 50 mL of CM2 without IL-2 was pre-warmed for each feeder lot to be tested. The designated feeder lot vials were removed from LN2 storage, placed in zipper storage bag, and placed on ice.

Vials were thawed inside closed zipper storage bag by immersing in a 37° C. water bath. Vials were removed from zipper bag, sprayed or wiped with 70% EtOH, and transferred to a BSC.

Using a transfer pipet, the contents of feeder vials were immediately transferred into 30 mL of warm CM2 in a 50 mL conical tube. The vial was washed with a small volume of CM2 to remove any residual cells in the vial and centrifuged at 400×CF for 5 minutes. Aspirated the supernatant and resuspended in 4 mL warm CM2 plus 3000 IU/mL IL-2. Removed 200 μL for cell counting using the automated cell counter. Recorded the counts.

Resuspended cells at $1.3\times10^7$ cells/mL in warm CM2 plus 3000 IU/mL IL-2. Diluted TIL cells from $1.3\times10^6$ cells/mL to $1.3\times10^5$ cells/mL.

Setup Co-Culture. Diluted TIL cells from $1.3\times10^6$ cells/mL to $1.3\times10^5$ cells/mL. Added 4.5 mL of CM2 medium to a 15 mL conical tube. Removed TIL cells from incubator and resuspended well using a 10 mL serological pipet. Removed 0.5 mL of cells from the $1.3\times10^6$ cells/mL TIL suspension and added to the 4.5 mL of medium in the 15 mL conical tube. Returned TIL stock vial to incubator. Mixed well. Repeated for the second TIL line.

Transferred flasks with pre-warmed media for a single feeder lot from the incubator to the BSC. Mixed feeder cells by pipetting up and down several times with a 1 mL pipet tip and transferred 1 mL ($1.3\times10^7$ cells) to each flask for that feeder lot. Added 60 μL of OKT3 working stock (10 μg/mL) to each flask. Returned the two control flasks to the incubator.

Transferred 1 mL ($1.3\times10^5$) of each TIL lot to the correspondingly labeled T25 flask. Returned flasks to the incubator and incubate upright. Did not disturb until Day 5. This procedure was repeated for all feeder lots tested.

Day 5, Media change. Prepared CM2 with 3000 IU/mL IL-2. 10 mL is needed for each flask. With a 10 mL pipette, transferred 10 mL warm CM2 with 3000 IU/mL IL-2 to each flask. Returned flasks to the incubator and incubated upright until day 7. Repeated for all feeder lots tested.

Day 7, Harvest. Removed flasks from the incubator and transfer to the BSC, care as taken not to disturb the cell layer on the bottom of the flask. Without disturbing the cells growing on the bottom of the flasks, 10 mL of medium was removed from each test flask and 15 mL of medium from each of the control flasks.

Using a 10 mL serological pipet, the cells were resuspended in the remaining medium and mix well to break up any clumps of cells. After thoroughly mixing cell suspension by pipetting, removed 200 μL for cell counting. Counted the TIL using the appropriate standard operating procedure in conjunction with the automatic cell counter equipment. Recorded counts in day 7. This procedure was repeated for all feeder lots tested.

Feeder control flasks were evaluated for replication incompetence and flasks containing TIL were evaluated for fold expansion from day 0.

Day 7, Continuation of Feeder Control Flasks to Day 14. After completing the day 7 counts of the feeder control flasks, 15 mL of fresh CM2 medium containing 3000 IU/mL IL-2 was added to each of the control flasks. The control flasks were returned to the incubator and incubated in an upright position until day 14.

Day 14, Extended Non-proliferation of Feeder Control Flasks. Removed flasks from the incubator and transfer to the BSC, care was taken not to disturb the cell layer on the bottom of the flask. Without disturbing the cells growing on the bottom of the flasks, approximately 17 mL of medium was removed from each control flasks. Using a 5 mL serological pipet, the cells were resuspended in the remaining medium and mixed well to break up any clumps of cells. The volumes were recorded for each flask.

After thoroughly mixing the cell suspension by pipetting, 200 μL was removed for cell counting. The TIL were counted using the appropriate standard operating procedure in conjunction with the automatic cell counter equipment and the counts were recorded. This procedure was repeated for all feeder lots tested.

B. Results and Acceptance Criteria Protocol

Results. The dose of gamma irradiation was sufficient to render the feeder cells replication incompetent. All lots were expected to meet the evaluation criteria and also demonstrated a reduction in the total viable number of feeder cells remaining on day 7 of the REP culture compared to day 0. All feeder lots were expected to meet the evaluation criteria of 100-fold expansion of TIL growth by day 7 of the REP culture. Day 14 counts of Feeder Control flasks were expected to continue the non-proliferative trend seen on day 7.

Acceptance Criteria. The following acceptance criteria were met for each replicate TIL line tested for each lot of feeder cells. Acceptance criteria were two-fold, as shown in Table 40 below.

TABLE 40

Embodiments of acceptance criteria.

| Test | Acceptance criteria |
|---|---|
| Irradiation of MNC and Replication Incompetence | No growth observed at 7 and 14 days |
| TIL expansion | At least a 100-fold expansion of each TIL (minimum of $1.3\times10^7$ viable cells) |

The dose of radiation was evaluated for its sufficiency to render the MNC feeder cells replication incompetent when cultured in the presence of 30 ng/mL OKT3 antibody and 3000 IU/mL IL-2. Replication incompetence was evaluated by total viable cell count (TVC) as determined by automated cell counting on day 7 and day 14 of the REP.

The acceptance criteria was "No Growth," meaning the total viable cell number has not increased on day 7 and day 14 from the initial viable cell number put into culture on Day 0 of the REP.

The ability of the feeder cells to support TIL expansion was evaluated. TIL growth was measured in terms of fold expansion of viable cells from the onset of culture on day 0 of the REP to day 7 of the REP. On day 7, TIL cultures achieved a minimum of 100-fold expansion, (i.e., greater than 100 times the number of total viable TIL cells put into culture on REP day 0), as evaluated by automated cell counting.

Contingency Testing of MNC Feeder Lots that do not meet acceptance criteria. In the event that an MNC feeder lot did not meet the either of the acceptance criteria outlined above, the following steps will be taken to retest the lot to rule out simple experimenter error as its cause.

If there are two or more remaining satellite testing vials of the lot, then the lot was retested. If there were one or no remaining satellite testing vials of the lot, then the lot was failed according to the acceptance criteria listed above.

In order to be qualified, the lot in question and the control lot had to achieve the acceptance criteria above. Upon meeting these criteria, the lot is released for use.

Example 4: Preparation of IL-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL TN acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution ($6\times10^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left(\frac{\text{Vial Mass (mg)} \times \text{Biological Activity}\left(\frac{IU}{\text{mg}}\right)}{6\times10^6\frac{IU}{\text{mL}}}\right) - HAc\ vol\ (\text{mL}) = 1\%\ HSA\ vol\ (\text{mL})$$

For example, according to CellGenix's rhIL-2 lot 10200121 COA, the specific activity for the 1 mg vial is $25\times10^6$ IU/mg. It recommends reconstituting the rhIL-2 in 2 mL 0.2% HAc.

$$\left(\frac{1\ \text{mg}\times25\times10^6\frac{IU}{\text{mg}}}{6\times10^6\frac{IU}{\text{mL}}}\right) - 2\text{mL} = 2.167\text{mL}\ HSA$$

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Expired 6 months after date of preparation. Rh-IL-2 labels included vendor and catalog number, lot number, expiration date, operator initials, concentration and volume of aliquot.

EXAMPLE 5: CRYOPRESERVATION PROCESS

This example describes a cryopreservation process method for TILs prepared with the procedure described herein using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 6: Tumor Expansion Processes with Defined Medium

The processes disclosed above may be performed substituting the CM1 and CM2 media with a defined medium according (e.g., CTS™ OpTmizer™ T-Cell Expansion SFM, ThermoFisher, including for example DM1 and DM2).

Example 7: Nsclc Treatment with Anti-Pd-1 Antibodies

Patient population:

Treatment naive NSCLC or post chemotherapy but anti-PD-1/PD-L1 naive Treatment schedules:

Tumor fragment, treat with up to 4 doses of anti-PD-1/PD-L1, treat the primary refractory patients with TIL product which is cryo-preserved and ready for use upon immediate progression. Primary refractory patients may have progressed after 2 doses.

Relapse patients can also be treated upon progression (the timing may vary from months to years later).

Full strength IL-2 up to 6 doses.

Patient populations to further consider with the same manufacturing permutations noted earlier:

- Treatment naive NSCLC or post chemotherapy but anti-PD-1/PD-L1 naive
- Treatment naive NSCLC or post chemotherapy but anti-PD-1/PD-L1 naive who have low expression of PD-L1
- Treatment naive NSCLC or post chemotherapy but anti-PD-1/PD-L1 naive who have low expression of PD-L1 and/or have bulky disease at baseline-(for example, bulky disease is indicated where the maximal tumor diameter is greater than 7 cm measured in either the transverse or coronal plane or swollen lymph nodes with a short-axis diameter of 20 mm or greater on CT were defined as bulky; see for example, Samejima, J., Japanese *Journal of Clinical Oncology,* 45(11): 1050-10541 2015, incorporated herein by reference)

Example 8: Exemplary Gen 2 Production of a Cryopreserved TIL Cell Therapy

This example describes the cGMP manufacture of Iovance Biotherapeutics, Inc. TIL Cell Therapy Process in G-REX Flasks according to current Good Tissue Practices and current Good Manufacturing Practices. This example describes an exemplary cGMP manufacture of TIL Cell Therapy Process in G-REX Flasks according to current Good Tissue Practices and current Good Manufacturing Practices.

TABLE 41

| Process Expansion Exemplary Plan. | | | | |
|---|---|---|---|---|
| Estimated Day (post-seed) | Activity | Target Criteria | Anticipated Vessels | Estimated Total Volume (mL) |
| 0 | Tumor Dissection | ≤50 desirable tumor fragments per G-REX-100MCS | G-REX-100MCS 1 flask | ≤1000 |
| 11 | REP Seed | 5 − 200 × $10^6$viable cells per G-REX-500MCS | G-REX-500MCS 1 flasks | ≤5000 |
| 16 | REP Split | 1 × $10^9$viable cells per G-REX-500MCS | G-REX-500MCS ≤5 flasks | ≤25000 |
| 22 | Harvest | Total available cells | 3-4 CS-750 bags | ≤530 |

TABLE 42

| Flask Volumes. | |
|---|---|
| Flask Type | Working Volume/Flask |
| G-REX-100MCS | 1000 |
| G-REX-500MCS | 5000 |

Day 0 CM1 Media Preparation. In the BSC added reagents to RPMI 1640 Media bottle. Added the following reagents t Added per bottle: Heat Inactivated Human AB Serum (100.0 mL); GlutaMax™ (10.0 mL); Gentamicin sulfate, 50 mg/mL (1.0 mL); 2-mercaptoethanol (1.0 mL)

Removed unnecessary materials from BSC. Passed out media reagents from BSC, left Gentamicin Sulfate and HBSS in BSC for Formulated Wash Media preparation.

Thawed IL-2 aliquot. Thawed one 1.1 mL IL-2 aliquot ($6\times10^6$ IU/mL) (BR71424) until all ice had melted. Recorded IL-2: Lot #and Expiry Transferred IL-2 stock solution to media. In the BSC, transferred 1.0 mL of IL-2 stock solution to the CM1 Day 0 Media Bottle prepared. Added CM1 Day 0 Media 1 bottle and IL-2 (6×106 IU/mL) 1.0 mL.

Passed G-REX100MCS into BSC. Aseptically passed G-REX100MCS (W3013130) into the BSC.

Pumped all Complete CM1 Day 0 Media into G-REX100MCS flask. Tissue Fragments Conical or GRex100MCS.

Day 0 Tumor Wash Media Preparation. In the BSC, added 5.0 mL Gentamicin (W3009832 or W3012735) to 1×500 mL HBSS Media (W3013128) bottle. Added per bottle: HBSS (500.0 mL); Gentamicin sulfate, 50 mg/mL (5.0 mL). Filtered HBSS containing gentamicin prepared through a 1L 0.22-micron filter unit (W1218810).

Day 0 Tumor Processing. Obtained tumor specimen and transferred into suite at 2-8° C. immediately for processing. Aliquoted tumor wash media. Tumor wash 1 is performed using 8" forceps (W3009771). The tumor is removed from the specimen bottle and transferred to the "Wash 1" dish prepared. This is followed by tumor wash 2 and tumor wash 3. Measured and assessed tumor. Assessed whether >30% of entire tumor area observed to be necrotic and/or fatty tissue. Clean up dissection if applicable. If tumor was large and >30% of tissue exterior was observed to be necrotic/fatty, performed "clean up dissection" by removing necrotic/fatty tissue while preserving tumor inner structure using a combination of scalpel and/or forceps. Dissect tumor. Using a combination of scalpel and/or forceps, cut the tumor specimen into even, appropriately sized fragments (up to 6 intermediate fragments). Transferred intermediate tumor fragments. Dissected tumor fragments into pieces approximately 3×3×3 mm in size. Stored Intermediate Fragments to prevent drying. Repeated intermediate fragment dissection. Determined number of pieces collected. If desirable tissue remains, selected additional favorable tumor pieces from the "favorable intermediate fragments" 6-well plate to fill the drops for a maximum of 50 pieces.

Prepared conical tube. Transferred tumor pieces to 50 mL conical tube. Prepared BSC for G-REX100MCS. Removed G-REX100MCS from incubator. Aseptically passed G-REX100MCS flask into the BSC. Added tumor fragments to G-REX100MCS flask. Evenly distributed pieces.

Incubated G-REX100MCS at the following parameters: Incubated G-REX flask: Temperature LED Display: 37.0+2.0° C.; $CO_2$ Percentage: 5.0+1.5% $CO_2$. Calculations: Time of incubation; lower limit=time of incubation+252 hours; upper limit=time of incubation+276 hours.

After process was complete, discarded any remaining warmed media and thawed aliquots of IL-2.

Day 11—Media Preparation. Monitored incubator. Incubator parameters: Temperature LED Display: 37.0+2.0° C.; $CO_2$ Percentage: 5.0+1.5% $CO_2$.

Warmed 3×1000 mL RPMI 1640 Media (W3013112) bottles and 3×1000 mL AIM-V (W3009501) bottles in an incubator for >30 minutes. Removed RPMI 1640 Media from incubator. Prepared RPMI 1640 Media. Filter Media. Thawed 3×1.1 mL aliquots of IL-2 (6×106 IU/mL) (BR71424). Removed AIM-V Media from the incubator. Add IL-2 to AIM-V. Aseptically transferred a 10 L Labtainer Bag and a repeater pump transfer set into the BSC.

Prepared 10 L Labtainer media bag. Prepared Baxa pump. Prepared 10 L Labtainer media bag. Pumped media into 10 L Labtainer. Removed pumpmatic from Labtainer bag.

Mixed media. Gently massaged the bag to mix. Sample media per sample plan. Removed 20.0 mL of media and place in a 50 mL conical tube. Prepared cell count dilution tubes. In the BSC, added 4.5 mL of AIM-V Media that had been labelled with "For Cell Count Dilutions" and lot number to four 15 mL conical tubes. Transferred reagents from the BSC to 2-8° C. Prepared 1 L Transfer Pack. Outside of the BSC weld (per Process Note 5.11) a 1L Transfer Pack to the transfer set attached to the "Complete CM2 Day 11 Media" bag prepared. Prepared feeder cell transfer pack. Incubated Complete CM2 Day 11 Media.

Day 11—TIL Harvest. Preprocessing table. Incubator parameters: Temperature LED display: 37.0+2.0° C.; $CO_2$ Percentage: 5.0+1.5% $CO_2$. Removed G-REX100MCS from incubator. Prepared 300 mL Transfer Pack. Welded transfer packs to G-REX100MCS.

Prepare flask for TIL Harvest and initiation of TIL Harvest. TIL Harvested. Using the GatheRex, transferred the cell suspension through the blood filter into the 300 mL transfer pack. Inspect membrane for adherent cells.

Rinsed flask membrane. Closed clamps on G-REX100MCS. Ensured all clamps are closed. Heat sealed the TIL and the "Supernatant" transfer pack. Calculated volume of TIL suspension. Prepared Supernatant Transfer Pack for Sampling.

Pulled Bac-T Sample. In the BSC, draw up approximately 20.0 mL of supernatant from the 1L "Supernatant" transfer pack and dispense into a sterile 50 mL conical tube.

Inoculated BacT per Sample Plan. Removed a 1.0 mL sample from the 50 mL conical labeled BacT prepared using an appropriately sized syringe and inoculated the anaerobic bottle.

Incubated TIL. Placed TIL transfer pack in incubator until needed. Performed cell counts and calculations. Determined the Average of Viable Cell Concentration and Viability of the cell counts performed. Viability+2. Viable Cell Concentration+2. Determined Upper and Lower Limit for counts. Lower Limit: Average of Viable Cell Concentration x 0.9. Upper Limit: Average of Viable Cell Concentration x 1.1. Confirmed both counts within acceptable limits. Determined an average Viable Cell Concentration from all four counts performed.

Adjusted Volume of TIL Suspension: Calculate the adjusted volume of TIL suspension after removal of cell count samples. Total TIL Cell Volume (A). Volume of Cell Count Sample Removed (4.0 mL) (B) Adjusted Total TIL Cell Volume C=A−B.

Calculated Total Viable TIL Cells. Average Viable Cell Concentration*: Total Volume; Total Viable Cells: C=A×B.

Calculation for flow cytometry: if the Total Viable TIL Cell count from was >$4.0\times10^7$, calculated the volume to obtain $1.0\times10^7$cells for the flow cytometry sample.

Total viable cells required for flow cytometry: $1.0\times10^7$cells. Volume of cells required for flow cytometry: Viable cell concentration divided by $1.0\times10^7$cells A.

Calculated the volume of TIL suspension equal to $2.0\times10^8$viable cells. As needed, calculated the excess volume of TIL cells to remove and removed excess TIL and placed TIL in incubator as needed. Calculated total excess TIL removed, as needed.

Calculated amount of CS-10 media to add to excess TIL cells with the target cell concentration for freezing is $1.0\times10^8$ cells/mL. Centrifuged excess TILs, as needed. Observed conical tube and added CS-10.

Filled Vials. Aliquoted 1.0 mL cell suspension, into appropriately sized cryovials. Aliquoted residual volume into appropriately sized cryovial. If volume is <0.5 mL, add CS10 to vial until volume is 0.5 mL.

Calculated the volume of cells required to obtain $1\times10^7$cells for cryopreservation. Removed sample for cryopreservation. Placed TIL in incubator.

Cryopreservation of sample. Observed conical tube and added CS-10 slowly and record volume of 0.5 mL of CS10 added.

Day 11—Feeder Cells. Obtained feeder cells. Obtained 3 bags of feeder cells with at least two different lot numbers from LN2 freezer. Kept cells on dry ice until ready to thaw. Prepared water bath or cryotherm. Thawed feeder cells at 37.0±2.0° C. in the water bath or cytotherm for ~3-5 minutes or until ice has just disappeared. Removed media from incubator. Pooled thawed feeder cells. Added feeder cells to transfer pack. Dispensed the feeder cells from the syringe into the transfer pack. Mixed pooled feeder cells and labeled transfer pack.

Calculated total volume of feeder cell suspension in transfer pack. Removed cell count samples. Using a separate 3 mL syringe for each sample, pulled 4×1.0 mL cell count samples from Feeder Cell Suspension Transfer Pack using the needless injection port. Aliquoted each sample into the cryovials labeled. Performed cell counts and determine multiplication factors, elected protocols and entered multiplication factors. Determined the average of viable cell concentration and viability of the cell counts performed. Determined upper and lower limit for counts and confirm within limits.

Adjusted volume of feeder cell suspension. Calculated the adjusted volume of feeder cell suspension after removal of cell count samples. Calculated total viable feeder cells. Obtained additional feeder cells as needed. Thawed additional feeder cells as needed. Placed the 4th feeder cell bag into a zip top bag and thaw in a 37.0±2.0° C. water bath or cytotherm for −3-5 minutes and pooled additional feeder cells. Measured volume. Measured the volume of the feeder cells in the syringe and recorded below (B). Calculated the new total volume of feeder cells. Added feeder cells to transfer pack.

Prepared dilutions as needed, adding 4.5 mL of AIM-V Media to four 15 mL conical tubes. Prepared cell counts. Using a separate 3 mL syringe for each sample, removed 4×1.0 mL cell count samples from Feeder Cell Suspension transfer pack, using the needless injection port. Performed cell counts and calculations. Determined an average viable cell concentration from all four counts performed. Adjusted volume of feeder cell suspension and calculated the adjusted volume of feeder cell suspension after removal of cell count samples. Total Feeder Cell Volume minues 4.0 mL removed. Calculated the volume of Feeder Cell Suspension that was required to obtain $5\times10^9$viable feeder cells. Calculated excess feeder cell volume. Calculated the volume of excess feeder cells to remove. Removed excess feeder cells.

Using a 1.0 mL syringe and 16G needle, drew up 0.15 mL of OKT3 and added OKT3. Heat sealed the feeder cell suspension transfer pack.

Day 11 G-REX Fill and Seed Set up G-REX500MCS. Removed "Complete CM2 Day 11 Media", from incubator and pumped media into G-REX500MCS. Pumped 4.5L of media into the G-REX500MCS, filling to the line marked on the flask. Heat sealed and incubated flask as needed. Welded the Feeder Cell suspension transfer pack to the G-REX500MCS. Added Feeder Cells to G-REX500MCS. Heat sealed. Welded the TIL Suspension transfer pack to the flask. Added TIL to G-REX500MCS. Heat sealed. Incubated G-REX500MCS at 37.0+2.0° C., $CO_2$ Percentage: 5.0+1.5% $CO_2$.

Calculated incubation window. Performed calculations to determine the proper time to remove G-REX500MCS from incubator on Day 16. Lower limit: Time of incubation +108 hours. Upper limit: Time of incubation+132 hours.

Day 11 Excess TIL Cryopreservation. Applicable: Froze Excess TIL Vials. Verified the CRF has been set up prior to freeze. Perform Cryopreservation. Transferred vials from Controlled Rate Freezer to the appropriate storage. Upon completion of freeze, transfer vials from CRF to the appropriate storage container. Transferred vials to appropriate storage. Recorded storage location in LN2.

Day 16 Media Preparation. Pre-warmed AIM-V Media. Calculated time Media was warmed for media bags 1, 2, and 3. Ensured all bags have been warmed for a duration between 12 and 24 hours. Setup 10 L Labtainer for Supernatant. Attached the larger diameter end of a fluid pump transfer set to one of the female ports of a 10 L Labtainer bag using the Luer connectors. Setup 10 L Labtainer for Supernatant and label. Setup 10 L Labtainer for Supernatant. Ensure all clamps were closed prior to removing from the BSC. NOTE: Supernatant bag was used during TIL Harvest, which may be performed concurrently with media preparation.

Thawed IL-2. Thawed 5×1.1 mL aliquots of IL-2 ($6\times10^6$ IU/mL) (BR71424) per bag of CTS AIM V media until all ice had melted. Aliquoted 100.0 mL GlutaMax™. Added IL-2 to GlutaMax™. Prepared CTS AIM V media bag for formulation. Prepared CTS AIM V media bag for formulation. Stage Baxa Pump. Prepared to formulate media. Pumped GlutaMax™+IL-2 into bag. Monitored parameters: Temperature LED Display: 37.0±2.0° C., $CO_2$ Percentage: 5.0±1.5% $CO_2$. Warmed Complete CM4 Day 16 Media. Prepared Dilutions.

Day 16 REP Spilt. Monitored Incubator parameters: Temperature LED display: 37.0±2.0° C., $CO_2$ Percentage: 5.0±1.5% $CO_2$. Removed G-REX500MCS from the incubator. Prepared and labeled 1 L Transfer Pack as TIL Suspension and weighed 1L.

Volume Reduction of G-REX500MCS. Transferred −4.5L of culture supernatant from the G-REX500MCS to the 10 L Labtainer.

Prepared flask for TIL harvest. After removal of the supernatant, closed all clamps to the red line.

Initiation of TIL Harvest. Vigorously tap flask and swirl media to release cells and ensure all cells have detached.

TIL Harvest. Released all clamps leading to the TIL suspension transfer pack. Using the GatheRex transferred the cell suspension into the TIL Suspension transfer pack. NOTE: Be sure to maintain the tilted edge until all cells and media are collected. Inspected membrane for adherent cells. Rinsed flask membrane. Closed clamps on G-REX500MCS. Heat sealed the Transfer Pack containing the TIL. Heat sealed the 10 L Labtainer containing the supernatant. Recorded weight of Transfer Pack with cell suspension and calculate the volume suspension. Prepared transfer pack for sample removal. Removed testing samples from cell supernatant.

Sterility & BacT testing sampling. Removed a 1.0 mL sample from the 15 mL conical labeled BacT prepared. Removed Cell Count Samples. In the BSC, using separate 3 mL syringes for each sample, removed 4×1.0 mL cell count samples from "TIL Suspension" transfer pack.

Removed *mycoplasma* samples. Using a 3 mL syringe, removed 1.0 mL from TIL Suspension transfer pack and place into 15 mL conical labeled "*Mycoplasma* diluent" prepared.

Prepared transfer pack for seeding. Placed TIL in incubator. Removed cell suspension from the BSC and place in incubator until needed. Performed cell counts and calculations. Diluted cell count samples initially by adding 0.5 mL of cell suspension into 4.5 mL of AIM-V media prepared which gave a 1:10 dilution. Determined the average of viable cell concentration and viability of the cell counts performed. Determined upper and lower limit for counts. Note: dilution may be adjusted according based off the expected concentration of cells. Determined an average viable cell concentration from all four counts performed. Adjusted volume of TIL suspension. Calculated the adjusted volume of TIL suspension after removal of cell count samples. Total TIL cell volume minus 5.0 mL removed for testing.

Calculated total viable TIL cells. Calculated the total number of flasks to seed. NOTE: The maximum number of G-REX500MCS flasks to seed was five. If the calculated number of flasks to seed exceeded five, only five were seeded using the entire volume of cell suspension available.

Calculate number of flasks for subculture. Calculated the number of media bags required in addition to the bag prepared. Prepared one 10 L bag of "CM4 Day 16 Media" for every two G-REX-500M flask needed as calculated. Proceeded to seed the first GREX-500M flask(s) while additional media is prepared and warmed. Prepared and warmed the calculated number of additional media bags determined. Filled G-REX500MCS. Prepared to pump media and pumped 4.5L of media into G-REX500MCS. Heat Sealed. Repeated Fill. Incubated flask. Calculated the target volume of TIL suspension to add to the new G-REX500MCS flasks. If the calculated number of flasks exceeds five only five will be seeded, USING THE ENTIRE VOLUME OF CELL SUSPENSION. Prepared Flasks for Seeding. Removed G-REX500MCS from the incubator. Prepared G-REX500MCS for pumping. Closed all clamps on except large filter line. Removed TIL from incubator. Prepared cell suspension for seeding. Sterile welded (per Process Note 5.11) "TIL Suspension" transfer pack to pump inlet line. Placed TIL suspension bag on a scale.

Seeded flask with TIL Suspension. Pump the volume of TIL suspension calculated into flask. Heat sealed. Filled remaining flasks.

Monitored Incubator. Incubator parameters: Temperature LED Display: 37.0+2.0° C., $CO_2$ Percentage: 5.0+1.5% $CO_2$. Incubated Flasks.

Determined the time range to remove G-REX500MCS from incubator on Day 22.

Day 22 Wash Buffer Preparation. Prepared 10 L Labtainer Bag. In BSC, attach a 4" plasma transfer set to a 10 L Labtainer Bag via luer connection. Prepared 10 L Labtainer Bag. Closed all clamps before transferring out of the BSC. NOTE: Prepared one 10 L Labtainer Bag for every two G-REX500MCS flasks to be harvested. Pumped Plasmalyte into 3000 mL bag and removed air from 3000 mL Origen bag by reversing the pump and manipulating the position of the bag. Added human albumin 25% to 3000 mL Bag. Obtain a final volume of 120.0 mL of human albumin 25%.

Prepared IL-2 diluent. Using a 10 mL syringe, removed 5.0 mL of LOVO Wash Buffer using the needleless injection port on the LOVO Wash Buffer bag. Dispensed LOVO wash buffer into a 50 mL conical tube.

CRF blank bag LOVO wash buffer aliquotted. Using a 100 mL syringe, drew up 70.0 mL of LOVO Wash Buffer from the needleless injection port.

Thawed one 1.1 mL of IL-2 (6×106 IU/mL), until all ice has melted. Added 50 μL IL-2 stock ($6\times10^6$ IU/mL) to the 50 mL conical tube labeled "IL-2 Diluent."

Cryopreservation preparation. Placed 5 cryo-cassettes at 2-8° C. to precondition them for final product cryopreservation.

Prepared cell count dilutions. In the BSC, added 4.5 mL of AIM-V Media that has been labelled with lot number and "For Cell Count Dilutions" to 4 separate 15 mL conical tubes. Prepared cell counts. Labeled 4 cryovials with vial number (1-4). Kept vials under BSC to be used.

Day 22 TIL Harvest. Monitored Incubator. Incubator Parameters Temperature LED display: 37±2.0° C., $CO_2$ Percentage: 5%1.5%. Removed G-REX500MCS Flasks from Incubator. Prepared TIL collection bag and labeled. Sealed off extra connections. Volume Reduction: Transferred −4.5L of supernatant from the G-REX500MCS to the Supernatant bag.

Prepared flask for TIL harvest. Initiated collection of TIL. Vigorously tap flask and swirl media to release cells. Ensure all cells have detached. Initiated collection of TIL. Released all clamps leading to the TIL suspension collection bag. TIL Harvest. Using the GatheRex, transferred the TIL suspension into the 3000 mL collection bag. Inspect membrane for adherent cells. Rinsed flask membrane. Closed clamps on G-Rex500MCS and ensured all clamps are closed. Transferred cell suspension into LOVO source bag. Closed all clamps. Heat Sealed. Removed 4×1.0 mL Cell Counts Samples Performed Cell Counts. Performed cell counts and calculations utilizing NC-200 and Process Note 5.14. Diluted cell count samples initially by adding 0.5 mL of cell suspension into 4.5 mL of AIM-V media prepared. This gave a 1:10 dilution. Determined the average viability, viable cell concentration, and total nucleated cell concentration of the cell counts performed. Determined Upper and Lower Limit for counts. Determined the average viability, viable cell concentration, and total nucleated cell concentration of the cell counts performed. Weighed LOVO source bag. Calculated total viable TIL Cells. Calculated total nucleated cells.

Prepared *Mycoplasma* Diluent. Removed 10.0 mL from one supernatant bag via luer sample port and placed in a 15 mL conical.

Performed "TIL G-REX Harvest" protocol and determined the final product target volume. Loaded disposable kit. Removed filtrate bag. Entered Filtrate capacity. Placed Filtrate container on benchtop. Attached PlasmaLyte. Verified that the PlasmaLyte was attached and observed that the PlasmaLyte is moving. Attached Source container to tubing and verified Source container was attached. Confirmed PlasmaLyte was moving.

Final Formulation and Fill. Target volume/bag calculation. Calculated volume of CS-10 and LOVO wash buffer to formulate blank bag. Prepared CRF Blank.

Calculated the volume of IL-2 to add to the Final Product. Final IL-2 Concentration desired (IU/mL)-300IU/mL. IL-2 working stock: $6\times10^4$ IU/mL. Assembled connect apparatus. Sterile welded a 4S-4M60 to a CC2 cell connection. Sterile welded the CS750 cryobags to the harness prepared. Welded CS-10 bags to spikes of the 4S-4M60.

Prepared TIL with IL-2. Using an appropriately sized syringe, removed amount of IL-2 determined from the "IL-2 $6\times10^4$" aliquot. Labeled formulated TIL Bag. Added the formulated TIL bag to the apparatus. Added CS10. Switched Syringes. Drew −10 mL of air into a 100 mL syringe and replaced the 60 mL syringe on the apparatus. Added CS10. Prepared CS-750 bags. Dispensed cells.

Removed air from final product bags and take retain. Once the last final product bag was filled, closed all clamps. Drew 10 mL of air into a new 100 mL syringe and replace the syringe on the apparatus. Dispensed retain into a 50 mL conical tube and label tube as "Retain" and lot number. Repeat air removal step for each bag.

Prepared final product for cryopreservation, including visual inspection. Held the cryobags on cold pack or at 2-8° C. until cryopreservation.

Removed cell count sample. Using an appropriately sized pipette, remove 2.0 mL of retain and place in a 15 mL conical tube to be used for cell counts. Performed cell counts and calculations. NOTE: Diluted only one sample to appropriate dilution to verify dilution is sufficient. Diluted additional samples to appropriate dilution factor and proceed with counts. Determined the Average of Viable Cell Concentration and Viability of the cell counts performed. Determined Upper and Lower Limit for counts. NOTE: Dilution may be adjusted according based off the expected concentration of cells. Determined the Average of Viable Cell Concentration and Viability. Determined Upper and Lower Limit for counts. Calculated IFN-γ. Heat Sealed Final Product bags.

Labeled and collected samples per exemplary sample plan below.

TABLE 43

Sample plan.

| Sample | Number of Containers | Sample Volume to Add to Each | Container Type |
|---|---|---|---|
| *Mycoplasma | 1 | 1.0 mL | 15 mL Conical |
| Endotoxin | 2 | 1.0 mL | 2 mL Cryovial |
| Gram Stain | 1 | 1.0 mL | 2 mL Cryovial |
| IFN-Y | 1 | 1.0 mL | 2 mL Cryovial |
| Flow Cytometry | 1 | 1.0 mL | 2 mL Cryovial |
| ** Bac-T Sterility | 2 | 1.0 mL | Bac-T Bottle |
| QC Retain | 4 | 1.0 mL | 2 mL Cryovial |
| Satellite Vials | 10 | 0.5 mL | 2 mL Cryovial |

Sterility and BacT testing. Testing Sampling. In the BSC, remove a 1.0 mL sample from the retained cell suspension collected using an appropriately sized syringe and inoculate the anaerobic bottle. Repeat the above for the aerobic bottle.

Final Product Cryopreservation. Prepared controlled rate freezer (CRF). Verified the CRF had been set up. Set up CRF probes. Placed final product and samples in CRF. Determined the time needed to reach 4° C. +1.5° C. and proceed with the CRF run. CRF completed and stored. Stopped the CRF after the completion of the run. Remove cassettes and vials from CRF. Transferred cassettes and vials to vapor phase LN2 for storage. Recorded storage location.

Post-Processing and analysis of final drug product included the following tests: (Day 22) Determination of CD3+cells on Day 22 REP by flow cytometry; (Day 22) Gram staining method (GMP); (Day 22) Bacterial endotoxin test by Gel Clot LAL Assay (GMP); (Day 16) BacT Sterility Assay (GMP); (Day 16) *Mycoplasma* DNA detection by TD-PCR (GMP); Acceptable appearance attributes; (Day 22) BacT sterility assay (GMP)(Day 22); (Day 22) IFN-gamma assay. Other potency assay as described herein are also employed to analyze TIL products.

Example 9: An Exemplary Embodiment of the Gen 3 Expansion Platform

DAY 0

Prepared tumor wash media. Media warmed prior to start. Added 5 mL of gentamicin (50 mg/mL) to the 500 mL bottle of HBSS. Added 5 mL of Tumor Wash Media to a 15 mL conical to be used for OKT3 dilution. Prepared feeder cell bags. Sterilely transfered feeder cells to feeder cell bags and stored at 37° C. until use or freeze. Counted feeder cells if at 37° C. Thawed and then counted feeder cells if frozen.

Optimal range for the feeder cell concentration is between 5x104 and $5\times10^6$ cells/mL. Prepared four conical tubes with 4.5 mL of AIM-V. Added 0.5 mL of cell fraction for each cell count. If total viable feeder cell number was $>1\times10^9$ cells, proceeded to adjust the feeder cell concentration. Calculated the volume of feeder cells to remove from the first feeder cell bag in order to add $1\times10^9$ cells to a second feeder cell bag.

Using the p1000 micropipette, transferred 900 μL of Tumor Wash Media to the OKT3 aliquot (100 μL). Using a syringe and sterile technique, drew up 0.6 mL of OKT3 and added into the second feeder cell bag. Adjusted media volume to a total volume of 2L. Transferred the second feeder cells bag to the incubator.

OKT3 formulation details: OKT3 may be aliquoted and frozen in original stock concentration from the vial (1 mg/mL) in 100 μL aliquots. ~10X aliquots per 1 mL vial. Stored at −80C. Day 0:15 μg/flask, i.e. 30 ng/mL in 500 mL-60 μL max ~ 1 aliquot.

Added 5 mL of Tumor Wash Medium into all wells of the 6-well plate labelled Excess Tumor Pieces. Kept the Tumor Wash Medium available for further use in keeping the tumor hydrated during dissection. Added 50 mL of Tumor Wash Medium to each 100 mm petri dish.

Dissected the tumor into 27 $mm^3$ fragments (3×3×3 mm), using the ruler under the Dissection dish lid as a reference. Dissected intermediate fragment until 60 fragments were reached. Counted total number of final fragments and prepared G-REX-100MCS flasks according to the number of final fragments generated (generally 60 fragments per flask).

Retained favorable tissue fragments in the conical tubes labeled as Fragments Tube 1 through Fragments Tube 4. Calculated the number of G-REX-100MCS flasks to seed with feeder cell suspension according to the number of fragments tubes originated.

Removed feeder cells bag from the incubator and seed the G-REX-100MCS. Label as DO (Day 0).

Tumor fragment addition to culture in G-REX-100 MCS. Under sterile conditions, unscrewed the cap of the G-REX-100MCS labelled Tumor Fragments Culture (DO) 1 and the 50 mL conical tube labelled Fragments Tube. Swirled the opened Fragments Tube 1 and, at the same time, slightly lifted the cap of the G-REX100MCS. Added the medium with the fragments to the G-REX100MCS while being swirled. Recorded the number of fragments transferred into the G-REX100MCS.

Once the fragments were located at the bottom of the GREX flask, drew 7 mL of media and created seven 1 mL aliquots-5 mL for extended characterization and 2 mL for sterility samples. Stored the 5 aliquots (final fragment culture supernatant) for extended characterization at −20° C. until needed.

Inoculated one anaerobic BacT/Alert bottle and one aerobic BacT/Alert bottle each with 1 mL of final fragment culture supernatant. Repeat for each flask sampled.

AT DAY 7-8

Prepared feeder cell bags. Thawed feeder bags for 3-5 minutes in 37° C. water bath when frozen. Counted feeder cells if frozen. Optimal range for the feeder cell concentration is between $5\times10^4$ and $5\times10^6$ cells/mL. Prepared four conical tubes with 4.5 mL of AIM-V. Added 0.5 mL of cell fraction for each cell count into a new cryovial tube. Mixed the samples well and proceeded with the cell count.

If total viable feeder cell number was $>2\times10^9$ cells, proceeded to the next step to adjust the feeder cell concentration. Calculated the volume of feeder cells to remove from the first feeder cell bag in order to add $2\times10^9$ cells to the second feeder cell bag.

Using the p1000 micropipette, transfer 900 μL of HBSS to a 100 μL OKT3 aliquot. Mix by pipetting up and down 3 times. Prepared two aliquots.

OKT3 formulation details: OKT3 may be aliquoted and frozen in original stock concentration from the vial (1 mg/mL) in 100 μL aliquots. −10x aliquots per 1 mL vial. Stored at −80C. Day7/8:30 μg/flask, i.e. 60 ng/mL in 500 mL-120 μl max ~ 2 aliquots.

Using a syringe and sterile technique, drew up 0.6 mL of OKT3 and added into the feeder cell bag, ensuring all added. Adjusted media volume to a total volume of 2 L. Repeated with second OKT3 aliquot and added to the feeder cell bag. Transferred the second feeder cells bag to the incubator.

Preparation of G-REX100MCS flask with feeder cell suspension. Recorded the number of G-REX-100MCS flasks to process according to the number of G-REX flasks generated on Day 0. Removed G-REX flask from incubator and removed second feeder cells bag from incubator.

Removal of supernatant prior to feeder cell suspension addition. Connected one 10 mL syringe to the G-REX100 flask and drew up 5 mL of media. Created five 1 mL aliquots −5 mL for extended characterization and stored the 5 aliquots (final fragment culture supernatant) for extended characterization at −20° C. until requested by sponsor. Labeled and repeated for each G-REX100 flask.

5-20×1 mL samples for characterization, depending on number of flasks:

5 mL=1 flask
10 mL=2 flasks
15 mL=3 flasks
20 mL=4 flasks

Continued seeding feeder cells into the G-REX100 MCS and repeated for each G-REX100 MCS flask. Using sterile transfer methods, gravity transferred 500 mL of the second feeder cells bag by weight (assume 1 g=1 mL) into each G-REX-100MCS flask and recorded amount. Labeled as Day 7 culture and repeated for each G-REX100 flask. Transferred G-REX-100MCS flasks to the incubator.

DAY 10-11

Removed the first G-REX-100MCS flask and using sterile conditions removed 7 mL of pre-process culture supernatant using a 10 mL syringe. Created seven 1 mL aliquots −5 mL for extended characterization and 2 mL for sterility samples.

Mixed the flask carefully and using a new 10 mL syringe remove 10 mL supernatant and transfer to a 15 mL tube labelled as D10/11 *mycoplasma* supernatant.

Mixed the flask carefully and using a new syringe removed the volume below according to how many flasks were to be processed:

1 flask=40 mL
2 flask=20 mL/flask
3 flask=13.3 mL/flask
4 flask=10 mL/flask

A total of 40 mL should be pulled from all flasks and pooled in a 50 mL conical tube labeled 'Day 10/11 QC Sample' and stored in the incubator until needed. Performed a cell count and allocated the cells.

Stored the 5 aliquots (pre-process culture supernatant) for extended characterization at <−20° C. until needed. Inoculated one anaerobic BacT/Alert bottle and one aerobic BacT/Alert bottle each with 1 mL of pre-process culture supernatant.

Continued with cell suspension transferred to the G-REX-500MCS and repeated for each G-REX-100MCS. Using sterile conditions, transferred the contents of each G-REX-100MCS into a G-REX-500MCS, monitoring about 100 mL of fluid transfer at a time. Stopped transfer when the volume of the G-REX-100MCS was reduced to 500 mL.

During transfer step, used 10 mL syringe and drew 10 mL of cell suspension into the syringe from the G-REX-100MCS. Followed the instructions according to the number of flasks in culture. If only 1 flask: Removed 20 mL total using two syringes. If 2 flasks: removed 10 mL per flask. If 3 flasks: removed 7 mL per flask. If 4 flasks: removed 5 mL per flask. Transferred the cell suspension to one common 50 mL conical tube. Keep in the incubator until the cell count step and QC sample. Total number of cells needed for QC was 20e6 cells: 4×0.5 mL cell counts (cell counts were undiluted first).

The quantities of cells needed for assays are as follows:

1. $10\times10^6$ cells minimum for potency assays, such as those described herein, or for an IFN-γ or granzyme B assay
2. $1\times10^6$ cells for *mycoplasma*
3. $5\times10^6$ cells for flow cytometry for CD3+/CD45+

Transferred the G-REX-500MCS flasks to the incubator.

Prepared QC Samples. At least $15\times10^8$ cells were needed for the assays in this embodiment. Assays included: Cell count and viability; *Mycoplasma* ($1\times10^6$ cells/average viable concentration;) flow ($5\times10^6$ cells/average viable concentration;) and IFN-g assay ($5\times10^6$ cells-$1\times10^6$ cells; 8-$10\times10^6$ cells are required for the IFN-γ assay.

Calculated the volume of cells fraction for cryopreservation at $10\times10^6$ cells/mL and calculated the number of vials to prepare

DAY 16-17

Wash Buffer preparation (1% HSA Plasmalyte A). Transferred HSA and Plasmalyte to 5 L bag to make LOVO wash buffer. Using sterile conditions, transferred a total volume of 125 mL of 25% HSA to the 5L bag. Removed and transferred 10 mL or 40 mL of wash buffer in the 'IL-2 $6\times10^4$ IU/mL' tube (10 mL if IL-2 was prepared in advance or 40 mL if IL-2 was prepared fresh).

Calculated volume of reconstituted IL-2 to add to Plasmalyte+1% HSA: volume of reconstituted IL-2=(Final concentration of IL-2×Final volume)/specific activity of the IL-2 (based on standard assay). The Final Concentration of IL-2 was $6\times10^4$ IU/mL. The final volume was 40 mL.

Removed calculated initial volume of IL-2 needed of reconstituted IL-2 and transfer to the 'IL-2 $6\times10^4$ IU/mL' tube. Added 100 μL of IL-2 $6\times10^6$ IU/mL from the aliquot prepared in advance to the tube labelled 'IL-2 $6\times10^4$ IU/mL' containing 10 mL of LOVO wash buffer.

Removed about 4500 mL of supernatant from the G-REX-500MCS flasks. Swirled the remaining supernatant and transferred cells to the Cell Collection Pool bag. Repeated with all G-REX-500MCS flasks.

Removed 60 mL of supernatant and add to supernatant tubes for quality control assays, including *mycoplasma* detection. Stored at +2-8° C.

Cell collection. Counted cells. Prepare four 15 mL conicals with 4.5 mL of AIM-V. These may be prepared in advance. Optimal range=is between 5 $\times10^4$ and $5\times10^6$ cells/mL. (1:10 dilution was recommended). For 1:10 dilution, to 4500 μL of AIM V prepared previously, add 500 μL of CF. Recorded dilution factor.

$$\text{Calculated the } TC \text{ (Total Cells) pre-}LOVO\text{ (live + dead)} = \text{Average Total Cell Concentration } (TC\ conc\ \text{pre } LOVO)\text{(live + dead)} \times \text{Volume of Source bag}$$

$$\text{Calculated the } TVC \text{ (Total Viable Cells) pre-}LOVO\text{ (live)} = \text{Average Total Viable Cell Concentration } (TVC\ \text{pre } LOVO)\text{ (live)} \times \text{Volume of } LOVO \text{ Source Bag}$$

When the total cell (TC) number was $>5\times10^9$, remove $5\times10^8$ cells to be cryopreserved as MDA retention samples. $5\times10^8$+avg TC concentration (step 14.44)=volume to remove.

When the total cell (TC) number was $<5\times10^9$, remove $4\times10^6$ cells to be cryopreserved as MDA retention samples. $4\times10^6$+avg TC concentration=volume to remove.

When the total cell number was determined, the number of cells to remove should allow retention of 150×109 viable cells. Confirm TVC pre-LOVO $5\times10^8$ or $4\times10^6$ or not applicable. Calculated the volume of cells to remove.

Calculated the remaining Total Cells Remaining in Bag. Calculated the TC (Total Cells) pre-LOVO. [Avg. Total cell concentration X Remaining Volume=TC pre-LOVO Remaining]

According to the total number of cells remaining, the corresponding process in Table 44 is selected.

TABLE 44

Total number of cells.

| Total cells: | Retentate (mL) |
|---|---|
| $0 < \text{Total cells} \le 31\times10^9$ | 115 |
| $31\times10^9 < \text{Total cells} \le 71\times10^9$ | 165 |
| $71\times10^9 < \text{Total Cells} \le 110\times10^9$ | 215 |
| $110\times10^9 < \text{Total Cells} \le 115\times10^9$ | 265 |

Chose the volume of IL-2 to add corresponding to the used process. Volume calculated as: Retentate Volume×2×300 IU/mL=IU of IL-2 required. IU of IL-2 required/6×104 IU/mL=Volume of IL-2 to add Post LOVO bag. Recorded all volumes added. Obtained samples in cryovial for further analyses.

Mixed the cell product well. Sealed all bags for further processing, included cryopreservation when applicable.

Performed endotoxin, IFN-γ, sterility, and other assays as needed on cryovial samples obtained.

Example 10: Gen 2 and Gen 3 Exemplary Processes

This example demonstrates the Gen 2 and Gen 3 processes. Process Gen 2 and Gen 3 TILs are generally composed of autologous TIL derived from an individual patient through surgical resection of a tumor and then expanded ex vivo. The priming first expansion step of the Gen 3 process was a cell culture in the presence of interleukin-2 (IL-2) and the monoclonal antibody OKT3, which targets the T-cell co-receptor CD3 on a scaffold of irradiated peripheral blood mononuclear cells (PBMCs).

The manufacture of Gen 2 TIL products consists of two phases: 1) pre-Rapid Expansion (Pre-REP) and 2) Rapid Expansion Protocol (REP). During the Pre-REP resected tumors were cut up into <50 fragments 2-3 mm in each dimension which were cultured with serum-containing culture medium (RPMI 1640 media containing 10% HuSAB supplemented) and 6,000 IU/mL of Interleukin-2 (IL-2) for a period of 11 days. On day 11 TIL were harvested and introduced into the large-scale secondary REP expansion. The REP consists of activation of $<200\times10^6$ of the viable cells from pre-REP in a co-culture of $5\times10^9$ irradiated allogeneic PBMCs feeder cells loaded with 150 μg of monoclonal anti-CD3 antibody (OKT3) in a 5 L volume of CM2 supplemented with 3000 IU/mL of rhIL-2 for 5 days. On day 16 the culture is volume reduced 90% and the cell fraction is split into multiple G-REX-500 flasks at $>1\times10^9$ viable lymphocytes/flask and QS to 5L with CM4. TIL are incubated an additional 6 days. The REP is harvested on day 22, washed, formulated, and cryo-preserved prior to shipping at −150° C. to the clinical site for infusion.

The manufacture of Gen 3 TIL products consists of three phases: 1) Priming First Expansion Protocol, 2) Rapid Second Expansion Protocol (also referred to as rapid expansion phase or REP), and 3) Subculture Split. To effect the Priming First Expansion TIL propagation, resected tumor was cut up into <120 fragments 2-3 mm in each dimension. On day 0 of the Priming First Expansion, a feeder layer of approximately $2.5\times10^8$ allogeneic irradiated PBMCs feeder cells loaded with OKT-3 was established on a surface area of approximately 100 $cm^2$ in each of 3 100 MCS vessels. The tumor fragments were distributed among and cultured in the 3 100 MCS vessels each with 500 mL serum-containing CM1 culture medium and 6,000 IU/mL of Interleukin-2 (IL-2) and 15 ug OKT-3 for a period of 7 days. On day 7, REP was initiated by incorporating an additional feeder cell layer of approximately $5\times10^8$ allogeneic irradiated PBMCs feeder cells loaded with OKT-3 into the tumor fragmented culture phase in each of the three 100 MCS vessels and culturing with 500 mL CM2 culture medium and 6,000 IU/mL IL-2 and 30 μg OKT-3. The REP initiation was enhanced by activating the entire Priming First Expansion culture in the same vessel using closed system fluid transfer of OKT3 loaded feeder cells into the 100MCS vessel. For Gen 3, the TIL scale up or split involved process steps where the whole cell culture was scaled to a larger vessel through closed system fluid transfer and was transferred (from 100 M flask to a 500 M flask) and additional 4 L of CM4 media was added. The REP cells were harvested on day 16, washed, formulated, and cryo-preserved prior to shipping at −150° C. to the clinical site for infusion.

Overall, the Gen 3 process is a shorter, more scalable, and easily modifiable expansion platform that will accommodate to fit robust manufacturing and process comparability.

TABLE 45

Comparison of Exemplary Gen 2 and Exemplary Gen 3 manufacturing process.

| Step | Process (Gen 2) | Process (Gen 3) |
|---|---|---|
| Pre REP-day 0 | Up to 50 fragments, 1 G-REX-100MCS, 11 days<br>In 1 L of CM1 media +<br>IL-2 (6000 IU/mL) | Whole tumor up to 120 fragments divided evenly among up to 3 flasks. 1 flask: 1-60 fragments<br>2 flasks: 61-89 fragments<br>3 flasks 90-120 fragments<br>7 days in 500 mL of CM1 media +<br>IL-2 (6000 IU/mL)<br>$2.5\times10^8$ feeder cells/flask<br>15 ug OKT-3/flask |
| REP Initiation | Direct to REP, Day 11, <<br>$200\times10^6$ TIL<br>(1)G-REX-500MCS in 5L CM2 media<br>IL-2 (3000 IU/mL)<br>$5\times10^9$ feeder cells<br>150 ug OKT-3 | Direct to REP, Day 7, all cells, same G-REX-100MCS<br>Add 500 CM2 media<br>IL-2 (6000 IU/mL)<br>$5\times10^8$ feeder cells/flask<br>30 ug OKT-3/flask |
| TIL propagation or Scale up | Volume reduce and split cell fraction in up to 5 G-REX-500MCS<br>4.5 L CM4 media + IL-2 (3000 IU/mL)<br>$\geq1\times10^9$ TVC / flask<br>Split day 16 | Each G-REX-100MCS(1L) transfers to 1 G-REX-500MCS<br>Add 4L CM4 media + IL-2 (3000 IU/mL)<br>Scale up on day 9 to 11 |
| Harvest | Harvest day 22,<br>LOVO-automated cell washer | Harvest day 16<br>LOVO- automated cell washer |
| Final formulation | Cryopreserved Product<br>300 IU/mL IL2- CS10 in LN. 20<br>multiple aliquots | Cryopreserved product<br>300 IU/mL IL-2-CS10 in LN.<br>multiple aliquots |
| Process time | 22 days | 16 days |

On day 0, for both processes, the tumor was washed 3 times and the fragments were randomized and divided into two pools; one pool per process. For the Gen 2 Process, the fragments were transferred to one-GREX 100MCS flask with 1 L of CM1 media containing 6,0001U/mL rhIL-2. For the Gen 3 Process, fragments were transferred to one G-REX-100MCS flask with 500 mL of CM1 containing 6,000 IU/mL rhIL-2, 15 ug OKT-3 and 2.5×108 feeder cells. Seeding of TIL for Rep initiation day occurred on different days according to each process. For the Gen 2 Process, in which the G-REX-100MCS flask was 90% volume reduced, collected cell suspension was transferred to a new G-REX-500MCS to start REP initiation on day 11 in CM2 media containing IL-2 (3000 IU/mL), plus $5\times10^9$ feeder cells and OKT-3 (30 ng/mL). Cells were expanded and split on day 16 into multiple G-REX-500 MCS flasks with CM4 media with IL-2 (3000 IU/mL) per protocol. The culture was then harvested and cryopreserved on day 22 per protocol. For the Gen 3 process, the REP initiation occurred on day 7, in which the same G-REX-100MCS used for REP initiation. Briefly, 500 mL of CM2 media containing IL-2 (6000 IU/mL) and $5\times10^8$ feeder cells with 30ug OKT-3 was added to each flask. On day 9-11 the culture was scaled up. The entire volume of the G-REX100M (1 L) was transferred to a G-REX-500MCS and 4L of CM4 containing IL-2 (3000 IU/mL) was added. Flasks were incubated 5 days. Cultures were harvested and cryopreserved on Day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

Media was warmed at 37° C. up to 24 hours in advance for L4055 tumor on REP initiation and scale-up.

Results. Gen 3 results fell within 30% of Gen 2 for total viable cells achieved. Gen 3 final product exhibited higher production of IFN-γ after restimulation. Gen 3 final product exhibited increased clonal diversity as measured by total unique CDR3 sequences present. Gen 3 final product exhibited longer mean telomere length.

Pre-REP and REP expansion on Gen 2 and Gen 3 processes followed the procedures described above. For each tumor, the two pools contained equal number of fragments. Due to the small size of tumors, the maximum number of fragments per flask was not achieved. Total pre-REP cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in Table 46 below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 46

Pre-REP cell counts

| | Tumor ID | | | | | |
|---|---|---|---|---|---|---|
| | L4054 | | L4055* | | M1085T | |
| | Process | | | | | |
| | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |
| Average TVC per fragment at pre-REP | 6.65E+06 | 2.06E+06 | 1.12E+06 | 5.75E+05 | 7.66E+05 | 2.18E+05 |
| Gen 3 extrapolated value at pre REP day 11 | N/A | 6.79E+07 | N/A | 2.17E+07 | N/A | 5.49E+06 |

*L4055, unfiltered media.

For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initiation TVC. As exhibited in Table 47, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 47

Total viable cell count and fold expansion on TIL final product.

| | Tumor ID | | | | | |
|---|---|---|---|---|---|---|
| | L4054 | | L4055 | | M1085T | |
| | Process | | | | | |
| | Gen 2 | Gen 3 | Gen 2 | Gen 3 | Gen 2 | Gen 3 |
| # Fragments | 21 | 21 | 24 | 24 | 16 | 16 |
| TVC/fragment (at Harvest) | 3.18E+09 | 8.77E+08 | 2.30E+09 | 3.65E+08 | 7.09E+08 | 4.80E+08 |
| REP initiation | 1.42E+08 | 4.32E+07 | 2.68E+07 | 1.38E+07 | 1.23E+07 | 3.50E+06 |
| Scale up | 3.36E+09 | 9.35E+08 | 3.49E+09 | 8.44E+08 | 1.99E+09 | 3.25E+08 |
| Harvest | 6.67E+10 | 1.84E+10 | 5.52E+10 | 8.76E+09 | 1.13E+10 | 7.68E+09 |
| Fold Expansion Harvest/ REP initiation | 468.4 | 425.9 | 2056.8 | 634.6 | 925.0 | 2197.2 |
| Gen 3 extrapolated value at REP harvest day 22 | N/A | 2.53E+10 | N/A | 1.20E+10 | N/A | 1.06E+10 |

* L4055, unfiltered media.

Table 48: % Viability of TIL final product: Upon harvest, the final TIL REP products were compared against release criteria for 0% viability. All of the conditions for the Gen 2 and Gen 3 processes surpassed the 70% viability criterion and were comparable across processes and tumors.

Upon harvest, the final TIL REP products were compared against release criteria for 00 viability. All of the conditions for the Gen 2 and Gen 3 processes surpassed the 70% o viability criterion and were comparable across processes and tumors.

TABLE 48

% Viability of REP (TIL Final Product)

| | Tumor ID | | | | | |
|---|---|---|---|---|---|---|
| | L4054 | | L4055 | | M1085T | |
| | Process | | | | | |
| | Gen 2 | Gen 3 | Gen 2 | Gen 3 | Gen 2 | Gen 3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

Due to the number of fragments per flask below the maximum required number, an estimated cell count at harvest day was calculated for each tumor. The estimation was based on the expectation that clinical tumors were large enough to seed 2 or 3 flasks on day 0.

TABLE 49

Extrapolated estimate cell count calculation to full scale 2 and 3 flask on Gen 3 Process.

| | Tumor ID | | | | | |
|---|---|---|---|---|---|---|
| | L4054 | | L4055 | | M1085T | |
| | Gen 3 Process | | | | | |
| | 2 flasks | 3 Flasks | 2 flasks | 3 Flasks | 2 flasks | 3 Flasks |
| Estimate Harvest | 3.68E+10 | 5.52E+10 | 1.75E+10 | 2.63E+10 | 1.54E+10 | 2.30E+10 |

Immunophenotyping—phenotypic marker comparisons on TIL final product. Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+cells was over 90%.

TIL harvested from the Gen 3 process showed a higher expression of CD8 and CD28 compared to TIL harvested from the Gen 2 process. The Gen 2 process showed a higher percentage of CD4+.

TIL harvested from the Gen 3 process showed a higher expression on central memory compartments compared to TIL from the Gen 2 process.

Activation and exhaustion markers were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes.

Interferon gamma secretion upon restimulation. On harvest day, day 22 for Gen 2 and day 16 for Gen 3, TIL underwent an overnight restimulation with coated anti-CD3 plates for L4054 and L4055. The restimulation on M1085T was performed using anti-CD3, CD28, and CD137 beads. Supernatant was collected after 24 hours of the restimulation in all conditions and the supernatant was frozen. IFNγ analysis by ELISA was assessed on the supernatant from both processes at the same time using the same ELISA plate. Higher production of IFNγ from the Gen 3 process was observed in the three tumors analyzed.

Measurement of IL-2 levels in culture media. To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carryover of the media throughout the process.

Metabolic substrate and metabolite analysis. The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes.

Spent media for L4054 and L4055 was collected at REP initiation, scale up, and harvest days for both process Gen 2 and Gen 3. The spent media collection was for Gen 2 on Day 11, day 16 and day 22; for Gen 3 was on day 7, day 11 and day 16. Supernatant was analyzed on a CEDEX Bio-analyzer for concentrations of glucose, lactic acid, glutamine, GlutaMax™, and ammonia.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with GlutaMax™, which is more stable in aqueous solutions and does not spontaneously degrade. In the two tumor lines, the Gen 3 arm showed a decrease in L-glutamine and GlutaMax™ during the process and an increase in ammonia throughout the REP. In the Gen 2 arm a constant concentration of L-glutamine and GlutaMax™, and a slight increase in the ammonia production was observed. The Gen 2 and Gen 3 processes were comparable at harvest day for ammonia and showed a slight difference in L-glutamine degradation.

Telomere repeats by Flow-FISH. Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis. To determine the clonal diversity of the cell products generated in each process, TIL final product harvested for L4054 and L4055, were sampled and assayed for clonal diversity analysis through sequencing of the CDR3 portion of the T-cell receptors.

Table 50 shows a comparison between Gen 2 and Gen 3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 50

Comparison of shared uCDR3 sequences between Gen 2 and Gen 3 processes on L4054.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4054 | 8915 | 4355 (48.85%) | 205 | 199 (97.07%) |
| Gen 3-L4054 | — | 18130 | — | 223 |

Table 51 shows a comparison between Gen 2 and Gen 3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 51

Comparison of shared uCDR3 sequences between Gen 2 and Gen 3 processes on L4055.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4055 | 12996 | 6599 (50.77%) | 1843 | 1833 (99.45%) |
| Gen 3-L4055 | — | 27246 | — | 2616 |

CM1 and CM2 media was prepared in advanced without filtration and held at 4 degree c. until use for tumor L4055 to use on Gen 2 and Gen 3 process.

Media was warmed up at 37 degree c. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

Conclusions. This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for Gen 3 process assuming the pre-REP harvest occurred at day 11 instead day 7 and REP Harvest at Day 22 instead day 16. In both cases, Gen 3 shows a closer number on TVC compared to the Gen 2 process, indicating that the early activation enhanced TIL growth.

In the case of extrapolated value for extra flasks (2 or 3) on Gen 3 process assuming a bigger size of tumor processed, and reaching the maximum number of fragments required per process as described. It was observed that a similar dose can be reachable on TVC at Day 16 Harvest for Gen 3 process compared to Gen 2 process at Day 22. This observation is important and indicates an early activation of the culture reduced TIL processing time.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization, a higher CD8+ and CD28+expression was observed on three tumors on Gen 3 process compared to Gen 2 process.

Gen 3 process showed slightly higher central memory compartments compared to Gen 2 process.

Gen 2 and Gen 3 process showed comparable activation and exhaustion markers, despite the shorter duration of the Gen 3 process.

IFN gamma (IFNγ) production was 3 times higher on Gen 3 final product compared to Gen 2 in the three tumors analyzed. This data indicates the Gen 3 process generated a highly functional and more potent TIL product as compared to the Gen 2 process, possibly due to the higher expression of CD8 and CD28 expression on Gen 3. Phenotypic characterization suggested positive trends in Gen 3 toward CD8+, CD28+expression on three tumors compared to Gen 2 process.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the non-execution of volume reduction removal in each day of the process and less volume media overall in the process, compared to Gen 2.

Overall Gen 3 process showed a reduction almost two times of the processing time compared to Gen 2 process, which would yield a substantial reduction on the cost of goods (COGs) for TIL product expanded by the Gen 3 process.

IL-2 consumption indicates a general trend of IL-2 consumption on Gen 2 process, and in Gen 3 process IL-2 was higher due to the non-removal of the old media.

The Gen 3 process showed a higher clonal diversity measured by CDR3 TCRab sequence analysis.

The addition of feeders and OKT-3 on day 0 of the pre-REP allowed an early activation of TIL and allowed for TIL growth using the Gen 3 process.

Table 52 describes various embodiments and outcomes for the Gen 3 process as compared to the current Gen 2 process.

TABLE 52

Exemplary Gen 3 process features.

| Step | Process Gen 2 embodiment | Process Gen 3 embodiment |
|---|---|---|
| Pre REP- | ≤50 fragments | ≤240 fragments |
| | 1X G-REX-100MCS | ≤60 fragments/flask |
| | | ≤4 flasks |
| day 0 | 1 L media | ≤2 L media (500 mL/flask) |
| | IL-2 (6000 IU/mL) | IL-2 (6000 IU/mL) |
| | 11 days | 2.5 × $10^8$ feeder cells/flask |
| | | 15 ug OKT3/flask |
| REP | Fresh TIL direct to REP | Fresh TIL direct to REP |
| | Day 11 | |
| Initiation | ≤200e$^6$ viable cells | Day 7 |
| | 5 × $10^9$ feeder cells | Activate entire culture |
| | G-REX-500MCS | 5 × $10^8$ feeder cells |
| | 5L CM2 media + IL-2 (3000 IU/mL) | 30 ug OKT3/flask |
| | 150 ug OKT3 | G-REX-100MCS |
| | | 500 mL media+ IL-2 (6000 IU/mL) |
| TIL Sub-culture or Scale up | ≤5 G-REX-500MCS | ≤4 G-REX-500MCS |
| | ≤1 × 10 viable cells/ flask | Scale up entire culture |
| | 5 L/flask | 4 L/flask |
| | Day 16 | Day 10-11 |
| Harvest | Harvest Day 22, | Harvest Day 16 |
| | LOVO-automated cell washer | LOVO-automated cell washer |
| | 2 wash cycles | 5 wash cycles |
| Final formulation | Cryopreserved Product | Cryopreserved product |
| | 300 IU/mL IL2- CS10 in LN,, | 300 IU/mL IL-2-CS10 in LN2, |
| | multiple aliquots | multiple aliquots |
| Process time | 22 days | 16 days |

Example 11: An Exemplary Gen 3 Process (Also Referred to as Gen 3.1)

This example describes further studies regarding the "Comparability between the Gen 2 and Gen 3 processes for TIL expansion". The Gen 3 process was modified to include an activation step early in the process with the goal of increasing the final total viable cell (TVC) output, while maintaining the phenotypic and functional profiles. As described below, a Gen 3 embodiment was modified as a further embodiment and is referred to herein in this example as Gen 3.1.

In some embodiments, the Gen 3.1 TIL manufacturing process has four operator interventions:

1. Tumor Fragment Isolation and Activation: On Day 0 of the process the tumor was dissected and the final fragments generated awe-3×3 mm each (up to 240 fragments total) and cultured in 1-4 G-REX100MCS flasks. Each flask contained up to 60 fragments, 500 mL of CM1 or DM1 media, and supplemented with 6,000 IU rhIL-2, 15 μg OKT3, and 2.5×$10^8$ irradiated allogeneic mononuclear cells. The culture was incubated at 37° C. for 6-8 days.
2. TIL Culture Reactivation: On Day 7-8 the culture was supplemented through slow addition of CM2 or DM1 media supplemented with 6,000 IU rhIL-2, 30 μg OKT3, and 5×$10^8$ irradiated allogeneic mononuclear cells in both cases. Care was taken to not disturb the existing cells at the bottom of the flask. The culture was incubated at 37° C. for 3-4 days.
3. Culture Scale Up: Occurs on day 10-11. During the culture scale-up, the entire contents of the G-REX100MCS was transferred to a G-REX500MCS flask containing 4L of CM4 or DM2 supplemented with 3,000 IU/mL of IL-2 in both cases. Flasks were incubated at 37° C. for 5-6 days until harvest.
4. Harvest/Wash/Formulate: On day 16-17 the flasks are volume reduced and pooled. Cells were concentrated and washed with PlasmaLyte A pH 7.4 containing 1% HSA. The washed cell suspension was formulated at a 1:1 ratio with CryoStor10 and supplemented with rhIL-2 to a final concentration of 300 IU/mL.

The DP was cryopreserved with a controlled rate freeze and stored in vapor phase liquid nitrogen. *Complete Standard TIL media 1, 2, or 4 (CM1, CM2, CM4) could be substituted for CTS™OpTmizer™ T-Cell serum free expansion Medium, referred to as Defined Medium (DM1 or DM2), as noted above.

Process description. On day 0, the tumor was washed 3 times, then fragmented in 3×3×3 final fragments. Once the whole tumor was fragmented, then the final fragments were randomized equally and divided into three pools. One randomized fragment pool was introduced to each arm, adding the same number of fragments per the three experimental matrices.

Tumor L4063 expansion was performed with Standard Media and tumor L4064 expansion was performed with Defined Media (CTS OpTmizer) for the entire TIL expansion process. Components of the media are described herein.

CM1 Complete Media 1: RPMI+Glutamine supplemented with 2 mM GlutaMax™, 10% Human AB Serum, Gentamicin (50ug/mL), 2-Mercaptoethanol (55 uM). Final media formulation supplemented with 60001U/mL IL-2.

CM2 Complete Media 2:50% CM1 medium+50% AIM-V medium. Final media formulation supplemented with 60001U/mL IL-2.

CM4 Complete Media 4: AIM-V supplemented with GlutaMax™ (2 mM). Final media formulation supplemented with 30001U/mL IL-2.

CTS OpTmizer CTS™OpTmizer™ T-Cell Expansion Basal Medium supplemented with CTS™ OpTmizer™ T-Cell Expansion Supplement (26 mL/L).

DM1: CTS™OpTmizer™ T-Cell Expansion Basal Medium supplemented with CTS™ OpTmizer™ T-Cell Expansion Supplement (26 mL/L), and CTS™ Immune Cell SR (3%), with GlutaMax™ (2 mM). Final formulation supplemented with 6,000 IU/mL of IL-2.

DM2: CTS™OpTmizer™ T-Cell Expansion Basal Medium supplemented with CTS™ OpTmizer™ T-Cell Expansion Supplement (26 mL/L), and CTS™ Immune Cell SR (3%), with GlutaMax™ (2 mM). Final formulation supplemented with 3,000 IU/mL of IL-2.

All types of media used, i.e., Complete (CM) and Defined (DM) media, were prepared in advance, held at 4° C. degree until the day before use, and warmed at 37° C. in an incubator for up to 24 hours in advance prior to process day.

TIL culture reactivation occurred on Day 7 for both tumors. Scale-up occurred on day 10 for L4063 and day 11 for L4064. Both cultures were harvested and cryopreserved on Day 16.

Results Achieved. Cells counted and % viability for Gen 3.0 and Gen 3.1 processes were determined. Expansion in all the conditions followed details described in this example.

For each tumor, the fragments were divided into three pools of equal numbers. Due to the small size of the tumors, the maximum number of fragments per flask was not achieved. For the three different processes, the total viable cells and cell viability were assessed for each condition. Cell counts were determined as TVC on day 7 for reactivation, TVC on day 10 (L4064) or day 11 (L4063) for scale-up, and TVC at harvest on day 16/17.

Cell counts for Day 7 and Day 10/11 were taken FIO. Fold expansion was calculated by dividing the harvest day 16/17 TVC by the day 7 reactivation day TVC. To compare the three arms, the TVC on harvest day was divided by the number of fragments added in the culture on Day 0 in order to calculate an average of viable cells per fragment.

Cell counts and viability assays were performed for L4063 and L4064. The Gen 3.1-Test process yielded more cells per fragment than the Gen 3.0 Process on both tumors.

Total viable cell count and fold expansion; % Viability during the process. On reactivation, scale up and harvest the percent viability was performed on all conditions. On day 16/17 harvest, the final TVC were compared against release criteria for % viability. All of the conditions assessed surpassed the 70% viability criterion and were comparable across processes and tumors.

Immunophenotyping—Phenotypic characterization on TIL final product. The final products were subjected to flow cytometry analysis to test purity, differentiation, and memory markers. Percent populations were consistent for TCRa/p, CD4+ and CD8+cells for all conditions.

Extended phenotypic analysis of REP TIL was performed. TIL product showed a higher percentage of CD4+cells for Gen 3.1 conditions compared to Gen 3.0 on both tumors, and higher percentage of CD28+cells from CD8+population for Gen 3.0 compared to Gen 3.1 conditions on both conditions.

TIL harvested from the Gen 3.0 and Gen 3.1 processes showed comparable phenotypic markers as CD27 and CD56 expression on CD4+ and CD8+cells, and a comparable CD28 expression on CD4+gated cells population. Memory markers comparison on TIL final product:

Frozen samples of TIL harvested on day 16 were stained for analysis. TIL memory status was comparable between Gen 3.0 and Gen 3.1 processes. Activation and exhaustion markers comparison on TIL final product:

Activation and exhaustion markers were comparable between the Gen 3.0 and Gen 3.1 processes gated on CD4+ and CD8+cells.

Interferon gamma secretion upon restimulation. Harvested TIL underwent an overnight restimulation with coated anti-CD3 plates for L4063 and L4064. Higher production of IFNγ from the Gen 3.1 process was observed in the two tumors analyzed compared to Gen 3.0 process.

Measurement of IL-2 levels in culture media. To compare the levels of IL-2 consumption between all of the conditions and processes, cell supernatants were collected at initiation of reactivation on Day 7, at scale-up Day 10 (L4064)/11 (L4063), and at harvest Day 16/17, and frozen. The supernatants were subsequently thawed and then analyzed. The quantity of IL-2 in cell culture supernatant was measured by the manufacturer protocol.

Overall Gen 3 and Gen 3.1 processes were comparable in terms of IL-2 consumption during the complete process assessed across same media conditions. IL-2 concentration (μg/mL) analysis on spent media collected for L4063 and L4064.

Metabolite analysis. Spent media supernatants was collected from L4063 and L4064 at reactivation initiation on day 7, scale-up on day 10 (L4064) or day 11 (L4063), and at harvest on days 16/17 for L4063 and L4064, for every condition. Supernatants were analyzed on a CEDEX Bio-analyzer for concentrations of glucose, lactate, glutamine, GlutaMax™, and ammonia.

Defined media has a higher glucose concentration of 4.5 g/L compared to complete media (2 g/L). Overall, the concentration and consumption of glucose were comparable for Gen 3.0 and Gen 3.1 processes within each media type.

An increase in lactate was observed and increase in lactate was comparable between the Gen 3.0 and Gen 3.1 conditions and between the two media used for reactivation expansion (complete media and defined media).

In some instances, the standard basal media contained 2 mM L-glutamine and was supplemented with 2 mM GlutaMax™ to compensate for the natural degradation of L-glutamine in culture conditions to L-glutamate and ammonia.

In some instances, defined (serum free) media used did not contain L-glutamine on the basal media, and was supplemented only with GlutaMax™ to a final concentration of 2 mM. GlutaMax™ is a dipeptide of L-alanine and L-glutamine, is more stable than L-glutamine in aqueous solutions and does not spontaneously degrade into glutamate and ammonia. Instead, the dipeptide is gradually dissociated into the individual amino acids, thereby maintaining a lower but sufficient concentration of L-glutamine to sustain robust cell growth.

In some instances, the concentration of glutamine and GlutaMax™ slightly decreased on the scale-up day, but at harvest day showed an increase to similar or closer levels compared to reactivation day. For L4064, glutamine and GlutaMax™ concentration showed a slight degradation in a similar rate between different conditions, during the whole process.

Ammonia concentrations were higher samples grown in standard media containing 2 mM glutamine+2 mM GlutaMax™) than those grown in defined media containing 2 mM GlutaMax™). Further, as expected, there was a gradual increase or accumulation of ammonia over the course of the culture. There were no differences in ammonia concentrations across the three different test conditions.

Telomere repeats by Flow—FISH. Flow-FISH technology was used to measure the average length of the telomere repeat on L4063 and L4064 under Gen 3 and Gen 3.1 processes. The determination of a relative telomere length (RTL) was calculated using Telomere PNA kit/FITC for flow cytometry analysis from DAKO. Telomere assay was performed. Telomere length in samples were compared to a control cell line (1301 leukemia). The control cell line is a tetraploid cell line having long stable telomeres that allows calculation of a relative telomere length. Gen 3 and Gen 3.1 processes assessed in both tumors showed comparable telomere length.

TCR Vβ repertoire Analysis

To determine the clonal diversity of the cell products generated in each process, TIL final products were assayed for clonal diversity analysis through sequencing of the CDR3 portion of the T-cell receptors.

Three parameters were compared between the three conditions:

- Diversity index of Unique CDR3 (uCDR3)
- % shared uCDR3
- For the top 80% of uCDR3:
  - Compare the % shared uCDR3 copies
  - Compare the frequency of unique clonotypes Control and Gen 3.1 Test, percentage shared unique CDR3 sequences on TIL harvested cell product for: 975 sequences are shared between Gen 3 and Gen 3.1 Test final product, equivalent to 88% of top 80% of unique CDR3 sequences from Gen 3 shared with Gen 3.1.

Control and Gen 3.1 Test, percentage shared unique CDR3 sequences on TIL harvested cell product for: 2163 sequences are shared between Gen 3 and Gen 3.1 Test final product, equivalent to 87% of top 80% of unique CDR3 sequences from Gen 3 shared with Gen 3.1.

The number of unique CD3 sequences identified from $1\times10^6$ cells collected on Harvest day 16, for the different processes. Gen 3.1 Test condition showed a slightly higher clonal diversity compared to Gen 3.0 based on the number of unique peptide CDRs within the sample.

The Shannon entropy diversity index is a reliable and common metric for comparison, because Gen 3.1 conditions on both tumors showed slightly higher diversity than Gen 3 process, suggesting that TCR Vβ repertoire for Gen 3.1 Test condition was more polyclonal than the Gen 3.0 process.

Additionally, the TCR Vβ repertoire for Gen 3.1 Test condition showed more than 87% overlap with the corresponding repertoire for Gen 3.0 process on both tumor L4063 and L4064.

The value of IL-2 concentration on spent media for Gen 3.1 Test L4064 on reactivation day was below to the expected value (similar to Gen 3.1 control and Gen 3.0 condition).

The low value could be due to a pipetting error, but because of the minimal sample taken it was not possible to repeat the assay.

Conclusions. Gen 3.1 test condition including feeders and OKT-3 on Day 0 showed a higher TVC of cell doses at Harvest day 16 compared to Gen 3.0 and Gen 3.1 control. TVC on the final product for Gen 3.1 test condition was around 2.5 times higher than Gen 3.0.

Gen 3.1 test condition with the addition of OKT-3 and feeders on day 0, for both tumor samples tested, reached a maximum capacity of the flask at harvest. Under these conditions, if a maximum of 4 flasks on day 0 is initiated, the final cell dose could be between $80\text{-}100\times10^9$ TILs.

All the quality attributes such as phenotypic characterization including purity, exhaustion, activation and memory markers on final TIL product were maintained between Gen 3.1 Test and Gen 3.0 process.

IFN-γ production on final TIL product was 3 times higher on Gen 3.1 with feeder and OKT-3 addition on day 0, compared to Gen 3.0 in the two tumors analyzed, suggesting Gen 3.1 process generated a potent TIL product.

No differences observed in glucose or lactate levels across test conditions. No differences observed on glutamine and ammonia between Gen 3.0 and Gen 3.1 processes across media conditions. The low levels of glutamine on the media are not limiting cell growth and suggest the addition of GlutaMax™ only in media is sufficient to give the nutrients needed to make cells proliferate.

The scale up on day 11 and day 10 respectively and did not show major differences in terms of cell number reached on the harvest day of the process and metabolite consumption was comparable in both cases during the whole process. This observation suggests of Gen 3.0 optimized process can have flexibility on processing days, thereby facilitating flexibility in the manufacturing schedule.

Gen 3.1 process with feeder and OKT-3 addition on day 0 showed a higher clonal diversity measured by CDR3 TCRab sequence analysis compared to Gen 3.0.

FIG. 32 describes an embodiment of the Gen 3 process (Gen 3 Optimized process). Standard media and CTS Optimizer serum free media can be used for Gen 3 Optimized process TIL expansion. In case of CTS Optimizer serum free media is recommended to increase the GlutaMax™ on the media to final concentration 4 mM.

Example 12: An Exemplary Embodiment of Selecting and Expanding PBLs from PBMCs in CLL Patients PBMCs are collected from patients and either frozen for later use, or used fresh. Enough volume of peripheral blood is collected to yield at least about 400,000,000 ($400\times10^6$) PBMCs for starting material in the method of the present invention. On Day 0 of the method, IL-2 at $6\times10^6$ IU/mL is either prepared fresh or thawed, and stored at 4° C. or on ice until ready to use. 200 mL of CM2 medium is prepared by combining 100 mL of CM1 medium (containing GlutaMAX®), then diluting it with 100 mL (1:1) with AIM-V to make CM2. The CM2 is protected from light, and sealed tightly when not in use.

All of the following steps are performed under sterile cell culture conditions. An aliquot of CM2 is warmed in a 50 mL conical tube in a 37° C. water bath for use in thawing and/or washing a frozen PBMC sample. If a frozen PBMC sample is used, the sample is removed from freezer storage and kept on dry ice until ready to thaw. When ready to thaw the PBMC cryovial, 5 mL of CM2 medium is placed in a sterile 50 mL conical tube. The PBMC sample cryovial is placed in a 37° C. water bath until only a few ice crystals remain. Warmed CM2 medium is added, dropwise, to the sample vial in a 1:1 volume ratio of sample:medium (about 1 mL). The entire contents is removed from the cryovial and transferred to the remaining CM2 medium in the 50 mL conical tube. An additional 1-2 mL of CM2 medium is used to rinse the cryovial and the entire contents of the cryovial is removed and transferred to the 50 mL conical tube. The volume in the conical tube is then adjusted with additional CM2 medium to 15 mL, and swirled gently to rinse the cells. The conical tube is then centrifuged at 400g for 5 minutes at room temperature in order to collect the cell pellet.

The supernatant is removed from the pellet, the conical tube is capped, and then the cell pellet is disrupted by, for example, scraping the tube along a rough surface. About 1 mL of CM2 medium is added to the cell pellet, and the pellet and medium are aspirated up and down 5-10 times with a pipette to break up the cell pellet. An additional 3-5 mL of CM2 medium is added to the tube and mixed via pipette to suspend the cells. At this point, the volume of the cell suspension is recorded. Remove 100 μL of the cell suspension from the tube for cell counting with an automatic cell counter, for example, a Nexcelom Cellometer K2. Determine the number of live cells in the sample and record.

Reserve a minimum of $5\times10^6$ cells for phenotyping and other characterization experiments. Spin the reserved cells at 400g for 5 minutes at room temperature to collect the cell pellet. Resuspend the cell pellet in freezing medium (sterile, heat-inactivated FBS containing 20% DMSO). Freeze one or two aliquots of the reserved cells in freezing medium, and slow-freeze the aliquots in a cell freezer (Mr. Frosty) in a −80° C. freezer. Transfer to liquid nitrogen storage after a minimum of 24 hours at −80° C.

For the following steps, use pre-cooled solutions, work quickly, and keep the cells cold. The next step is to purify the T-cell fraction of the PBMC sample. This is completed using a Pan T-cell Isolation Kit (Miltenyi, catalog #130-096-535). Prepare the cells for purification by washing the cells with a sterile-filtered wash buffer containing PBS, 0.5% BSA, and 2 mM EDTA at pH 7.2. The PBMC sample is centrifuged at 400g for 5 minutes to collect the cell pellet. The supernatant is aspirated off and the cell pellet is resuspended in 40 μL of wash buffer for every $10^7$ cells. Add 10 μL of Pan T Cell Biotin-Antibody Cocktail for every $10^7$ cells. Mix well and incubate for 5 minutes in refrigerator or on ice. Add 30 μL of wash buffer for every $10^7$ cells. Add 20 μL of Pan T-cell MicroBead Cocktail for every $10^7$ cells. Mix well and incubate for 10 minutes in refrigerator or on ice. Prepare an LS column and magnetically separate cells from the microbeads. The LS column is placed in the QuadroMACS magnetic field. The LS column is washed with 3 mL of cold wash buffer, and the wash is collected and discarded. The cell suspension is applied to the column and the flow-through (unlabeled cells) is collected. This flow-through is the enriched T-cell fraction (PBLs). Wash the column with 3 mL of wash buffer and collect the flow-through in the same tube as the initial flow-through. Cap the tube and place on ice. This is the T-cell fraction, or PBLs. Remove the LS column from the magnetic field, wash the column with 5 mL of wash buffer, and collect the non-T-cell fraction (magnetically labeled cells) into another tube. Centrifuge both fractions at 400g for 5 minutes to collect the cell pellets. Supernatants are aspirated from both samples, disrupt the pellet, and resuspend the cells in 1 mL of CM2 medium supplemented with 3000 IU/mL IL-2 to each pellet, and pipette up and down 5-10 times to break up the pellets. Add 1-2 mL of CM2 to each sample, and mix each sample well, and store in tissue culture incubator for next steps. Remove about a 50 μL aliquot from each sample, count cells, and record count and viability.

The T-cells (PBLs) are then cultured with Dunabeads™ Human T-Expander CD3/CD28. A stock vial of Dynabeads is vortexed for 30 seconds at medium spead. A required aliquot of beads is removed from the stock vial into a sterile 1.5 mL microtube. The beads are washed with bead wash solution by adding 1 mL of bead wash to the 1.5 mL microtube containing the beads. Mix gently. Place the tube onto the DynaMag™-2 magnet and let sit for 30 minutes while beads draw toward the magnet. Aspirate the wash solution off the beads and remove tube from the magnet. 1 mL of CM2 medium supplemented with 3000 IU/mL IL-2 is added to the beads. The entire contents of the microtube is transferred to a 15 or 50 mL conical tube. Bring the beads to a final concentration of about 500,000/mL using CM2 medium with IL-2.

The T-cells (PBLs) and beads are cultured together as follows. On day 0: In a G-Rex-REX 24 well plate, in a total of 7 mL per well, add 500,000 T-cells, 500,000 CD3/CD28 Dynabeads, and CM2 supplemented with IL-2. The G-Rex-REX plate is placed into a humidified 37° C., 5% $CO_2$ incubator until the next step in the process (on Day 4). Remaining cells are frozen in CS10 cryopreservation medium using a Mr. Frosty cell freezer. The non-T-cell fraction of cells are frozen in CS10 cryopreservation medium using a Mr. Frosty cell freezer. On day 4, medium is exchanged. Half of the medium (about 3.5 mL) is removed from each well of the G-rex plate. A sufficient volume (about 3.5 mL) of CM4 medium supplemented with 3000 IU/mL IL-2 warmed to 37° C. is added to replace the medium removed from each sample well. The G-rex plate is returned to the incubator.

On day 7, cells are prepared for expansion by REP. The G-rex plate is removed from the incubator and half of medium is removed from each well and discarded. The cells are resuspended in the remaining medium and transferred to a 15 mL conical tube. The wells are washed with 1 mL each of CM4 supplemented with 3000 IU/mL IL-2 warmed to 37° C. and the wash medium is transferred to the same 15 mL tube with the cells. A representative sample of cells is removed and counted using an automated cell counter. If there are less than $1\times10^6$ live cells, the Dynabead expansion process at Day 0 is repeated. The remainder of the cells are frozen for back-up expansion or for phenotyping and other characterization studies. If there are $1\times10^6$ live cells or more, the REP expansion is set up in replicate according to the protocol from Day 0. Alternatively, with enough cells, the expansion may be set up in a G-rex TOM culture flask using $10\text{-}15\times10^6$ PBLs per flask and a 1:1 ratio of Dynabeads: PBLs in a final volume of 100 mL/well of CM4 medium supplemented with 3000 IU/mL IL-2. The plate and/or flask is returned to the incubator. Excess PBLs may be aliquotted and slow-frozen in a Mr. Frosty cell freezer in a −80° C. freezer, and the transferred to liquid nitrogen storage after a minimum of 24 hours at −80° C. These PBLs may be used as back-up samples for expansion or for phenotyping or other characterization studies.

On Day 11, the medium is exchanged. Half of the medium is removed from either each well of the G-rex plate or the flask and replaced with the same amount of fresh CM4 medium supplemented with 3000 IU/mL IL-2 at 37° C.

On Day 14, the PBLs are harvested. If the G-rex plate is used, about half of the medium is removed from each well of the plate and discarded. The PBLs and beads are suspended in the remaining medium and transferred to a sterile 15 mL conical tube (Tube 1). The wells are washed with 1-2 mL of fresh AIM-V medium warmed to 37° C., and the wash is transferred to Tube 1. Tube 1 is capped and placed in the DynaMag™-15 Magnet for 1 minute to allow the beads to be drawn to the magnet. The cell suspension is transferred into a new 15 mL tube (Tube 2), and the beads are washed with 2 mL of fresh AIM-V at 37° C. Tube 1 is placed back in the magnet for an additional 1 minute, and the wash medium is then transferred to Tube 2. The wells may be combined if desired, after the final washing step. Remove a representative sample of cells and count, record count and viability. Tubes may be placed in the incubator while counting. Additional AIM-V medium may be added to the Tube 2 if cells appear very dense. If a flask is used, the volume in the flask should be reduced to about 10 mL. The contents of the flask is mixed and transferred to a 15 mL conical tube (Tube A). The flask is washed with 2 mL of the AIM-V medium as described above and the wash medium is also transferred to Tube A. Tube A is capped and placed in the DynaMag™-15 Magnet for 1 minute to allow the beads to be drawn to the magnet. The cell suspension is transferred into a new 15 mL tube (Tube B), and the beads are washed with 2 mL of fresh AIM-V at 37° C. Tube A is placed back in the magnet for an additional 1 minute, and the wash medium is then transferred to Tube B. The wells may be combined if desired, after the final washing step. Remove a representative sample of cells and count, record count and viability. Tubes may be placed in the incubator while counting. Additional AIM-V medium may be added to the Tube B if cells appear very dense. Cells may be used fresh or frozen in CS10 preservation medium at desired concentrations.

Example 13: A Phase 2, Multicenter Study of Autologous Tumor Infiltrating Lymphocytes in Patients with Solid Tumors Study Design Overview This example describes a prospective, open-label, multi-cohort, non-randomized, multicenter Phase 2 study evaluating ACT using TIL in combination with pembrolizumab or TIL as a single therapy, using TILs prepared as described in the present application as well as in this example.

Objectives:

Primary:

To evaluate the efficacy of autologous TIL in combination with pembrolizumab in MM, HNSCC, or NSCLC patients or TIL as a single therapy in relapsed or refractory (r/r) NSCLC patients, who had previously progressed on or after treatment with CPIs, as determined by objective response rate (ORR), using the Response Evaluation Criteria in Solid Tumors (RECIST 1.1), as assessed by Investigator.

To characterize the safety profile of TIL in combination with pembrolizumab in MM, HNSCC, and NSCLC patients or TIL as a single therapy in r/r NSCLC patients as measured by the incidence of Grade >3 treatment-emergent adverse events (TEAEs).

Secondary:

To further evaluate the efficacy of autologous TIL in combination with pembrolizumab in MM, HNSCC, and NSCLC patients or TIL as a single therapy in r/r NSCLC patients using complete response (CR) rate, duration of response (DOR), disease control rate (DCR), progression-free survival (PFS) using RECIST 1.1, as assessed by Investigator, and overall survival (OS).

Cohorts:

Cohort TA: TIL therapy in combination with pembrolizumab in patients with Stage IIIC or Stage IV unresectable or MM with <3 prior lines of systemic therapy excluding immunotherapy. If previously treated, patients must have had radiographically documented progression on or after most recent therapy.

Cohort 2A: TIL therapy in combination with pembrolizumab in patients with advanced, recurrent or metastatic HNSCC (e.g., Stages T1N1-N2B, T2-4N0-N2b) with <3 prior lines of systemic therapy, excluding immunotherapy. If previously treated, patients must have had radiographically documented progression on or after most recent therapy.

Cohort 3A: TIL therapy in combination with pembrolizumab in patients with locally advanced or metastatic (Stage III-IV) NSCLC with <3 prior lines of systemic therapy, excluding immunotherapy. If previously treated, patients must have had radiographically documented progression on or after most recent therapy.

Cohort 3B: TIL therapy as a single agent in patients Stage III or Stage IV NSCLC who have previously received systemic therapy with CPIs (e.g., anti-PD-1/anti-PD-L1) as part of 5 3 prior lines of systemic therapy. If previously treated, patients must have had radiographically documented progression on or after most recent therapy.

Patients in Cohorts 3A and 3B (NSCLC) with oncogene-driven tumors with available effective targeted therapy must have received at least one line of targeted therapy.

All patients received autologous cryopreserved TIL therapy (with or without pembrolizumab, depending on cohort assignment), preceded by a nonmyeloablative lymphodepletion (NMA-LD) preconditioning regimen consisting of cyclophosphamide and fludarabine. Following TIL infusion, up to 6 IV interleukin-2 (IL-2) doses maximum were administered.

The following general study periods took place in all 4 cohorts, unless specified otherwise.

Screening and Tumor Resection: Up to 4 weeks (28 days) from study entry; manufacturing of the TIL Product: approximately <22 days from tumor resection; and treatment period, as discussed below.

Treatment Period (Cohorts 1A, 2A, and 3A): up to 2 years, including NMA-LD (7 days), TIL infusion (1 day) followed by IL-2 administrations (1 to 4 days).Patients receive a single infusion of pembrolizumab after the completion of their tumor resection for TIL production and baseline scans but before the initiation of the NMA-LD regimen. The next dose of pembrolizumab will be no earlier than following the completion of IL-2 and continue Q3W ±3 days thereafter for <2 years (24 months) or until disease progression or unacceptable toxicity, whichever occurs first. The end-of-treatment (EOT) visit occurred within 30 days after the last dose of pembrolizumab. The visit could be combined with end-of-assessment (EOA) visit if applicable (e.g., pembrolizumab discontinuation occurred at disease progression or at the start of new anticancer therapy).

Treatment Period (Cohort 3B): up to 12 days, including NMA-LD (7 days), TIL, infusion (1 day) followed by IL-2 administrations (1 to 4 days). The EOT visit occurred once a patient received the last dose of IL-2. The EOT visit was performed within 30 days after treatment discontinuation and it may be combined with any scheduled visit occurring within this interval during the assessment period.

Assessment Period: began after TIL infusion on Day 0 and ends upon disease progression, with the start of a new anticancer therapy, partial withdrawal of consent to study assessments, or 5 years (Month 60), whichever occurred first. An end-of-assessment (EOA) visit occurred once a patient reached disease progression or started a new anti-cancer therapy.

The TIL autologous therapy with the TILs prepared as described herein was comprised of the following steps:

1. Tumor resection to provide the autologous tissue that serves as the source of the TIL cellular product;
2. TIL product produced at a central Good Manufacturing Practice (GMP) facility;
3. A 7-day NMA-LD preconditioning regimen;
4. Cohorts 1A, 2A, and 3A: Patients receive a single infusion of pembrolizumab after the completion of their tumor resection for TIL production and baseline scans but before the initiation of NMA-LD regimen. The next dose of pembrolizumab will be no earlier than following the completion of IL-2 and continue Q3W ±3 days thereafter.
5. Infusion of the autologous TIL product (Day 0); and
6. IV IL-2 administrations for up to 6 doses maximum.

In Cohorts TA, 2A, and 3A, the next dose of pembrolizumab was no earlier than following the completion of IL-2 and continue Q3W ±3 days thereafter for <2 years (24 months), or until disease progression or unacceptable toxicity, whichever occurred first.

Figure 7:
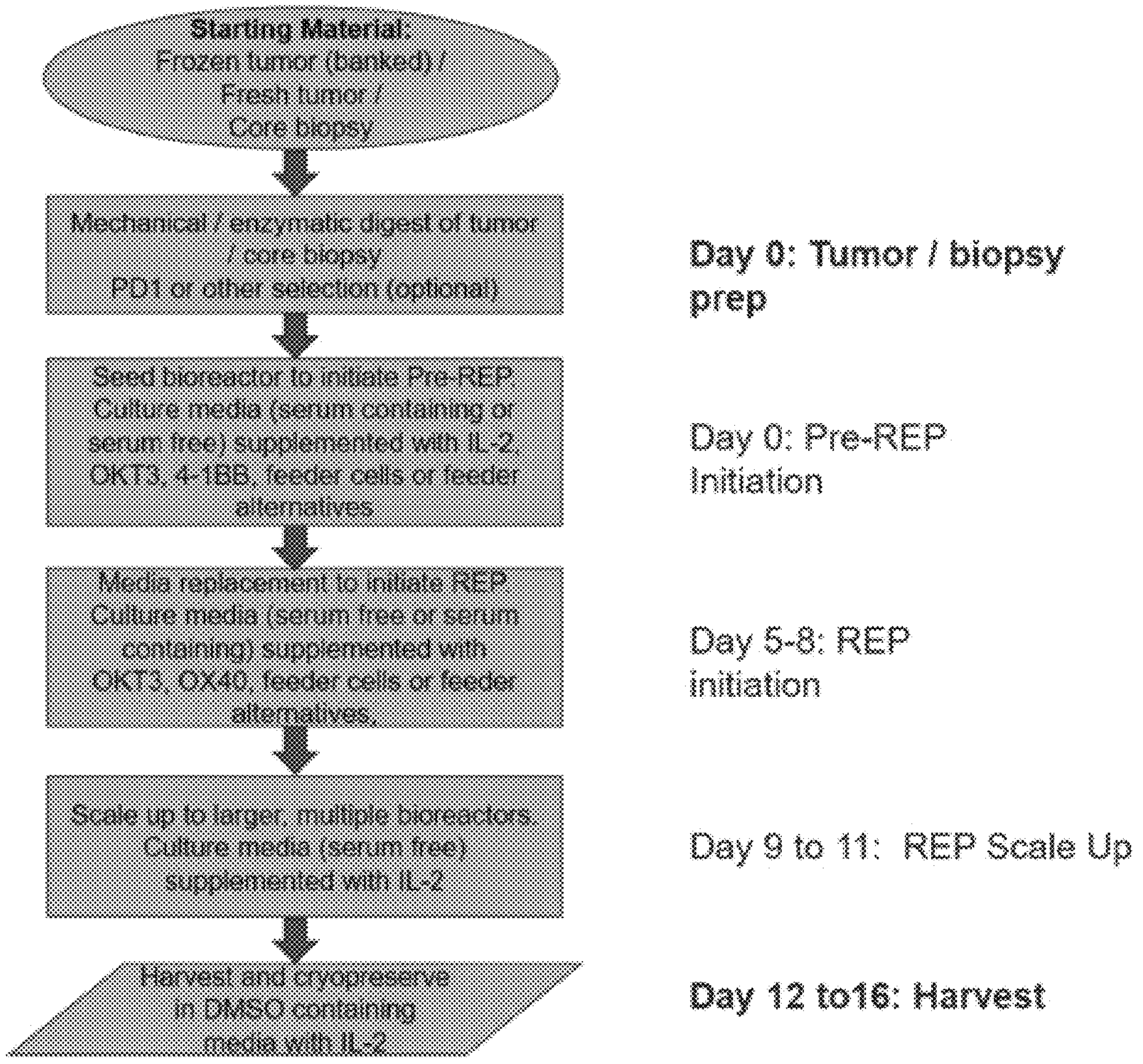
FIG. 7: Exemplary Gen 3 type process for NSCLC tumors.

Flowcharts for Cohorts TA, 2A, and 3A can be found in FIG. 7. The Flowchart for Cohort 3B can be found in FIG. 8. Patients were assigned to the appropriate cohort by tumor indication.

TIL Therapy+Pembrolizumab (Cohorts 1A, 2A, and 3A)

Patients were screened and scheduled for surgery for tumor resection. Patients then had one or more tumor lesions resected, which were sent to a central manufacturing facility for TIL production.

Next, the NMA-LD regimen was imitated and consisted of 2 days of IV cyclophosphamide (60 mg/kg) with mesna (per site standard of care or USPI/SmPC) on Days −7 and Day −6 followed by 5 days of IV fludarabine (25 mg/m$^2$: Day −5 through Day −1).

Patients in Cohorts TA, 2A, and 3A received a single infusion of pembrolizumab after the completion of their tumor resection for TIL production and baseline scans and before the initiation of NMA-LD regimen. IL-2 administrations at a dose of 600,000 IU/kg IV begun as soon as 3 hours after, but no later than 24 hours after, completion of the TIL infusion on Day 0. Additional IL-2 administrations will be given approximately every 8 to 12 hours for up to 6 doses maximum. The second dose of pembrolizumab was no earlier than following the completion of IL-2. Patients should have recovered from all IL-2-related toxicities (Grade ≤2), prior to the second pembrolizumab administration. Pembrolizumab will continue Q3W 3 days thereafter for ≤2 years (24 months) or until disease progression or unacceptable toxicity, whichever occurred first.

TIL Therapy as a Single Agent (Cohort 3B)

Patients were screened and scheduled for surgery for tumor resection. Patients then had one or more tumor lesions resected, which were sent to a central manufacturing facility for TIL production.

Next, the NMA-LD regimen consisted of 2 days of IV cyclophosphamide (60 mg/kg) with mesna (per site standard of care or USPI/SmPC) on Day −7 and Day −6 followed by 5 days of IV fludarabine (25 mg/m$^2$: Day −5 through Day −1).

Infusion of the tumor-derived autologous TIL product occurred no sooner than 24 hours after last dose of fludarabine. IL-2 administrations at a dose of 600,000 IU/kg IV may have begun as soon as 3 hours after, but no later than 24 hours after, completion of the TIL infusion.

Additional IL-2 administrations were given approximately every 8 to 12 hours for up to 6 doses maximum.

Production and Expansion of Tumor Infiltrating Lymphocytes

Figure 9:
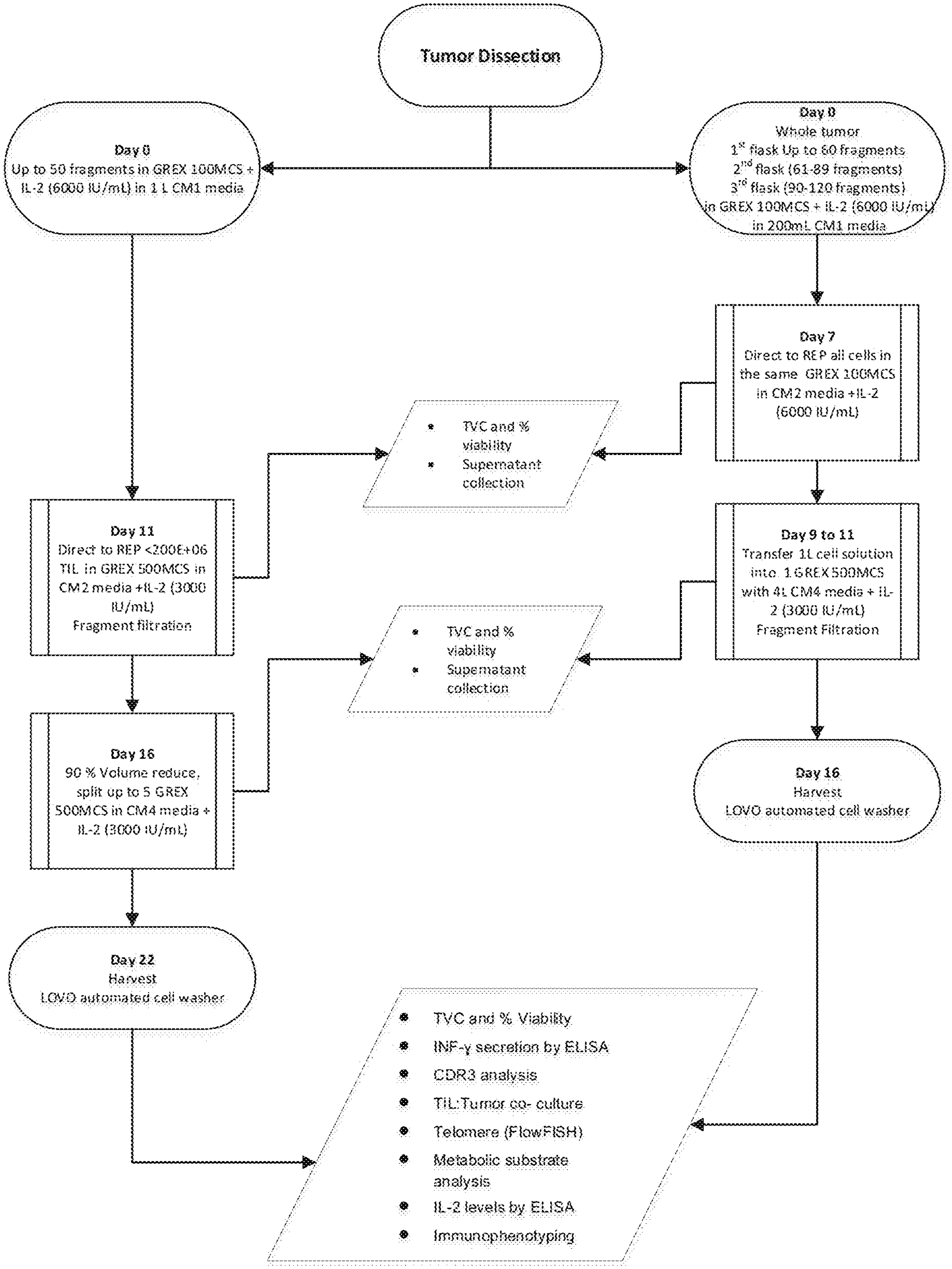
FIG. 9: Provides an experimental flow chart for comparability between Gen 2 (Gen 2) versus Gen 3.
Figure 10:
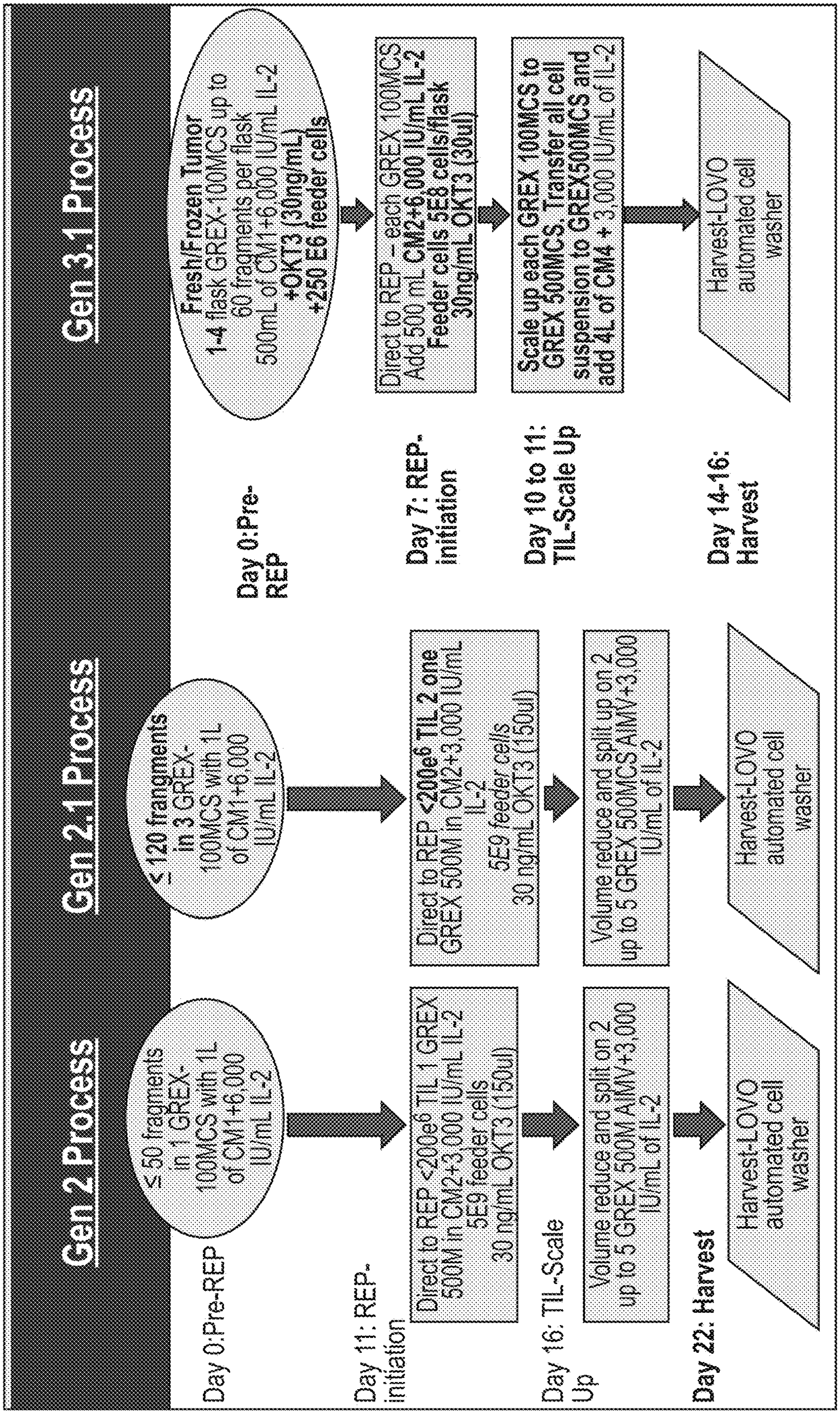
FIG. 10: Shows a comparison between various Gen 2 (2A process) and the Gen 3.1 process embodiment.
Figure 16:
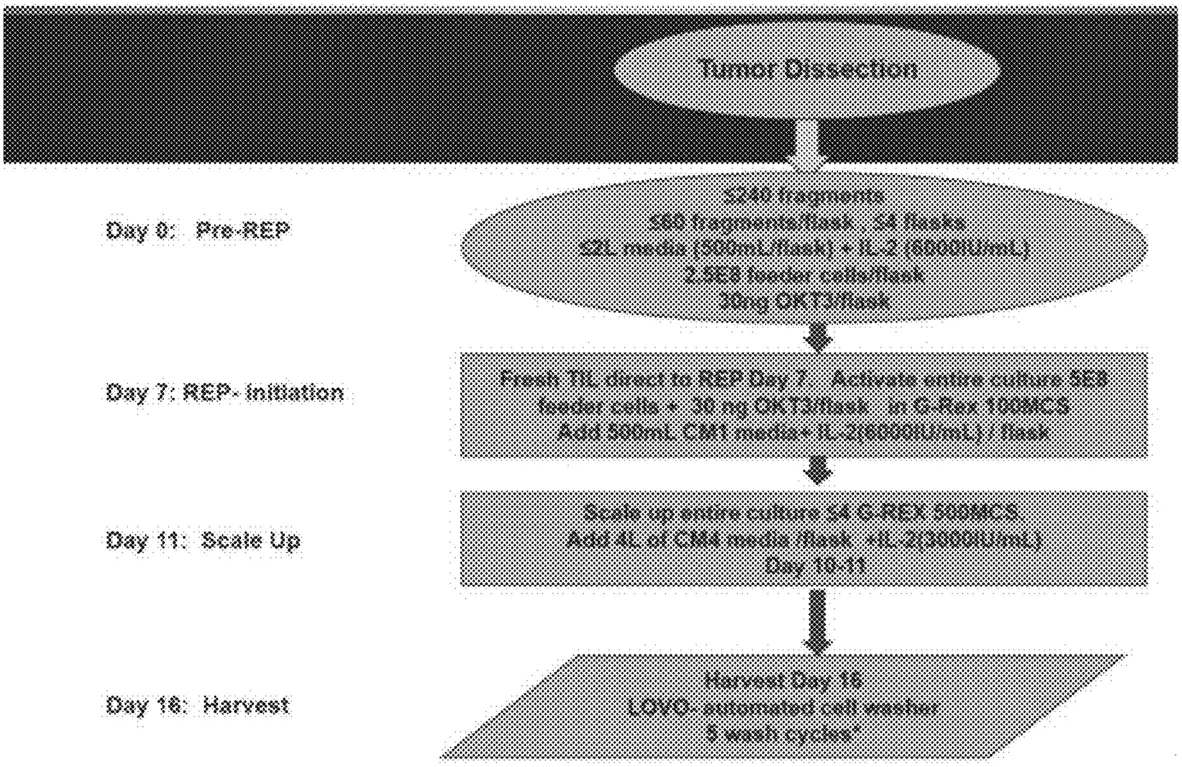
FIG. 16: Schematic of an exemplary embodiment of the Gen 3 process (a 16-day process).
Figure 17:
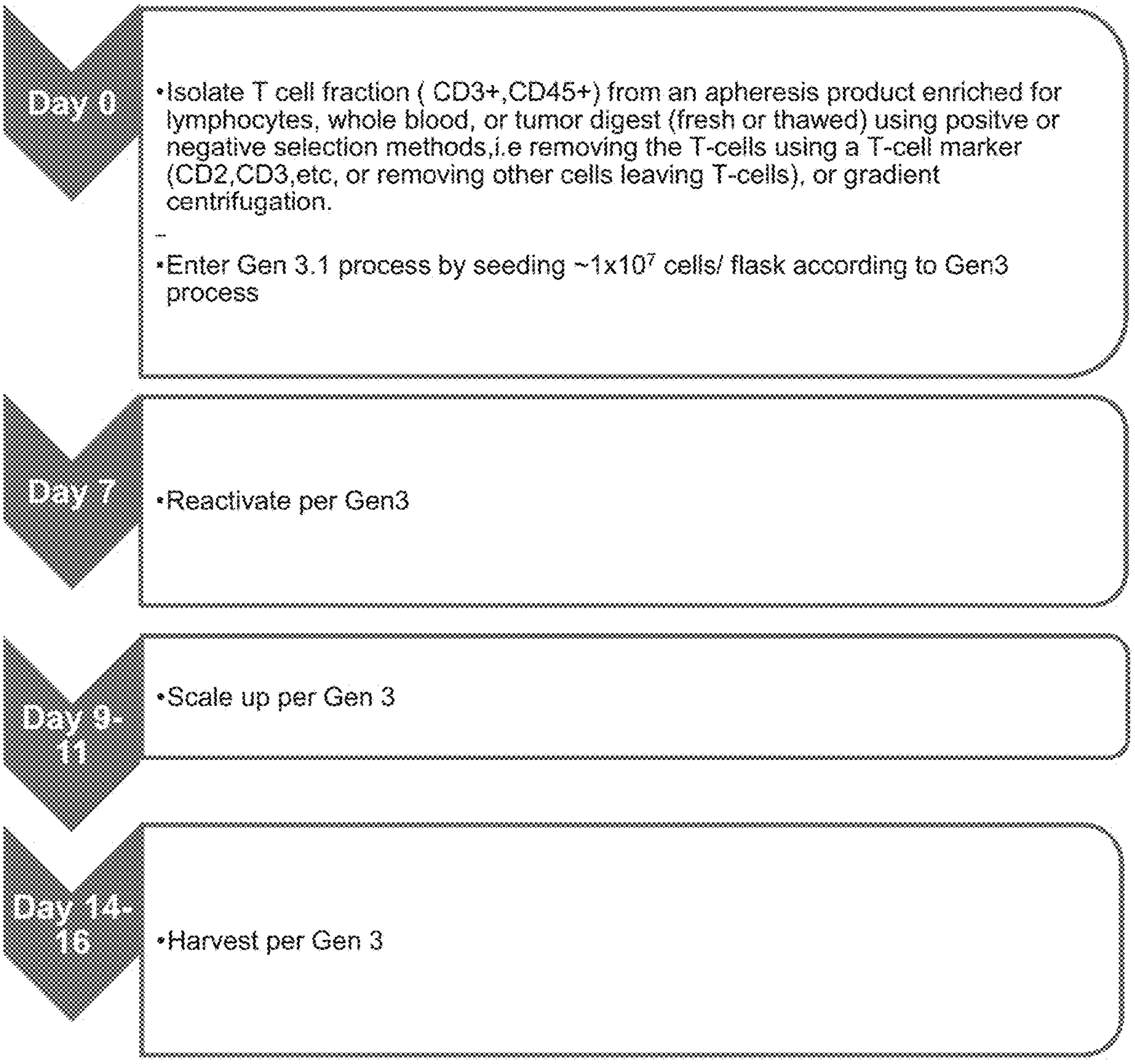
FIG. 17: Schematic of an exemplary embodiment of a method for expanding T cells from hematopoietic malignancies using Gen 3 expansion platform.

The TIL autologous cellular product was composed of viable cytotoxic T lymphocytes derived from a patient's tumor/lesion, which are manufactured ex vivo at a central GMP facility. An exemplary flow diagram depicting the TIL production process is provided in FIG. 9, for example.

The TIL manufacturing process begun at the clinical site after surgical excision of a primary or secondary metastatic tumor lesion(s) of>1.5 cm in diameter in each individual patient. Multiple tumor lesions from various anatomical locations can be excised to compile a total aggregate of tumor tissue; however, the aggregate should not exceed 4.0 cm in diameter, or 10 g in weight, due to the limited quantity of the biopreservation media present in the transport bottle.

Once the tumor lesion(s) was placed in the biopreservation transport bottle, it is shipped at 2° C. to 8° C. using an express courier to a central GMP manufacturing facility. Upon arrival, the tumor specimen(s) were dissected into fragments, which were then cultured in a pre-rapid expansion protocol (Pre-REP) with human recombinant IL-2 for ~−11 days.

These pre-REP cells were then further expanded using a rapid expansion protocol (REP) for 11 days in the presence of IL-2, OKT3 (a murine monoclonal antibody to human CD3, also known as [muromonab-CD3]) and irradiated allogenic peripheral blood mononuclear cells (PBMC) as feeder cells.

The expanded cells were then harvested, washed, formulated, cryopreserved, and shipped to the clinical site via an express courier. The dosage form of the TIL cellular product was a cryopreserved autologous "live-cell suspension" that was ready for infusion into the patient from whom the TIL were derived. Patients were to receive the full dose of product that was manufactured and released, which contained between $1\times10^9$ and $150\times10^9$ viable cells per the product specification. Clinical experience indicated that objective tumor responses were achieved across this dose range, which has also been shown to be safe (Radvanyi L.G., et al., *Clin Cancer Res.* 2012; 18(24):6758-70). The full dose of product was provided in up to four infusion bags.

Preparation of Patients to Receive the TIL Cellular Product

The NMA-LD preconditioning regimen used in this study (i.e., 2 days of cyclophosphamide plus mesna, followed by 5 days of fludarabine) was based on the method developed and tested by the National Cancer Institute (Rosenberg S.A., et al., *Clin Cancer Res.* 2011; 17(13):4550-7; Radvanyi L.G., et al., *Clin Cancer Res.* 2012; 18(24):6758-70; Dudley M.E., et al., *J Clin Oncol.* 2008; 26(32):5233-9; Pilon-Thomas S, et al., *J Immunother.* 2012; 35(8):615-20; Dudley M.E., et al., *J Clin Oncol.* 2005; 23(10):2346-57; and Dudley M.E., et al., *Science.* 2002; 298(5594):850-4). Following the 7-day preconditioning regimen, the patient was infused with the TIL cellular product.

The TIL infusion was followed by the administration of IV IL-2 (600,000 IU/kg) every 8 to 12 hours, with the first dose administered between 3 and 24 hours after the completion of the TIL infusion and continuing for up to 6 doses maximum. Per institutional standards, the doses of IL-2 can be calculated on the basis of actual weight.

Selection of Patient Populations

Cohort 1A:

Patients had a confirmed diagnosis of unresectable MM (Stage IIIC or Stage IV, histologically confirmed as per American Joint Committee on Cancer [AJCC] staging system). Ocular melanoma patients were excluded. Patients must not have received prior immuno-oncology targeted agents. If BRAF-mutation positive, patient could have received prior BRAF/MEKtargeted therapy.

Cohort 2A:

Patients had advanced, recurrent and/or metastatic HNSCC and can be treatment naive; histologic diagnosis of the primary tumor is required via the pathology report. Patients must not have received prior immunotherapy regimens.

Cohort 3A:

Patients had a confirmed diagnosis of Stage III or Stage IV NSCLC (squamous, adenocarcinoma, large cell carcinoma). Patients with oncogene-driven tumors with available effective targeted therapy had received at least one line of targeted therapy.

Cohort 3B:

Patients had a confirmed diagnosis of Stage III or Stage IV NSCLC (squamous, adenocarcinoma, large cell carcinoma) and had previously received systemic therapy with CPIs (e.g., anti-PD-1/anti-PD-L1). Patients with oncogene-driven tumors with available effective targeted therapy had received at least one line of targeted therapy.

All patients had received up to 3 prior systemic anticancer therapies (see, inclusion criteria below), excluding immunotherapy for Cohorts 1A, 2A, and 3A. If previously treated, patients had radiographically confirmed progression on or after most recent therapy.

Inclusion Criteria

Patients must have met ALL of the following inclusion criteria for participation in the study:

1. All patients had a histologically or pathologically confirmed diagnosis of malignancy of their respective histologies:
   - Unresectable or metastatic melanoma (Cohort 1A)
   - Advanced, recurrent or metastatic squamous cell carcinoma of the head and neck (Cohort 2A)
   - Stage III or Stage IV NSCLC (squamous, nonsquamous, adenocarcinoma, large cell carcinoma) (Cohorts 3A and 3B).
2. Cohorts 1A, 2A, and 3A only: Patients were immunotherapy naive. If previously treated, patients had progressed on or after most recent therapy. Cohorts 1A, 2A, and 3A may have received up to 3 prior systemic anticancer therapies, specifically:
   - In Cohort 1A: Patients with unresectable or metastatic melanoma (Stage IIIC or Stage IV); if BRAF mutation-positive, patients could have received a BRAF inhibitor.
   - In Cohort 2A: Patients with unresectable or metastatic HNSCC. Those who had received initial chemoradiotherapy were allowed.
   - In Cohort 3A: Patients with Stage III or Stage IV NSCLC (squamous, nonsquamous, adenocarcinoma, or large cell carcinoma) and who were immunotherapy naive and progressed after <3 lines of prior systemic therapy in the locally advanced or metastatic setting. Patients who received systemic therapy in the adjuvant or neoadjuvant setting, or as part of definitive chemoradiotherapy, were eligible and were considered to have had one line of therapy if the disease has progressed within 12 months of completion of prior systemic therapy. Patients with known oncogene drivers (e.g., EGFR, ALK, ROS) who had mutations that were sensitive to targeted therapies must had progressed after at least 1 line of targeted therapy.
3. Cohort 3B only: Patients with Stage III or Stage IV NSCLC (squamous, nonsquamous, adenocarcinoma, or large cell carcinoma) who had previously received systemic therapy with CPIs (e.g., anti-PD-1/anti-PD-L1) as part of <3 prior lines of systemic therapy.
   - Patients had radiographically confirmed progression on or after most recent therapy.
   - Patients who received systemic therapy in the adjuvant or neoadjuvant setting, or as part of definitive chemoradiotherapy, were eligible and were considered to have had 1 line of therapy if the disease had progressed within 12 months of completion of prior systemic therapy.
   - Patients with known oncogene drivers (e.g., EGFR, ALK, ROS) who had mutations that are sensitive to targeted therapies must have progressed after at least 1 line of targeted therapy.
4. Patients had at least 1 resectable lesion (or aggregate lesions) of a minimum 1.5 cm in diameter post-resection for TIL investigational product production. It was encouraged that tumor tissue be obtained from multiple and diverse metastatic lesions, as long as the surgical resection did not pose additional risks to the patient.
   - If the lesion considered for resection for TIL generation is within a previously irradiated field, the lesion must have demonstrated radiographic progression prior to resection.
   - Patients must have an adequate histopathology specimen for protocol-required testing.
5. Patients had remaining measurable disease as defined by the standard and well known RECIST 1.1 guidelines (see, for example, Eisenhauer, *European Journal of Cancer* 45:228-247 (2009), also available on the World Wide Web at project.eortc.org/recist/wp-content/uploads/sites/4/2015/03/RECISTGuidelines.pdf) following tumor resection for TIL manufacturing:
   - Lesions in previously irradiated areas were not be selected as target lesions unless there had been demonstrated progression of disease in those lesions;
   - Lesions that were partially resected for TIL generation that were still measurable per RECIST may be selected as nontarget lesions but could not serve as a target lesion for response assessment.
6. Patients were ≥18 years at the time of consent.
7. Patients had an Eastern Cooperative Oncology Group (ECOG) performance status of 0 or 1, and an estimated life expectancy of ≥3 months.
8. Patients of childbearing potential or those with partners of childbearing potential had to be willing to practice an approved method of highly effective birth control during treatment and continue for 12 months after receiving all protocol-related therapy (Note: Females of reproductive potential were to use effective contraception during treatment and for 12 months after their last dose of IL-2, or 4 months after their last dose of pembrolizumab whichever occurred later). Males could not donate sperm during the study or for 12 months after treatment discontinuation, whichever occurred later.
9. Patients had the following hematologic parameters:
   - Absolute neutrophil count (ANC) >1000/mm$^3$;
   - Hemoglobin >9.0 g/dL;
   - Platelet count >100,000/mm$^3$.

10. Patients had adequate organ function:
   Serum alanine aminotransferase (ALT)/serum glutamic-pyruvic transaminase (SGPT) and aspartate aminotransferase (AST)/SGOT <3 times the upper limit of normal (ULN), patients with liver metastasis <5 times ULN.
   An estimated creatinine clearance >40 mL/min using the Cockcroft Gault formula at Screening.
   Total bilirubin 2 mg/dL.
   Patients with Gilbert's Syndrome must have a total bilirubin <3 mg/dL.
11. Patients were seronegative for the human immunodeficiency virus (HIV1 and HIV2). Patients with positive serology for hepatitis B virus surface antigen (HBsAg), hepatitis B core antibody (anti HBc), or hepatitis C virus (anti-HCV) indicating acute or chronic infection were enrolled depending on the viral load based on polymerase chain reaction (PCR) and the local prevalence of certain viral exposures.
12. Patients had a washout period from prior anticancer therapy(ies) of a minimum duration, as detailed below prior to the first study treatment (i.e., start ofNMA-LD or pembrolizumab):
   Targeted therapy: prior targeted therapy with an epidermal growth factor receptor (EGFR), MEK, BRAF, ALK, ROS1 or other-targeted agents (e.g., erlotinib, afatinib, dacomitinib, osimertinib, crizotinib, ceritinib, lorlatinib) was allowed provided the washout is a minimum of 14 days prior to the start of treatment.
   Chemotherapy: adjuvant, neoadjuvant or definitive chemotherapy/chemoradiation was allowed provided the washout is a minimum of 21 days prior to the start of treatment.
   Immunotherapy for Cohort 3B only, prior checkpoint-targeted therapy with an anti-PD-1, other mAbs, or vaccines were allowed with a washout period of >21 days before the start of NMA-LD.
   Palliative radiation therapy: prior external beam radiation was allowed provided all radiation-related toxicities were resolved to Grade 1 or baseline, excluding alopecia, skin pigmentation change, or other clinically insignificant events, e.g., small area radiation dermatitis or rectal or urinary urgency
   The tumor lesion(s) being assessed as target for response via RECIST 1.1 were outside of the radiation portal; however, if within the portal, they must have demonstrated progression (see Inclusion Criterion above).
   Surgery/pre-planned procedure: previous surgical procedure(s) was permitted provided that wound healing had occurred, all complications had resolved, and at least 14 days have elapsed (for major operative procedures) prior to the tumor resection.
13. Patients had recovered from all prior anticancer treatment-related adverse events (TRAEs) to Grade <1 (per Common Terminology Criteria for Adverse Events [CTCAE]), except for alopecia or vitiligo, prior to cohort assignment.
14. Patients with stable Grade >2 toxicity from prior anticancer therapy were considered on a case by case basis after consultation with the Medical Monitor.
15. Cohorts 1A, 2A, and 3A patients with irreversible toxicity not reasonably expected to be exacerbated by treatment with pembrolizumab were included only after consultation with the Medical Monitor. For patients in Cohort 3B only, patients with documented Grade >2 or higher diarrhea or colitis as a result of a previous treatment with immune checkpoint inhibitor CPI(s) must have been asymptomatic for at least 6 months or had a normal by visual assessment colonoscopy post-treatment prior to tumor resection.
16. Patients must have provided written authorization for use and disclosure of protected health information.

Exclusion Criteria

Patients who meet ANY of the following criteria were excluded from the study:

1. Patients with melanoma of uveal/ocular origin
2. Patients who had received an organ allograft or prior cell transfer therapy that included a nonmyeloablative or myeloablative chemotherapy regimen within the past 20 years. (Note: This criterion was applicable for patients undergoing retreatment with TIL, with the exception that they had a prior NMA-LD regimen with their
prior TIL treatment.)
3. Patients with symptomatic and/or untreated brain metastases.
   Patients with definitively-treated brain metastases will be considered for enrollment
after discussion with Medical Monitor; if, prior to the start of treatment the patient is
clinically stable for >2 weeks, there are no new brain lesions via magnetic resonance
imaging (MRI) post-treatment, and the patient does not require ongoing
corticosteroid treatment.
4. Patients who are on a systemic steroid therapy within 21 days of enrollment.
5. Patients who are pregnant or breastfeeding.
6. Patients who had an active medical illness(es), which in the opinion of the Investigator, posed increased risks for study participation; such as systemic infections (e.g., syphilis or any other infection requiring antibiotics), coagulation disorders, or other active major medical illnesses of the cardiovascular, respiratory, or immune systems.
7. Patients may not have active or prior documented autoimmune or inflammatory disorders (including pneumonitis, inflammatory bowel disease [e.g., colitis or Crohn's disease], diverticulitis [with the exception of diverticulosis], systemic lupus erythematosus, sarcoidosis syndrome, or Wegener syndrome [granulomatosis with polyangiitis, Graves' disease, rheumatoid arthritis, hypophysitis, uveitis, etc.]). The following were exceptions to this criterion:
   Patients with vitiligo or alopecia.
   Patients with hypothyroidism (e.g., following Hashimoto syndrome) stable on
   hormone replacement.
   Any chronic skin condition that did not require systemic therapy.
   Patients with celiac disease controlled by diet alone.
8. Patients who had received a live or attenuated vaccination within 28 days prior to the start of treatment.
9. Patients who had any form of primary immunodeficiency (such as severe combined immunodeficiency disease [SCID] and acquired immune deficiency syndrome [AIDS]).
10. Patients with a history of hypersensitivity to any component of the study drugs. TILs were not administered to patients with a known hypersensitivity to any component of TIL product formulation including, but not limited to any of the following:

NMA-LD (cyclophosphamide, mesna, and fludarabine)

Proleukin®, aldesleukin, IL-2

Antibiotics of the aminoglycoside group (i.e., streptomycin, gentamicin [excluding those who are skin-test negative for gentamicin hypersensitivity])

Any component of the TIL product formulation including dimethyl sulfoxide

[DMSO], HSA, IL-2, and dextran-40

Pembrolizumab

11. Patients who had a left ventricular ejection fraction (LVEF)<45% or who are New York Heart Association Class II or higher. A cardiac stress test demonstrating any irreversible wall movement abnormality in any patients >60 years of age or in patients who have a history of ischemic heart disease, chest pain, or clinically significant atrial and/or ventricular arrhythmias.

Patients with an abnormal cardiac stress test could be enrolled if they had adequate ejection fraction and cardiology clearance with approval of the Sponsor's Medical Monitor.

12. Patients who had obstructive or restrictive pulmonary disease and have a documented FEV1 (forced expiratory volume in 1 second) of <60% of predicted normal.

If a patient was not able to perform reliable spirometry due to abnormal upper airway anatomy (i.e., tracheostomy), a 6-minute walk test was used to assess pulmonary function. Patients who were unable to walk a distance of at least 80% predicted for age and sex or demonstrates evidence of hypoxia at any point during the test (SpO2<90%) are excluded.

13. Patients who had another primary malignancy within the previous 3 years (except for those which did not require treatment or had been curatively treated greater than 1 year ago, and in the judgment of the Investigator, did not pose a significant risk of recurrence including, but not limited to, non-melanoma skin cancer, DCIS, LCIS, prostate cancer Gleason score ≤6 or bladder cancer).

14. Participation in another clinical study with an investigational product within 21 days of the initiation of treatment.

Study Endpoints and Planned Analyses

The primary and secondary endpoints were analyzed separately by cohort.

Primary Endpoints:

The ORR was defined as the proportion of patients who achieved either a confirmed PR or CR as best response as assessed by Investigators per RECIST 1.1 among the efficacy analysis set.

Objective response was evaluated per each disease assessment and the ORR was expressed as a binomial proportion with the corresponding 2-sided 90% CI. The primary analysis for each cohort occurred when all treated patients per cohort have an opportunity to be followed for 12 months, unless progressed/expired or discontinued early from the assessment period.

The safety primary endpoint was measured by any Grade 3 or higher TEAE incidence rate within each cohort expressed as binomial proportions with the corresponding 2-sided 90% CI.

Secondary Endpoints:

Efficacy:

The secondary efficacy endpoints were defined as follows:

CR rate as based on responders who achieved confirmed CR as assessed by Investigators. DCR was derived as the sum of the number of patients who achieved confirmed PR/CR or sustained SD (at least 6 weeks) divided by the number of patients in the efficacy analysis set x 100%. The CR rate and DCR was summarized using a point estimate and its 2-sided 90% CI.

DOR was defined among patients who achieved objective response. It was measured from the first-time response (PR/CR) criteria are met until the first date that recurrent or progressive disease was objectively documented, or receipt of subsequent anticancer therapy or the patient dies (whichever is first recorded). Patients not experiencing PD or have not died prior to the time of data cut or the final database lock will have their event times censored on the last date that an adequate assessment of tumor status is made.

PFS was defined as the time (in months) from the time of lymphodepletion to PD, or death due to any cause, whichever event is earlier. Patients not experiencing PD or not having expired at the time of the data cut or the final database lock had their event times censored on the last date that an adequate assessment of tumor status is made.

OS was defined as the time (in months) from the time of lymphodepletion to death due to any cause. Patients not having expired by the time of data cut or the final database lock had their event times censored on the last date of their known survival status.

DOR, PFS, and OS was subjected to right censoring. The Kaplan-Meier method will be used to summarize the time-to-event efficacy endpoints. The baseline data for the tumor assessment was the last scan before the lymphodepletion for all cohorts.

The above efficacy parameters will be estimated for applicable cohort for subsets defined by baseline disease characteristics; BRAF status (Cohort TA only), HPV status (Cohort 2A only), squamous or non-squamous lung disease (Cohorts 3A and 3B only), and anti-PD-L1 status.

Example 14: A Phase 2, Multicenter Study of Autologous Tumor Infiltrating Lymphocytes in Patients with Solid Tumors Study Design Overview This example describes a prospective, open-label, multi-cohort, non-randomized, multicenter Phase 2 study evaluating ACT using TIL in combination with pembrolizumab or TIL as a single therapy, using TILs prepared as described in the present application as well as in this example.

Objectives:

Primary:

To evaluate the efficacy of autologous TIL in combination with pembrolizumab in MM, HNSCC, or NSCLC patients or TIL as a single therapy in relapsed or refractory (r/r) NSCLC patients, who had previously progressed on or after treatment with CPIs, as determined by objective response rate (ORR), using the Response Evaluation Criteria in Solid Tumors (RECIST 1.1), as assessed by Investigator.

To characterize the safety profile of TIL in combination with pembrolizumab in MM, HNSCC, and NSCLC patients or TIL as a single therapy in r/r NSCLC patients as measured by the incidence of Grade >3 treatment-emergent adverse events (TEAEs).

Secondary:

To further evaluate the efficacy of autologous TIL in combination with pembrolizumab in MM, HNSCC, and NSCLC patients or TIL as a single therapy in r/r NSCLC patients using complete response (CR) rate, duration of response (DOR), disease control rate (DCR), progression-free survival (PFS) using RECIST 1.1, as assessed by Investigator, and overall survival (OS).

Cohorts:

Cohort 1A: TIL therapy in combination with pembrolizumab in patients with Stage IIIC or Stage IV unresectable or MM with <3 prior lines of systemic therapy excluding immunotherapy. If previously treated, patients must have had radiographically documented progression on or after most recent therapy.

Cohort 2A: TIL therapy in combination with pembrolizumab in patients with advanced, recurrent or metastatic HNSCC (e.g., Stages T1N1-N2B, T2-4N0-N2b) with <3 prior lines of systemic therapy, excluding immunotherapy. If previously treated, patients must have had radiographically documented progression on or after most recent therapy.

Cohort 3A: TIL therapy in combination with pembrolizumab in patients with locally advanced or metastatic (Stage III-IV) NSCLC with <3 prior lines of systemic therapy, excluding immunotherapy. If previously treated, patients must have had radiographically documented progression on or after most recent therapy.

Cohort 3B: TIL therapy as a single agent in patients Stage III or Stage IV NSCLC who have previously received systemic therapy with CPIs (e.g., anti-PD-1/anti-PD-L1) as part of ≤3 prior lines of systemic therapy. If previously treated, patients must have had radiographically documented progression on or after most recent therapy.

Patients in Cohorts 3A and 3B (NSCLC) with oncogene-driven tumors with available effective targeted therapy must have received at least one line of targeted therapy.

All patients received autologous cryopreserved TIL therapy (with or without pembrolizumab, depending on cohort assignment), preceded by a nonmyeloablative lymphodepletion (NMA-LD) preconditioning regimen consisting of cyclophosphamide and fludarabine. Following TIL infusion, up to 6 IV interleukin-2 (IL-2) doses maximum were administered.

The following general study periods took place in all 4 cohorts, unless specified otherwise.

Screening and Tumor Resection: Up to 4 weeks (28 days) from study entry; manufacturing of the TIL Product: approximately <22 days from tumor resection; and treatment period, as discussed below.

Treatment Period (Cohorts 1A, 2A, and 3A): up to 2 years, including NMA-LD (7 days), TIL infusion (1 day) followed by IL-2 administrations (1 to 4 days).Patients receive a single infusion of pembrolizumab after the completion of their tumor resection for TIL production and baseline scans but before the initiation of the NMA-LD regimen. The next dose of pembrolizumab will be no earlier than following the completion of IL-2 and continue Q3W ±3 days thereafter for <2 years (24 months) or until disease progression or unacceptable toxicity, whichever occurs first. The end-of-treatment (EOT) visit occurred within 30 days after the last dose of pembrolizumab. The visit could be combined with end-of-assessment (EOA) visit if applicable (e.g., pembrolizumab discontinuation occurred at disease progression or at the start of new anticancer therapy).

Treatment Period (Cohort 3B): up to 12 days, including NMA-LD (7 days), TIL, infusion (1 day) followed by IL-2 administrations (1 to 4 days). The EOT visit occurred once a patient received the last dose of IL-2. The EOT visit was performed within 30 days after treatment discontinuation and it may be combined with any scheduled visit occurring within this interval during the assessment period.

Assessment Period: began after TIL infusion on Day 0 and ends upon disease progression, with the start of a new anticancer therapy, partial withdrawal of consent to study assessments, or 5 years (Month 60), whichever occurred first. An end-of assessment (EOA) visit occurred once a patient reached disease progression or started a new anti-cancer therapy.

The TIL autologous therapy with the TILs prepared as described herein was comprised of the following steps:

1. Tumor resection to provide the autologous tissue that serves as the source of the TIL cellular product;
2. TIL product produced at a central Good Manufacturing Practice (GMP) facility;
3. A 7-day NMA-LD preconditioning regimen;
4. Cohorts 1A, 2A, and 3A: Patients receive a single infusion of pembrolizumab after the completion of their tumor resection for TIL production and baseline scans but before the initiation of NMA-LD regimen. The next dose of pembrolizumab will be no earlier than following the completion of IL-2 and continue Q3W ±3 days thereafter.
5. Infusion of the autologous TIL product (Day 0); and
6. IV IL-2 administrations for up to 6 doses maximum.

In Cohorts 1A, 2A, and 3A, the next dose of pembrolizumab was no earlier than following the completion of IL-2 and continue Q3W ±3 days thereafter for <2 years (24 months), or until disease progression or unacceptable toxicity, whichever occurred first.

Flowcharts for Cohorts 1A, 2A, and 3A can be found in FIG. 7. The Flowchart for Cohort 3B can be found in FIG. 8. Patients were assigned to the appropriate cohort by tumor indication.

TIL Therapy+Pembrolizumab (Cohorts 1A, 2A, and 3A)

Patients were screened and scheduled for surgery for tumor resection. Patients then had one or more tumor lesions resected, which were sent to a central manufacturing facility for TIL production.

Next, the NMA-LD regimen was imitated and consisted of 2 days of IV cyclophosphamide (60 mg/kg) with mesna (per site standard of care or USPI/SmPC) on Days −7 and Day −6 followed by 5 days of IV fludarabine (25 mg/m$^2$: Day −5 through Day −1).

Patients in Cohorts 1A, 2A, and 3A received a single infusion of pembrolizumab after the completion of their tumor resection for TIL production and baseline scans and before the initiation of NMA-LD regimen. IL-2 administrations at a dose of 600,000 IU/kg IV begun as soon as 3 hours after, but no later than 24 hours after, completion of the TIL infusion on Day 0. Additional IL-2 administrations will be given approximately every 8 to 12 hours for up to 6 doses maximum. The second dose of pembrolizumab was no earlier than following the completion of IL-2. Patients should have recovered from all IL-2-related toxicities (Grade ≤2), prior to the second pembrolizumab administration. Pembrolizumab will continue Q3W 3 days thereafter for 2 years (24 months) or until disease progression or unacceptable toxicity, whichever occurred first.

TIL Therapy as a Single Agent (Cohort 3B)

Patients were screened and scheduled for surgery for tumor resection. Patients then had one or more tumor lesions resected, which were sent to a central manufacturing facility for TIL production.

Next, the NMA-LD regimen consisted of 2 days of IV cyclophosphamide (60 mg/kg) with mesna (per site standard of care or USPI/SmPC) on Day −7 and Day −6 followed by 5 days of IV fludarabine (25 mg/m$^2$: Day −5 through Day −1).

Infusion of the tumor-derived autologous TIL product occurred no sooner than 24 hours after last dose of fludarabine. IL-2 administrations at a dose of 600,000 IU/kg IV may have begun as soon as 3 hours after, but no later than 24 hours after, completion of the TIL infusion.

Additional IL-2 administrations were given approximately every 8 to 12 hours for up to 6 doses maximum.

Production and Expansion of Tumor Infiltrating Lymphocytes

The TIL autologous cellular product was composed of viable cytotoxic T lymphocytes derived from a patient's tumor/lesion, which are manufactured ex vivo at a central GMP facility. An exemplary flow diagram depicting the TIL production process is provided in FIG. 9, for example.

The TIL manufacturing process begun at the clinical site after surgical excision of a primary or secondary metastatic tumor lesion(s) of ≥1.5 cm in diameter in each individual patient. Multiple tumor lesions from various anatomical locations can be excised to compile a total aggregate of tumor tissue; however, the aggregate should not exceed 4.0 cm in diameter, or 10 g in weight, due to the limited quantity of the biopreservation media present in the transport bottle.

Once the tumor lesion(s) was placed in the biopreservation transport bottle, it is shipped at 2° C. to 8° C. using an express courier to a central GMP manufacturing facility. Upon arrival, the tumor specimen(s) were dissected into fragments, which were then cultured in a pre-rapid expansion protocol (Pre-REP) with human recombinant IL-2 for ~–11 days.

These pre-REP cells were then further expanded using a rapid expansion protocol (REP) for 11 days in the presence of IL-2, OKT3 (a murine monoclonal antibody to human CD3, also known as [muromonab-CD3]) and irradiated allogenic peripheral blood mononuclear cells (PBMC) as feeder cells.

The expanded cells were then harvested, washed, formulated, cryopreserved, and shipped to the clinical site via an express courier. The dosage form of the TIL cellular product was a cryopreserved autologous "live-cell suspension" that was ready for infusion into the patient from whom the TIL were derived. Patients were to receive the full dose of product that was manufactured and released, which contained between $1\times10^9$ and $150\times10^9$ viable cells per the product specification. Clinical experience indicated that objective tumor responses were achieved across this dose range, which has also been shown to be safe (Radvanyi L.G., et al., *Clin Cancer Res.* 2012; 18(24):6758-70). The full dose of product was provided in up to four infusion bags.

Preparation of Patients to Receive the TIL Cellular Product

The NMA-LD preconditioning regimen used in this study (i.e., 2 days of cyclophosphamide plus mesna, followed by 5 days of fludarabine) was based on the method developed and tested by the National Cancer Institute (Rosenberg S.A., et al., *Clin Cancer Res.* 2011; 17(13):4550-7; Radvanyi L.G., et al., *Clin Cancer Res.* 2012; 18(24):6758-70; Dudley M.E., et al., *J Clin Oncol.* 2008; 26(32):5233-9; Pilon-Thomas S, et al., *J Immunother.* 2012; 35(8):615-20; Dudley M.E., et al., *J Clin Oncol.* 2005; 23(10):2346-57; and Dudley M.E., et al., *Science.* 2002; 298(5594):850-4). Following the 7-day preconditioning regimen, the patient was infused with the TIL cellular product.

The TIL infusion was followed by the administration of IV IL-2 (600,000 IU/kg) every 8 to 12 hours, with the first dose administered between 3 and 24 hours after the completion of the TIL infusion and continuing for up to 6 doses maximum. Per institutional standards, the doses of IL-2 can be calculated on the basis of actual weight.

Selection of Patient Populations

Cohort 1A:

Patients had a confirmed diagnosis of unresectable MM (Stage IIIC or Stage IV, histologically confirmed as per American Joint Committee on Cancer [AJCC] staging system). Ocular melanoma patients were excluded. Patients must not have received prior immuno-oncology targeted agents. If BRAF-mutation positive, patient could have received prior BRAF/MEKtargeted therapy.

Cohort 2A:

Patients had advanced, recurrent and/or metastatic HNSCC and can be treatment naive; histologic diagnosis of the primary tumor is required via the pathology report. Patients must not have received prior immunotherapy regimens.

Cohort 3A:

Patients had a confirmed diagnosis of Stage III or Stage IV NSCLC (squamous, adenocarcinoma, large cell carcinoma). Patients with oncogene-driven tumors with available effective targeted therapy had received at least one line of targeted therapy.

Cohort 3B:

Patients had a confirmed diagnosis of Stage III or Stage IV NSCLC (squamous, adenocarcinoma, large cell carcinoma) and had previously received systemic therapy with CPIs (e.g., anti-PD-1/anti-PD-L1). Patients with oncogene-driven tumors with available effective targeted therapy had received at least one line of targeted therapy.

All patients had received up to 3 prior systemic anticancer therapies (see, inclusion criteria below), excluding immunotherapy for Cohorts 1A, 2A, and 3A. If previously treated, patients had radiographically confirmed progression on or after most recent therapy.

Inclusion Criteria

Patients must have met ALL of the following inclusion criteria for participation in the study:

1. All patients had a histologically or pathologically confirmed diagnosis of malignancy of their respective histologies:
   - Unresectable or metastatic melanoma (Cohort 1A)
   - Advanced, recurrent or metastatic squamous cell carcinoma of the head and neck (Cohort 2A)
   - Stage III or Stage IV NSCLC (squamous, nonsquamous, adenocarcinoma, large cell carcinoma) (Cohorts 3A and 3B).
2. Cohorts 1A, 2A, and 3A only: Patients were immunotherapy naive. If previously treated, patients had progressed on or after most recent therapy. Cohorts 1A, 2A, and 3A may have received up to 3 prior systemic anticancer therapies, specifically:
   - In Cohort TA: Patients with unresectable or metastatic melanoma (Stage IIIC or Stage IV); if BRAF mutation-positive, patients could have received a BRAF inhibitor.
   - In Cohort 2A: Patients with unresectable or metastatic HNSCC. Those who had received initial chemoradiotherapy were allowed.
   - In Cohort 3A: Patients with Stage III or Stage IV NSCLC (squamous, nonsquamous, adenocarcinoma, or large cell carcinoma) and who were immunotherapy naive and progressed after <3 lines of prior systemic therapy in the locally advanced or metastatic setting. Patients who received systemic therapy in the adjuvant or neoadjuvant setting, or as part of definitive chemoradiotherapy, were eligible and were considered to have had one line of therapy if the disease has progressed within 12 months of completion of prior systemic therapy. Patients with known oncogene drivers (e.g., EGFR, ALK, ROS) who had mutations that were sensitive to targeted therapies must had progressed after at least 1 line of targeted therapy.

3. Cohort 3B only: Patients with Stage III or Stage IV NSCLC (squamous, nonsquamous, adenocarcinoma, or large cell carcinoma) who had previously received systemic therapy with CPIs (e.g., anti-PD-1/anti-PD-L1) as part of <3 prior lines of systemic therapy.
   Patients had radiographically confirmed progression on or after most recent therapy.
   Patients who received systemic therapy in the adjuvant or neoadjuvant setting, or as part of definitive chemoradiotherapy, were eligible and were considered to have had 1 line of therapy if the disease had progressed within 12 months of completion of prior systemic therapy.
   Patients with known oncogene drivers (e.g., EGFR, ALK, ROS) who had mutations that are sensitive to targeted therapies must have progressed after at least 1 line of targeted therapy.
4. Patients had at least 1 resectable lesion (or aggregate lesions) of a minimum 1.5 cm in diameter post-resection for TIL investigational product production. It was encouraged that tumor tissue be obtained from multiple and diverse metastatic lesions, as long as the surgical resection did not pose additional risks to the patient.
   If the lesion considered for resection for TIL generation is within a previously irradiated field, the lesion must have demonstrated radiographic progression prior to resection.
   Patients must have an adequate histopathology specimen for protocol-required testing.
5. Patients had remaining measurable disease as defined by the standard and well known RECIST 1.1 guidelines (see, for example, Eisenhauer, *European Journal of Cancer* 45:228-247 (2009), also available on the World Wide Web at project.eortc.org/recist/wp-content/uploads/sites/4/2015/03/RECISTGuidelines.pdf) following tumor resection for TIL manufacturing:
   Lesions in previously irradiated areas were not be selected as target lesions unless there had been demonstrated progression of disease in those lesions;
   Lesions that were partially resected for TIL generation that were still measurable per RECIST may be selected as nontarget lesions but could not serve as a target lesion for response assessment.
6. Patients were >18 years at the time of consent.
7. Patients had an Eastern Cooperative Oncology Group (ECOG) performance status of 0 or 1, and an estimated life expectancy of >3 months.
8. Patients of childbearing potential or those with partners of childbearing potential had to be willing to practice an approved method of highly effective birth control during treatment and continue for 12 months after receiving all protocol-related therapy (Note: Females of reproductive potential were to use effective contraception during treatment and for 12 months after their last dose of IL-2, or 4 months after their last dose of pembrolizumab whichever occurred later). Males could not donate sperm during the study or for 12 months after treatment discontinuation, whichever occurred later.
9. Patients had the following hematologic parameters:
   Absolute neutrophil count (ANC) >1000/mm$^3$;
   Hemoglobin >9.0 g/dL;
   Platelet count >100,000/mm$^3$.
10. Patients had adequate organ function:
   Serum alanine aminotransferase (ALT)/serum glutamic-pyruvic transaminase (SGPT) and aspartate aminotransferase (AST)/SGOT <3 times the upper limit of normal (ULN), patients with liver metastasis <5 times ULN.
   An estimated creatinine clearance >40 mL/min using the Cockcroft Gault formula at Screening.
   Total bilirubin <2 mg/dL.
   Patients with Gilbert's Syndrome must have a total bilirubin <3 mg/dL.
11. Patients were seronegative for the human immunodeficiency virus (HIV1 and HIV2). Patients with positive serology for hepatitis B virus surface antigen (HBsAg), hepatitis B core antibody (anti HBc), or hepatitis C virus (anti-HCV) indicating acute or chronic infection were enrolled depending on the viral load based on polymerase chain reaction (PCR) and the local prevalence of certain viral exposures.
12. Patients had a washout period from prior anticancer therapy(ies) of a minimum duration, as detailed below prior to the first study treatment (i.e., start ofNMA-LD or pembrolizumab):
   Targeted therapy: prior targeted therapy with an epidermal growth factor receptor (EGFR), MEK, BRAF, ALK, ROS1 or other-targeted agents (e.g., erlotinib, afatinib, dacomitinib, osimertinib, crizotinib, ceritinib, lorlatinib) was allowed provided the washout is a minimum of 14 days prior to the start of treatment.
   Chemotherapy: adjuvant, neoadjuvant or definitive chemotherapy/chemoradiation was allowed provided the washout is a minimum of 21 days prior to the start of treatment.
   Immunotherapy for Cohort 3B only, prior checkpoint-targeted therapy with an anti-PD-1, other mAbs, or vaccines were allowed with a washout period of >21 days before the start of NMA-LD.
   Palliative radiation therapy: prior external beam radiation was allowed provided all radiation-related toxicities were resolved to Grade 1 or baseline, excluding alopecia, skin pigmentation change, or other clinically insignificant events, e.g., small area radiation dermatitis or rectal or urinary urgency
   The tumor lesion(s) being assessed as target for response via RECIST 1.1 were outside of the radiation portal; however, if within the portal, they must have demonstrated progression (see Inclusion Criterion above).
   Surgery/pre-planned procedure: previous surgical procedure(s) was permitted provided that wound healing had occurred, all complications had resolved, and at least 14 days have elapsed (for major operative procedures) prior to the tumor resection.
13. Patients had recovered from all prior anticancer treatment-related adverse events (TRAEs) to Grade <1 (per Common Terminology Criteria for Adverse Events [CTCAE]), except for alopecia or vitiligo, prior to cohort assignment.
14. Patients with stable Grade >2 toxicity from prior anticancer therapy were considered on a case by case basis after consultation with the Medical Monitor.
15. Cohorts 1A, 2A, and 3A patients with irreversible toxicity not reasonably expected to be exacerbated by treatment with pembrolizumab were included only after consultation with the Medical Monitor. For patients in Cohort 3B only, patients with documented Grade >2 or higher diarrhea or colitis as a result of a previous treatment with immune checkpoint inhibitor CPI(s) must have been asymptomatic for at least 6 months or had a normal by visual assessment colonoscopy post-treatment prior to tumor resection.

16. Patients must have provided written authorization for use and disclosure of protected health information.

Exclusion Criteria

Patients who meet ANY of the following criteria were excluded from the study:

1. Patients with melanoma of uveal/ocular origin
2. Patients who had received an organ allograft or prior cell transfer therapy that included a nonmyeloablative or myeloablative chemotherapy regimen within the past 20 years. (Note: This criterion was applicable for patients undergoing retreatment with TIL, with the exception that they had a prior NMA-LD regimen with their prior TIL treatment.)

3. Patients with symptomatic and/or untreated brain metastases.

Patients with definitively-treated brain metastases will be considered for enrollment after discussion with Medical Monitor; if, prior to the start of treatment the patient is clinically stable for ≥2 weeks, there are no new brain lesions via magnetic resonance imaging (MRI) post-treatment, and the patient does not require ongoing corticosteroid treatment.

4. Patients who are on a systemic steroid therapy within 21 days of enrollment.
5. Patients who are pregnant or breastfeeding.
6. Patients who had an active medical illness(es), which in the opinion of the Investigator, posed increased risks for study participation; such as systemic infections (e.g., syphilis or any other infection requiring antibiotics), coagulation disorders, or other active major medical illnesses of the cardiovascular, respiratory, or immune systems.
7. Patients may not have active or prior documented autoimmune or inflammatory disorders (including pneumonitis, inflammatory bowel disease [e.g., colitis or Crohn's disease], diverticulitis [with the exception of diverticulosis], systemic lupus erythematosus, sarcoidosis syndrome, or Wegener syndrome [granulomatosis with polyangiitis, Graves' disease, rheumatoid arthritis, hypophysitis, uveitis, etc.]). The following were exceptions to this criterion:

Patients with vitiligo or alopecia.

Patients with hypothyroidism (e.g., following Hashimoto syndrome) stable on hormone replacement.

Any chronic skin condition that did not require systemic therapy.

Patients with celiac disease controlled by diet alone.

8. Patients who had received a live or attenuated vaccination within 28 days prior to the start of treatment.
9. Patients who had any form of primary immunodeficiency (such as severe combined immunodeficiency disease [SCID] and acquired immune deficiency syndrome [AIDS]).
10. Patients with a history of hypersensitivity to any component of the study drugs. TILs were not administered to patients with a known hypersensitivity to any component of TIL product formulation including, but not limited to any of the following:

NMA-LD (cyclophosphamide, mesna, and fludarabine)

Proleukin®, aldesleukin, IL-2

Antibiotics of the aminoglycoside group (i.e., streptomycin, gentamicin [excluding those who are skin-test negative for gentamicin hypersensitivity])

Any component of the TIL product formulation including dimethyl sulfoxide

[DMSO], HSA, IL-2, and dextran-40

Pembrolizumab

11. Patients who had a left ventricular ejection fraction (LVEF)<45% or who are New York Heart Association Class II or higher. A cardiac stress test demonstrating any irreversible wall movement abnormality in any patients >60 years of age or in patients who have a history of ischemic heart disease, chest pain, or clinically significant atrial and/or ventricular arrhythmias.

Patients with an abnormal cardiac stress test could be enrolled if they had adequate ejection fraction and cardiology clearance with approval of the Sponsor's Medical Monitor.

12. Patients who had obstructive or restrictive pulmonary disease and have a documented FEV1 (forced expiratory volume in 1 second) of <60% of predicted normal.

If a patient was not able to perform reliable spirometry due to abnormal upper airway anatomy (i.e., tracheostomy), a 6-minute walk test was used to assess pulmonary function. Patients who were unable to walk a distance of at least 80% predicted for age and sex or demonstrates evidence of hypoxia at any point during the test (SpO2<90%) are excluded.

13. Patients who had another primary malignancy within the previous 3 years (except for those which did not require treatment or had been curatively treated greater than 1 year ago, and in the judgment of the Investigator, did not pose a significant risk of recurrence including, but not limited to, non-melanoma skin cancer, DCIS, LCIS, prostate cancer Gleason score 6 or bladder cancer).
14. Participation in another clinical study with an investigational product within 21 days of the initiation of treatment.

Study Endpoints and Planned Analyses

The primary and secondary endpoints were analyzed separately by cohort.

Primary Endpoints:

The ORR was defined as the proportion of patients who achieved either a confirmed PR or CR as best response as assessed by Investigators per RECIST 1.1 among the efficacy analysis set.

Objective response was evaluated per each disease assessment and the ORR was expressed as a binomial proportion with the corresponding 2-sided 90% CI. The primary analysis for each cohort occurred when all treated patients per cohort have an opportunity to be followed for 12 months, unless progressed/expired or discontinued early from the assessment period.

The safety primary endpoint was measured by any Grade 3 or higher TEAE incidence rate within each cohort expressed as binomial proportions with the corresponding 2-sided 90% CI.

Secondary Endpoints:

Efficacy:

The secondary efficacy endpoints were defined as follows:

CR rate as based on responders who achieved confirmed CR as assessed by Investigators. DCR was derived as the sum of the number of patients who achieved confirmed PR/CR or sustained SD (at least 6 weeks) divided by the number of patients in the efficacy analysis set x 100%. The CR rate and DCR was summarized using a point estimate and its 2-sided 90% CI.

DOR was defined among patients who achieved objective response. It was measured from the first-time response (PR/CR) criteria are met until the first date that recurrent or progressive disease was objectively documented, or receipt of subsequent anticancer therapy or the patient dies (whichever is first recorded). Patients not experiencing PD or have not died prior to the time of data cut or the final database lock will have their event times censored on the last date that an adequate assessment of tumor status is made.

PFS was defined as the time (in months) from the time of lymphodepletion to PD, or death due to any cause, whichever event is earlier. Patients not experiencing PD or not having expired at the time of the data cut or the final database lock had their event times censored on the last date that an adequate assessment of tumor status is made.

OS was defined as the time (in months) from the time of lymphodepletion to death due to any cause. Patients not having expired by the time of data cut or the final database lock had their event times censored on the last date of their known survival status.

DOR, PFS, and OS was subjected to right censoring. The Kaplan-Meier method will be used to summarize the time-to-event efficacy endpoints. The baseline data for the tumor assessment was the last scan before the lymphodepletion for all cohorts.

The above efficacy parameters will be estimated for applicable cohort for subsets defined by baseline disease characteristics; BRAF status (Cohort TA only), HPV status (Cohort 2A only), squamous or non-squamous lung disease (Cohorts 3A and 3B only), and anti-PD-L1 status.

Example 15: A Phase 2, Multicenter Study of Autologous Tumor Infiltrating Lymphocytes in Patients with Solid Tumors The study in this example is a phase 2, multicenter, global, open label study of autologous tumor infiltrating lymphocytes (TIL) in patients with select solid tumors (metastatic melanoma, head and neck squamous cell cancer, and non-small cell lung cancer (NSCLC)). The example uses the TIL product manufactured according to the Examples herein, including Examples 10-17, as well as dresibed in throughout the present application, which is cryopreserved and has a 22-day manufacturing process. A single infusion of TIL produce was given after patients had completed the preparatory regimen of non-myeloablative lymphodepletion with cyclophosphamide (60 mg/kg ×2 days) and fludarabine (25 $mg^2/m$×5 days). There are 4 patient cohorts as described below:

- Cohort TA (combination cohort): Stage IIIC or IV unresectable or metastatic melanoma patients who are immunotherapy naive with <3 prior lines of systemic therapy. These patients will be receiving TIL product in combination with pembrolizumab.
- Cohort 2A (combination cohort): Advanced, recurrent or metastatic head and neck squamous cell carcinoma patients who are immunotherapy naive with <3 prior lines of systemic therapy. These patients will be receiving TIL product in combination with pembrolizumab.
- Cohort 3A (combination cohort): Locally advanced or metastatic (Stage III-IV) NSCLC patients who are immunotherapy naive with 3 prior lines of systemic therapy. These patients will be receiving TIL product in combination with pembrolizumab.
- Cohort 3B (single agent cohort): Stage III-IV NSCLC patients who have previously received systemic therapy with checkpoint inhibitors (anti-PD-1/anti-PD-L1) as part of <3 prior lines of systemic therapy. These patients will be receiving TIL product as single agent.

Two patients with NSCLC have been enrolled in Cohort 3B (TIL alone post immune checkpoint inhibitor) who had completed their first response assessment visit at day 42) are described below.

Patient A is a 63-year old female diagnosed with Stage IVA lung adenocarcinoma. She had received 3 prior lines of systemic therapy which included pembrolizumab, carboplatin/bevacizumab and vinorelbine. Her best response to prior pembrolizumab therapy was progressive disease; to carboplatin/bevacizumab was a partial response, and her vinorelbine response was non-evaluable (she discontinued prior to response assessment). She underwent left lower lobe lung resection for TIL generation and was infused with $3.75\times10^9$ cells of TIL product. The patient had her first response assessment (Day 42) visit, at which computerized tomography (CT) scans showed a 4% reduction in the tumor load compared to baseline scans, which is a stable disease response per RECIST 1.1.

Patient B is a 70-year old female diagnosed with Stage IVB basaloid squamous cell carcinoma. She had received 3 prior lines of therapy which included carboplatin/abraxane, nivolumab and cisplatin/gemcitabine. Her best response to prior carbo/abraxane was not evaluable (therapy discontinued due to toxicity); to nivolumab was progressive disease and for cisplatin/gemcitabine was a partial response. She underwent splenic lesion resection for TIL generation and was infused with $39\times10^9$ cells of TIL product. The patient had her first response assessment (Day 42) visit, at which CT scans showed a 44% reduction in the tumor load compared to baseline scans, which is a partial response per RECIST 1.1.

Example 16: A Phase 2, Multicenter Study of Autologous Tumor Infiltrating Lymphocytes in Patients with Locally Advanced or Metastatic Non-Small-Cell Lung Cancer This example relates to treatment of patients with locally advanced, unresectable or metastatic non-small-cell lung cancer (NSCLC) without any actionable driver mutations who have disease progression on or following a single line of approved systemic therapy consisting of combined checkpoint inhibitor (CPI)+chemotherapy ±bevacizumab (including bevacizumab (AVASTIN), a VEGFA inhibitor) and the cohorts for treatment are summarized below:

- Cohort 1: Patients whose tumors did not express programmed cell death-ligand 1 (PD-L1) (tumor proportion score [TPS]<1%) prior to their CPI treatment.
- Cohort 2: Patients whose tumors expressed PD-L1 (TPS >1%) prior to their CPI treatment. Cohort 3: Patients whose tumors did not express PD-L1 (TPS <1%) prior to their CPI treatment and who are unable to safely undergo a surgical harvest for TIL generation due to at least one of the followin:
  - Unacceptable surgical risk, or
  - Surgically approachable lesion was required for Response Evaluation Criteria in Solid Tumors (RECIST) v1.1 assessment.
- Cohort 4: Retreatment cohort: Patients who had been previously treated with TIL-based immunotherapy in Cohort 1, 2 or 3 of this study.

Treatment will be given using autologous TIL-based immunotherapy derived from an individual patient's tumor for patient-directed therapy Study Details Autologous TIL Therapy Regimen The TIL-based immunotherapy treatment regimen involved a course of the NMA-LD preparative regimen using cyclophosphamide and fludarabine for a total of 5 days prior to TIL-based immunotherapy infusion, and a limited course of IL-2 administration (up to six doses) following the TIL-based immunotherapy infusion. The NMA-LD preparative regimen and IL-2 were included in the regimen to support the engraftment, expansion, and activation of the transferred TIL Several preparative regimens had been used in conjunction with TIL therapies. NMA-LD preparative regimens included cyclophosphamide/fludarabine, total body irradiation (TBI), or the combination of both. The present exemplary study utilized the cy-flu regimen. The NMA-LD preparative regimen used in the current study was based on the method developed and tested by the National Cancer Institute (NCI), which involves 2 days of cyclophosphamide concomitant with 5 days of fludarabine in an effort to shorten the duration of the hospital stay of patients. Each patient would undergo an NMA-LD preparative regimen prior to infusion of TIL-based immunotherapy.

Brief Description of the Treatment

The therapy was a ready-to-infuse, autologous TIL-based immunotherapy. The TIL-based immunotherapy was composed of autologous TIL, which were obtained from an individual patient's tumor and expanded ex vivo through cell culture in the presence of the cytokine IL-2 and a murine monoclonal antibody (mAb) to human CD3 (OKT3).

The final drug product was a cryopreserved live-cell suspension that was formulated for IV infusion. The ex vivo expanded autologous TIL were formulated in CryoStor® CS10 cryopreservation medium/PlasmaLyte (final dimethyl sulfoxide [DMSO] concentration: 5%), with 0.5% human serum albumin (HSA) and 300 IU/mL (12 ng/mL) of IL-2. The formulated product was frozen at a controlled rate to <−150° C. in vapor phase liquid nitrogen, shipped in a cryoshipper to the appropriate clinical site, and thawed before use for infusion into the patient.

Production and Expansion of TIL

Figure 34:
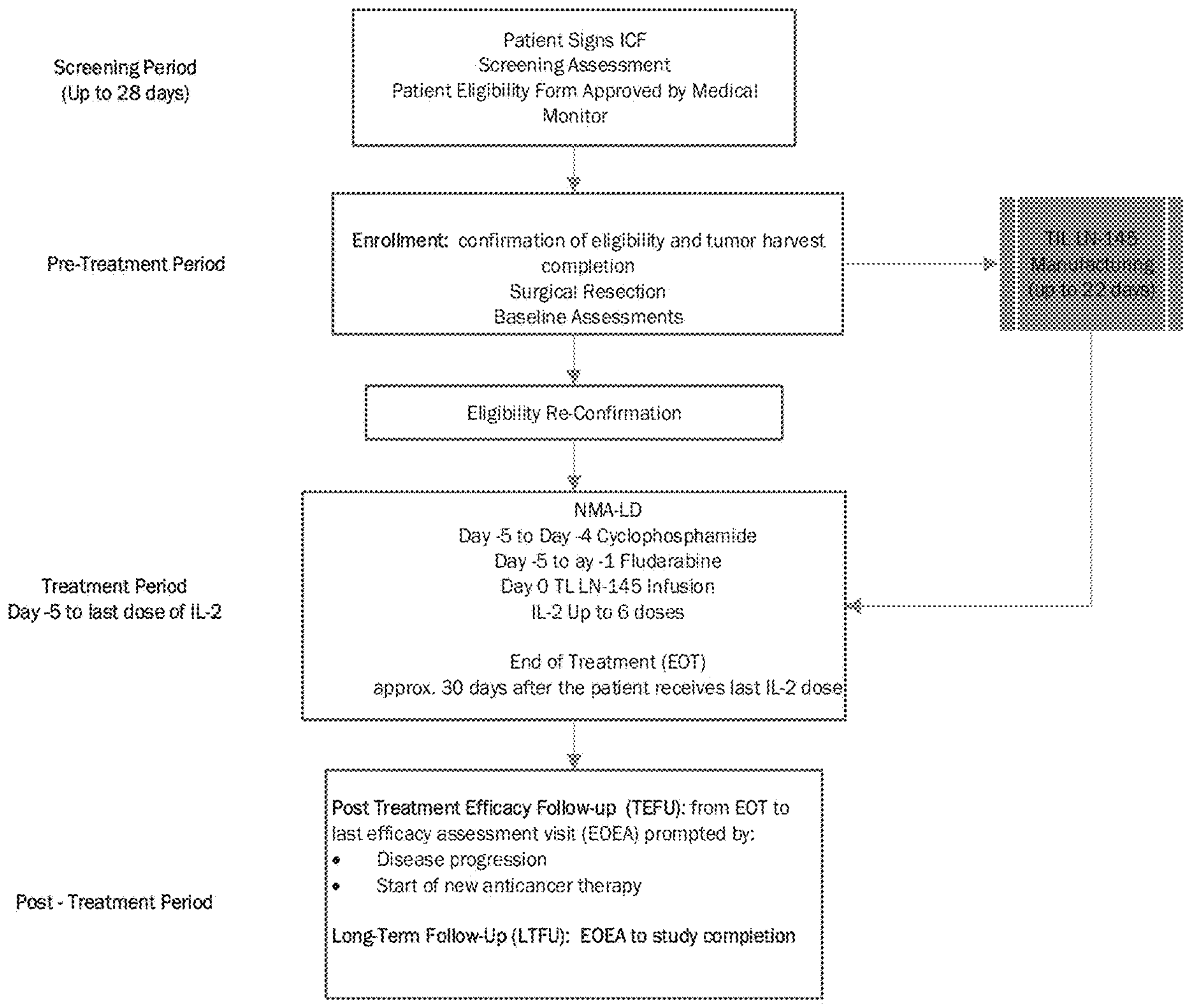
FIG. 34: Diagram of Study Design related to study described in Example 19.
Figure 35:
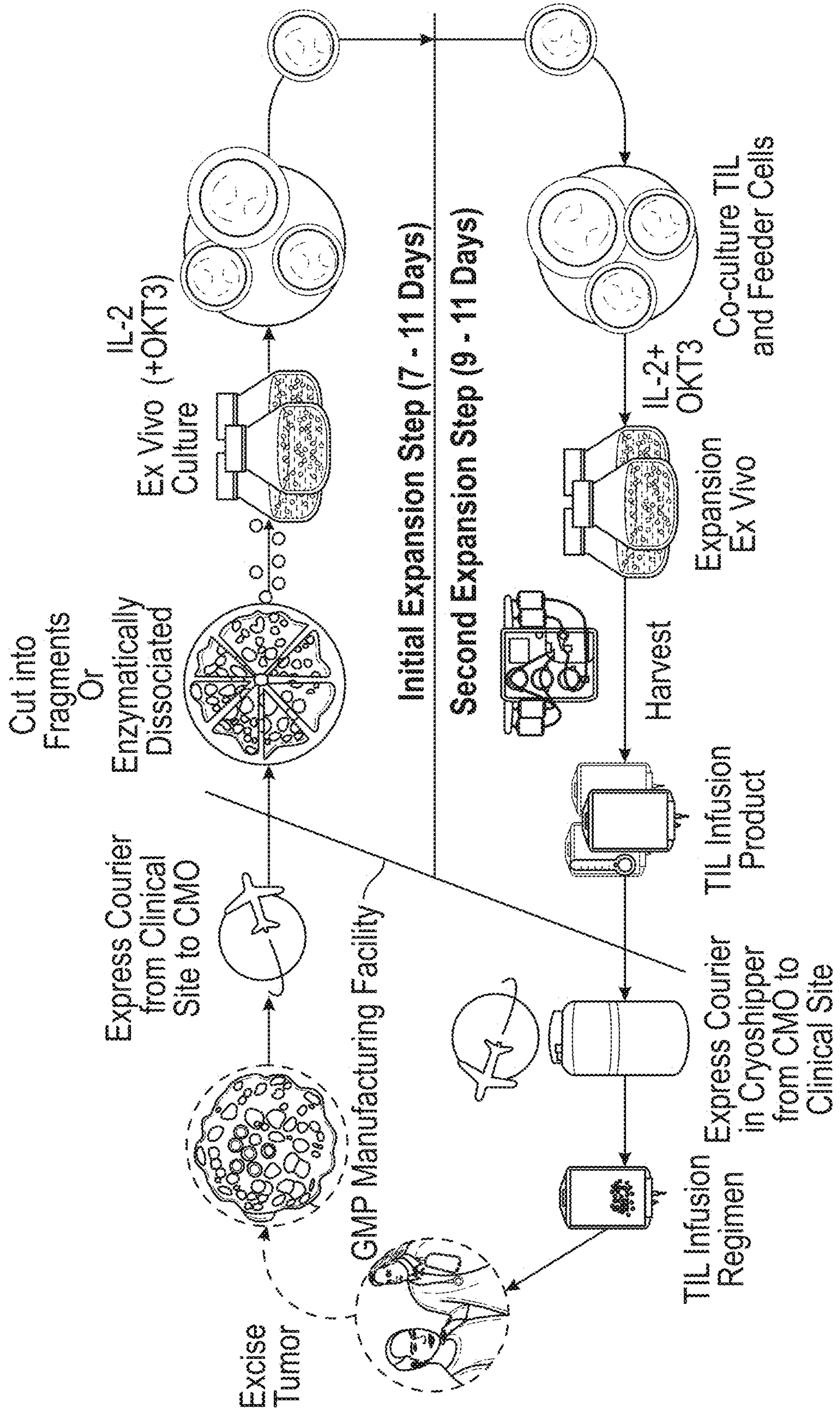
FIG. 35: Schematic of TIL-based immunotherapy banufacturing process related to the study described in Example 19. Abbreviations: CMO=contract manufacturing organization; GMP=Good Manufacturing Practices; IL-2=interleukin-2; OKT3=monoclonal antibody to CD3; TIL=tumor infiltrating lymphocytes.

The manufacturing process began at the clinical site with the surgical resection or core biopsy of a tumor lesion containing viable tumor material. An aggregate of multiple separate lesion biopsies could also be resected from the patient and was encouraged if patient safety allows. The tumor specimen was placed in transport media and shipped by express courier at 2-8° C. to the Good Manufacturing Practices (GMP) manufacturing facility. Upon arrival at the GMP manufacturing facility, the tumor specimen was dissected into fragments, which are then activated (initial expansion step) to generate the minimum number of viable cells required for the rapid expansion protocol (REP) stage. The tumors could also be enzymatically dissociated, and TIL could be selected for expression of biomarkers prior to proceeding to the REP. The REP stage (second expansion step) further expands the cells in the presence of IL-2, OKT3, and irradiated allogeneic peripheral blood mononuclear cells (PBMC). The REP-expanded cells are then harvested, washed, and formulated in a blood transport/infusion bag for shipment by courier to the clinical site. A diagram of the manufacturing process for TIL-based immunotherapy is provided in FIGS. 34 and 35.

Each cryopreservation bag of the TIL-based immunotherapy final product was labeled with a patient-specific label. TIL-based immunotherapy was shipped from the manufacturing facility to clinical sites for administration to patients.

This example related to a prospective, open-label, multicohort, non-randomized, multicenter phase 2 study evaluating TIL-based immunotherapy in patients with locally advanced unresectable or metastatic NSCLC.

The following cohorts were studied:

Cohort 1: TIL-based immunotherapy as single-agent therapy in patients with Stage IV NSCLC whose tumors did not express PD-L1 (tumor proportion score [TPS]<1%) prior to their CPI treatment without a known actionable driver mutation, who had disease progression on or following a single line of approved systemic therapy consisting of combined CPI+chemotherapy ±bevacizumab, who had at least one resectable lesion (or aggregate lesions) of a minimum 1.5 cm in diameter for TIL production and, following the resection, had at least one remaining measurable lesion, as defined by RECIST 1.1..

Cohort 2: TIL-based immunotherapy as single-agent therapy in patients with Stage IV NSCLC whose tumors expressed PD-L1 (TPS >1%) prior to their CPI treatment, without any known actionable driver mutations, who had disease progression on or following a single line of approved systemic therapy consisting of combined CPI+chemotherapy ±bevacizumab, and who had at least one resectable lesion (or aggregate lesions) of a minimum 1.5 cm in diameter for TIL production and, following the resection, had at least one remaining measurable lesion, as defined by RECIST 1.1.

Cohort 3: TIL-based immunotherapy as single-agent therapy in patients with Stage IV NSCLC whose tumors did not express PD-L1 (TPS <1%) prior to their CPI treatment, without any known actionable driver mutations, who had disease progression on or following a single line of approved systemic therapy consisting of combined CPI+chemotherapy bevacizumab, and who were unable to safely undergo a surgical harvest for TIL generation due to at least one of the following: 1) unacceptable surgical risk, or 2) surgically approachable lesion is required for RECIST assessment.

Cohort 4: TIL-based immunotherapy single agent therapy as retreatment in patients who previously received TIL-based immunotherapy as part of their participation in Cohorts 1, 2or 3.

For Cohorts 1, 2, 3, and 4, all patients received autologous cryopreserved TIL-based immunotherapy, preceded by a nonmyeloablative lymphodepletion (NMA-LD) preconditioning regimen consisting of cyclophosphamide and fludarabine. Following TIL-based immunotherapy infusion, up to 6 doses of IV IL-2 (such as aldesleukin or a biosimilar or variant thereof) were administered. Alternatively, descrescendo IL-2 or low-dose IL-2 may be used as set forth herein.

The autologous TIL therapy with TIL-based immunotherapy included the following general steps:

- Tumor harvest to provide the autologous tissue that served as the source of the autologous TIL cellular product,
- Production of autologous TIL-based immunotherapy investigational product (IP) at a central Good Manufacturing Practice (GMP) facility,
- A 5-day nonmyeloablative lymphodepletion (NMA-LD) preconditioning regimen,
- Infusion of the TIL-based immunotherapy product (Day 0), and
- Administration of <6 doses IV IL-2.

Primary Objectives:

Evaluated the efficacy of TIL-based immunotherapy in patients with locally advanced unresectable or metastatic NSCLC without an actionable driver mutation who have disease progression on or following a single line of approved systemic therapy consisting of combined checkpoint inhibitor(s) (CPI[s])+chemotherapy ±bevacizumab, as determined by objective response rate (ORR), using the Response Evaluation Criteria in Solid Tumors (RECIST 1.1), as assessed by the Independent Review Committee (IRC) (Cohorts 1 and 2) or by the Investigator Cohort 3 and Cohort 4).

Secondary Objectives:

Evaluated the efficacy of TIL-based immunotherapy as determined by ORR, using RECIST 1.1, and as assessed by the Investigator (Cohorts 1 and 2).

Further evaluated the efficacy of TIL-based immunotherapy using complete response (CR) rate; duration of response (DOR); disease control rate (DCR); progression-free survival (PFS) using RECIST 1.1, as assessed by the IRC (Cohorts 1 and 2) and Investigator (all cohorts); and overall survival (OS).

Characterized the safety profile of TIL-based immunotherapy in NSCLC patients, as measured by the incidence of Grade >3 treatment-emergent adverse events (TEAEs).

For Cohort 3 only: Evaluated the efficiency of generating TIL-based immunotherapy from core biopsies.

Exploratory Objectives:

Evaluated the persistence of TIL-based immunotherapy and to identify immune correlates that may affect response, outcome, and toxicity variables.

Assessed respective, indication-specific, health-related quality of life (HRQoL) parameters.

Endpoints—Primary Endpoint:

ORR was assessed per RECIST 1.1 by the IRC (Cohorts 1 and 2) or by the Investigator (Cohorts 3 and 4).

Endpoints—Secondary Endpoints:

Incidence of severity, seriousness, relationship to study treatment, and characteristics of treatment-emergent adverse events (TEAEs), including serious AEs (SAEs), therapy-related AEs, and AEs leading to early discontinuation from treatment or withdrawal from the Assessment Period or death.

CR (complete response) rate, DOR (duration of response), DCR (disease control rate), and PFS (progression-free survival) as assessed by IRC per RECIST 1.1 (Cohorts 1 and 2).

ORR (objective response rate), CR rate, DOR, DCR, and PFS as assessed by the Investigator per RECIST 1.1 (all cohorts).

OS (overall survival).

Percentage successful TIL products generated from core biopsies (Cohort 3).

Endpoints—Exploratory Endpoints:

In vivo persistence of the T cells comprising the TIL product was assessed by monitoring the presence of TIL product-specific T-cell receptor-beta complementarity determining region 3 (CDR3) sequences in the patient's blood over time. The CDR3 sequences present in the product and peripheral blood samples were identified using deep sequencing.

Exploratory endpoints aimed at identifying predictive and pharmacodynamic clinical biomarkers of the activity of TIL-based immunotherapy:

- Phenotypic and functional characteristics of TIL-based immunotherapy;
- Immune profile of the tumor tissues;
- Gene expression profiles of the TIL product, tumor tissues, and/or PBMCs;
- Mutational landscape of the tumors;
- Circulating immune factors; and
- Immune composition of PBMC.

HRQoL (health-related quality of life) as assessed per the European Organization for Research and Treatment of Cancer (EORTC) quality of life questionnaire (QLQ) C30 and QLQ LC13.

Study Design Details:

A prospective, open-label, multi-cohort, non-randomized, multicenter phase 2 study evaluated adoptive cell therapy (ACT) with TIL-based immunotherapy.

All patients received TIL-based immunotherapy, consisting of these steps:

- Tumor harvest provided the autologous tissue that serves as the source of the autologous TIL cellular product,
- Production of autologous TIL-based immunotherapy investigational product (IP) at a central Good Manufacturing Practice (GMP) facility,
- A 5-day nonmyeloablative lymphodepletion (NMA-LD) preconditioning regimen,
- Infusion of the TIL-based immunotherapy product (Day 0), and
- Administration of <6 doses IV IL-2.

The following general sequential periods will occur in all 4 cohorts, unless otherwise specified:

1. Screening Period: From informed consent form (ICF) signature to enrollment
2. Pre-treatment Period: From enrollment to initiation of preparative NMA-LD regimen.
3. Treatment Period: From initiation of preparative NMA-LD to End of Treatment (EOT) Visit. This consisted of 8 to 9 days of therapy, including NMA-LD (Days −5 to −1), TIL-based immunotherapy infusion (Day 0), followed by IL-2 administrations (Days 0 or 1 to 3 or 4). The EOT occurred approximately 30 days after Day 0.
4. Posttreatment Follow-up period, which is composed of:
   a. Posttreatment Efficacy Follow-up Period (TEFU): From EOT Visit to study completion (at 5 years [Month 60] after treatment) or the End of Efficacy Assessment (EOEA) Visit, which would be prompted by disease progression or start of a new anticancer therapy, whichever occurs first.
   b. Long-Term Follow-up Period (LTFU): From EOEA, as described above, to study completion (at 5 years [Month 60] after treatment).

Figure 36:
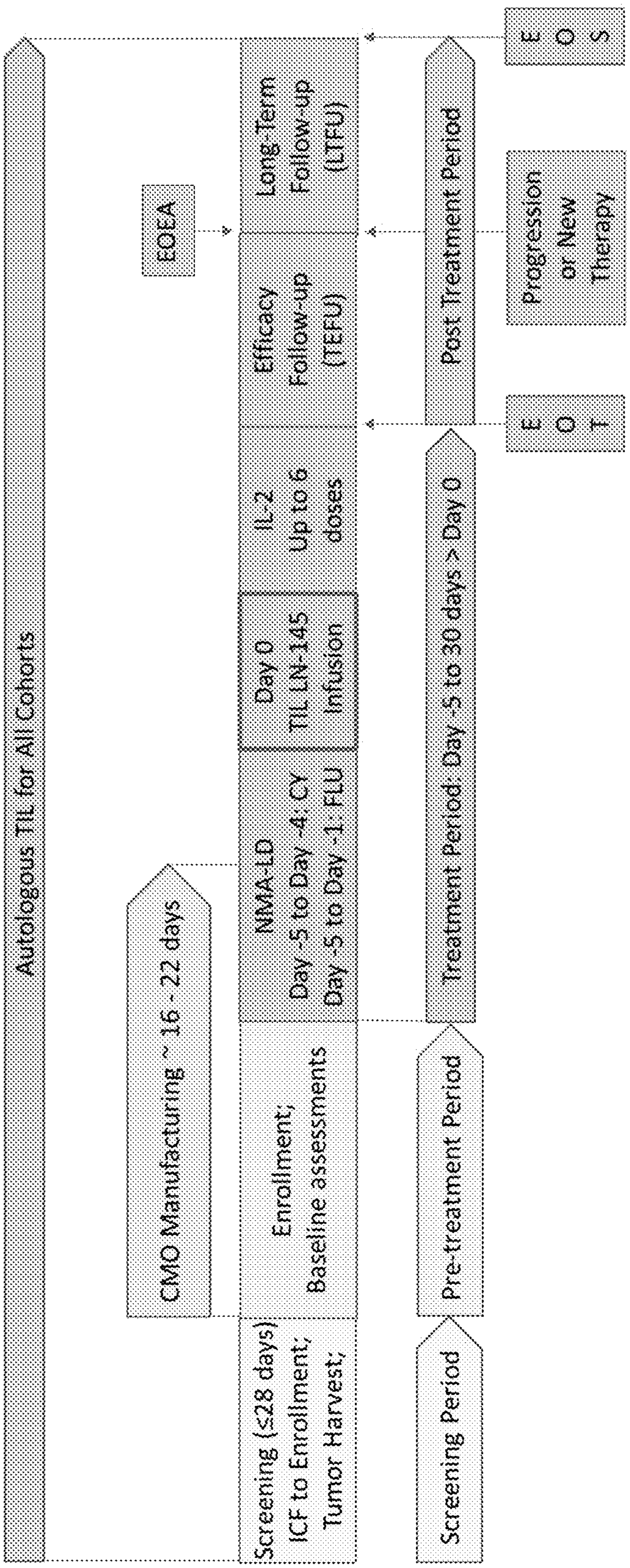
FIG. 36: Study Flowchart (all four cohorts).

Study participants (enrolled patients) will transition early to LTFU (e.g., at partial withdrawal of consent, or if is determined that they would not receive TIL-based immunotherapy for any reason). Early study withdrawal was prompted by either consent withdrawal, death, lost to follow-up, or study termination by Sponsor. A flowchart for the study design is presented in FIG. 36.

Detailed Doses and Treatment Schedule:

TIL-Based Immunotherapy

Patients will undergo a 5-day preconditioning NMA-LD regimen that was initiated prior to the planned TIL-based immunotherapy infusion on Day 0 (i.e., Days −5 through −1). The NMA LD regimen consisted of 2 days of intravenous (IV) cyclophosphamide (60 mg/kg) with mesna (per site standard of care or USPI/SmPC) on Days −5 and −4, and 5 days of fludarabine IV (25 mg/m$^2$, Days −5 through −1).

IL-2 IV administrations at a dose of 600,000 IU/kg began as soon as 3 hours after, but no later than 24 hours after, completion of the TIL-based immunotherapy infusion on Day 0. Additional IL-2 doses were given approximately every 8 to 12 hours for up to 6 total doses.

TABLE 53

| Treatment administration regimen Treatment Administration | | | | | | | | | | |
|---|---|---|---|---|---|---|---|---|---|---|
| | −5 | −4 | −3 | −2 | −1 | 0 | 1 | 2 | 3 | 4 |
| Cyclophosphamide 60 mg/kg | X | X | | | | | | | | |
| Mesna | X | X | | | | | | | | |
| Fludarabine 25 mg/m$^2$/day | X | X | X | X | X | | | | | |
| TIL-based immunotherapy infusion | | | | | | X | | | | |
| IL-2 600,000 IU/kg | | | | | | (X)[a] | X | X | X | (X)[a] |

[a]( ) = If applicable.

Mesna Preparation

Mesna was administered to reduce the risk of hemorrhagic cystitis related to cyclophosphamide administration. Mesna was administered as a continuous or intermittent infusion as per local standards.

The total dose of mesna was not adjusted if the amount of cyclophosphamide is reduced. Dilute the volume of mesna injection or infusion per institutional standard.

Infusion of Cyclophosphamide and Mesna

Cyclophosphamide (60 mg/kg) in a total volume of 250 mL or 500 mL (e.g., 5% dextrose in water [D5W] or 0.9% sodium chloride [NaCl]).

Mesna (15 mg/kg), if infused continuously, was infused over approximately 2 hours with cyclophosphamide (on Days −5 and −4), then at a rate of 3 mg/kg/hour for the remaining 22 hours in a suitable diluent over 24 hours starting concomitantly with each cyclophosphamide dose.

The total dose administered was at least 1.3 times that of the dose of cyclophosphamide. Higher or continued doses of mesna could be administered for prevention of hemorrhagic cystitis.

Infusion of Fludarabine

Fludarabine (25 mg/m$^2$) was to be given IV over approximately 30 minutes once daily for 5 consecutive days during Day −5 to Day −1.

Duration of Participation:

Overall, the study participation time will be up to 5 years from treatment to completion.

Selected Inclusion Criteria:

Had histologically or pathologically confirmed diagnosis of NSCLC (squamous, nonsquamous, adenocarcinoma, large cell, or mixed histologies), and must have documented PD-L1 expression status, as determined by the tumor proportion score (TPS) prior to the CPI treatment that they received (i.e., the historic TPS that informed the initial treatment choice) (TPS <1% for Cohorts 1 and 3, and TPS >1% for Cohort 2).

Have received a single line of systemic therapy that included CPI and chemotherapy concurrently, with documented radiographic disease progression on or following this single line of systemic therapy.

Prior systemic therapy in the adjuvant or neoadjuvant setting, or as part of definitive chemoradiotherapy was not counted as a line of therapy if the disease had not progressed during or within 12 months of the completion of such therapy. Prior TIL treatment on this protocol did not count as a line of therapy for Cohort 4 (retreatment) patients.

Had documented exercise tolerance no less than 85% of their age-expected normal range and no signs or symptoms of ischemia or clinically significant arrhythmias.

Had Eastern Cooperative Oncology Group (ECOG) performance status of 0 or 1 and an estimated life expectancy of >6 months, in the Investigator's opinion.

Cohorts 1 and 2: Must have had at least one resectable lesion (or aggregate lesions) of a minimum 1.5 cm in diameter for TIL production.

Cohort 3 only: Patients must have had a single RECIST 1.1 measurable lesion and no additional lesion available for surgical harvest, or be unable to safely undergo a surgical harvest for TIL generation, but able to safely have tumor harvest via radiology guided core biopsy sufficient for TIL generation.

Cohort 4: Followed either paradigm.

All Cohorts: If the lesion considered for harvest was within a previously irradiated field, the lesion must have demonstrated radiographic progression prior to harvest and the irradiation must have been completed at least 3 months prior to enrollment. Patients must have an adequate histopathology specimen for protocol-required testing.

Following tumor harvest for TIL manufacturing, all patients must have had at least one remaining measurable lesions, as defined by RECIST 1.1, with the following considerations:

- Lesions in previously irradiated areas were not selected as target lesions unless there had been demonstrated progression in those lesions and the irradiation has been completed at least 3 months prior to enrollment.
- Cohorts 1 and 2 only: Lesions that were surgically partially resected for TIL generation that were still measurable per RECIST v1.1 could be selected as nontarget lesions but could not serve as a target lesion for response assessment.
- Cohort 3 only: If no other lesion was available for core biopsy for TIL generation, the single RECIST v1.1 measurable lesion may have served as both, the harvest site for the core biopsies, and the lesion for response monitoring.
- Cohort 4: May follow either paradigm but must have had at least 1 RECIST v1.1 measurable lesion to follow for response.

Efficacy Assessment:

The following efficacy parameters for TIL-based immunotherapy as a single therapy in patients with NSCLC were investigated in each cohort: ORR, CR rate, DOR, DCR, PFS, and OS.

Statistical Considerations:

The statistical analyses were based on the estimation of efficacy and safety parameters and will be performed by cohort. No formal statistical comparisons were applied between cohorts.

The primary efficacy endpoint was ORR as assessed per RECIST v1.1 by the IRC (Cohorts 1 and 2) or by the Investigator (Cohorts 3 and 4).

The ORR, CR rates, and the DCRs were summarized using point estimates and 2-sided 95% confidence limits based on the Clopper-Pearson exact method. Kaplan-Meier methods were used to summarize time-to-event efficacy endpoints, such as DOR, PFS, and OS. DOR analyses were performed for patients who achieve objective responses.

The safety analyses were descriptive and based on the summarization of TEAEs, SAEs, and AEs leading to discontinuation from the study, vital signs, and clinical laboratory tests.

Sample Size Determination:

The total number of planned patients infused with TIL-based immunotherapy in Cohorts 1, 2 and 3 was approximately 95.

Cohort 1 and 2: Approximately 40 patients in each cohort. For each cohort, Simon's two-stage design (Simon, 1989) with minimax was used to test the null hypothesis of <10% ORR against the alternative hypothesis of ORR >10%. In the first stage, twenty-five patients were accrued. If there are 2 or fewer patients responding to the therapy in these 25 patients, the cohort could be terminated. Otherwise, expansion into Stage 2 to a total of 40 patients occurred concurrently with the analysis of Stage 1. At the end of the second stage, if at least 7 patients respond to therapy among the total of 40 patients, the null hypothesis was rejected. This 2-stage design provided 70% power to reject the null hypothesis of 10% ORR based on an assumption of 20% ORR for TIL-based immunotherapy at a one-sided alpha level of 0.1.

Cohort 3: Approximately 15 patients were planned, which provided an estimated ORR with a half-width 90% confidence interval (CI) of <0.23 by the Clopper-Pearson exact method.

Cohort 4: Retreatment cohort: Patients who had been previously treated with TIL-based immunotherapy in Cohort 1, 2 or 3 of this study.

Example 17: Complete Response (Cr) to Iovance Tumor Infiltrating Lymphocytes (Til) Alone Administered to a Patient with Relapsed Non-Small Cell Lung Cancer (Nsclc): Case Report

Introduction

NSCLC is the most common and lethal cancer with a world-wide prevalence of over 2 million and 1.7 million deaths annually. Treatment options are limited, and prognosis remains poor for patients with relapsed metastatic NSCLC (mNSCLC) after failing standard of care therapies including platinum-doublet chemotherapy and checkpoint inhibitors (CPI). There remains a significant unmet medical need in NSCLC for patients who progress after CPI.

Adoptive cell therapy with tumor infiltrating lymphocytes (TIL) has demonstrated responses in various malignancies including, melanoma, cervical cancer, NSCLC and HNSCC alone or in combination with checkpoint inhibitors (CPI).

The safety and efficacy of TIL therapy, in a case study of a mNSCLC heavily pre-treated patient with PD-L1 expression level less than <1%, is presented.

Methods

We report on a 72-year-old female, never-smoker with metastatic NSCLC diagnosed after presenting with cough and cold symptoms. The workup included a chest computer tomography (CT) showing a 135 mm lung mass. Staging identified pulmonary, splenic and nodular lymphatic lesions (T4N1M1b; Stage IVB), PD-L1<1%). Biopsy confirmed a basaloid squamous cell carcinoma. Therapy was initiated with carboplatin and +Nab paclitaxel but was discontinued after 3 cycles due to an allergic reaction and poor tolerability. The second-line of therapy consisted of was nivolumab which was, discontinued after 4 cycles due to disease progression. The patient had a PD-L1 level of less than 1%. A third-line regimen of gemcitabine and cisplatin doublet therapy was then administered. Cisplatin was discontinued after 4 cycles and gemcitabine was completed after 6 cycles. After an initial response, disease progression was observed.

Approximately 4 months after completing gemcitabine, with disease progressing rapidly below the diaphragm, the patient enrolled in (NCT03645928), a prospective, open-label, multi-cohort, non-randomized, multicenter phase 2 study evaluating ACT with TIL. The patient had an ECOG performance status of 1, baseline target lesion sum-of-diameters SOD of 50 mm and had an increase of 127% in her SOD from screening to baseline on study prior to receiving TIL. The patient underwent tumor resection for TIL generation and received TIL as a single therapy and a one-time treatment. Preconditioning chemotherapy consisted of cyclophosphamide/fludarabine, then TIL followed by 3 doses of 600,000 IU/kg IL-2 (i.e., aldesleukin). Treatment tolerability and safety were assessed on an ongoing basis along with efficacy evaluation by the Investigator using RECIST v1.1.

Results

Adverse events were consistent with the known toxicities of the lymphodepletion and IL-2. Treatment emergent adverse events were acute, self-limiting, manageable, and short in duration. Adverse events >G3 were limited to G4 pancytopenia, and G3 hypotension and bacteremia. The patient experienced no serious adverse events.

At week 6, a partial response with PR (44% decrease) in target lesions was observed at the patient's first assessment. At 7 months after administration of TIL, when reduction of sum of diameters (SODs) was at a 48% decrease, a positron-emission tomography (PET) CT was conducted and showed no metabolic activity within the residual CT lesion. The patient is considered a complete response (CR) by PET-CT. The examination was ongoing at 15 months post TIL administration and total SOD reduction reached 60%. The patient has required no other anti-cancer therapy to be administered since the TIL administration.

CONCLUSIONS

This case presentation demonstrates that treatment with TILs as described in the present application can offer a therapeutic option for patients with metastatic NSCLC who have disease progression on mNSCLC after multiple lines of standard of care therapies, including CPI. Enrollment is ongoing and studies to continue to monitor and evaluate impact of TIL in NSCLC patients.

Example 18: Exemplary Production of a Cryopreserved Til Cell Therapy

This example describes an exemplarity cGMP manufacture of TIL Cell Therapy Process in G-REX Flasks according to current Good Tissue Practices and current Good Manufacturing Practices.

TABLE 54

Process Expansion Examplary Plan

| Estimated Day (post-seed) | Activity | Target Criteria | Anticipated Vessels | Estimated Total Volume (mL) |
|---|---|---|---|---|
| 0 | Tumor Dissection | ≤ 50 desirable tumor fragments per G-REX100MCS | G-REX100MCS 1 flask | ≤1000 |

TABLE 54-continued

| Process Expansion Examplary Plan | | | | |
|---|---|---|---|---|
| Estimated Day (post-seed) | Activity | Target Criteria | Anticipated Vessels | Estimated Total Volume (mL) |
| 11 | REP Seed | 5 - 200 × $10^6$ viable cells per G-REX500MCS | G-REX500MCS 1 flasks | ≤5000 |
| 16 | REP Split | 1 × $10^9$ viable cells per G-REX500MCS | G-REX500MCS ≤5 flasks | ≤25000 |
| 22 | Harvest | Total available cells | 3-4 CS-750 bags | ≤530 |

TABLE 55

| Flask Volumes | |
|---|---|
| Flask Type | Working Volume/Flask |
| G-REX100MCS | 1000 |
| G-REX500MCS | 5000 |

Process Information—Primary

Day 0 CM1 Media Preparation

In the BSC added reagents to RPMI 1640 Media bottle. Added the following reagents t Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

Removed unnecessary materials from BSC. Passed out media reagents from BSC, left Gentamicin Sulfate and HBSS in BSC for Formulated Wash Media preparation.

Thawed IL-2 aliquot. Thawed one 1.1 mL IL-2 aliquot (6×106 IU/mL) (BR71424) until all ice had melted. Recorded IL-2: Lot #and Expiry Transferred IL-2 stock solution to media. In the BSC, transferred 1.0 mL of IL-2 stock solution to the CM1 Day 0 Media Bottle prepared. Added CM1 Day 0 Media 1 bottle and IL-2 (6×106 IU/mL) 1.0 mL.

Passed G-REX100MCS into BSC. Aseptically passed G-REX100MCS (W3013130) into the BSC.

Pumped all Complete CM1 Day 0 Media into G-REX100MCS flask. Tissue Fragments Conical or GRex100MCS.

Day 0 Tumor Wash Media Preparation

In the BSC, added 5.0 mL Gentamicin (W3009832 or W3012735) to 1×500 mL HBSS Media (W3013128) bottle. Added per bottle: HBSS (500.0 mL); Gentamicin sulfate, 50 mg/mL (5.0 mL). Filtered HBSS containing gentamicin prepared through a 1L 0.22-micron filter unit (W1218810).

Day 0 Tumor Processing

Obtained Tumor. Obtained tumor specimen from QAR and transferred into suite at 2-8° C. immediately for processing.

Aliquoted Tumor Wash Media.

Tumor Wash 1 Using 8" forceps (W3009771), removed the tumor from the specimen bottle and transferred to the “Wash 1” dish prepared. Followed by Tumor Wash 2 and Tumor Wash 3.

Measured Tumor. Assessed Tumor. Assessed whether >30% of entire tumor area observed to be necrotic and/or fatty tissue. If applicable: Clean-Up Dissection. If tumor was large and >30% of tissue exterior was observed to be necrotic/fatty, performed “clean up dissection” by removing necrotic/fatty tissue while preserving tumor inner structure using a combination of scalpel and/or forceps.

Dissect TumorUsing a combination of scalpel and/or forceps, cut the tumor specimen into even, appropriately sized fragments (up to 6 intermediate fragments). Transferred intermediate tumor fragments. Dissected Tumor Fragmentsinto pieces approximately 3×3×3 mm in size. Stored Intermediate Fragments to Prevent Drying.

Repeated Intermediate Fragment Dissection. Determined number of pieces collected. If desirable tissue remains, selected additional Favorable Tumor Pieces from the “favorable intermediate fragments” 6-well plate to fill the drops for a maximum of 50 pieces.

Prepared Conical Tube. Transferred Tumor Pieces to 50 mL Conical Tube. Prepared BSC for G-REX100MCS. Removed G-REX100MCS from Incubator. Aseptically passed G-REX100MCS flask into the BSC. Added tumor fragments to G-REX100MCS flask. Evenly distributed pieces.

Incubated G-REX100MCS at the following parameters: Incubated G-REX flask: Temperature LED Display: 37.0+2.0° C.; $CO_2$ Percentage: 5.0+1.5% $CO_2$. Calculations: Time of incubation; lower limite=time of incubation+252 hours; upper limit =time of incubation+276 hours.

After process was complete, discarded any remaining warmed media and thawed aliquots of IL-2.

Day 11—Media Preparation

Monitored Incubator. Monitored Incubator. Incubator parameters: Temperature LED Display: 37.0+2.0° C.; $CO_2$ Percentage: 5.0+1.5% $CO_2$.

Warmed 3×1000 mL RPMI 1640 Media (W3013112) bottles and 3×1000 mL AIM-V (W3009501) bottles in an incubator for >30 minutes. Removed RPMI 1640 Media from incubator. Prepared RPMI 1640 Media. Filter Media. Thawed 3×1.1 mL aliquots of IL-2 (6×106 IU/mL) (BR71424). Removed AIM-V Media from the incubator. Add IL-2 to AIM-V. Aseptically transferred a 10 L Labtainer Bag and a repeater pump transferr set into the BSC.

Prepared 10 L Labtainer media bag. Prepared Baxa pump. Prepared 10 L Labtainer media bag. Pumped media into 10 L Labtainer. Removed pumpmatic from Labtainer bag.

Mixed media. Gently massaged the bag to mix. Sample media per sample plan. Removed 20.0 mL of media and place in a 50 mL conical tube.

Prepared Cell Count Dilution Tubes In the BSC, added 4.5 mL of AIM-V Media that had been labelled with “For Cell Count Dilutions” and lot number to four 15 mL conical tubes. Transferred reagents from the BSC to 2-8° C. Prepared 1L Transfer Pack.

Outside of the BSC weld (per Process Note 5.11) a 1L Transfer Pack to the transfer set attached to the “Complete CM2 Day 11 Media” bag prepared. Prepared feeder cell transfer pack. Incubated Complete CM2 Day 11 Media.

Day 11—TIL Harvest

Preprocessing table. Incubator parameters: Temperature LED Display: 37.0+2.0° C.; $CO_2$ Percentage: 5.0+1.5%

$CO_2$. Removed G-REX100MCS from incubator. Prepared 300 mL Transfer Pack. Welded transfer packs to G-REX100MCS.

Prepare flask for TIL Harvest and nitiation of TIL Harvest. TIL Harvested. Using the GatheRex, transferred the cell suspension through the blood filter into the 300 mL transfer pack. Inspect membrane for adherent cells.

Rinsed flask membrane. Closed clamps on G-REX100MCS. Ensured all clamps are closed. Heat sealed the TIL and the "Supernatant" transfer pack. Calculated volume of TIL suspension. Prepared Supernatant Transfer Pack for Sampling.

Pulled Bac-T Sample. In the BSC, draw up approximately 20.0 mL of supernatant from the 1L "Supernatant" transfer pack and dispense into a sterile 50 mL conical tube.

Inoculated BacT per Sample Plan. Removed a 1.0 mL sample from the 50 mL conical labeled BacT prepared using an appropriately sized syringe and inoculated the anaerobic bottle.

Incubated TIL. Placed TIL Transfer Pack in incubator until needed. Performed cell counts and calculations. Determined the Average of Viable Cell Concentration and Viability of the cell counts performed. Viability −2. Viable Cell Concentration −2.

Determined Upper and Lower Limit for counts. Lower Limit: Average of Viable Cell Concentration x 0.9. Upper Limit: Average of Viable Cell Concentration x 1.1. Confirmed both counts within acceptable limits. Determined an average Viable Cell Concentration from all four counts performed.

Adjusted Volume of TIL Suspension. Calculate the adjusted volume of TIL suspension after removal of cell count samples. Total TIL Cell Volume (A). Volume of Cell Count Sample Removed (4.0 ml) (B) Adjusted Total TIL Cell Volume C=A-B.

Calculated Total Viable TIL Cells. Average Viable Cell Concentration*: Total Volume; Total Viable Cells: C=A ×B.

Calculation for flow cytometry: if the Total Viable TIL Cell count from was $>4.0\times10^7$, calculated the volume to obtain $1.0\times10^7$ cells for the flow cytometry sample.

Total viable cells required for flow cytometry: $1.0\times10^7$ cells. Volume of cells required for flow cytometry: Viable cell concentration divided by $1.0\times10^7$ cells A.

Calculated the volume of TIL suspension equal to $2.0\times10^8$ viable cells. As needed, calculated the excess volume of TIL cells to remove and removed excess TIL and placed TIL in incubator as needed. Calculated total excess TIL removed, as needed.

Calculated amount of CS-10 media to add to excess TIL cells with the target cell concentration for freezing is $1.0\times10^8$ cells/mL. Centrifuged excess TILs, as needed. Observed conical tube and added CS-10.

Filled Vials. Aliquoted 1.0 mL cell suspension, into appropriately sized cryovials. Aliquoted residual volume into appropriately sized cryovial per SOP-00242. If volume is <0.5 mL, add CS10 to vial until volume is 0.5 mL.

TIL Cryopreservation of Sample

Calculated the volume of cells required to obtain $1\times10^7$ cells for cryopreservation. Removed sample for Cryopreservation. Placed TIL in Incubator. Cryopreservation of sample.

Observed conical tube and added CS-10 slowly and record volume of 0.5 mL of CS10 added.

Day 11—Feeder Cells

Obtained feeder cells. Obtained 3 bags of feeder cells with at least two different lot numbers from LN2 freezer. Kept cells on dry ice until ready to thaw. Prepared waterbath or Cryotherm. Thawed Feeder Cells at 37.0±2.0° C. water bath or cytotherm for −3-5 minutes or until ice has just disappeared. Removed media from incubator. Pooled thawed feeder cells. Added feeder cells to transfer pack. Dispensed the feeder cells from the syringe into the transfer pack. Mixed pooled feeder cells and labeled transfer pack.

Calculated total volume of feeder cell suspension in Transfer Pack

Removed cell count samples. Using a separate 3 mL syringe for each sample, pulled 4×1.OmL cell count samples from Feeder Cell Suspension Transfer Pack using the needless injection port. Aliquoted each sample into the cryovials labeled. Performed Cell Counts and Determine Multiplication FactorSelected protocols and entered multiplication factors. Determined the Average of Viable Cell Concentration and Viability of the cell counts performed. Determined Upper and Lower Limit for counts and confirm within limits.

Adjusted Volume of Feeder Cell Suspension. Calculated the adjusted volume of Feeder Cell suspension after removal of cell count samples. Calculated Total Viable Feeder Cells. Obtained additional Feeder Cells as needed. Thawed Additional Feeder Cells as needed. Placed the 4th Feeder Cell bag into a zip top bag and thaw in a 37.0±2.0° C. water bath or cytotherm for ~3-5 minutes and pooled additional feeder cells. Measured Volume. Measured the volume of the feeder cells in the syringe and recorded below (B). Calculated the new total volume of feeder cells. Added Feeder Cells to Transfer Pack.

Prepared dilutions as needed, adding 4.5 mL of AIM-V Media to four 15 mL conical tubes. Prepared cell counts. Using a separate 3mLsyringe for each sample, removed 4 ×1.0 mL cell count samples from Feeder Cell Suspension transfer pack, using the needless injection port. Performed cell counts and calculations. Determined an average Viable Cell Concentration from all four counts performed. Adjusted Volume of Feeder Cell suspension and calculated the adjusted volume of Feeder Cell suspension after removal of cell count samples. Total Feeder Cell Volume minus 4.0 mL removed. Calculated the volume of Feeder Cell Suspension that was required to obtain $5\times10^9$ viable feeder cells. Calculated excess feeder cell volume. Calculated the volume of excess feeder cells to remove. Removed excess feeder cells.

Using a 1.0 mL syringe and 16G needle, drew up 0.15 mL of OKT3 and added OKT3. Heat sealed the Feeder Cell Suspension transfer pack.

Day 11 G-REX Fill and Seed

Set up G-REX500MCS. Removed "Complete CM2 Day 11 Media", from incubator and pumped media into G-REX500MCS. Pumped 4.5L of media into the G-REX500MCS, filling to the line marked on the flask. Heat sealed and incubated flask as needed. Welded the Feeder Cell suspension transfer pack to the G-REX500MCS. Added Feeder Cells to G-REX500MCS. Heat sealed. Welded the TIL Suspension transfer pack to the flask. Added TIL to G-REX500MCS. Heat sealed. Incubated G-REX500MCS at 37.0+2.0° C., $CO_2$ Percentage: 5.0+1.5% $CO_2$.

Calculated incubation window. Performed calculations to determine the proper time to remove G-REX500MCS from incubator on Day 16. Lower limit: Time of incubation +108 hours. Upper limit: Time of incubation+132 hours.

Day 11 Excess TIL Cryopreservation

Applicable: Froze Excess TIL Vials. Verified the CRF has been set up prior to freeze. Perform Cryopreservation. Transferred vials from Controlled Rate Freezer to the appropriate storage. Upon completion of freeze, transfer vials from CRF to the appropriate storage container. Transferred vials to appropriate storage. Recorded storage location in LN2.

Day 16 Media Preparation

Pre-warmed AIM-V Media. Calculated time Media was warmed for media bags 1, 2, and 3. Ensured all bags have been warmed for a duration between 12 and 24 hours. Setup 10 L Labtainer for Supernatant. Attached the larger diameter end of a fluid pump transfer set to one of the female ports of a 10 L Labtainer bag using the Luer connectors. Setup 10 L Labtainer for Supernatant and label. Setup 10 L Labtainer for Supernatant. Ensure all clamps were closed prior to removing from the BSC. NOTE: Supernatant bag was used during TIL Harvest, which may be performed concurrently with media preparation.

Thawed IL-2. Thawed 5×1.1 mL aliquots of IL-2 ($6\times10^6$ IU/mL) (BR71424) per bag of CTS AIM V media until all ice had melted. Aliquoted 100.0 mL GlutaMax. Added IL-2 to GlutaMax. Prepared CTS AIM V media bag for formulation. Prepared CTS AIM V media bag for formulation. Stage Baxa Pump. Prepared to formulate media. Pumped GlutaMax+IL-2 into bag. Monitored parameters: Temperature LED Display: 37.0+2.0° C., $CO_2$ Percentage: 5.0+1.5% $CO_2$. Warmed Complete CM4 Day 16 Media. Prepared Dilutions.

Day 16 REP Spilt

Monitored Incubator parameters: Temperature LED Display: 37.0+2.0° C., $CO_2$ Percentage: 5.0+1.5% $CO_2$. Removed G-REX500MCS from the incubator. Prepared and labeled 1L Transfer Pack as TIL Suspension and weighed 1L.

Volume Reduction of G-REX500MCS. Transferred −4.5L of culture supernatant from the G-REX500MCS to the 10 L Labtainer per SOP-01777.

Prepared flask for TIL Harvest. After removal of the supernatant, closed all clamps to the red line.

Initiation of TIL Harvest. Vigorously tap flask and swirl media to release cellsensure all cells have detached.

TIL Harvest. Released all clamps leading to the TIL suspension transfer pack. Using the GatheRex transferred the cell suspension into the TIL Suspension transfer pack. NOTE: Be sure to maintain the tilted edge until all cells and media are collected. Inspected membrane for adherent cells. Rinsed flask membrane. Closed clamps on G-REX500MCS. Heat sealed the Transfer Pack containing the TIL. Heat sealed the 10 L Labtainer containing the supernatant. Recorded weight of Transfer Pack with cell suspension and calculate the volume suspension. Prepared transfer pack for sample removal. Removed testing samples from cell supernatant.

Sterility & BacT Testing Sampling: removed a 1.0 mL sample from the 15 mL conical labeled BacT prepared. Removed Cell Count Samples. In the BSC, using separate 3 mL syringes for each sample, removed 4×1.0 mL cell count samples from "TIL Suspension" transfer pack.

Removed *Mycoplasma* Samples. Using a 3 mL syringe, removed 1.0 mL from TIL Suspension transfer pack and place into 15 mL conical labeled "*Mycoplasma* diluent" prepared.

Prepared Transfer Pack for Seeding. Placed TIL in Incubator. Removed cell suspension from the BSC and place in incubator until needed. Performed cell counts and calculations. Diluted cell count samples initially by adding 0.5 mL of cell suspension into 4.5 mL of AIM-V media prepared which gave a 1:10 dilution. Determined the Average of Viable Cell Concentration and Viability of the cell counts performed. Determined Upper and Lower Limit for counts. NOTE: Dilution may be adjusted according based off the expected concentration of cells. Determined an average Viable Cell Concentration from all four counts performed.

Adjusted Volume of TIL Suspension. Calculated the adjusted volume of TIL suspension after removal of cell count samples. Total TIL Cell Volume minus 5.0 mL removed for testing.

Calculated Total Viable TIL Cells. Calculated the total number of flasks to seed. NOTE: The maximum number of G-REX500MCS flasks to seed was five. If the calculated number of flasks to seed exceeded five, only five were seeded USING THE ENTIRE VOLUME OF CELL SUSPENSION AVAILABLE.

Calculate number of flasks for subculture. Calculated the number of media bags required in addition to the bag prepared. Prepared one 10 L bag of "CM4 Day 16 Media" for every two G-REX-500M flask needed as calculated. Proceeded to seed the first GREX-500M flask(s) while additional media is prepared and warmed. Prepared and warmed the calculated number of additional media bags determined. Filled G-REX500MCS. Prepared to pump media and pumped 4.5L of media into G-REX500MCS. Heat Sealed. Repeated Fill. Incubated flask. Calculated the target volume of TIL suspension to add to the new G-REX500MCS flasks. If the calculated number of flasks exceeds five only five will be seeded, USING THE ENTIRE VOLUME OF CELL SUSPENSION. Prepared Flasks for Seeding. Removed G-REX500MCS from the incubator. Prepared G-REX500MCS for pumping. Closed all clamps on except large filter line. Removed TIL from incubator. Prepared cell suspension for seeding. Sterile welded (per Process Note 5.11) "TIL Suspension" transfer pack to pump inlet line. Placed TIL suspension bag on a scale.

Seeded flask with TIL Suspension. Pump the volume of TIL suspension calculated into flask. Heat sealed. Filled remaining flasks.

Monitored Incubator. Incubator parameters: Temperature LED Display: 37.0+2.0° C., $CO_2$ Percentage: 5.0+1.5% $CO_2$. Incubated Flasks.

Determined the time range to remove G-REX500MCS from incubator on Day 22.

Day 22 Wash Buffer Preparation

Prepared 10 L Labtainer Bag. In BSC, attach a 4" plasma transfer set to a 10 L Labtainer Bag via luer connection. Prepared 10 L Labtainer Bag. Closed all clamps before transferring out of the BSC. NOTE: Prepared one 10 L Labtainer Bag for every two G-REX500MCS flasks to be harvested. Pumped Plasmalyte into 3000 mL bag and removed air from 3000 mL Origen bag by reversing the pump and manipulating the position of the bag. Added Human Albumin 25% to 3000 mL Bag. Obtain a final volume of 120.0 mL of Human Albumin 25%.

Prepared IL-2 Diluent. Using a 10 mL syringe, removed 5.0 mL of LOVO Wash Buffer using the needleless injection port on the LOVO Wash Buffer bag. Dispensed LOVO wash buffer into a 50 mL conical tube.

CRF Blank Bag LOVO Wash Buffer Aliquotted. Using a 100 mL syringe, drew up 70.0 mL of LOVO Wash Buffer from the needleless injection port.

Thawed IL-2. Thawed one 1.1 mL of IL-2 (6×106 IU/mL)), until all ice has melted. IL-2 Preparation. Added 50 μL IL-2 stock (6×106 IU/mL) to the 50 mL conical tube labeled "IL-2 Diluent."

Cryopreservation Prep. Placed 5 cryo-cassettes at 2-8° C. to precondition them for final product cryopreservation.

Prepared Cell Count Dilutions. In the BSC, added 4.5 mL of AIM-V Media that has been labelled with lot number and "For Cell Count Dilutions" to 4 separate 15 mL conical tubes. Prepared Cell Counts. Labeled 4 cryovials with vial number (1-4). Kept vials under BSC to be used.

Day 22 TIL Harvest

Monitored Incubator. Incubator Parameters Temperature LED display: 37 2.0° C., $CO_2$ Percentage: 5%+1.5%. Removed G-REX500MCS Flasks from Incubator. Prepared TIL collection bag and labeled. Sealed off extra connections. Volume Reduction: Transfered –4.5L of supernatant from the G-REX500MCS to the Supernatant bag.

Prepared flask for TIL Harvest. Initiated collection of TIL. Vigorously tap flask and swirl media to release cells. Eusure all cells have detached. Initiated collection of TIL. Released all clamps leading to the TIL suspension collection bag. TIL Harvest. Using the GatheRex, transferred the TIL suspension into the 3000 mL collection bag. Inspect membrane for adherent cells. Rinsed flask membrane. Closed clamps on G-Rex500MCS and ensured all clamps are closed. Transferred cell suspension into LOVO source bag. Closed all clamps. Heat Sealed. Removed 4×1.0 mL Cell Counts Samples Performed Cell Counts. Performed cell counts and calculations utilizing NC-200 and Process Note 5.14. Diluted cell count samples initially by adding 0.5 mL of cell suspension into 4.5 mL of AIM-V media prepared. This gave a 1:10 dilution. Determined the Average Viability, Viable Cell Concentration, and Total Nucleated Cell concentration of the cell counts performed. Determined Upper and Lower Limit for counts. Determined the Average Viability, Viable Cell Concentration, and Total Nucleated Cell concentration of the cell counts performed. Weighed LOVO Source Bag. Calculated Total Viable TIL Cells.

Calculated Total Nucleated Cells.

Prepared *Mycoplasma* Diluent. Removed 10.0 mL from one supernatant bag via luer sample port and placed in a 15 mL conical.

LOVO

Performed “TIL G-REX Harvest” protocol and determined the final product target volume. Loaded disposable kit. Removed filtrate bag. Entered Filtrate capacity. Placed Filtrate container on benchtop. Attached PlasmaLyte. Verified that the PlasmaLyte was attached and observed that the PlasmaLyte is moving. Attached Source container to tubing and verified Source container was attached. Confirmed PlasmaLyte was moving.

Final Formulation and Fill

Target volume/bag calculation. Calculated volume of CS-10 and LOVO wash buffer to formulate blank bag. Prepared CRF Blank.

Calculated the volume of IL-2 to add to the Final Product. Final IL-2 Concentration desired (IU/mL)—300IU/mL. IL-2 working stock: $6\times10^4$ IU/mL. Assembled Connect apparatus. Sterile welded a 4S-4M60 to a CC2 Cell Connection. Sterile welded (per Process Note 5.11) the CS750 Cryobags to the harness prepared. Welded CS-10 bags to spikes of the 4S-4M60.Prepared TIL with IL-2. Using an appropriately sized syringe, removed amount of IL-2 determined from the “IL-2 6x104” aliquot. Labeled Forumlated TIL Bag. Added the Formulated TIL bag to the apparatus. Added CS10. Switched Syringes. Drew ~10 mL of air into a 100 mL syringe and replaced the 60 mL syringe on the apparatus. Added CS10. Prepared CS-750 bags. Dispensed cells.

Removed air from final product bags and take retain. Once the last final product bag was filled, closed all clamps. Drew 10 mL of air into a new 100 mL syringe and replace the syringe on the apparatus. Dispensed retain into a 50 mL conical tube and label tube as “Retain” and lot number. Repeat air removal step for each bag.

Prepared final product for cryopreservation, including visual inspection. Held the cryobags on cold pack or at 2-8° C. until cryopreservation.

Removed Cell Count Sample. Using an appropriately sized pipette, remove 2.0 mL of retain and place in a 15 mL conical tube to be used for cell counts. Performed cell counts and calculations. NOTE: Diluted only one sample to appropriate dilution to verify dilution is sufficient. Diluted additional samples to appropriate dilution factor and proceed with counts. Determined the Average of Viable Cell Concentration and Viability of the cell counts performed. Determined Upper and Lower Limit for counts. NOTE: Dilution may be adjusted according based off the expected concentration of cells. Determined the Average of Viable Cell Concentration and Viability. Determined Upper and Lower Limit for counts. Calculated IFN-γ. Heat Sealed Final Product Bags.

Labeled and Collected Samples per exemplary Sample Plan below.

TABLE 56

Sample Plan

| Sample | Number of Containers | Sample Volume to Add to Each | Container Type |
|---|---|---|---|
| *Mycoplasma | 1 | 1.0 mL | 15 mL Conical |
| Endotoxin | 2 | 1.0 mL | 2 mL Cryovial |
| Gram Stain | 1 | 1.0 mL | 2 mL Cryovial |
| IFN-g | 1 | 1.0 mL | 2 mL Cryovial |
| Flow Cytometry | 1 | 1.0 mL | 2 mL Cryovial |
| **Bac-T Sterility | 2 | 1.0 mL | Bac-T Bottle |
| QC Retain | 4 | 1.0 mL | 2 mL Cryovial |
| Satellite Vials | 10 | 0.5 mL | 2 mL Cryovial |

Sterility & BacT. Testing Sampling. In the BSC, remove a 1.OmL sample from the retained cell suspension collected using an appropriately sized syringe and inoculate the anaerobic bottle. Repeat the above for the aerobic bottle Final Product Cryopreservation Prepared Controlled Rate Freezer. Verified the CRF had been set up. Set up CRF probes. Placed final product and samples in CRF. Determined the time needed to reach 4° C.±1.5° C. and proceed with the CRF run. CRF Completed and Stored. Stopped the CRF after the completion of the run. Remove cassettes and vials from CRF. Transferred cassettes and vials to vapor phase LN2 for storage. Recorded storage location Post Processing Summary Post-Processing: Final Drug Product (Day 22) Determination of CD3+Cells on Day 22 REP by Flow Cytometry (Day 22) Gram Staining Method (GMP)

(Day 22) Bacterial Endotoxin Test by Gel Clot LAL Assay (GMP)

(Day 16) BacT Sterility Assay (GMP)

(Day 16) *Mycoplasma* DNA Detection by TD-PCR (GMP)

Acceptable Appearance Attributes (Day 22) BacT Sterility Assay (GMP)(Day 22)

(Day 22) IFN-gamma Assay

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treating non-small cell lung cancer (NSCLC) in a patient in need thereof, the method comprising administering a therapeutically effective population of tumor infiltrating lymphocytes (TILs) to the patient, wherein the patient is refractory or resistant to an immune-checkpoint inhibitor (ICI) treatment, wherein the refractory or resistant NSCLC has been previously treated with an ICI and has progressed on or after the treatment with the ICI, and wherein the patient has a predetermined absence of one or more driver mutations, and wherein the one or more driver mutations comprise an EGFR mutation; and further wherein the TILs are administered as a single agent.

2. The method of claim 1, wherein the patient has a predetermined tumor proportion score (TPS) of PD-L1 of <1% prior to ICI treatment or TPS prior to ICI treatment is unknown, or a TPS score of PD-L1 of ≥1% prior to ICI treatment.

3. The method of claim 1, wherein the patient has a TPS of PD-L1 of <1% prior to ICI treatment or TPS prior to ICI treatment is unknown.

4. The method of claim 1, wherein the patient has a TPS of PD-L1 of 2 1% prior to ICI treatment.

5. The method of claim 1, wherein the therapeutically effective population of TILs is produced using a tumor sample from surgical resection.

6. The method of claim 1, wherein the therapeutically effective population of TILs is produced using a tumor sample from needle biopsy, core biopsy, or small biopsy.

7. The method of claim 1, wherein the one or more driver mutations further comprise one or more of an ALK-mutation, a c-ROS-mutation (ROS1-mutation), or a ROS1 fusion.

8. The method of claim 1, wherein the patient has a NSCLC that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNA11 inhibitor.

9. The method of claim 1, wherein the NSCLC is refractory or resistant to treatment with an anti-PD-1 and/or anti-PD-L1 antibody, wherein the refractory or resistant NSCLC has been previously treated with an anti-PD-1 and/or anti-PD-L1 antibody and has progressed on or after the treatment with the anti-PD-1 and/or anti-PD-L1 antibody.

10. The method of claim 1, wherein the NSCLC is refractory or resistant to treatment with a chemotherapeutic agent, wherein the refractory or resistant NSCLC has been previously treated with a chemotherapeutic agent and has progressed on or after the treatment with the chemotherapeutic agent.

11. The method of claim 1, wherein the NSCLC is refractory or resistant to a VEGF-A inhibitor, wherein the refractory or resistant NSCLC has been previously treated with a VEGF-A inhibitor and has progressed on or after the treatment with the VEGF-A inhibitor.

12. The method of claim 1, wherein the NSCLC has been previously treated with an anti-PD-1 or an anti-PD-L1 antibody and has been previously treated with a chemotherapeutic agent.

13. The method of claim 1, wherein the NSCLC has been previously treated with an anti-PD-1 and/or anti-PD-L1 antibody and has been previously treated with a chemotherapeutic agent and/or a VEGF-A inhibitor.

14. The method of claim 13, wherein the NSCLC has progressed on concurrent or sequential front-line PD-1/PD-L1 inhibitor+chemotherapy±bevacizumab.

15. The method of claim 1, wherein the NSCLC has been previously treated with an anti-PD-1 and/or anti-PD-L1 antibody and has bulky disease at baseline.

16. The method of claim 1, wherein the NSCLC has been treated with a chemotherapeutic agent and has bulky disease at baseline.

17. The method of claim 1, wherein the refractory or resistant NSCLC has been previously treated with a chemotherapeutic agent but is not being currently treated with a chemotherapeutic agent and has bulky disease at baseline.

18. The method of claim 1, wherein the NSCLC has been treated with a chemotherapeutic agent and/or VEGF-A inhibitor but is not being currently treated with a chemotherapeutic agent and/or VEGF-A inhibitor and has bulky disease at baseline.

19. The method of claim 1, wherein the patient has one or more genomic alterations except for EGFR, ALK and ROS1.

20. The method of claim 19, wherein the patient has been treated with a targeted therapy in addition to ICI treatment and chemotherapy.

* * * * *